(12) United States Patent
Gutierrez et al.

(10) Patent No.: US 7,834,000 B2
(45) Date of Patent: *Nov. 16, 2010

(54) CGRP RECEPTOR ANTAGONISTS

(75) Inventors: Corey Gutierrez, San Diego, CA (US);
Andreas Termin, Encinitas, CA (US);
Sara Hadida-Ruah, La Jolla, CA (US);
Pramod Joshi, San Diego, CA (US);
Daniele Bergeron, La Mesa, CA (US);
Sanghee Yoo, San Diego, CA (US);
Hayley Binch, San Diego, CA (US); Jon Come, Cambridge, MA (US); Jingrong Cao, Newton, MA (US); Suganthi Nanthakumar, Newton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/818,224

(22) Filed: Jun. 13, 2007

(65) Prior Publication Data

US 2008/0004261 A1    Jan. 3, 2008

Related U.S. Application Data

(60) Provisional application No. 60/813,178, filed on Jun. 13, 2006.

(51) Int. Cl.
| | |
|---|---|
| C07D 243/04 | (2006.01) |
| C07D 239/80 | (2006.01) |
| C07D 401/14 | (2006.01) |
| C07D 403/14 | (2006.01) |
| C07D 417/14 | (2006.01) |
| C07D 205/04 | (2006.01) |
| C07D 241/04 | (2006.01) |
| A61K 31/397 | (2006.01) |
| A61K 31/4025 | (2006.01) |
| A61K 31/427 | (2006.01) |
| A61K 31/437 | (2006.01) |
| A61K 31/438 | (2006.01) |
| A61K 31/496 | (2006.01) |
| A61K 31/517 | (2006.01) |
| A61K 31/551 | (2006.01) |

(52) U.S. Cl. ............... 514/211.08; 514/303; 514/266.1; 514/266.2; 514/266.21; 514/266.23; 514/266.24; 514/326; 514/255.05; 514/278; 540/567; 544/235; 544/405; 546/118; 546/209; 546/17

(58) Field of Classification Search ....................... None
See application file for complete search history.

(56) References Cited

U.S. PATENT DOCUMENTS 7,476,665 B2 * 1/2009 Burgey et al. ............... 514/221

FOREIGN PATENT DOCUMENTS

| WO | 03104236 A1 | 12/2003 |
| WO | 2004017965 A1 | 3/2004 |
| WO | 2004092166 A2 | 10/2004 |
| WO | WO2007/146349 | * 6/2006 |

OTHER PUBLICATIONS

Recober, et al. Curr. Opin. Neurol. 22, pp. 241-246 (2009).*
Hay, et al. Maturitas 64, pp. 104-108 (2009).*
Yu, et al. Neurosci. and Biobehav. Rev. 33, pp. 1185-1191 (2009).*
Schafer et al. Drug Discovery Today 2008, 13 (21/22), 913-916.*
Horig et al. Journal of Translational Medicine 2004, 2(44).*
PCT/US2007/013896: International Search Report dated Jul. 23, 2008.

* cited by examiner

*Primary Examiner*—Kamal A Saeed
*Assistant Examiner*—Michael Barker
(74) *Attorney, Agent, or Firm*—Michael C. Badia

(57) ABSTRACT

The present invention relates to CGRP receptor antagonists, pharmaceutical compositions thereof, and methods therewith for treating CGRP receptor-mediated diseases and conditions.

20 Claims, No Drawings

CGRP RECEPTOR ANTAGONISTS

CROSS REFERENCE TO RELATED APPLICATIONS

The present application claims the benefit under 35 U.S.C. §119 of U.S. provisional application Ser. No. 60/813,178 titled "CGRP RECEPTOR ANTAGONISTS" filed Jun. 13, 2006, the entire contents of which is hereby incorporated by reference.

TECHNICAL FIELD OF THE INVENTION

The present invention relates to CGRP receptor antagonists, pharmaceutical compositions thereof, and methods therewith for treating CGRP receptor-mediated diseases and conditions.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP (8-37), a peptide CGRP antagonist (Williamson et al., Cephalalgia, 1997, 17, 525-531). Trigeminal ganglion stimulation increased facial blood flow in the rat, which was inhibited by CGRP (8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist. In recently reported clinical trials, the CGRP receptor antagonist BIBN 4096 BS was reported to be effective in treating acute attacks of migraine (Olesen et al., N. Engl. J. Med. 2004, 350:1104-1110).

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr. Opin. Inves. Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists of CGRP receptors, pharmaceutical compositions thereof, and uses therewith.

SUMMARY OF THE INVENTION

The present invention provides compounds of formula I:

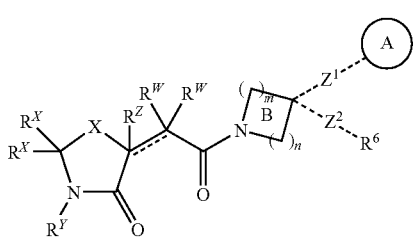

or a pharmaceutically acceptable salt thereof.

These compounds are useful as antagonists of CGRP receptors and thus treating CGRP-mediated conditions. The present invention also provides pharmaceutical compositions thereof and uses therewith.

DETAILED DESCRIPTION OF THE INVENTION

2. Compounds and Definitions:

Compounds of this invention include those described generally above, and are further illustrated by the classes, subclasses, and species disclosed herein. As used herein, the following definitions shall apply unless otherwise indicated.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic or tricyclic $C_8$-$C_{14}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. Suitable cycloaliphatic groups include cycloalkyl, bicyclic cycloalkyl (e.g., decalin), bridged bicycloalkyl such as norbornyl or [2.2.2]bicyclo-octyl, or bridged tricyclic such as adamantyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring atom is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, or nitrogen (including, any oxidized forms thereof, e.g., S=O, $SO_2$, etc.; the quaternized form of any basic nitrogen or; a substitutable nitrogen of a heterocyclic ring, for example N (as in 3,4-dihydro-2H-pyrrolyl), NH (as in pyrrolidinyl) or NR[+] (as in N-substituted pyrrolidinyl)).

The terms "haloaliphatic" and "haloalkoxy" means aliphatic or alkoxy, as the case may be, substituted with one or more halo atoms. The term "halogen" or "halo" means F, Cl, Br, or I. Examples of haloaliphatic include —$CHF_2$, —$CH_2F$, —$CF_3$, —$CF_2$—, or perhaloalkyl, such as, —$CF_2CF_3$.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroaralkoxy and the like) group may contain one or more substituents. Suitable substituents on the unsaturated carbon atom of an aryl or heteroaryl group are selected from halo; —R°; —OR°; —SR°; 1,2-methylene-dioxy; 1,2-ethylenedioxy; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O)R°; —NR°C(O)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(O)N(R°)$_2$; —OC(O)N(R°)$_2$; —S(O)$_2$R°; —SO$_2$N(R°)$_2$; —S(O)R°; —NR°SO$_2$N(R°)$_2$; —NR°SO$_2$R°; —C(=S)N(R°)$_2$; —C(=NH)—N(R°)$_2$; or —(CH$_2$)$_{0-2}$NHC(O)R° wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halo, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halo, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

Optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halo, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R$^+$ is unsubstituted.

The term "spirocyclic ring system" refers to a moiety comprising two or more rings, wherein at least one ring has two points of attachment to another ring through a common carbon ring atom.

As detailed above, in some embodiments, two independent occurrences of R° (or R$^+$, or any other variable similarly defined herein), are taken together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

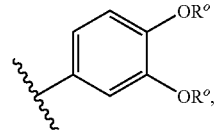

these two occurrences of R° are taken together with the oxygen atoms to which they are bound to form a fused 6-membered oxygen containing ring:

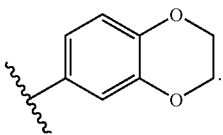

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes—in biological assays.

The term "aryl-C1-C6 aliphatic-" and similar such terms mean that the aryl group is linked to the core molecule by a C1 to C6 aliphatic linker. For instance, the term "aryl-C2-alkyl- means a —CH$_2$CH$_2$Ph group or a phenylethyl group is attached to the core molecule.

In one embodiment, the present invention provides compounds of formula I:

I wherein:

X is S, SO, or SO$_2$;

$Z^1$ is a bond or NR$^7$, O, S, CH$_2$, C(O), or NR$^7$C(O)NR$^7$, wherein R$^7$ is hydrogen, C1-C4 aliphatic or C(O)C1-C4 aliphatic;

$Z^2$ is a bond, O, CH$_2$O, or C(O);

ring A is phenyl or a 4-7 membered heterocyclic or heteroaryl ring or a 10-14 membered bicyclic heteroaryl or heterocyclic ring, wherein said heterocyclic or heteroaryl ring has 1-4 heteroatoms selected from O, N, or S; wherein ring A is optionally substituted with up to 5 R$^1$ substituents;

wherein:

$Z^2$ is a bond, $Z^1$ is a bond, NR$^7$, O, S, CH$_2$, C(O), or NR$^7$C(O)NR$^7$; or wherein:

$Z^1$, $Z^2$, and R$^6$ are absent, ring A is not aromatic, and ring A together with ring B form a spirocyclic ring system;

R$^6$ is hydrogen or C1-C4 aliphatic;

m is 1-3;

n is 1-3; provided that m+n is ≦4;

R$^Y$ is aryl, heteroaryl, cycloaliphatic, C1-C6 aliphatic, aryl-C1-C6 aliphatic-, heteroaryl-C1-C6 aliphatic-, heterocyclyl-C1-C6 aliphatic- or cycloaliphatic-C1-C6 aliphatic-; wherein R$^Y$ is optionally substituted with up to 5 R$^2$ substituents;

R$^X$ is hydrogen, aryl, heteroaryl, C1-C6 aliphatic, aryl-C1-C6 aliphatic-, heteroaryl-C1-C6 aliphatic-, wherein R$^X$ is optionally substituted with up to 5 R$^3$ substituents;

or two R$^X$, taken together with the carbon atom that they are attached to, form a 3-9 membered monocyclic, a 9-14 membered bicyclic, or a 12-14 membered tricyclic aryl, heteroaryl or heterocyclic ring system wherein each heteroaryl or heterocyclic ring has up to 3 heteroatoms selected from O, S, and N; wherein said ring system formed by two R$^X$ is optionally substituted with up to 5 R$^4$ substituents;

R$^Z$ is absent, hydrogen, CN, C1-C6 aliphatic, halo-C1-C6 aliphatic, O—C1-C6 aliphatic, O-(halo-C1-C6 aliphatic), halo, aryl-C1-C6 aliphatic, or heteroaryl-C1-C6 aliphatic;

----- is a single or a double bond; provided that when it is a double bond, then R$^Z$ and one of R$^W$ is absent;

each R$^W$ is independently absent, hydrogen, halo, oxo, C1-C6 aliphatic, halo-C1-C6 aliphatic, —O—C1-C6 aliphatic, —O-(halo-C1-C6 aliphatic), aryl, aryl-C1-C6 aliphatic-, C3-C7 cycloaliphatic; or two R$^W$ taken together form an optionally substituted C3-C7 cycloaliphatic or heterocyclic ring, wherein said heterocyclic ring has up to 3 heteroatoms selected from O, S, and N; wherein said ring formed by two R$^W$ is optionally substituted with up to 5 R$^5$ substituents;

wherein each occurrence of R$^1$, R$^2$, R$^3$, R$^4$, and R$^5$ is independently Q-R$^M$;

wherein Q is a bond or is a C1-C6 aliphatic chain wherein up to two non-adjacent methylene units of Q are optionally and independently replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR;

wherein each occurrence of R$^M$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R';

wherein each occurrence of R is independently selected from hydrogen or a C$_{1-6}$ aliphatic group optionally substituted with 0-5 occurrences of R$^K$; and each occurrence of R$^K$ is independently selected from —R$^V$, halogen, —NO$_2$, —CN, —OR$^V$, —SR$^V$, —N(R$^V$)$_2$, —NR$^V$COR$^V$, —NR$^V$CON(R$^V$)$_2$, —NR$^V$CO$_2$R$^V$, —COR$^V$, —CO$_2$R$^V$, —OCOR$^V$, —CON(R$^V$)$_2$, —C(=N—CN), —OCON(R$^V$)$_2$, —SOR$^V$, —SO$_2$R$^V$, —SO$_2$N(R$^V$)$_2$, —NR$^V$SO$_2$R$^V$, —NR$^V$SO$_2$N(R$^V$)$_2$, —COCOR$^V$, —COCH$_2$COR$^V$, —OP(O)(OR$^V$)$_2$, —P(O)(OR$^V$)$_2$, —OP(O)$_2$OR$^V$, —P(O)$_2$OR$^V$, —PO(R$^V$)$_2$, or —OPO(R$^V$)$_2$, wherein R$^V$ is hydrogen or unsubstituted C$_{1-6}$ aliphatic; and wherein each occurrence of R' is independently hydrogen, a C$_{1-6}$ aliphatic group optionally substituted with 0-5 occurrences of R$^{M1}$; and each occurrence of R$^{M1}$ is independently selected from —R$^T$, halogen, —NO$_2$, —CN, —OR$^T$, —SR$^T$, —N(R$^T$)$_2$, —NR$^T$COR$^T$, —NR$^T$CON(R$^T$)$_2$, —NR$^T$CO$_2$R$^T$, —COR$^T$, —CO$_2$R$^T$, —OCOR$^T$, —CON(R$^T$)$_2$, —C(=N—CN), —OCON(R$^T$)$_2$, —SOR$^T$, —SO$_2$R$^T$, —SO$_2$N(R$^T$)$_2$, —NR$^T$SO$_2$R$^T$, —NR$^T$SO$_2$N(R$^T$)$_2$, —COCOR$^T$, —COCH$_2$COR$^T$, —OP(O)(OR$^T$)$_2$, —P(O)(OR$^T$)$_2$, —OP(O)$_2$OR$^T$, —P(O)$_2$OR$^T$, —PO(R$^T$)$_2$, or —OPO(R$^T$)$_2$, wherein R$^T$ is hydrogen or unsubstituted C$_{1-6}$ aliphatic; or R' is a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur wherein said monocyclic or bicyclic ring is optionally substituted with 0-5 occurrences of R$^U$; and each occurrence of R$^U$ is independently selected from a 3-8-membered saturated, partially unsaturated, or fully unsaturated monocyclic ring optionally substituted with 0-3 occurrences of —R$^{Q1}$ and having 0-3 heteroatoms independently selected from nitrogen, oxygen, or sulfur, or R$^U$ is —R$^Q$, halogen, =O, =NR$^Q$, —NO$_2$, —CN, —OR$^Q$, —SR$^Q$, —N(R$^Q$)$_2$, —NR$^Q$COR$^Q$, —NR$^Q$CON(R$^Q$)$_2$, —NR$^Q$CO$_2$R$^Q$, —COR$^Q$, —CO$_2$R$^Q$, —OCOR$^Q$, —CON(R$^Q$)$_2$, —C(=N—CN), —OCON(R$^Q$)$_2$, —SOR$^Q$, —SO$_2$R$^Q$, —SO$_2$N(R$^Q$)$_2$, —NR$^Q$SO$_2$R$^Q$, —NR$^Q$SO$_2$N(R$^Q$)$_2$, —COCOR$^Q$, —COCH$_2$COR$^Q$, —OP(O)(OR$^Q$)$_2$, —P(O)(OR$^Q$)$_2$, —OP(O)$_2$OR$^Q$, —P(O)$_2$OR$^Q$, —PO(R$^Q$)$_2$, or —OPO(R$^Q$)$_2$, wherein R$^Q$ and R$^{Q1}$ are hydrogen or unsubstituted C$_{1-6}$ aliphatic; or R and R', two occurrences of R, or two occurrences of R', are taken together with the atom(s) to which they are bound to form a 3-12 membered saturated, partially unsaturated, or fully unsaturated monocyclic or bicyclic ring having 0-4 heteroatoms independently selected from nitrogen, oxygen, or sulfur wherein said monocyclic or bicyclic ring is optionally substituted with 0-5 occurrences of R$^{T1}$; and each occurrence of R$^{T1}$ is independently selected from —R$^S$, halogen, =O, =NR$^S$, —NO$_2$, —CN, —OR$^S$, —SR$^S$, —N(R$^S$)$_2$, —NR$^S$COR$^S$, —NR$^S$CON(R$^S$)$_2$, —NR$^S$CO$_2$R$^S$, —COR$^S$, —CO$_2$R$^S$, —OCOR$^S$, —CON(R$^S$)$_2$, —C(=N—CN), —OCON(R$^S$)$_2$, —SOR$^S$, —SO$_2$R$^S$, —SO$_2$N(R$^S$)$_2$, —NR$^S$SO$_2$R$^S$, —NR$^S$SO$_2$N(R$^S$)$_2$, —COCOR$^S$, —COCH$_2$COR$^S$, —OP(O)(OR$^S$)$_2$, —P(O)(OR$^S$)$_2$, —OP(O)$_2$OR$^S$, —P(O)$_2$OR$^S$, —PO(R$^S$)$_2$, or —OPO(R$^S$)$_2$, wherein R$^S$ is hydrogen or unsubstituted C$_{1-6}$ aliphatic.

In one embodiment of formula I, Z$^2$ is a bond, R$^6$ is hydrogen, and Z$^1$ is a bond.

In another embodiment of formula I, Z$^2$ is a bond, R$^6$ is hydrogen, and Z$^1$ is NR$^7$, O, S, CH$_2$, C(O), or NR$^7$C(O)NR$^7$.

In one embodiment of formula I, Z$^2$-R$^6$ is other than hydrogen and Z$^1$ is a bond.

In one embodiment of formula I, Z$^2$-R$^6$ is other than hydrogen and Z$^1$ is NR$^7$, O, S, CH$_2$, C(O), or NR$^7$C(O)NR$^7$.

In one embodiment of formula I, ----- is a single bond.

In one embodiment of formula I, ----- is a single bond and both of R$^W$ are hydrogen.

In one embodiment of formula I, R$^Z$, if present, is C1-C6 alkyl, halo-C1-C6 alkyl- or —O—C1-C6 alkyl.

In one embodiment of formula I, R$^Z$, if present, is fluoro, methyl, ethyl, n-propyl, CF$_3$, CHF$_2$, OMe or OEt.

In one embodiment of formula I, at least one R$^W$ is C1-C6 alkyl, halo-C1-C6 alkyl or —O—C1-C6 alkyl.

In one embodiment of formula I, at least one R$^W$ is fluoro, methyl, ethyl, n-propyl, CF$_3$, CHF$_2$, OMe or OEt.

In one embodiment of formula I, one R$^W$ is hydrogen and the other R$^W$ is C1-C6 alkyl, halo-C1-C6 alkyl- or —O—C1-C6 alkyl.

In one embodiment of formula I, one of R$^W$ is hydrogen and the other R$^W$ is fluoro, methyl, ethyl, n-propyl, CF$_3$, CHF$_2$, OMe or OEt.

In one embodiment of formula I, R$^Y$ is C1-C6 aliphatic optionally substituted with one or more halo, OH, —C1-C4 alkoxy, —C1-C4 alkoxy carbonyl, or di-(C1-C4 alkyl)amino-.

In one embodiment of formula I, R$^Y$ is methyl, ethyl, propyl, isopropyl, butyl, t-butyl, 3,3-dimethyl-butyl, 3-methyl-butyl, 2-methyl-propyl, 2-methoxy-ethyl, 3-ethoxypropyl, 1-(methoxy carbonyl)-3-methyl-butyl, 1-(hydroxy methyl)-3-methyl-butyl, allyl, acetenyl, 2-(diethylamino)ethyl, 1-methyl-2-methoxy-ethyl, 3-hydroxy-2,2-dimethyl-propyl, 2,2,2-trifluoroethyl, 3,3,3-trifluoro-propyl, or 2,2,3,3,3-pentafluoro-propyl.

In one embodiment of formula I, R$^Y$ is methyl, ethyl, propyl, isopropyl, butyl, t-butyl, 3,3-dimethyl-butyl, 3-methyl-butyl or 2-methyl-propyl.

In one embodiment of formula I, R$^Y$ is C3-C8 cycloaliphatic or a C3-C8 cycloaliphatic substituted C1-C6 aliphatic-.

In one embodiment of formula I, R$^Y$ is C3-C6 cycloalkyl or a C3-C6 cycloalkyl substituted C1-C6 alkyl-.

In one embodiment of formula I, R$^Y$ is cyclopropyl, cyclohexyl, cyclohexylmethyl-, cyclopropylmethyl-, or cyclohexylethyl-.

In one embodiment of formula I, R$^Y$ is pyridyl (C1-C6)-alkyl-, tetrahydrofuranyl (C1-C6 alkyl)-, or N—(C1-C4 alkyl)-pyrrolidinyl-(C1-C6 alkyl)-.

In one embodiment of formula I, tetrahydrofuran-2-yl-methyl-, pyridin-3-yl-methyl-, pyridin-4-yl-ethyl-, pyridin-2-yl-ethyl-, pyridin-4-yl-methyl-, 1H-indazol-5-yl, or 2-(N-methyl)-pyrrolidin-2-yl-ethyl-.

In one embodiment of formula I, R$^Y$ is phenyl or (phenyl)-substituted C1-C6 aliphatic-each optionally substituted with up to 5 R$^2$ substituents independently selected from halogen or a 5-6 membered heterocyclyl ring having 1-3 heteroatoms selected from N, O, or S.

In one embodiment of formula I, R$^Y$ is phenyl, 2,6-difluorophenyl, benzyl, 4-fluorophenylmethyl-, 4-morpholinophenyl-, 2-piperidinylphenyl- or phenylethyl-.

In one embodiment of formula I, one R$^X$ is hydrogen and the other R$^X$ is an aryl or heteroaryl ring optionally substituted with up to 5 R$^3$ substituents independently selected from C1-C6 aliphatic, phenyl, halogen, C$_3$-C$_6$ cycloaliphatic or a 4-7 membered heterocyclic ring wherein said heterocyclic ring is optionally substituted with up to 3 R$^U$ substituents wherein said heteroaryl or heterocyclic ring has up to three heteroatoms selected from N, O, or S.

In one embodiment of formula I, one R$^X$ is hydrogen and the other R$^X$ is phenyl or pyridyl with up to 2 R$^3$ substituents independently selected from halogen or a 4-7 membered heterocyclic ring wherein said heterocyclic ring is optionally substituted with up to 2 R$^U$ substituents wherein said heterocyclic ring has up to three heteroatoms selected from N, O, or S.

In one embodiment of formula I, one R$^X$ is hydrogen and the other R$^X$ is phenyl substituted with a 4-7 membered heterocyclic ring in the 2 position and a halogen in the 3 position.

In one embodiment of formula I, one R$^X$ is hydrogen and the other R$^X$ is phenyl, or phenyl substituted with piperazine, 4-methyl-piperazin-1-yl, 4-ethyl-piperazin-1-yl, 4-propyl-piperazin-1-yl, 4-butyl-piperazin-1-yl, 4-isopropyl-piperazin-1-yl, 4-t-butylpiperazin-1-yl, 4-cyclopropylpiperazin-1-yl, 4-t-butoxycarbonyl-piperazin-1-yl, 4-hydroxy-piperidinyl, 4-ethoxycarbonyl-piperidin-1-yl, morpholin-4-yl, 1-H-pyrazol-1-yl, imidazol-1-yl, pyrrolidin-1-yl, 3-dimethylamino-pyrrolidin-1-yl, 4-(piperidin-1-yl)piperidine, pyridyl (1-methylpiperidin-4-yl)piperazin-1-yl, or 1-(2,2,2-trifluoroethyl)piperazin-1-yl.

In one embodiment of formula I, one R$^X$ is hydrogen and the other R$^X$ is pyridyl, or pyridyl substituted with piperazine, 4-methyl-piperazin-1-yl, 4-ethyl-piperazin-1-yl, 4-propyl-piperazin-1yl, 4-butyl-piperazin-1yl, 4-isopropyl-piperazin-1yl, 4-t-butylpiperazin-1yl, 4-cyclopropylpiperazin-1-yl, 4-t-butoxycarbonyl-piperazin-1-yl, 4-hydroxy-piperidinyl, 4-ethoxycarbonyl-piperidin-1-yl, morpholin-4-yl, 1-H-pyrazol-1-yl, imidazol-1-yl, pyrrolidin-1-yl, 3-dimethylamino-pyrrolidin-1-yl, 4-(piperidin-1-yl)piperidine, pyridyl (1-methylpiperidin-4-yl)piperazin-1-yl, or 1-(2,2,2-trifluoroethyl)piperazin-1-yl.

In one embodiment of formula I, one R$^X$ is hydrogen and the other R$^X$ is phenyl or heteroaryl optionally substituted with one or more substituents independently selected from C1-C6 aliphatic, cyano, halo, halo-C1-C6 aliphatic-, aryl-C1-C6 aliphatic-, heteroaryl-C1-C6 aliphatic-, aralkyloxy, di(C1-C6 aliphatic)amino-, —O—C1-C6 aliphatic, —S(O)—C1-C6 aliphatic, or —S(O)$_2$—C1-C6 aliphatic.

In one embodiment of formula I, one R$^X$ is hydrogen and the other R$^X$ is a C3-C7 cycloaliphatic or a heterocyloaliphatic ring optionally substituted with up to five R$^3$ substituents and having up to three heteroatoms selected from O, N, or S, wherein said ring is optionally fused to one or more phenyl or heteroaryl rings.

In one embodiment of formula I, said $R^X$ is selected from cyclopentyl, cyclohexyl, cyclohexenyl, cycloheptyl, tetrahydro-2H-pyranyl, tetrahydro-2H-thiopyranyl, 9H-fluoren-9-yl or piperidinyl.

In one embodiment of formula I, two $R^X$, taken together with the carbon atom that they are attached to, form a 3-9 membered monocyclic, a 9-14 membered bicyclic, or a 12-14 membered tricyclic aryl, heteroaryl or heterocyclic ring system wherein each heteroaryl or heterocyclic ring has up to 3 heteroatoms selected from O, S, and N; wherein said ring system formed by two $R^X$ is optionally substituted with up to 5 $R^4$ substituents.

In one embodiment of formula I, said ring system is selected from 9H-fluoroen-9-yl, tetrahydro-2H-pyran-4-yl, tetrahydro-2H-thiopyran-4-yl, cyclobutyl, cyclopentyl, cyclohexyl, cycloheptyl, cyclohexenyl, piperidinyl, or 1-benzyl-piperidin-4-yl.

In another embodiment of formula I, said compound is of formula I-A:

I-A wherein:

ring A is a 4-7 membered heterocyclic ring that forms a spirocyclic ring system with said piperidine ring through carbon atom CA, wherein ring A is optionally fused with a phenyl or heteroaryl ring that is optionally substituted with up to 5 $R^1$ substituents;

wherein said ring A, in addition to the nitrogen ring atom, has up to two additional ring heteroatoms selected from O, N, or S;

wherein ring A, in addition to the oxo group, is optionally substituted with up to 5 $R^1$ substituents;

$R^1$, $R^X$, $R^Y$, $R^Z$, $R^W$, and X are as defined herein.

In one embodiment of formula I-A, ----- is a single bond and $R^Z$, if present, is hydrogen.

In one embodiment of formula I-A, ----- is a single bond and $R^Z$ is C1-C6 alkyl, halo-C1-C6 alkyl-, or —O—C1-C6 alkyl.

In one embodiment of formula I-A, $R^Z$, if present, is fluoro, methyl, ethyl, n-propyl, $CF_3$, $CHF_2$, OMe or OEt.

In one embodiment of formula I-A, at least one $R^W$ is C1-C6 alkyl, halo-C1-C6 alkyl- or —O—C1-C6 alkyl.

In one embodiment of formula I-A, at least one $R^W$ is fluoro, methyl, ethyl, n-propyl, $CF_3$, $CHF_2$, OMe or OEt.

In one embodiment of formula I-A, ----- is a single bond, one $R^W$ is hydrogen and the other $R^W$ is C1-C6 alkyl, halo-C1-C6 alkyl or —O—C1-C6 alkyl.

In one embodiment of formula I-A, one $R^W$ is hydrogen and the other $R^W$ is fluoro, methyl, ethyl, n-propyl, $CF_3$, $CHF_2$, OMe or OEt.

In one embodiment of formula I-A, ----- is a single bond and each $R^W$ is hydrogen.

In one embodiment of formula I-A, $R^Y$ is C1-C6 aliphatic optionally substituted with one or more halo, OH, C1-C4 alkoxy, C1-C4 alkoxy carbonyl, or di-(C1-C4 alkyl)amino-.

In one embodiment of formula I-A, $R^Y$ is methyl, ethyl, propyl, isopropyl, butyl, t-butyl, 3,3-dimethyl-butyl, 3-methyl-butyl, 2-methyl-propyl, 2-methoxy-ethyl, 3-ethoxypropyl, 1-(methoxy carbonyl)-3-methyl-butyl, 1-(hydroxy methyl)-3-methyl-butyl, allyl, acetenyl, 2-(diethylamino) ethyl, 1-methyl-2-methoxy-ethyl, 3-hydroxy-2,2-dimethyl-propyl, 2,2,2-trifluoroethyl, 3,3,3-trifluoro-propyl, or 2,2,3,3, 3-pentafluoro-propyl.

In one embodiment of formula I-A, $R^Y$ is methyl, ethyl, propyl, isopropyl, butyl, t-butyl, 3,3-dimethyl-butyl, 3-methyl-butyl or 2-methyl-propyl.

In one embodiment of formula I-A, $R^Y$ is C3-C8 cycloaliphatic or a C3-C8 cycloaliphatic substituted C1-C6 aliphatic-.

In one embodiment of formula I-A, $R^Y$ is C3-C6 cycloalkyl or a C3-C6 cycloalkyl substituted C1-C6 alkyl-.

In one embodiment of formula I-A, $R^Y$ is cyclopropyl, cyclohexyl, cyclohexylmethyl-, cyclopropylmethyl-, or cyclohexylethyl-.

In one embodiment of formula I-A, $R^Y$ is pyridyl (C1-C6) alkyl-, tetrahydrofuranyl (C1-C6 alkyl)-, N—(C1-C4 alkyl)-pyrrolidinyl-(C1-C6 alkyl)-.

In one embodiment of formula I-A, $R^Y$ is tetrahydrofuran-2-yl-methyl-, pyridin-3-yl-methyl-, pyridin-4-yl-ethyl-, pyridin-2-yl-ethyl-, pyridin-4-yl-methyl-, 1H-indazol-5-yl, or 2-(N-methyl)-pyrrolidin-2-yl-ethyl-.

In one embodiment of formula I-A, $R^Y$ is phenyl or (phenyl)-substituted C1-C6 aliphatic-optionally substituted with up to 5 $R^2$ substituents independently selected from halogen or a 5-6 membered heterocyclyl ring having 1-3 heteroatoms selected from N, O, or S.

In one embodiment of formula I-A, $R^Y$ is phenyl, 2,6-difluorophenyl, benzyl, 4-fluorophenylmethyl-, 4-morpholinophenyl-, 2-piperidinylphenyl- or phenylethyl-.

In one embodiment of formula I-A, ----- is a single bond, one $R^X$ is hydrogen and the other $R^X$ is an aryl or heteroaryl ring optionally substituted with up to 5 $R^3$ substituents independently selected from C1-C6 aliphatic, phenyl, halogen, $C_3$-$C_6$ cycloaliphatic or a 4-7 membered heterocyclic ring with up to 3 $R^U$ substituents wherein said heteroaryl or heterocyclic ring has up to three heteroatoms selected from N, O, or S.

In one embodiment of formula I-A, one $R^X$ is hydrogen and the other $R^X$ is phenyl or pyridyl with up to 2 $R^5$ substituents independently selected from halogen or a 4-7 membered heterocyclic ring with up to 2 $R^U$ substituents wherein said heterocyclic ring has up to three heteroatoms selected from N, O, or S.

In one embodiment of formula I-A, one $R^X$ is hydrogen and the other $R^X$ is phenyl substituted with a 4-7 membered heterocyclic ring in the 2 position and a halogen in the 3 position.

In one embodiment of formula I-A, one $R^X$ is hydrogen and the other $R^X$ is phenyl, or phenyl substituted with piperazine, 4-methyl-piperazin-1-yl, 4-ethyl-piperazin-1yl, 4-propyl-piperazin-1yl, 4-butyl-piperazin-1yl, 4-isopropyl-piperazin-1yl, 4-t-butylpiperazin-1yl, 4-cyclopropylpiperazin-1-yl, 4-t-butoxycarbonyl-piperazin-1-yl, 4-hydroxy-piperidinyl, 4-ethoxycarbonyl-piperidin-1-yl, morpholin-4-yl, 1-H-pyrazol-1-yl, imidazol-1-yl, pyrrolidin-1-yl, 3-dimethylamino-pyrrolidin-1-yl, 4-(piperidin-1-yl)piperidine, pyridyl (1-methylpiperidin-4-yl)piperazin-1-yl, or 1-(2,2,2-trifluoroethyl) piperazin-1-yl.

In one embodiment of formula I-A, one $R^X$ is hydrogen and the other $R^X$ is pyridyl, or pyridyl substituted with piperazine, 4-methyl-piperazin-1-yl, 4-ethyl-piperazin-1yl, 4-propyl-piperazin-1yl, 4-butyl-piperazin-1yl, 4-isopropyl-piperazin-1yl, 4-t-butylpiperazin-1-yl, 4-cyclopropylpiperazin-1-yl, 4-t-butoxycarbonyl-piperazin-1-yl, 4-hydroxy-piperidinyl, 4-ethoxycarbonyl-piperidin-1-yl, morpholin-4-yl, 1-H-pyrazol-1-yl, imidazol-1-yl, pyrrolidin-1-yl, 3-dimethylamino-pyrrolidin-1-yl, 4-(piperidin-1-yl)piperidine, pyridyl (1-methylpiperidin-4-yl)piperazin-1-yl, 1-(2,2,2-trifluoroethyl) piperazin-1-yl.

In one embodiment of formula I-A, one $R^X$ is hydrogen and the other $R^X$ is phenyl or heteroaryl optionally substituted with one or more substituents independently selected from C1-C6 aliphatic, cyano, halo, halo-C1-C6 aliphatic-, aryl-C1-C6 aliphatic-, heteroaryl-C1-C6 aliphatic-, aralkyloxy, di(C1-C6 aliphatic)amino-, —O—C1-C6 aliphatic, —S(O)—C1-C6 aliphatic, or —S(O)$_2$—C1-C6 aliphatic.

In one embodiment of formula I-A, at least one $R^X$ is hydrogen and the other $R^X$ is a C3-C7 cycloaliphatic or a heterocycloaliphatic ring optionally substituted with up to five $R^3$ substituents and having up to three heteroatoms selected from O, N, or S, wherein said ring is optionally fused to one or more phenyl or heteroaryl rings.

In one embodiment of formula I-A, said $R^X$ is selected from cyclopentyl, cyclohexyl, cyclohexenyl, cycloheptyl, tetrahydro-2H-pyranyl, tetrahydro-2H-thiopyranyl, 9H-fluoren-9-yl or piperidinyl.

In one embodiment of formula I-A, ----- is a single bond, two $R^X$, taken together with the carbon atom that they are attached to, form a 3-9 membered monocyclic, a 9-14 membered bicyclic, or a 12-14 membered tricyclic aryl, heteroaryl or heterocyclic ring system wherein each heteroaryl or heterocyclic ring has up to 3 heteroatoms selected from O, S, and N; wherein said ring system formed by two $R^X$ is optionally substituted with up to 5 $R^4$ substituents.

In one embodiment of formula I-A, said ring system is selected from 9H-fluoroen-9-yl, tetrahydro-2H-pyran-4-yl, tetrahydro-2H-thiopyran-4-yl, cyclobutyl, cyclopentyl, cyclohexyl, cycloheptyl, cyclohexenyl, piperidinyl, or 1-benzyl-piperidin-4-yl.

In one embodiment of formula I or I-A, ring A is selected from:

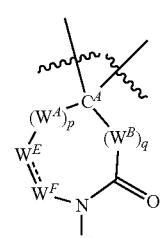

A-i

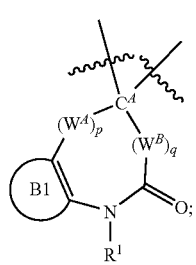

A-ii

-continued

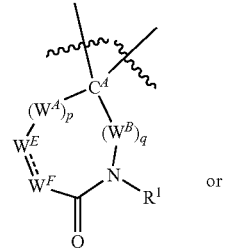

A-iii or

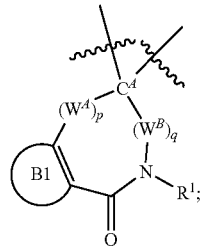

A-iv wherein:
p is 0-2;
q is 0-2; provided that p+q≦2;
each of $W^A$ and $W^B$ is independently selected from $NR^1$, O, S, SO, SO$_2$, $C(R^1)_2$, or =$CR^1$ (when p or q is 2);
$W^E$ is —$C(R^1)_2$, =$C(R^1)$—, =N—, or —$N(R^1)$—;
$W^F$ is absent or is selected from —$C(R^1)_2$, =$C(R^1)$—, =N—, or —$N(R^1)$—; provided that both of $W^E$ and $W^F$ are not simultaneously =N— or —$N(R^1)$—;
ring B1 is a phenyl or 5-6 membered heteroaryl ring optionally substituted with up to 5 $R^1$ substituents; and
$R^1$ is as defined herein.

In another embodiment of formula I or I-A, ring A has formula A-i.

In one embodiment of formula I or I-A, ring A has formula A-ii.

In one embodiment of formula I or I-A, ring A has formula A-iii.

In one embodiment of formula I or I-A, ring A has formula A-iv.

In one embodiment of formula I or I-A, both, $W^E$ and $W^F$ are =$C(R^1)$.

In one embodiment of formula I or I-A, $W^E$ is =$C(R^1)$— and $W^F$ is =N—.

In one embodiment of formula I or I-A, p is 0 and q is 0.
In one embodiment of formula I or I-A, p is 1 and q is 0.
In one embodiment of formula I or I-A, p is 0 and q is 2.
In one embodiment of formula I or I-A, $W^A$ is $NR^1$.
In one embodiment of formula I or I-A, $W^A$ is O.
In one embodiment of formula I or I-A, $W^A$ is $C(R^1)_2$.
In one embodiment of formula I or I-A, $W^A$ is $C(R^1)_2$ and $R^1$ is hydrogen.
In one embodiment of formula I or I-A, $W^B$ is $NR^1$.
In one embodiment of formula I or I-A, $W^B$ is O.
In one embodiment of formula I or I-A, $W^B$ is $C(R^1)_2$.
In one embodiment of formula I or I-A, $W^B$ is $C(R^1)_2$ and $R^1$ is hydrogen.
In one embodiment of formula I or I-A, p is 2 and $W^A$ is $C(R^1)_2$—$C(R^1)_2$ or —$CR^1$=$CR^1$—
In one embodiment of formula I or I-A, q is 2 and $W^B$ is $C(R^1)_2$—$C(R^1)_2$ or —$CR^1$=$CR^1$—
In one embodiment of formula I or I-A, ring A is selected from:

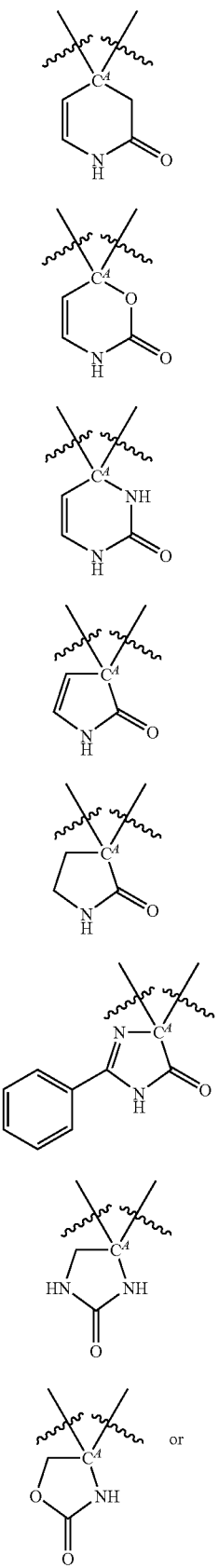
A-i-a
A-i-b
A-i-c
A-i-d
A-i-h
A-i-i
A-i-j
A-i-k
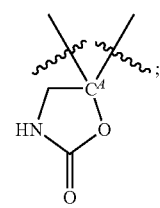
A-i-l
wherein said ring is optionally substituted with up to 4 $R^1$ substituents.
In one embodiment of formula I or I-A, ring A is selected from:
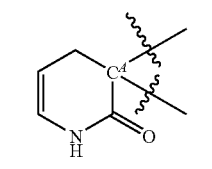
A-i-e
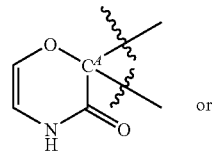
A-i-f
or
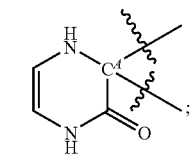
A-i-g
;
wherein said ring is optionally substituted with up to 4 $R^1$ substituents.
In one embodiment of formula I or I-A, ring A is selected from:
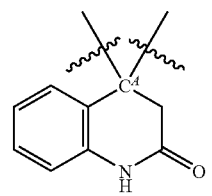
A-ii-a
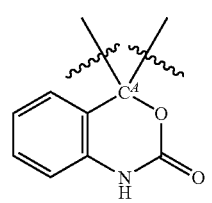
A-ii-b -continued

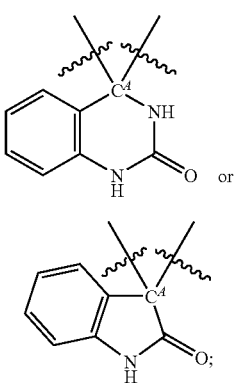
A-ii-c

A-ii-d wherein said ring system is optionally substituted with up to 4 R¹ substituents.

In one embodiment of formula I or I-A, ring A is selected from:

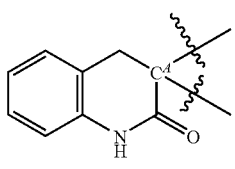
A-ii-e

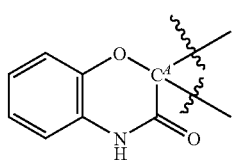
A-ii-f

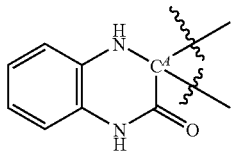
A-ii-g

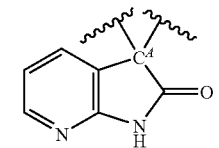
A-ii-h

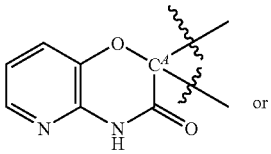
A-ii-i

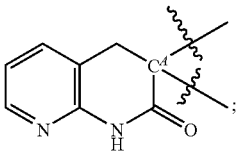
A-ii-j wherein said ring system is optionally substituted with up to 4 R¹ substituents.

In another embodiment of formula I or I-A, the compound is of formula I-B:

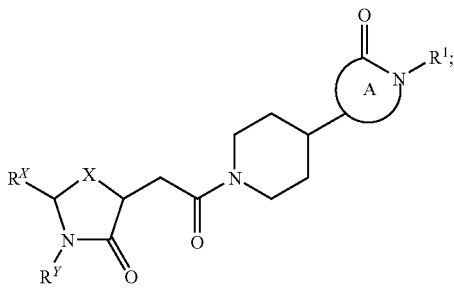
I-B wherein ring A is a 4-7 membered heterocyclic ring optionally fused with an phenyl or heteroaryl ring that is optionally substituted with up to 5 R¹ substituents;

wherein said ring A, in addition to the nitrogen ring atom, contains up to two additional ring heteroatoms selected from O, N, or S;

wherein ring A, in addition to the oxo group, is optionally substituted with up to 5 R¹ substituents;

$R^1$, $R^X$, $R^Y$, and X are as defined herein.

In one embodiment of formula I-B, $R^Y$ is C1-C6 aliphatic optionally substituted with one or more halo, OH, C1-C4 alkoxy, C1-C4 alkoxy carbonyl, or di-(C1-C4 alkyl)amino-.

In one embodiment of formula I-B, $R^Y$ is methyl, ethyl, propyl, isopropyl, butyl, t-butyl, 3,3-dimethyl-butyl, 3-methyl-butyl, 2-methyl-propyl, 2-methoxy-ethyl, 3-ethoxypropyl, 1-(methoxy carbonyl)-3-methyl-butyl, 1-(hydroxy methyl)-3-methyl-butyl, allyl, acetenyl, 2-(diethylamino) ethyl, 1-methyl-2-methoxy-ethyl, 3-hydroxy-2,2-dimethyl-propyl, 2,2,2-trifluoroethyl, 3,3,3-trifluoro-propyl, or 2,2,3,3, 3-pentafluoro-propyl.

In one embodiment of formula I-B, $R^Y$ is methyl, ethyl, propyl, isopropyl, butyl, t-butyl, 3,3-dimethyl-butyl, 3-methyl-butyl or 2-methyl-propyl.

In one embodiment of formula I-B, $R^Y$ is $C_3$-$C_8$ cycloaliphatic or a C3-C8 cycloaliphatic substituted C1-C6 aliphatic-.

In one embodiment of formula I-B, $R^Y$ is $C_3$-$C_6$ cycloalkyl or C3-C6 cycloalkyl substituted C1-C6 alkyl-.

In one embodiment of formula I-B, $R^Y$ is cyclopropyl, cyclohexyl, cyclohexylmethyl-, cyclopropylmethyl-, or cyclohexylethyl-.

In one embodiment of formula I-B, $R^Y$ is pyridyl (C1-C6) alkyl-, tetrahydrofuranyl (C1-C6 alkyl)-, N—(C1-C4 alkyl)-pyrrolidinyl-(C1-C6 alkyl)-.

In one embodiment of formula I-B, $R^Y$ is tetrahydrofuran-2-yl-methyl-, pyridin-3-yl-methyl-, pyridin-4-yl-ethyl-, pyridin-2-yl-ethyl-, pyridin-4-yl-methyl-, 1H-indazol-5-yl, or 2-(N-methyl)-pyrrolidin-2-yl-ethyl-.

In one embodiment of formula I-B, $R^Y$ is phenyl or (phenyl)-substituted C1-C6 aliphatic each optionally substituted with up to 5 R² substituents independently selected from halogen or a 5-6 membered heterocyclyl ring having 1-3 heteroatoms selected from N, O, or S.

In one embodiment of formula I-B, $R^Y$ is phenyl, 2,6-difluorophenyl, benzyl, 4-fluorophenylmethyl-, 4-morpholinophenyl-, 2-piperidinylphenyl- or phenylethyl-.

In one embodiment of formula I-B, $R^X$ is an aryl or heteroaryl ring optionally substituted with up to 5 R³ substituents independently selected from C1-C6 aliphatic, phenyl, halogen, $C_3$-$C_6$ cycloaliphatic or a 4-7 membered heterocyclic ring with up to 3 $R^U$ substituents wherein said heteroaryl or heterocyclic ring has up to three heteroatoms selected from N, O, or S.

In one embodiment of formula I-B, $R^X$ is phenyl or pyridyl with up to 2 $R^3$ substituents independently selected from halogen or a 4-7 membered heterocyclic ring wherein said heterocyclic ring is optionally substituted with up to 2 $R^U$ substituents wherein said heterocyclic ring has up to three heteroatoms selected from N, O, or S.

In one embodiment of formula I-B, $R^X$ is phenyl substituted with a 4-7 membered heterocyclic ring in the 2 position and a halogen in the 3 position.

In one embodiment of formula I-B, $R^X$ is pyridyl, phenyl, or phenyl substituted with piperazine, 4-methyl-piperazin-1-yl, 4-ethyl-piperazin-1yl, 4-propyl-piperazin-1yl, 4-butyl-piperazin-1-yl, 4-isopropyl-piperazin-1-yl, 4-t-butylpiperazin-1-yl, 4-cyclopropylpiperazin-1-yl, 4-t-butoxycarbonyl-piperazin-1-yl, 4-hydroxy-piperidinyl, 4-ethoxycarbonyl-piperidin-1-yl, morpholin-4-yl, 1-H-pyrazol-1-yl, imidazol-1-yl, pyrrolidin-1-yl, 3-dimethylamino-pyrrolidin-1-yl, 4-(piperidin-1-yl)piperidine, pyridyl (1-methylpiperidin-4-yl)piperazin-1-yl, or 1-(2,2,2-trifluoroethyl)piperazin-1-yl.

In one embodiment of formula I-B, $R^X$ is phenyl or heteroaryl optionally substituted with one or more substituents independently selected from C1-C6 aliphatic, cyano, halo, halo-C1-C6 aliphatic-, aryl-C1-C6 aliphatic-, heteroaryl-C1-C6 aliphatic-, aralkyloxy, di(C1-C6 aliphatic)amino-, —O—C1-C6 aliphatic, —S(O)—C1-C6 aliphatic, or —S(O)$_2$—C1-C6 aliphatic.

In one embodiment of formula I-B, $R^X$ is a C3-C7 cycloaliphatic or a heterocycloaliphatic ring optionally substituted with up to five $R^3$ substituents and having up to three heteroatoms selected from O, N, or S, wherein said ring is optionally fused to one or more phenyl or heteroaryl rings.

In one embodiment of formula I-B, said fused ring is selected from cyclopentyl, cyclohexyl, cyclohexenyl, cycloheptyl, tetrahydro-2H-pyranyl, tetrahydro-2H-thiopyranyl, 9H-fluoren-9-yl or piperidinyl.

In one embodiment of formula I-B, ring A is selected from:

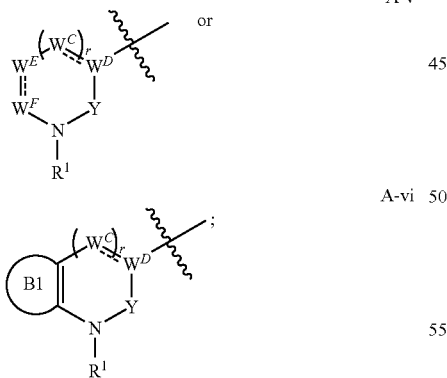

A-v or

A-vi wherein:
$W^C$ is —C($R^1$)$_2$, C(O), or =C$R^1$—;
r is 0-2;
$W^D$ is N or =C—;
$W^E$ is —C($R^1$)$_2$, =C($R^1$)—, =N—, or —N($R^1$)—;
$W^F$ is absent or is selected from —C($R^1$)$_2$, =C($R^1$)—, =N—, or —N($R^1$)—; provided that both of $W^E$ and $W^F$ are not simultaneously =N— or —N($R^1$)—;

Y is C(O), S(O), or S(O)$_2$;
ring B1 is a phenyl or 5-6 membered heteroaryl ring optionally substituted with up to 5 $R^1$ substituents; and ----- is a single or a double bond;
$R^1$ is as defined herein.

In one embodiment of formula I-B, $W^C$ is —C($R^1$)$_2$.
In another embodiment of formula I-B, $W^C$ is =C$R^1$—.
In one embodiment of formula I-B, $W^C$ is C(O).
In one embodiment of formula I-B, r is 0.
In one embodiment of formula I-B, r is 1.
In one embodiment of formula I-B, r is 2.
In one embodiment of formula I-B, $W^D$ is N.
In one embodiment of formula I-B, $W^D$ is =C—.
In one embodiment of formula I-B, Y is C(O).
In one embodiment of formula I-B, Y is S(O).
In one embodiment of formula I-B, Y is S(O)$_2$.
In one embodiment of formula I-B, ring A is selected from:

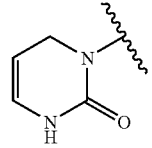

A-v-a

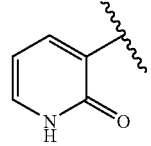

A-v-b

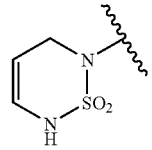

A-v-c

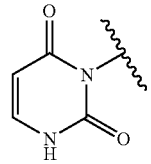

A-v-d

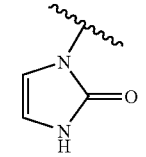

A-v-e

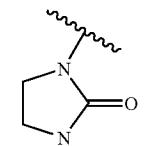

A-v-f

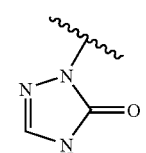

A-v-g

-continued

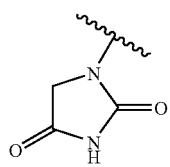
A-v-h

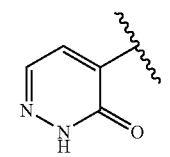
A-v-i

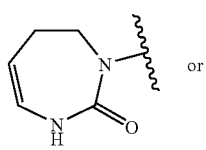
A-v-j  or

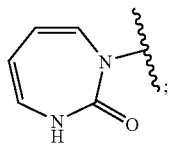
A-v-k
;

wherein said ring is optionally substituted with up to 4 R¹ substituents.

In one embodiment of formula I-B, ring A is selected from:

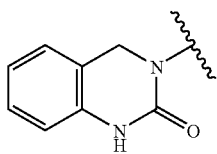
A-vi-a

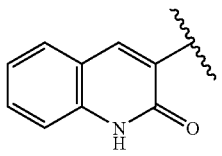
A-vi-b

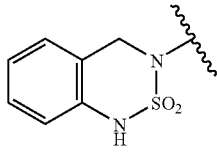
A-vi-c

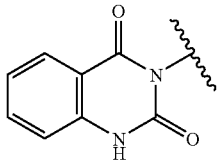
A-vi-d

-continued

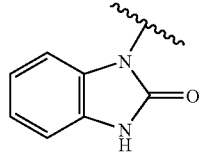
A-vi-e

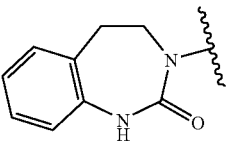
A-vi-f

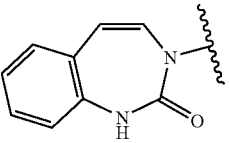
A-vi-g

A-vi-h

A-vi-I

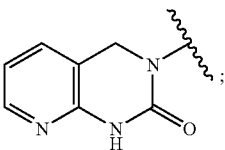
;

wherein said ring is optionally substituted with up to 4 R¹ substituents.

In one embodiment of formula I-B, ring A is optionally substituted with up to 5 substituents selected from C1-C6 aliphatic, C1-C6 aliphatic-oxy, C1-C6 haloaliphatic, CN, halo, oxo, optionally substituted C3-C7 cycloaliphatic, or an optionally substituted ring selected from phenyl, furanyl, pyrrolyl, pyrrolinyl, pyrrolidinyl, imadazolyl, imidazolinyl, imidazolidinyl, pyrazolyl, pyrazolinyl, pyrazolidinyl, pyridyl, pyrimidinyl, piperidinyl, piperazinyl, or morpholinyl.

In one embodiment of formula I-B, in R¹, Q is a bond.
In one embodiment of formula I-B, in R¹, Q-R$^M$ is Q-R'.
In one embodiment of formula I-B, Q is present and R is hydrogen.
In one embodiment of formula I-B, Q is present and R is C1-C6 aliphatic.
In one embodiment of formula I-B, R is methyl, ethyl, propyl, or butyl.
In one embodiment of formula I-B, R' is hydrogen.
In one embodiment of formula I-B, R' is a C1-C8 aliphatic group, optionally substituted with up to 3 substituents selected from halo, CN, CF₃, CHF₂, OCF₃, or OCHF₂, wherein up to two methylene units of said C1-C8 aliphatic is optionally replaced with —CO—, —CONH(C1-C4 alkyl)-, —CO₂—, —OCO—, —N(C1-C4 alkyl)CO₂—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO₂N(C1-C4 alkyl)-, N(C1-C4 alkyl)SO₂—, or —N(C1-C4 alkyl)SO₂N(C1-C4 alkyl)-.

In one embodiment of formula I-B, R' is a 3-8 membered saturated, partially unsaturated, or fully unsaturated monocyclic ring having 0-3 heteroatoms independently selected from nitrogen, oxygen, or sulfur, wherein R' is optionally substituted with up to 3 substituents selected from halo, CN, $CF_3$, $CHF_2$, $OCF_3$, $OCHF_2$, or C1-C6 alkyl, wherein up to two methylene units of said C1-C6 alkyl is optionally replaced with —CO—, —CONH(C1-C4 alkyl)-, —$CO_2$—, —OCO—, —N(C1-C4 alkyl)$CO_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —$SO_2$N(C1-C4 alkyl)-, N(C1-C4 alkyl)$SO_2$—, or —N(C1-C4 alkyl)$SO_2$N(C1-C4 alkyl)-.

In one embodiment of formula I-B, R' is an 8-12 membered saturated, partially unsaturated, or fully unsaturated bicyclic ring system having 0-5 heteroatoms independently selected from nitrogen, oxygen, or sulfur; wherein R' is optionally substituted with up to 3 substituents selected from halo, CN, $CF_3$, $CHF_2$, $OCF_3$, $OCHF_2$, or C1-C6 alkyl, wherein up to two methylene units of said C1-C6 alkyl is optionally replaced with —CO—, —CONH(C1-C4 alkyl)-, —$CO_2$—, —OCO—, —N(C1-C4 alkyl)$CO_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —$SO_2$N(C1-C4 alkyl)-, N(C1-C4 alkyl)$SO_2$—, or —N(C1-C4 alkyl)$SO_2$N(C1-C4 alkyl)-.

In one embodiment of formula I-B, two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein R' is optionally substituted with up to 3 substituents selected from halo, CN, $CF_3$, $CHF_2$, $OCF_3$, $OCHF_2$, or C1-C6 alkyl, wherein up to two methylene units of said C1-C6 alkyl is optionally replaced with —CO—, —CONH(C1-C4 alkyl)-, —$CO_2$—, —OCO—, —N(C1-C4 alkyl)$CO_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —$SO_2$N(C1-C4 alkyl)-, N(C1-C4 alkyl)$SO_2$—, or —N(C1-C4 alkyl)$SO_2$N(C1-C4 alkyl)-.

In one embodiment, compounds of the present invention include those in Table 1 and Table 1A.

In another embodiment, compounds of the present invention include those in Table 1.

In another embodiment, compounds of the present invention include those in Table 1A.

In another embodiment, compounds of the present invention include those in Table 1A and Table 1 except for compound numbers 85, 97, and 105.

In another embodiment, compounds of the present invention include those in Table 1 except for compound numbers 85, 97, and 105.

In one embodiment, the present invention provides compounds of formula I':

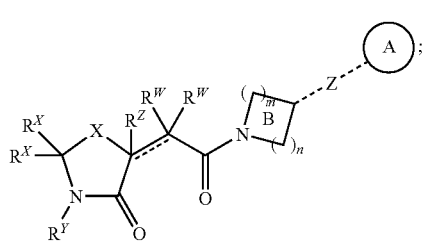

wherein:
X is S, SO, or $SO_2$;
Z is present or absent;
wherein:
when Z is present, then ring A is attached to ring B through a single bond;
when Z is absent, then ring A together with ring B forms a spirocyclic ring system;
ring A is a 4-7 membered heterocyclic or heteroaryl ring or a 10-14 membered bicyclic heterocyclic ring, wherein ring A has 1-4 heteroatoms selected from O, N, or S;
wherein ring A is optionally substituted with up to 5 $R^1$ substituents;
m is 1-3;
n is 1-3; provided that m+n is $\leq 4$;
$R^Y$ is aryl, heteroaryl, cycloaliphatic, C1-C6 aliphatic, arylaliphatic, or cycloaliphatic-aliphatic; wherein $R^Y$ is optionally substituted with up to 5 $R^2$ substituents;
$R^X$ is hydrogen, halo, aryl, heteroaryl, C1-C6 aliphatic, aryl-C1-C6 aliphatic, heteroaryl-C1-C6 aliphatic, wherein $R^X$ is optionally substituted with up to 5 $R^3$ substituents;
or two $R^X$, taken together with the carbon atom that they are attached to, form a 3-9 membered cycloaliphatic or heterocyclic ring, wherein said heterocyclic ring has up to 3 heteroatoms selected from O, S, and N; wherein said ring is optionally substituted with up to 3 $R^3$ substituents;
wherein said ring formed by two $R^X$ is optionally substituted with up to 5 $R^4$ substituents;
$R^Z$ is absent, hydrogen, CN, C1-C6 aliphatic, halo-C1-C6 aliphatic, O—C1-C6 aliphatic, O-(halo-C1-C6 aliphatic), halo, aryl-C1-C6 aliphatic, or heteroaryl-C1-C6 aliphatic;
----- is a single or a double bond; provided that when it is a double bond, then $R^Z$ and one of $R^W$ is absent;
$R^W$ is independently hydrogen, halo, oxo, C1-C6 aliphatic, halo-C1-C6 aliphatic, O—$C_1$-$C_6$ aliphatic, O-(halo-C1-C6 aliphatic), aryl, aryl-C1-C6 aliphatic, C3-C7 cycloaliphatic; or
two $R^W$ taken together form an optionally substituted C3-C7 cycloaliphatic or heterocyclic ring, wherein said heterocyclic ring has up to 3 heteroatoms selected from O, S, and N; wherein said ring formed by two $R^W$ is optionally substituted with up to 5 $R^S$ substituents;
wherein each occurrence of $R^1$, $R^2$, $R^3$, $R^4$, and $R^S$ is independently Q-$R^M$;
wherein Q is a bond or is a $C_1$-$C_6$ aliphatic chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2$NR, $NRSO_2$NR, O, S, or NR;
wherein each occurrence of $R^M$ is independently selected from R', halogen, $NO_2$, CN, OR', SR', N(R')$_2$, NR'C(O)R', NR'C(O)N(R')$_2$, $NR'CO_2R'$, C(O)R', $CO_2R'$, OC(O)R', C(O)N(R')$_2$, OC(O)N(R')$_2$, SOR', $SO_2R'$, $SO_2$N(R')$_2$, $NR'SO_2R'$, $NR'SO_2$N(R')$_2$, C(O)C(O)R', or C(O)$CH_2$C(O)R', wherein each occurrence of R is independently selected from hydrogen or an optionally substituted $C_{1-6}$ aliphatic group;
wherein each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form a 5-8 membered cycloalkyl, heterocyclyl, aryl, or heteroaryl ring having 0-3 heteroatoms independently selected from nitrogen, oxygen, or sulfur.

In one embodiment, ----- is a double bond and $R^Z$ and one of $R^W$ is absent;

In another embodiment, ----- is a single bond. In another embodiment, one or $R^W$ is hydrogen and the other is not. In another embodiment, both of $R^W$ are hydrogen.

In one embodiment, m is 1 and n is 1. In another embodiment, m is 1 and n is 2. Or, m is 2 and n is 1. Or, m is 2 and n is 2.

In another embodiment, $R^Z$ is C1-C6 alkyl or halo-C1-C6 alkyl. Or, $R^Z$ is —O—$C_1$-$C_6$ alkyl. Exemplary $R^Z$ include fluoro, methyl, ethyl, n-propyl, $CF_3$, $CHF_2$, OMe, OEt, etc.

In another embodiment, $R^W$ is C1-C6 alkyl or halo-C1-C6 alkyl. Or, $R^W$ is —O—C1-C6 alkyl. Exemplary $R^W$ include fluoro, methyl, ethyl, n-propyl, $CF_3$, $CHF_2$, OMe, OEt, etc.

In another embodiment, two $R^W$, taken together with the carbon atom they are attached to, form an optionally substituted $C_3$-$C_9$ cycloalkyl or a 3-9 membered heterocyclyl ring. Exemplary such rings include cyclopropyl, cyclopentyl, or cyclohexyl.

In one embodiment, $R^Y$ is C1-C6 aliphatic optionally substituted with one or more halo, OH, C1-C4 alkoxy, C1-C4 alkoxy carbonyl, or di-(C1-C4 alkyl)amino. Exemplary embodiments include methyl, ethyl, propyl, isopropyl, butyl, t-butyl, 3,3-dimethyl-butyl, 3-methyl-butyl, 2-methyl-propyl, 2-methoxy-ethyl, 3-ethoxypropyl, 1-(methoxy carbonyl)-3-methyl-butyl, 1-(hydroxy methyl)-3-methyl-butyl, allyl, acetenyl, 2-(diethylamino)ethyl, 1-methyl-2-methoxy-ethyl, 3-hydroxy-2,2-dimethyl-propyl, 2,2,2-trifluoroethyl, 3,3,3-trifluoro-propyl, or 2,2,3,3,3-pentafluoro-propyl.

In another embodiment, $R^Y$ is $C_3$-$C_8$ cycloaliphatic or $C_3$-$C_8$ cycloaliphatic substituted C1-C6 aliphatic. In one embodiment, $R^Y$ is $C_3$-$C_6$ cycloalkyl or $C_3$-$C_6$ cycloalkyl substituted C1-C6 alkyl. Exemplary embodiments include cyclopropyl, cyclohexyl, cyclohexylmethyl, cyclopropylmethyl, or cyclohexylethyl.

In another embodiment, $R^Y$ is pyridyl (C1-C6) alkyl, tetrahydrofuranyl (C1-C6 alkyl), N—(C1-C4 alkyl)-pyrrolidinyl-(C1-C6 alkyl). Exemplary embodiments include tetrahydrofuran-2-ylmethyl, pyridin-3-yl-methyl, pyridin-4-yl-ethyl, pyridin-2-yl-ethyl, pyridin-4-yl-methyl, 1H-indazol-5-yl, or 2-(N-methyl)-pyrrolidin-2-yl-ethyl.

In another embodiment, $R^Y$ is optionally substituted phenyl or (optionally substituted phenyl)-substituted C1-C6 aliphatic. Exemplary embodiments include phenyl, 2,6-difluorophenyl, benzyl, 4-fluorophenylmethyl, or phenylethyl.

In one embodiment, both $R^X$ are hydrogen.

In one embodiment, $R^X$ is a phenyl or a heteroaryl, such as pyridyl, wherein said phenyl or heteroaryl is optionally substituted with an optionally substituted 3-7 membered heterocyclic or heteroaryl ring having up to three heteroatoms selected from O, S, or N. Exemplary $R^X$ include phenyl, pyridyl, or phenyl substituted with piperazine, 4-methyl-piperazin-1-yl, 4-t-butoxycarbonyl-piperazin-1-yl, 4-hydroxypiperidinyl, 4-ethoxycarbonyl-piperidin-1-yl, morpholin-4-yl, 1-H-pyrazol-1-yl, imidazol-1-yl or pyridyl.

In another embodiment, $R^X$ is phenyl or heteroaryl optionally substituted with one or more substituents independently selected from C1-C6 aliphatic, cyano, halo, halo-C1-C6 aliphatic, aryl-C1-C6 aliphatic, heteroaryl-C1-C6 aliphatic, aralkyloxy, di(C1-C6 aliphatic)amino, O—C1-C6 aliphatic, S(O)—C1-C6 aliphatic, or $S(O)_2$—C1-C6 aliphatic.

In another embodiment, $R^X$ is an optionally substituted C3-C7 cycloaliphatic or a heterocycloaliphatic ring having up to three heteroatoms selected from O, N, or S, wherein said ring is optionally fused to one or more phenyl or heteroaryl ring. Exemplary rings include cyclopentyl, cyclohexyl, cyclohexenyl, cycloheptyl, tetrahydro-2H-pyranyl, tetrahydro-2H-thiopyranyl, 9H-fluoren-9-yl, piperidinyl, etc.

In another embodiment, two $R^X$, taken together with the carbon atom that they are attached to, form an optionally substituted 3-9 membered cycloaliphatic or heterocyclic, monocyclic, bicyclic, or tricyclic ring. Exemplary embodiments include 9H-fluoroen-9-yl, tetrahydro-2H-pyran-4-yl, tetrahydro-2H-thiopyran-4-yl, cyclobutyl, cyclopentyl, cyclohexyl, cycloheptyl, cyclohexenyl, piperidinyl, or 1-benzyl-piperidin-4-yl.

In another embodiment, the present invention provides compounds of formula I'-A:

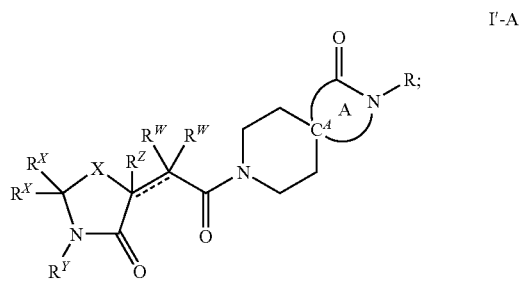

I'-A wherein:

ring A is a 4-7 membered heterocyclic ring that forms a spirocyclic ring system with said piperidine ring through carbon atom $C^A$, wherein said heterocyclic ring is optionally fused with an optionally substituted phenyl or heteroaryl ring;

wherein said ring A, in addition to the nitrogen ring atom, up to two additional ring heteroatoms selected from O, N, or S;

wherein ring A, in addition to the oxo group, is optionally substituted with up to 5 $R^1$ substituents;

$R^1$, $R^X$, $R^Y$, $R^Z$, $R^W$, and X are as defined above.

In one embodiment, ----- is a double bond and $R^Z$ and one of $R^W$ is absent;

In another embodiment, ----- is a single bond.

In another embodiment, $R^Z$ is C1-C6 alkyl or halo-C1-C6 alkyl. Or, $R^Z$ is —O—$C_1$-$C_6$ alkyl. Exemplary $R^Z$ include methyl, ethyl, n-propyl, $CF_3$, $CHF_2$, OMe, OEt, etc.

In another embodiment, $R^W$ is C1-C6 alkyl or halo-C1-C6 alkyl. Or, $R^W$ is —O—C1-C6 alkyl. Exemplary $R^W$ include methyl, ethyl, n-propyl, $CF_3$, $CHF_2$, OMe, OEt, etc.

In another embodiment, two $R^W$, taken together with the carbon atom they are attached to, form an optionally substituted C3-C9 cycloalkyl or a 3-9 membered heterocyclyl ring. Exemplary such rings include cyclopropyl, cyclopentyl, or cyclohexyl.

In one embodiment, ring A is selected from:

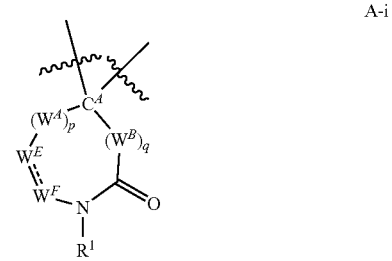

A-i

-continued

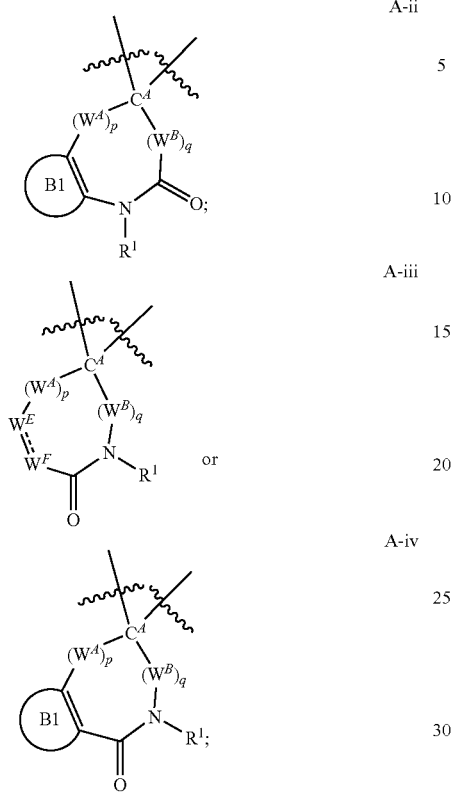

wherein:
p is 0-2;
q is 0-2; provided that p+q≦2;
each of $W^A$ and $W^B$ is independently selected from $NR^1$, O, S, SO, $SO_2$, $C(R^1)_2$, or $=CR^1$ (when p or q is 2);
$W^E$ is $-C(R^1)_2$, $=C(R^1)-$, $=N-$, or $-N(R^1)-$;
$W^F$ is absent or is selected from $-C(R^1)_2$, $=C(R^1)-$, $=N-$, or $-N(R^1)-$; provided that both of $W^E$ and $W^F$ are not simultaneously $=N-$ or $-N(R^1)-$;
ring B1 is an optionally substituted phenyl or 5-6 membered heteroaryl ring;
$R^1$ is as defined above.

In one embodiment, ring A has formula A-i. In another embodiment, ring A has formula A-ii. Or, ring A has formula A-iii. Or, ring A has formula A-iv.

In one embodiment, both, $W^E$ and $W^F$ are $=C(R^1)$. In another embodiment, $W^E$ is $=C(R^1)-$ and $W^F$ is $=N-$.

In one embodiment, p is 0 and q is 0. In another embodiment, p is 1 and q is 0. In another embodiment, p is 0 and q is 1. In yet another embodiment, both p and q are 1. Or, p is 0 and q is 2. Or, p is 2 and q is 0.

In one embodiment, $W^A$ is $NR^1$. In another embodiment, $W^A$ is O. Or, $W^A$ is $C(R^1)_2$. In one embodiment $R^1$ is hydrogen.

In one embodiment, $W^B$ is $NR^1$. In another embodiment, $W^B$ is O. Or, $W^B$ is $C(R^1)_2$. In one embodiment $R^1$ is hydrogen.

In another embodiment, p is 2 and $W^A$ is $C(R^1)_2-C(R^1)_2$ or $-CR^1=CR^1-$.

In another embodiment, q is 2 and $W^B$ is $C(R^1)_2-C(R^1)_2$ or $-CR^1=CR^1-$.

In one embodiment, ring A is selected from:

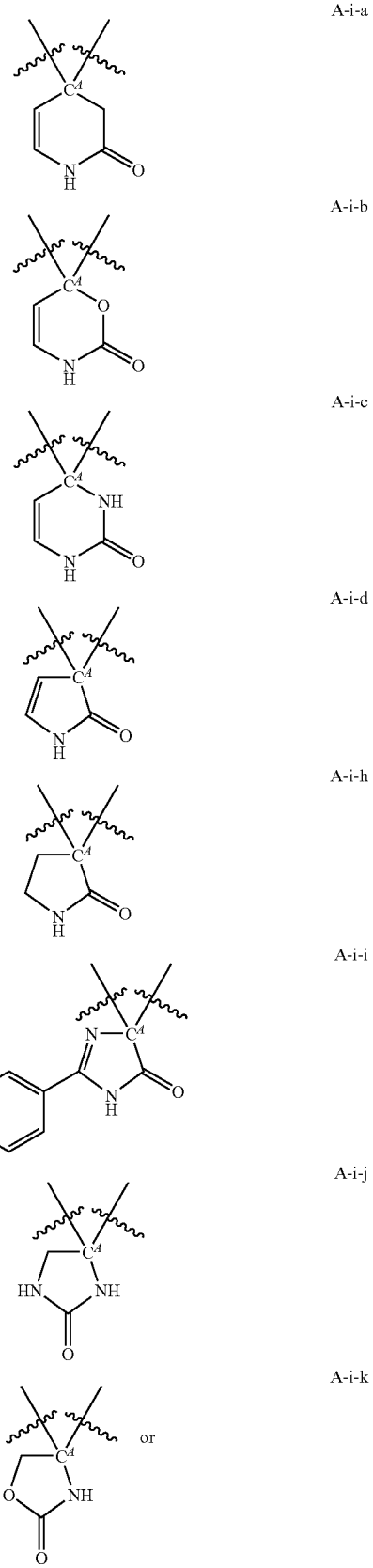

-continued

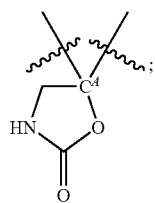
A-i-l wherein said ring is optionally substituted with up to 4 R¹ substituents.

In another embodiment, ring A is selected from:

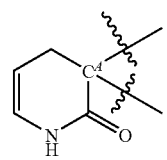
A-i-e

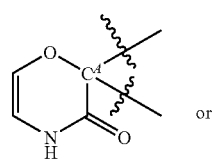
A-i-f or

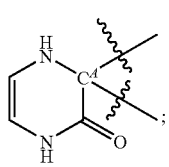
A-i-g wherein said ring is optionally substituted with up to 4 R¹ substituents.

In another embodiment, ring A is selected from:

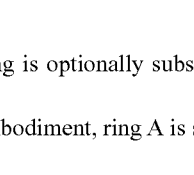
A-ii-a

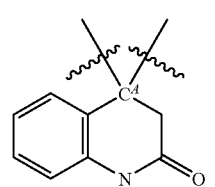
A-ii-b

A-ii-c

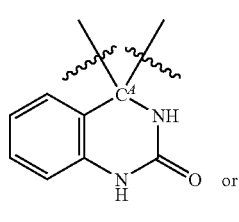
A-ii-c or

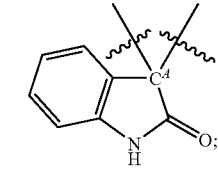
A-ii-d wherein said ring system is optionally substituted with up to 4 R¹ substituents.

In another embodiment, ring A is selected from:

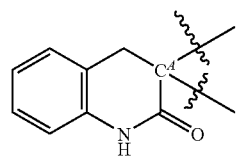
A-ii-e

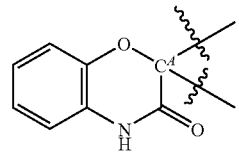
A-ii-f

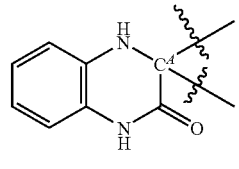
A-ii-g

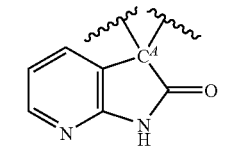
A-ii-h

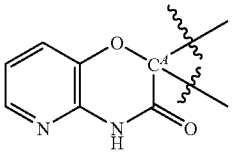
A-ii-i or

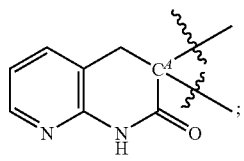
A-ii-j wherein said ring system is optionally substituted with up to 4 R¹ substituents.

In another embodiment, the compounds of the present invention have formula I'-B:

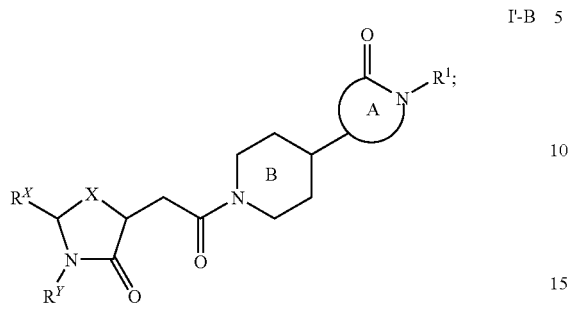

I'-B wherein said ring A, in addition to the nitrogen ring atom, contains up to two additional ring heteroatoms selected from O, N, or S;

wherein ring A, in addition to the oxo group, is optionally substituted with up to 5 $R^1$ substituents;

$R^1$, $R^X$, $R^Y$, and X are as defined above.

In one embodiment, ring A is selected from:

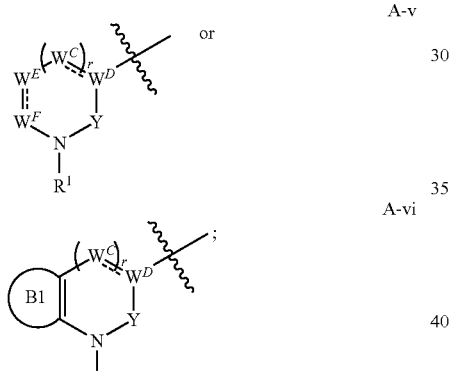

A-v or

A-vi wherein:
$W^C$ is —C($R^1$)$_2$, C(O), or =C$R^1$—;
r is 0-2;
$W^D$ is N or =C—;
$W^E$ is —C($R^1$)$_2$, =C($R^1$)—, =N—, or —N($R^1$)—;
$W^F$ is absent or is selected from —C($R^1$)$_2$, =C($R^1$)—, =N—, or —N($R^1$)—; provided that both of
$W^E$ and $W^F$ are not simultaneously =N— or —N($R^1$)—;
Y is C(O), S(O), or S(O)$_2$;
ring B1 is an optionally substituted phenyl or a heteroaryl ring;
----- is a single or a double bond;
$R^1$ is as defined above.

In one embodiment, $W^C$ is —C($R^1$)$_2$. Or, $W^C$ is =C$R^1$—. Or, $W^C$ is C(O).

In one embodiment, r is 0. Or, r is 1. Or, r is 2.
In another embodiment, $W^D$ is N. Or, W is =C—.
In one embodiment, Y is C(O). Or, Y is S(O). Or, Y is S(O)$_2$.

In one embodiment, ring A is selected from:

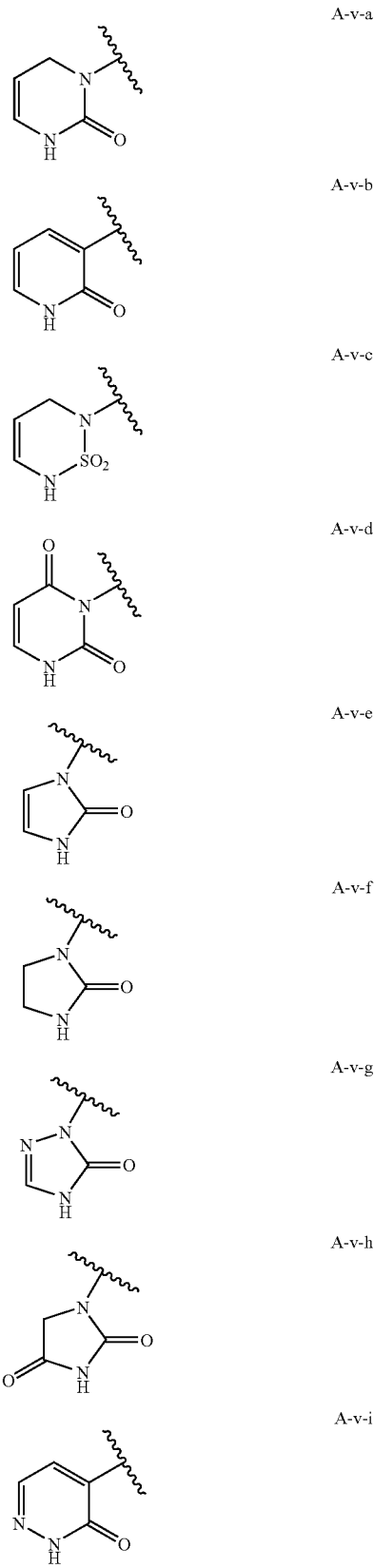

A-v-a

A-v-b

A-v-c

A-v-d

A-v-e

A-v-f

A-v-g

A-v-h

A-v-i

-continued

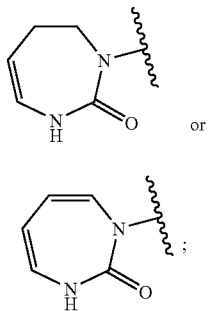

A-v-j

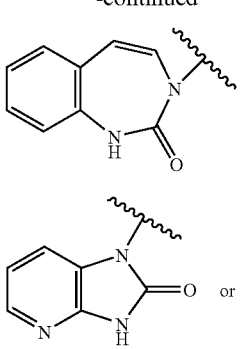

A-vi-g

A-v-k

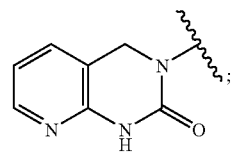

A-vi-h wherein said ring is optionally substituted with up to 4 R¹ substituents.

In one embodiment, ring A is selected from:

A-vi-I

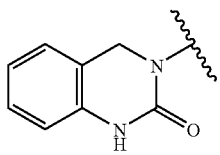

A-vi-a wherein said ring is optionally substituted with up to 4 R¹ substituents.

In one embodiment, ring A is optionally substituted with up to 5 substituents selected from C1-C6 aliphatic, C1-C6 aliphatic-oxy, C1-C6 haloaliphatic, CN, halo, oxo, optionally substituted C3-C7 cycloaliphatic, or an optionally substituted ring selected from phenyl, furanyl, pyrrolyl, pyrrolinyl, pyrrolidinyl, imadazolyl, imidazolinyl, imidazolidinyl, pyrazolyl, pyrazolinyl, pyrazolidinyl, pyridyl, pyrimidinyl, piperidinyl, piperazinyl, or morpholinyl.

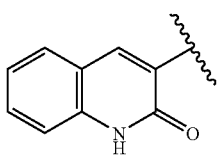

A-vi-b

In one embodiment Q is absent. In another embodiment, Q-R$^M$ is R'.

In one embodiment, R is hydrogen. Or, R is C1-C6 aliphatic. Exemplary R includes C1-C6 alkyl, e.g., methyl, ethyl, propyl, or butyl.

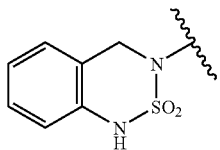

A-vi-c

In one embodiment, R' is hydrogen.

In one embodiment, R' is a C1-C8 aliphatic group, optionally substituted with up to 3 substituents selected from halo, CN, CF$_3$, CHF$_2$, OCF$_3$, or OCHF$_2$, wherein up to two methylene units of said C1-C8 aliphatic is optionally replaced with —CO—, —CONH(C1-C4 alkyl)-, —CO$_2$—, —OCO—, —N(C1-C4 alkyl)CO$_2$—, —O—, —N(C1-C4 alkyl)CON (C1-C4 alkyl)-, —OCON(C1-C4 alkyl)-, —N(C1-C4 alkyl) CO—, —S—, —N(C1-C4 alkyl)-, —SO$_2$N(C1-C4 alkyl)-, N(C1-C4 alkyl)SO$_2$—, or —N(C1-C4 alkyl)SO$_2$N(C1-C4 alkyl)-.

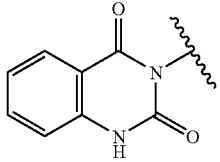

A-vi-d

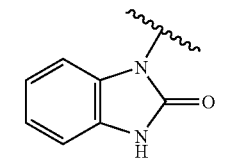

A-vi-e

In one embodiment, R' is a 3-8 membered saturated, partially unsaturated, or fully unsaturated monocyclic ring having 0-3 heteroatoms independently selected from nitrogen, oxygen, or sulfur, wherein R' is optionally substituted with up to 3 substituents selected from halo, CN, CF$_3$, CHF$_2$, OCF$_3$, OCHF$_2$, or C1-C6 alkyl, wherein up to two methylene units of said C1-C6 alkyl is optionally replaced with —CO—, —CONH(C1-C4 alkyl)-, —CO$_2$—, —OCO—, —N(C1-C4 alkyl)CO$_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO$_2$N(C1-C4 alkyl)-, N(C1-C4 alkyl) SO$_2$—, or —N(C1-C4 alkyl)SO$_2$N(C1-C4 alkyl)-.

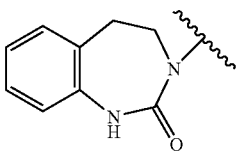

A-vi-f

In one embodiment, R' is an 8-12 membered saturated, partially unsaturated, or fully unsaturated bicyclic ring system having 0-5 heteroatoms independently selected from nitrogen, oxygen, or sulfur; wherein R' is optionally substituted with up to 3 substituents selected from halo, CN, CF$_3$, CHF$_2$, OCF$_3$, OCHF$_2$, or C1-C6 alkyl, wherein up to two methylene units of said C1-C6 alkyl is optionally replaced with —CO—, —CONH(C1-C4 alkyl)-, —CO$_2$—, —OCO—, —N(C1-C4 alkyl)CO$_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO$_2$N(C1-C4 alkyl)-, N(C1-C4 alkyl)SO$_2$—, or —N(C1-C4 alkyl)SO$_2$N(C1-C4 alkyl)-.

In one embodiment, two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein R' is optionally substituted with up to 3 substituents selected from halo, CN, CF$_3$, CHF$_2$, OCF$_3$, OCHF$_2$, or C1-C6 alkyl, wherein up to two methylene units of said C1-C6 alkyl is optionally replaced with —CO—, —CONH(C1-C4 alkyl)-, —CO$_2$—, —OCO—, —N(C1-C4 alkyl)CO$_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO$_2$N(C1-C4 alkyl)-, N(C1-C4 alkyl)SO$_2$—, or —N(C1-C4 alkyl)SO$_2$N(C1-C4 alkyl)-.

Exemplary compounds of the present invention are shown in Table 1 and Table 1A below.

TABLE 1

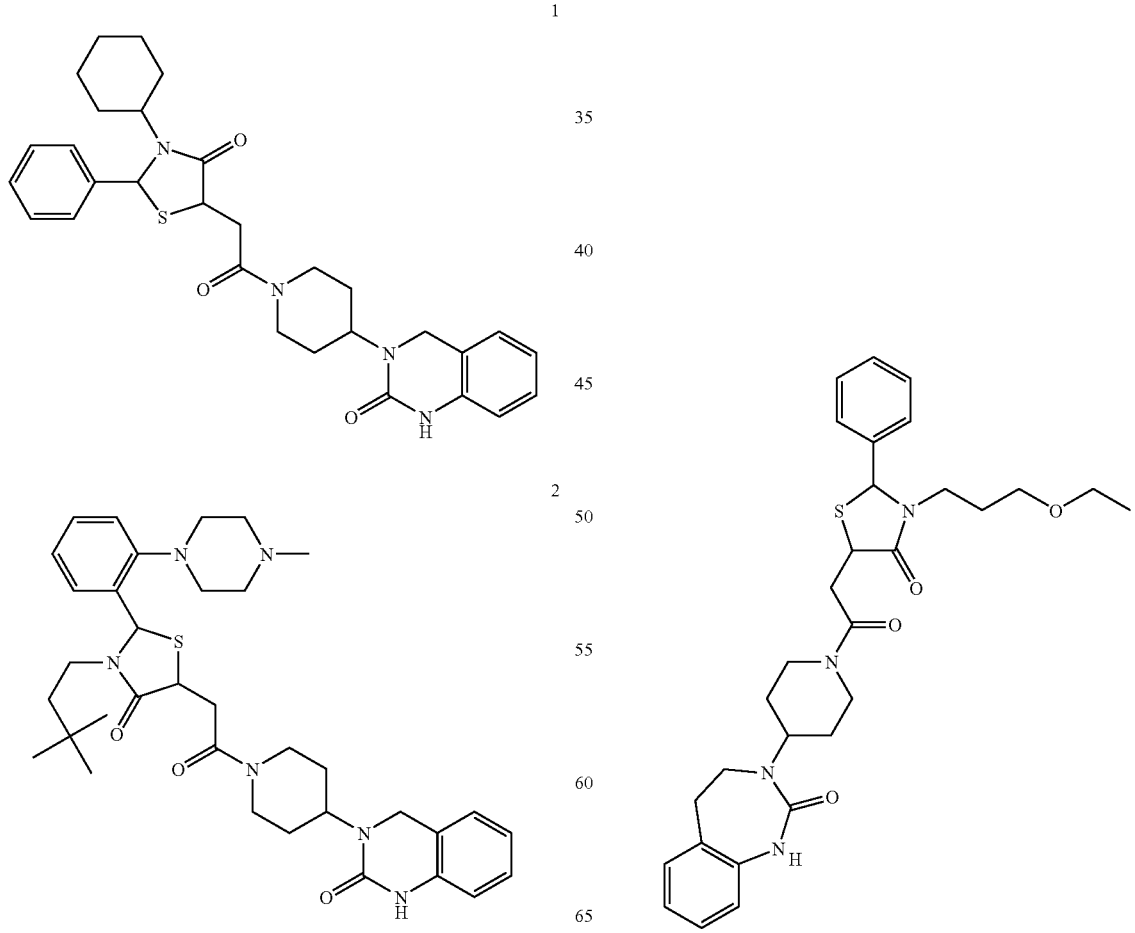

TABLE 1-continued

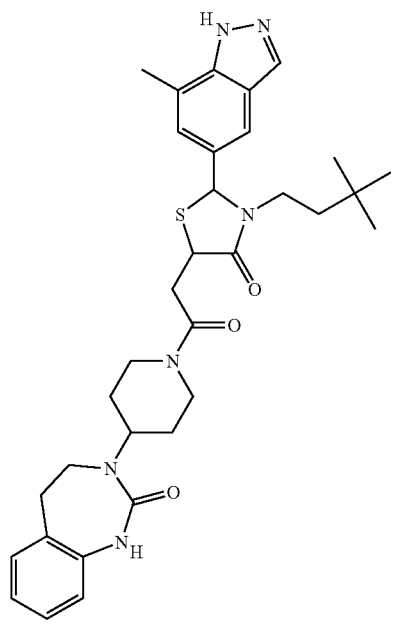

TABLE 1-continued

TABLE 1-continued
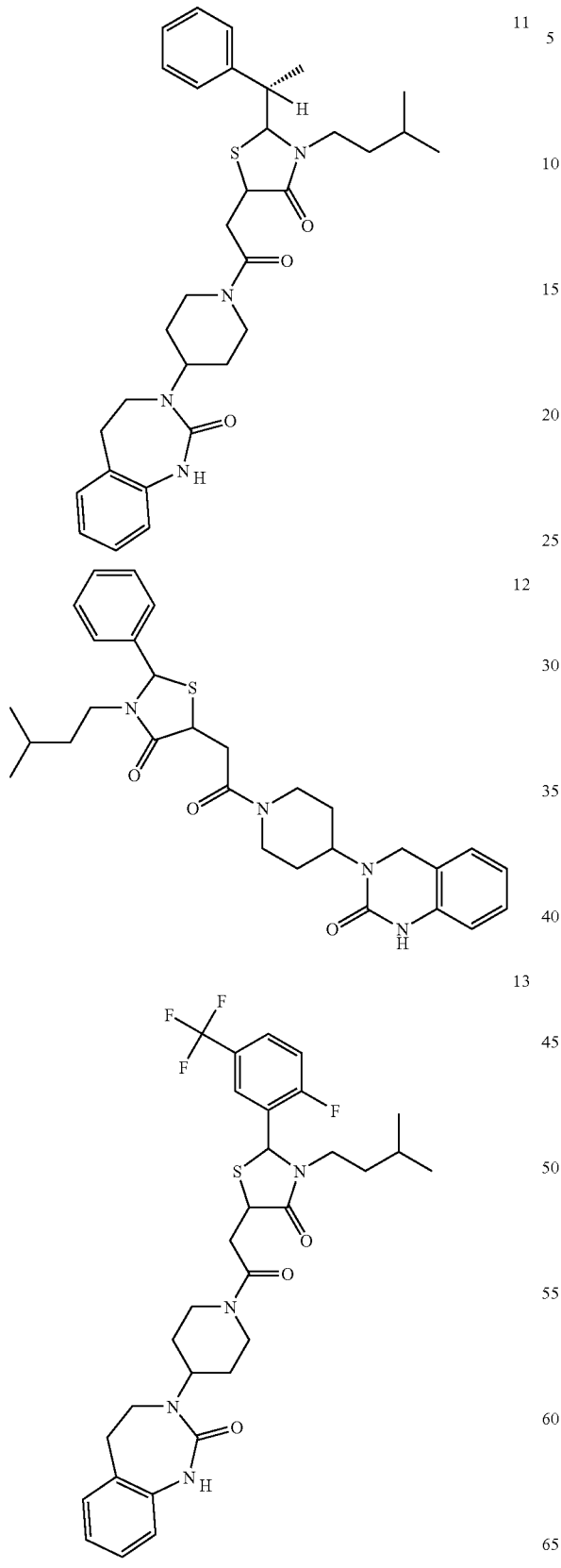
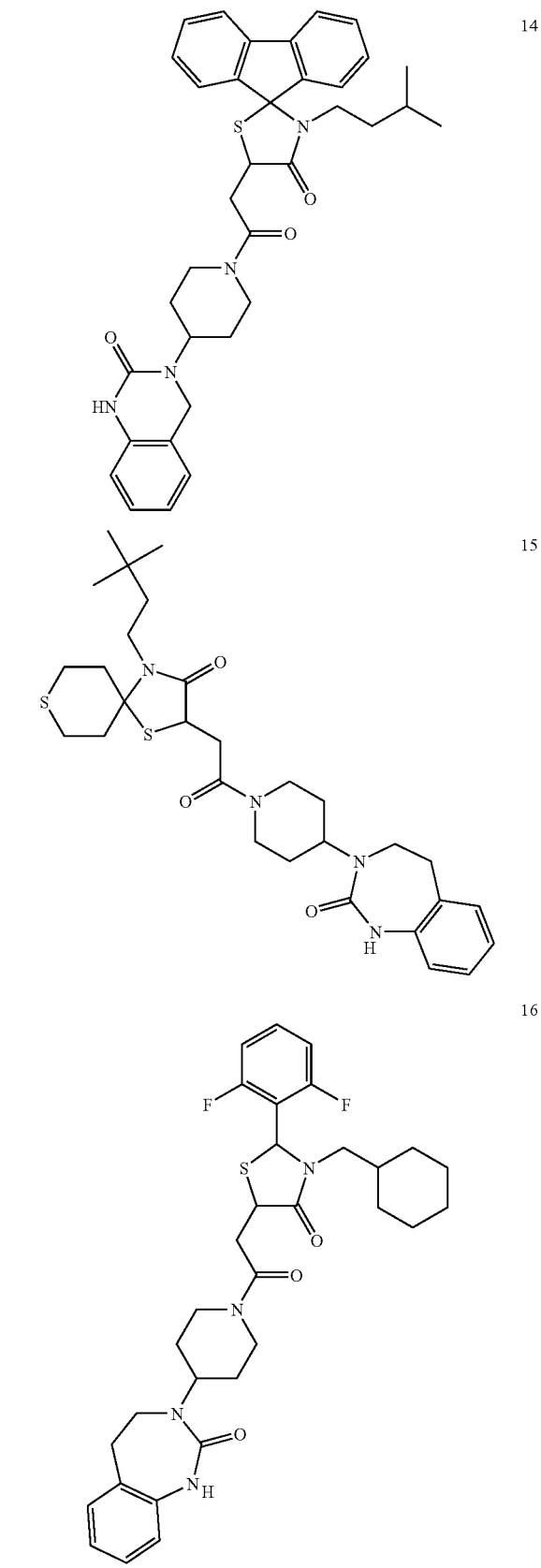

TABLE 1-continued
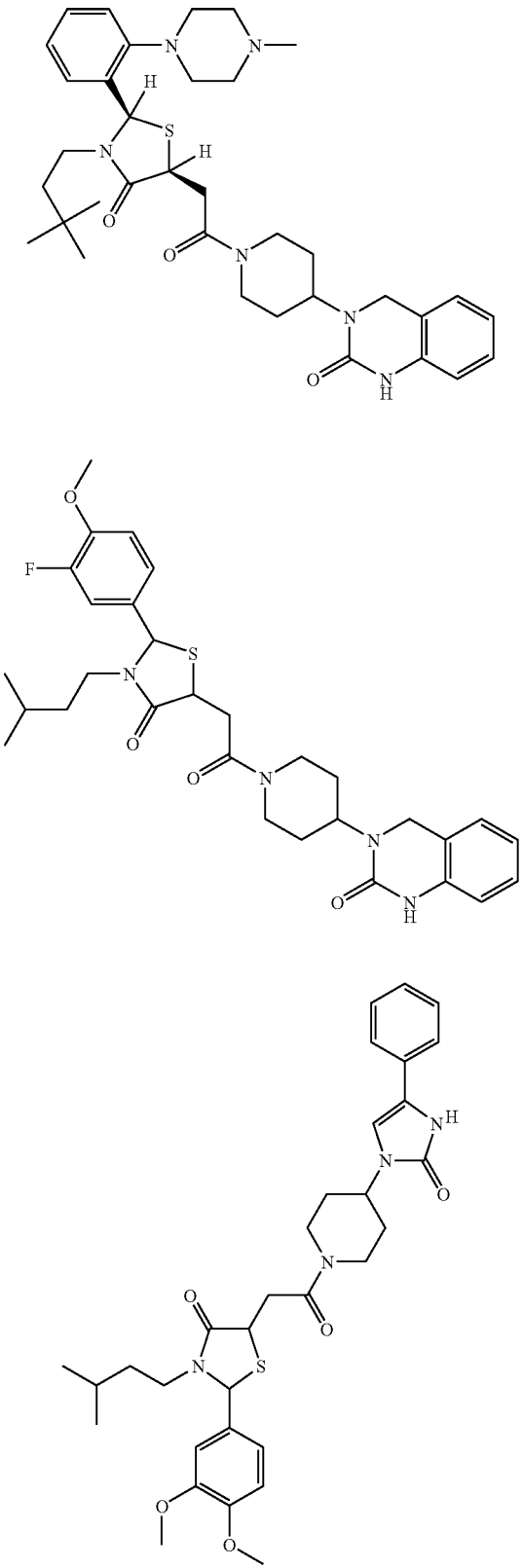
TABLE 1-continued
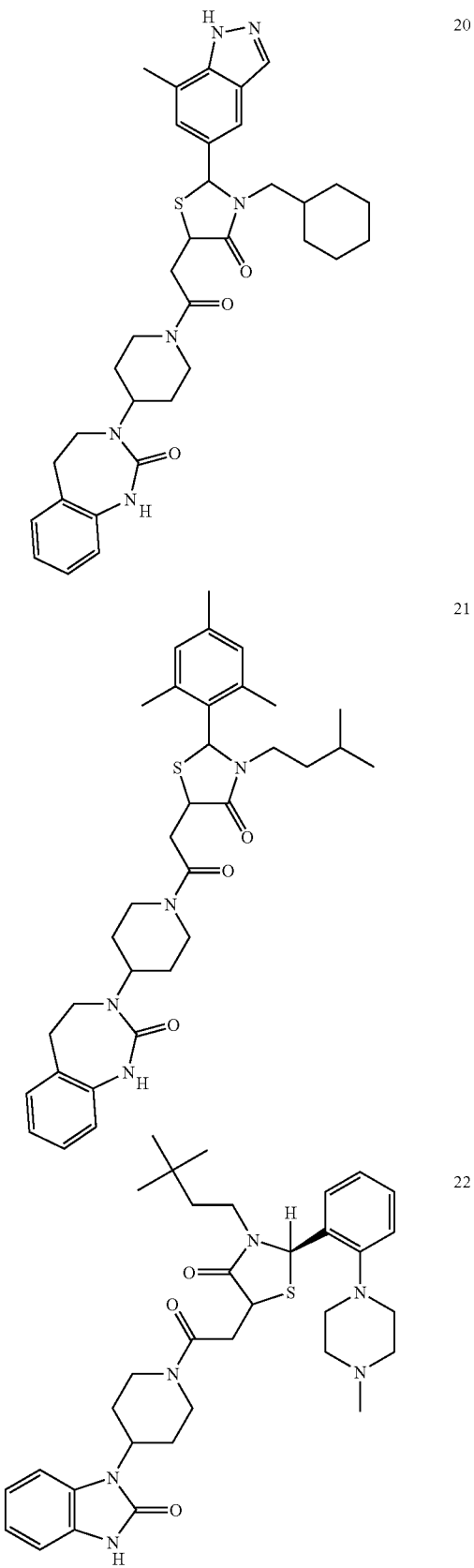

TABLE 1-continued
23
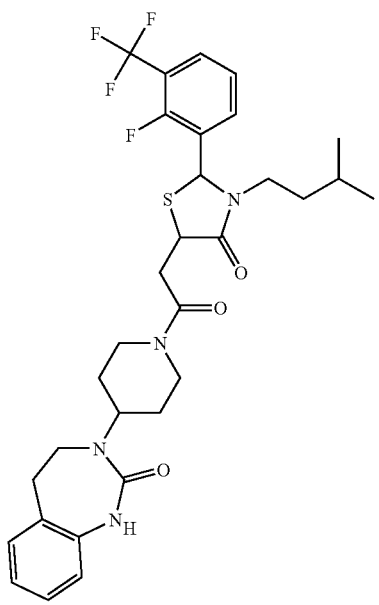
24
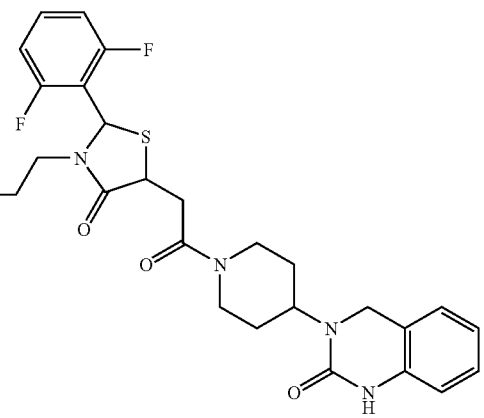
25
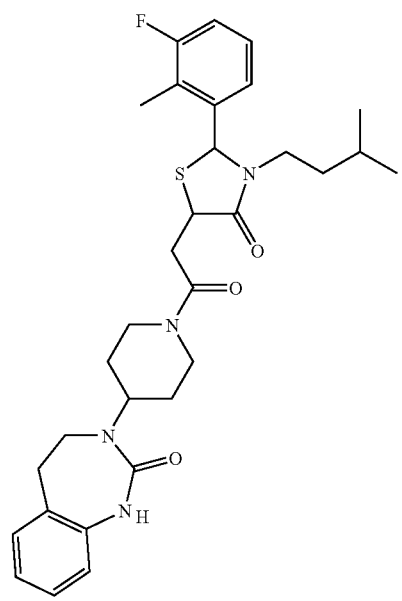
26
27
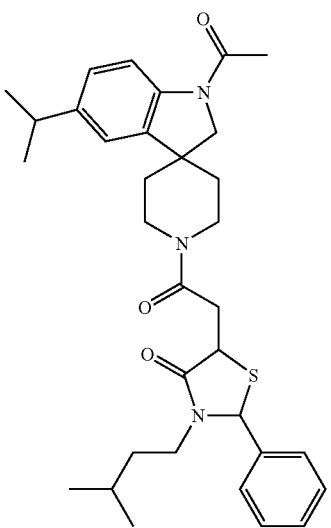

TABLE 1-continued
28
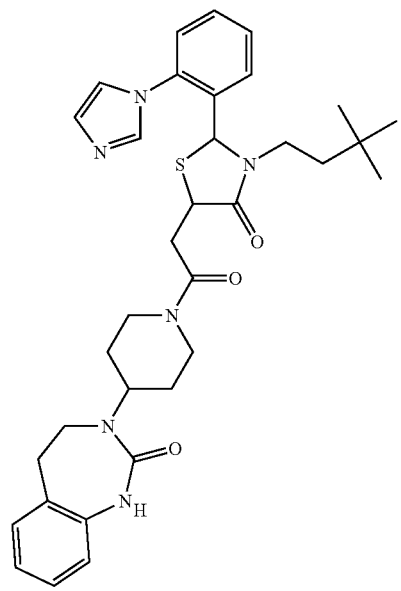
29
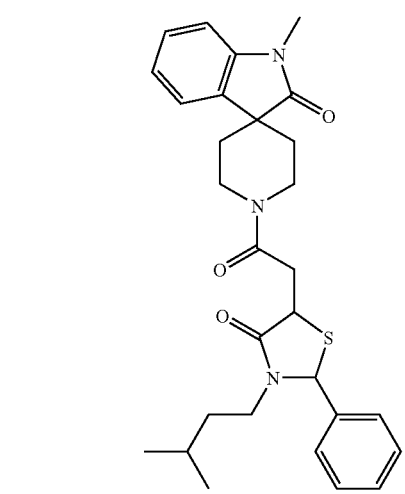
30
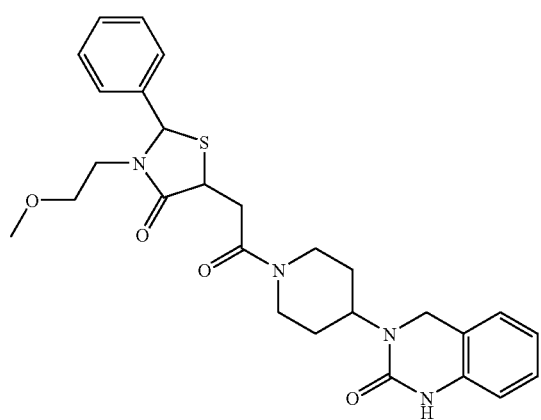
TABLE 1-continued
31
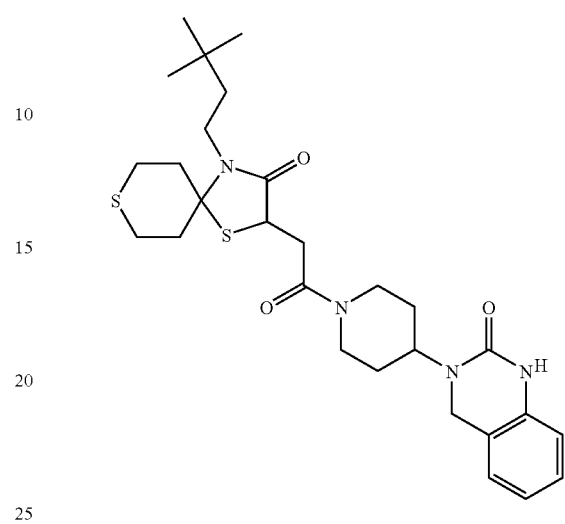
32
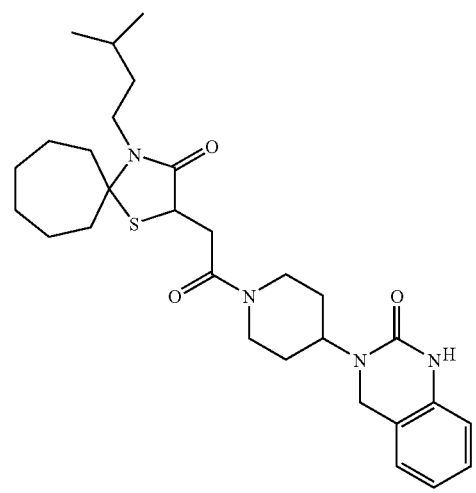
33
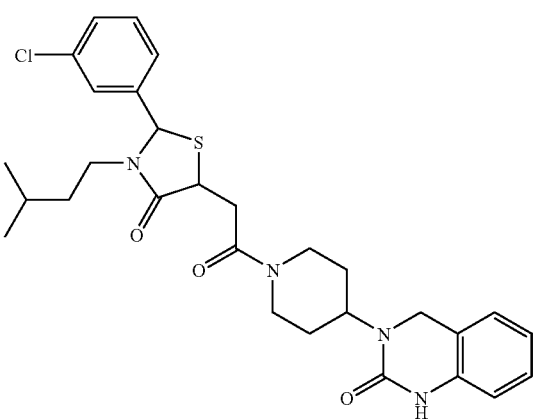

TABLE 1-continued
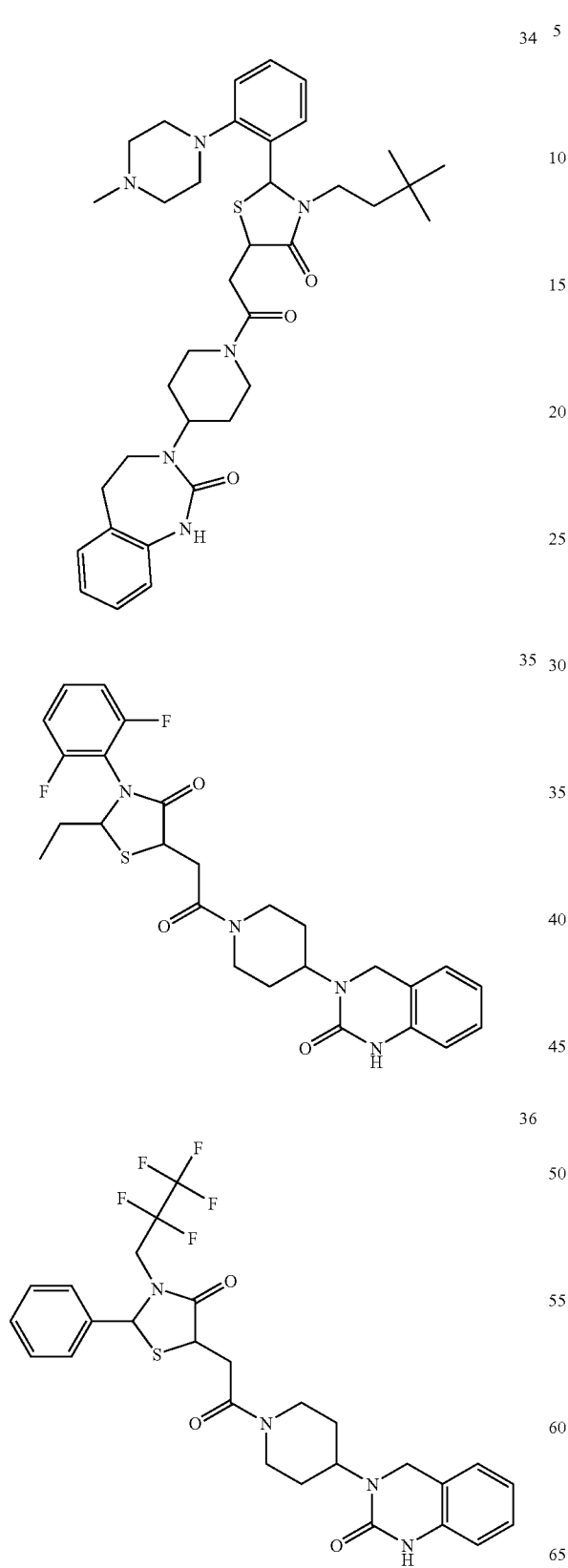
TABLE 1-continued
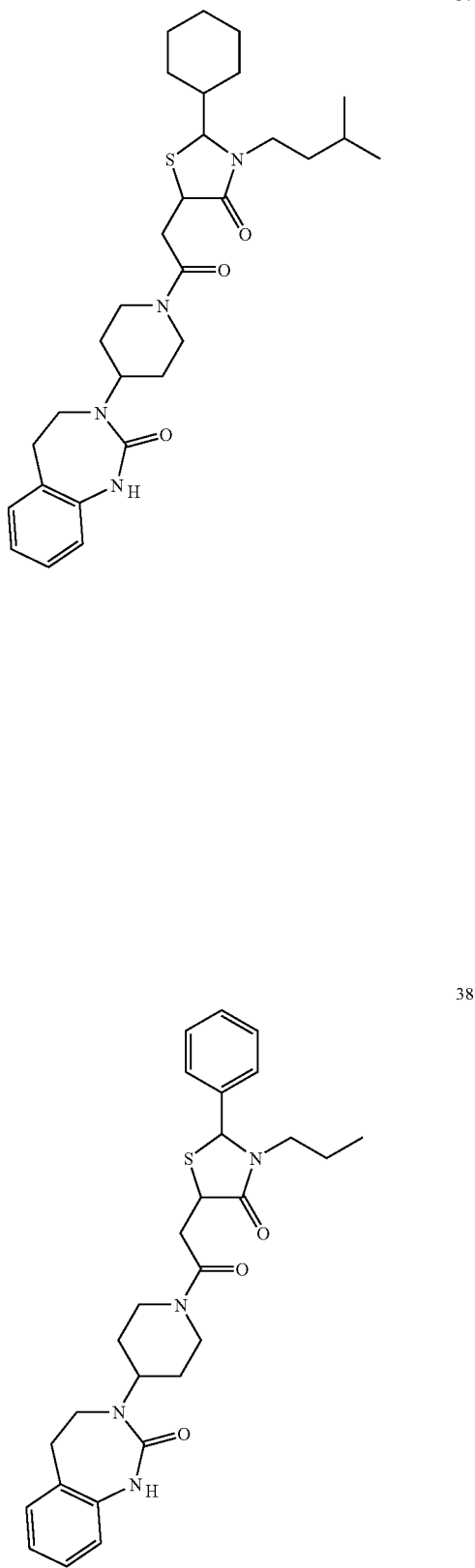

TABLE 1-continued
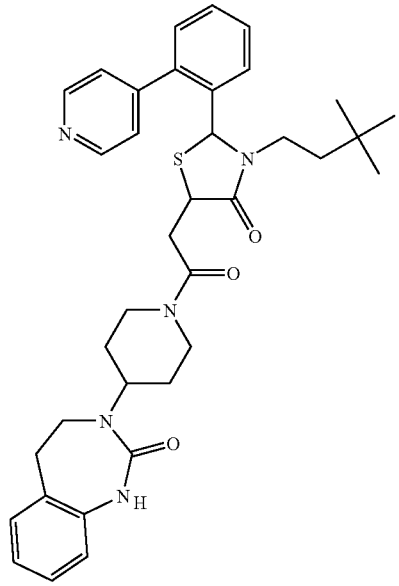
39
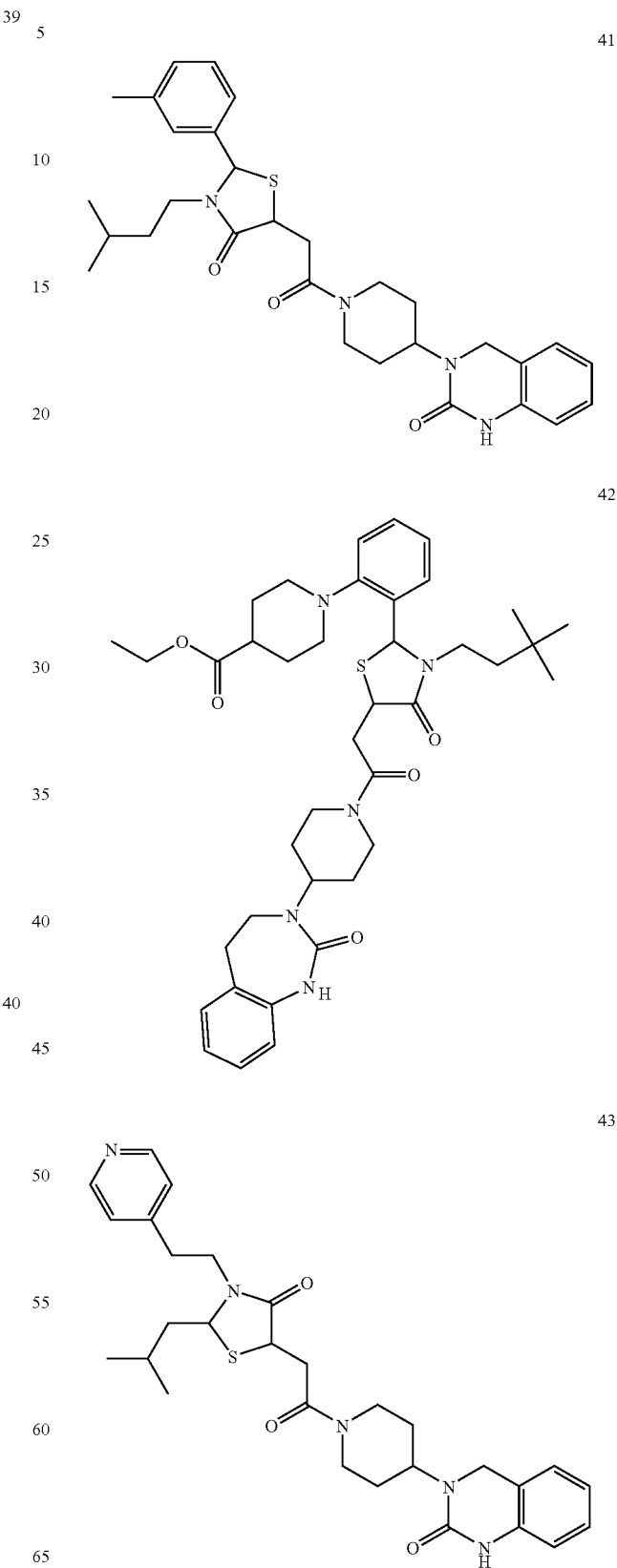

TABLE 1-continued
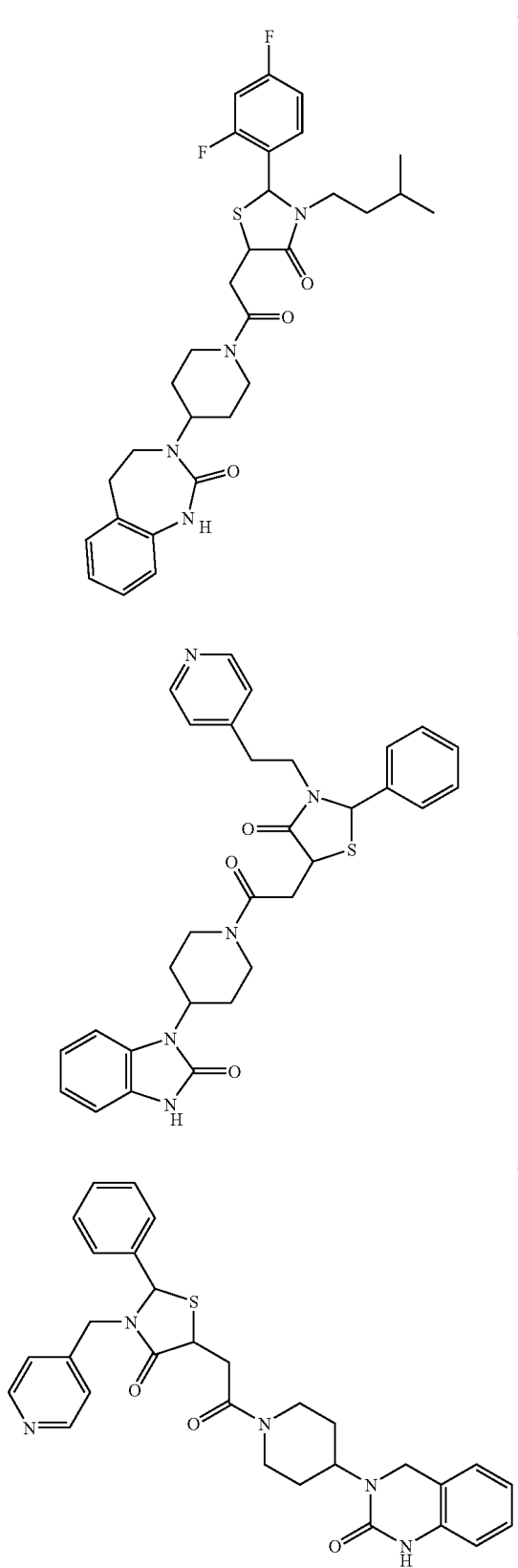
TABLE 1-continued
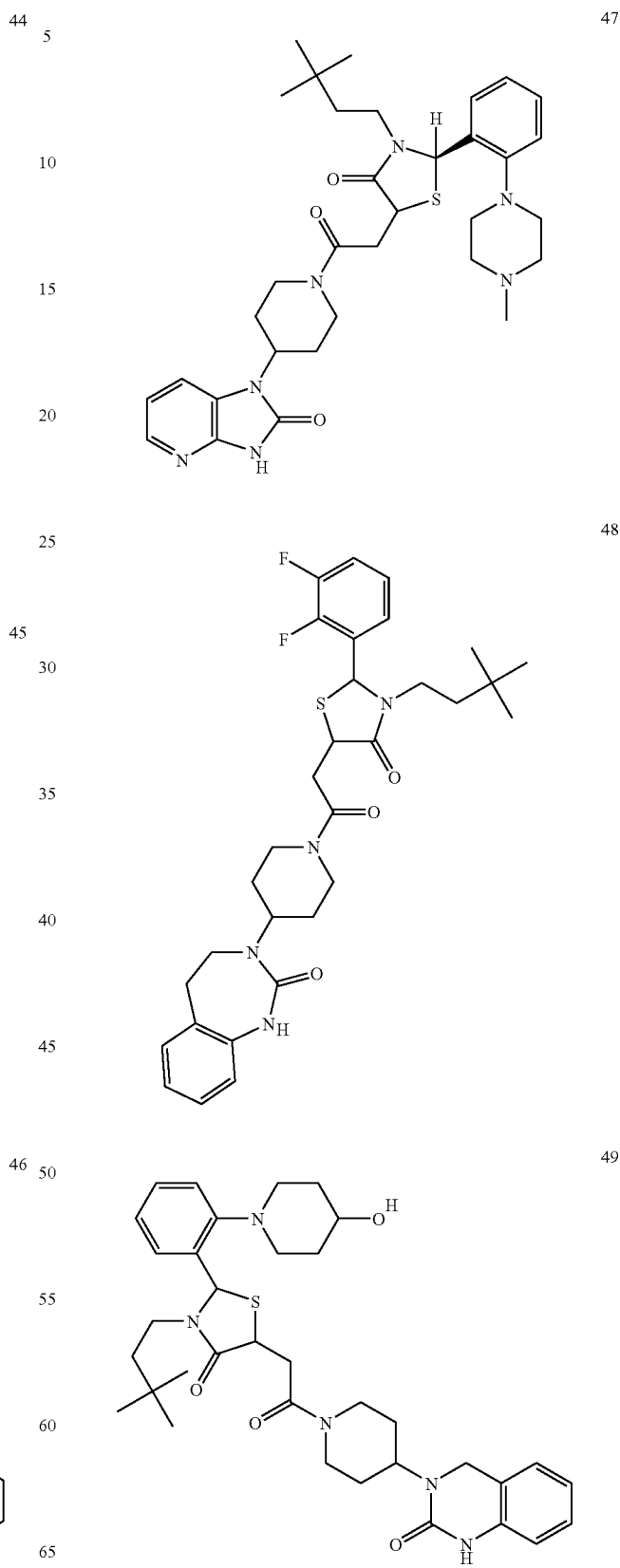

TABLE 1-continued
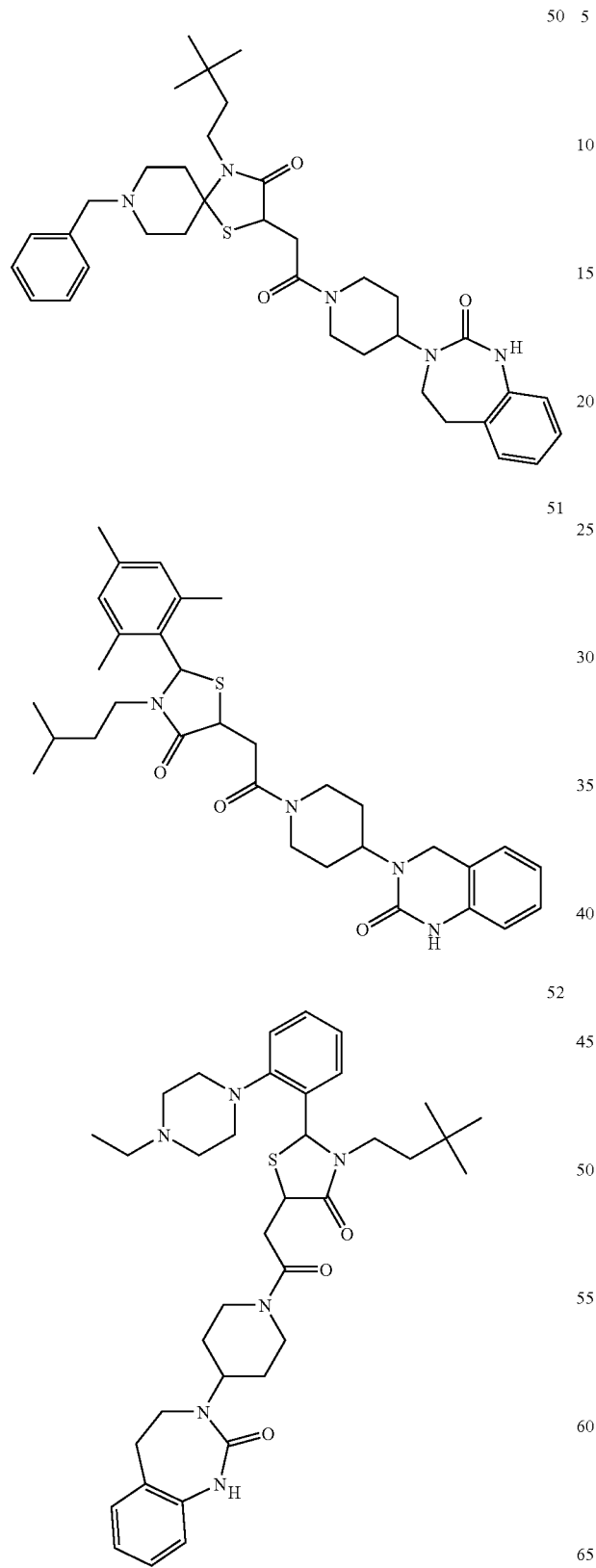
TABLE 1-continued
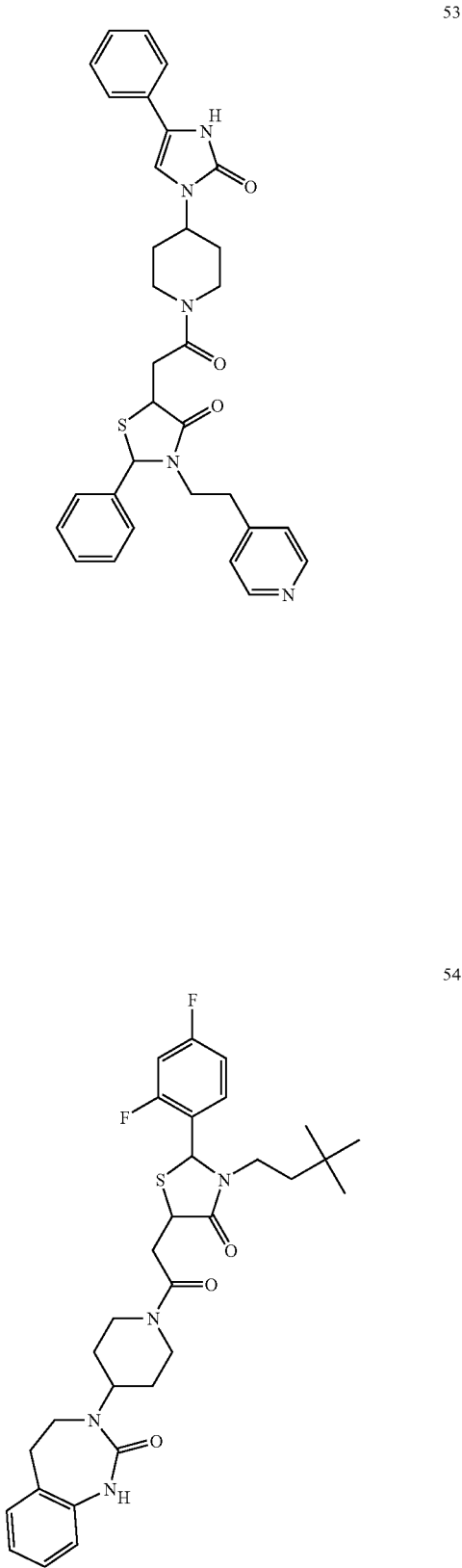

TABLE 1-continued
55
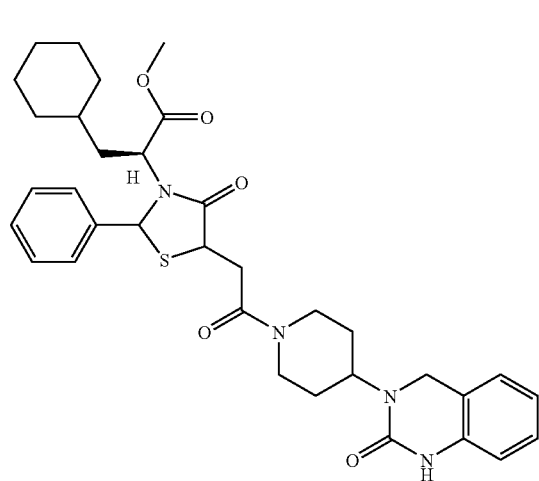
56
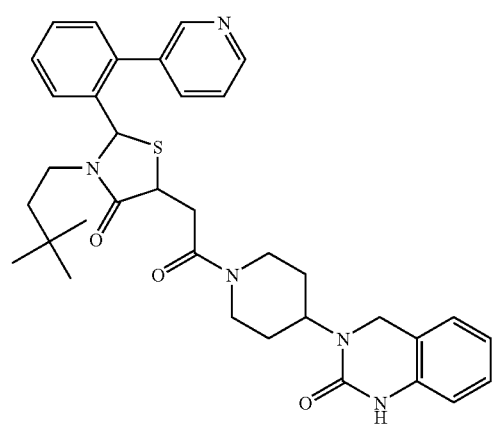
57
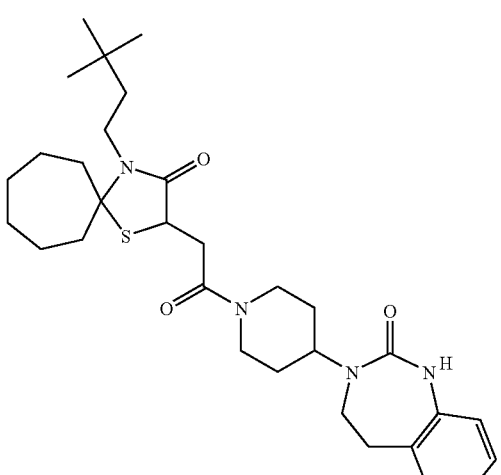
TABLE 1-continued
58
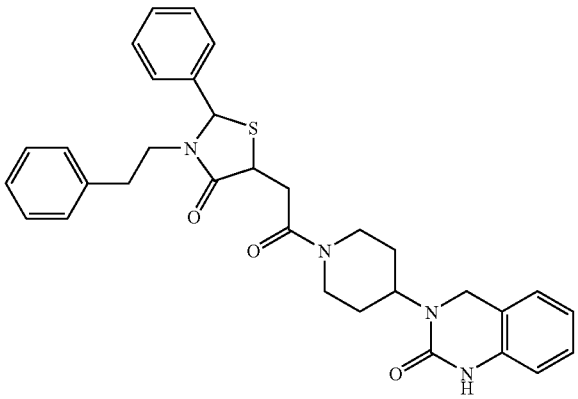
59
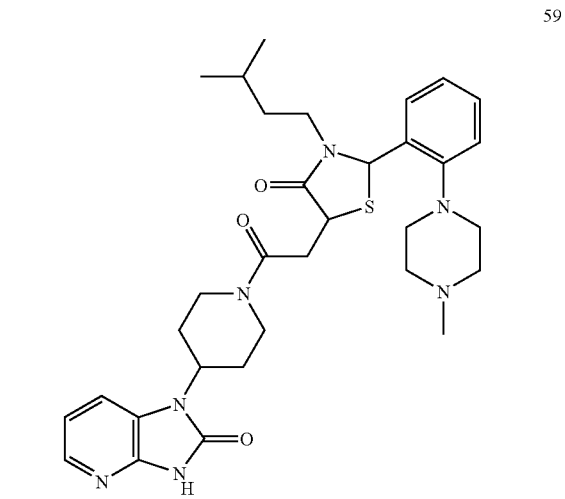
60

TABLE 1-continued
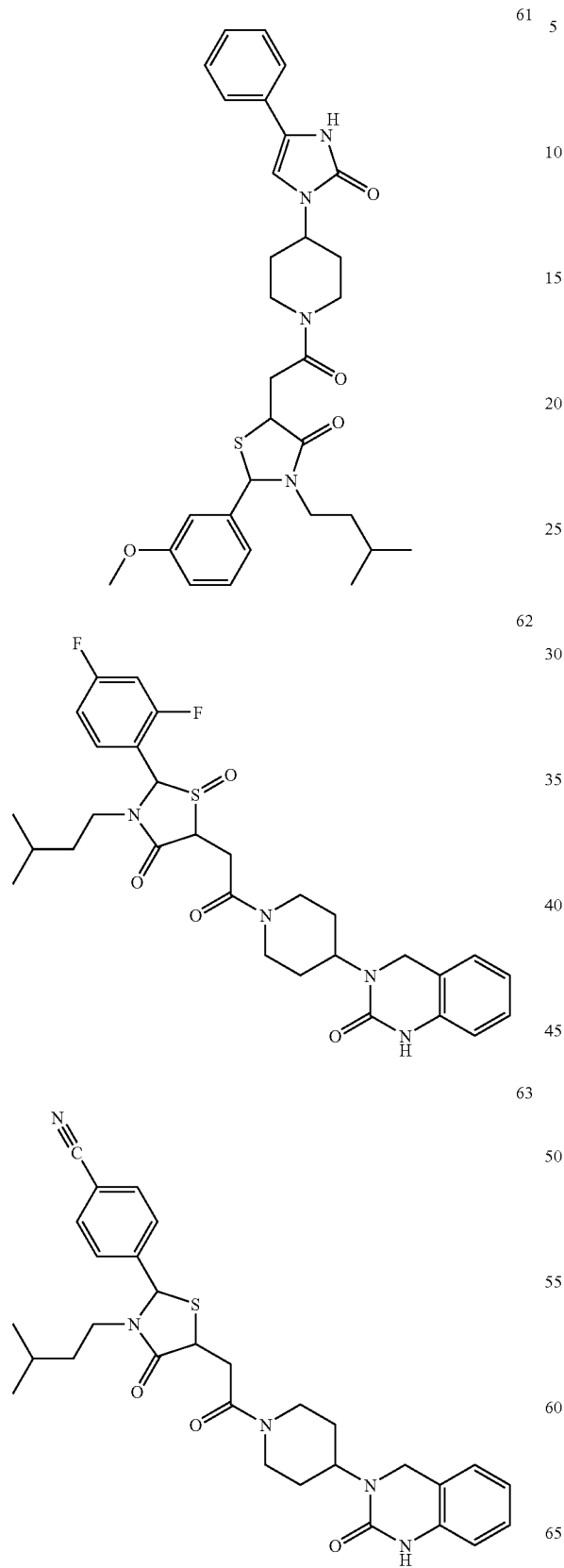
TABLE 1-continued
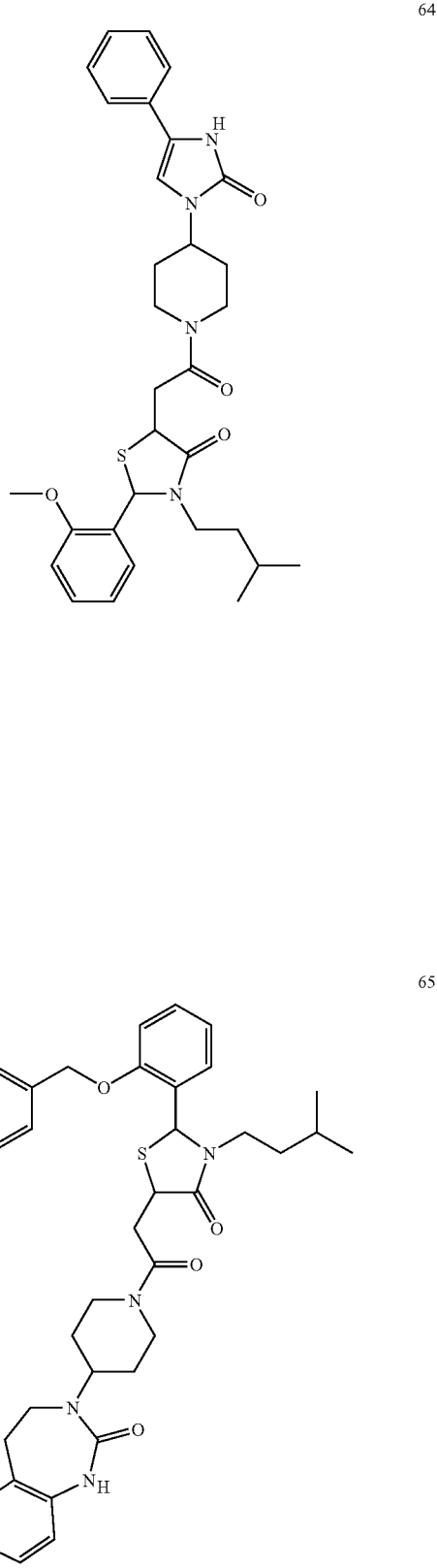

TABLE 1-continued
66
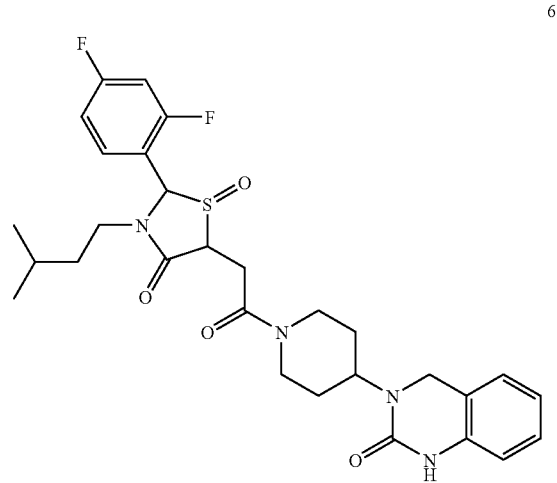
67
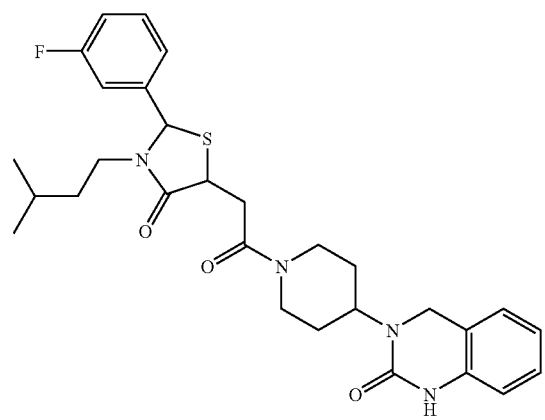
68
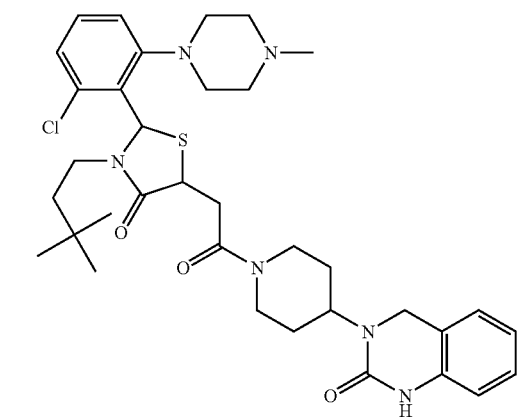
TABLE 1-continued
69
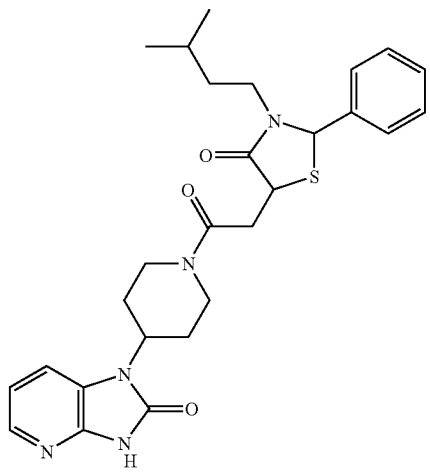
70
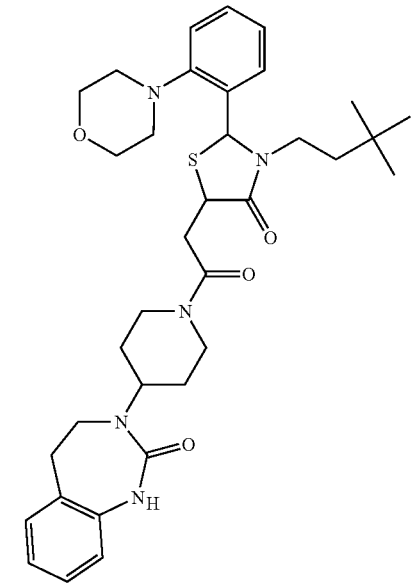
71
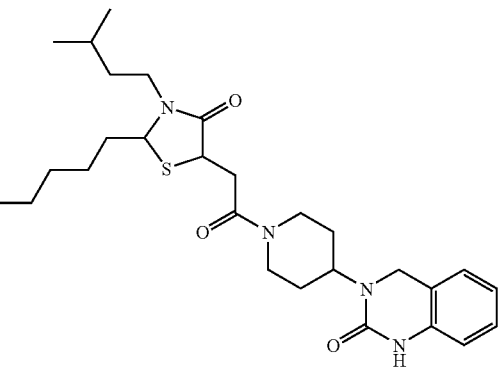

TABLE 1-continued
| | |
|---|---|
| 72 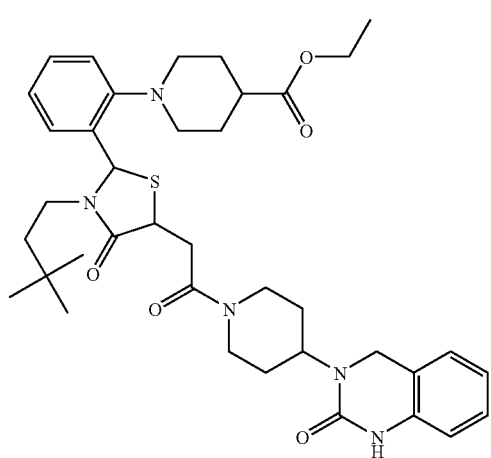 | 74 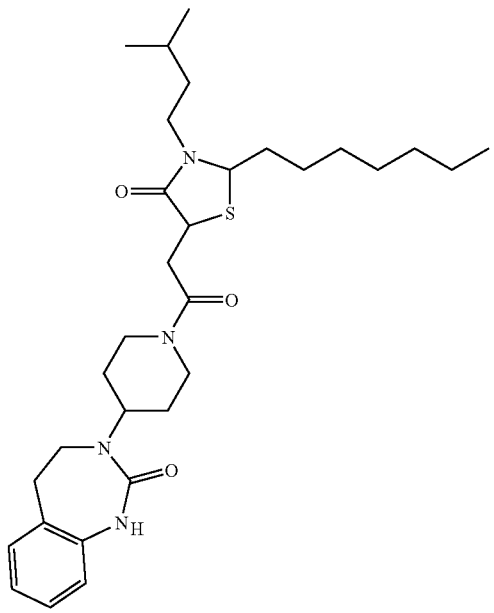 |
| 73 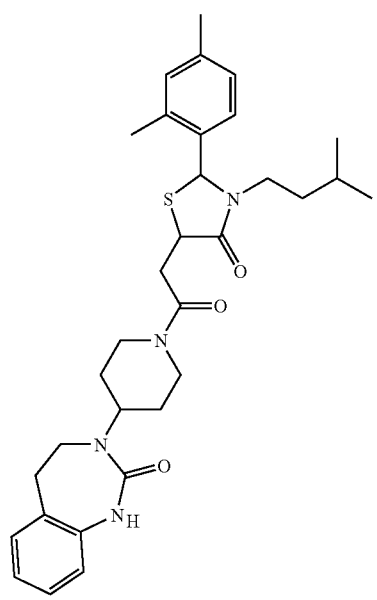 | 75 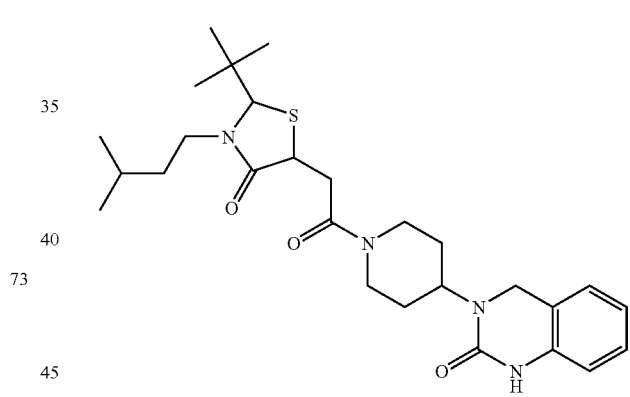 |
| | 76 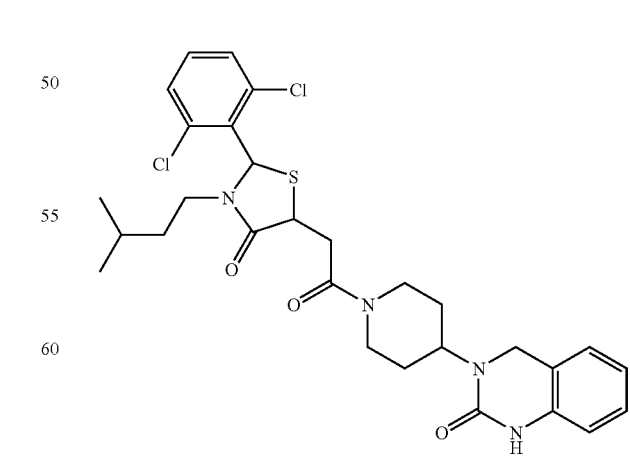 |

TABLE 1-continued
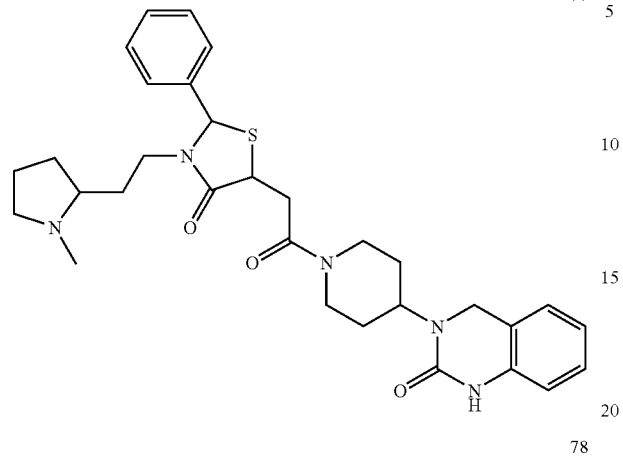
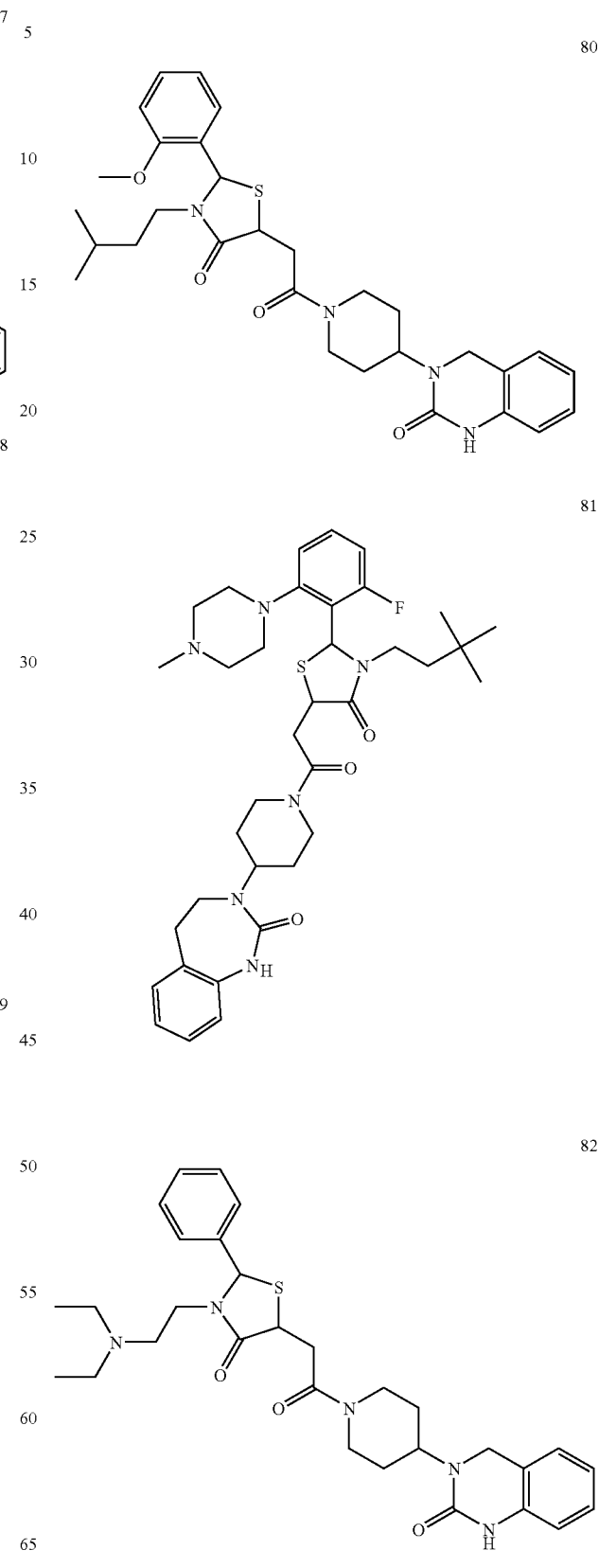

TABLE 1-continued
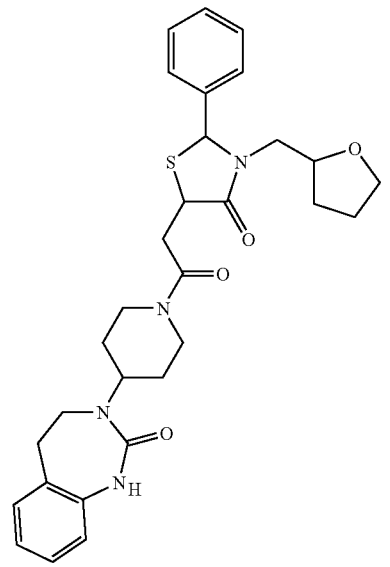
83
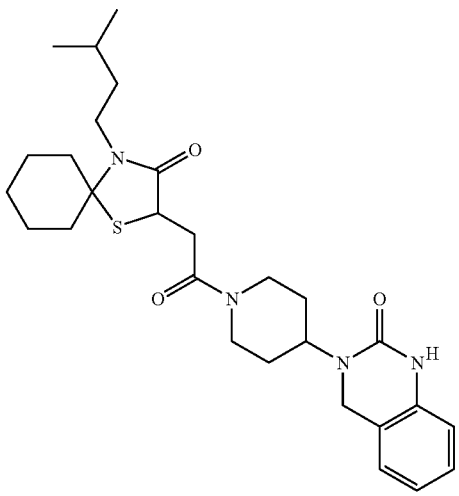
86
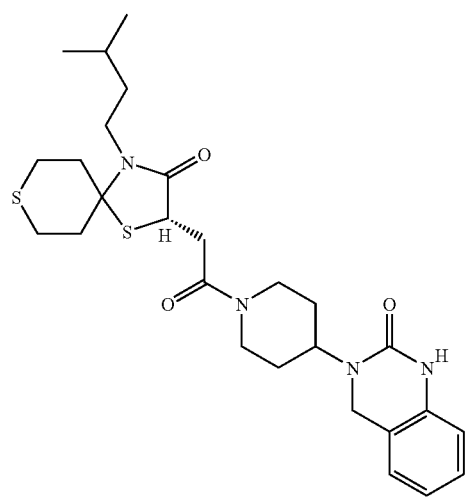
84
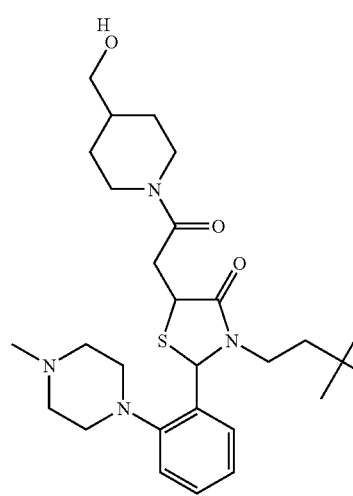
85
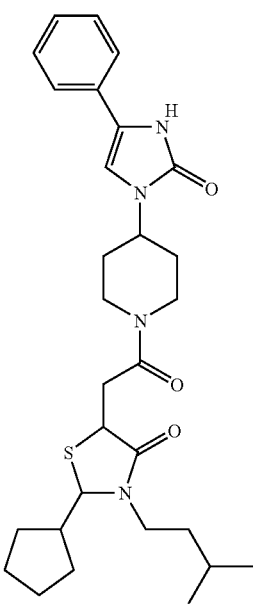
87

TABLE 1-continued
| 88 | 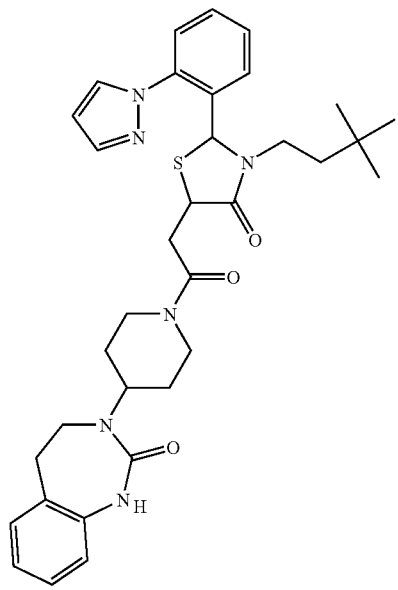 |
| --- | --- |
| 89 | 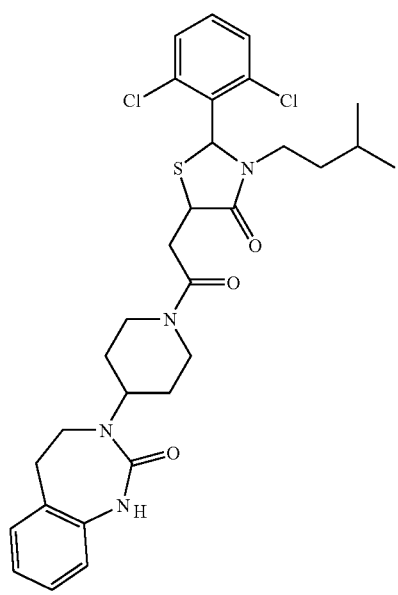 |
TABLE 1-continued
| 90 | 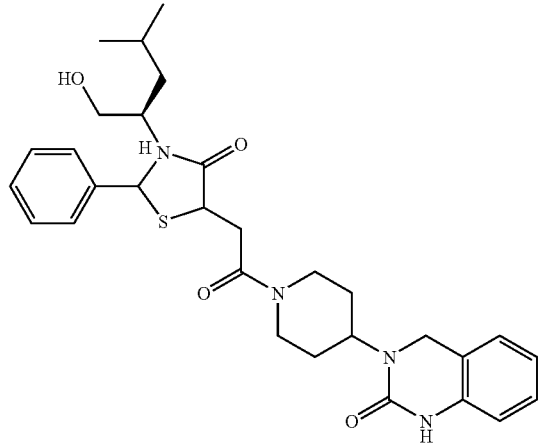 |
| --- | --- |
| 91 | 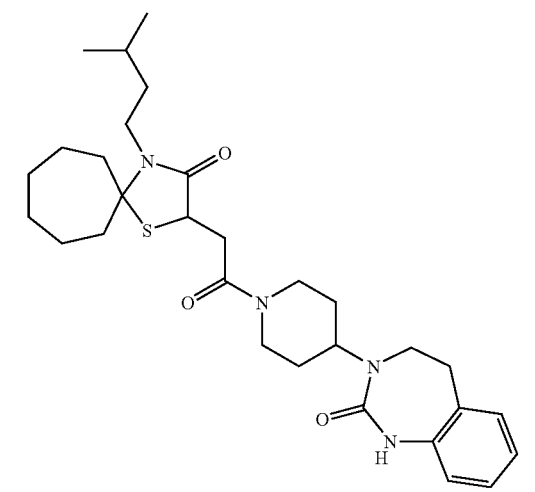 |
| 92 | 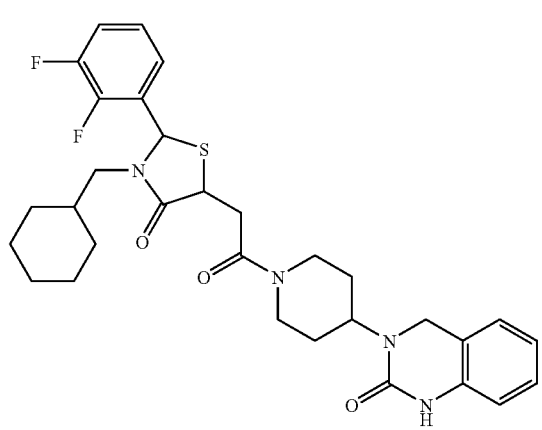 |

TABLE 1-continued
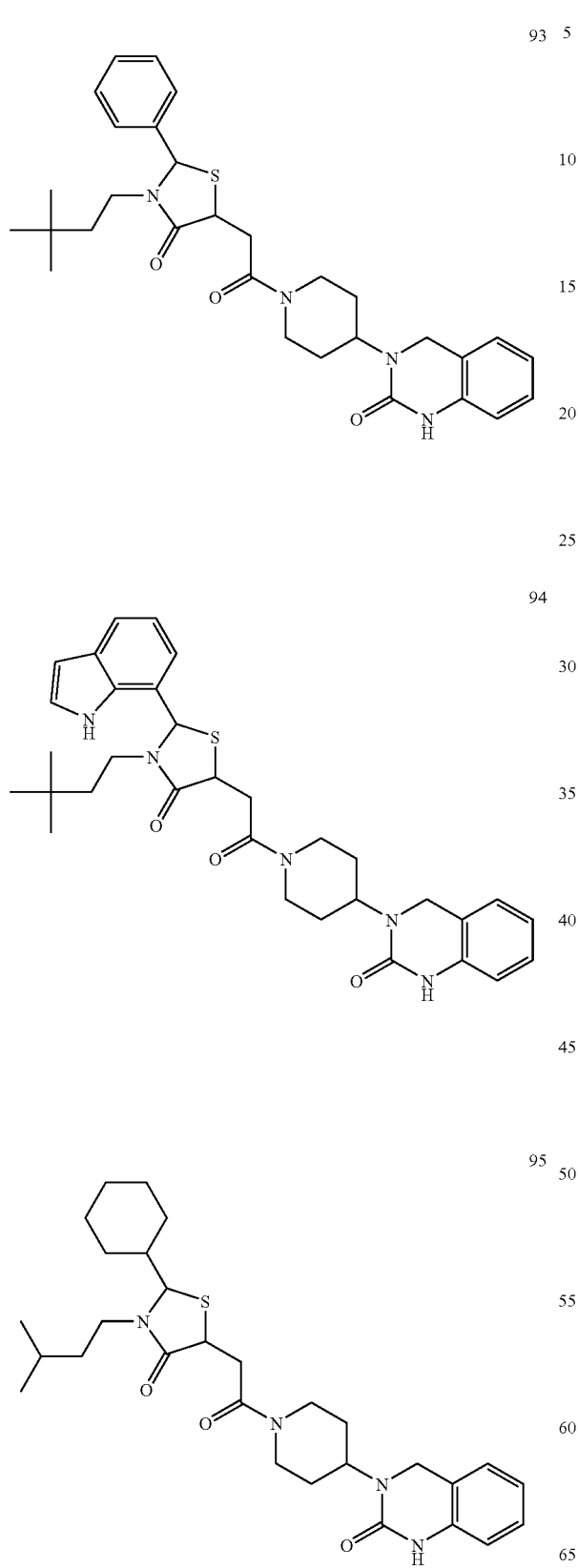
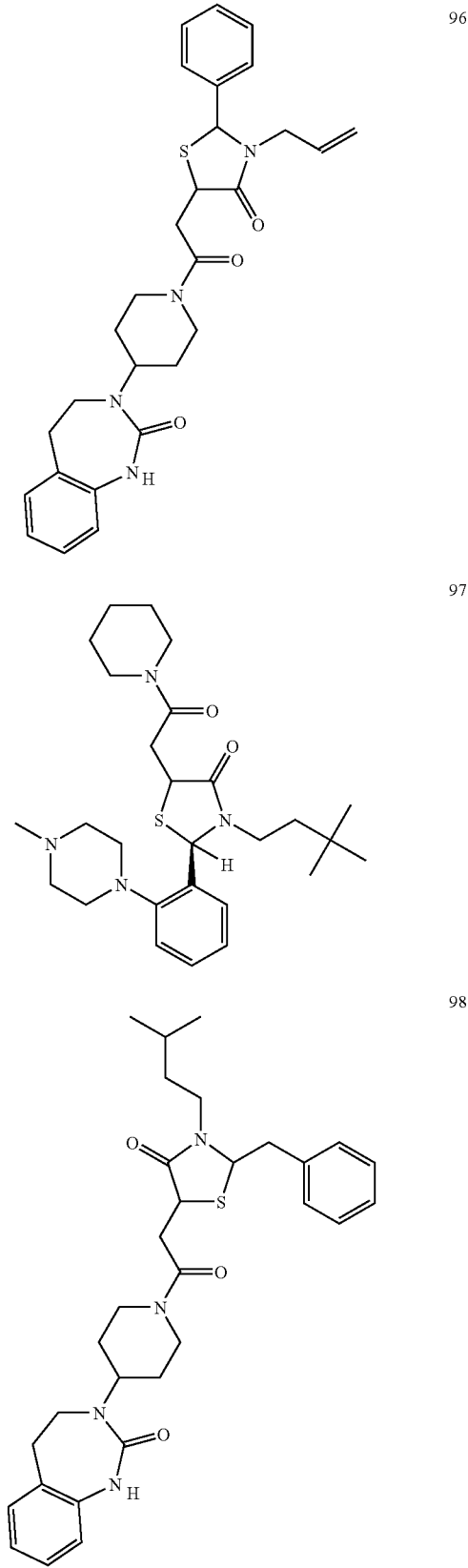

TABLE 1-continued
99
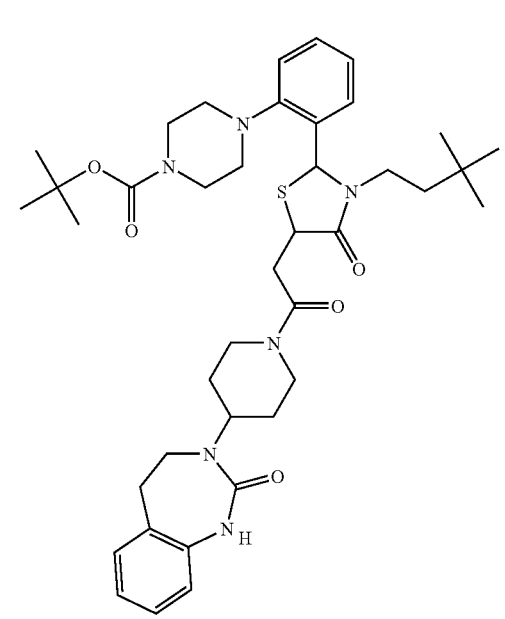
100
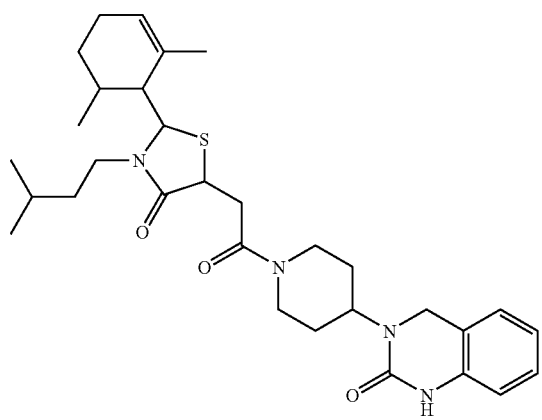
101
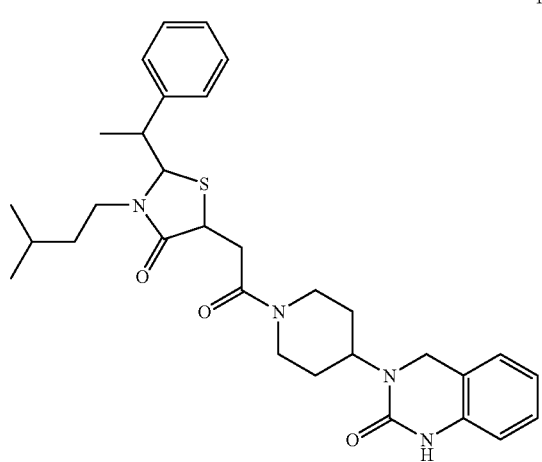
TABLE 1-continued
102
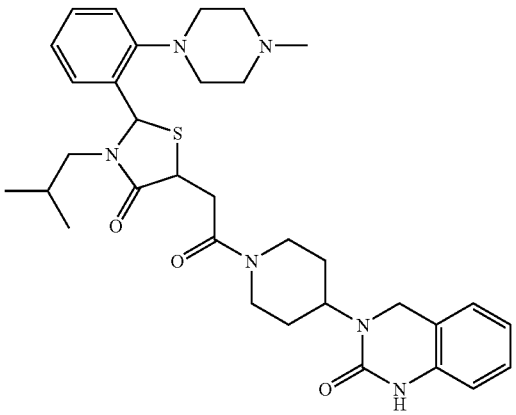
103
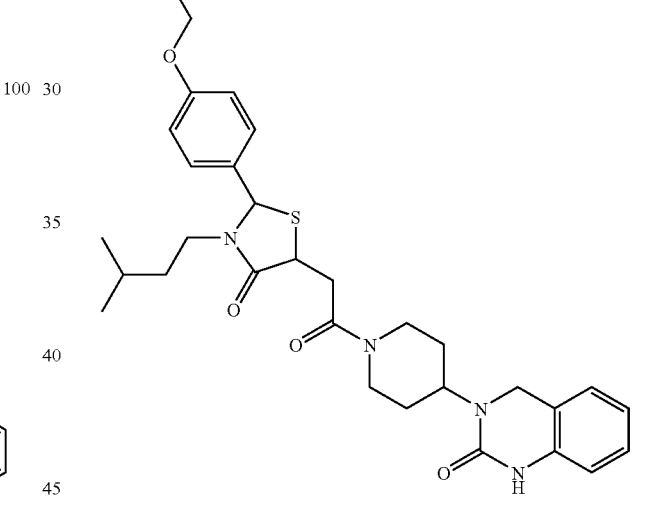
104
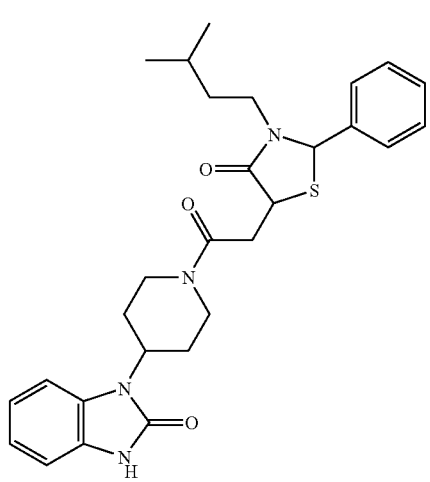

TABLE 1-continued
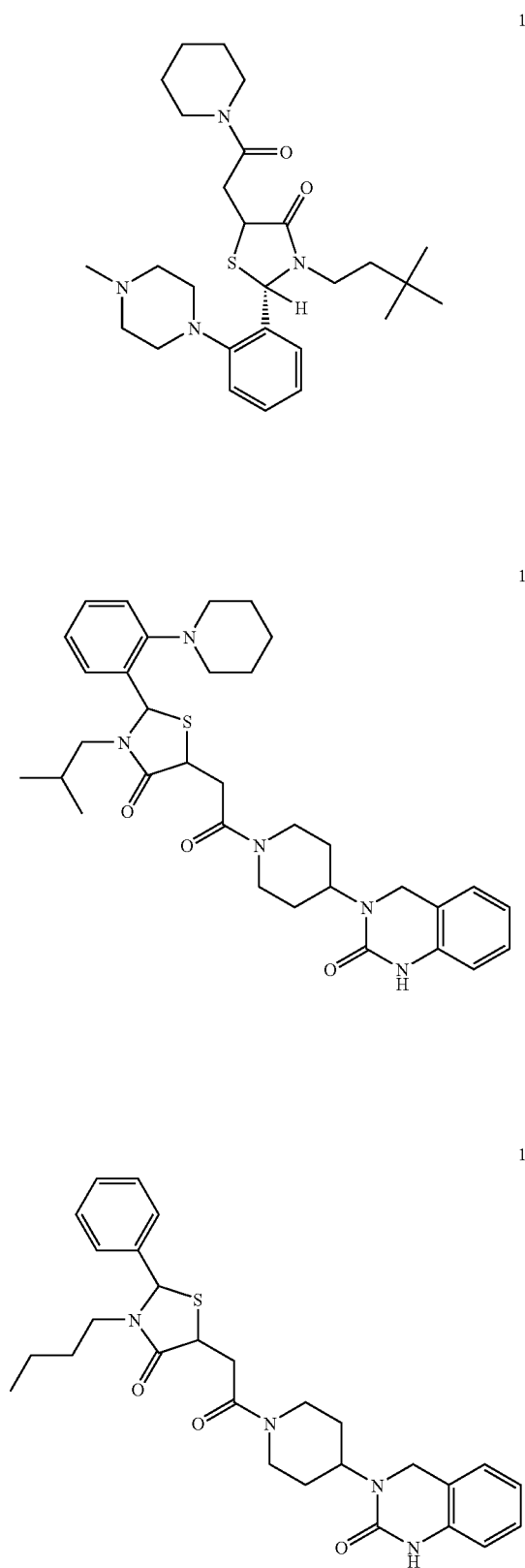
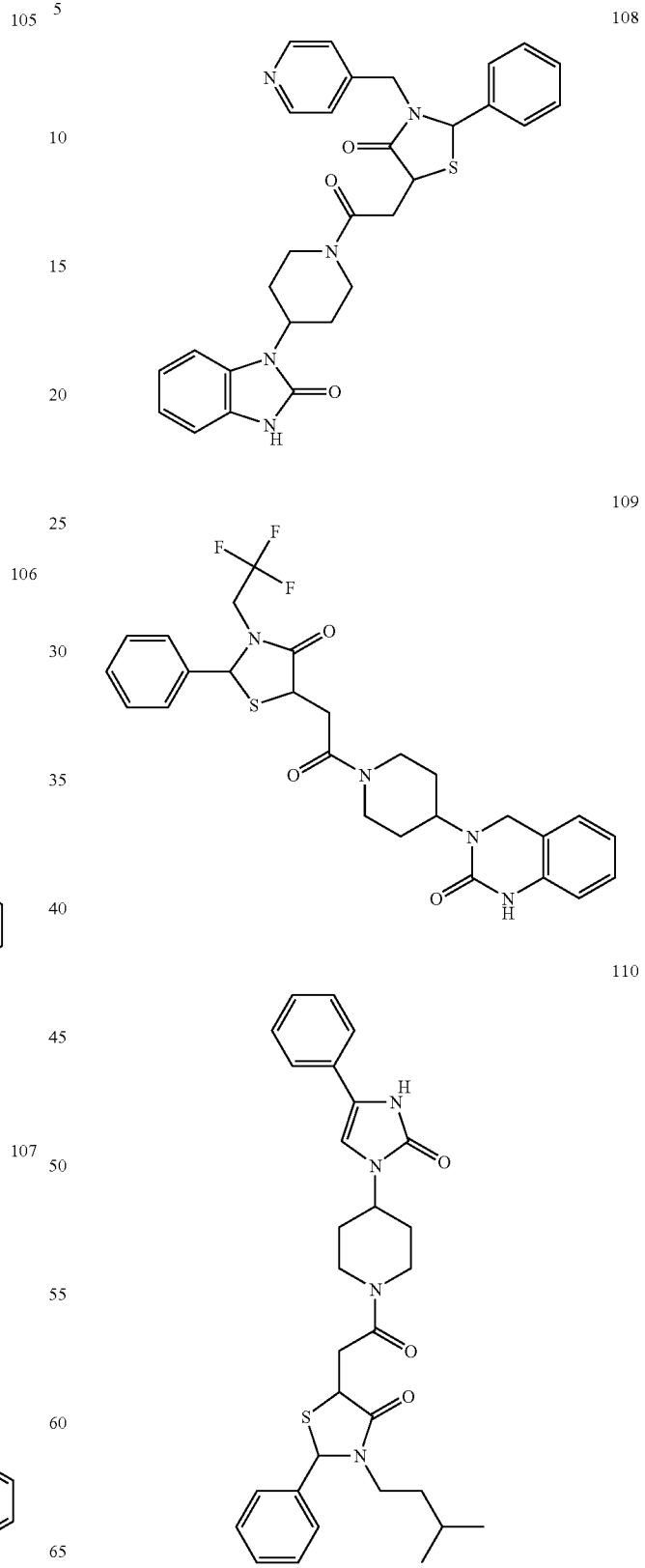

TABLE 1-continued
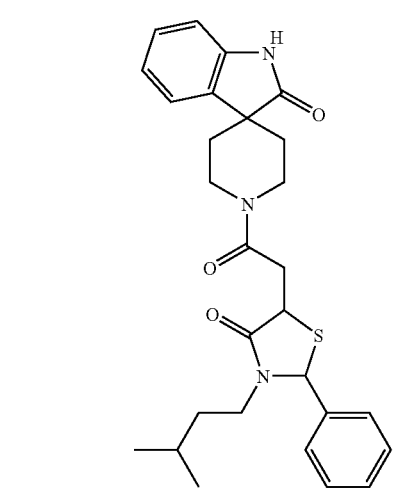
111
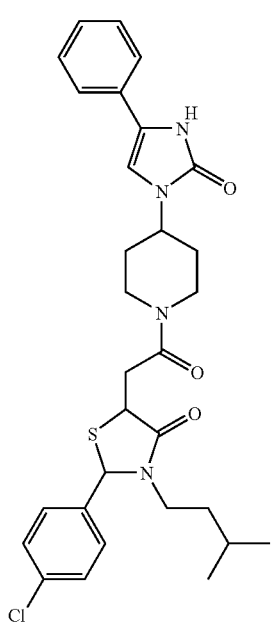
112
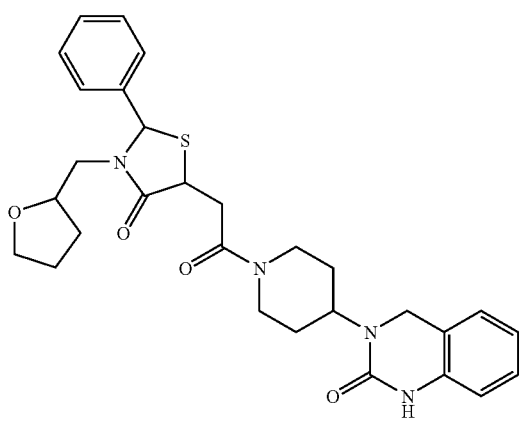
113
TABLE 1-continued
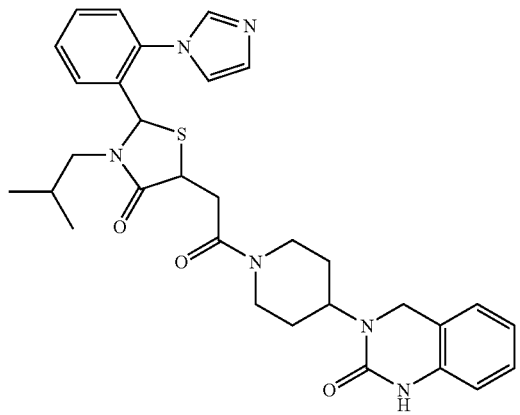
114
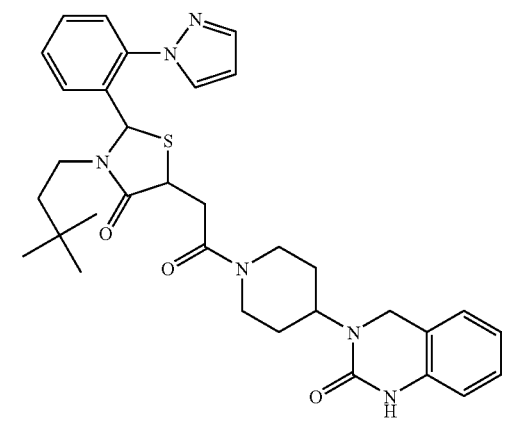
115
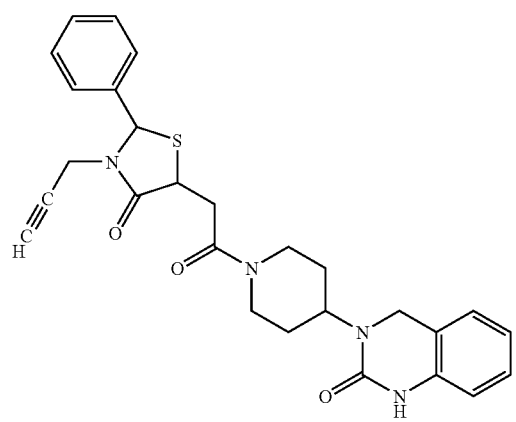
116

TABLE 1-continued
117
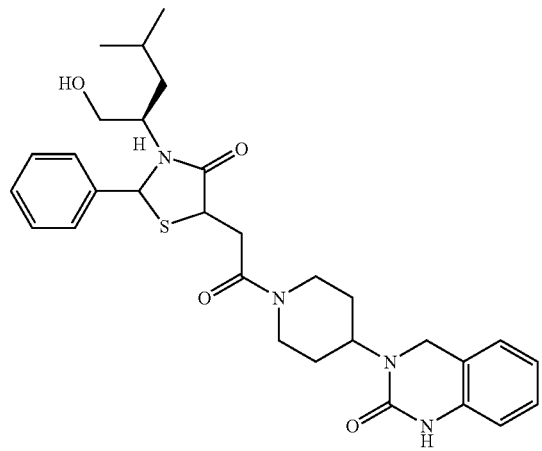
118
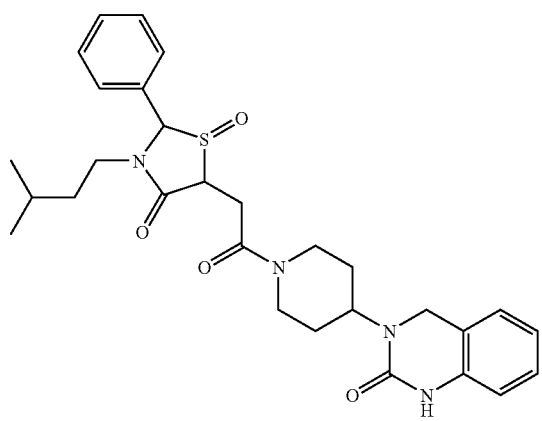
119
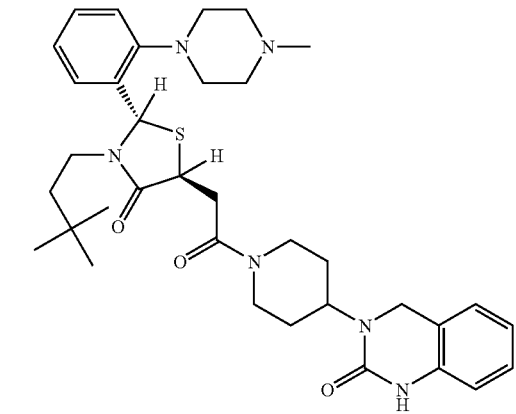
TABLE 1-continued
120
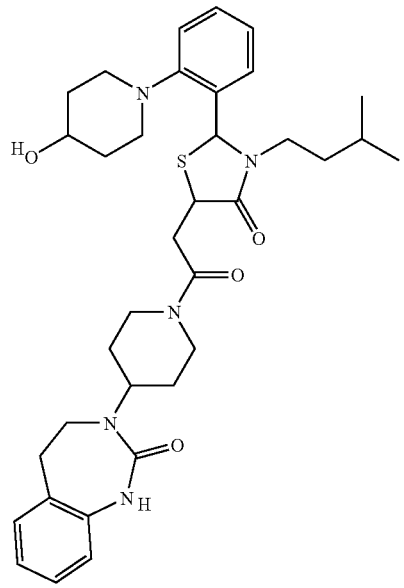
121
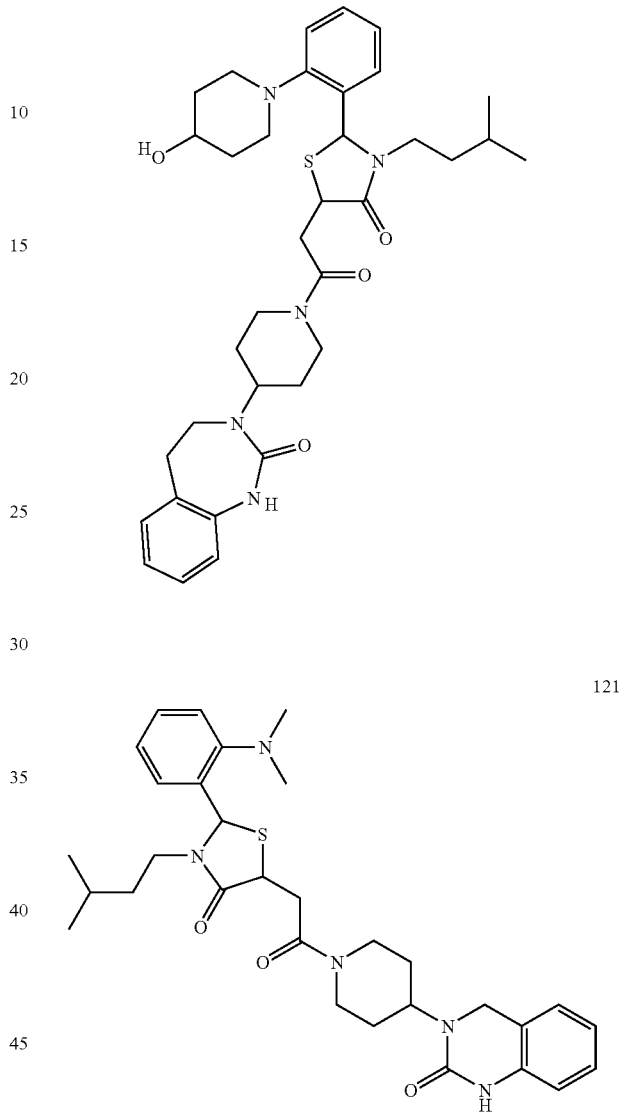
122
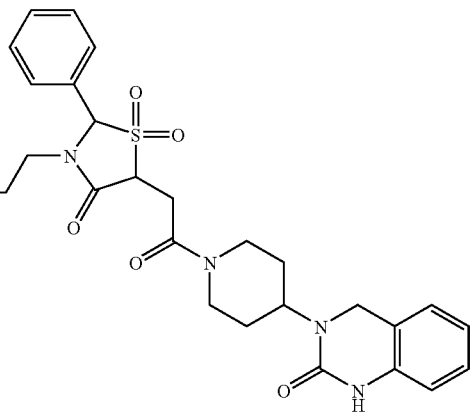

TABLE 1-continued
123
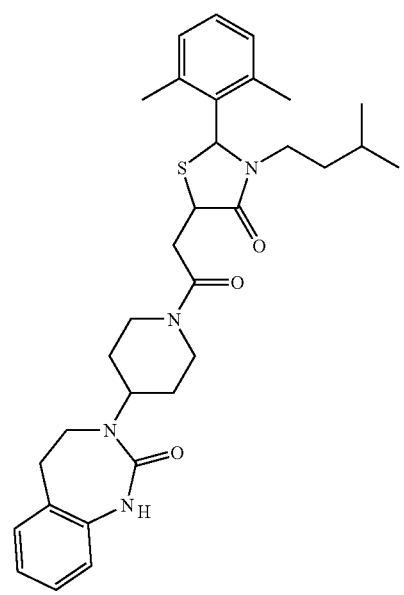
124
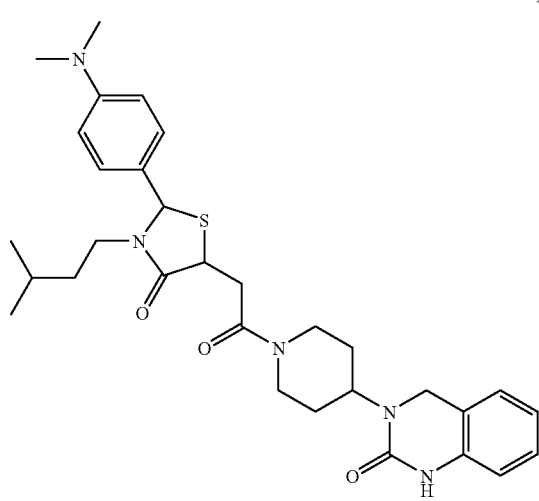
TABLE 1-continued
125
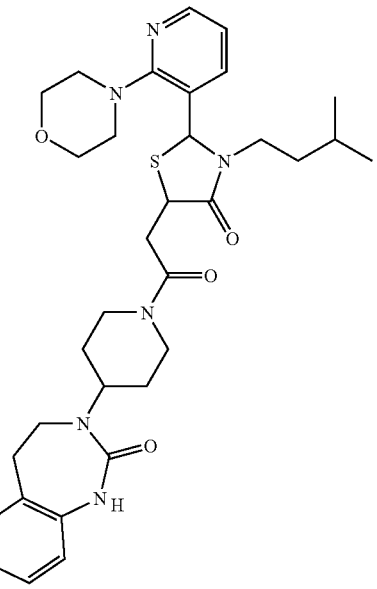
126
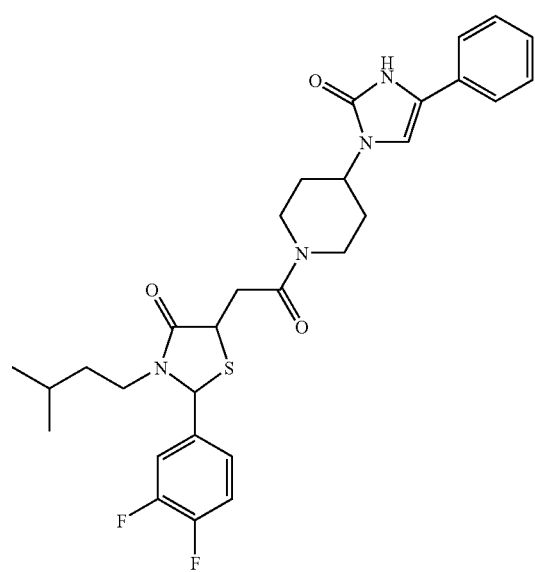
127

TABLE 1-continued
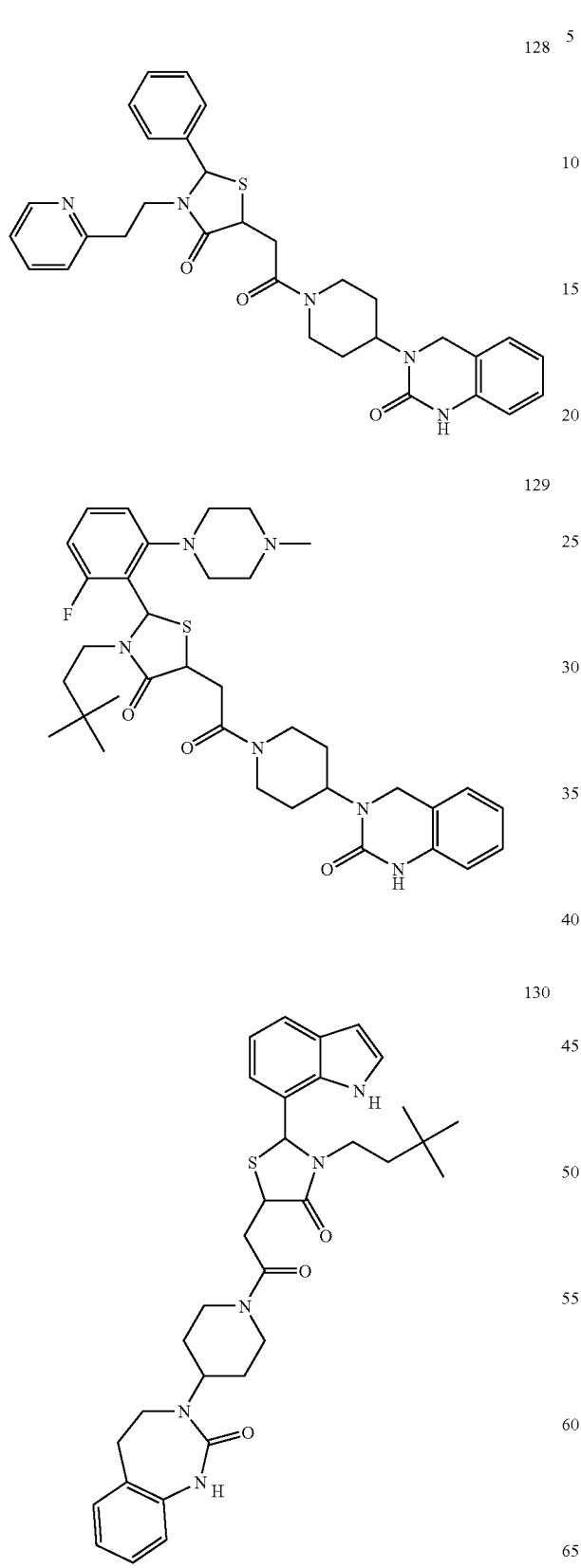
128
129
130
TABLE 1-continued
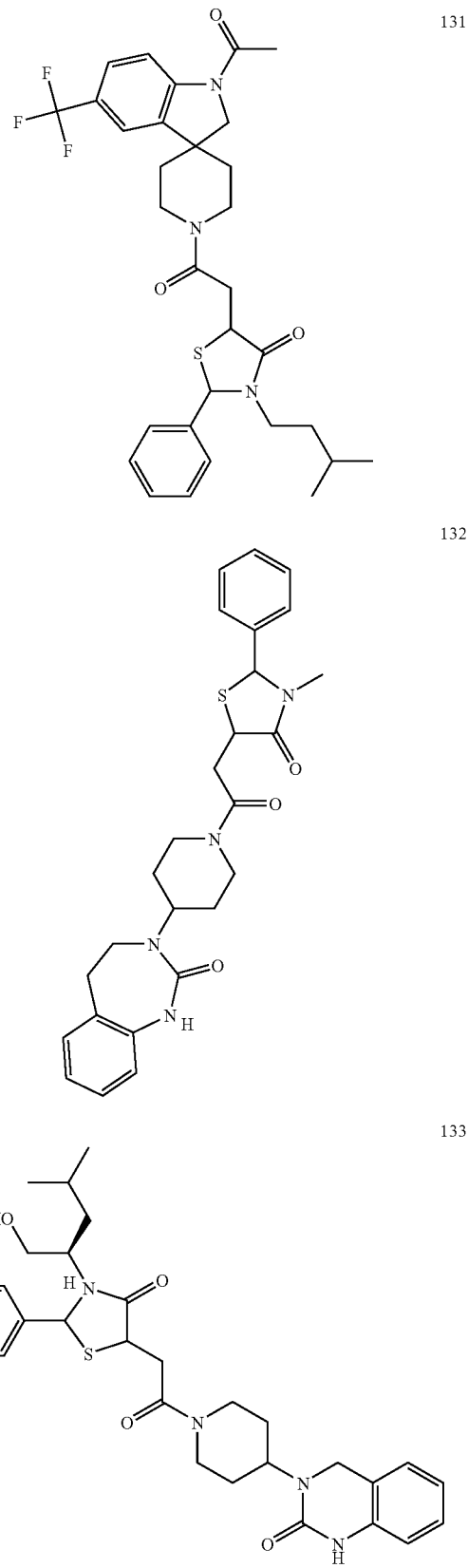
131
132
133

TABLE 1-continued
134
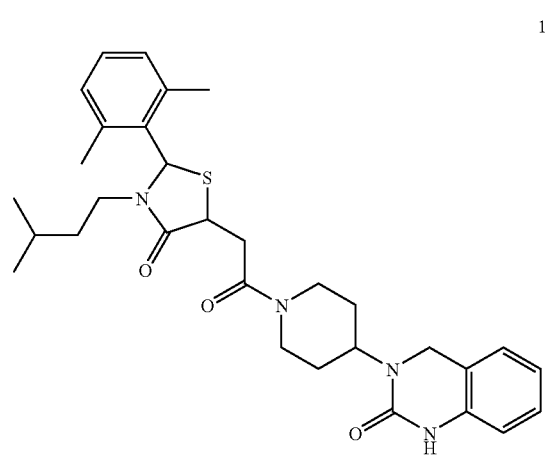
135
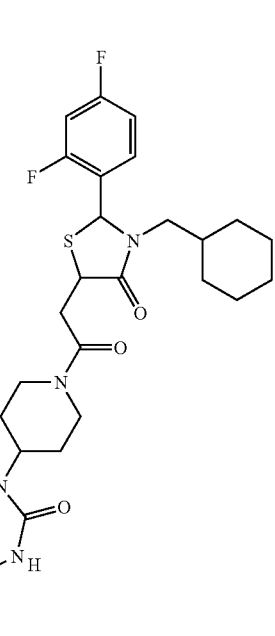
136
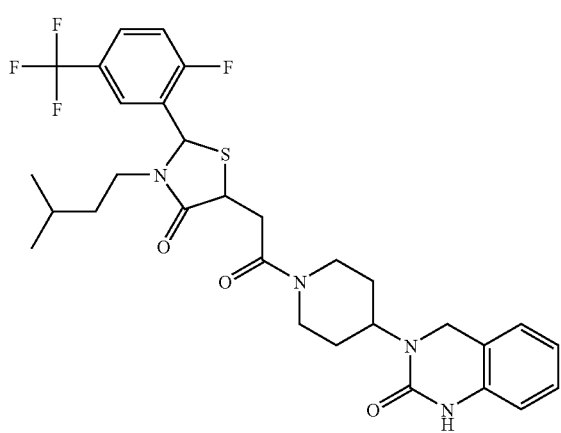
TABLE 1-continued
137
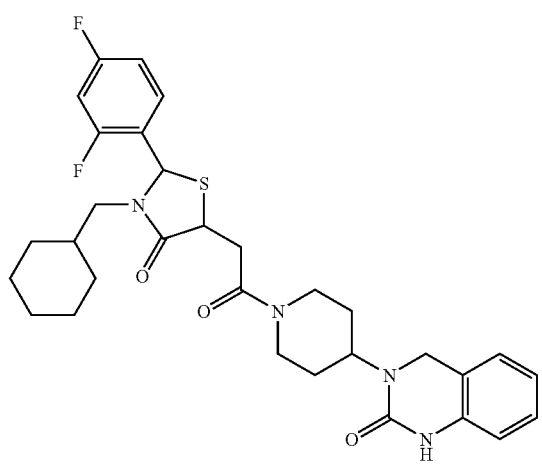
138
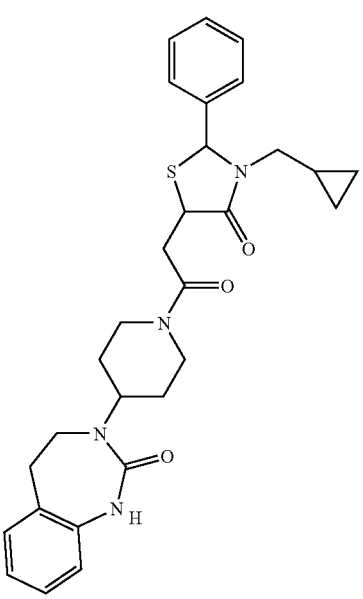
139
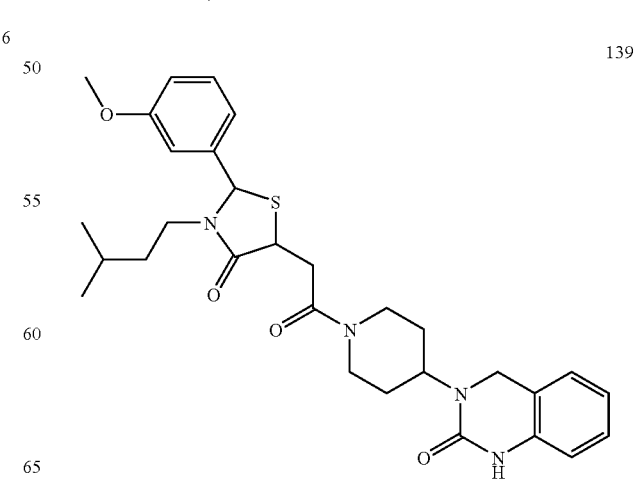

TABLE 1-continued
140 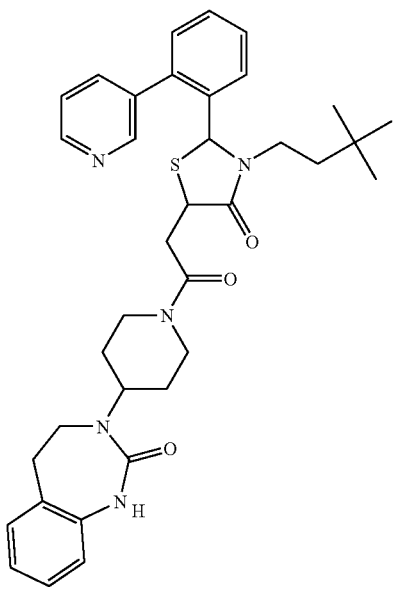
141 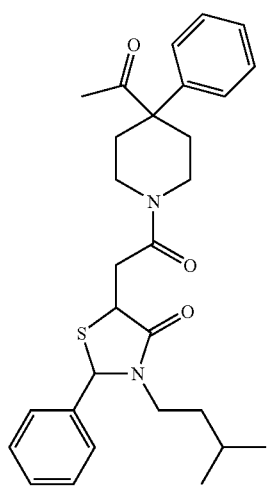
142 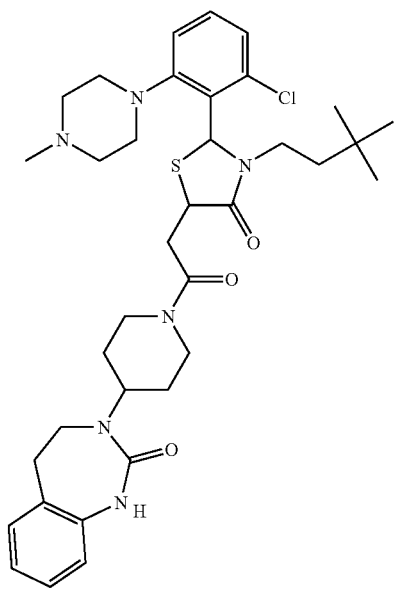
143 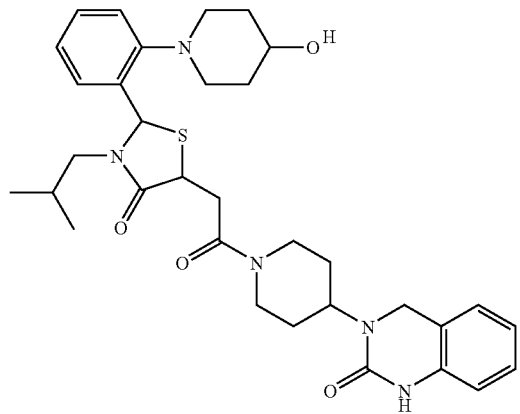
144

TABLE 1-continued
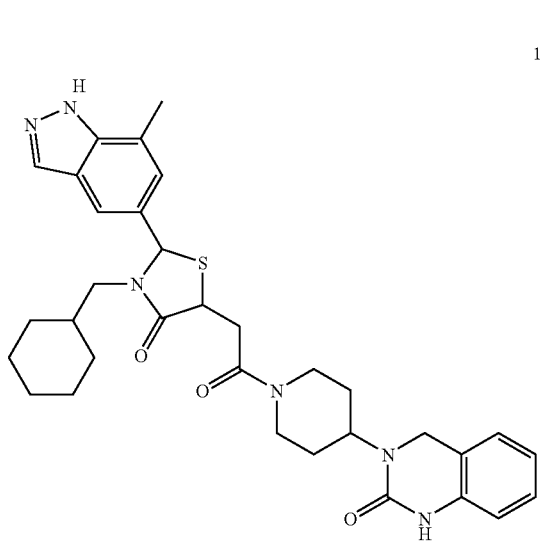
145
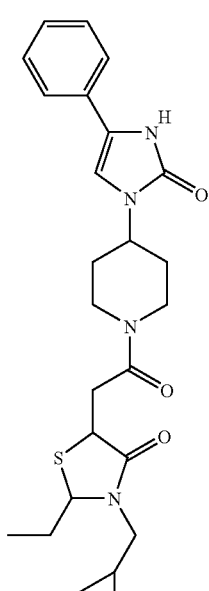
146
TABLE 1-continued
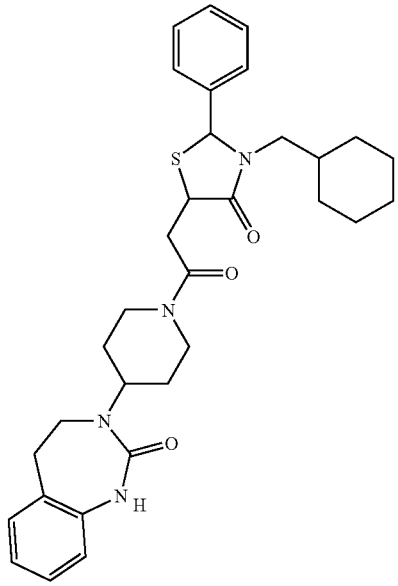
147
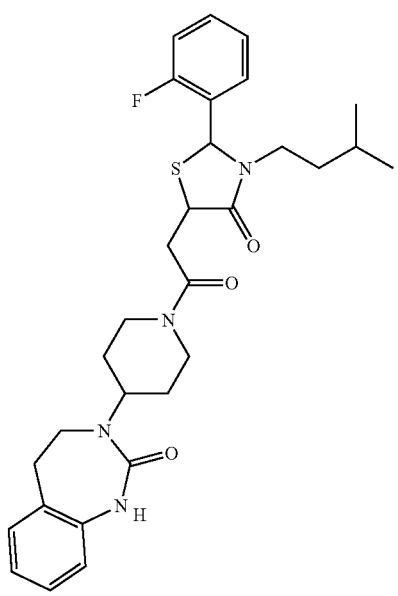
148
149

TABLE 1-continued
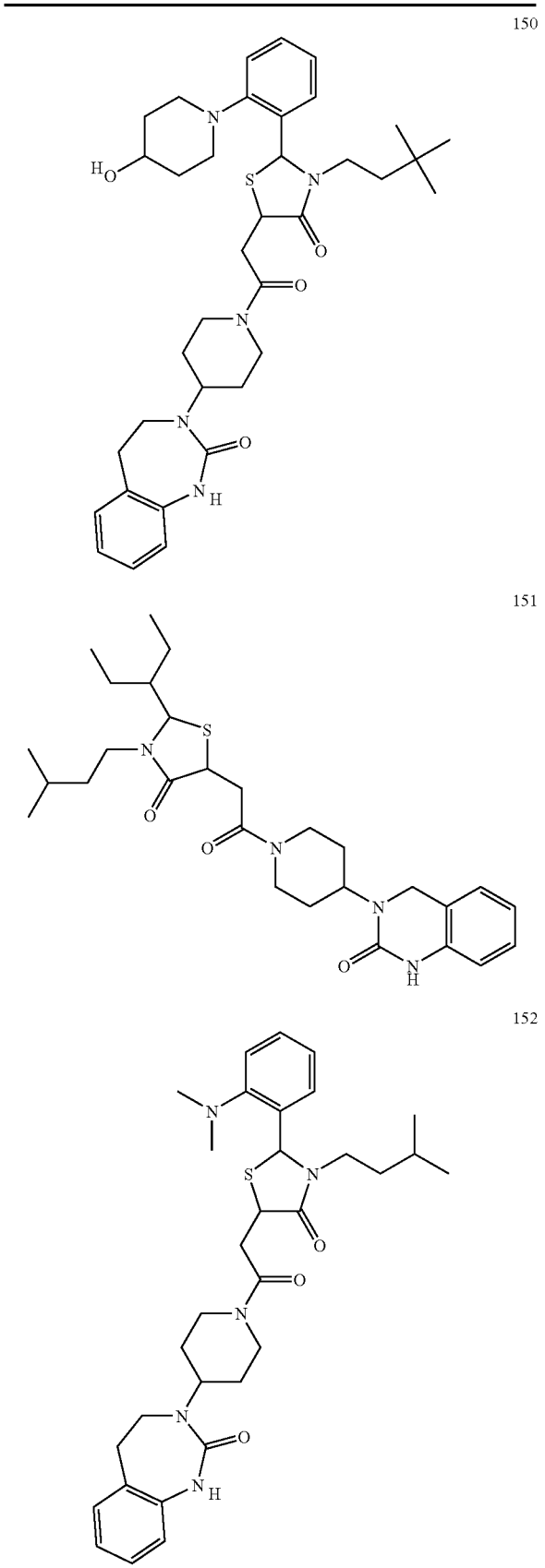
150
151
152
TABLE 1-continued
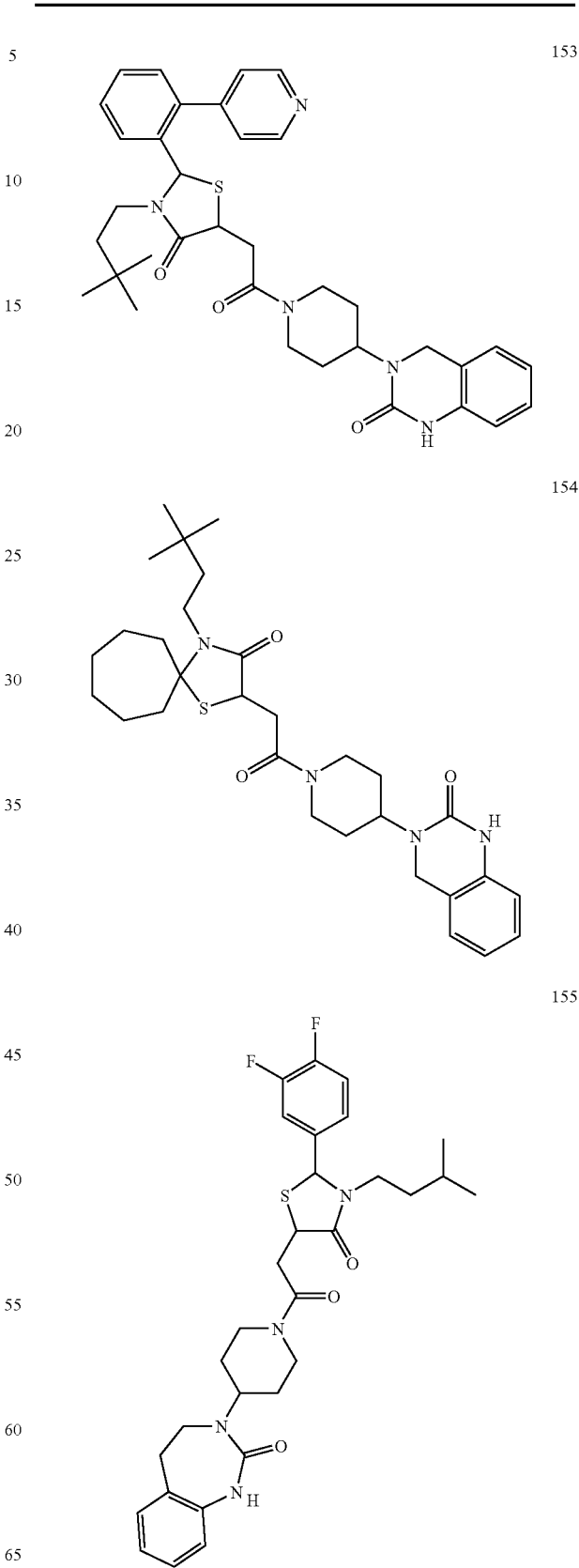
153
154
155

US 7,834,000 B2
TABLE 1-continued | TABLE 1-continued
156 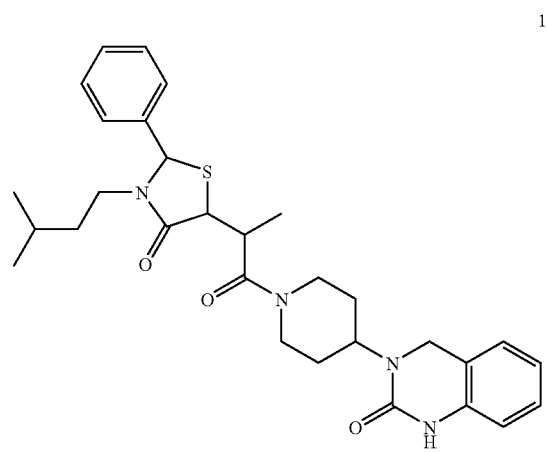
157 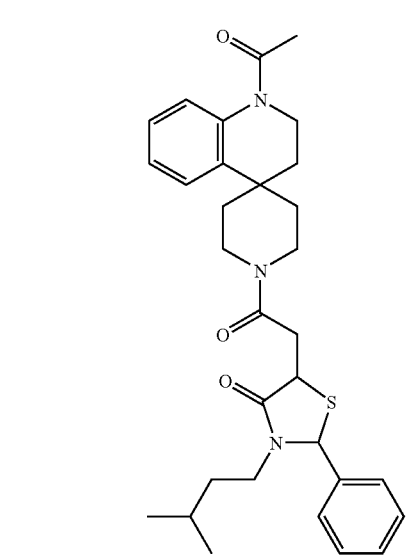
158 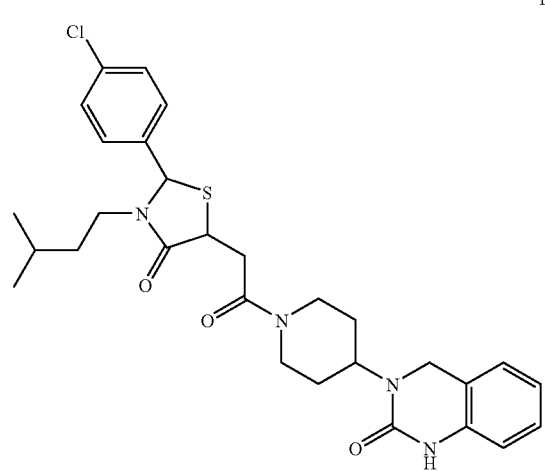
159 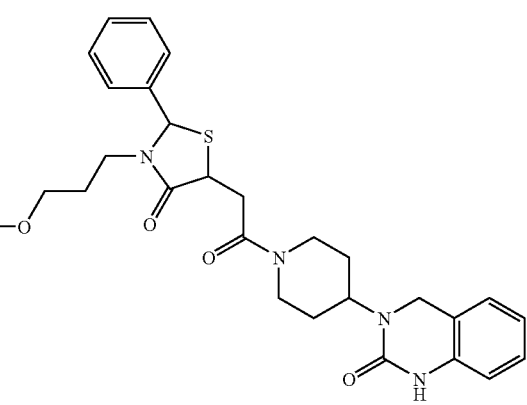
160 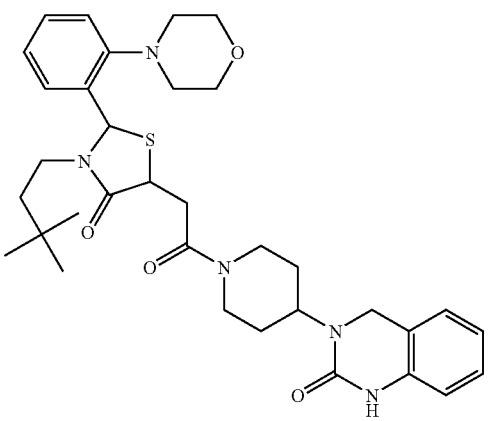
161 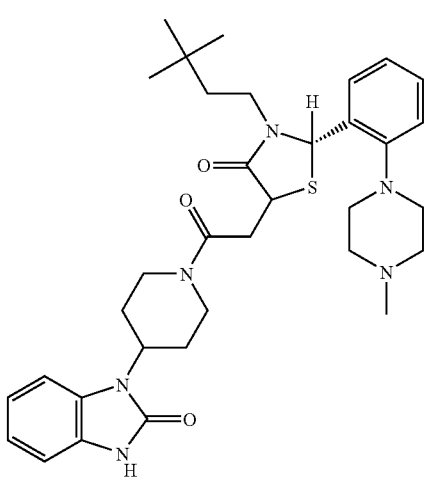

TABLE 1-continued
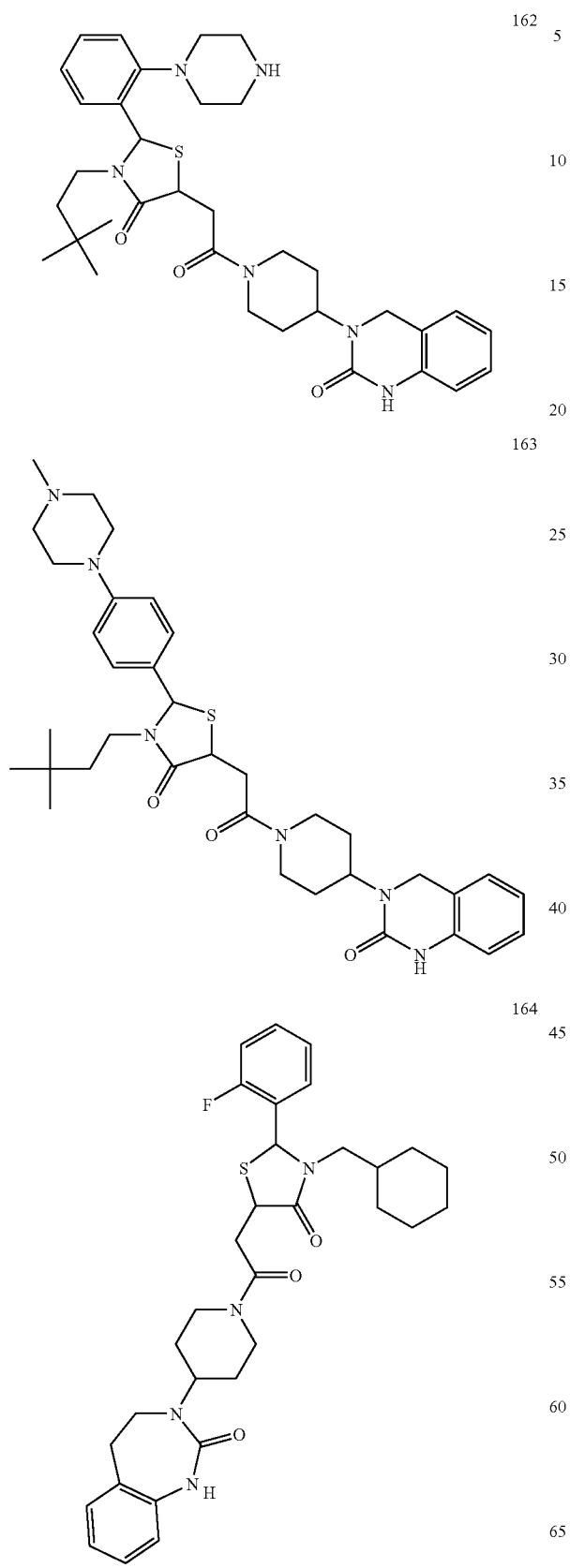

TABLE 1-continued
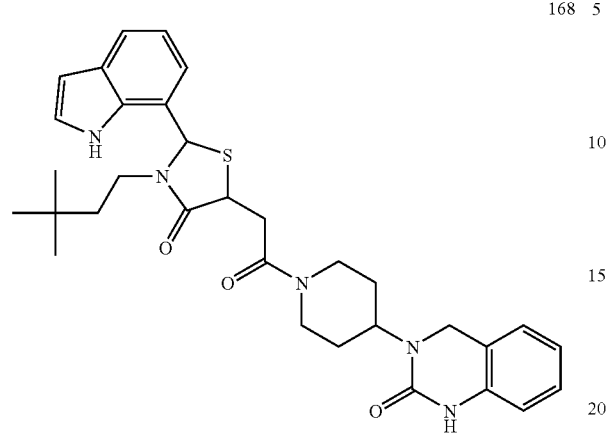
168
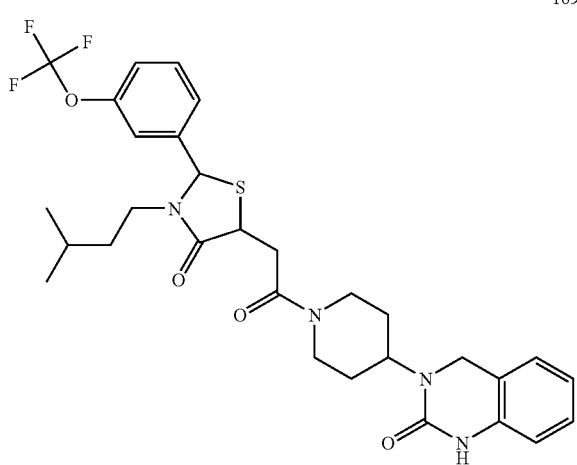
169
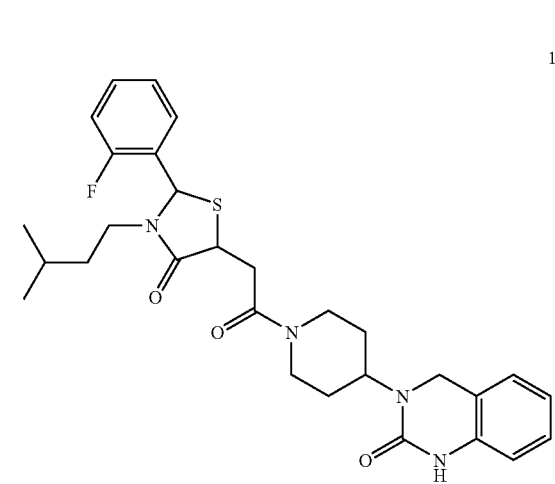
170
TABLE 1-continued
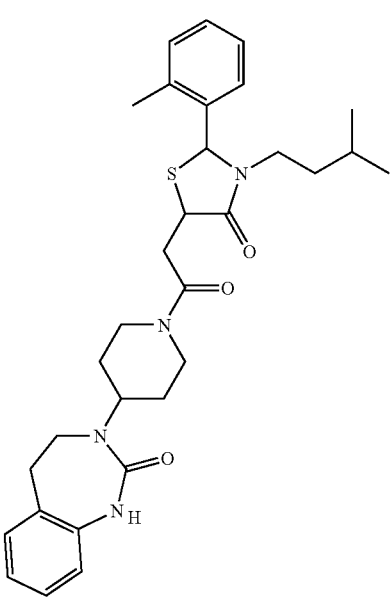
171
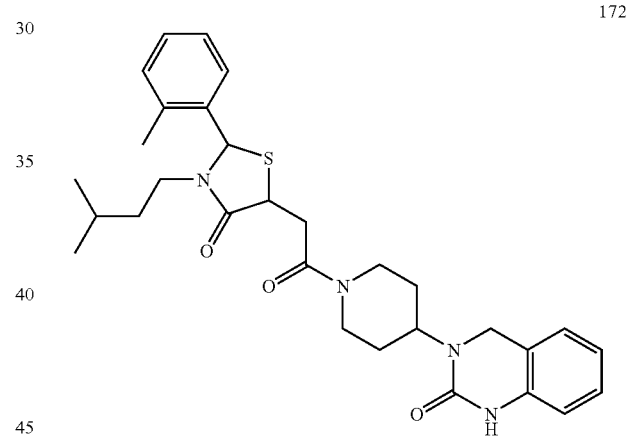
172
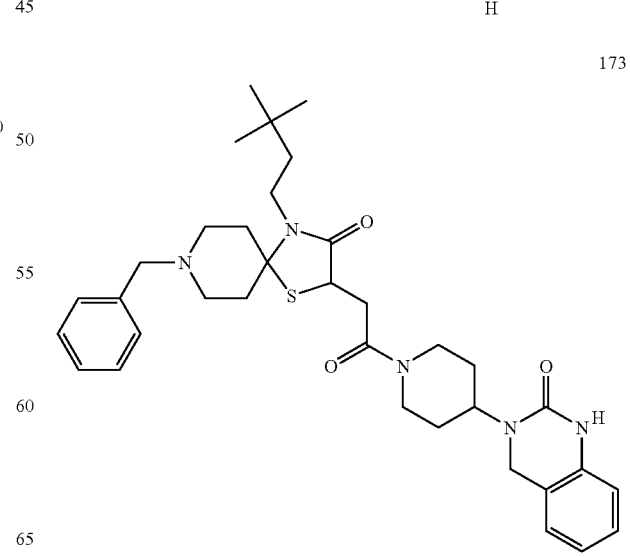
173

TABLE 1-continued
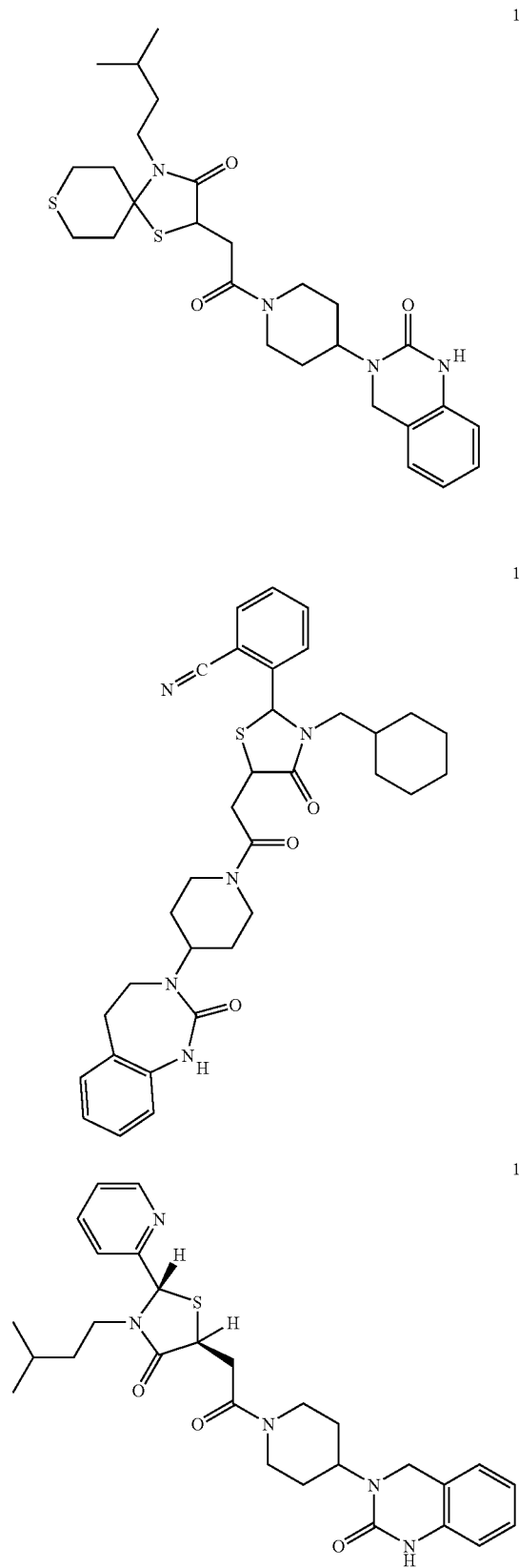
174
175
176
TABLE 1-continued
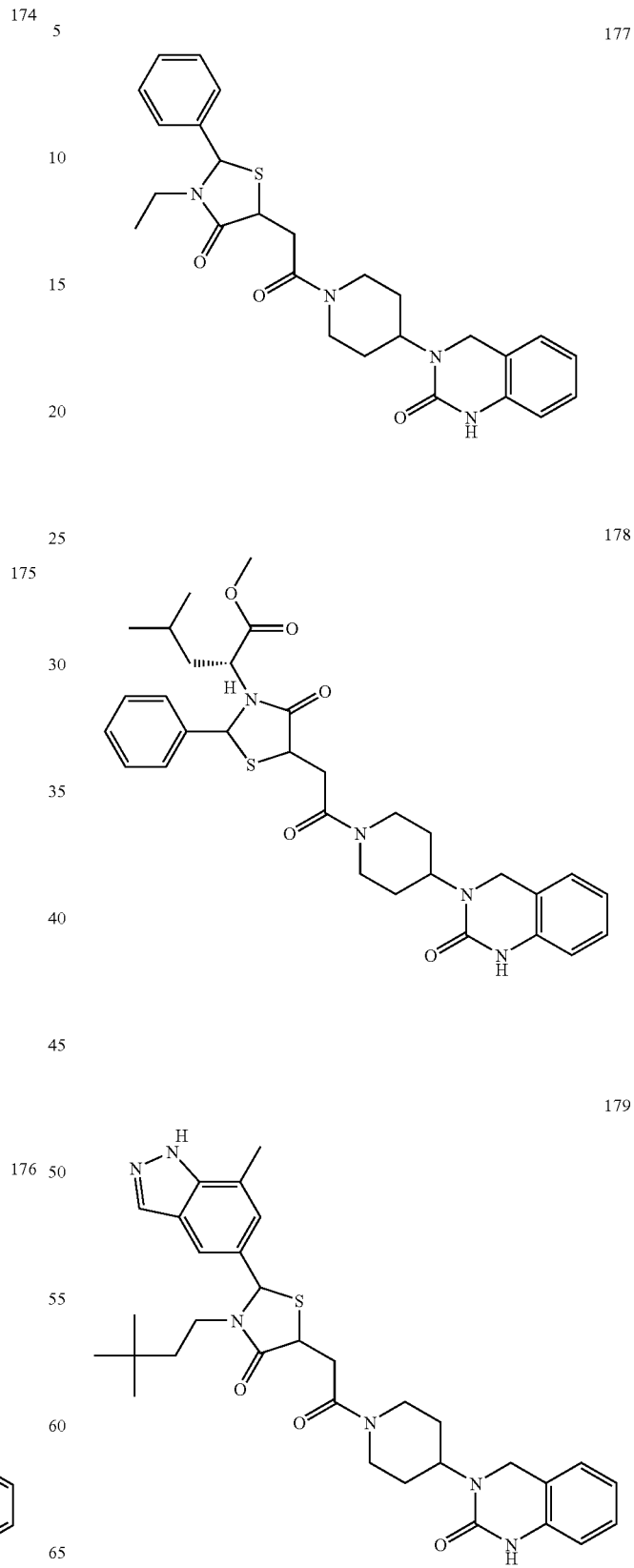
177
178
179

TABLE 1-continued
| 180 | 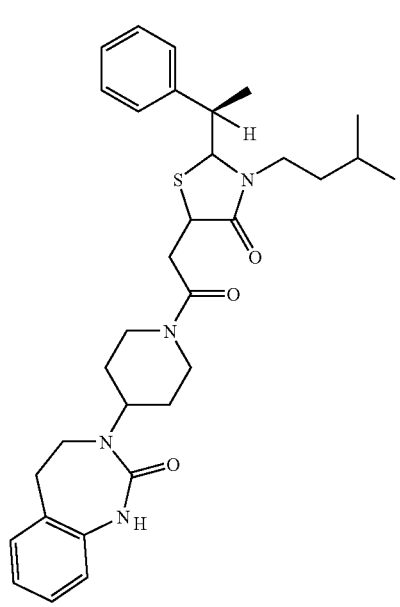 |
| --- | --- |
| 181 | 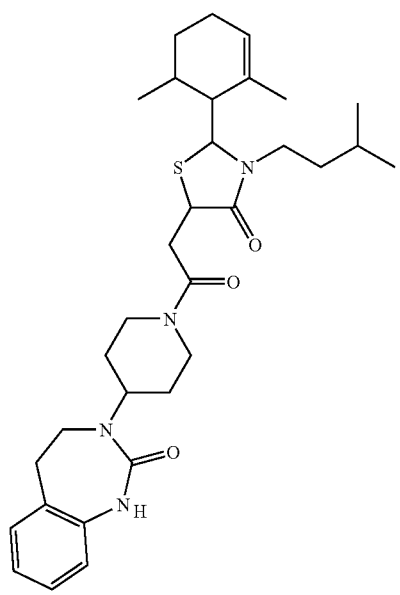 |
| 182 | 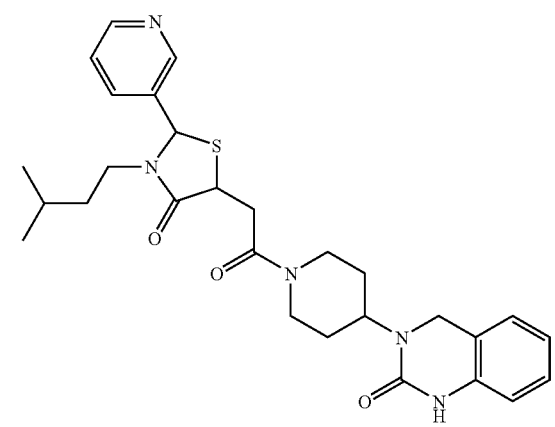 |
| 183 | 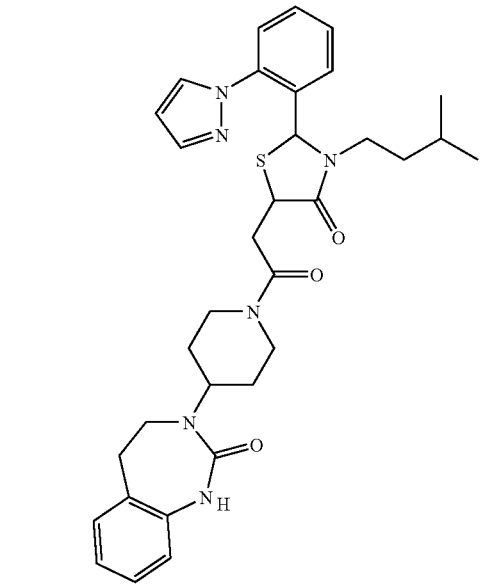 |
| 184 | 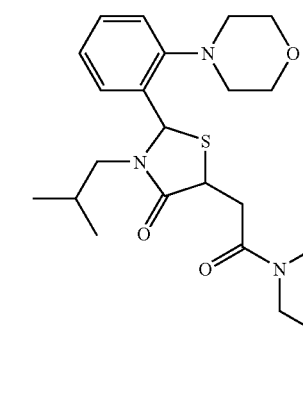 |

TABLE 1-continued
185
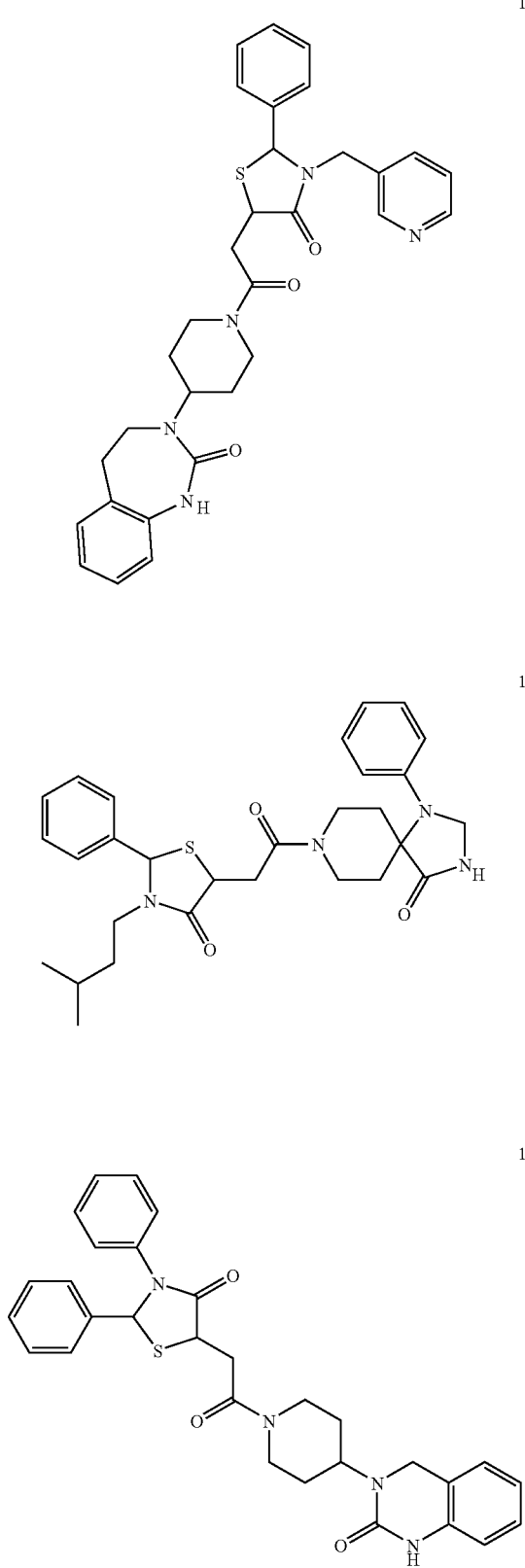
186
187
TABLE 1-continued
188
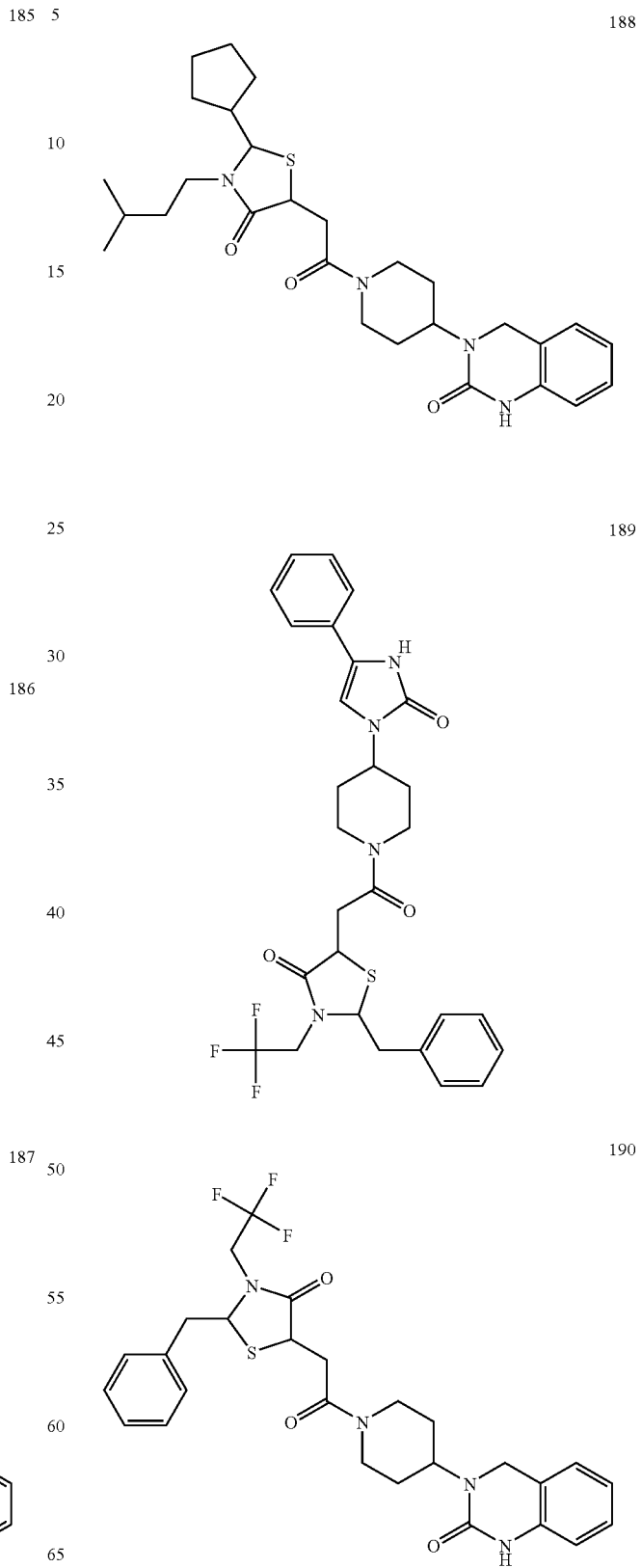
189
190

TABLE 1-continued
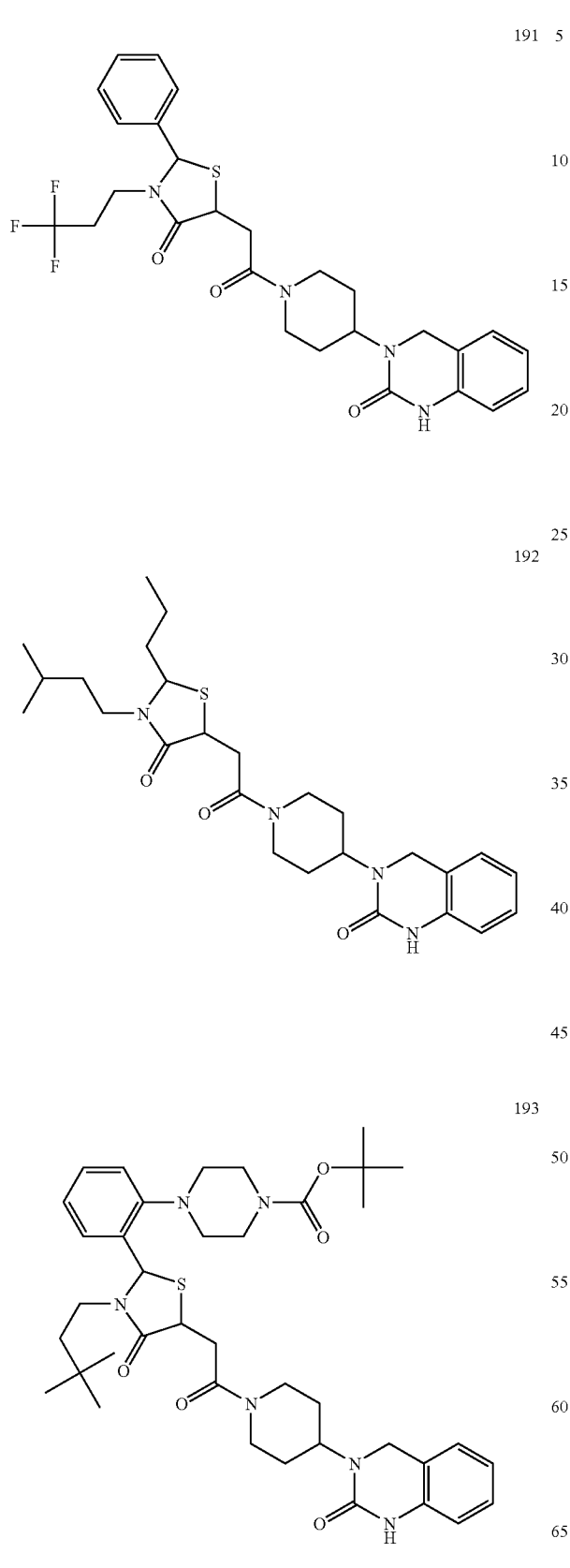
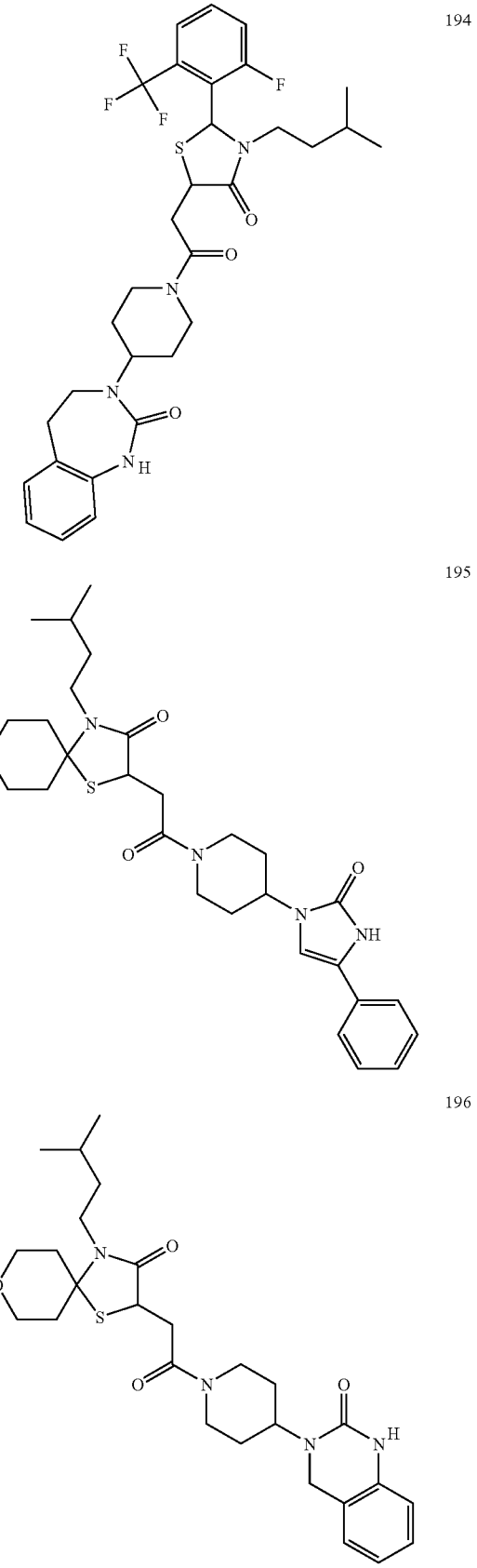

TABLE 1-continued
197
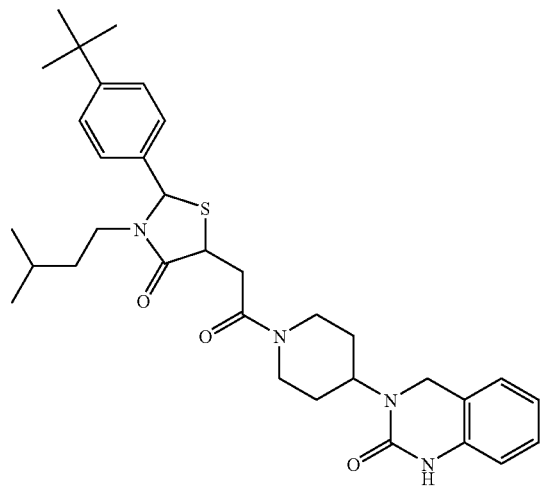
198
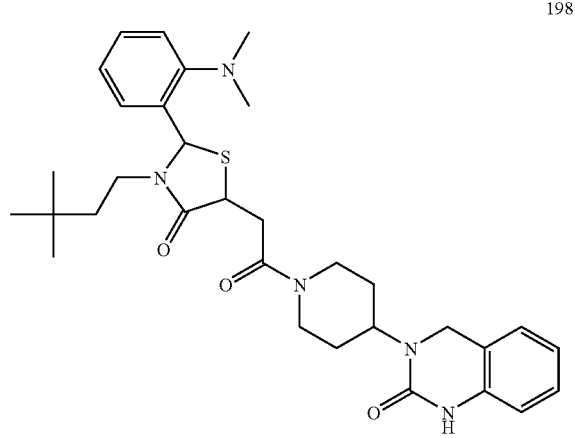
199
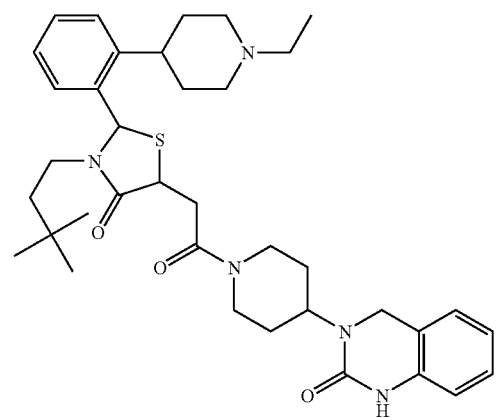
TABLE 1-continued
200
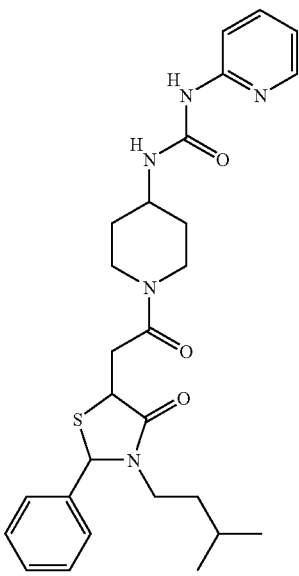
201
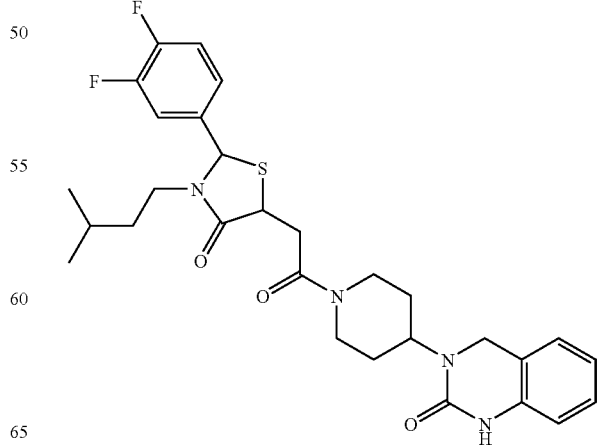
202

TABLE 1-continued
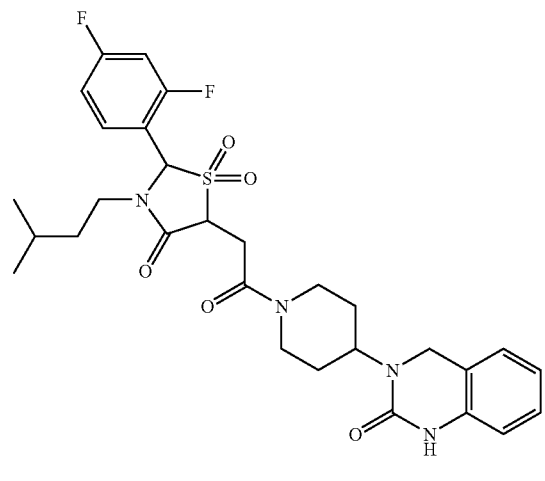
203
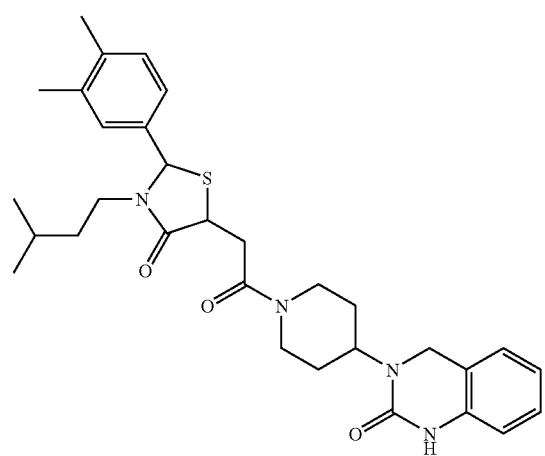
204
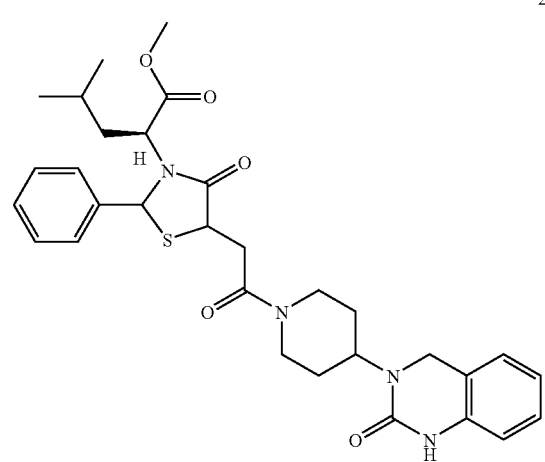
205
TABLE 1-continued
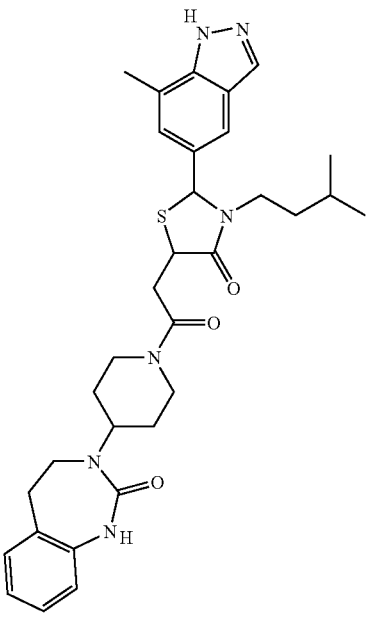
206
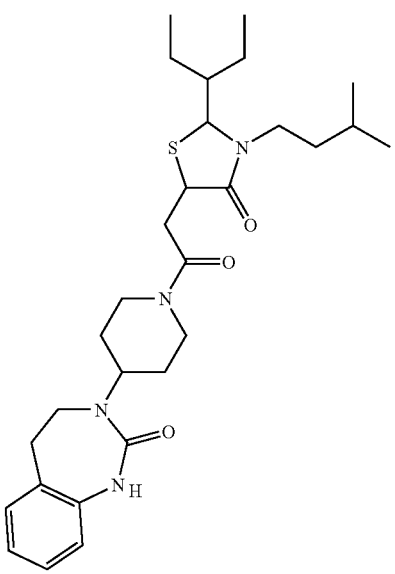
207
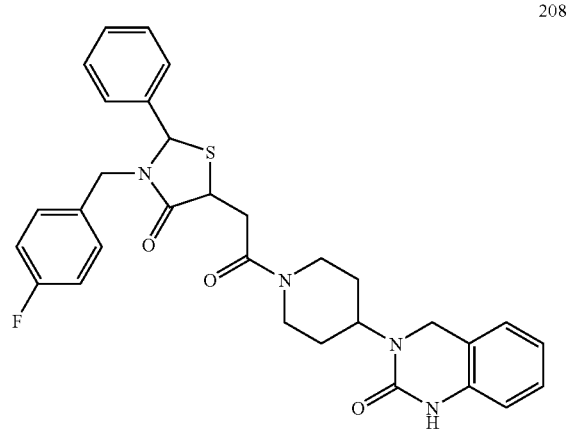
208

TABLE 1-continued
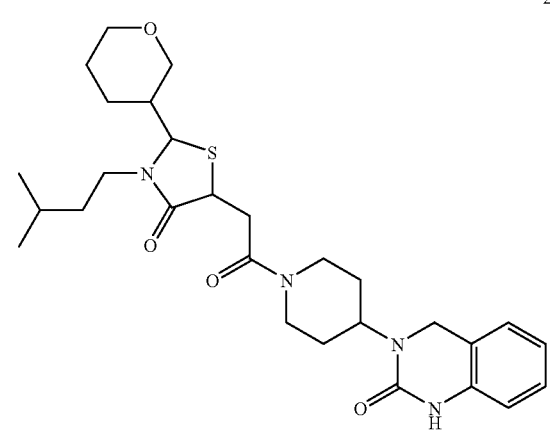
209
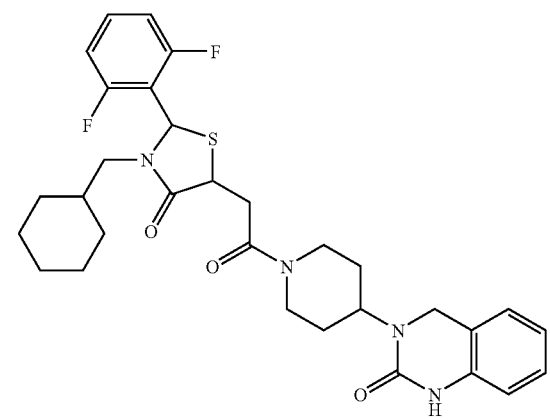
210
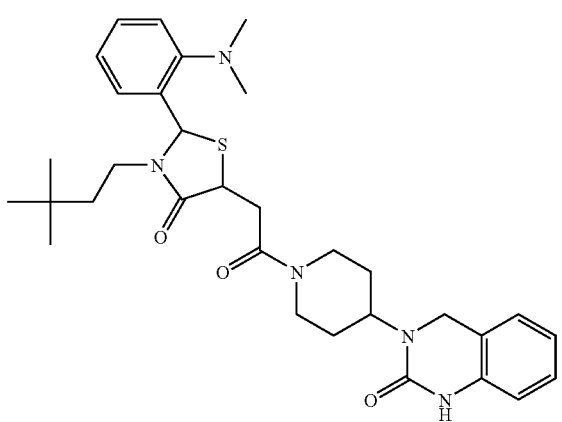
211
TABLE 1-continued
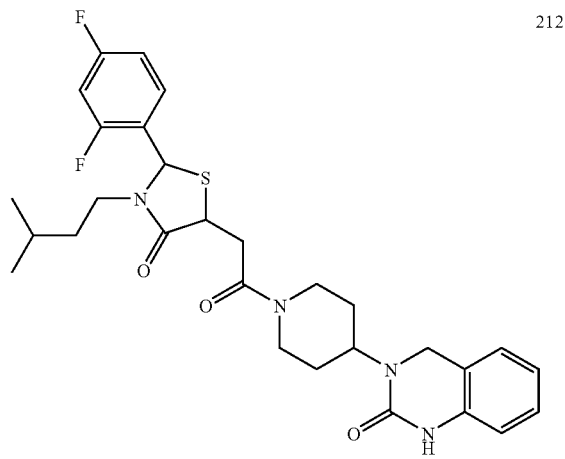
212
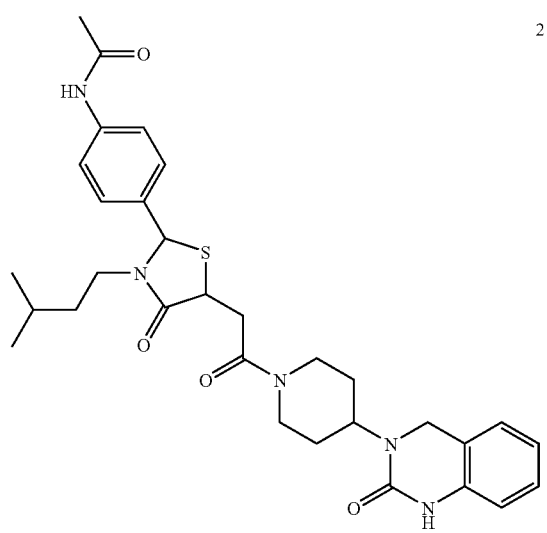
213
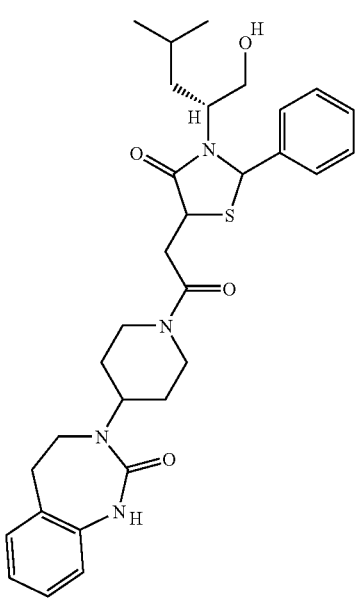
214

TABLE 1-continued
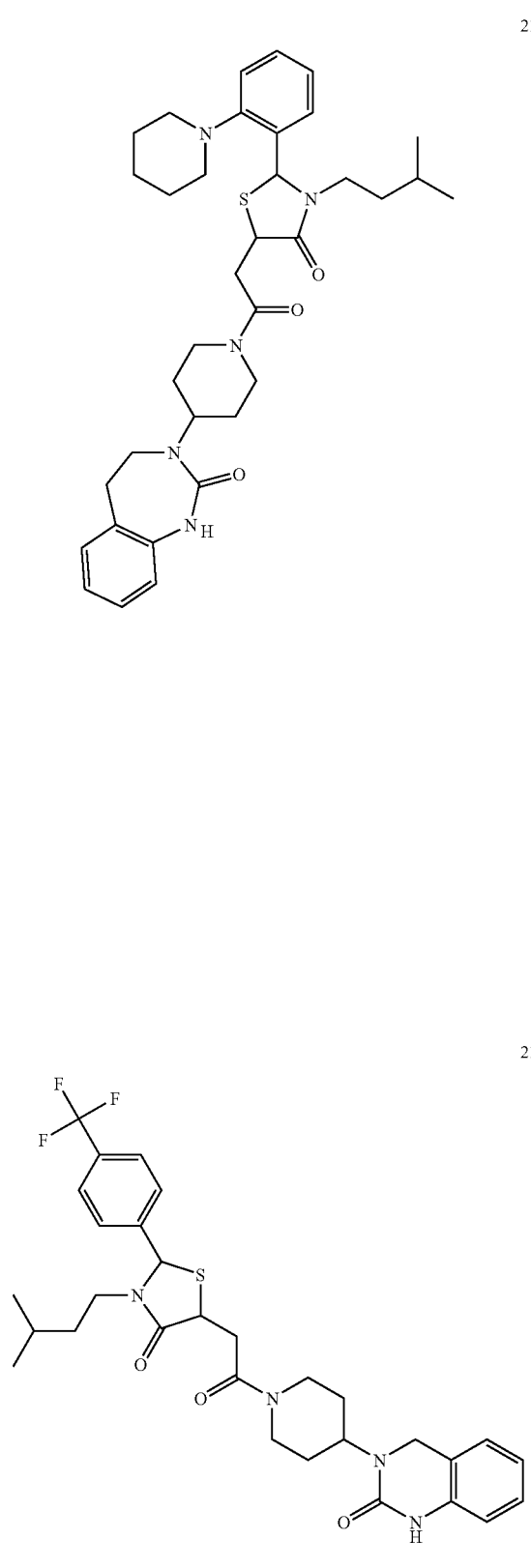
TABLE 1-continued
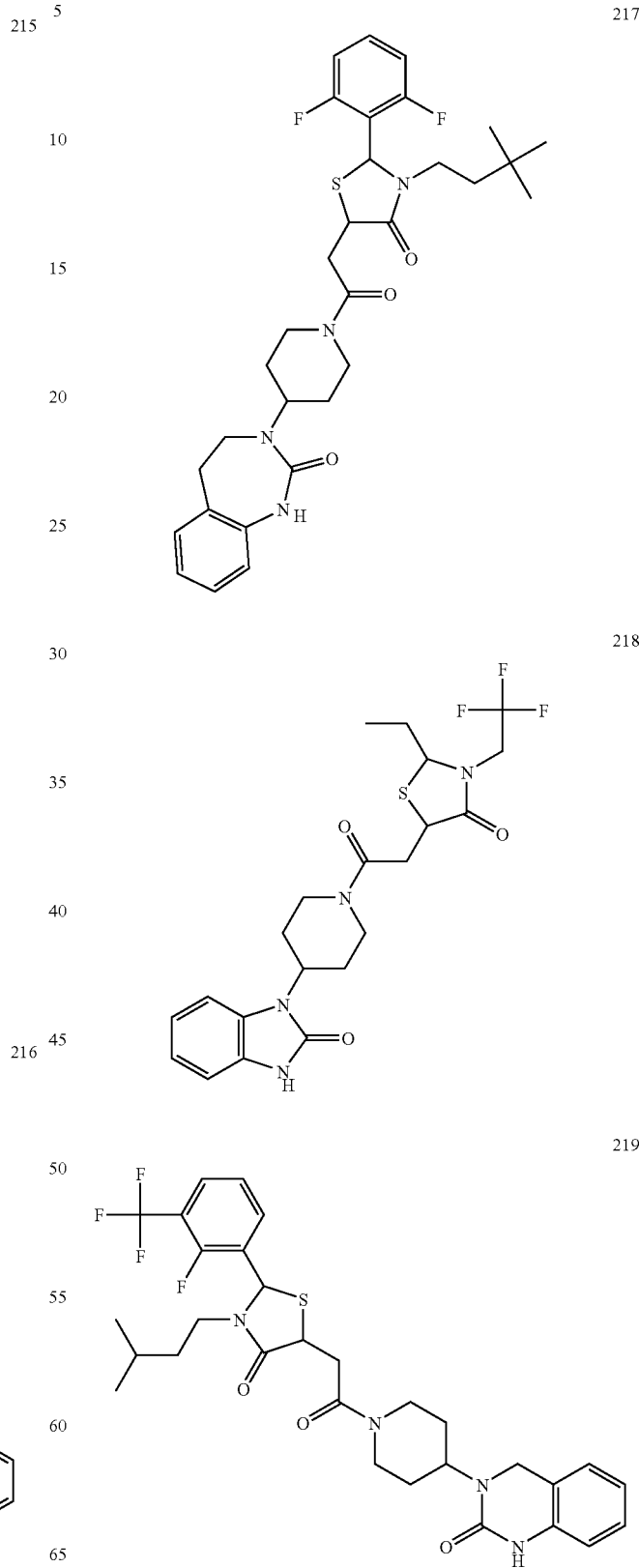

TABLE 1-continued
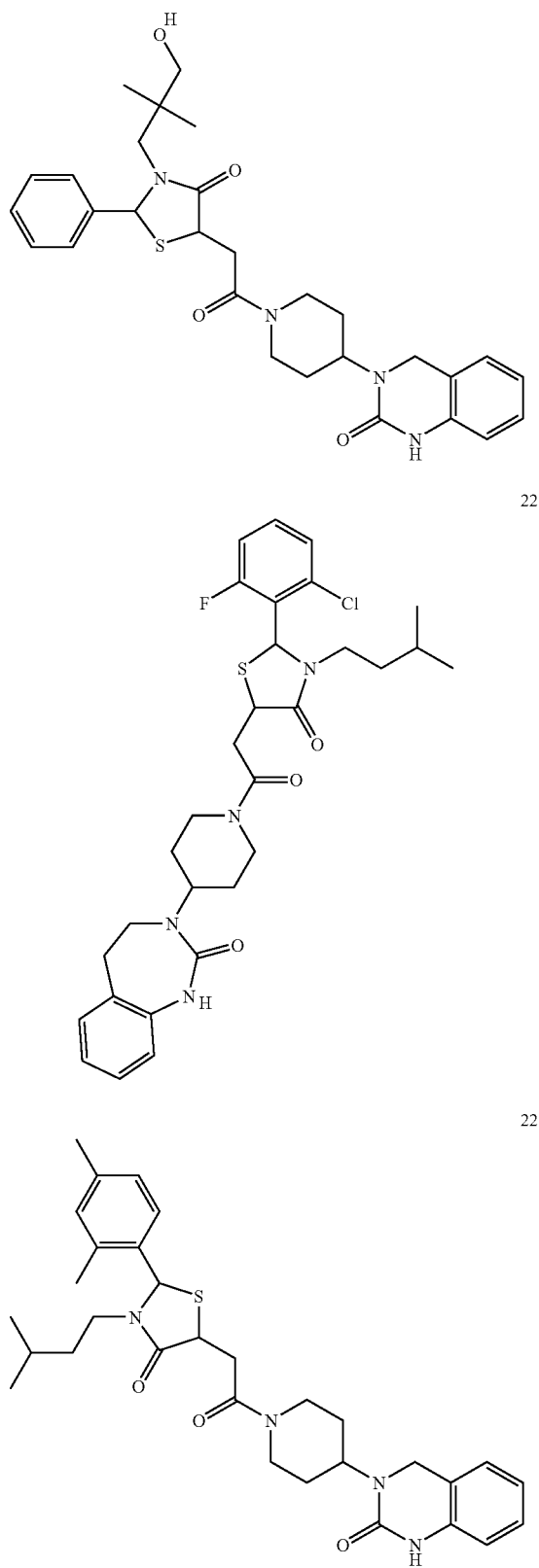
TABLE 1-continued
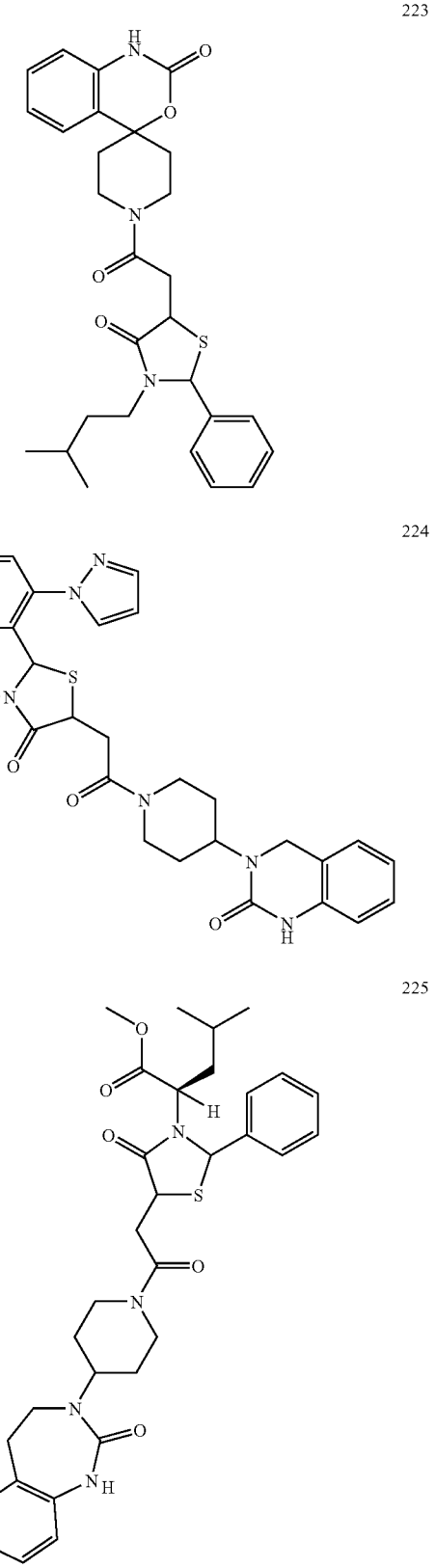

TABLE 1-continued
226 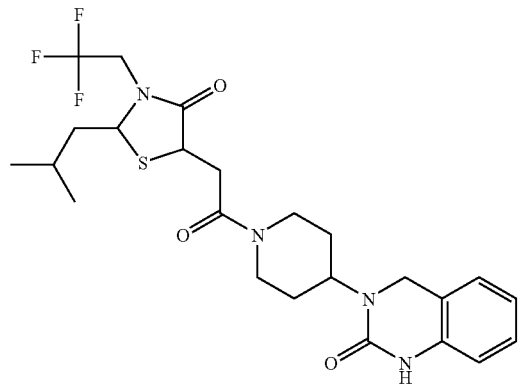
227 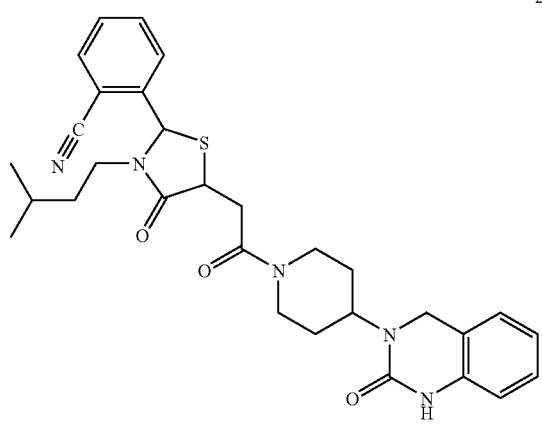
228 
229 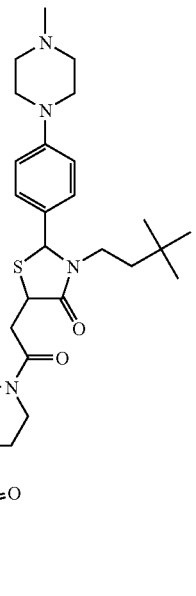
230 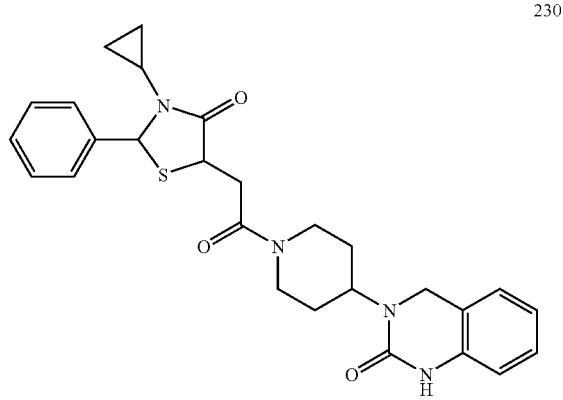
231 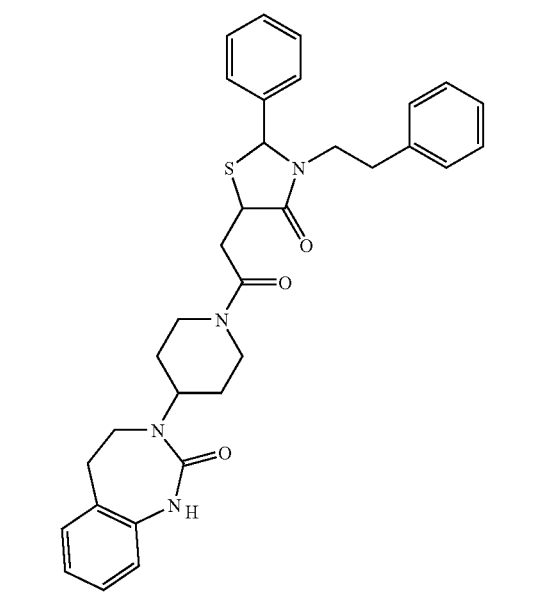

TABLE 1-continued
232
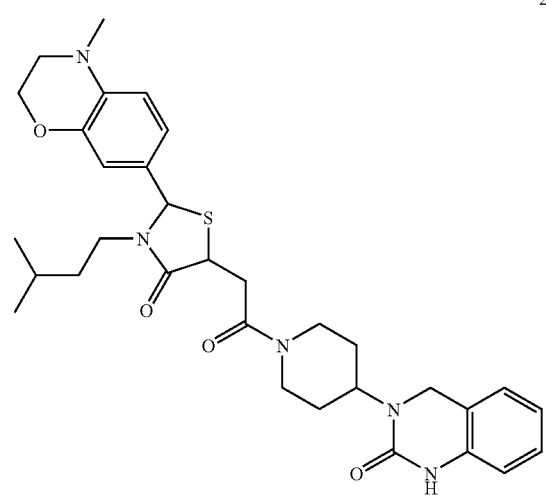
233
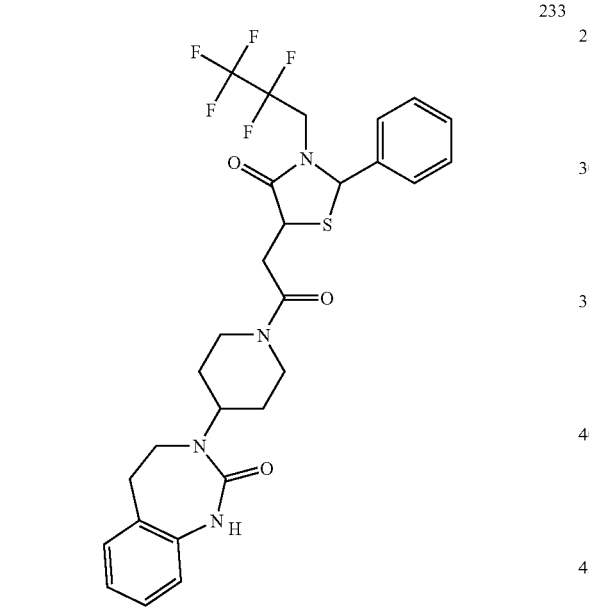
234
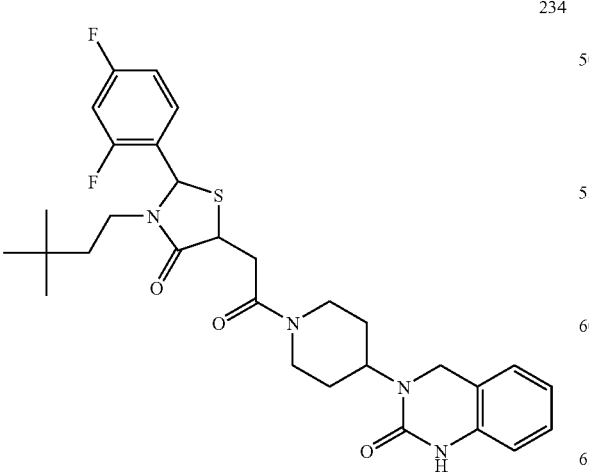
TABLE 1-continued
235
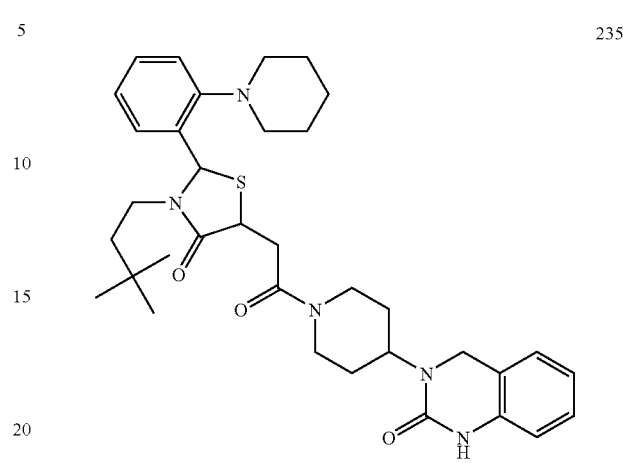
236
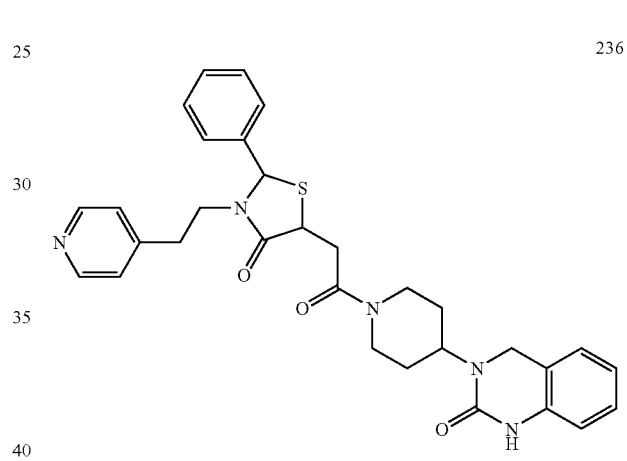
237
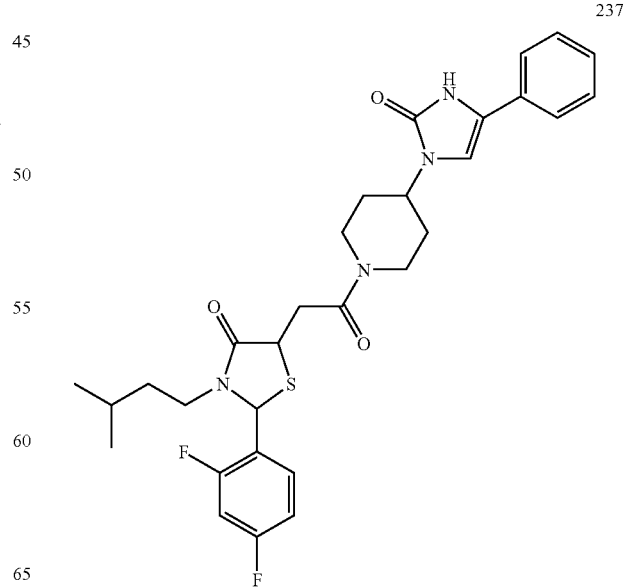

TABLE 1-continued
238
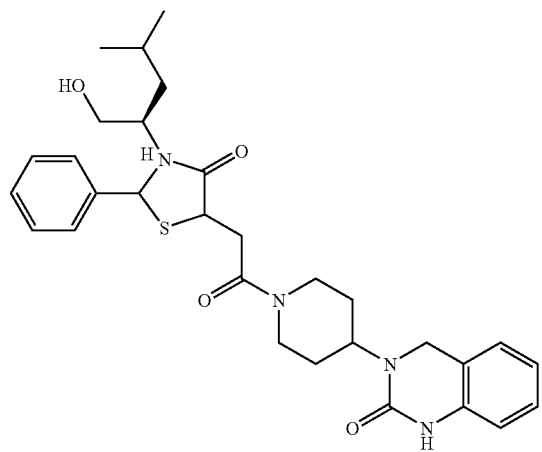
239
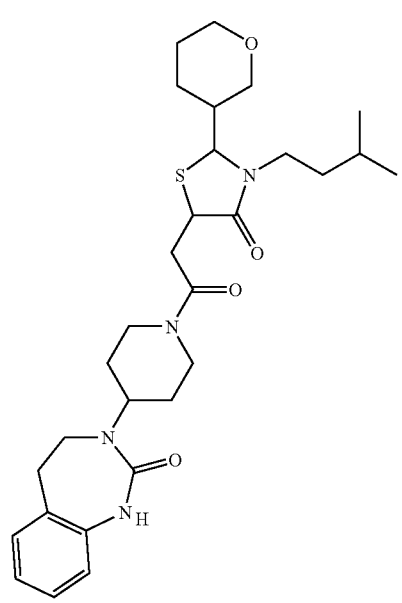
240
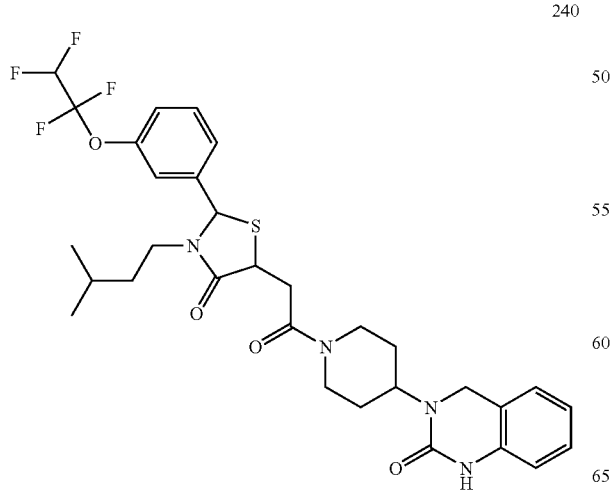
TABLE 1-continued
241
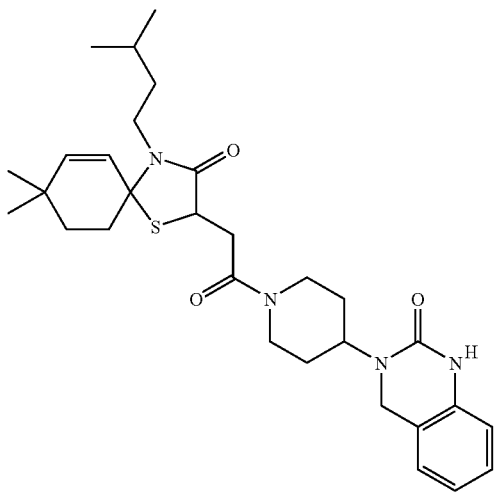
242
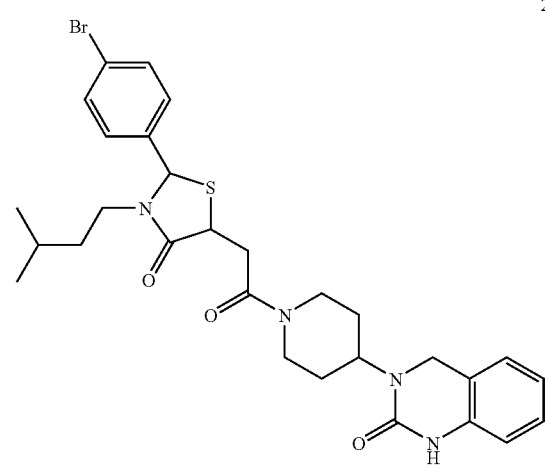
243
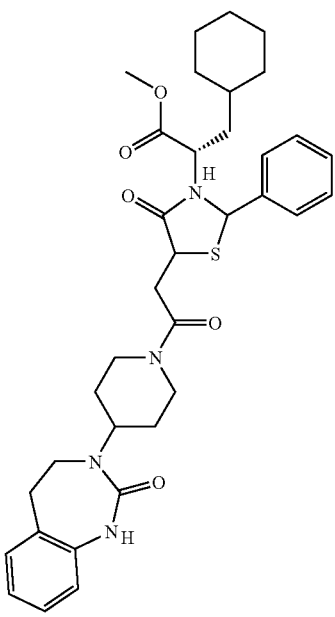

TABLE 1-continued
244
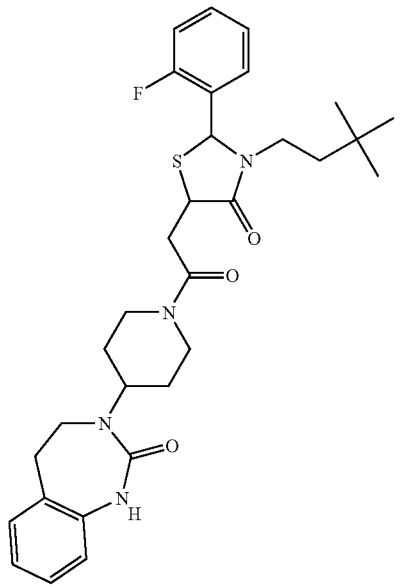
245
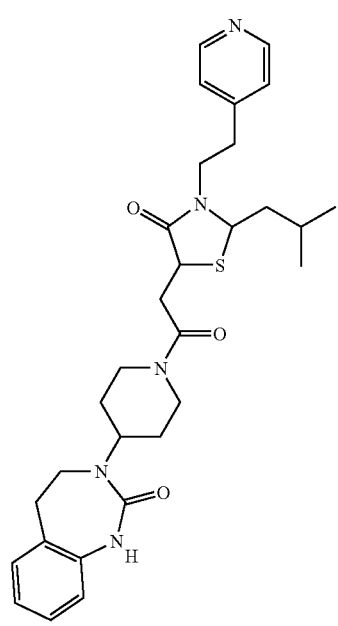
TABLE 1-continued
246
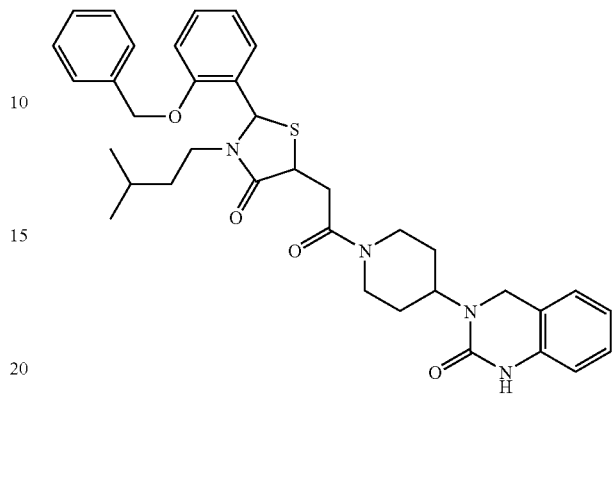
247

TABLE 1-continued
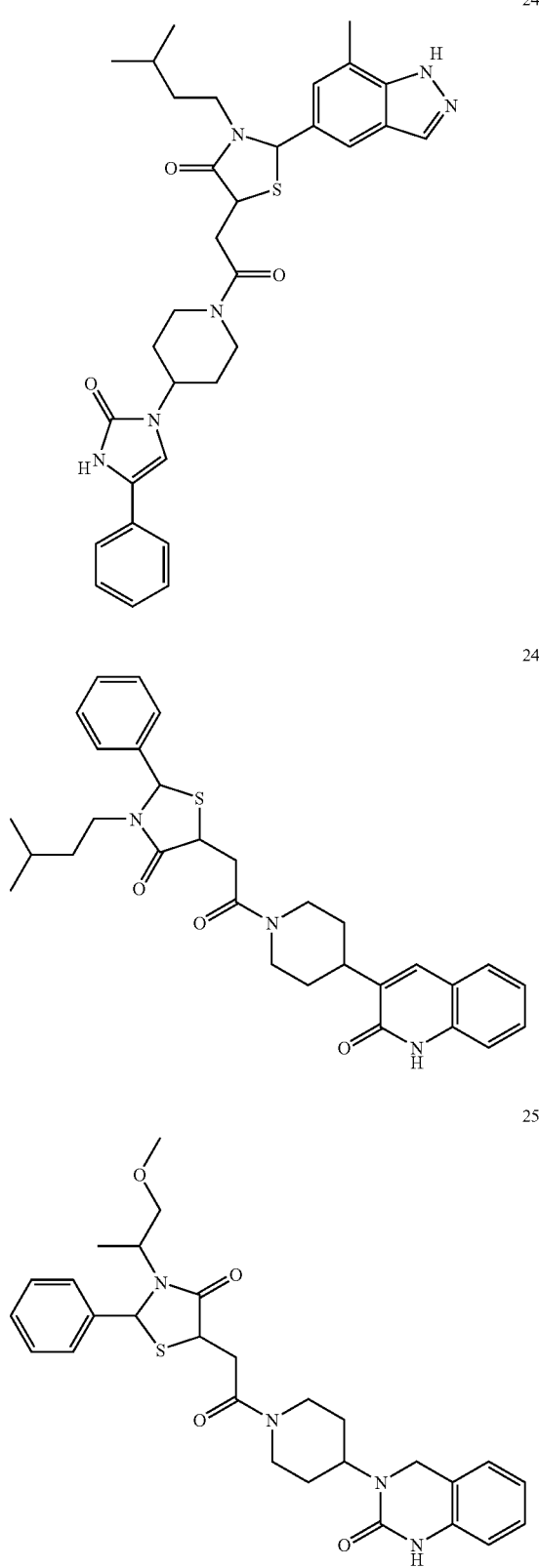
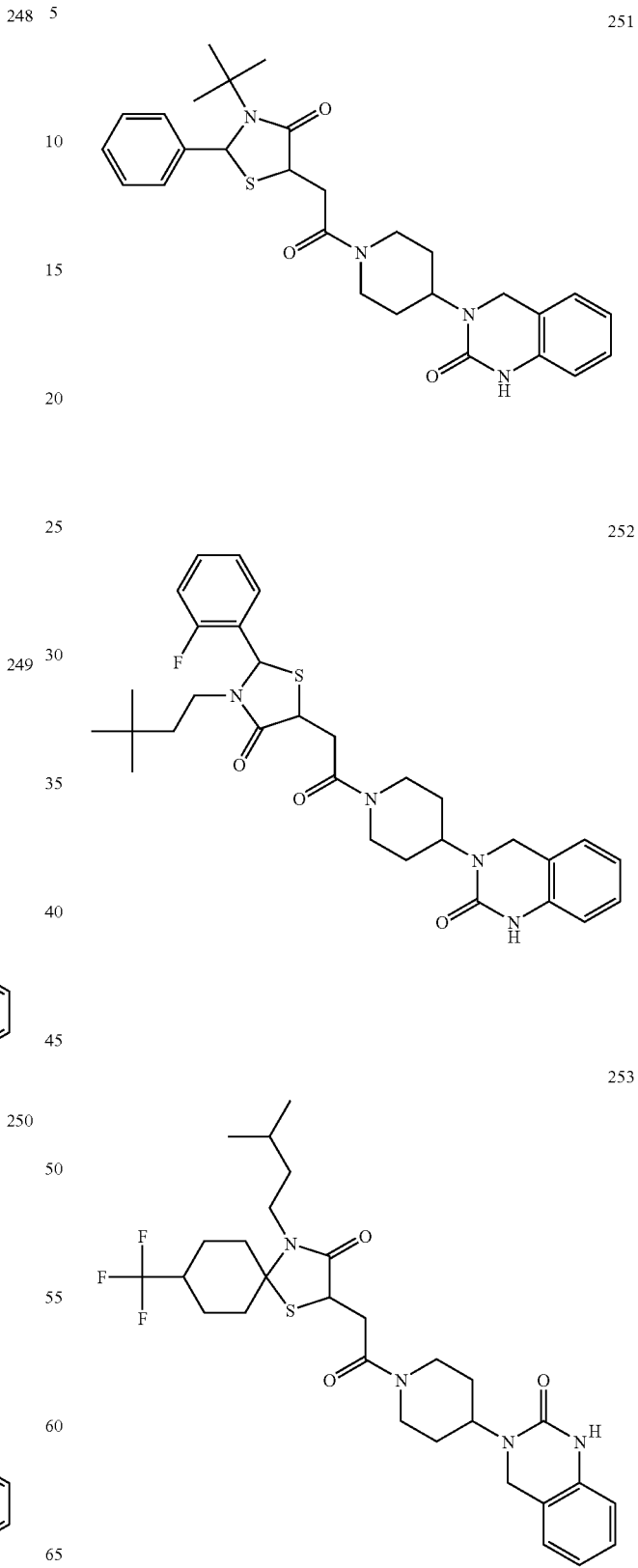

TABLE 1-continued
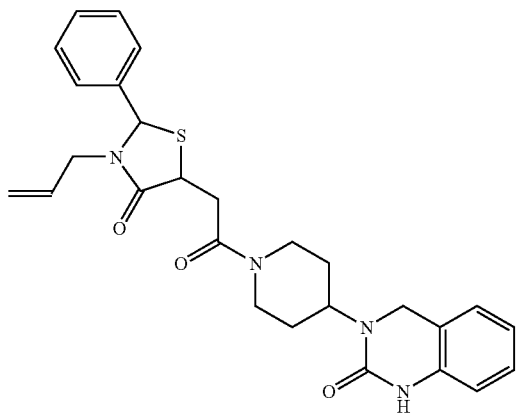
254
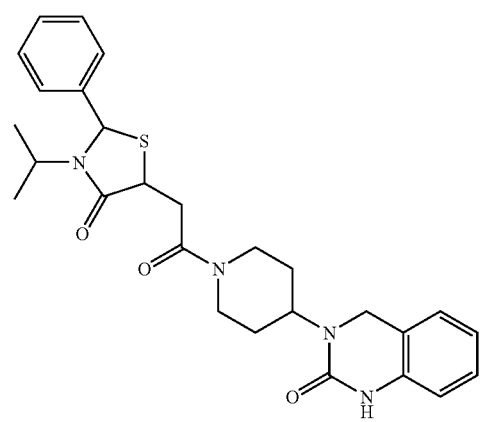
255
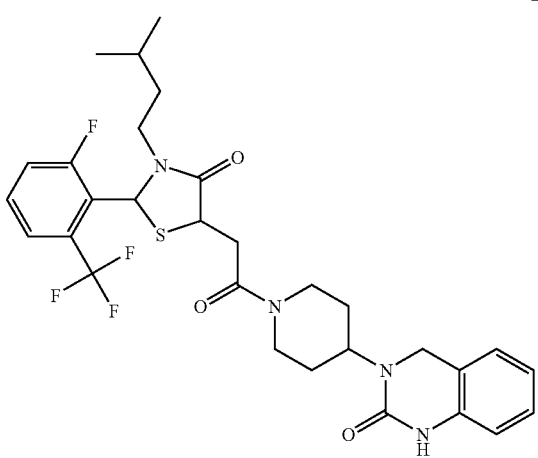
256
TABLE 1-continued
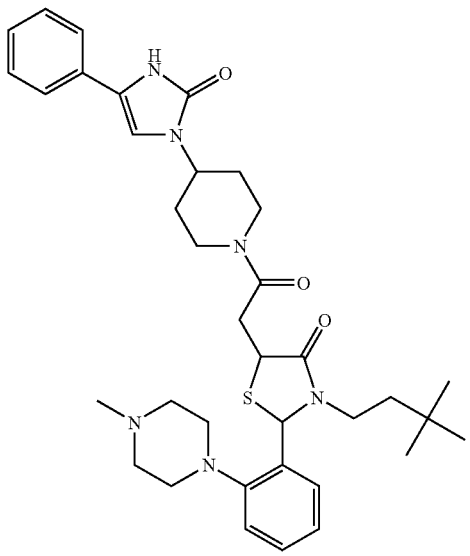
257
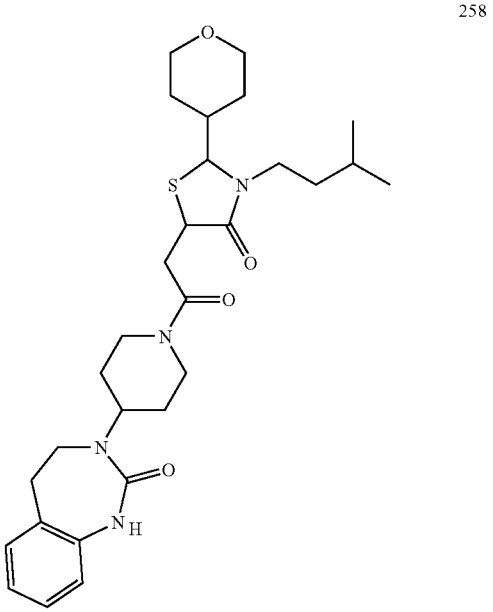
258
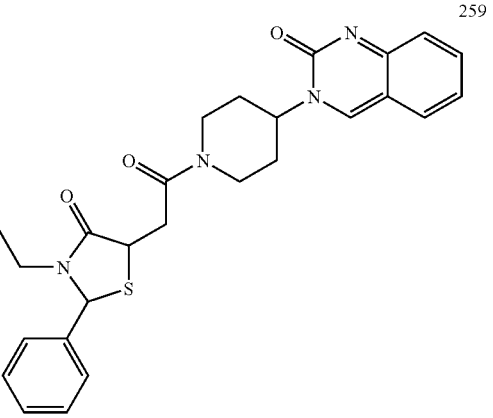
259

TABLE 1-continued
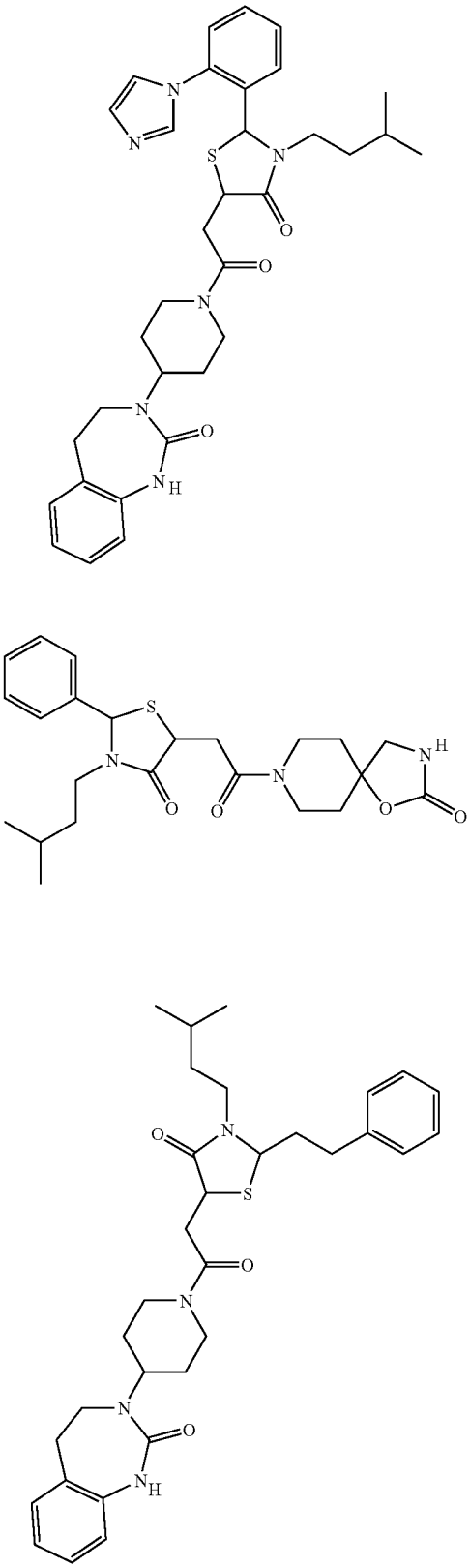
TABLE 1-continued
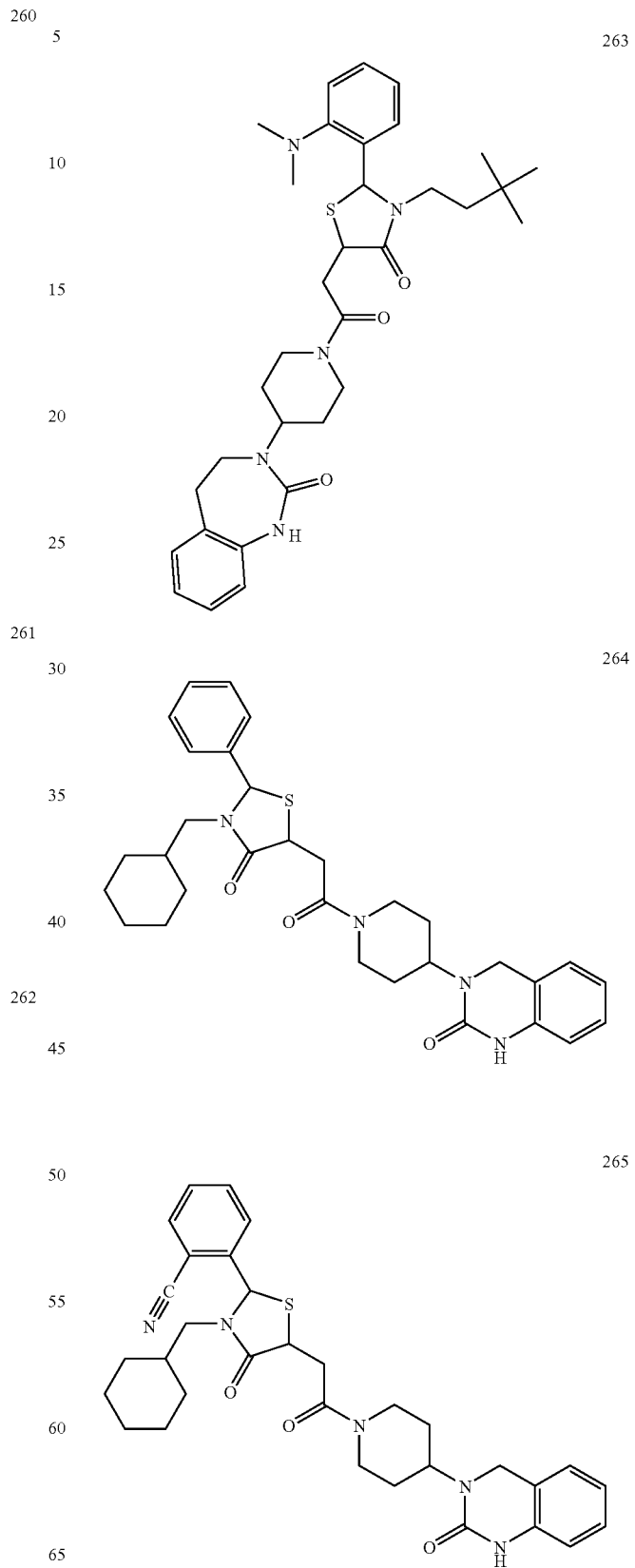

TABLE 1-continued
266
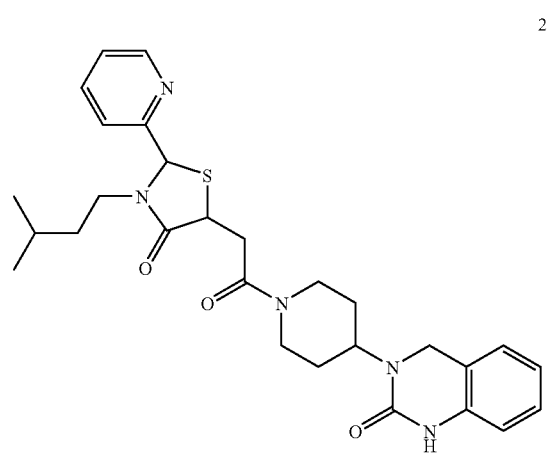
267
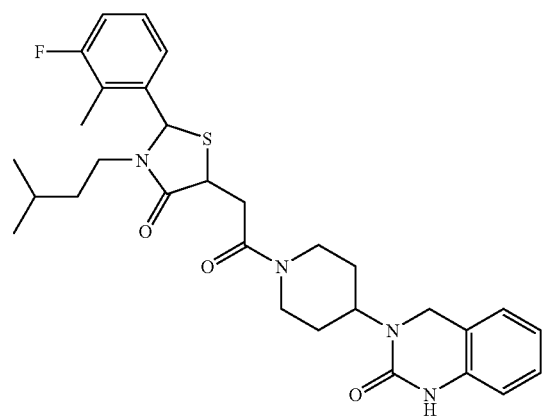
268
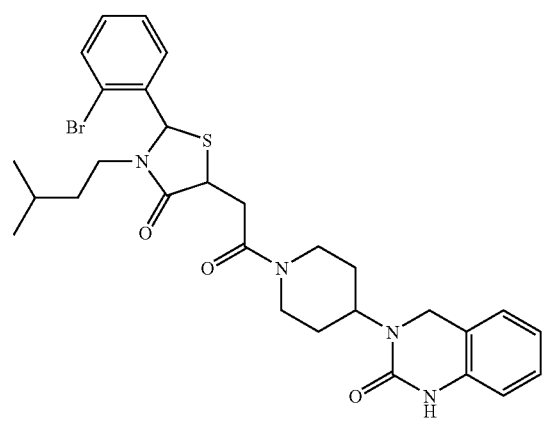
TABLE 1-continued
269
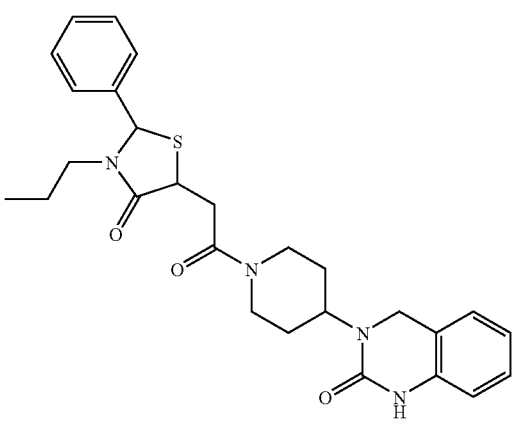
270
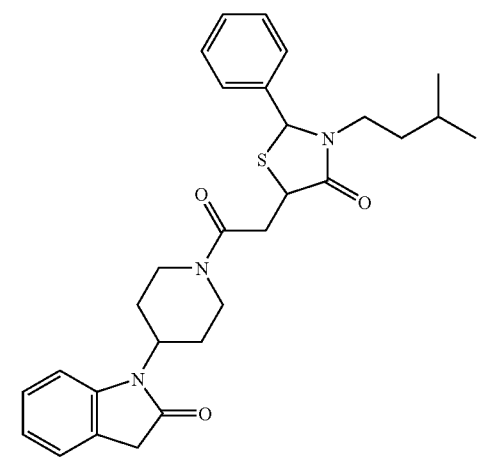
271
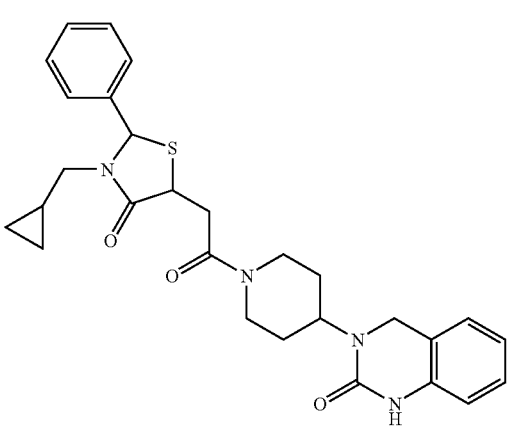

TABLE 1-continued
| | |
|---|---|
| 272 | 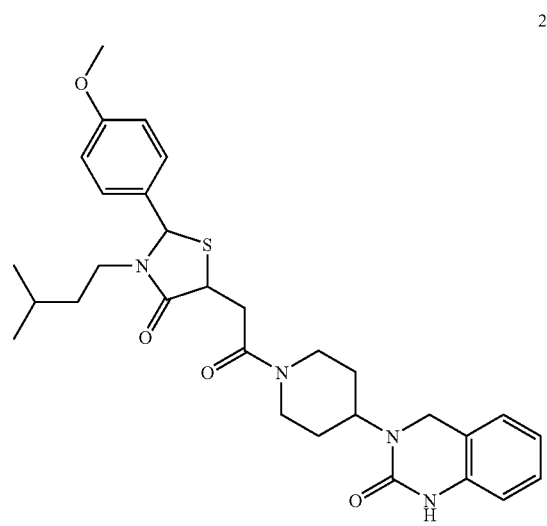 |
| 273 | 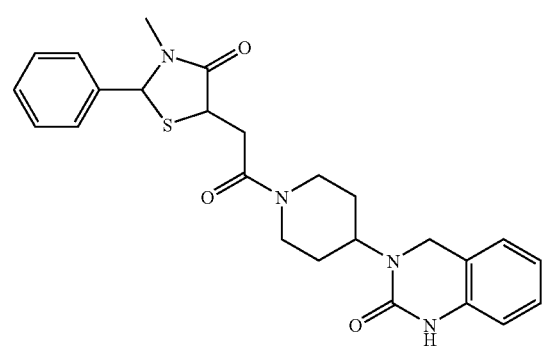 |
| 274 | 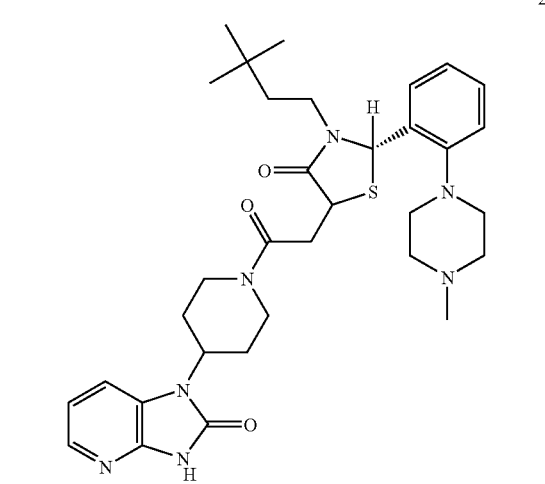 |
TABLE 1-continued
| | |
|---|---|
| 275 | |
| 276 | |
| 277 | |
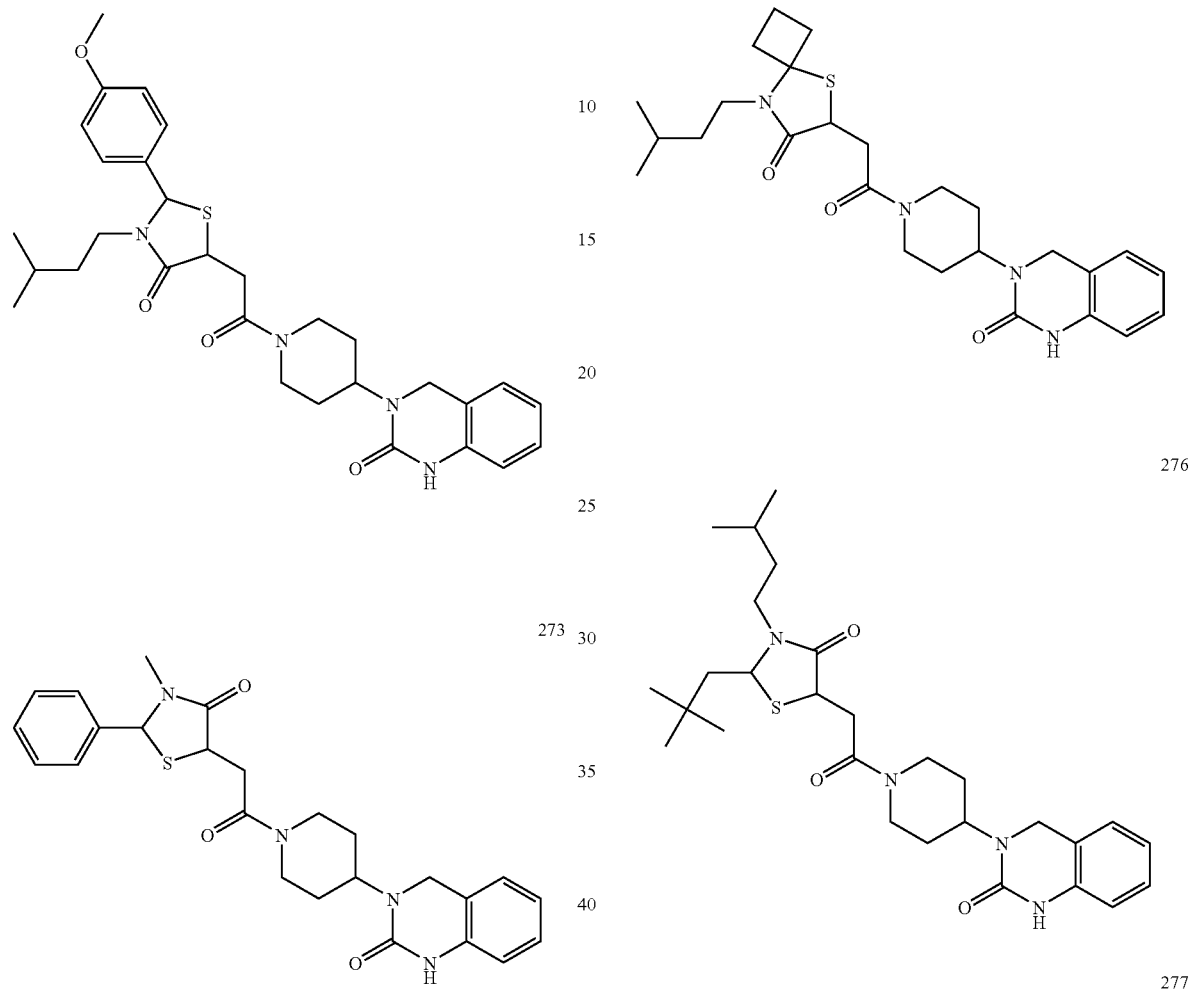
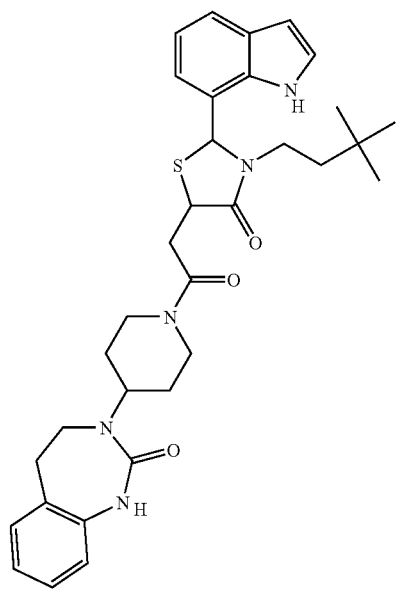

TABLE 1-continued
278
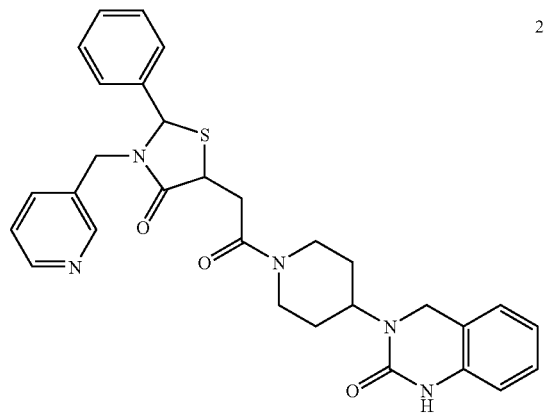
279
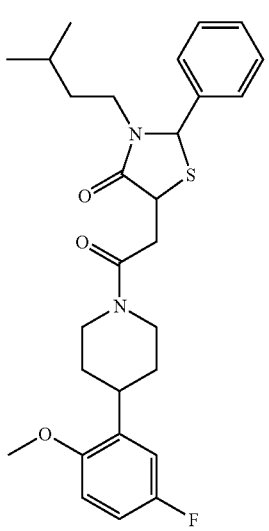
280
281
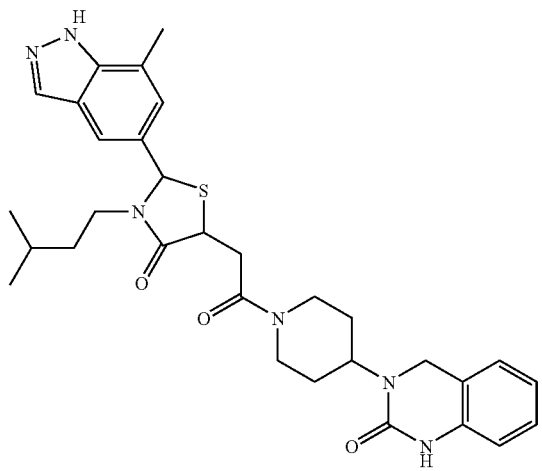
282
283
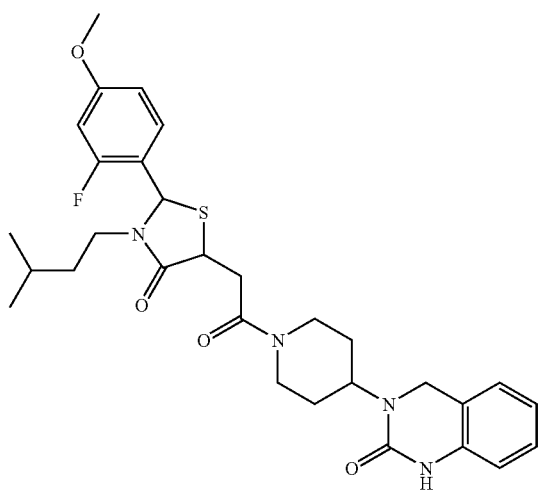

TABLE 1-continued
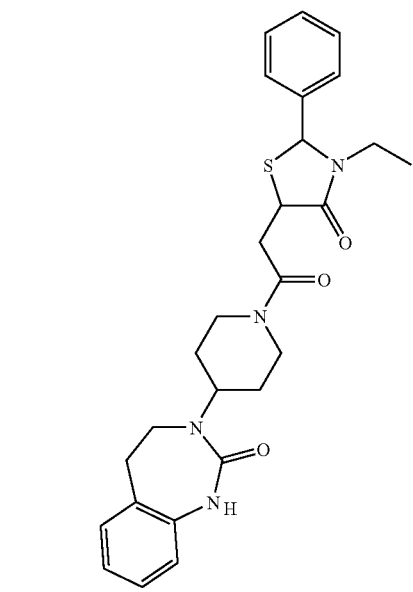
284
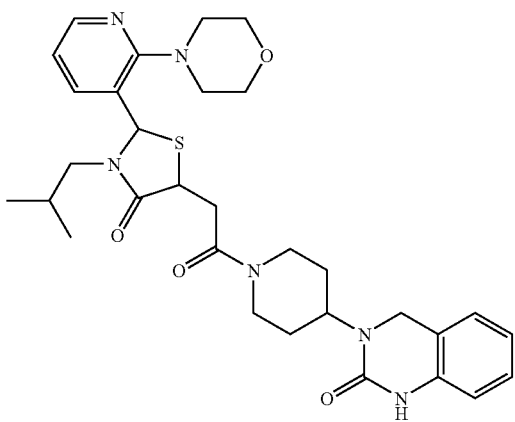
285
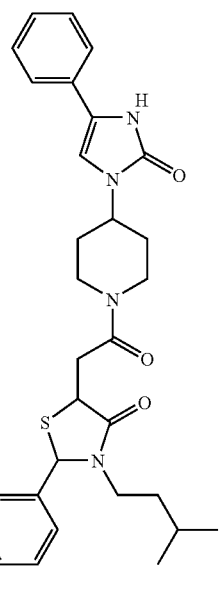
286
TABLE 1-continued
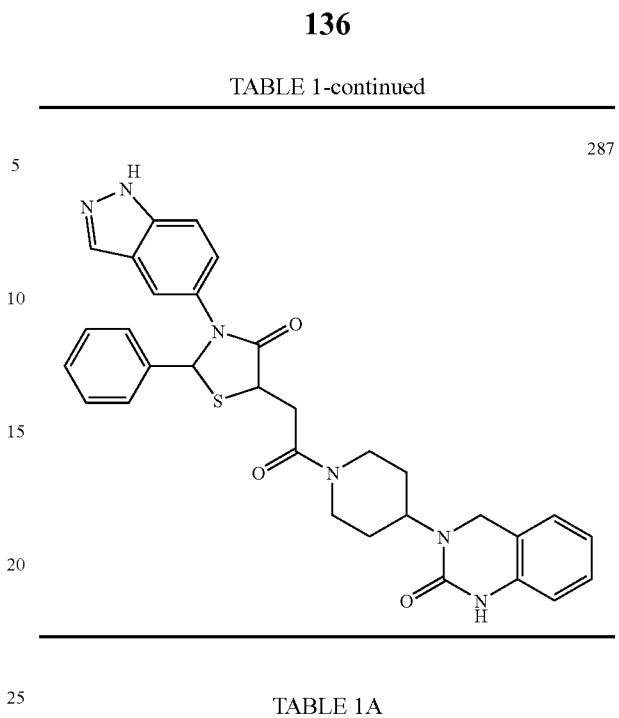
287
TABLE 1A
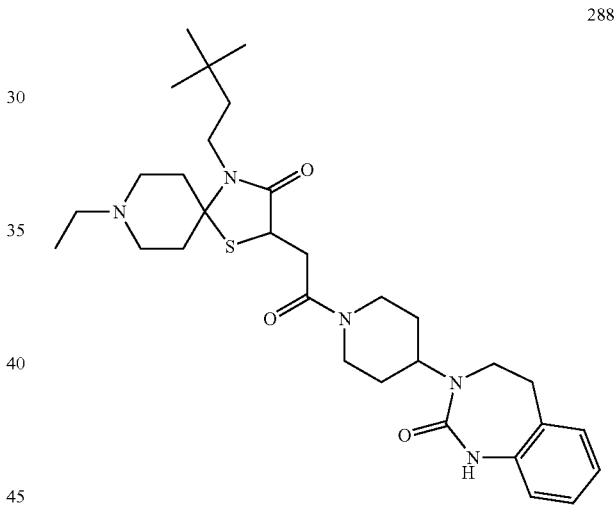
288
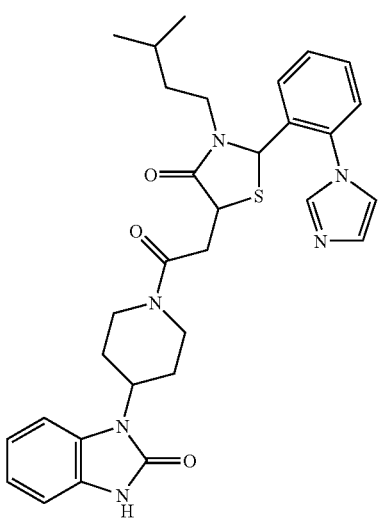
289

TABLE 1A-continued
290
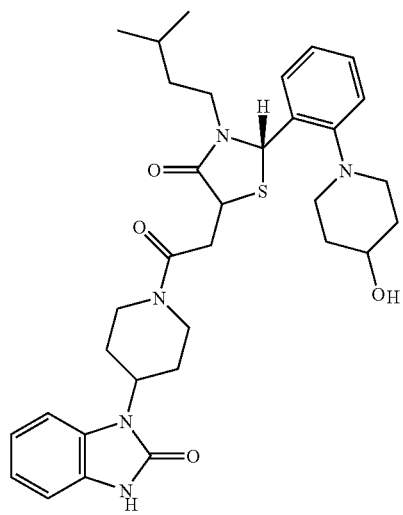
291
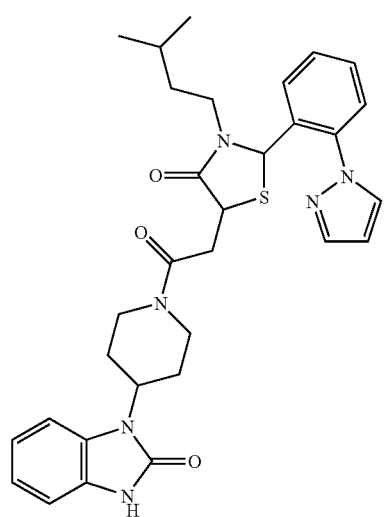
292
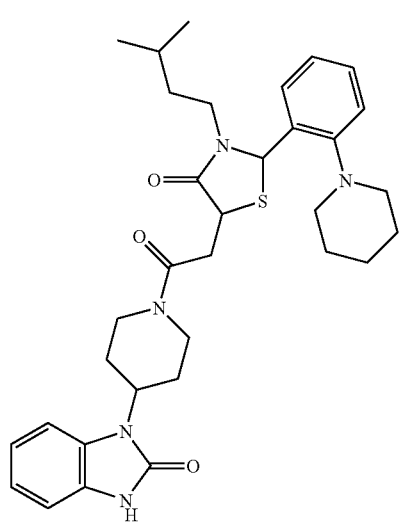
TABLE 1A-continued
293
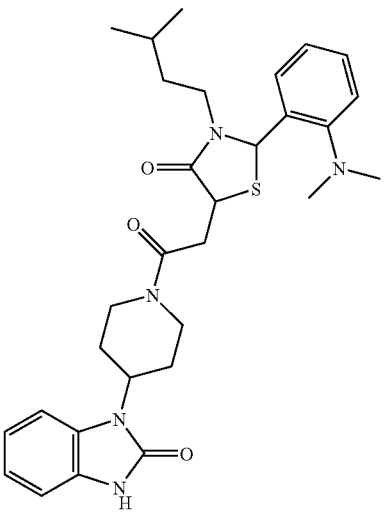
294
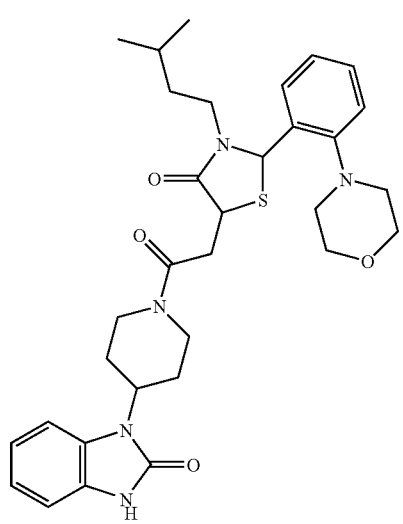
295
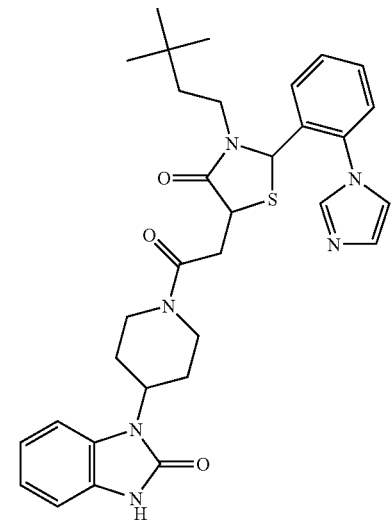

TABLE 1A-continued
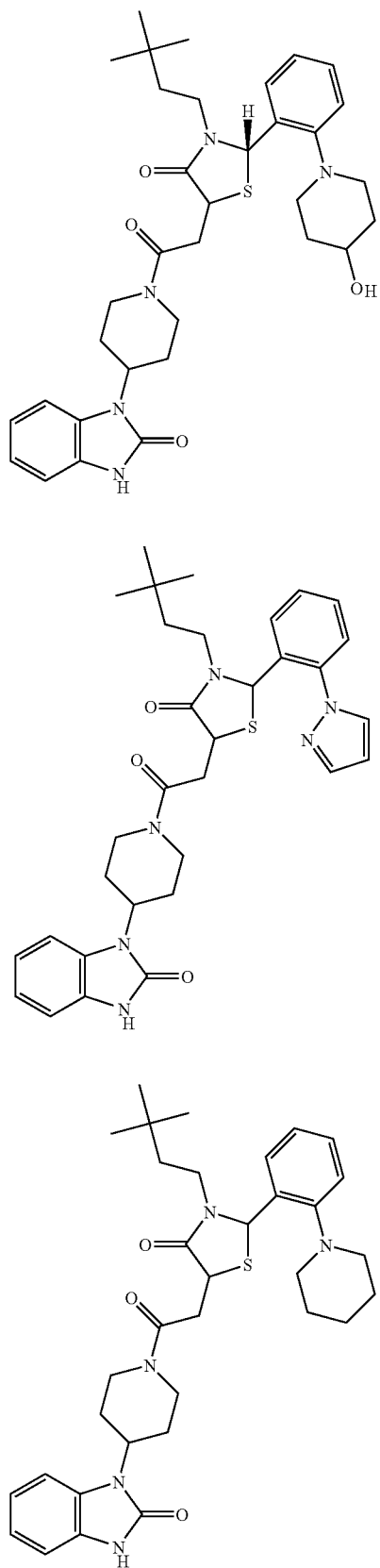
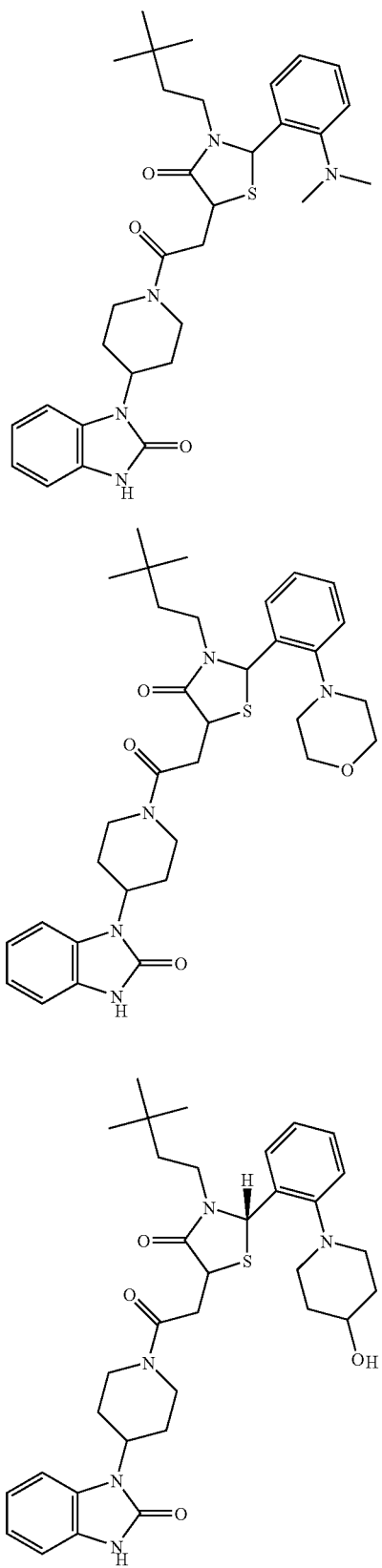

TABLE 1A-continued
302
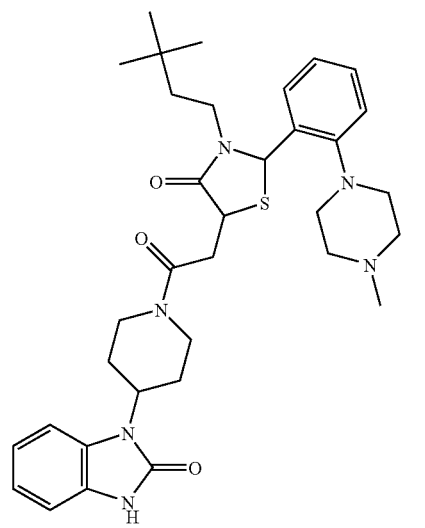
303
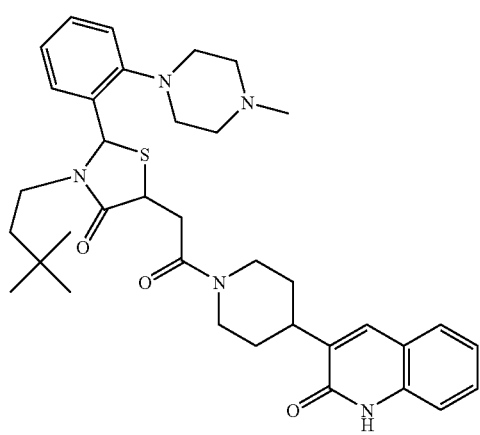
304
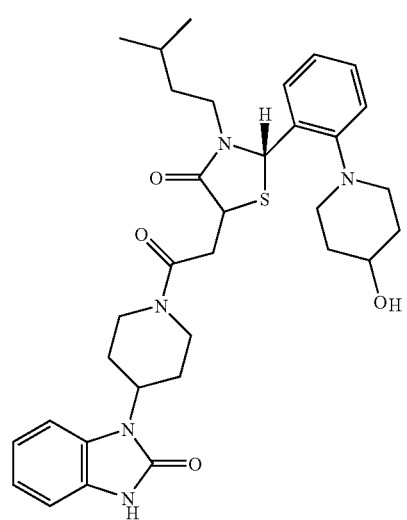
TABLE 1A-continued
305
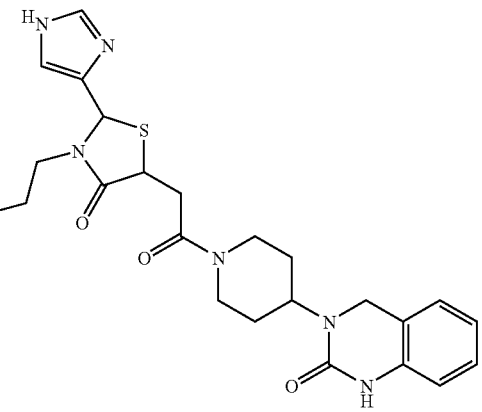
306
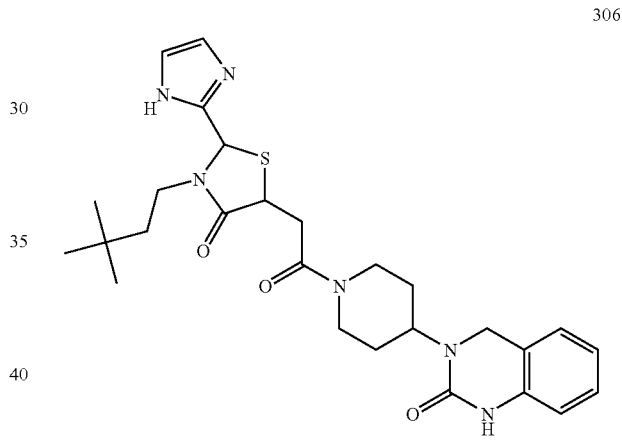
307
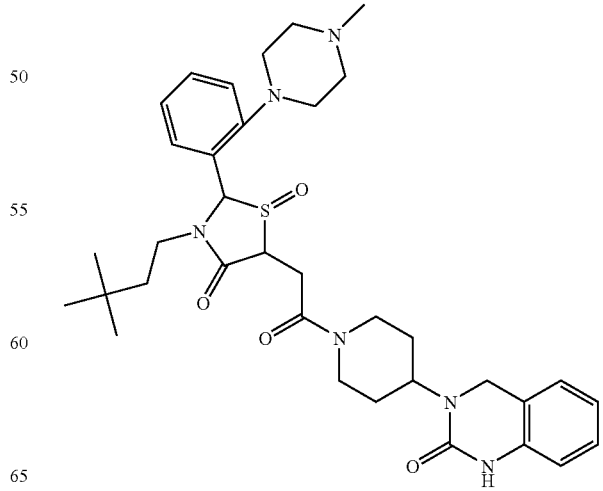

TABLE 1A-continued
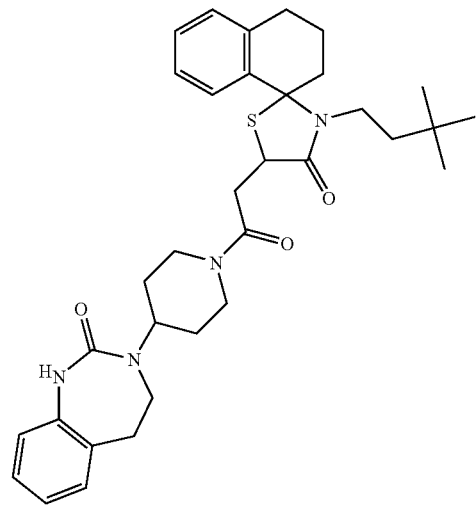
308
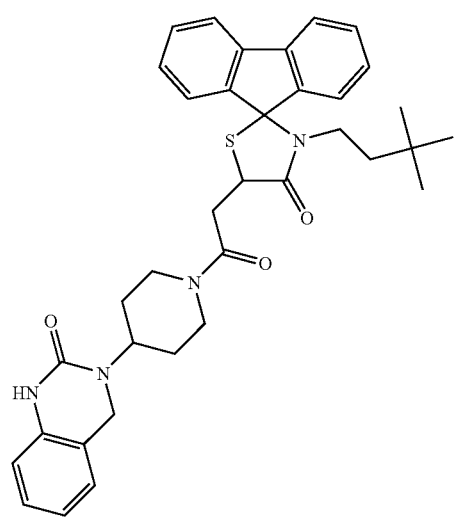
309
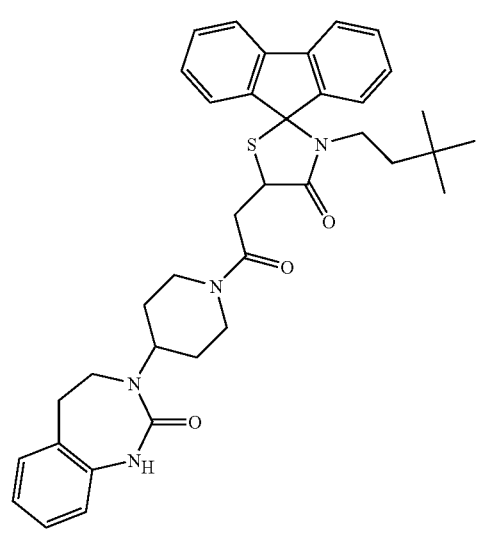
310
TABLE 1A-continued
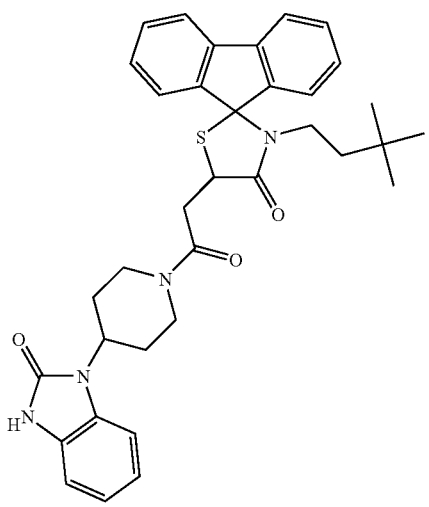
311
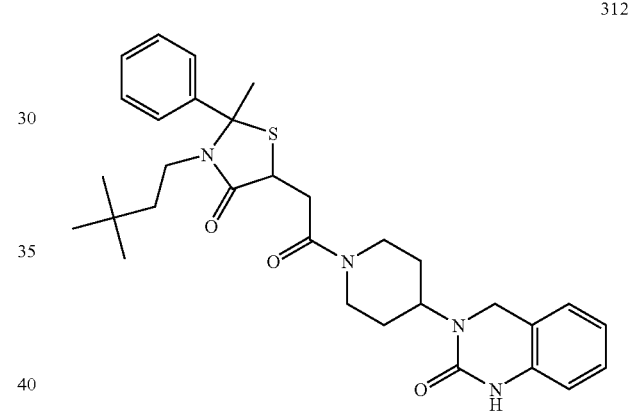
312
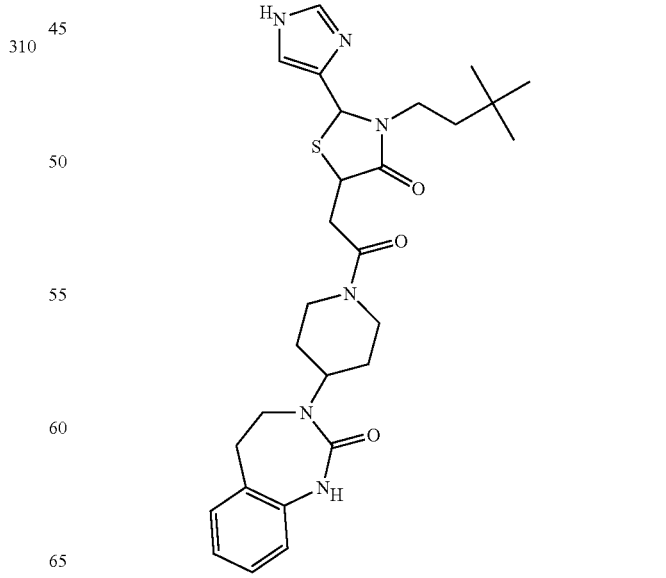
313

TABLE 1A-continued
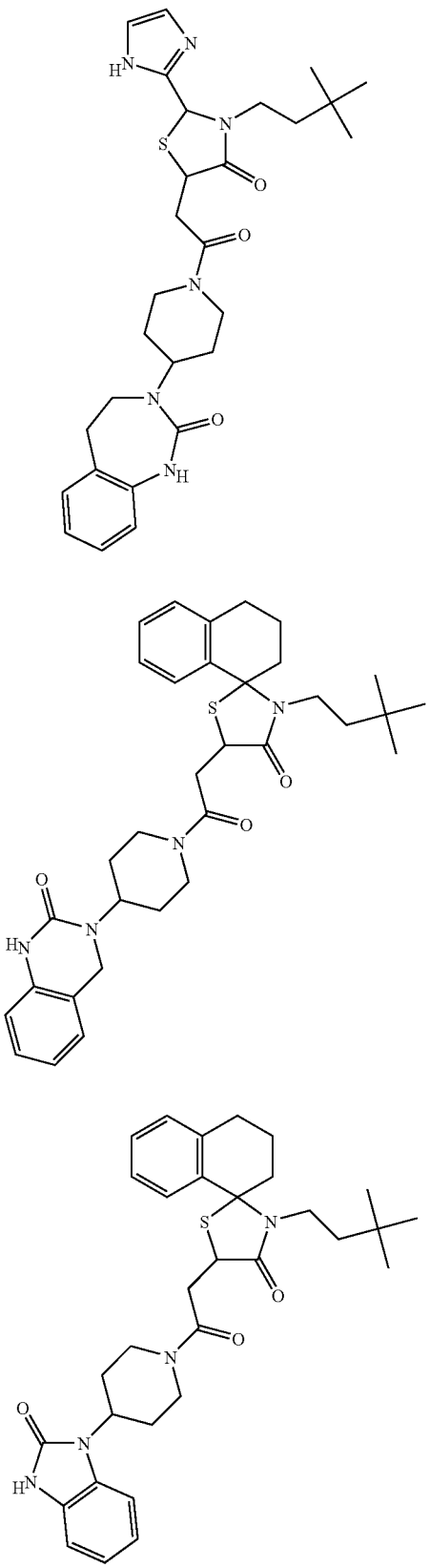
314
315
316
TABLE 1A-continued
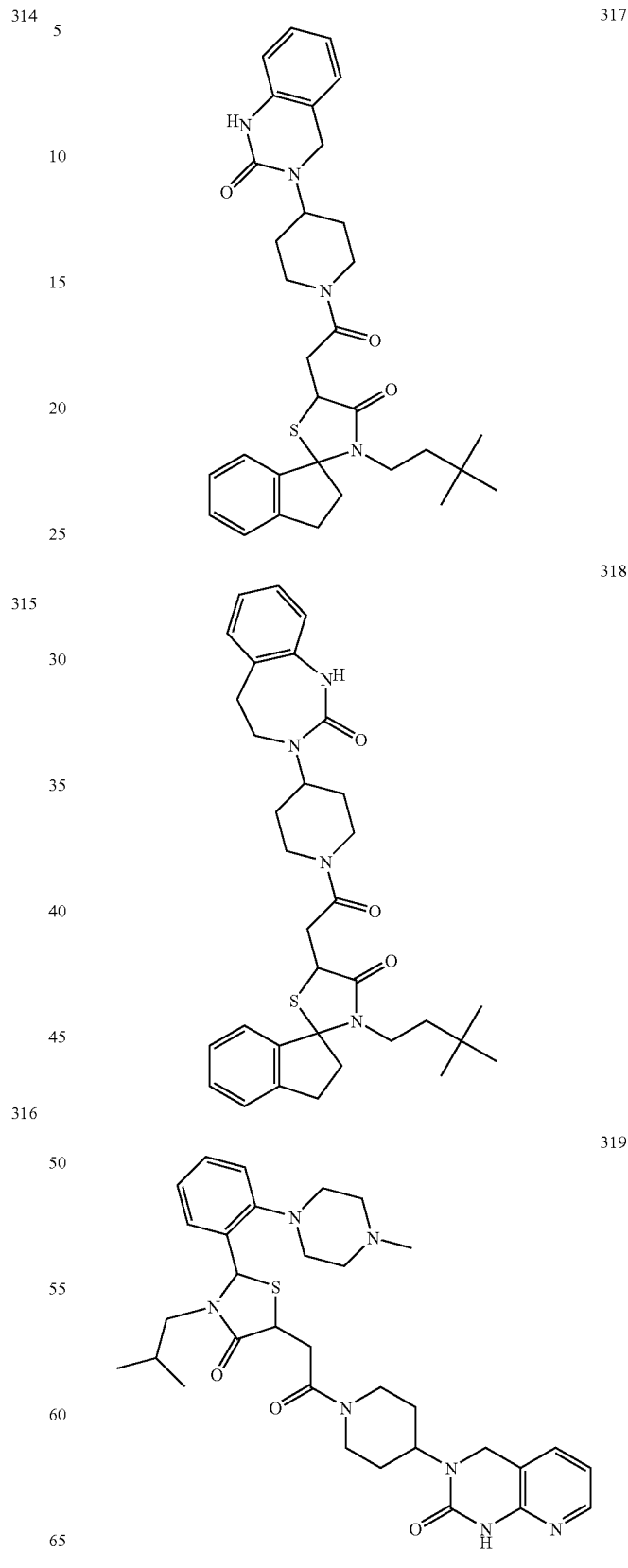
317
318
319

TABLE 1A-continued
320
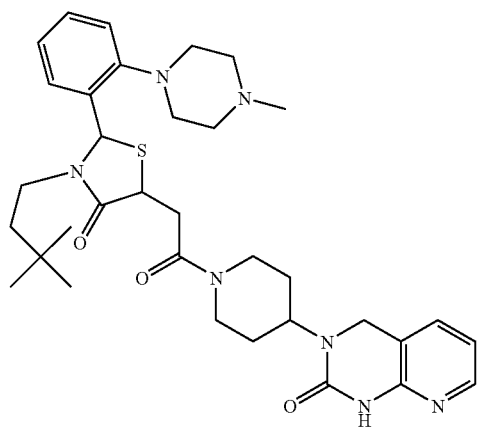
321
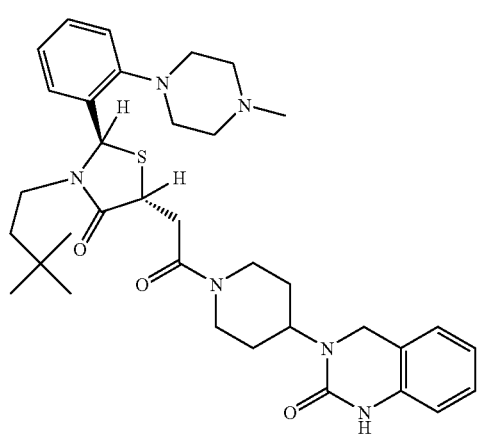
322
TABLE 1A-continued
323
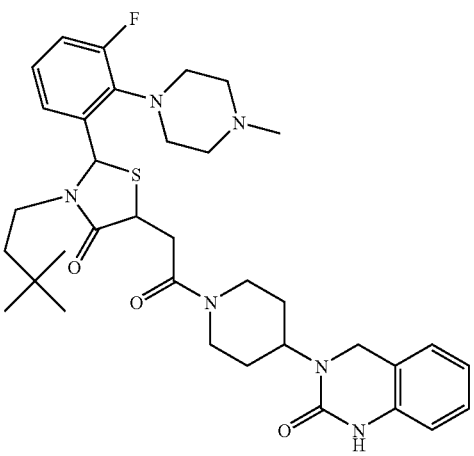
324
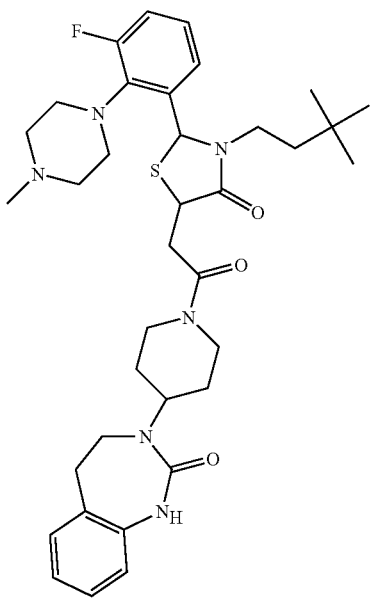
325
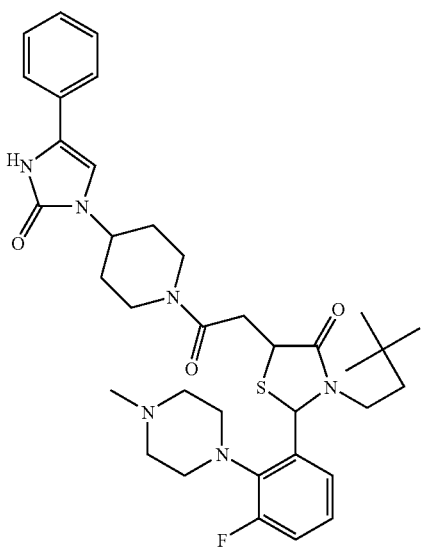

TABLE 1A-continued
326
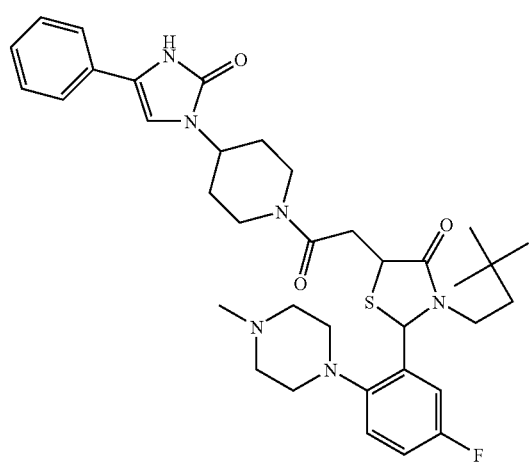
327
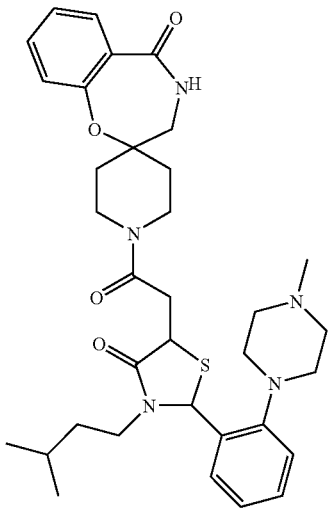
328
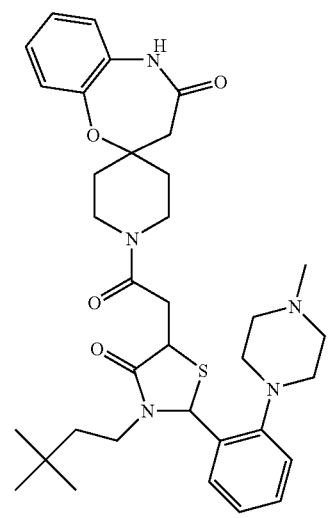
TABLE 1A-continued
329
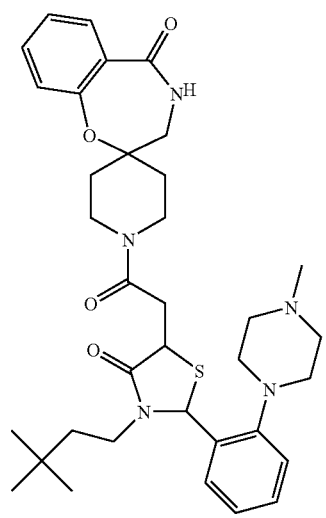
330
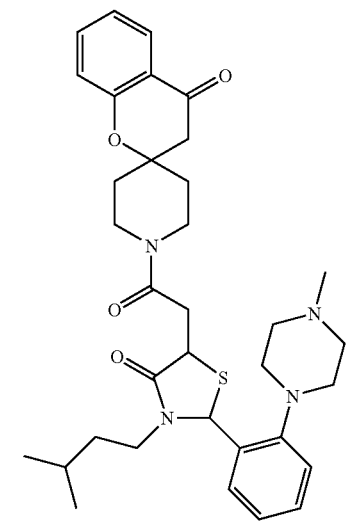
331

TABLE 1A-continued
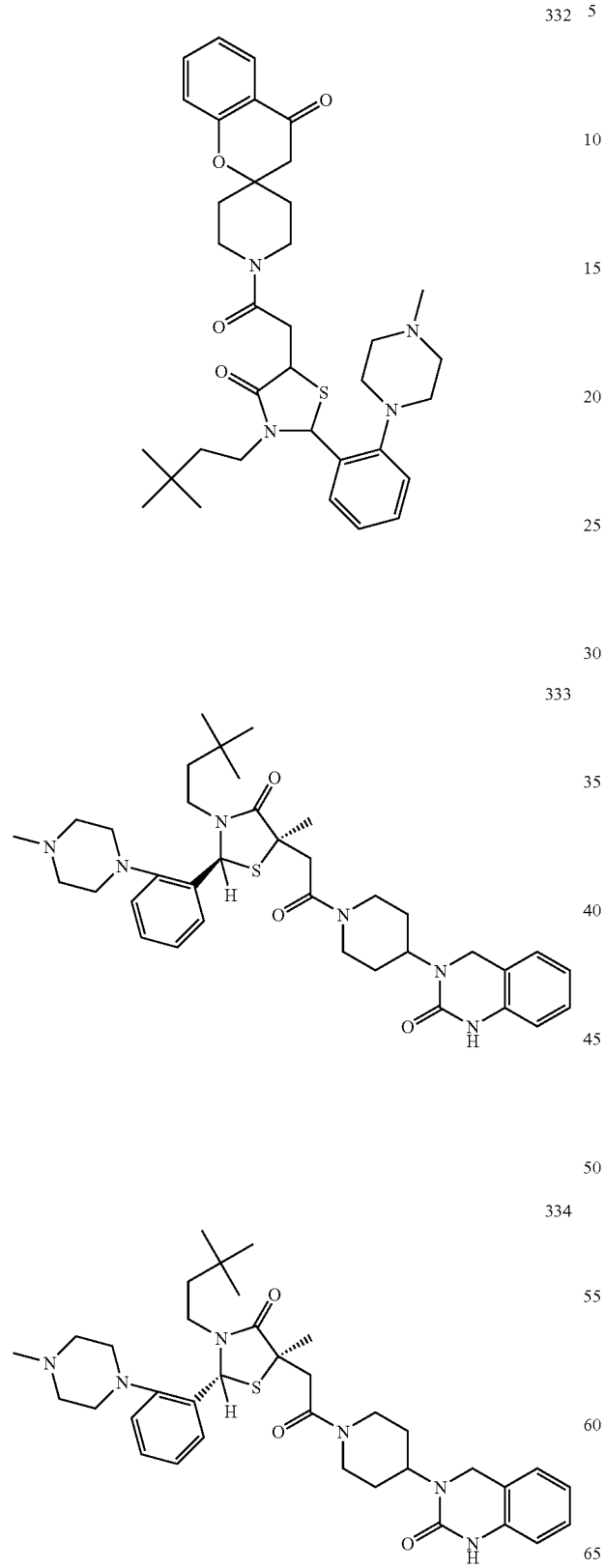
332
333
334
TABLE 1A-continued
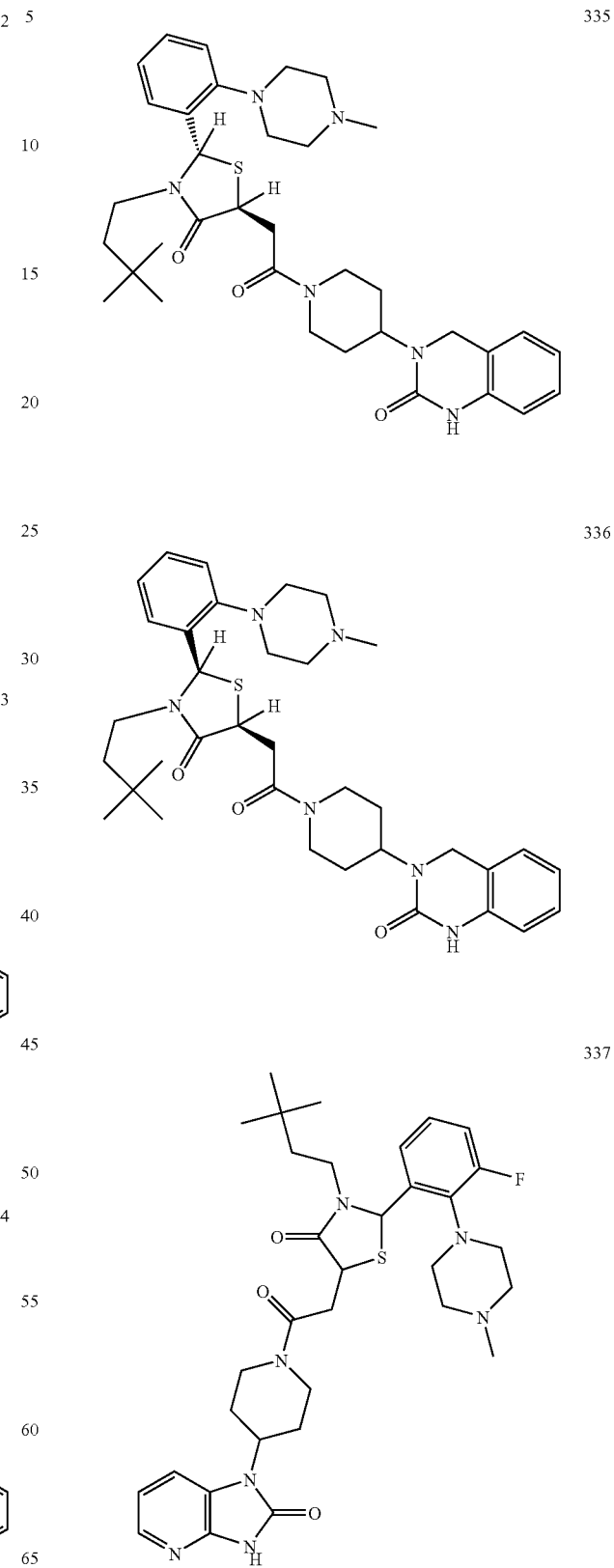
335
336
337

TABLE 1A-continued
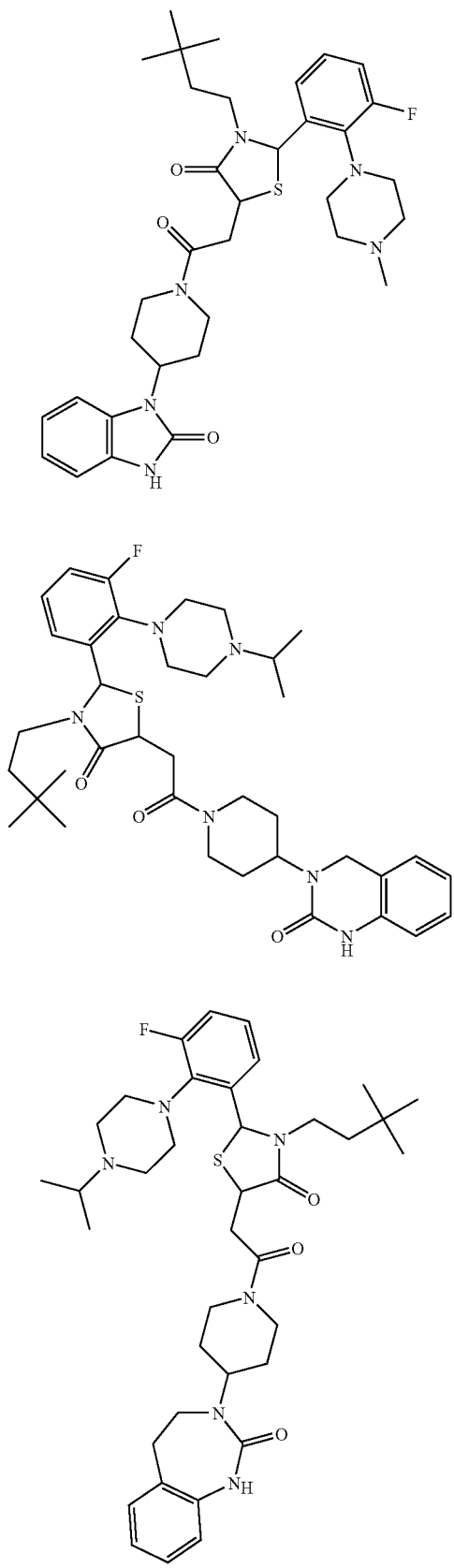
TABLE 1A-continued
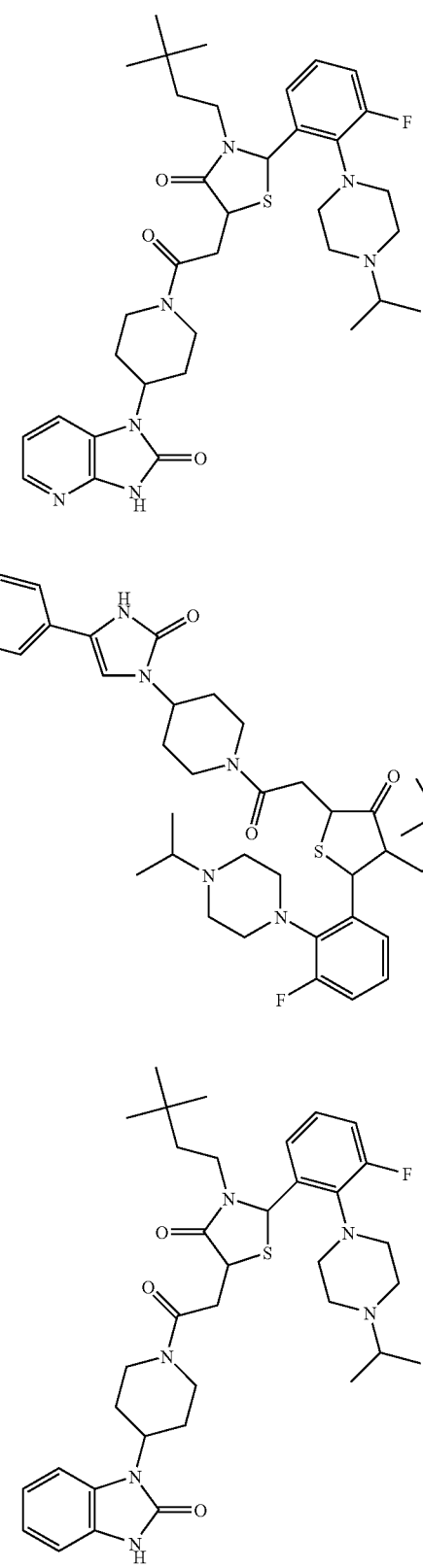

TABLE 1A-continued
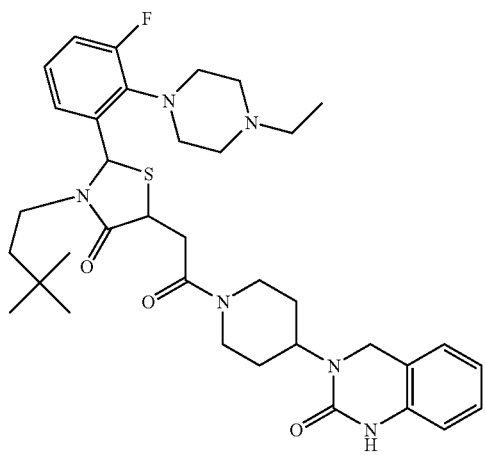
344
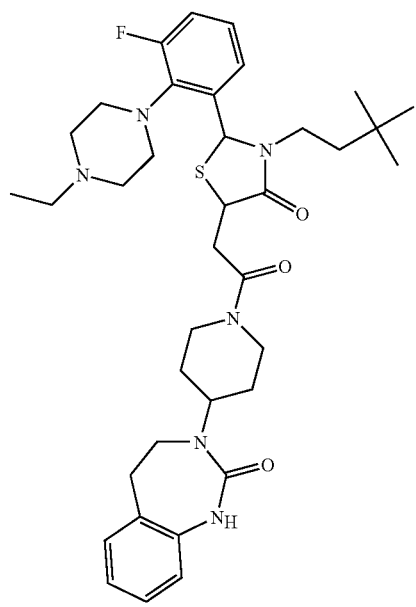
345
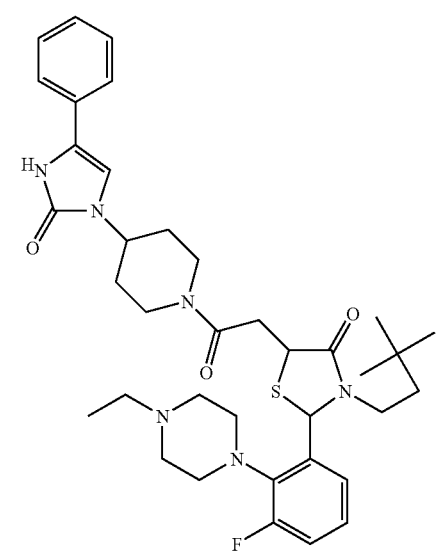
346
TABLE 1A-continued
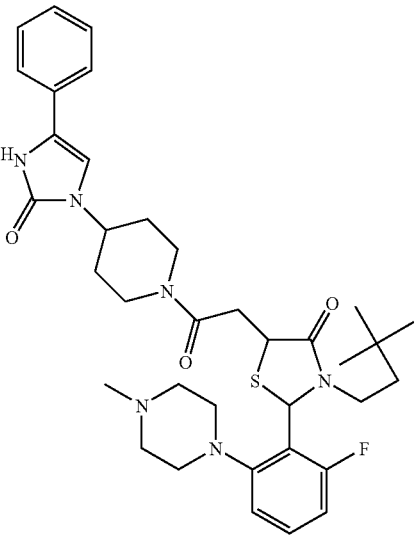
347
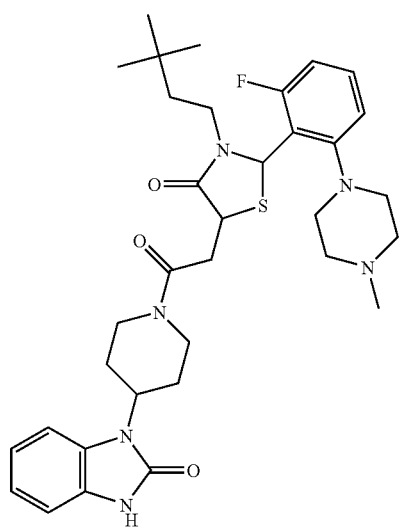
348
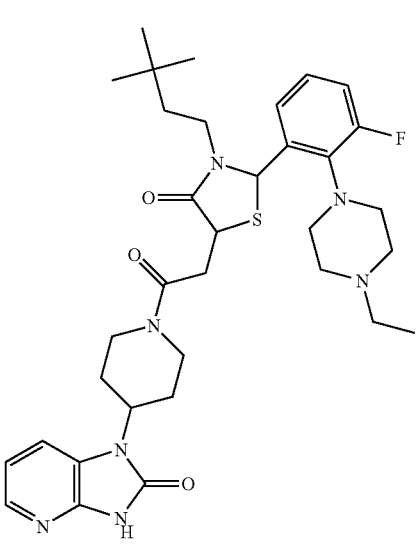
349

TABLE 1A-continued
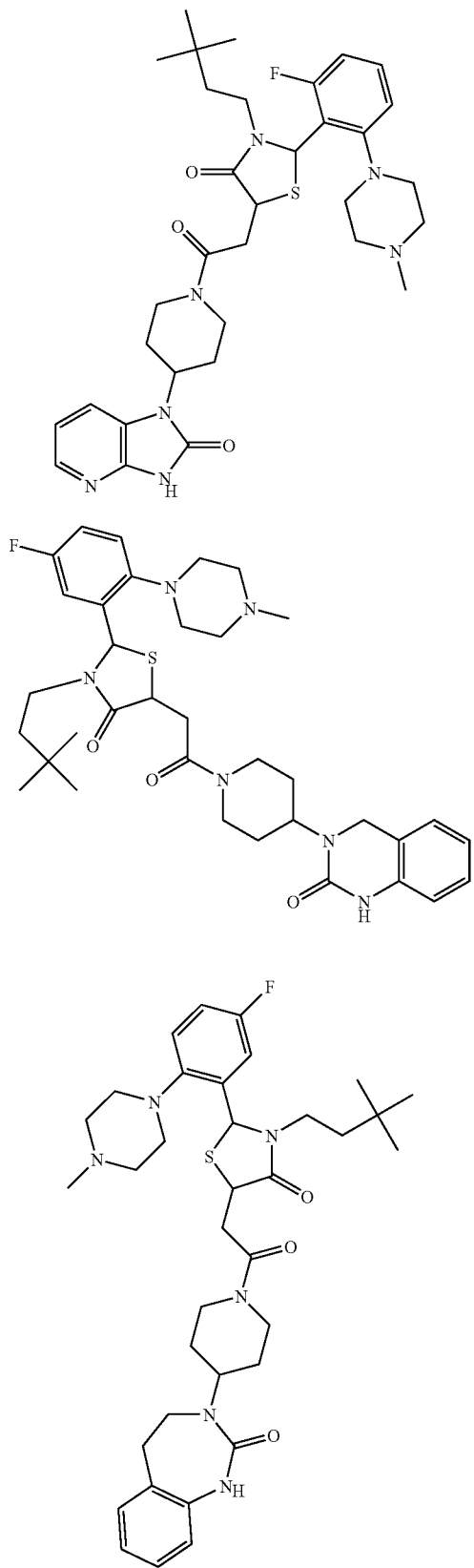
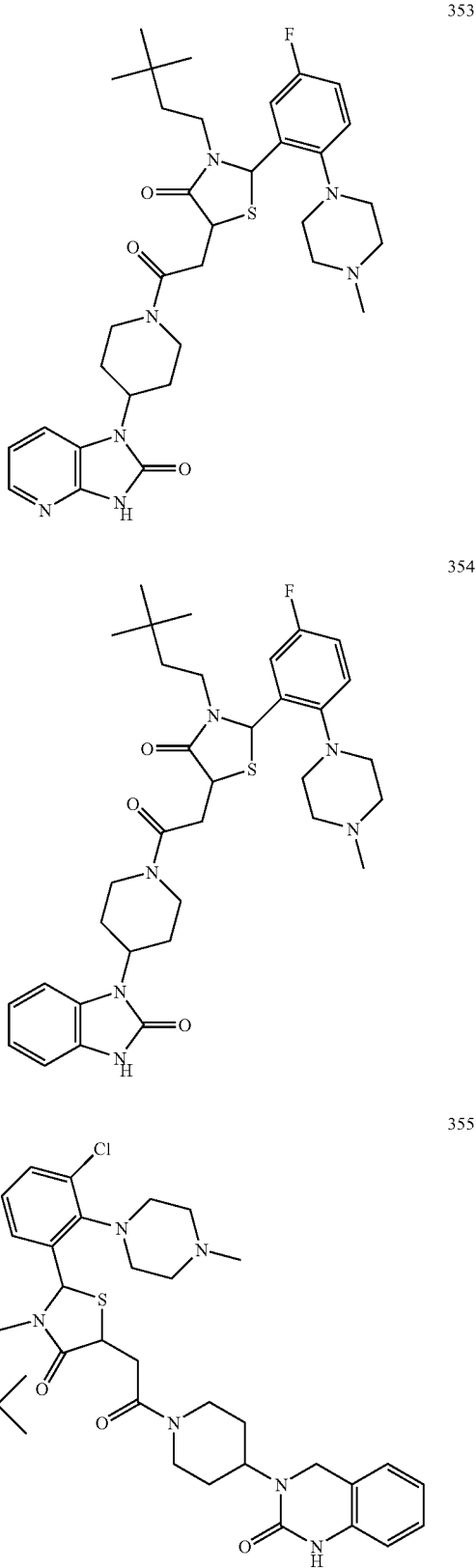

TABLE 1A-continued
356
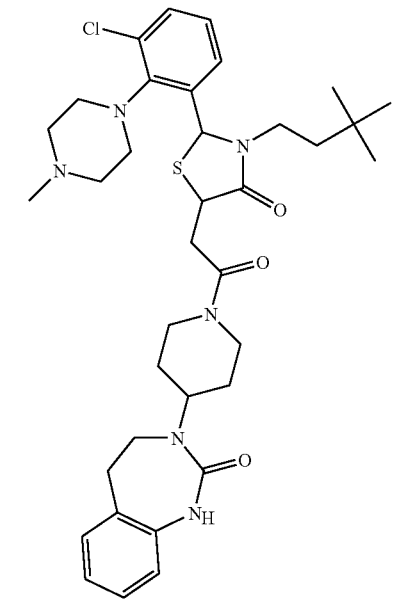
357
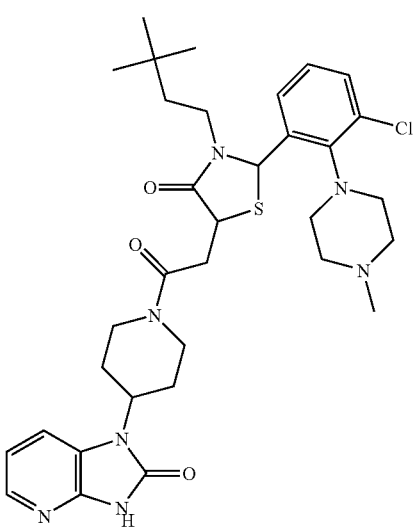
358
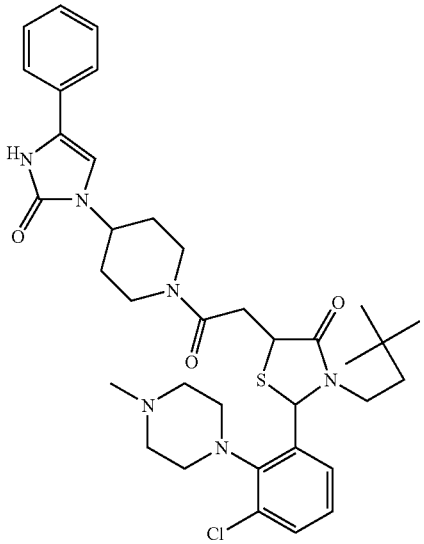
359
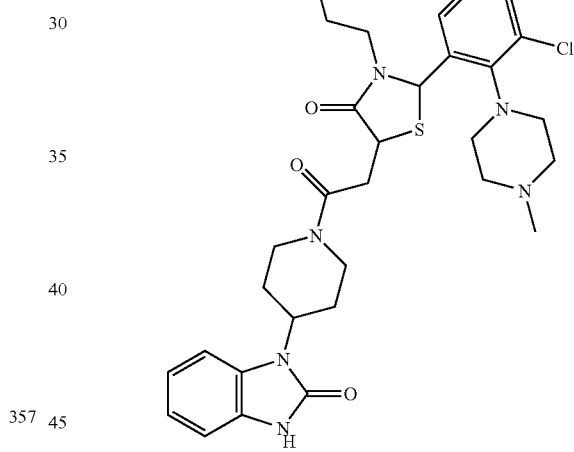
360
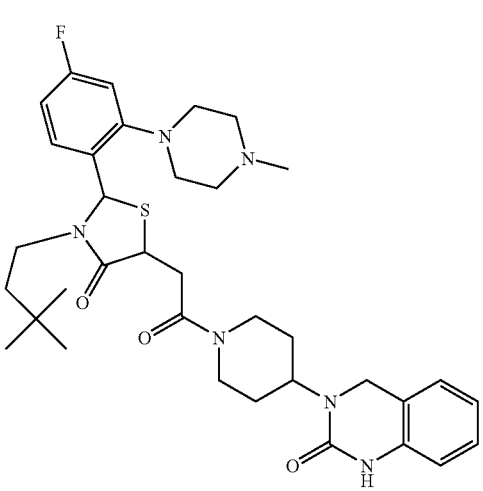

TABLE 1A-continued
161
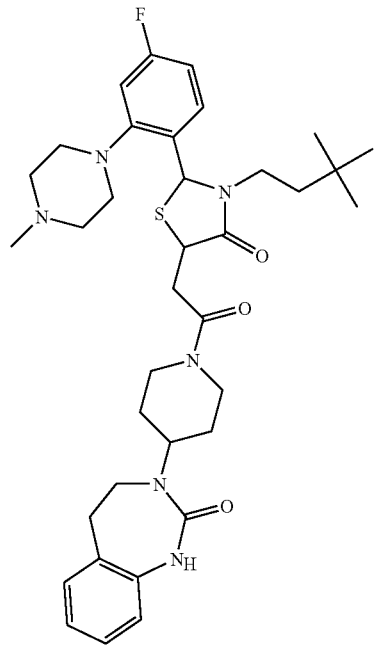
362
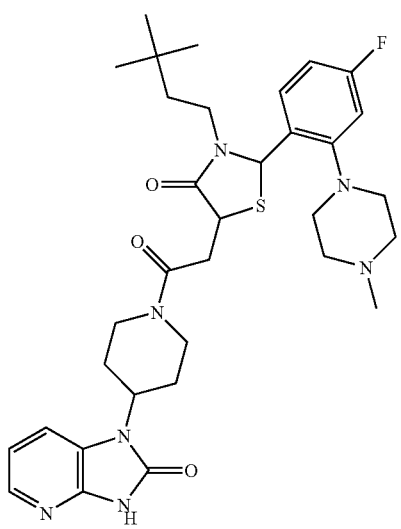
TABLE 1A-continued
361
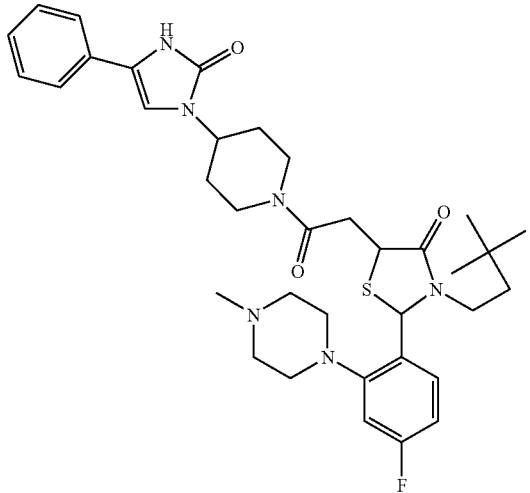
363
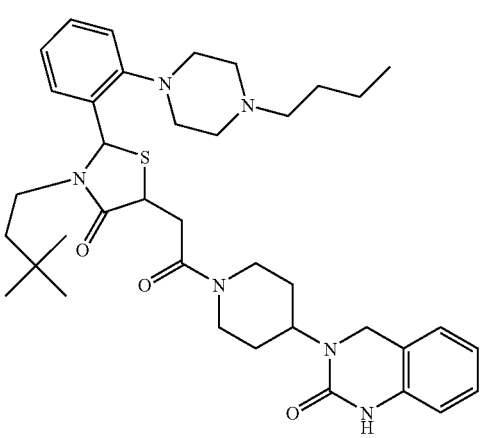
364
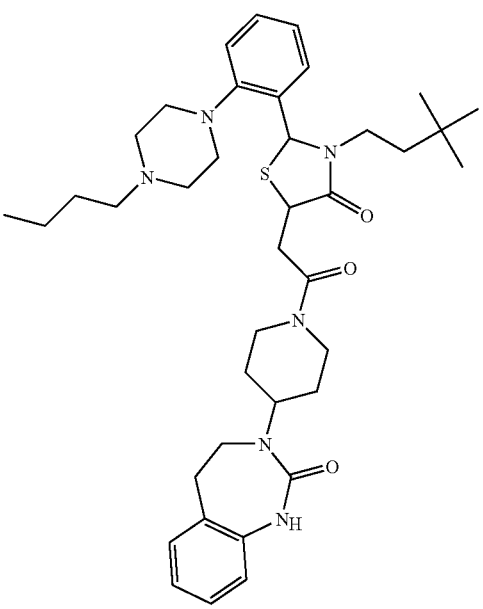
365

TABLE 1A-continued
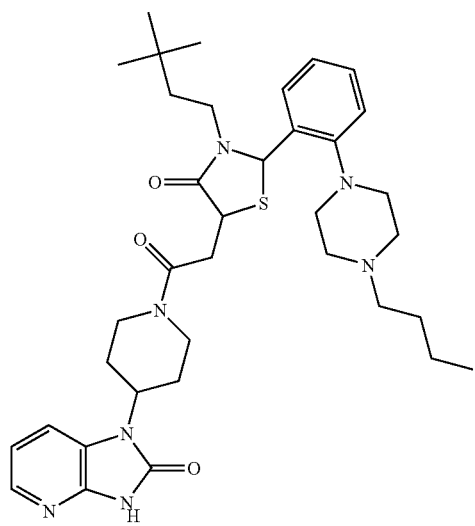
366
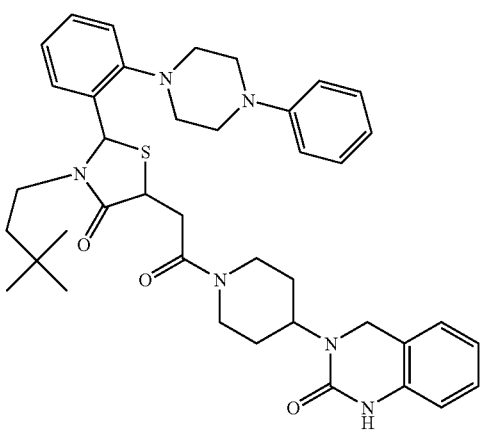
367
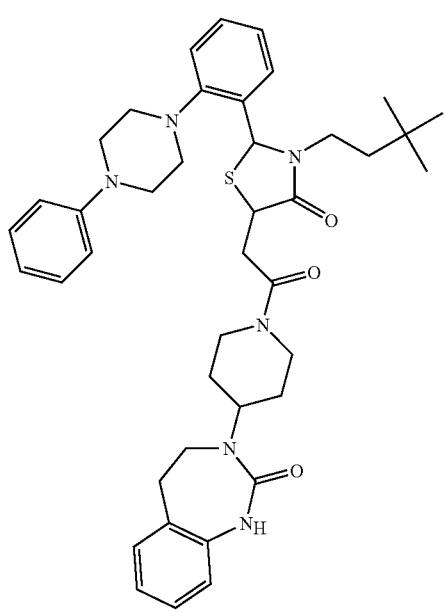
368
TABLE 1A-continued
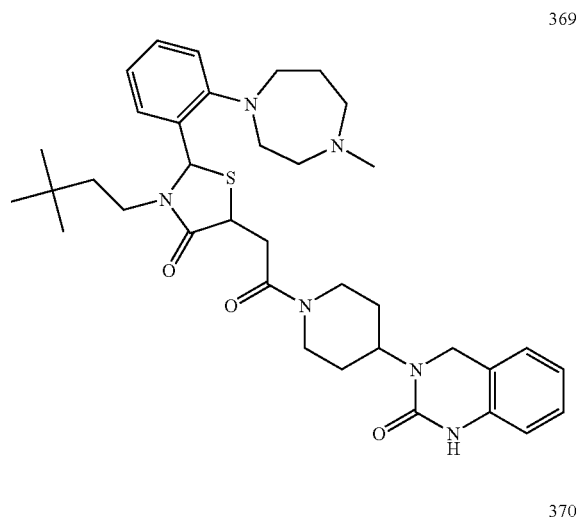
369
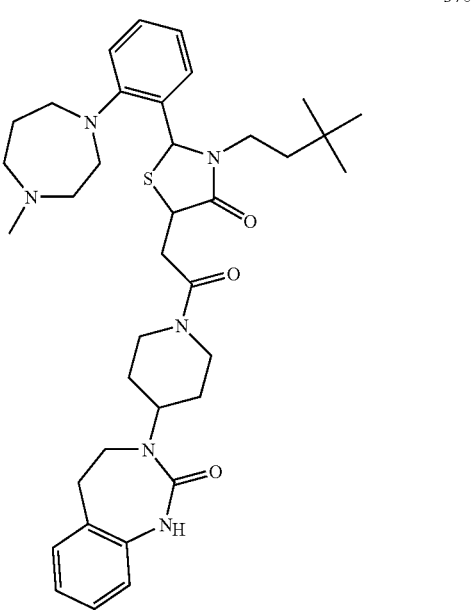
370
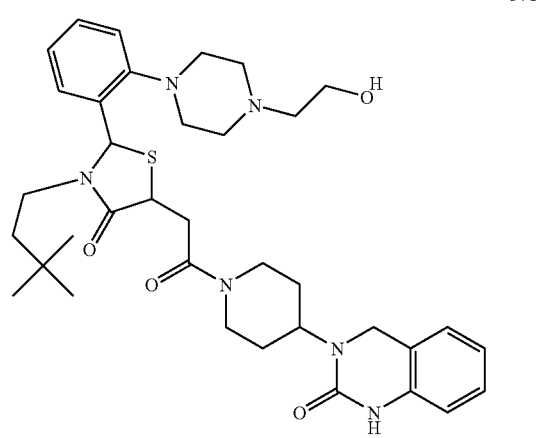
371

TABLE 1A-continued
372
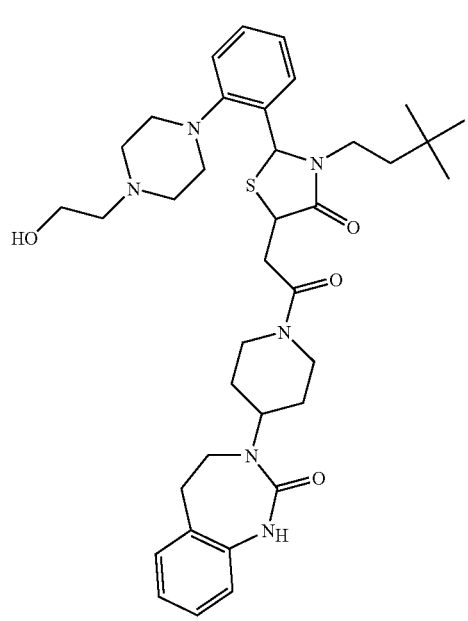
373
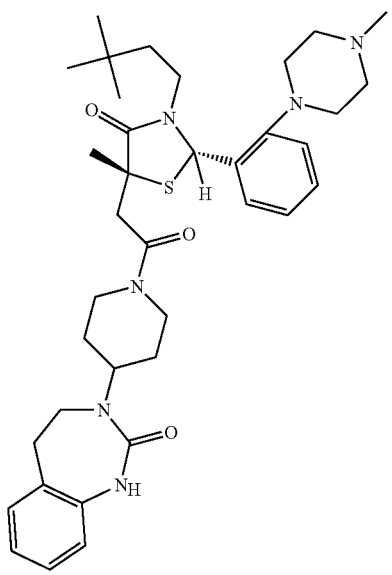
374
TABLE 1A-continued
375
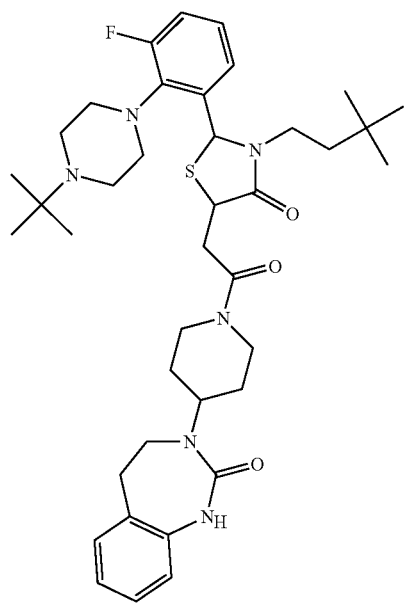
376

TABLE 1A-continued
377
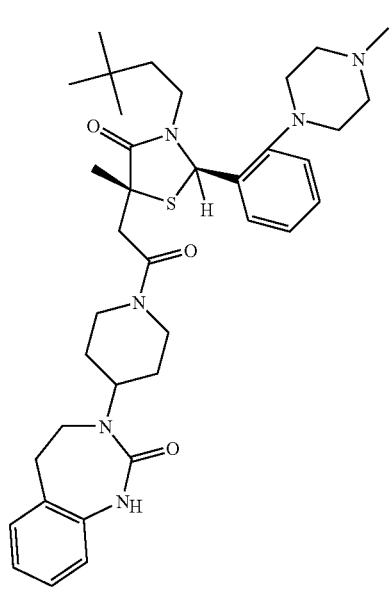
379
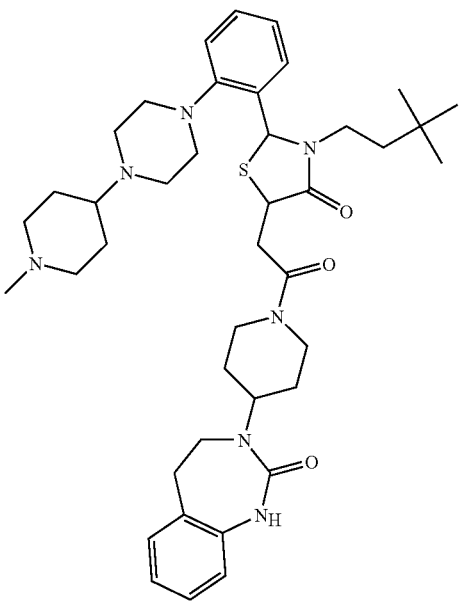
378
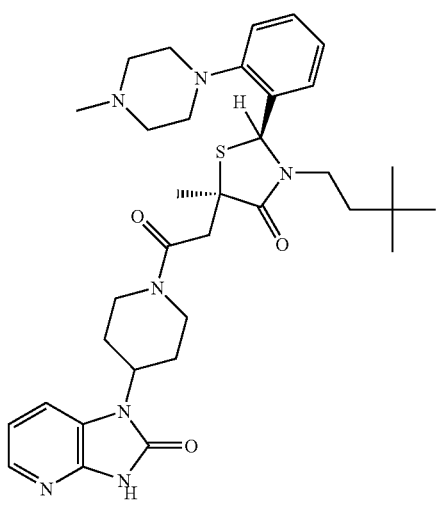
380
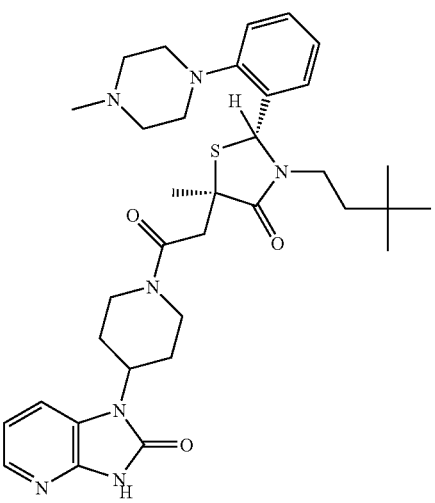

TABLE 1A-continued
381
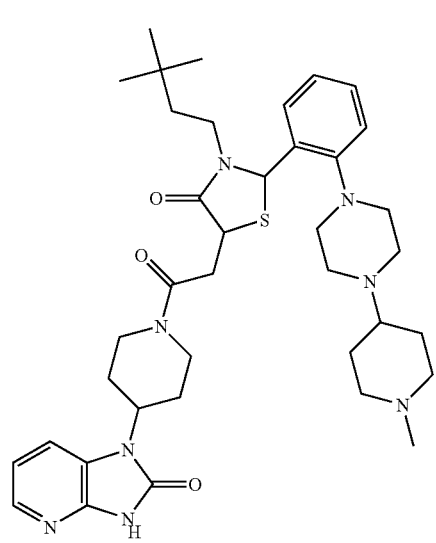
382
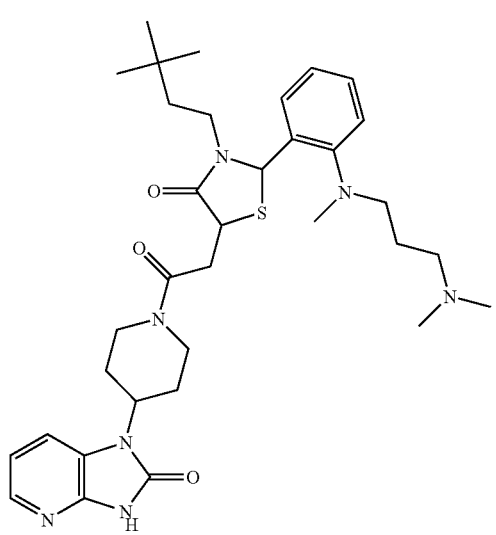
TABLE 1A-continued
383
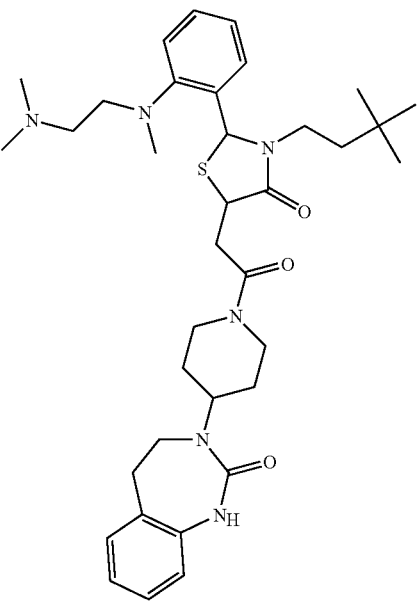
384
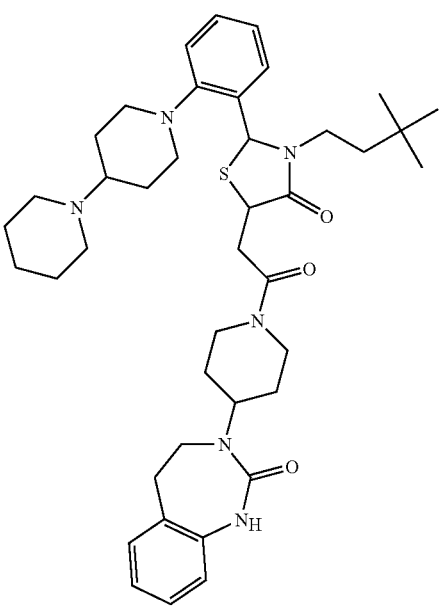

TABLE 1A-continued
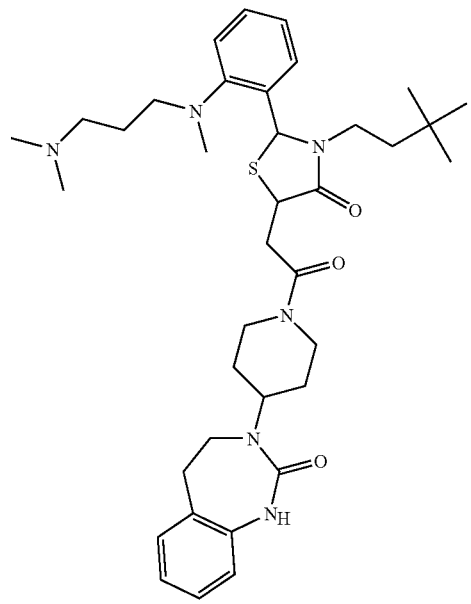
385
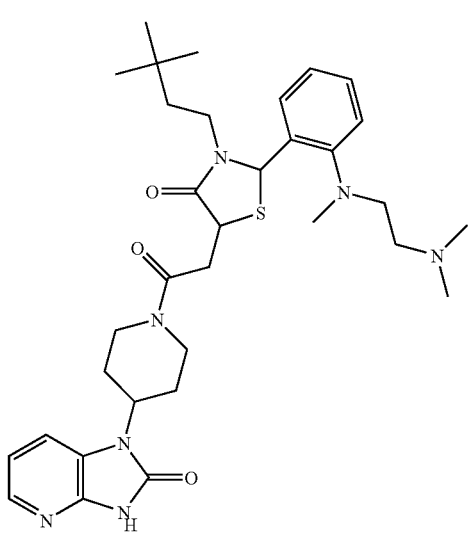
386
TABLE 1A-continued
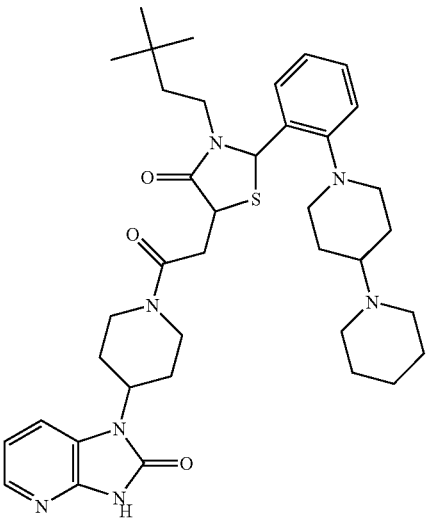
387
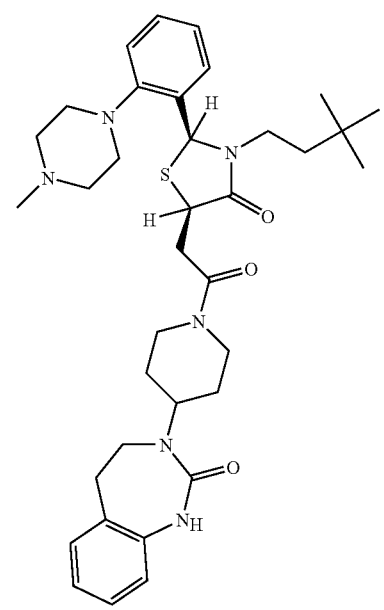
388

TABLE 1A-continued
389
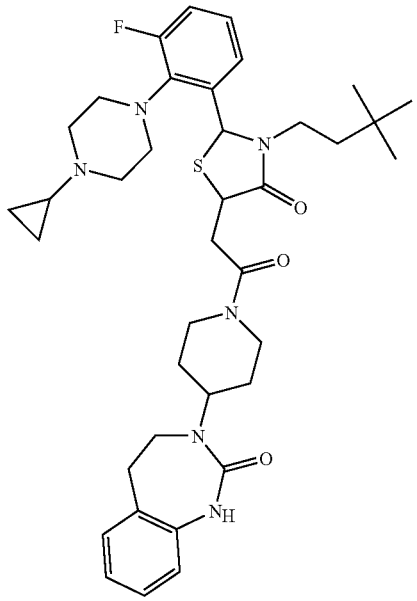
390
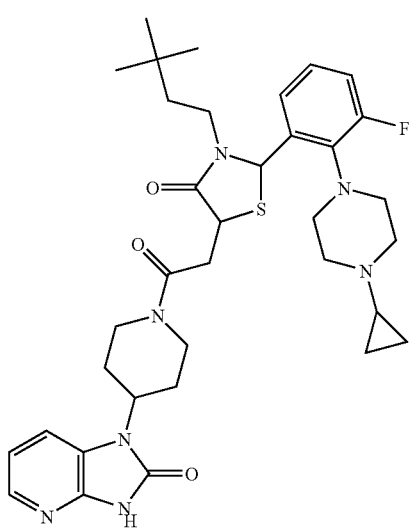
TABLE 1A-continued
391
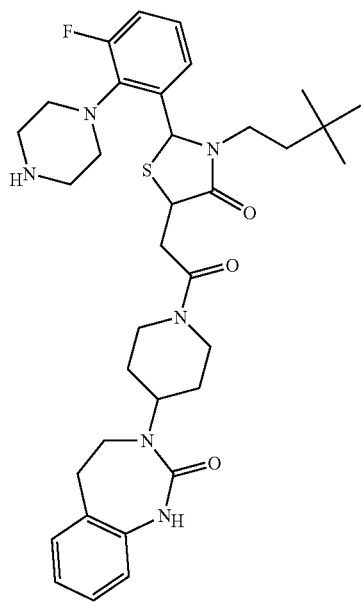
392
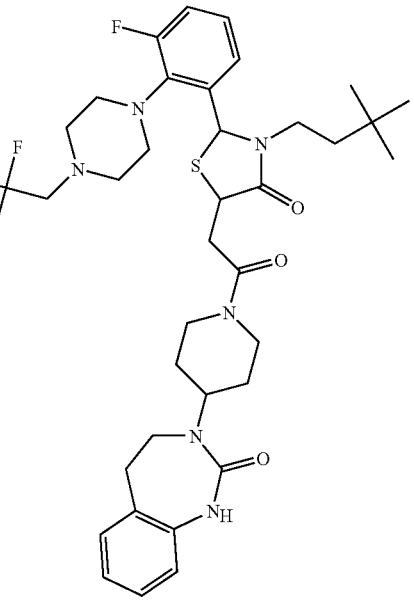

TABLE 1A-continued
393
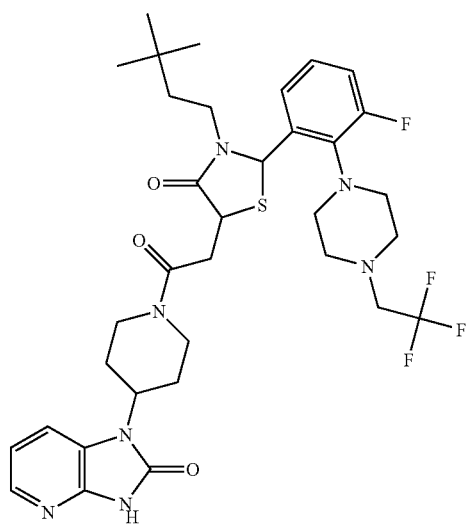
394
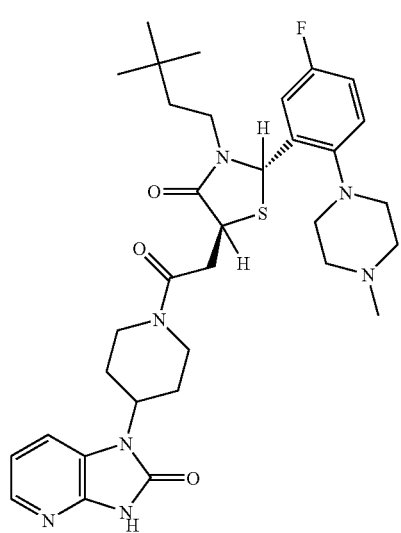
TABLE 1A-continued
395
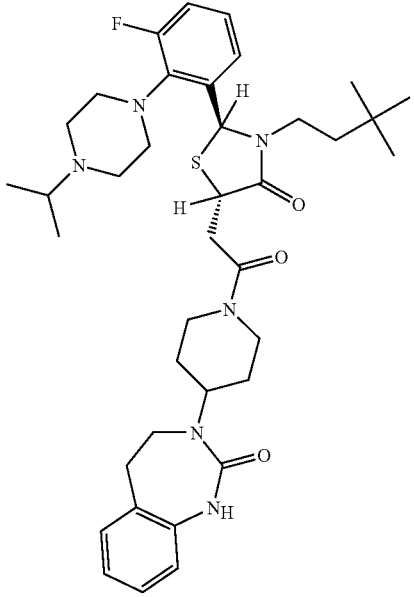
396
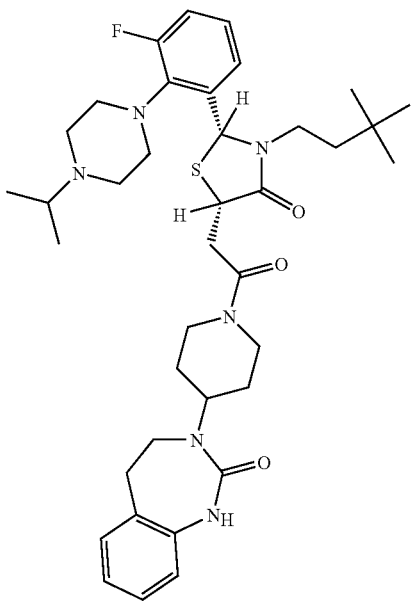

TABLE 1A-continued
397
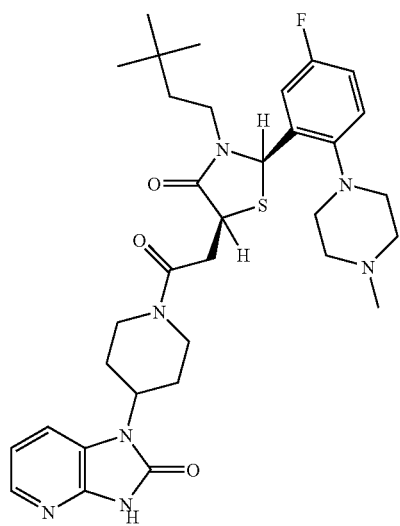
398
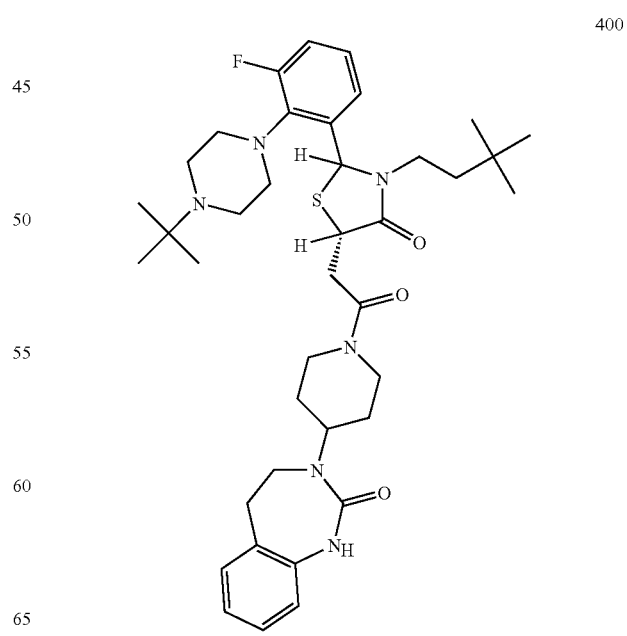
TABLE 1A-continued
399
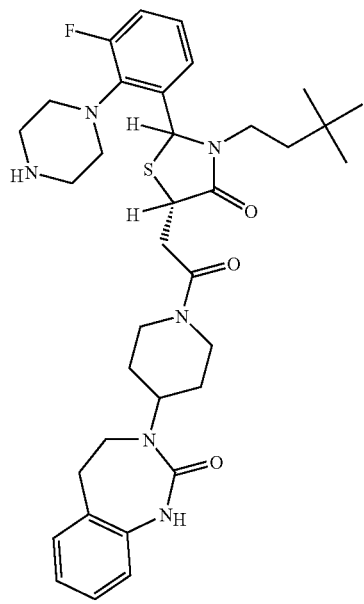
400

TABLE 1A-continued
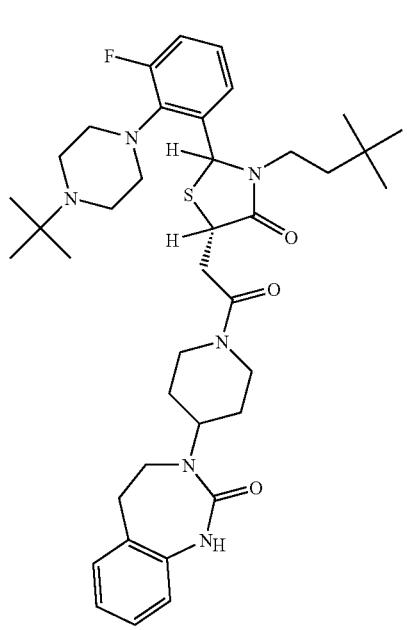
401
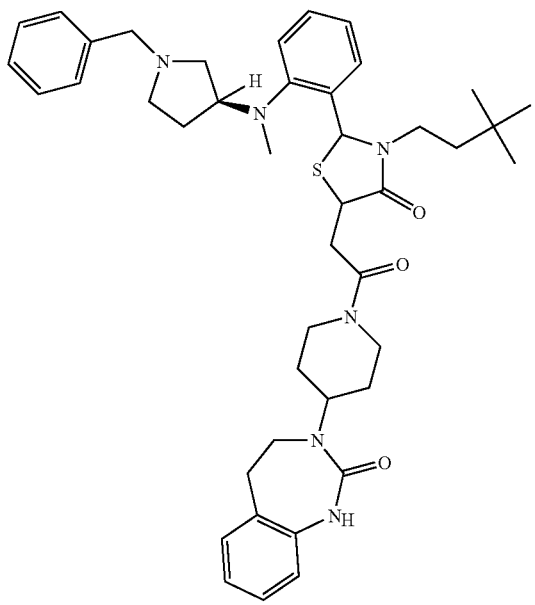
403
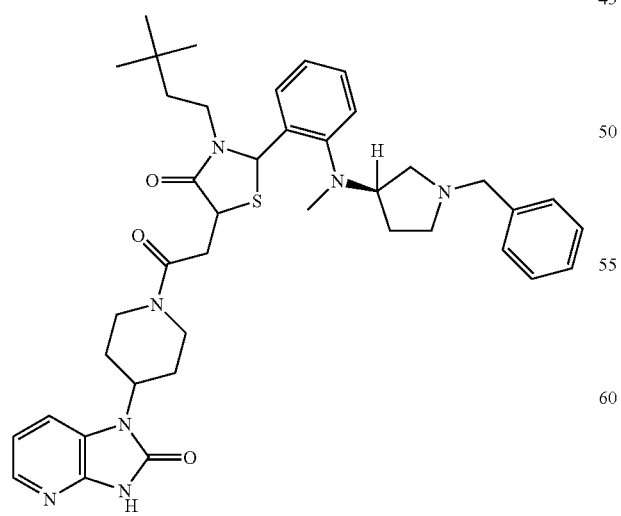
402
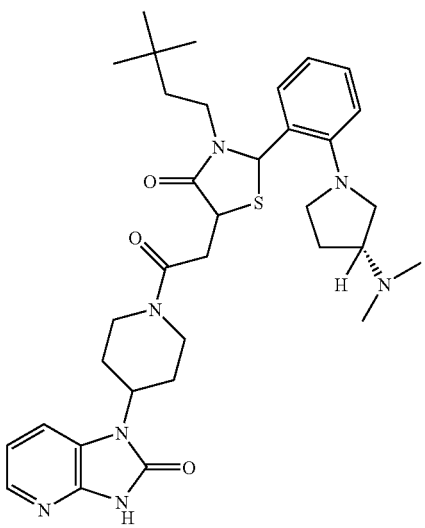
404

181
TABLE 1A-continued
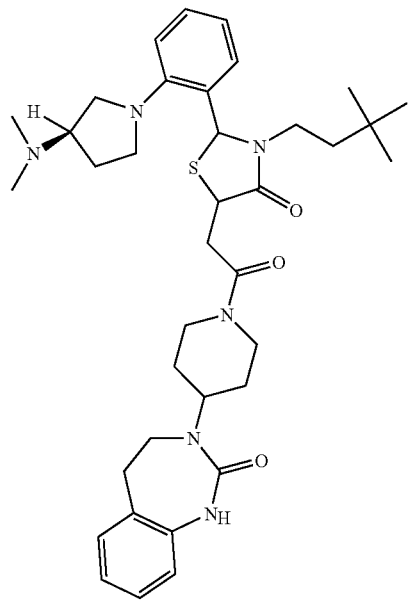
405
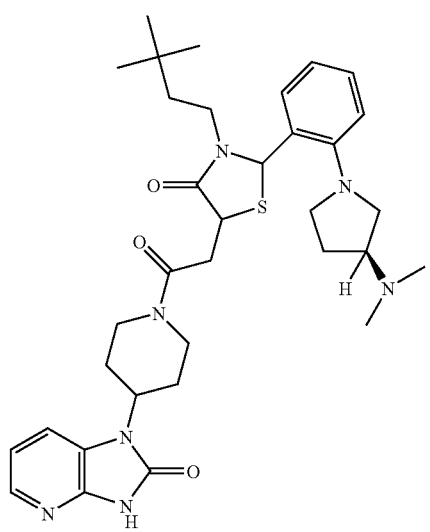
406
182
TABLE 1A-continued
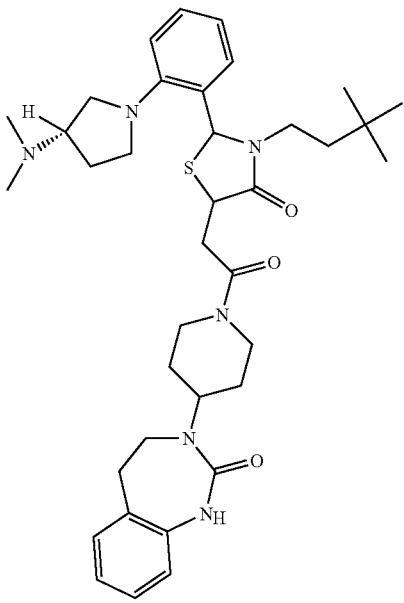
407
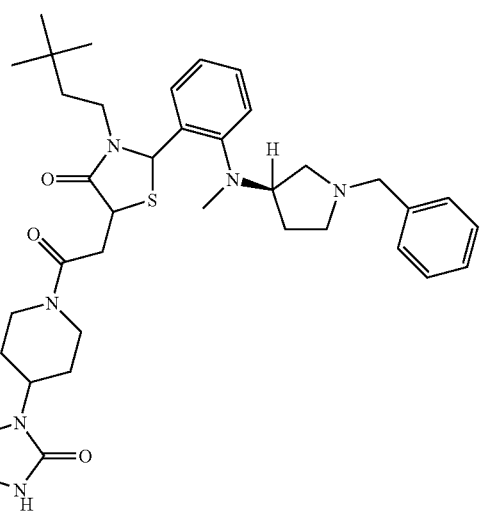
408

TABLE 1A-continued
409
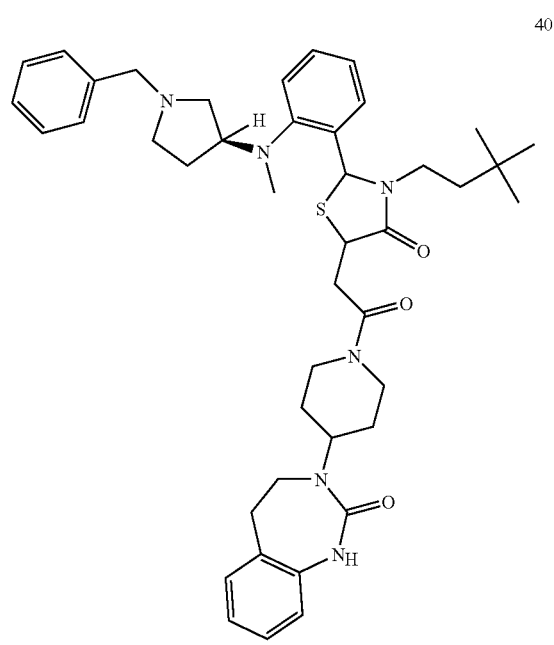
410
411
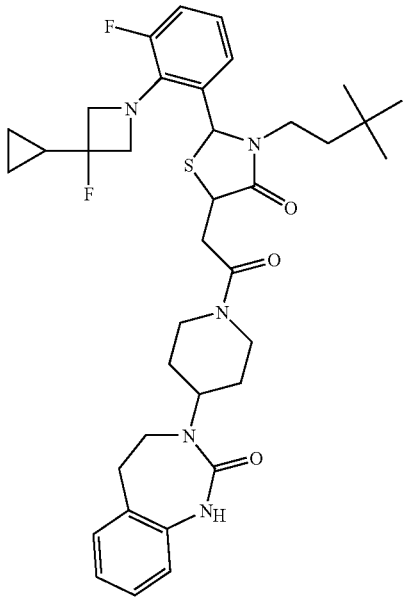
412
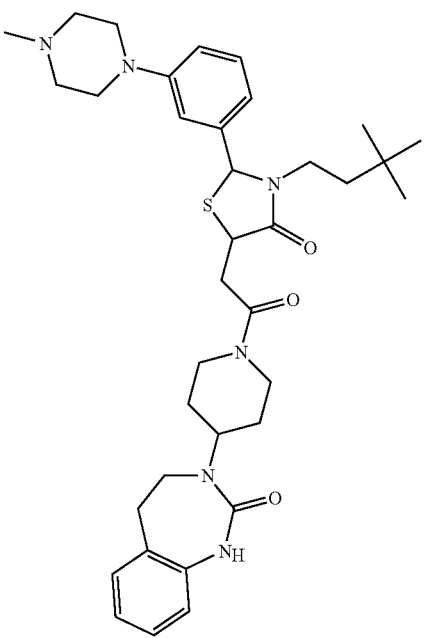

TABLE 1A-continued
413
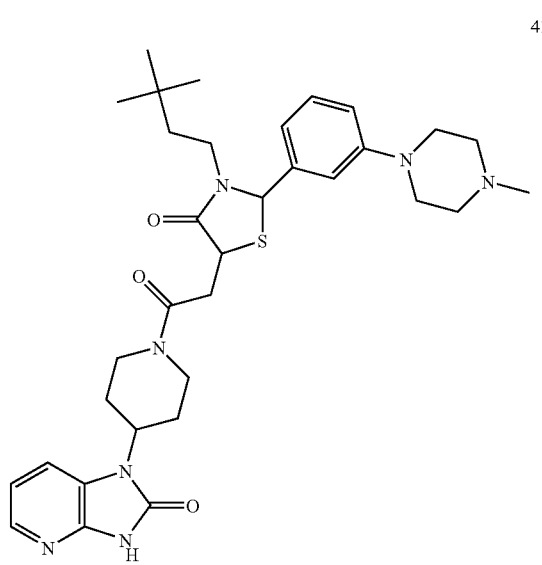
414
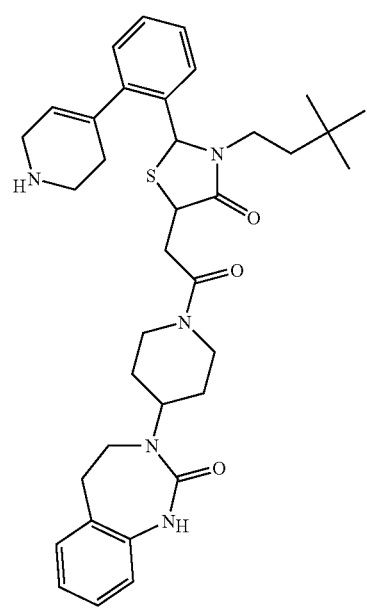
TABLE 1A-continued
415
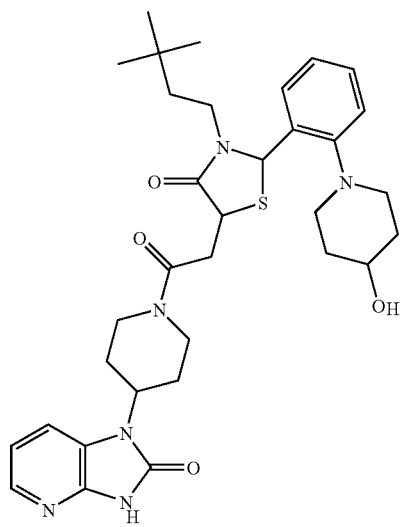
416
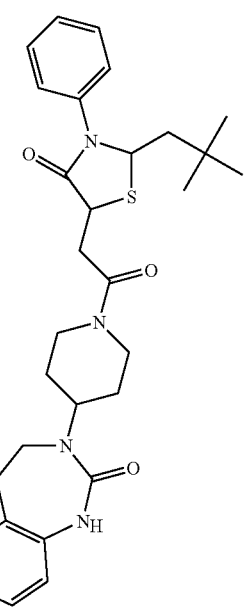

TABLE 1A-continued
417
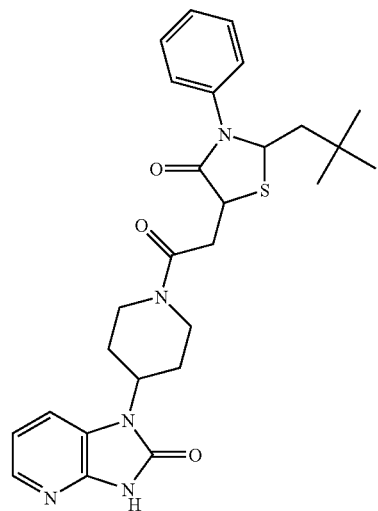
418
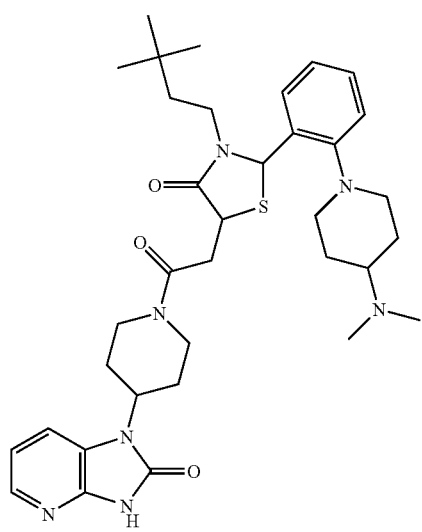
TABLE 1A-continued
419
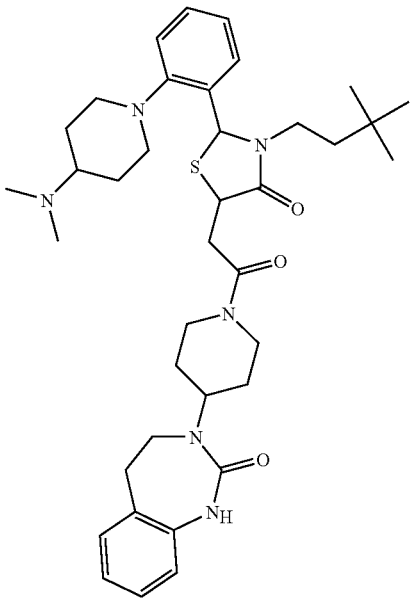
420
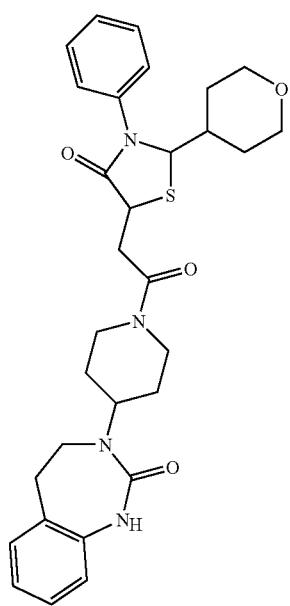

TABLE 1A-continued
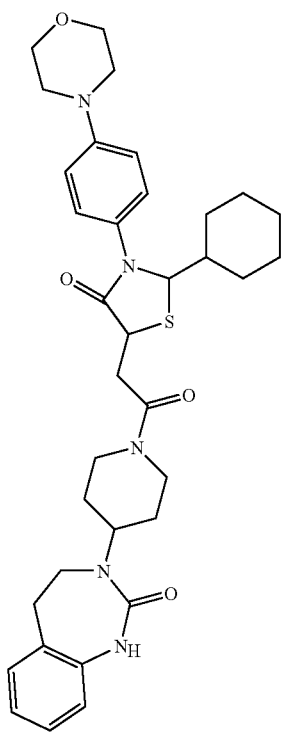
421
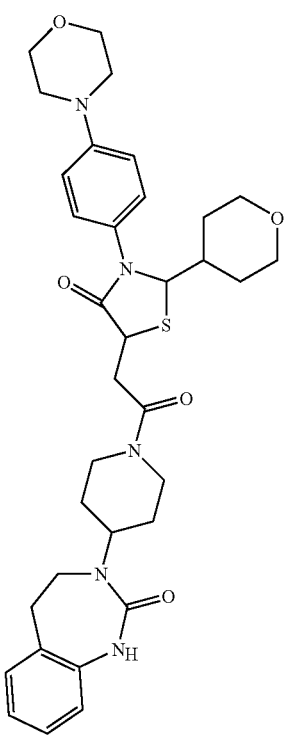
422
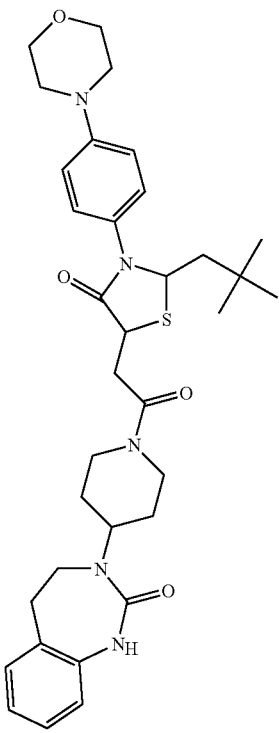
423
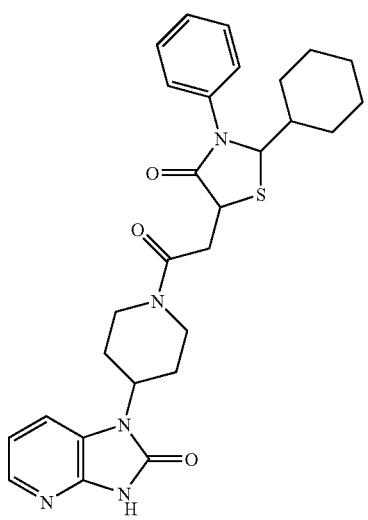
424

TABLE 1A-continued
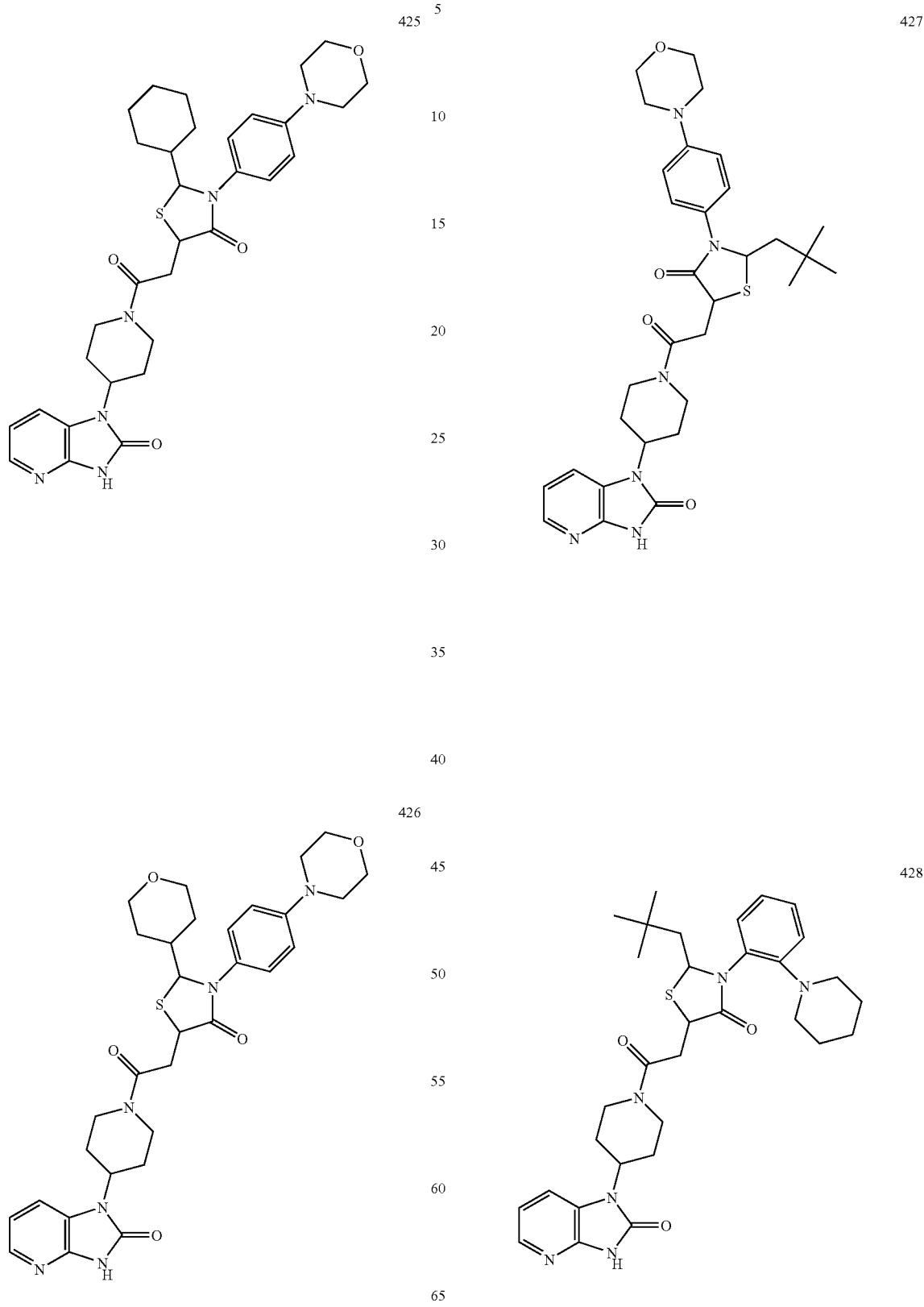

TABLE 1A-continued
429
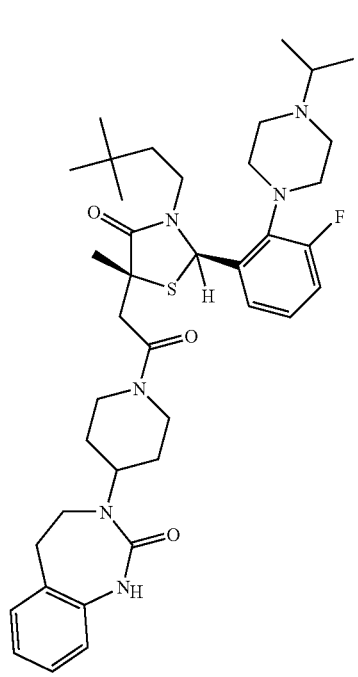
430
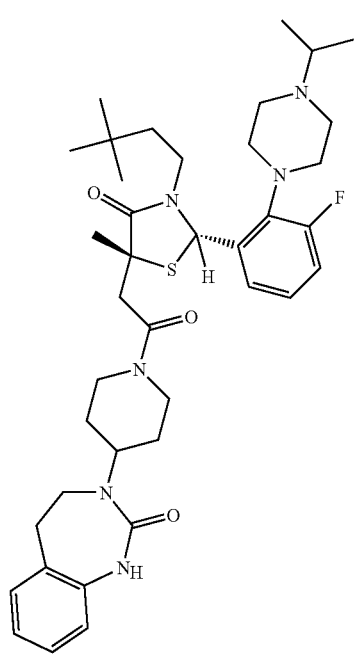
TABLE 1A-continued
431
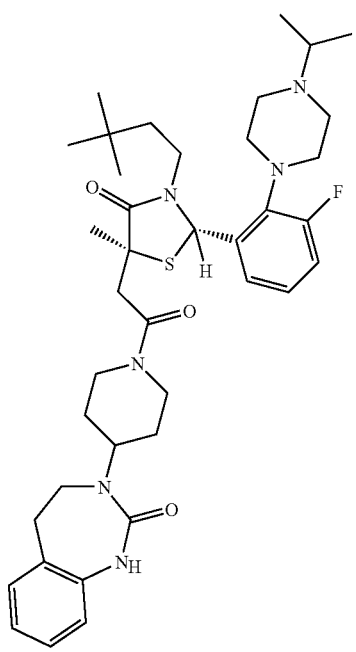
432
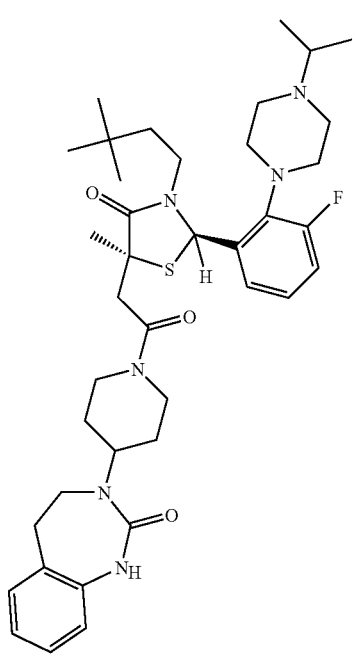

TABLE 1A-continued
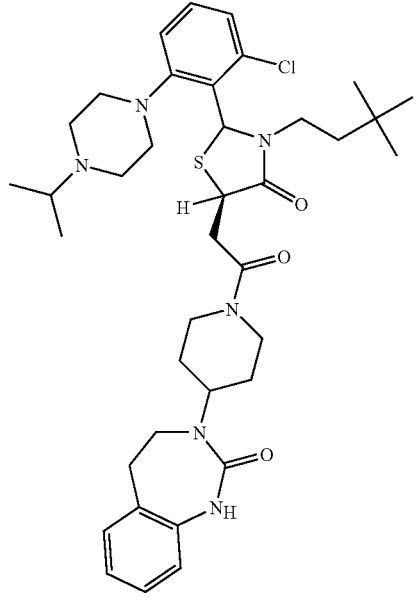
433
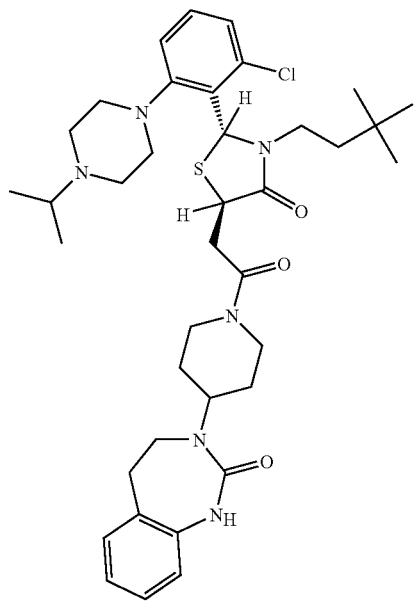
434
TABLE 1A-continued
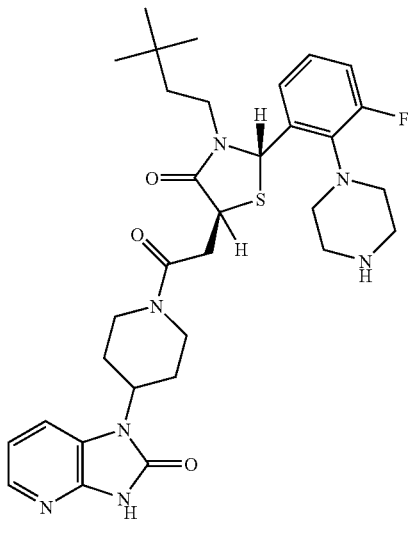
435
436
437

TABLE 1A-continued
438
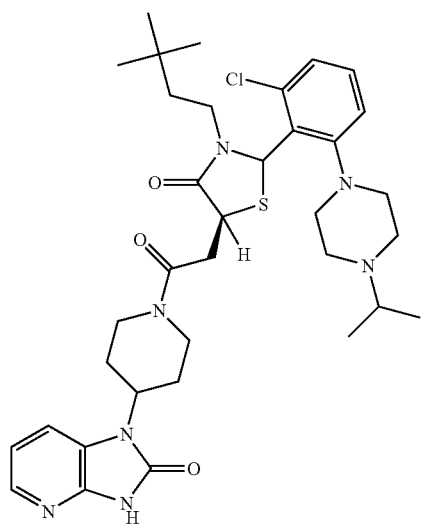
439
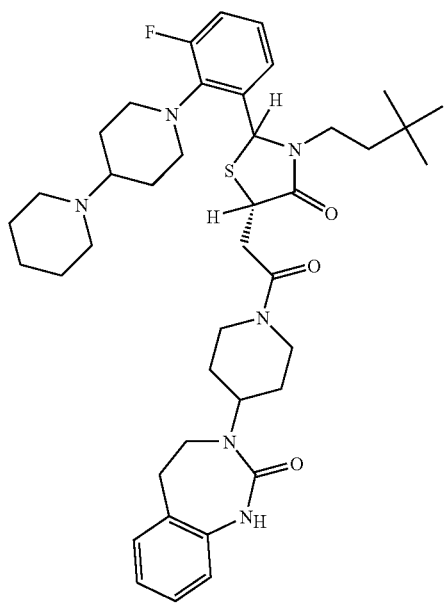
TABLE 1A-continued
440
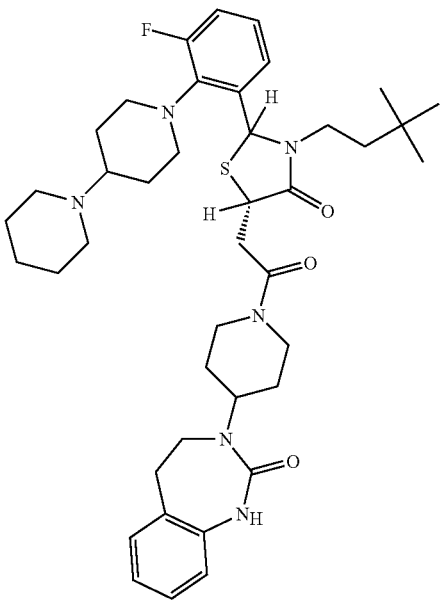
441
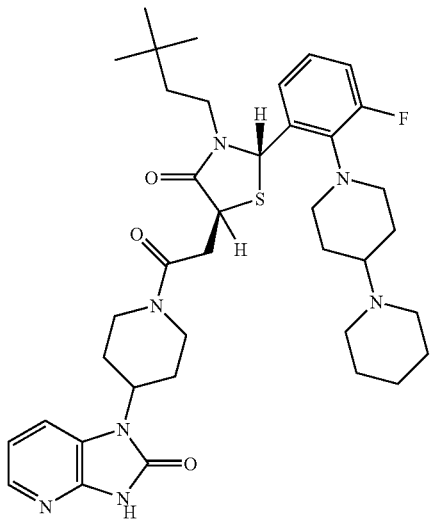

TABLE 1A-continued
442
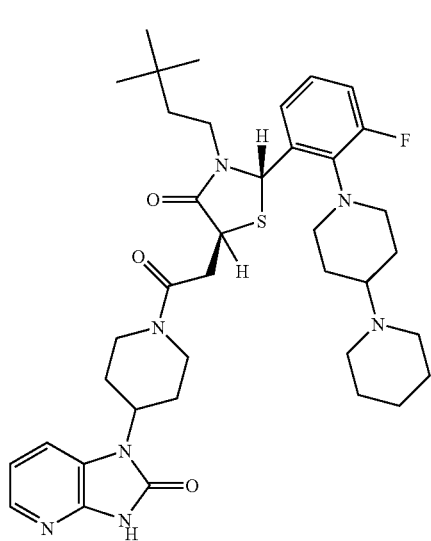
444
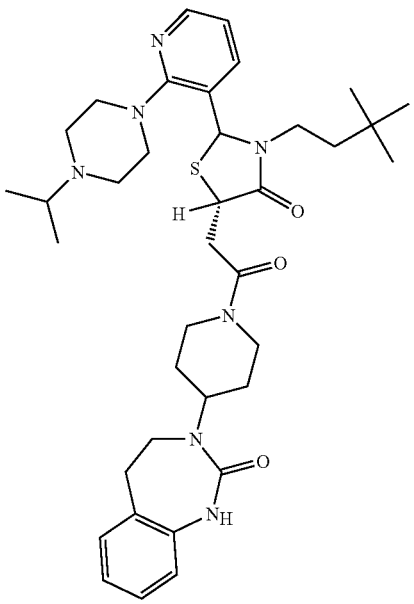
443
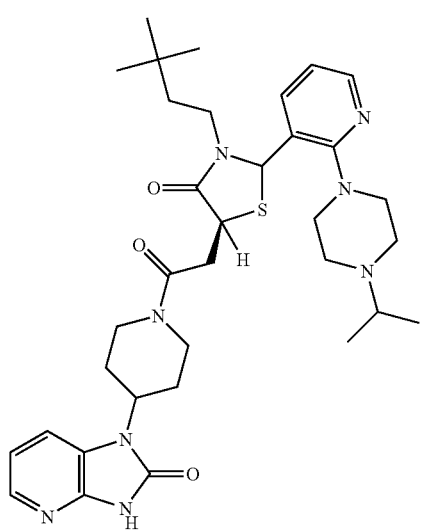
445
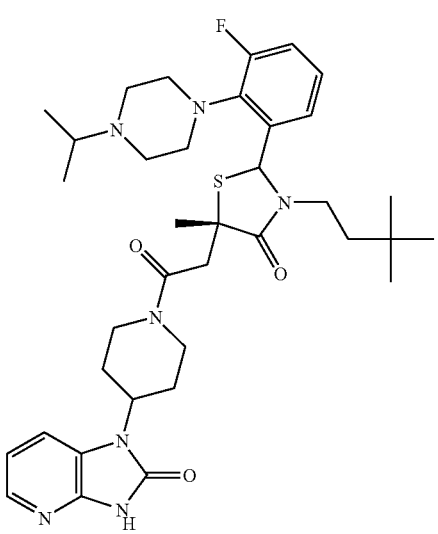

TABLE 1A-continued
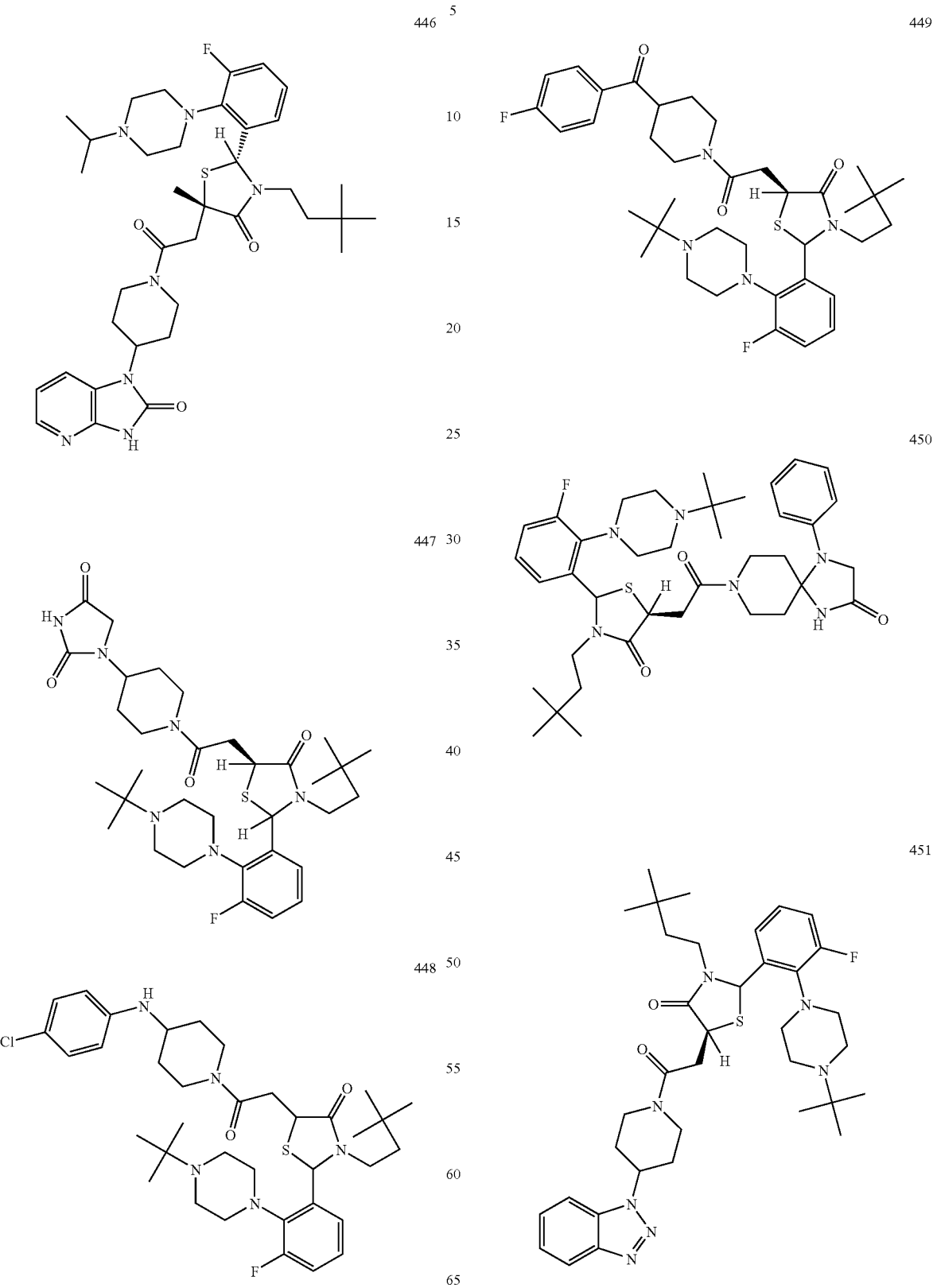

TABLE 1A-continued
452
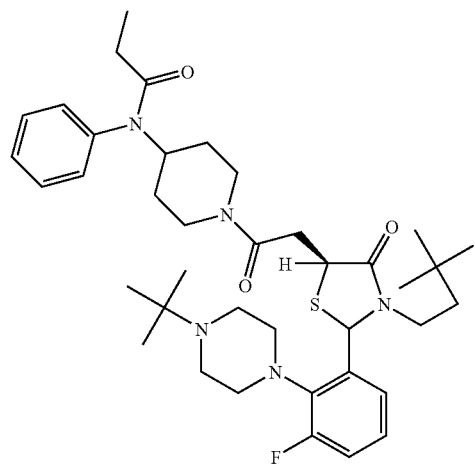
453
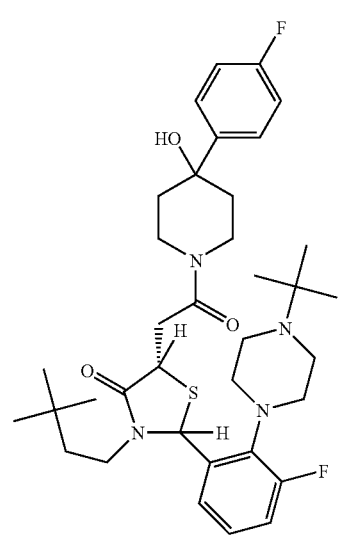
454
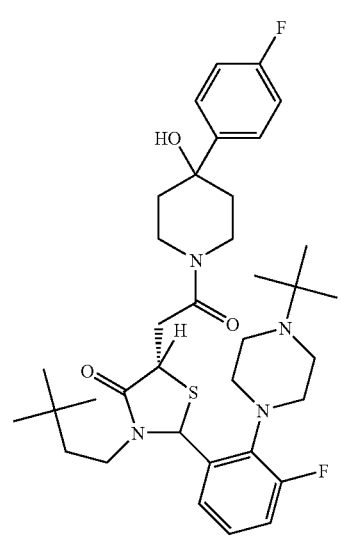
TABLE 1A-continued
455
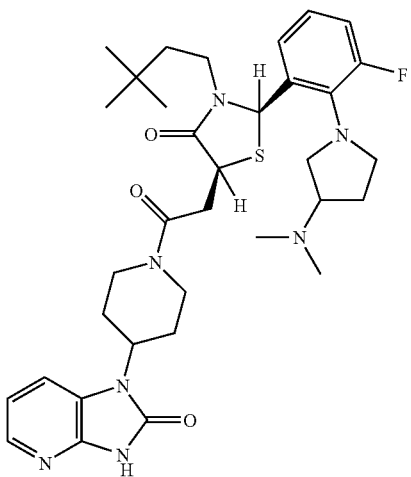
456
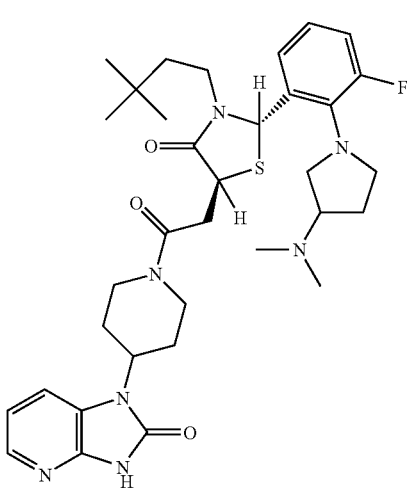
457
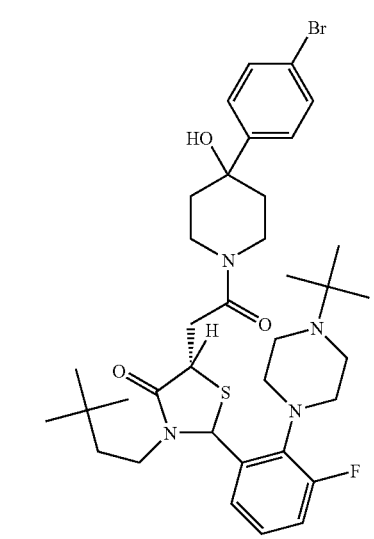

TABLE 1A-continued
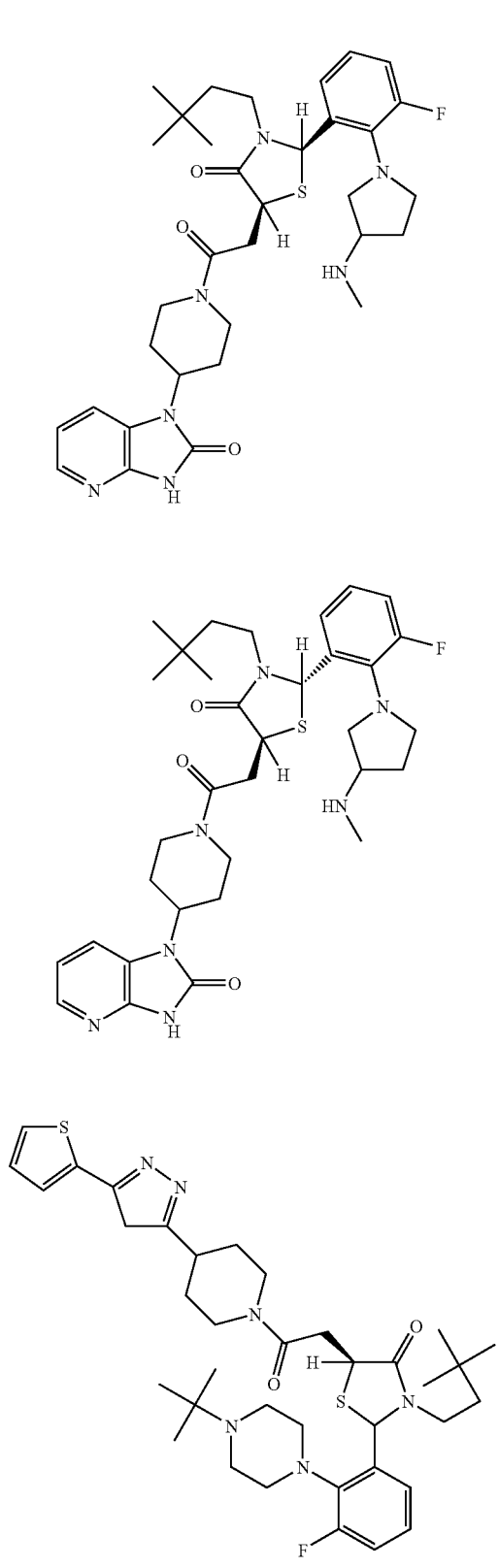
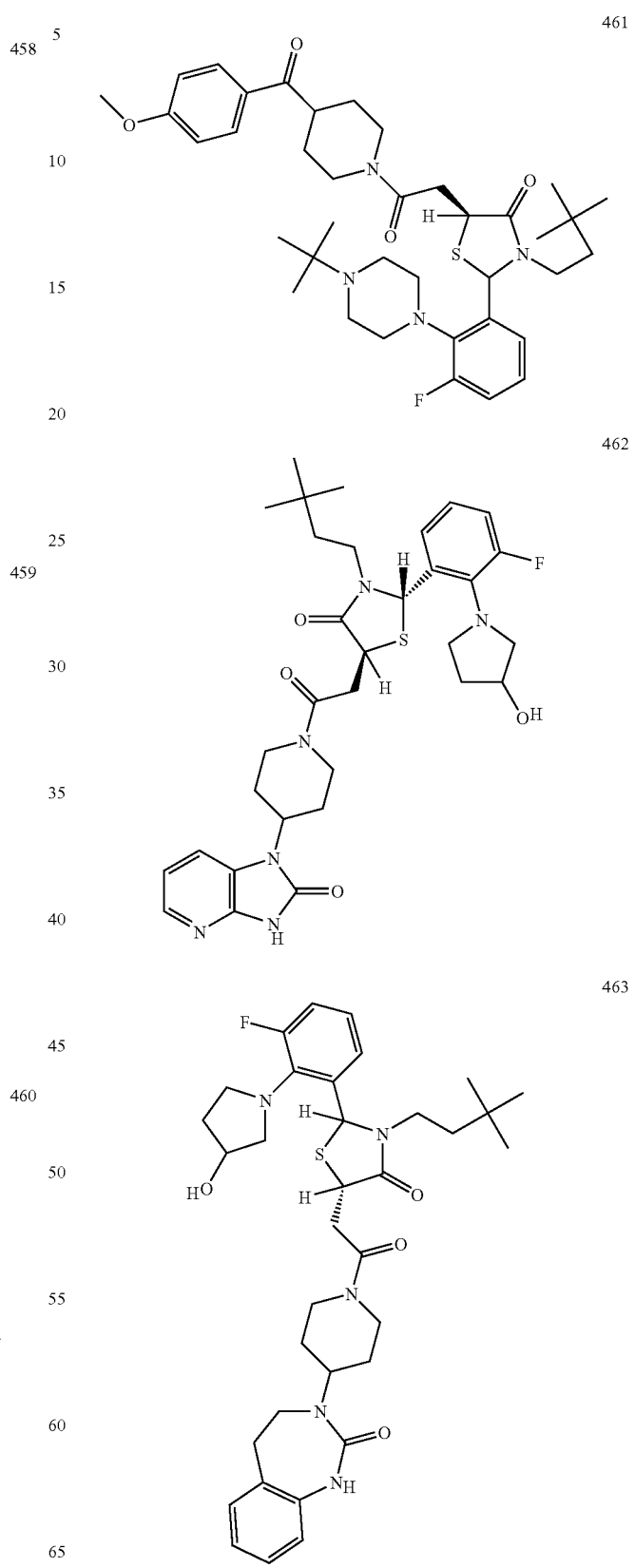

TABLE 1A-continued
464
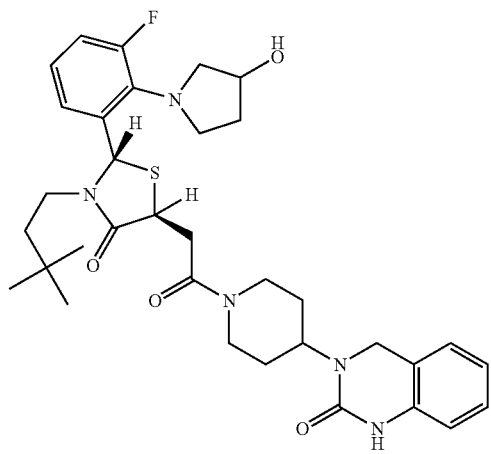
465
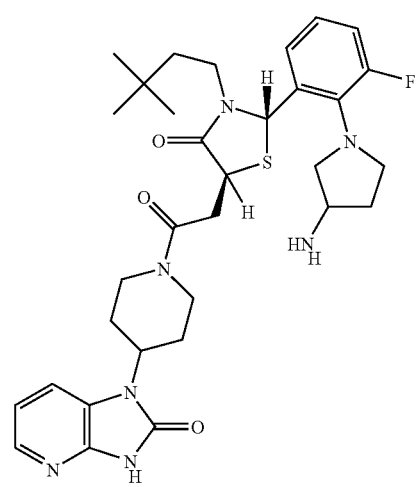
466
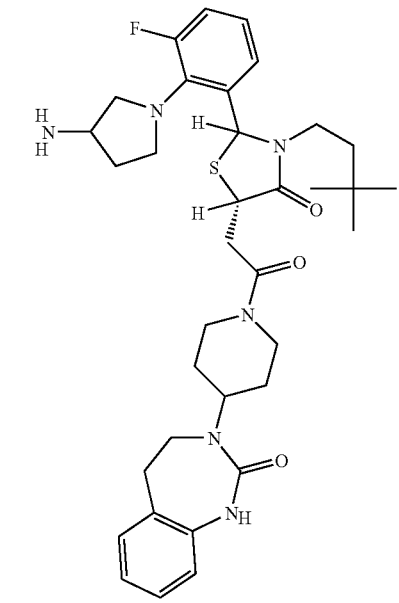
TABLE 1A-continued
467
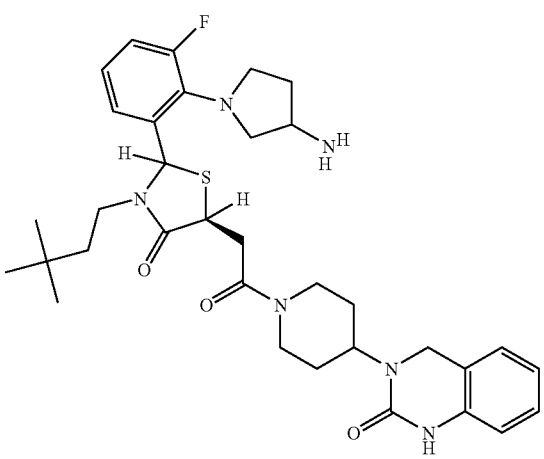
468
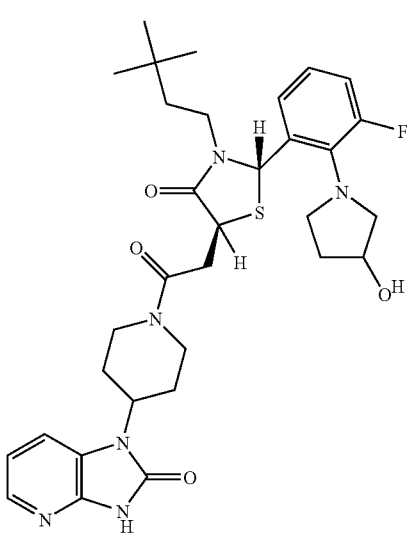
469
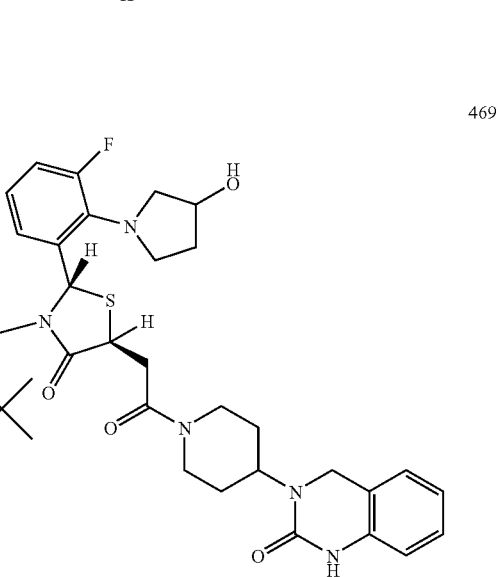

TABLE 1A-continued
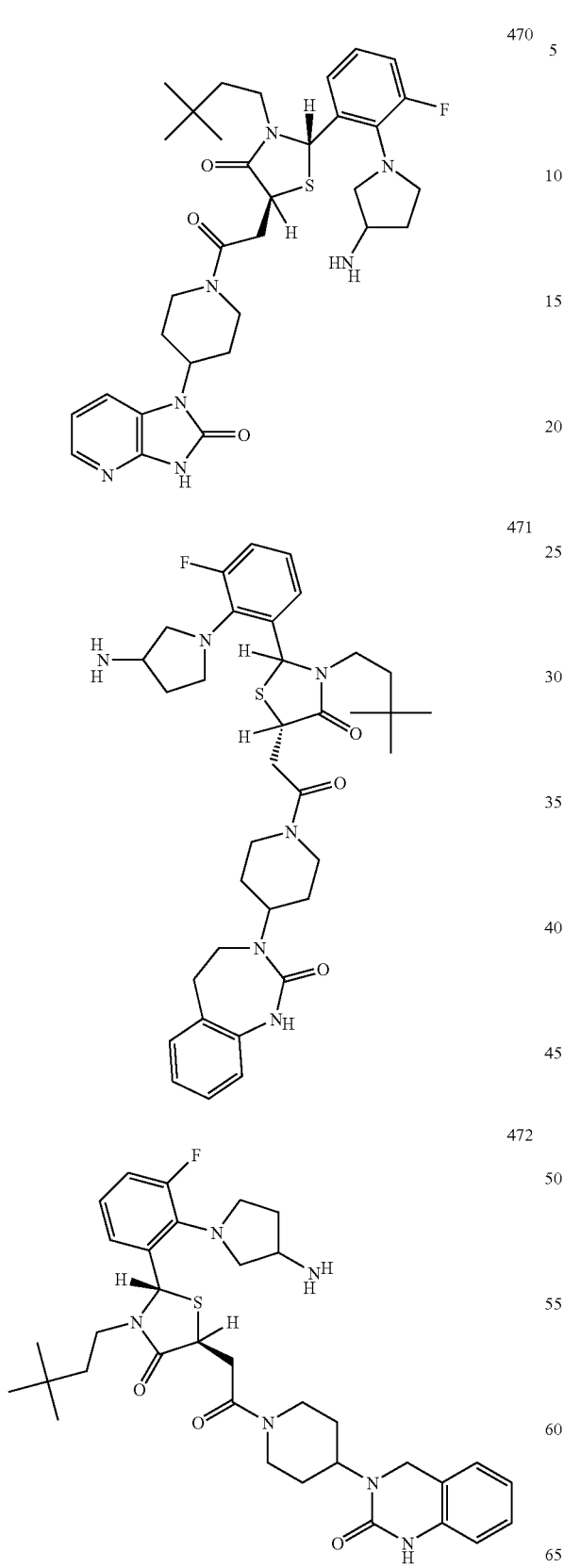
TABLE 1A-continued
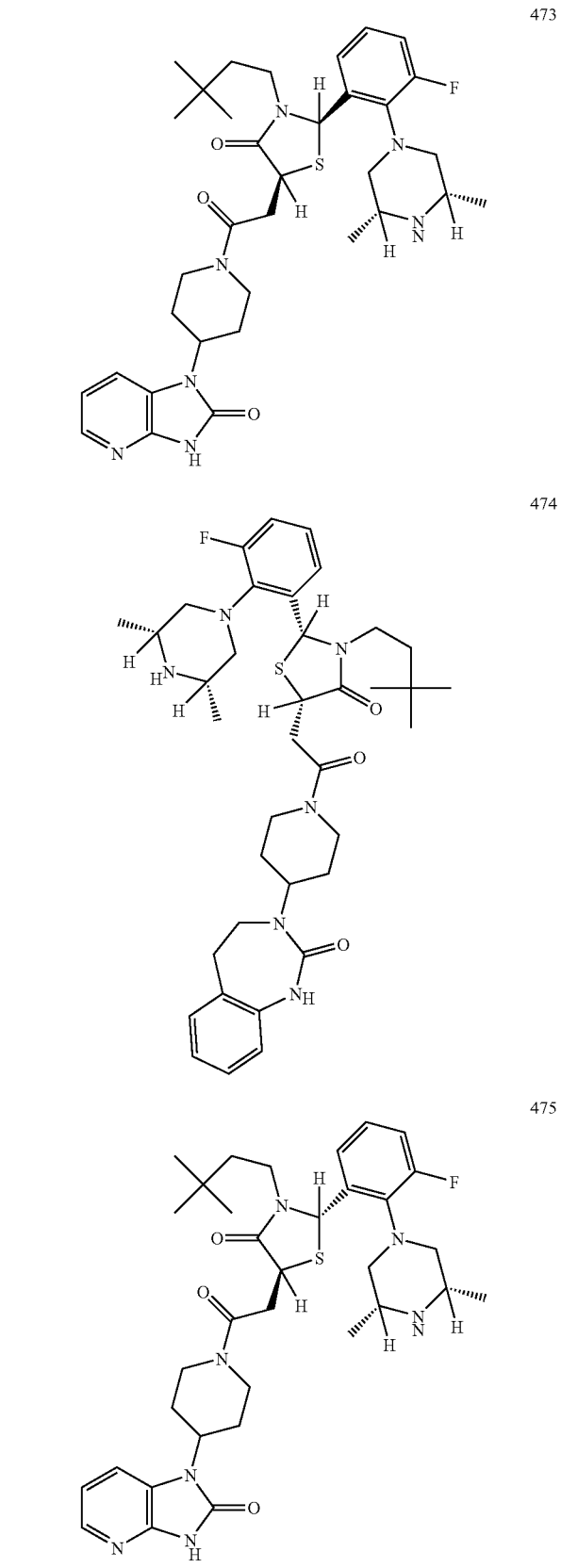

TABLE 1A-continued

476

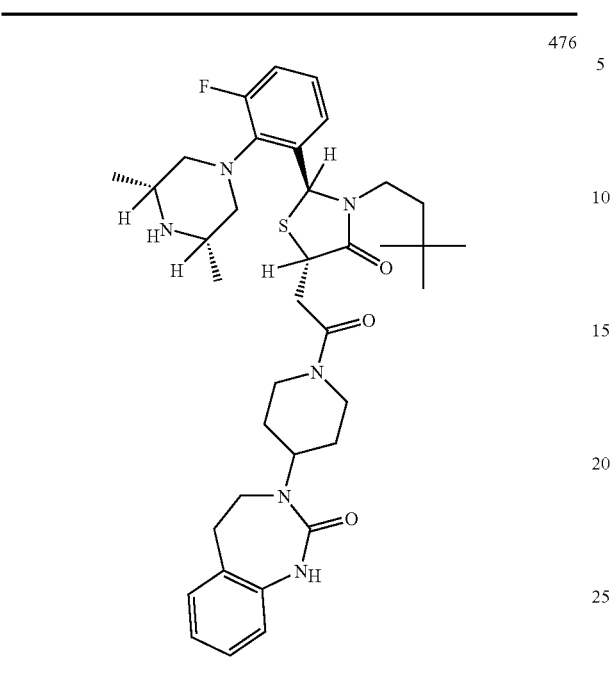

477

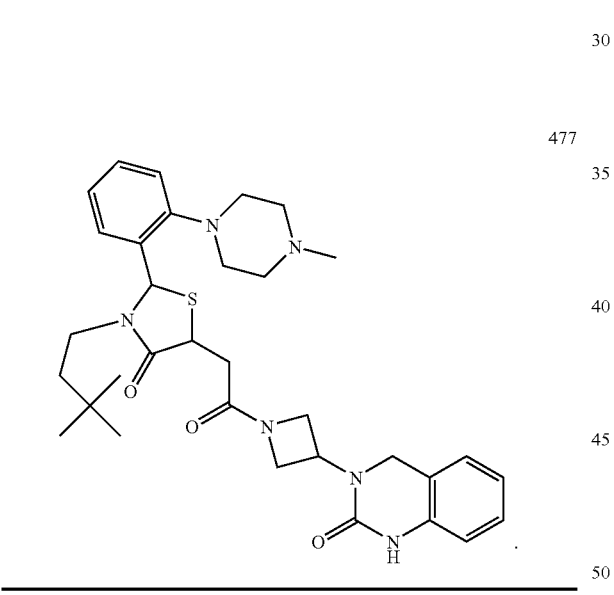

Compounds of the present invention may be readily prepared by methods well known in the art. Synthetic schemes for preparing the compounds of the present invention are shown below for illustrative purposes.

Scheme 1: Preparation of compounds of formula I:

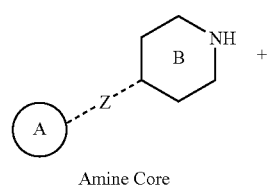

Amine Core

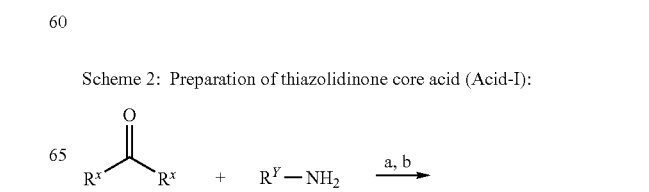

Thiazolidinone Acid Core a) HATU, D$^i$PEA, DMF, RT, 16 h.

Compounds of formula I are prepared as shown in Scheme 1 above, wherein an amine core, containing the ring A, and the thiazolidinone acid core are combined under suitable conditions to provide compounds of formula I.

Scheme 1A: Preparation of compounds of formula I:

Amine Core

Thiazolidinone Acid Core (I)

Scheme 2: Preparation of thiazolidinone core acid (Acid-I):

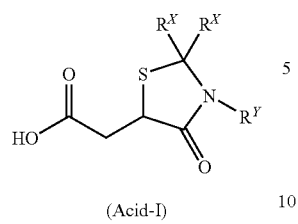

(Acid-I)

a) DMF or Toluene or benzene, 4Å molecular sieves, 80° C., 1-2 h
b) Mercaptosuccinic acid, 80° C., 16 h Scheme 3: Preparation of thiazolidinone core acid (Acid-II):

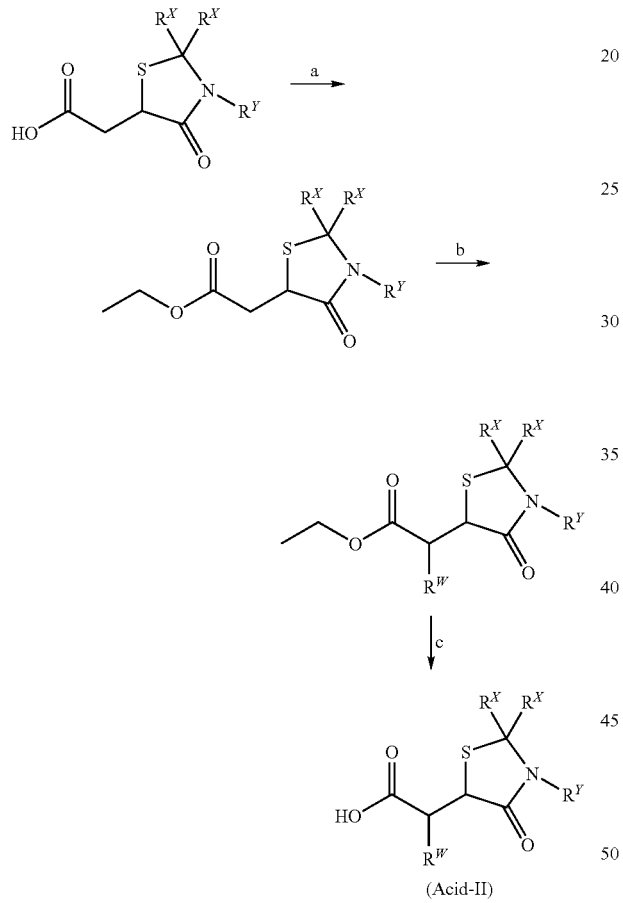

(Acid-II)

a) EtOH/H$_2$SO$_4$, 80° C., 24 h
b) LiHMDS, THF, 15 min, then R$^W$—LG, 0° C., to RT, 16 h
  NaOH (aq.), MeOH; wherein LG is a suitable leaving group.

Scheme 4: Preparation of thiazolidinone core acid (Acid-III):

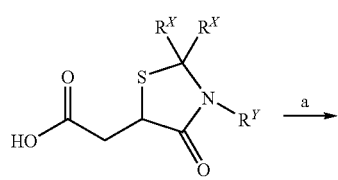

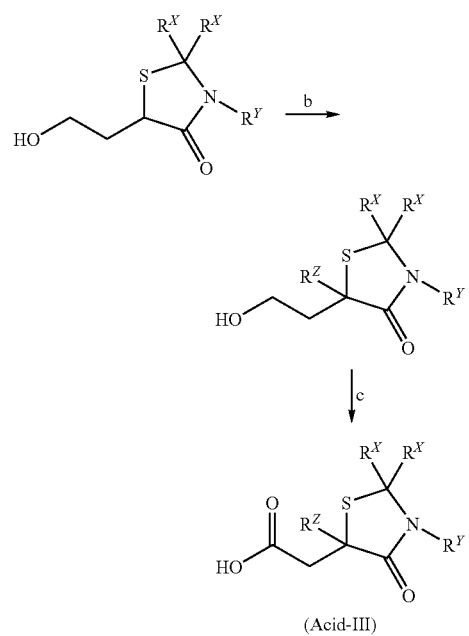

(Acid-III)

a) BOP, D$^i$PEA, THF, 6 h, then NaBH$_4$, RT
b) LiCl, LiHMDS, R$^Z$—LG, -78 C. ° C. to -40° C.;
  wherein LG is a suitable leaving group
c) Jones oxidation, 0° C.

Scheme 5: Preparation of thiazolidinone core acid (Acid-IV):

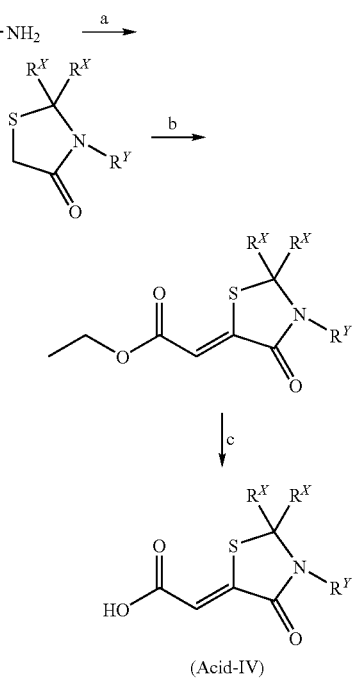

(Acid-IV)

a) THF/trimethoxyorthoformate, thioacetic acid, 80° C., 16 h or
  DMF, 2 h, 80° C., then thioacetic acid, 80° C., 16 h.
b) LDA, -78 C. ° C. to RT, then ethyl glyoxalate, RT, 16 h
c) NaOH (aq.), MeOH.

Scheme 6: Preparation of thiazolidinone core acid (Acid V):

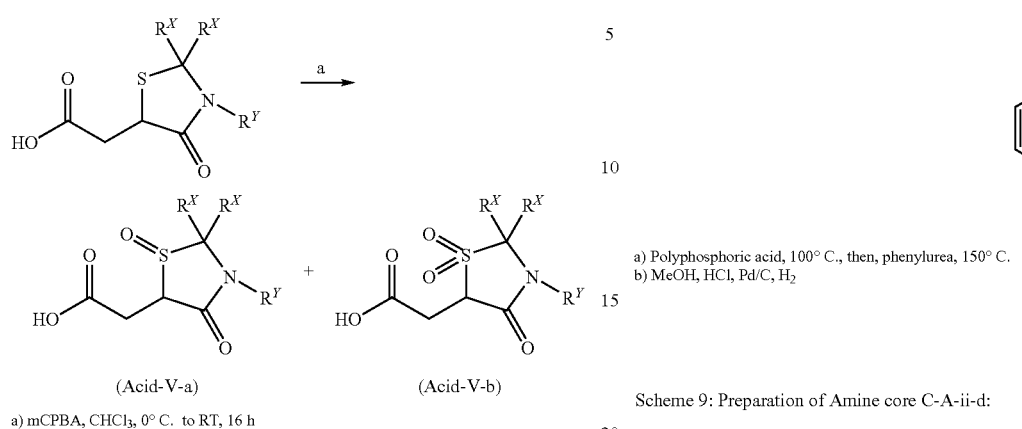

a) mCPBA, CHCl₃, 0° C. to RT, 16 h

Scheme 7: Preparation of Amine core (C-A-i-d):

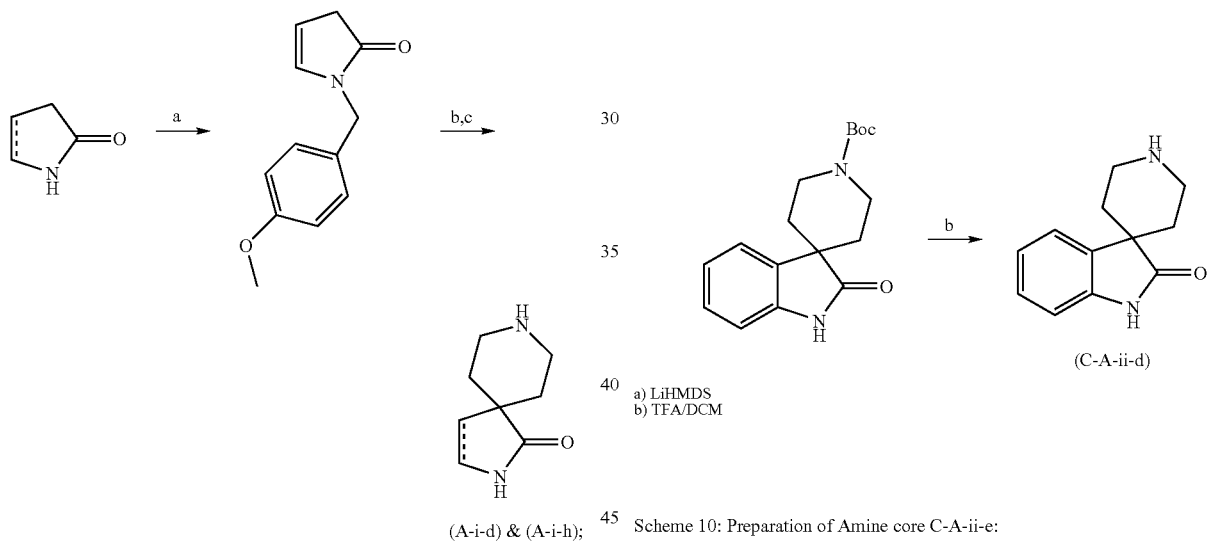

(A-i-d) & (A-i-h);

a) 4-Methoxybenzylchloride, TEA, DMF
b) tert-butyl bis(2-chloroethyl)carbamate, LDA, THF
c) TFA/DCM Amine core C-A-i-e, wherein ring A is A-i-e (see, supra) can be prepared using the method of Scheme 7.

Scheme 8: Preparation of Amine core C-A-ii-c:

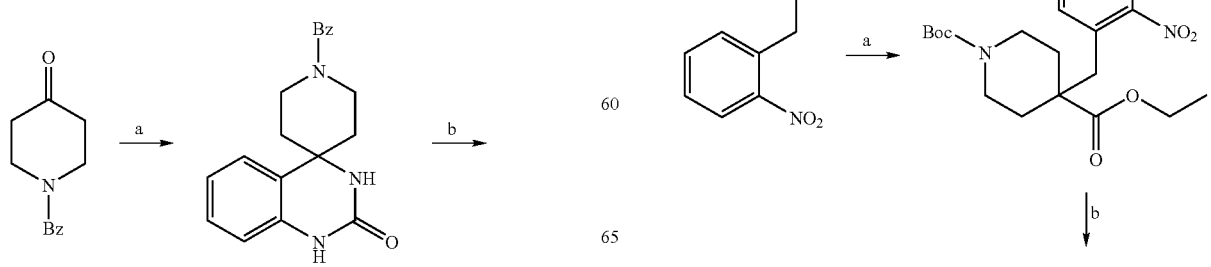

-continued

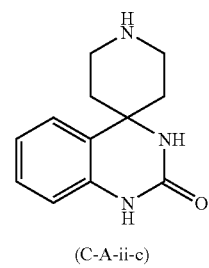

(C-A-ii-c)

a) Polyphosphoric acid, 100° C., then, phenylurea, 150° C.
b) MeOH, HCl, Pd/C, H₂

Scheme 9: Preparation of Amine core C-A-ii-d:

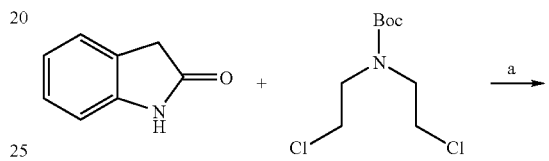

(C-A-ii-d)

a) LiHMDS
b) TFA/DCM

Scheme 10: Preparation of Amine core C-A-ii-e:

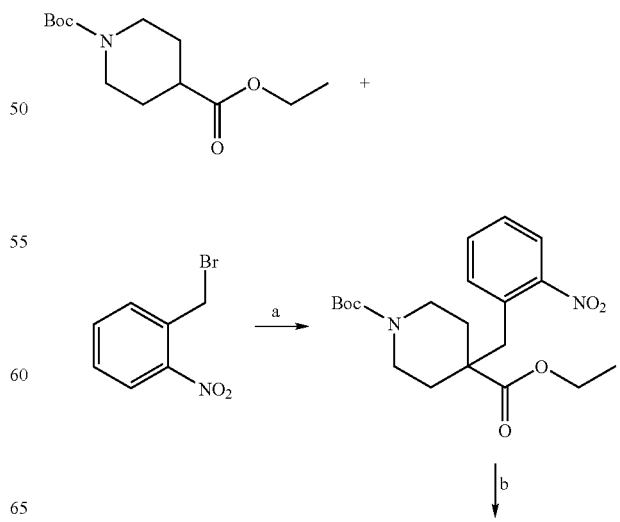

-continued

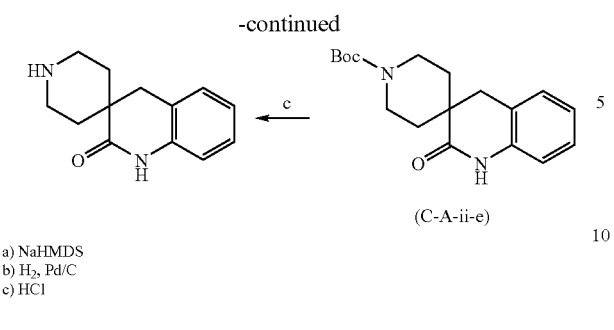

(C-A-ii-e)

a) NaHMDS
b) H$_2$, Pd/C
c) HCl

Scheme 11: Preparation of Amine core C-A-v-e:

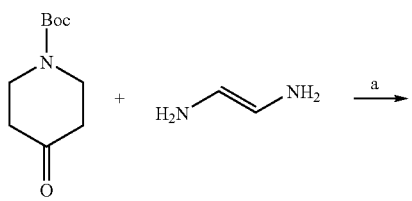

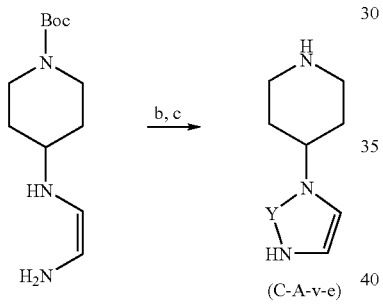

(C-A-v-e)

a) NaBH$_4$CN
b) CDI or SOCl$_2$ or 1,1'-Sulfonyldiimidazole
c) TFA/DCM

Amine cores C-A-v-a, C-A-v-c, and C-A-v-f, containing ring A embodiments, A-v-a, A-v-c, and A-v-f, respectively, can be readily prepared using the method of Scheme 11.

Scheme 12: Alternative Preparation of Amine core C-A-v-e:

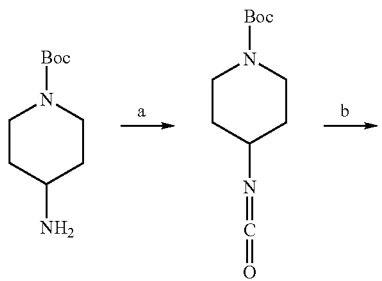

-continued

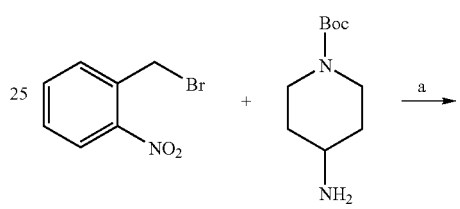

(C-A-v-e)

a) COCl$_2$
b) Aminoacetaldehyde dimethylacetal
c) TFA/DCM

Scheme 13: Preparation of Amine Core C-A-vi-a:

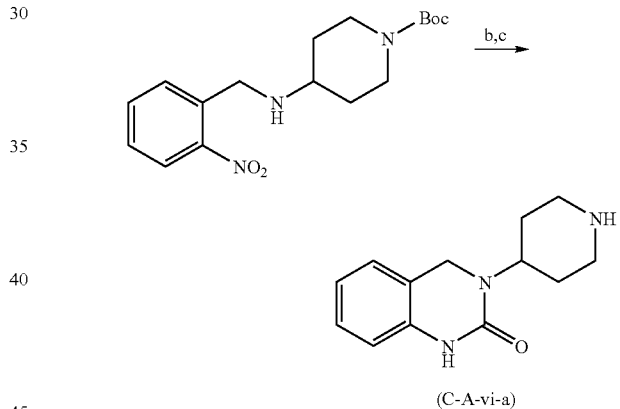

(C-A-vi-a)

a) TEA, DCM, RT, 16 h
b) CDI, THF/DCM, 16h.
c) TFA/DCM

Scheme 14: Preparation of Amine core C-A-vi-c:

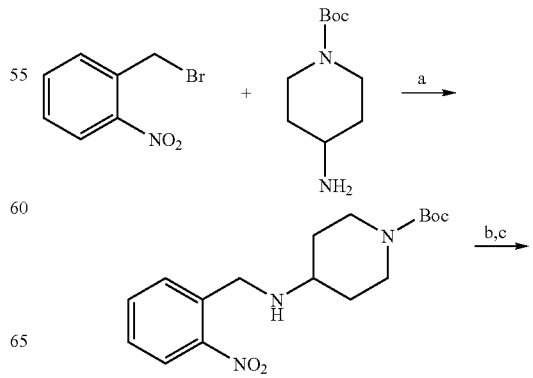

-continued

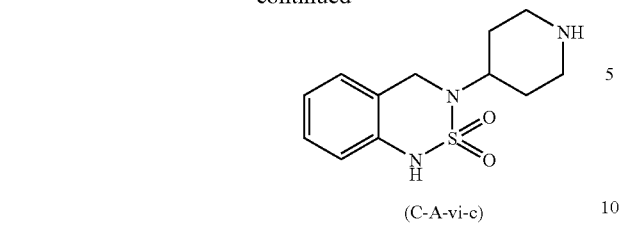

(C-A-vi-c)

a) TEA, DCM, RT, 16 h
b) 1,1′-Sulfonyldiimidazole, THF/DCM.
c) TFA/DCM

-continued

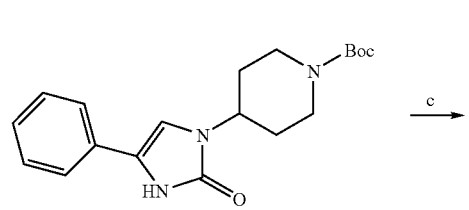

c →

Scheme 15: Preparation of Amine Core C-A-vi-f:

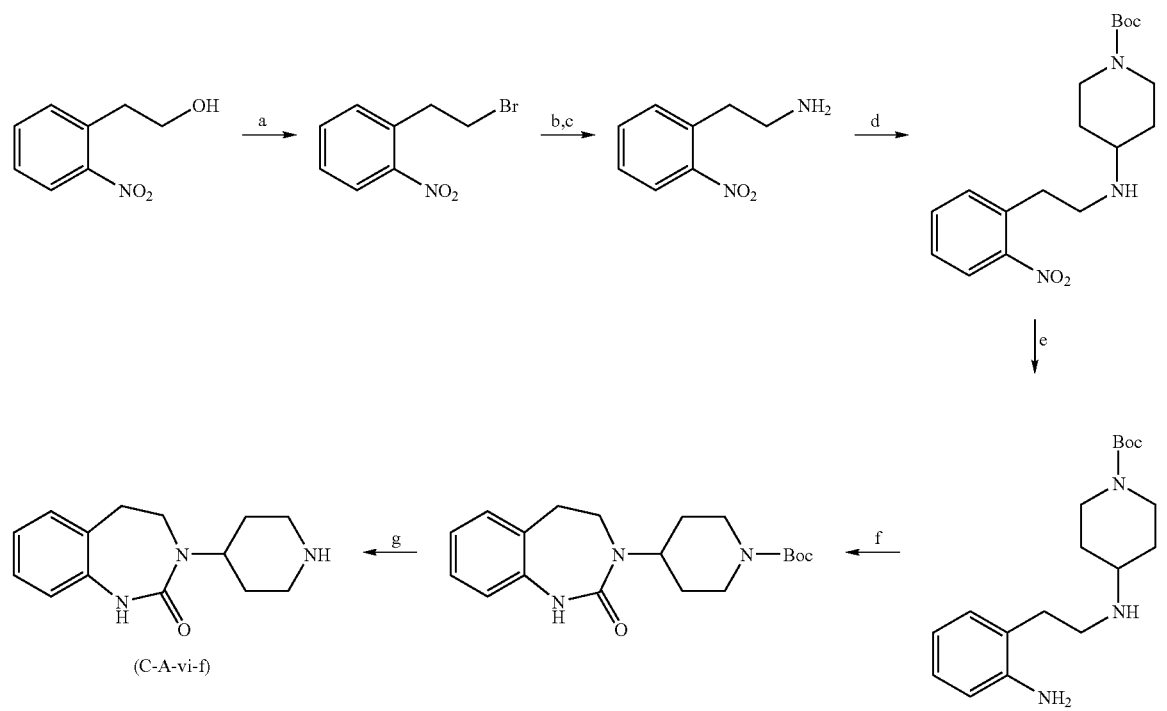

(C-A-vi-f)

a) PPh$_3$, CBr$_4$, DCM, 0° C. to RT, overnight
b) NaN$_3$, H$_2$O, CH$_3$CN
c) 1) PPh$_3$, toluene, RT, 16 hours;
   2) Acetic acid/48% HBr in Acetic acid, 100° C. 1h.
d) tert-butyl 4-oxopiperidine-1-carboxylate, NaBH(OAc)$_3$, AcOH, DMF
e) CDI, THF
f) TFA/DCM Scheme 16: Preparation of Amine Core A-v-e:

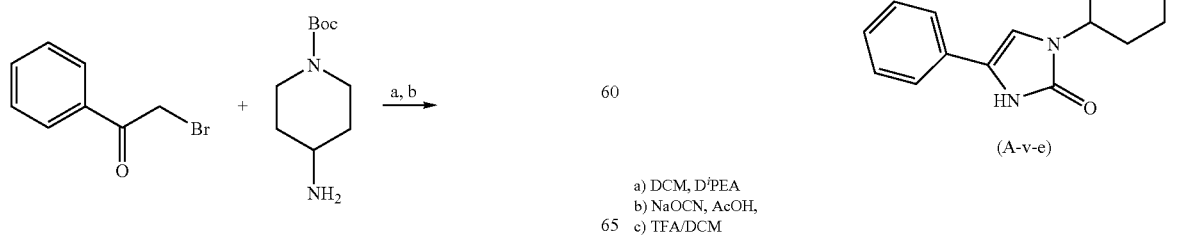

a) DCM, D$^i$PEA
b) NaOCN, AcOH,
c) TFA/DCM

-continued

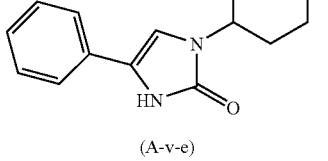

(A-v-e)

Scheme 17: Preparation of Amine Core A-v-f:
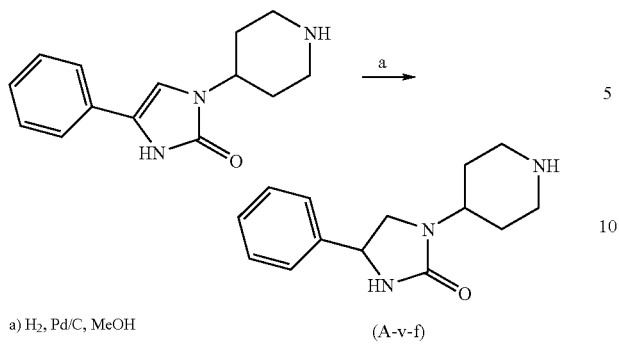
a) H₂, Pd/C, MeOH
(A-v-f)
Scheme 18: Preparation of Amine Core A-v-g:
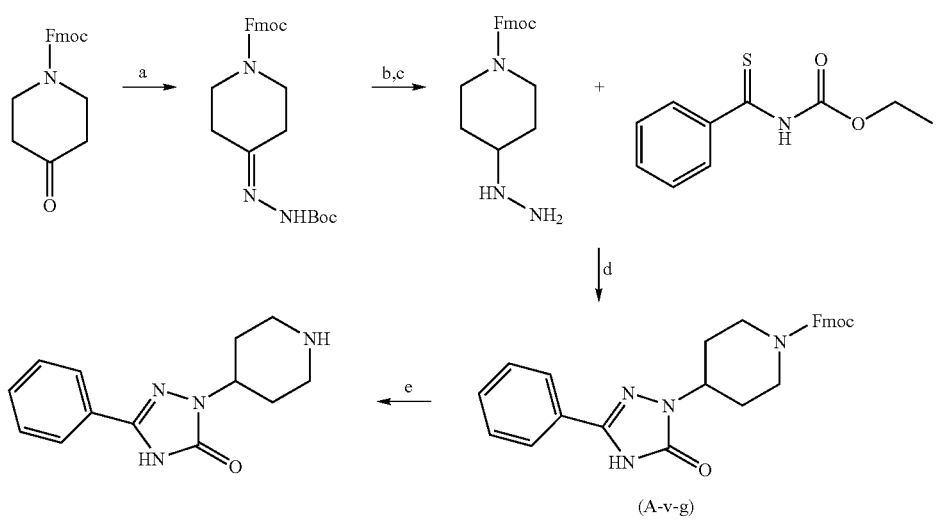
(A-v-g)
a) H₂NNHBoc, EtOH
b) PtO₂, AcOH, H₂
c) TFA
d) D^iPEA, THF
e) Et₂NH, THF
Scheme 19: Preparation of Amine Core A-vi-h:
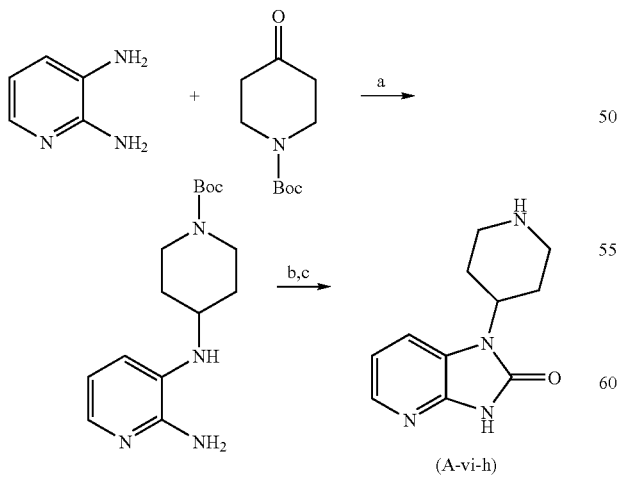
(A-vi-h)
a) NaBH(OAc)3, DCE
b) CDI, CH₃CN
c) HCl, Et₂O Scheme 20: Preparation of Amine Core A-vi-i:

(A-vi-i)

a) 2,4-Dimethoxybenzylamine, DMA, TEA
b) LiAlH₃, THF
c) tert-butyl 4-oxopiperidine-1-carboxylate, NaBH(OAc)3, AcOH, DCE
d) CDI, DMF
e) TFA/DCM Scheme 21: Preparation of Amine Core A-ii-h:

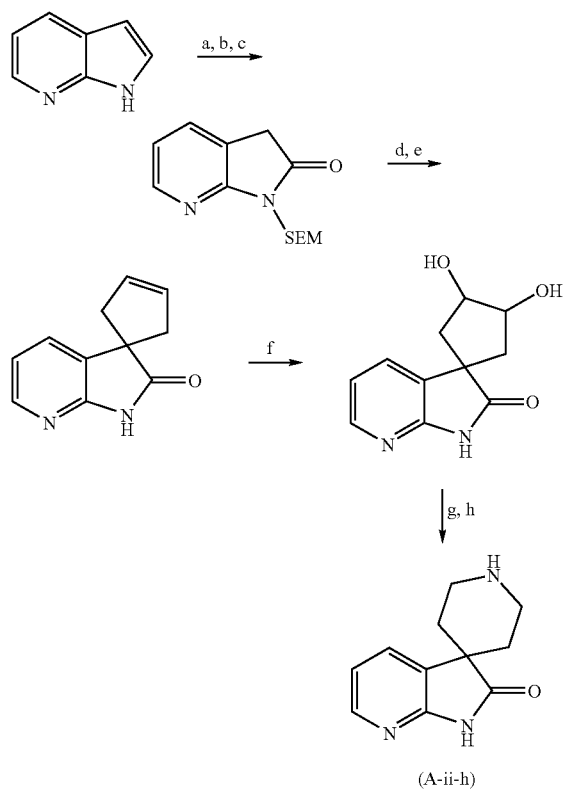

(A-ii-h)

a) NaH, SEM-Cl, DMF
b) Pyridinehydrobromide perbromide, dioxane
c) Zn, AcOH
d) cis-1,4-dichlorobut-2-ene, Cs₂CO₃, DMF
e) TFA/DCM
f) OsO₄, Me₃N-O, DCM
g) NaIO₄, EtOH, H₂O
h) NH₄OH, H₂, Pd/C Scheme 22: Preparation of Amine Core A-ii-i:

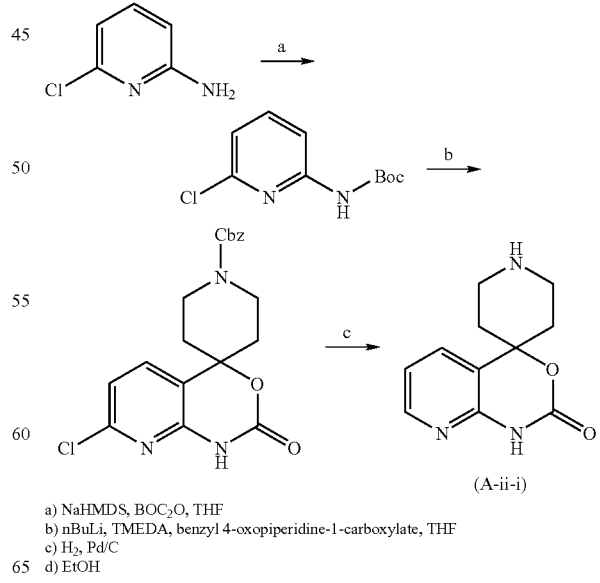

(A-ii-i)

a) NaHMDS, BOC₂O, THF
b) nBuLi, TMEDA, benzyl 4-oxopiperidine-1-carboxylate, THF
c) H₂, Pd/C
d) EtOH Scheme 23: Preparation of Amine Core A-i-h:
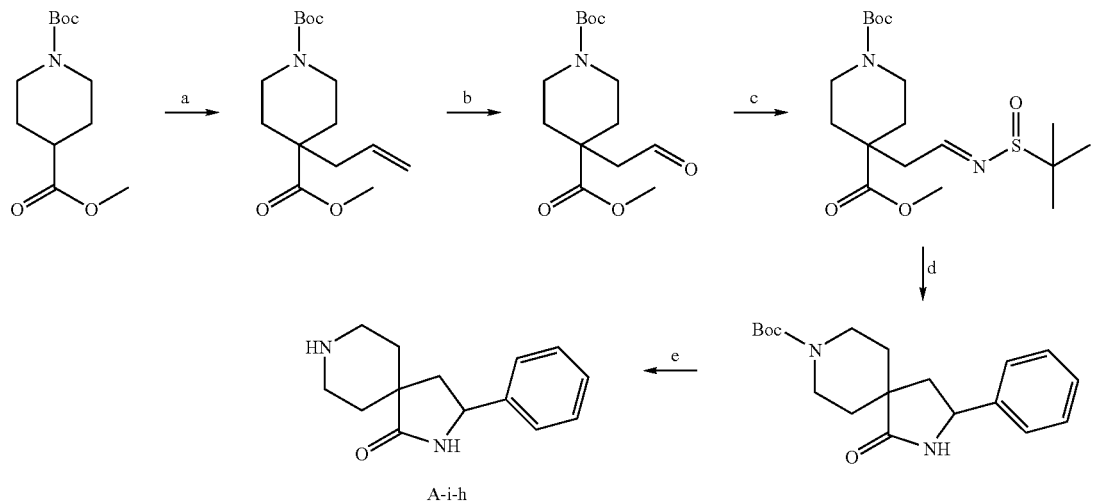
a) KHMDS, allylbromide, THF
b) O$_3$, MeOH, DCM, then Me$_2$S
c) $^t$BuSONH$_2$, CuSO$_4$, DCE
d) PhLi, Et$_2$O
e) HCl, MeOH
Scheme 24: Preparation of Amine Core A-ii-j:
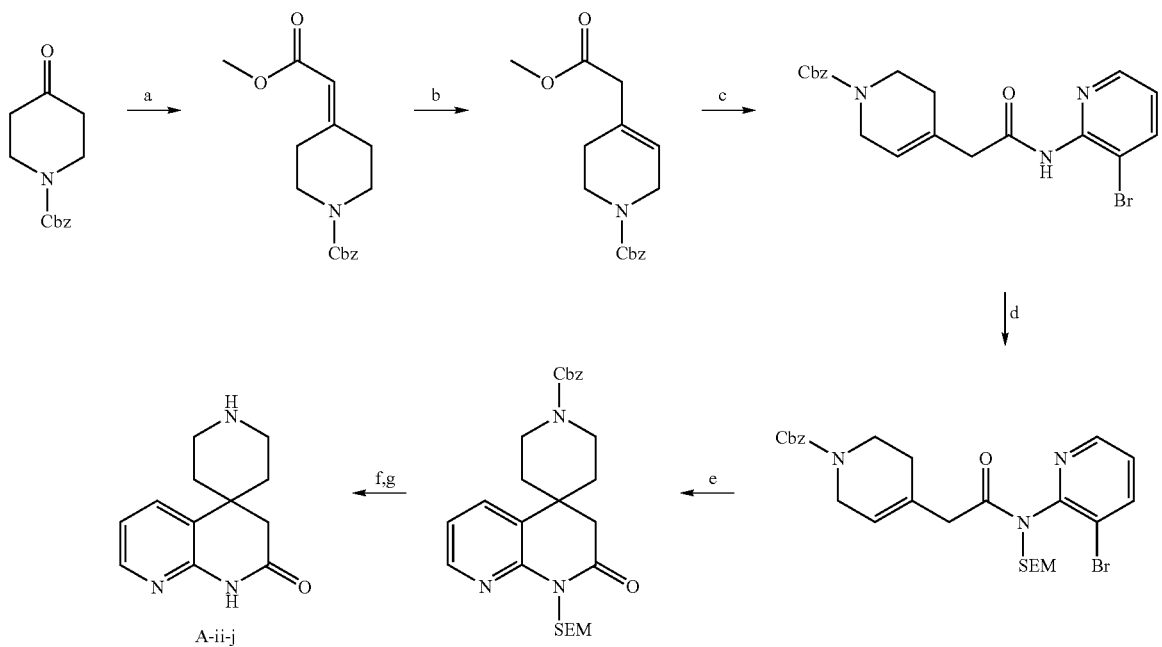
a) (2-Methoxy-2-oxoethyl)(triphenyl)phosphonium chloride, benzene
b) DBU, DMF
c) 3-Bromo-2-aminopyridine, AlMe$_3$, DCE
d) NaH, SEM-Cl, THF
e) Pd($^t$Bu$_3$)$_2$, dicyclohexylmethylamine, dioxane
f) TFA
g) H$_2$, Pd/C Scheme 25: Preparation of Amine Core A-i-i:
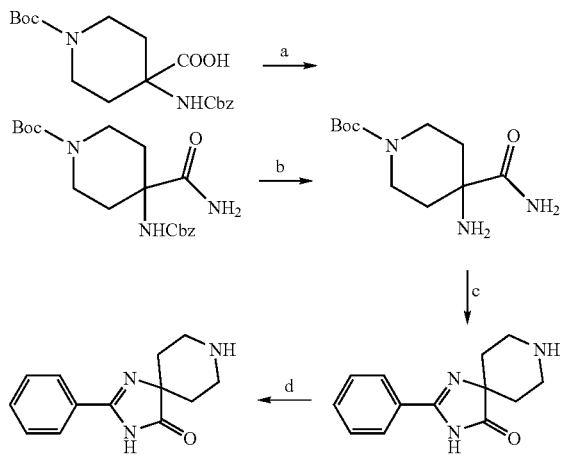
a) EDC, HOBt, NH$_3$, TEA, DMF
b) H$_2$, Pd/C, EtOH
c) 1-(Trimethoxymethyl)benzene, toluene
d) TFA/DCM
Scheme 26: Preparation of Amine Core A-i-j:
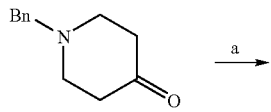
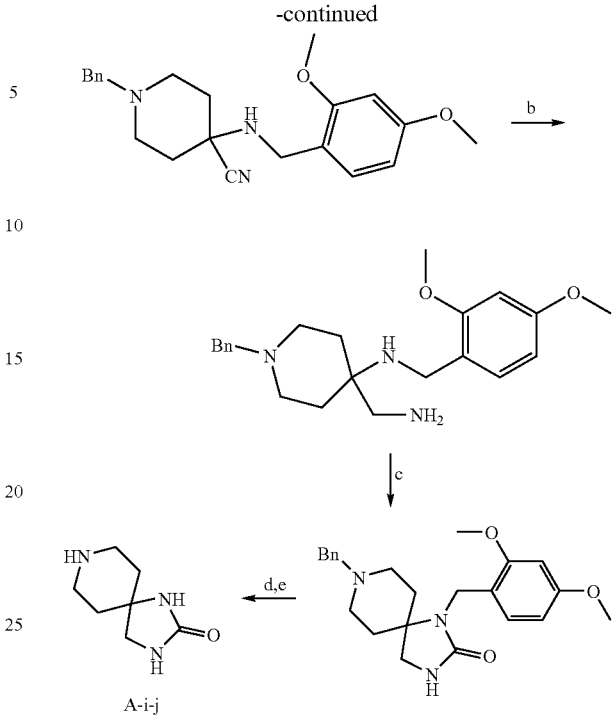
a) 2,4-Dimethoxybenzylamine, TMSCN
b) H$_2$, Rh/alumina
c) CDI
d) TFA/DCM
e) H$_2$, Pd/C
Scheme 27: Preparation of Amine Core A-i-k:
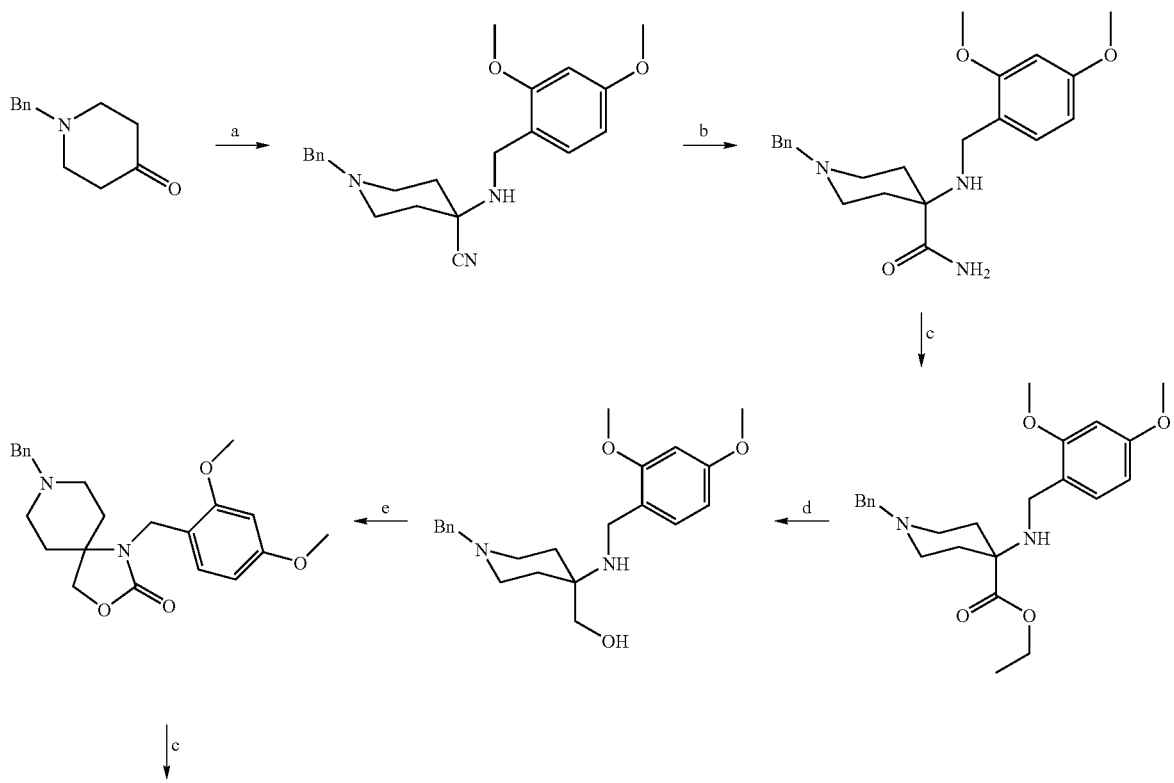

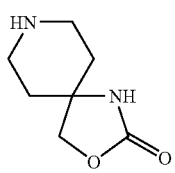

A-i-k a) 2,4-Dimethoxybenzylamine, TMSCN
b) H$_2$SO$_4$
c) 1) KOH
   2) H$_2$SO$_4$, KOH
d) LiAlH$_4$
e) CDI
f) 1) TFA/DCM
   2) H$_2$, Pd/C Scheme 28: Preparation of Amine Core A-i-l:

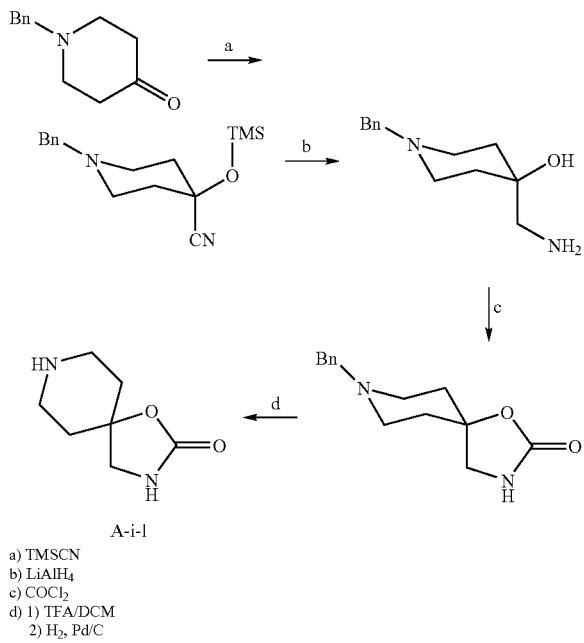

A-i-l a) TMSCN
b) LiAlH$_4$
c) COCl$_2$
d) 1) TFA/DCM
   2) H$_2$, Pd/C

Amine core A-i-a may be prepared according to the method disclosed in WO2005097795. Amine core A-ii-a may be prepared according to the method disclosed in US2006293281. Amine core A-ii-a wherein the fused 6-membered ring is pyridyl may be prepared according to the method disclosed in WO2007016087. Amine core A-v-b may be prepared according to the method disclosed in WO2006044504. Amine core A-v-i may be prepared according to the method disclosed in WO2006044504. Amine core A-vi-b as the HCl salt may be prepared according to the method disclosed in WO2005056550. Amine core A-vi-d may be prepared according to the method disclosed in Chem. Pharm. Bull., 34(5), pp. 1907-1916 (1986). Amine core A-vi-e is commercially available. Amine core A-v-h may be prepared according to the method disclosed in WO2007016087. Other amine cores not described in the schemes, experimentals, or referenced herein, can be prepared by methods known to one of skill in the art.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an active metabolite or residue thereof. As used herein, the term "active metabolite or residue thereof" means that a metabolite or residue thereof is also an antagonist of CGRP.

Pharmaceutically acceptable salts are well known in the art. For example, S. M. Berge, et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar--agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The compounds of the present invention are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; encephalitis; brain trauma; epilepsy; neurodegenerative diseases; skin diseases; neurogenic cutaneous redness, skin rosaceousness and erythema; tinnitus; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The compounds of the present invention are further useful in a method for the prevention, treatment, control, amelioration, or reduction of risk of the diseases, disorders and conditions noted herein.

The compounds of the present invention are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-inflammatory or analgesic agent or an anti-migraine agent, such as an ergotamine or 5-HT.sub.1 agonists, especially a 5-HT.sub.1B/1D agonist, for example sumatriptan, naratriptan, zolmitriptan, eletriptan, almotriptan, frovatriptan, donitriptan, and rizatriptan; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as aspirin, ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or a steroidal analgesic. Similarly, the instant compounds may be administered with a pain reliever such as acetaminophen, phenacetin, codeine, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; a tricyclic antidepressant, for example amitriptyline, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with ergot alkaloids, for example ergotamine, ergonovine, ergonovine, methylergonovine, metergoline, ergoloid mesylates, dihydroergotamine, dihydroergocomine, dihydroergocristine, dihydroergocryptine, dihydro-I-ergocryptine, dihydro-.theta.-ergocryptine, ergotoxine, ergocomine, ergocristine, ergocryptine, I-ergocryptine, .theta.-ergocryptine, ergosine, ergostane, bromocriptine, or methysergide.

Additionally, the present compounds may be used in conjunction with a beta-adrenergic antagonist such as timolol, propanolol, atenolol, or nadolol, and the like; a MAO inhibitor, for example phenelzine; a calcium channel blocker, for example flunarizine, nimodipine, lomerizine, verapamil, nifedipine, prochlorperazine or gabapentin; neuroleptics such as olanzapine and quetiapine; an anticonvulsant such as topiramate, zonisamide, tonabersat, carabersat or divalproex sodium; an angiotensin II antagonist, for example losartan and candesartan cilexetil; an angiotensin converting enzyme inhibitor such as lisinopril; or botulinum toxin type A.

The present compounds may be used in conjunction with a potentiator such as caffeine, an H2-antagonist, simethicone, aluminum or magnesium hydroxide; a decongestant such as phenylephrine, phenylpropanolamine, pseudoephedrine, oxymetazoline, epinephrine, naphazoline, xylometazoline, propylhexedrine, or levo-desoxy-ephedrine; an antitussive such as codeine, hydrocodone, caramiphen, carbetapentane, or dextromethorphan; a diuretic; a prokinetic agent such as metoclopramide or domperidone, and a sedating or non-sedating antihistamine.

In a particularly preferred embodiment the present compounds are used in conjunction with an anti-migraine agent, such as: an ergotamine; a 5-HT.sub.1 agonist, especially a 5-HT.sub.1B/1D agonist, in particular, sumatriptan, naratriptan, zolmitriptan, eletriptan, almotriptan, frovatriptan, donitriptan and rizatriptan; and a cyclooxygenase inhibitor, such as a selective cyclooxygenase-2 inhibitor, in particular, rofecoxib, etoricoxib, celecoxib, meloxicam, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

In order that the invention described herein may be more fully understood, the following examples are set forth. It should be understood that these examples are for illustrative purposes only and are not to be construed as limiting this invention in any manner.

EXAMPLES

General LC/MS Methods

LC/MS data were acquired using a PESciex API-150-EX LC/MS, Shimadzu LC-8A pumps, Gilson 215 autosampler, Gilson 819 injection module, 3.0 mL/min flow rate, 10-99% $CH_3CN$ (0.035% TFA)/$H_2O$ (0.05% TFA) gradient, Phenomenex Luna 5u C18 column (50×4.60 mm), Shimadzu SPD-10A UV/Vis detector, Cedex 75 ELSD detector.

Mass Spec Method for Separating Diasteromeric Mixtures:

A Semi-Prep Gilson HPLC was used to purify various diastereomeric mixtures in the present invention using Gilson 322 pumps, a Gilson 215 liquid handler, a Gilson 819 injection module. Flow rate was 15.0 mL/min using a gradient of 20-70% CH3CN (0.1% TFA)/H2O (0.1% TFA) on an Agilent Zorbax, SB-C18 column (21.2×100 mm, 5 um) monitoring with a Gilson 156 UV/Vis detector.

tert-Butyl 4-(1,2-dihydro-2-oxo-5-phenylimidazol-3-yl)piperidine-1-carboxylate

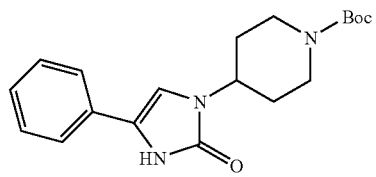

tert-Butyl 4-(1,2-dihydro-2-oxo-5-phenylimidazol-3-yl) piperidine-1-carboxylate was synthesised as described in J. Med. Chem., 2005, 48, 5921. A solution of 2-bromo-1-phenylethanone (5 g, 25 mmol) in DCM (10 ml) was added dropwise to a stirred solution of tert-butyl 4-aminopiperidine-1-carboxylate (6 g, 30 mmol) and D'PEA (9.84 ml, 57.5 ml) in DCM (50 ml) over 1 hour, the reaction mixture was then stirred at room temperature for 16 hours. Sodium cyanate (3.41 g, 52.5 mmol) was added, the reaction mixture was then cooled to 0° C., the pH was brought to pH 4 with acetic acid and the reaction mixtures was stirred from 0° C. to RT over 16 hours. The reaction mixture was poured into water and extracted with DCM (3×). Organics combined, washed with water (3×), brine, dried (MgSO$_4$) and evaporated to dryness. The residue was triturated with ether, filtered and the solid was washed with ether to give a pale yellow solid (4.04 g, 47%). LC/MS (10% to 99%): M/Z (M+H)$^+$ (obs)=344; $t_R$=3.01.

5-Phenyl-3-(piperidin-4-yl)-1H-imidazol-2(3H)-one

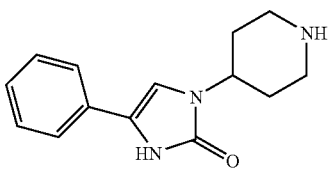

To a solution of tert-butyl 4-(1,2-dihydro-2-oxo-5-phenylimidazol-3-yl)piperidine-1-carboxylate (4 g) in DCM (20 ml) was added TFA (4 ml) and the reaction mixture was stirred at RT for 4 hours. Evaporation gave the TFA salt of the desired product (Quant.). LC/MS (10% to 99%): M/Z (M+H)$^+$ (obs)=244; $t_R$=1.06.

tert-Butyl 4-(2-nitrobenzylamino)piperidine-1-carboxylate

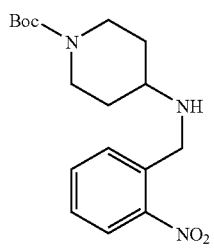

A solution of 1-(bromomethyl)-2-nitrobenzene (13.2 g, 61 mmol) in DCM (60 ml) was added dropwise to a solution of tert-butyl 4-aminopiperidine-1-carboxylate (14.6 g, 73 mmol) and TEA (13.4 ml, 91 mmol) in DCM (100 ml), followed by stirring the reaction mixture for a further 16 hours. The reaction mixture was then poured into water, and the layers separated. The aqueous layer was then extracted with DCM (2×). The organic layers were combined, washed with water (2×), brine, dried (MgSO$_4$) and evaporated to dryness. The residue was taken up in EtOAc and filtered through a large plug of silica. The silica was washed with EtOAc until TLC analysis show no further material was eluting. Evaporation gave the product as an orange oil (24 g, 74%). LC/MS (10% to 99%): M/Z (M+H)$^+$ (obs)=336; $t_R$=2.23.

tert-Butyl 4-(2-aminobenzylamino)piperidine-1-carboxylate

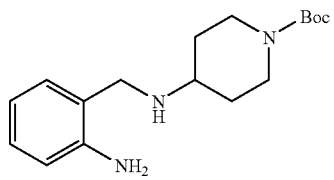

A solution of tert-Butyl 4-(2-nitrobenzylamino)piperidine-1-carboxylate (24 g, 71.6 mmol) in MeOH (150 ml) was stirred under an atmosphere of hydrogen for 24 hours. The reaction mixture was filtered and evaporated to give the crude amine, which was used without further purification.

tert-Butyl 4-(1,2-dihydro-2-oxoquinazolin-3(4H)-yl) piperidine-1-carboxylate

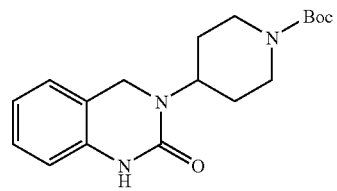

To a solution of tert-butyl 4-(2-nitrobenzylamino)piperidine-1-carboxylate (13.2 g, 43.2 mmol) in THF (400 ml) was added a solution of CDI (7.7 g, 47.5 mmol) in 1:1 DCM:THF (100 ml) dropwise over 1 hour followed by stirring the reaction mixture for a further 16 hours. The reaction mixture was evaporated to give an oil that, when treated with EtOAc, precipitated the desired product. The precipitate was washed with cold EtOAc and dried to give a yellow solid (3.5 g). LC/MS (10% to 99%): M/Z (M+H)$^+$ (obs)=332; $t_R$=3.01.

3,4-Dihydro-3-(piperidin-4-yl)quinazolin-2(1H)-one

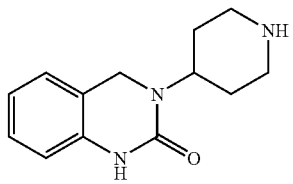

To a solution of tert-Butyl 4-(1,2-dihydro-2-oxoquinazolin-3(4H)-yl)piperidine-1-carboxylate (3.5 g, 10.6 mmol) in DCM (20 ml) was added TFA (15 ml) and the reaction mixture was stirred at RT for 2 h. The reaction mixture was evaporated, then co-evaporated with EtOH (2×), to give the TFA salt of the desired product (Quant.). LC/MS (10% to 99%): M/Z (M+H)$^+$ (obs)=232; $t_R$=0.38.

1-(2-Bromoethyl)-2-nitrobenzene

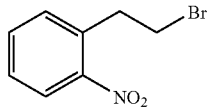

To a solution of 1-(2-hydroxyethyl)-2-nitrobenzene (21 ml, 150 mmol) and triphenylphosphine (39.2 g, 150 mmol) in DCM (400 ml) at 0° C. was add CBr₄ (49.5 g, 150 mmol) in portions and the reaction mixture was stirred from 0° C. to RT overnight. The reaction mixture was quenched with sat. aq. Na₂CO₃, the layers were separated and the organic layer was washed with brine, dried (MgSO₄) and evaporated to dryness. The residue was treated with EtOAc and the precipitated Ph₃O was filtered and the solvent removed. This was repeated twice more. Purification by column chromatography (0% to 10% EtOAc in Hx) gave an oil that solidified on standing.

2-(2-Nitrophenyl)ethanamine

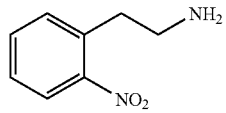

To a solution of 1-(2-Bromoethyl)-2-nitrobenzene (6.96 g, 30.5 mmol) in CH₃CN was added a solution of NaN₃ (6 g, 91.6 mmol) in water (20 ml) and the reaction mixture was refluxed for 20 hours. The solution was cooled and extracted with DCM (3×). The organics were combined, washed with brine, dried (MgSO₄) and evaporated to dryness. The residue was taken up in toluene (160 ml) and to this was added PPh₃ (8 g, 30.5 mmol) and the reaction mixture was stirred at RT for 16 hours. The solvent was evaporated to dryness and the residue was treated with acetic acid (30 ml) and 48% HBr in acetic acid (30 ml) at 100° C. for 1 h. The reaction mixture was cooled, concentrated and extracted with DCM. The aqueous was brought to pH ~10 with NaOH (aq.) and extracted with EtOAc (3×). The organics were combined, washed with brine, dried (MgSO₄) and evaporated to dryness (4.2 g).

tert-Butyl 4-(2-nitrophenethylamino)piperidine-1-carboxylate

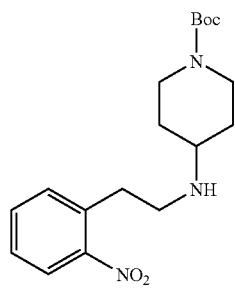

A stirred solution of 2-(2-nitrophenyl)ethanamine (4 g, 24 mmol) and tert-butyl 4-oxopiperidine-1-carboxylate (4.8 g, 24 mmol) in MeOH (48 ml) was brought to pH 5 by the addition of acetic acid. NaBH3CN (2.3 g, 36 mmol) was added and the reaction mixture was stirred at RT for 3 hours. The solvent was evaporated and the residue was taken up in EtOAc and sat. aq. Na₂CO₃. The layers were separated and the organic layer was washed with brine, dried (Na₂SO₄) and evaporated to dryness. Purification by column chromatography (0% to 7% MeOH in DCM) gave the desired product. LC/MS (10% to 99%): M/Z (M+H)⁺ (obs)=350; $t_R$=2.22.

tert-Butyl 4-(2-aminophenethylamino)piperidine-1-carboxylate

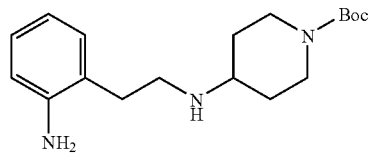

To a solution of tert-butyl 4-(2-nitrophenethylamino)piperidine-1-carboxylate (10.5 g) in EtOH (180 ml) was added 10% Pd/C (1.05 g) and the reaction mixture was stirred at RT under an atmosphere of H₂ overnight. The reaction mixture was filtered and the resulting solution was evaporated to dryness giving the desired product (9.6 g). LC/MS (10% to 99%): M/Z (M+H)⁺ (obs)=320; $t_R$=2.06.

tert-Butyl 4-(1,2,4,5-tetrahydro-2-oxobenzo[d][1,3]diazepin-3-yl)piperidine-1-carboxylate

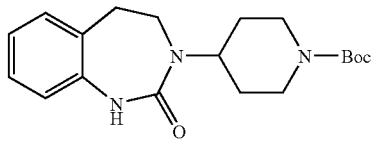

To a solution of tert-butyl 4-(2-aminophenethylamino)piperidine-1-carboxylate (6.9 g, 30 mmol) in DMF (110 ml) was added CDI (4.86 g, 30 mmol) in portions followed by stirring the reaction mixture at RT for 2 h. The reaction mixture was diluted with water and extracted with EtOAc. The organics were combined, washed with water, brine, and evaporated to dryness to give the desired product. LC/MS (10% to 99%): M/Z (M+H)⁺ (obs)=346; $t_R$=3.24.

4,5-Dihydro-3-(piperidin-4-yl)-1H-benzo[d][1,3]diazepin-2(3H)-one

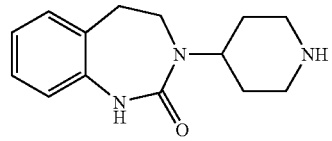

To a solution of tert-butyl 4-(1,2,4,5-tetrahydro-2-oxobenzo[d][1,3]diazepin-3-yl)piperidine-1-carboxylate (10 g, 2.89 mmol) in DCM (5 ml) was added TFA (5 ml) and the reaction mixture was stirred at RT for 1 h. The reaction mixture was evaporated, then co-evaporated with EtOH (2×), to give the TFA salt of the desired product (Quant.). LC/MS (10% to 99%): M/Z (M+H)+ (obs)=246; $t_R$=1.75.

tert-Butyl 4-(2-aminopyridin-3-ylamino)piperidine-1-carboxylate

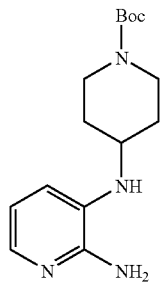

To a solution of 2,3-diaminopyridine (3.0 g, 27.5 mmol) in DCE (45 ml) was added tert-butyl 4-oxopiperidine-1-carboxylate (5.75 g, 28.8 mmol) and the reaction mixture stirred for 5 min at RT before the portion-wise addition of NaBH(Oac)$_3$ (8.7 g, 41.7 mmol) and continued stirring at RT until the reaction judged complete by LCMS. The reaction was quenched with 5% NaOH, the layers separated and the organic layer was dried over Na$_2$SO$_4$. Evaporation gave the desired product as a brown solid (4.96 g). LC/MS (10% to 99%): M/Z (M+H)+ (obs)=293; $t_R$=2.31.

tert-Butyl 4-(2,3-dihydro-2-oxoimidazo[4,5-b]pyridin-1-yl)piperidine-1-carboxylate

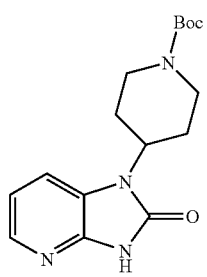

To a solution of tert-Butyl 4-(2-aminopyridin-3-ylamino)piperidine-1-carboxylate (3.0 g, 10.3 mmol) in CH$_3$CN (206 ml) at RT was added CDI (4.2 g, 25.7 mmol) in portions and the reaction mixture was stirred at RT for 16 hours. The reaction mixture was evaporated to dryness and the residue was take up in DCM and water. The layers were separated and the organic layer was washed with brine, dried (Na$_2$SO$_4$) and evaporated to dryness. Purification by column chromatography (1-10% MeOH in DCM) gave the desired solid as a beige solid (3.55 g). LC/MS (10% to 99%): M/Z (M+H)+ (obs)=319; $t_R$=2.31.

1-(Piperidin-4-yl)-1H-imidazo[4,5-b]pyridin-2(3H)-one

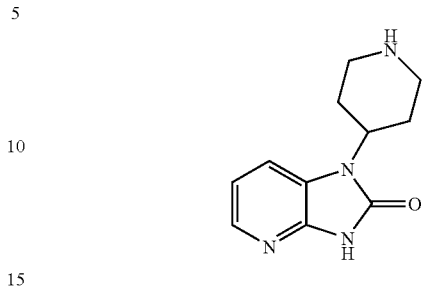

A solution of tert-butyl 4-(2,3-dihydro-2-oxoimidazo[4,5-b]pyridin-1-yl)piperidine-1-carboxylate (3.39 g, 10.7 mmol) in 2N HCl in Et$_2$O (20 ml) was stirred from 0° C. to RT over 2 h. The solvent was evaporated and the residue triturated with Et$_2$O, filtered washed with Et$_2$O and dried to give the bis-HCl Salt of the desired product (2.62 g). LC/MS (10% to 99%): M/Z (M+H)+ (obs)=219; $t_R$=0.36.

2-(2,4-Dimethoxybenzylamino)pyridine-3-carbonitrile

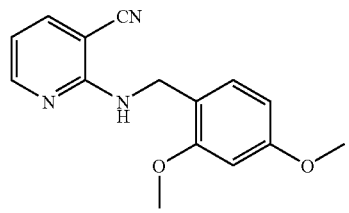

To a solution of 2-chloro-3-cyanopyridine (4.0 g, 28.9 mmol) in DMA (58 ml) was added 2,4-dimethoxybenzealdehyde (5.2 ml, 34.6 mmol) and TEA (4.8 ml (34.6 mmol) and the reaction mixture stirred at 80° C. for 4 hours. The reaction mixture was poured into water and extracted with Et$_2$O. The organics were combined, dried (Na$_2$SO$_4$) and evaporated to dryness. Column chromatography (0.5% to 5% EtOAc (with 0.1% TEA) in DCM) gave the desired product. LC/MS (10% to 99%): M/Z (M+H)+ (obs)=270; $t_R$=3.05.

N-(2,4-Dimethoxybenzyl)-3-(aminomethyl)pyridin-2-amine

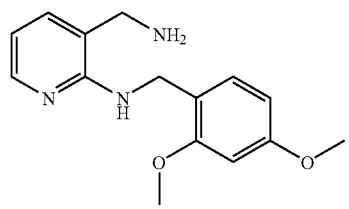

A solution of 2-(2,4-Dimethoxybenzylamino)pyridine-3-carbonitrile (0.55 g, 2.04 mmol) and LiAlH$_4$ (2.2 ml of 1N, 4.4 mmol) was stirred at RT until the reaction was judged complete by LCMS. The reaction was quenched with sat. aq. Na$_2$CO$_3$ and the layers were separated. The organic layer was dried (Na$_2$SO$_4$) and the solvents removed under reduced pressure giving the desired product which was used without further purification. LC/MS (10% to 99%): M/Z (M+H)$^+$ (obs)=274; t$_R$=0.28.

tert-Butyl-4-((2-(2,4-dimethoxybenzylamino)pyridin-3-yl)methylamino)piperidine-1-carboxylate

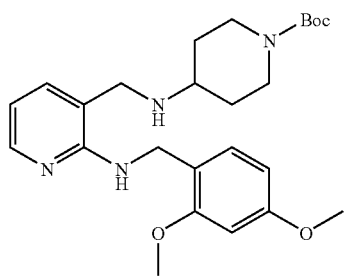

To a stirred solution of N-(2,4-Dimethoxybenzyl)-3-(aminomethyl)pyridin-2-amine (2.04 mmol) and tert-butyl 4-oxopiperidine-1-carboxylate (0.41 g, 2.04 mmol) in DCE (8 ml) and AcOH (115 µL, 2.04 mmol) was added NaBH(OAc)$_3$ (0.43 g, 2.04 mmol) and the reaction stirred at RT until judged complete by LCMS. The reaction mixture was diluted with DCM and sat. aq. Na$_2$CO$_3$, the layers were separated and the organic layer was dried (Na2SO3) and evaporated to dryness. Purification by column chromatography (MeOH/DCM) gave the desired product (0.64 g, 69%). LC/MS (10% to 99%): M/Z (M+H)$^+$ (obs)=457; t$_R$=2.19.

tert-Butyl 4-(1-(2,4-dimethoxybenzyl)-1,2-dihydro-2-oxopyrido[2,3-d]pyrimidin-3(4H)-yl)piperidine-1-carboxylate

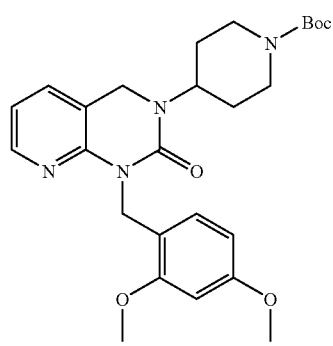

To a solution of tert-butyl 4-((2-(2,4-dimethoxybenzylamino)pyridin-3-yl)methylamino)piperidine-1-carboxylate (2.89 g, 6.33 mmol) in DMF (42 ml) was added CDI (1.23 g, 7.6 mmol) in portions and the reaction mixture was stirred at 120° C. for 2 hours. A further portion of CDI was added (0.82 g) was added and the reaction mixture stirred at 130° C. for 6 hours, followed by stirring at RT for 16 hours. The reaction was diluted with water and extracted with DCM. The organics were combined, dried (NaSO4) and evaporated to dryness. Purification by column chromatography (10 to 80% EtOAc in Hx) gave the desired product (1.17 g). LC/MS (10% to 99%): M/Z (M+H)$^+$ (obs)=483; t$_R$=3.58.

3,4-Dihydro-3-(piperidin-4-yl)pyrido[2,3-d]pyrimidin-2(1H)-one

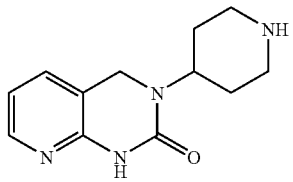

2-(4-Oxo-2-phenyl-3-((pyridin-4-yl)methyl)thiazolidin-5-yl)acetic acid

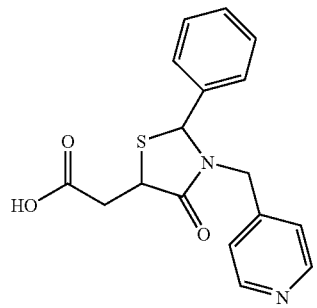

A solution of benzaldehyde (0.75 mmol, 79.6 mg) and 2-(pyridin-4-yl)ethanamine (97.3 mg, 0.9 mmol) in DMF (0.5 ml) with 4 Å molecular sieves was heated at 80° C. for 2 hours. A solution of mercaptosuccinic acid (1.13 mmol, 168 mg) in DMF (0.2 ml) was added and the reaction was heated at 80° C. for an additional 16 hours. The reaction mixture was diluted with water and extracted with EtOAc. The organic layer was washed with 1N HCl, water and evaporated to dryness to give the desired product which was used without further purification. LC/MS (10% to 99%): M/Z (M+H)$^+$ (obs)=329; t$_R$=1.95.

1-(1-(2-(4-Oxo-2-phenyl-3-((pyridin-4-yl)methyl)thiazolidin-5-yl)acetyl)piperidin-4-yl)-1H-benzo[d]imidazol-2(3H)-one (Compound # 45)

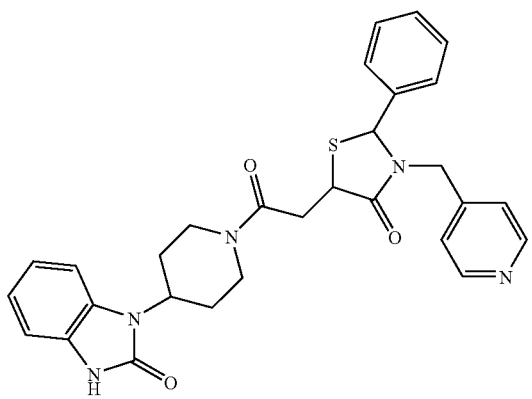

To a solution of 2-(4-oxo-2-phenyl-3-((pyridin-4-yl)methyl)thiazolidin-5-yl)acetic acid (0.15 mmol, 49 mg), 1-(piperidin-4-yl)-1H-benzo[d]imidazol-2(3H)-one (0.15 mmol, 33 mg) and DIPEA (0.375 mmol, 65.3 µl) in 4:1 CH$_3$CN:DMF (0.5 ml) was added HATU (0.18 mmol, 68 mg) and the reaction mixture was stirred at room temperature for 16 h. Purification by preparative reverse phase HPLC using 10%/99% CH$_3$CN (0.035% TFA)/H$_2$O (0.05% TFA) gave the title compound. LC/MS (10% to 99%): M/Z (M+H)$^+$ (obs)=528.1; t$_R$=2.28. H NMR (400 MHz, CDCl3) δ 9.00 (s, 1H), 8.60 (d, J=6.3 Hz, 2H), 7.40-7.38 (m, 2H), 7.33-7.29 (m, 5H), 7.06-6.92 (m, 4H), 5.55-5.53 (m, 1H), 4.55 (d, J=4.4 Hz, 2H), 4.45-4.42 (m, 3H), 4.07 (d, m, 2H), 3.42-3.41 (m, 1H), 3.20-3.15 (m, 1H), 3.01-2.90 (m, 1H), 2.66 (m, 2H), 1.88 (m, 2H) ppm.

2-(3-Methyl-4-oxo-2-phenylthiazolidin-5-yl)acetic acid

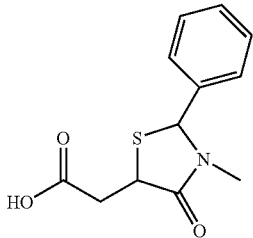

A solution of benzaldehyde (0.75 mmol, 79.6 mg) and methylamine hydrochloride (60.8 mg, 0.9 mmol) in DMF (0.5 ml) with 4 Å molecular sieves was heated at 80° C. for 2 hours. A solution of mercaptosuccinic acid (1.13 mmol, 168 mg) in DMF (0.2 ml) was added and the reaction was heated at 80° C. for an additional 16 hours. The reaction mixture was diluted with water and extracted with EtOAc. The organic layer was washed with 1N HCl, water and evaporated to dryness to give the desired product which was used without further purification.

3,4-Dihydro-3-(1-(2-(3-methyl-4-oxo-2-phenylthiazolidin-5-yl)acetyl)piperidin-4-yl)quinazolin-2(1H)-one (Compound # 273)

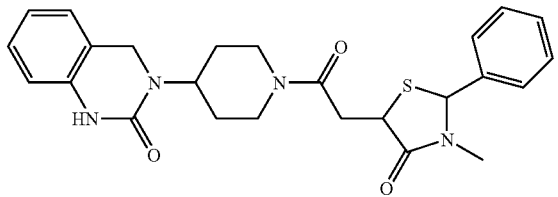

To a solution of 2-(3-methyl-4-oxo-2-phenylthiazolidin-5-yl)acetic acid (0.2 mmol, 50 mg), 3,4-dihydro-3-(piperidin-4-yl)quinazolin-2(1H)-one TFA salt (0.15 mmol, 49 mg) and D$^i$PEA (0.375 mmol, 65.3 µl) in 4:1 CH$_3$CN:DMF (0.5 ml) was added HATU (0.18 mmol, 68 mg) and the reaction mixture was stirred at room temperature for 16 h. Purification by preparative reverse phase HPLC using 10%-99% CH$_3$CN (0.035% TFA)/H$_2$O (0.05% TFA) gave the title compound. LC/MS (10% to 99%): M/Z (M+H)$^+$ (obs)=465.5; t$_R$=2.18. $^1$H NMR (400 MHz, CDCl3) δ 7.34-7.22 (m, 5H), 7.12 (t, J=7.5 Hz, 1H), 7.00 (d, J=7.5 Hz, 2H), 6.95-6.89 (m, 2H), 6.61 (d, J=7.8 Hz, 2H), 5.46-5.41 (m, 1H), 4.70 (m, 1H), 4.56 (m, 1H), 4.26 (m, 3H), 3.86 (m, 1H), 3.50 (m, 1H), 3.32 (m, 1H), 3.12-3.08 (m, 1H), 2.89-2.73 (m, 1H), 1.69 (m, 3H) ppm.

2-(3-Isopropyl-4-oxo-2-phenylthiazolidin-5-yl)acetic acid

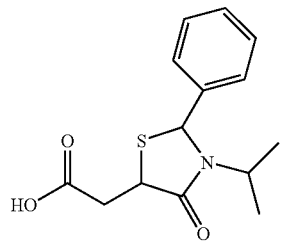

A solution of benzaldehyde (0.75 mmol, 79.6 mg) and isopropylamine (53.1 mg, 0.9 mmol) in DMF (0.5 ml) with 4 Å molecular sieves was heated at 80° C. for 2 hours. A solution of mercaptosuccinic acid (1.13 mmol, 168 mg) in DMF (0.2 ml) was added and the reaction was heated at 80° C. for an additional 16 hours. The reaction mixture was diluted with water and extracted with EtOAc. The organic layer was washed with 1N HCl, water and evaporated to dryness to give the desired product which was used without further purification.

3,4-Dihydro-3-(1-(2-(3-isopropyl-4-oxo-2-phenylthiazolidin-5-yl)acetyl)piperidin-4-yl) quinazolin-2(1H)-one (Compound #255)

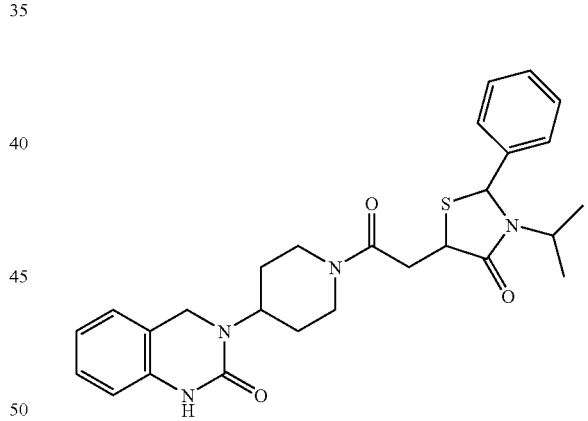

To a solution of 2-(3-isopropyl-4-oxo-2-phenylthiazolidin-5-yl)acetic acid (0.2 mmol, 56 mg), 1-(piperidin-4-yl)-1H-benzo[d]imidazol-2(3H)-one (0.15 mmol, 33 mg) and DIPEA (0.375 mmol, 65.3 µl) in 4:1 CH$_3$CN:DMF (0.5 ml) was added HATU (0.18 mmol, 68 mg) and the reaction mixture was stirred at room temperature for 16 h. Purification by preparative reverse phase HPLC using 10%-99% CH$_3$CN (0.035% TFA)/H$_2$O (0.05% TFA) gave the title compound. LC/MS (10% to 99%): M/Z (M+H)$^+$ (obs)=493.5; t$_R$=3.1. H NMR (400 MHz, CDCl$_3$) δ 7.31-7.25 (m, 5H), 7.14-7.10 (m, 1H), 7.05 (s, 1H), 7.00 (m, 1H), 6.93-6.89 (m, 1H), 6.62 (d, J=7.8 Hz, 1H), 5.56 (m, 1H), 4.72 (m, 1H), 4.47-4.41 (m, 2H), 4.27-4.19 (m, 2H), 4.02-3.96 (m, 1H), 3.87 (m, 1H), 3.36-3.29 (m, 1H), 3.13-3.10 (m, 1H), 2.70 (m, 2H), 1.70-1.60 (m, 3H), 1.20 (dd, J=2.0, 6.9 Hz, 3H), 0.94 (m, 3H).

2-(3-Isopentyl-4-oxo-2-phenylthiazolidin-5-yl)acetic acid

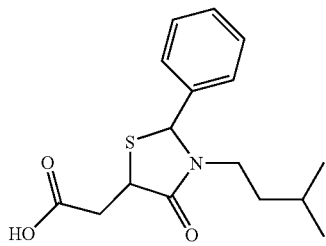

A solution of benzealdehyde (5.06 ml, 50 mmol) and isopentylamine (5.82 ml, 50 mmol) was stirred at 80° C. for 2 hours before the addition of mercaptosuccinic acid (7.51 g, 50 mmol) and a further 16 hours of stirring at 80° C. The reaction mixture was poured into water and extracted with EtOAc. The organics combined, dried and evaporated to dryness. Purification by column chromatography (EtOAc/Hx) gave the desired product as a yellow oil (11.3 g).

Ethyl 2-(3-isopentyl-4-oxo-2-phenylthiazolidin-5-yl) acetate

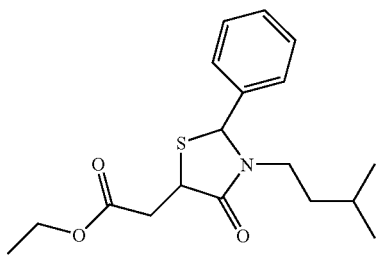

A solution of 2-(3-Isopentyl-4-oxo-2-phenylthiazolidin-5-yl)acetic acid (2.2 g, 7.2 mmol) in EtOH (20 ml) and $H_2SO_4$ (1 ml) was refluxed for 16 hours. The solution was evaporated to dryness and the residue was taken up in EtOAc and washed with sat. aq. $Na_2CO_3$ (3×), brine and evaporated to give the desired product as an oil.

Ethyl 2-(3-isopentyl-4-oxo-2-phenylthiazolidin-5-yl) propanoate

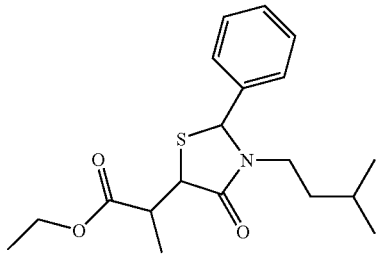

To a stirred solution of ethyl 2-(3-isopentyl-4-oxo-2-phenylthiazolidin-5-yl)acetate (84 mg, 0.25 mmol) in THF at 0° C. was added LiHMDS (0.28 ml of 1 N, 0.28 mmol) dropwise and the reaction mixture was stirred from 0° C. to RT over 16 hours. The reaction mixture was poured in to 1 N HCl and extracted with EtOAc (4×). The organics were combined, dried ($MgSO_4$) and evaporated to dryness. Purification by preparative TLC (7:1; Hx:EtOAc) gave the desired product as an oil (12 mg).

2-(3-Isopentyl-4-oxo-2-phenylthiazolidin-5-yl)propanoic acid

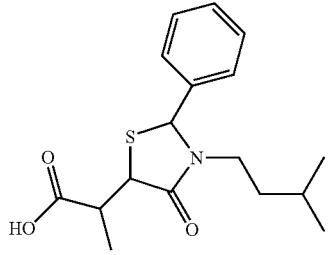

A solution 2-(3-isopentyl-4-oxo-2-phenylthiazolidin-5-yl)propanoic acid (12 mg, 0.034 mmol) and NaOH aq. (0.068 ml of 1N, 0.068 mmol) in MeOH (0.2 ml) was stirred at 60° C. for 16 hours. The solution was neutralized with 1 N HCl (0.068 ml of 1 N), the solvents removed and the crude product used with out further purification.

3-(1-(2-(3-Isopentyl-4-oxo-2-phenylthiazolidin-5-yl)propanoyl)piperidin-4-yl)-3,4-dihydroquinazolin-2(1H)-one (Compound #156)

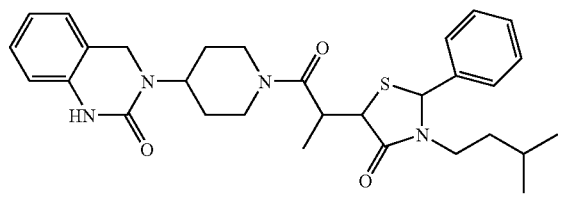

To a solution of 2-(3-Isopentyl-4-oxo-2-phenylthiazolidin-5-yl)propanoic acid (11 mg, 0.034 mmol), 3,4-Dihydro-3-(piperidin-4-yl)quinazolin-2(1H)-one TFA (17 mg, 0.051 mmol) and D$^i$PEA (24 ul, 0.14 mmol) in DMF (0.2 ml) was added HATU (17 mg, 0.044 mmol) and the reaction mixture was stirred at RT for 16 hours. Purification by preparative reverse phase HPLC using 10%-99% $CH_3CN$ (0.035% TFA)/ $H_2O$ (0.05% TFA) gave the title compound.

3-Isopentyl-2-phenylthiazolidin-4-one

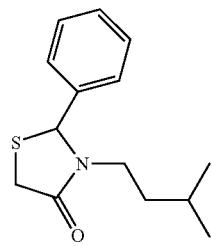

A solution of isopentylamine (0.58 ml, 5 mmol), benzealdehyde (1 ml, 10 mmol) and mercaptoacetic acid (1.05 ml g, 15 mmol) in THF (7 ml) and trimethoxyorthoformate (2 ml) was stirred at 75° C. for 16 hours. The R$^M$ was poured in to water and extracted with EtOAc (3×). The organics were combined, washed with 1N HCl (2×), brine, dried (MgSO₄) and evaporated to dryness. Purification by column chromatography (10-25% EtOAc in Hx) gave the desired product as an oil (1.07 g, 86%).

Ethyl 2-(3-isopentyl-4-oxo-2-phenylthiazolidin-5-ylidene)acetate

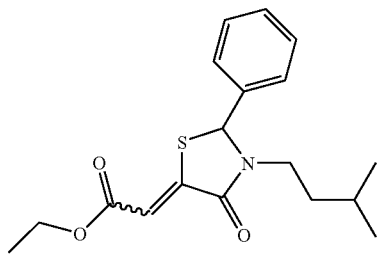

To a stirred solution of 3-isopentyl-2-phenylthiazolidin-4-one (0.25 g, 1 mmol) in THF was added LDA (1.1 ml of ~1 M in THF; freshly prepared from nBuLi and Diisopropylamine) at −78° C. and the reaction mixture was allowed to warm to room temperature. Ethyl glyoxalate (0.24 ml of ~50% w/v in toluene, 1.2 mmol) was added and the reaction mixture was stirred at room temperature for 16 hours. The reaction mixture was poured into 1 N HCl and extracted with EtOAc (3×). The organics were combined, washed with brine, dried (MgSO₄) and evaporated to dryness. Purification by column chromatography (5 to 15% EtOAc in Hx) gave the desired product as an oil.

2-(3-Isopentyl-4-oxo-2-phenylthiazolidin-5-ylidene) acetic acid

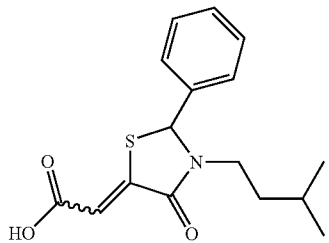

To a solution of ethyl 2-(3-isopentyl-4-oxo-2-phenylthiazolidin-5-ylidene)acetate (0.031 g, 0.1 mmol) and aq. NaOH (0.3 ml of 1 N) in MeOH was stirred at 40° C. for 2 hours. HCl (0.5 ml of 1 N) was added and the MeOH was evaporated. Water and EtOAc was added and the layers separated. The aqueous layer was extracted with EtOAc (2×), all organic layers were combined, dried (MgSO₄) and evaporated to dryness to give the desired product as an orange oil (11 mg, 36%).

3,4-Dihydro-3-(1-(2-(3-isopentyl-4-oxo-2-phenylthiazolidin-5-ylidene)acetyl)piperidin-4-yl)quinazolin-2(1H)-one

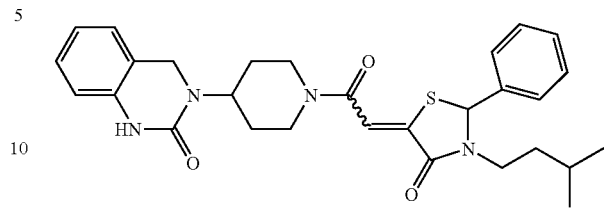

To a solution of 2-(3-isopentyl-4-oxo-2-phenylthiazolidin-5-ylidene)acetic acid (11 mg, 0.036 mmol), 3,4-Dihydro-3-(piperidin-4-yl)quinazolin-2(1H)-one TFA (18 mg, 0.054 mmol) and D$^i$PEA (22 ul, 0.14 mmol) in DMF (0.2 ml) was added HATU (16 mg, 0.043 mmol) and the reaction mixture was stirred at RT for 16 hours. Purification by preparative reverse phase HPLC using 10%-99% CH₃CN (0.035% TFA)/ H₂O (0.05% TFA) gave the title compound.

Preparation A: Synthesis of 1'H-spiro[piperidine-4,4'-quinolin]-2'(3'H)-one

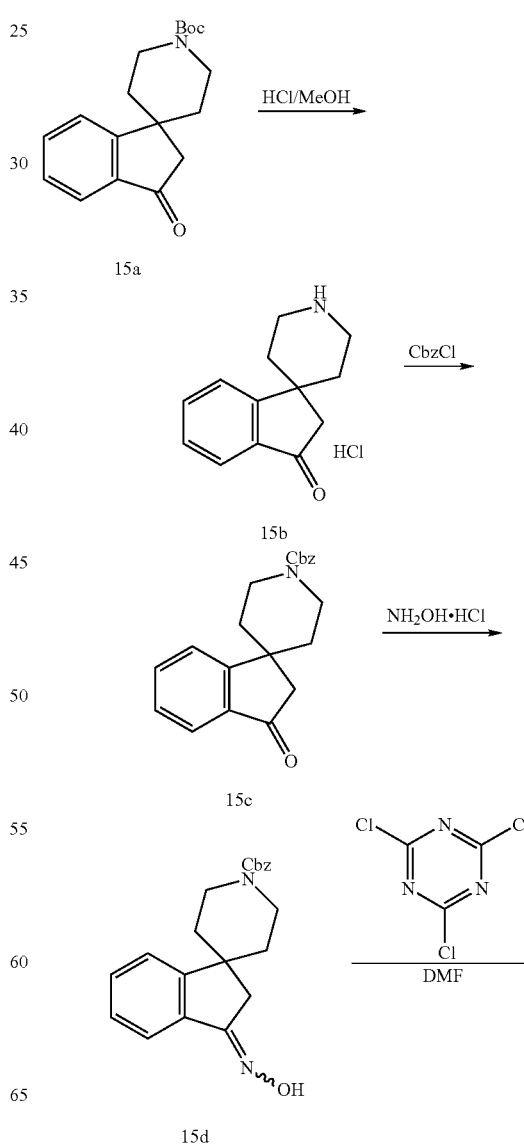

-continued

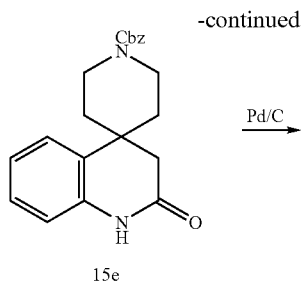

15e → 15f (Pd/C)

The mixture of tert-butyl 3-oxo-2,3-dihydrospiro[indene-1,4'-piperidine]-1'-carboxylate (20 g, 66.4 mmol) and MeOH/HCl (2.5 mol/L, 100 mL) were stirred overnight. After evaporation the residue was washed by petroleum ether to provide spiro[indene-1,4'-piperidin]-3(2H)-one hydrochloride (15.4 g, 97.6%).

To a solution spiro[indene-1,4'-piperidin]-3(2H)-one hydrochloride (5.0 g, 24.84 mmol) and $Et_3N$ (7.54 g, 74.53 mol) in $CH_2Cl_2$ (50 mL) was added drop-wise Cbz-Cl (4.66 g, 27.33 mmol) at 0° C. The reaction was allowed to warm to room temperature and stirred overnight. The precipitate was filtered, washed with $Et_2O$ and dried to furnish benzyl 3-oxo-2,3-dihydrospiro[indene-1,4'-piperidine]-1'-carboxylate (6.1 g, yield 99%).

A solution of benzyl 3-oxo-2,3-dihydrospiro[indene-1,4'-piperidine]-1'-carboxylate (3 g, 10.3 mmol) in EtOH (30 mL) containing $NH_2OH \cdot HCl$ (1.43 g, 20.6 mmol) and NaOAc (1.52 g, 18.53 mmol) was heated under reflux for 1.5 h. The solvent was removed by evaporation and the residue was partitioned between $CH_2Cl_2$ and water. The organic phase was washed with brine, dried over $Na_2SO_4$, and concentrated to provide benzyl 3-(hydroxyimino)-2,3-dihydrospiro[indene-1,4'-piperidine]-1'-carboxylate (3.14 g, yield 99%), which was used directly in the next step.

2,4,6-trichloro-[1,3,5]-triazine (1.32 g, 7.16 mmol) was added to DMF (9.6 mL) maintained at 25° C. The reaction was monitored by TLC until TCT was consumed. Then benzyl 3-(hydroxyimino)-2,3-dihydrospiro[indene-1,4'-piperidine]-1'-carboxylate (1.6 g, 4.77 mmol) in DMF (17 mL) was added. After the addition, the mixture was stirred at room temperature overnight. Water was added. The mixture was extracted with EtOAc. The combined organic layers were washed with sat. $Na_2CO_3$, followed by 1N HCl and brine, dried over $Na_2SO_4$ and concentrated. The residue was purified by prep HPLC to obtain benzyl 2'-oxo-2',3'-dihydro-1'H-spiro[piperidine-4,4'-quinoline]-1-carboxylate (260 mg, yield 16%).

The mixture of benzyl 2'-oxo-2',3'-dihydro-1'H-spiro[piperidine-4,4'-quinoline]-1-carboxylate (1.2 g, 3.4 mmol) and Pd/C (200 mg) in MeOH (20 mL) was hydrogenated under atmosphere pressure at room temperature for 3 h. The catalyst was filtered and the filtrate was concentrated under reduced pressure. The residue was purified by preparative HPLC twice to give 1'H-spiro[piperidine-4,4'-quinolin]-2'(3'H)-one (110 mg, 11%) as a TFA salt. $^1$H NMR ($CDCl_3$) δ 7.65 (d, J=7.5 Hz, 1H), 7.29–7.45 (m, 3H), 3.45 (d, J=12.3 Hz, 2H), 3.20 (t, J=12.3 Hz, 2H), 2.96 (s, 2H), 2.10–2.21 (m, 2H), 1.70 (d, J=14.1 Hz, 2H). MS (ESI) m/z 217.06 [M+H]$^+$.

Preparation B: Synthesis of spiro[4H-3,1-benzoxazine-4,4'-piperidin]-2(1H)-one

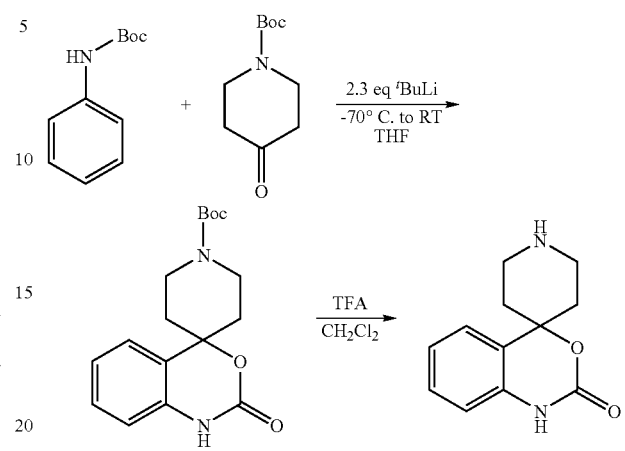

N-Boc-aniline (16.12 g, 83.4 mmol) was dissolved in anhydrous tetrahydrofuran (120 mL) and cooled to −70° C. To this solution was added dropwise, under nitrogen, a 1.7 M solution of tert-butyllithium in pentane (110 mL, 187 mmol) at −70° C. After 30 min at −70° C., the solution was warmed to −20° C. and maintained at that temperature for 2 h. The solution was again cooled to −70° C. and treated dropwise with a solution of N-Boc-4-piperidone (15.98 g, 80.2 mmol) in anhydrous tetrahydrofuran (50 mL). The solution was slowly warmed to room temperature, treated with potassium tert-butoxide (25 mg) and stirred at room temperature overnight under nitrogen. The solution was diluted with diethyl ether (300 mL), cooled in an ice-$H_2O$ bath and adjusted to pH 7 with 1.0 N HCl (aq). The layers were separated and the aqueous layer extracted once with diethyl ether (100 mL). The pooled organic layers were washed with $H_2O$ and saturated brine, then dried over $Na_2SO_4$ and filtered. The filtrate was concentrated under reduced pressure to afford 39.09 g crude product as a viscous pale yellow oil. The crude product was purified via silica gel flash chromatography (25-50% ethyl acetate in hexanes) to afford tert-butyl 2-oxo-1,2-dihydrospiro[benzo[d][1,3]oxazine-4,4'-piperidine]-1'-carboxylate as a pale yellow solid (8.687 g, 34% yield). LC/MS m/z 319.0 [M+H]$^+$, retention time 2.72 min (RP—$C_{18}$, 10-99% $CH_3CN$/0.05% TFA); $^1$H-NMR (400 MHz, $CDCl_3$) δ 9.06 (br s, 1H), 7.28 (m, 1H), 7.12 (m, 2H), 6.91 (d, J=8.5 Hz, 1H), 4.12 (br d, J=9.9 Hz, 2H), 3.36 (br t, J=12.4 Hz, 2H), 2.13 (br d, J=13.1 Hz, 2H), 1.98 (m, 2H), 1.51 (s, 9H).

tert-Butyl 2-oxo-1,2-dihydrospiro[benzo[d][1,3]oxazine-4,4'-piperidine]-1'-carboxylate (6.71 g, 21.1 mmol) was dissolved in dichloromethane (50 mL), treated with trifluoroacetic acid (20 mL) and stirred at room temperature for 45 min. The reaction was concentrated under reduced pressure, re-dissolved in acetonitrile and re-concentrated under reduced pressure. The crude TFA salt was cooled in an ice-$H_2O$ bath, dissolved in ice-cold saturated brine (20 mL) and $H_2O$ (50 mL) and basified with ice-cold 35% NaOH (aq). A small amount of product (obtained from extraction with 50 mL ethyl acetate) was added to the aqueous layer to initiate crystallization. The suspension obtained was cooled in an ice-$H_2O$ bath, filtered, rinsed with ice-cold $H_2O$ and dried to afford 3.071 g spiro[benzo[d][1,3]oxazine-4,4'-piperidin]-2(1H)-one free base as a white crystalline solid. An additional 800 mg free base was obtained via extraction of the mother liquor with ethyl acetate (10×50 mL) and subsequent trituration of the crude free base with acetonitrile (overall yield=84%). LC/MS m/z 219.2 [M+H]⁺, retention time 0.58 min (RP—C₁₈, 10-99% CH₃CN/0.05% TFA); ¹H-NMR (400 MHz, DMSO-d₆) δ 10.17 (br s, 1H), 7.23 (m, 2H), 7.02 (m, 1H), 6.87 (dd, J=8.2, 1.2 Hz, 1H), 2.89 (m, 2H), 2.82 (m, 2H), 1.84 (m, 4H).

1-Benzyl-4-(2-chloroquinolin-3-yl)piperidin-4-ol

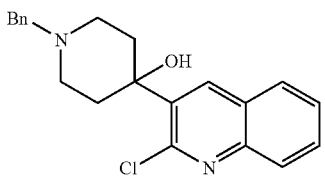

To a solution of LDA (3.4 ml of 2 M in Hept/THF) at −78° C. in THF (5 ml) was added a solution of 2-chloroquinoline (1.0 g. 6.11 mmol) in THF (10 ml) dropwise, and the reaction mixture stirred at −78° C. for 1 hour before a solution of 1-benzylpiperidin-4-one (1.22 g, 6.22 mmol) in THF (2 ml) was added dropwise. The reaction mixture was stirred from −78° C. to RT over two hours, cooled to −20° C., quenched with water and extracted with EtOAc. The organics combined, dried (Na₂SO₄) and evaporated to dryness. Purification by column chromatography (1 to 15% MeOH in DCM) gave the desired product. LC/MS (10% to 99%): M/Z (M+H)⁺ (obs)=353; t_R=24.

3-(1-Benzyl-1,2,3,6-tetrahydropyridin-4-yl)quinolin-2(1H)-one

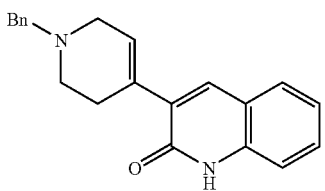

A solution of 1-Benzyl-4-(2-chloroquinolin-3-yl)piperidin-4-ol (1 g, 2.84 mmol) in 6 N HCl (9 ml) was heated at 100° C. for 8 h. The reaction mixture was cooled, water was added and the precipitated product was filtered and dried (0.27 g). LC/MS (10% to 99%): M/Z (M+H)⁺ (obs)=317; t_R=2.18.

3-(Piperidin-4-yl)quinolin-2(1H)-one

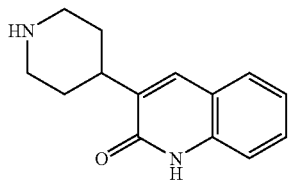

A solution of 3-(1-Benzyl-1,2,3,6-tetrahydropyridin-4-yl) quinolin-2(1H)-one (0.25 g. 0.29 mmol) and 10% Pd/C (130 mg) in MeOH (20 ml) was stirred at 40° C. for 6 hours. The catalysis was filtered and solvent evaporated affording the desired product. LC/MS (10% to 99%): M/Z (M+H)⁺ (obs) =229; t_R=1.27.

Analytical data for certain compounds of the present invention are shown below in Table 2.

TABLE 2

| Cmpd # | LC/MS M + 1 | LC/RT min |
|---|---|---|
| 1 | 533.5 | 3.36 |
| 2 | 633. | 1.45 |
| 3 | 603.5 | 3.35 |
| 4 | 551.5 | 3.22 |
| 5 | 599.5 | 3.07 |
| 6 | 549.5 | 1.98 |
| 7 | 632.7 | 2.34 |
| 8 | 549.5 | 3.63 |
| 9 | 507.5 | 3.24 |
| 10 | 620.5 | 1.89 |
| 11 | 563.5 | 3.77 |
| 12 | 521. | 3.31 |
| 13 | 621.5 | 3.77 |
| 14 | 595.5 | 3.8 |
| 15 | 559.3 | 3.72 |
| 16 | 597.5 | 3.62 |
| 17 | 633. | 1.47 |
| 18 | 569.5 | 3.37 |
| 19 | 593.5 | 3.17 |
| 20 | 615.5 | 3.23 |
| 21 | 577.7 | 3.94 |
| 22 | 619.7 | 1.39 |
| 23 | 621.5 | 3.8 |
| 24 | 507.3 | 3.25 |
| 25 | 571.5 | 3.72 |
| 26 | 567.5 | 3.72 |
| 27 | 562.4 | 3.28 |
| 28 | 615.7 | 1.41 |
| 29 | 506.4 | 2.96 |
| 30 | 509.7 | 2.91 |
| 31 | 545.7 | 3.64 |
| 32 | 527.3 | 1.98 |
| 33 | 555.3 | 3.55 |
| 34 | 647. | 1.46 |
| 35 | 529.3 | 3.12 |
| 36 | 583.3 | 1.86 |
| 37 | 541.7 | 3.8 |
| 38 | 507.5 | 3.25 |
| 39 | 626.7 | 1.53 |
| 40 | 633.5 | 1.42 |
| 41 | 535.5 | 3.54 |
| 42 | 704.7 | 2.23 |
| 43 | 536.3 | 2.24 |
| 44 | 571.3 | 3.57 |
| 45 | 542.5 | 2.13 |
| 46 | 542.5 | 2.39 |
| 47 | 620.5 | 1.27 |
| 48 | 585.3 | 3.82 |
| 49 | 634.5 | 1.74 |
| 50 | 632.7 | 1.49 |
| 51 | 563.7 | 2.08 |
| 52 | 661.7 | 1.47 |
| 53 | 568.5 | 2.22 |
| 54 | 585.3 | 3.84 |
| 55 | 619.5 | 3.68 |
| 56 | 612.5 | 1.52 |
| 57 | 555.5 | 2.13 |
| 58 | 555.3 | 3.37 |
| 59 | 606.4 | 2.39 |
| 60 | 601.5 | 1.37 |
| 61 | 563.5 | 3.34 |
| 62 | 573.4 | 3.06 |
| 63 | 546.5 | 3.27 |
| 64 | 563.5 | 3.36 |
| 65 | 641.3 | 3.89 |
| 66 | 573.4 | 3.05 |
| 67 | 539.5 | 3.45 |
| 68 | 667.5 | 1.42 |

TABLE 2-continued

| Cmpd # | LC/MS M + 1 | LC/RT min |
|---|---|---|
| 69 | 508.6 | 3.1 |
| 70 | 634.5 | 1.93 |
| 71 | 543.5 | 2.31 |
| 72 | 690.5 | 2.16 |
| 73 | 563.5 | 3.82 |
| 74 | 557.5 | 4.15 |
| 75 | 501.5 | 3.5 |
| 76 | 589.5 | 1.98 |
| 77 | 562.5 | 2.41 |
| 78 | 535.5 | 3.51 |
| 79 | 587.3 | 3.79 |
| 80 | 551.5 | 3.47 |
| 81 | 665.7 | 1.46 |
| 82 | 550.5 | 2.42 |
| 83 | 549.5 | 3.12 |
| 84 | 531. | 1.78 |
| 85 | 517.5 | 1.21 |
| 86 | 513.3 | 3.53 |
| 87 | 525.5 | 3.5 |
| 88 | 615.5 | 1.88 |
| 89 | 603.5 | 3.77 |
| 90 | 551.5 | 3.22 |
| 91 | 541.5 | 2.05 |
| 92 | 583.5 | 3.6 |
| 93 | 535.5 | 3.51 |
| 94 | 574.5 | 2. |
| 95 | 527.3 | 1.96 |
| 96 | 505.3 | 3.2 |
| 97 | 487.5 | 1.41 |
| 98 | 549.7 | 3.63 |
| 99 | 733.7 | 2.26 |
| 100 | 553.5 | 2.08 |
| 101 | 549.5 | 1.89 |
| 102 | 619.5 | 2.58 |
| 103 | 579.5 | 3.64 |
| 104 | 507. | 3.22 |
| 105 | 487.5 | 1.37 |
| 106 | 604.7 | 2.21 |
| 107 | 507.5 | 3.27 |
| 108 | 528.1 | 2.28 |
| 109 | 533.3 | 3.11 |
| 110 | 533. | 3.28 |
| 111 | 492.5 | 3.43 |
| 112 | 567.5 | 3.53 |
| 113 | 535.5 | 2.95 |
| 114 | 587.5 | 1.32 |
| 115 | 601.5 | 1.84 |
| 116 | 489.5 | 3. |
| 117 | 551.5 | 3.12 |
| 118 | 537.4 | 2.95 |
| 119 | 633. | 1.41 |
| 120 | 634.5 | 1.74 |
| 121 | 564.7 | 1.84 |
| 122 | 553.6 | 3.16 |
| 123 | 563.7 | 3.79 |
| 124 | 564.7 | 2.91 |
| 125 | 621.5 | 3.22 |
| 126 | 565.5 | 3.55 |
| 127 | 569.5 | 3.44 |
| 128 | 556.5 | 2.39 |
| 129 | 651.5 | 1.39 |
| 130 | 588.5 | 2.13 |
| 131 | 588.4 | 3.22 |
| 132 | 479.3 | 3.02 |
| 133 | 551.5 | 3.22 |
| 134 | 549.5 | 1.98 |
| 135 | 597.5 | 3.65 |
| 136 | 607.3 | 1.96 |
| 137 | 583.5 | 3.58 |
| 138 | 519.5 | 3.28 |
| 139 | 551.5 | 3.44 |
| 140 | 626.5 | 1.58 |
| 141 | 493.1 | 3.76 |
| 142 | 681.7 | 1.47 |
| 143 | 538.7 | 3.52 |
| 144 | 620.7 | 1.68 |
| 145 | 601.5 | 3.15 |
| 146 | 469.5 | 2.56 |
| 147 | 561.5 | 3.7 |
| 148 | 522. | 1.52 |
| 149 | 553.5 | 3.57 |
| 150 | 648.7 | 1.79 |
| 151 | 515.7 | 1.96 |
| 152 | 578.5 | 1.89 |
| 153 | 612.5 | 1.46 |
| 154 | 541.7 | 2.06 |
| 155 | 571.5 | 3.6 |
| 156 | 535. | 3.52 |
| 157 | 534.4 | 2.77 |
| 158 | 555.3 | 3.6 |
| 159 | 537.5 | 3.06 |
| 160 | 620.5 | 1.89 |
| 161 | 619.7 | 1.38 |
| 162 | 619.7 | 1.36 |
| 163 | 633.5 | 1.37 |
| 164 | 579.5 | 3.62 |
| 165 | 571.5 | 3.75 |
| 166 | 573.5 | 1.91 |
| 167 | 477.3 | 4.08 |
| 168 | 574.5 | 2.05 |
| 169 | 605.5 | 3.61 |
| 170 | 539.5 | 3.38 |
| 171 | 549.5 | 3.62 |
| 172 | 535.5 | 3.45 |
| 173 | 618.7 | 1.41 |
| 174 | 531.5 | 3.37 |
| 175 | 586.5 | 3.47 |
| 176 | 522. | 1.52 |
| 177 | 479.5 | 3. |
| 178 | 579.5 | 3.39 |
| 179 | 589.5 | 3.3 |
| 180 | 563.7 | 3.67 |
| 181 | 567.5 | 3.95 |
| 182 | 522.5 | 2.54 |
| 183 | 601.7 | 1.83 |
| 184 | 606.5 | 1.83 |
| 185 | 556.5 | 2.48 |
| 186 | 521.6 | 2.67 |
| 187 | 527.3 | 3.19 |
| 188 | 513.5 | 3.52 |
| 189 | 559.3 | 3.13 |
| 190 | 547.3 | 3.15 |
| 191 | 547.5 | 1.74 |
| 192 | 487.5 | 1.82 |
| 193 | 719.7 | 2.21 |
| 194 | 621.5 | 3.79 |
| 195 | 525.5 | 3.41 |
| 196 | 515.7 | 3.07 |
| 197 | 577.7 | 3.84 |
| 198 | 578.5 | 1.64 |
| 199 | 647.7 | 1.41 |
| 200 | 510.8 | 2.76 |
| 201 | 529.5 | 1.56 |
| 202 | 557.5 | 3.44 |
| 203 | 589.4 | 3.21 |
| 204 | 549.5 | 3.58 |
| 205 | 579.5 | 3.39 |
| 206 | 589.7 | 3.15 |
| 207 | 529.5 | 3.79 |
| 208 | 559.5 | 3.38 |
| 209 | 529.5 | 1.61 |
| 210 | 583.5 | 3.53 |
| 211 | 578.5 | 1.92 |
| 212 | 557.5 | 3.44 |
| 213 | 578.4 | 2.95 |
| 214 | 565.5 | 3.22 |
| 215 | 618.7 | 2.28 |
| 216 | 589.5 | 3.57 |
| 217 | 585.3 | 3.77 |
| 218 | 471.3 | 2.79 |
| 219 | 607.5 | 1.99 |
| 220 | 537.5 | 3. |

TABLE 2-continued

| Cmpd # | LC/MS M + 1 | LC/RT min |
|---|---|---|
| 221 | 587.5 | 3.7 |
| 222 | 549.5 | 1.98 |
| 223 | 508.2 | 2.53 |
| 224 | 587.5 | 1.78 |
| 225 | 593.5 | 3.53 |
| 226 | 513.3 | 3.29 |
| 227 | 546.5 | 3.28 |
| 228 | 581.3 | 3.27 |
| 229 | 647.7 | 1.42 |
| 230 | 491.3 | 2.97 |
| 231 | 569.5 | 3.5 |
| 232 | 592.5 | 3.38 |
| 233 | 597.3 | 1.91 |
| 234 | 571.5 | 3.77 |
| 235 | 618.7 | 2.28 |
| 236 | 556.5 | 2.2 |
| 237 | 569.5 | 3.43 |
| 238 | 551.5 | 3.13 |
| 239 | 543.5 | 3.3 |
| 240 | 637.4 | 3.61 |
| 241 | 539.5 | 3.57 |
| 242 | 601.3 | 3.64 |
| 243 | 633.5 | 3.8 |
| 244 | 567.5 | 3.79 |
| 245 | 550.5 | 2.53 |
| 246 | 627.5 | 2.06 |
| 247 | 651.5 | 3.69 |
| 248 | 587.5 | 3.02 |
| 249 | 518.2 | 3.49 |
| 250 | 523.5 | 3.04 |
| 251 | 507.5 | 3.24 |
| 252 | 553.3 | 3.72 |
| 253 | 581.3 | 3.6 |
| 254 | 491.3 | 3.06 |
| 255 | 493.5 | 3.1 |
| 256 | 607.5 | 1.98 |
| 257 | 645.7 | 1.38 |
| 258 | 543.5 | 3.25 |
| 259 | 519. | 3.07 |
| 260 | 601.5 | 1.34 |
| 261 | 446.5 | 3.03 |
| 262 | 563.7 | 3.75 |
| 263 | 592.7 | 1.98 |
| 264 | 547.5 | 3.57 |
| 265 | 572.7 | 3.4 |
| 266 | 522.5 | 2.96 |
| 267 | 553.5 | 1.91 |
| 268 | 601.3 | 3.61 |
| 269 | 493.3 | 3.13 |
| 270 | 506.4 | 2.77 |
| 271 | 505.5 | 3.14 |
| 272 | 551.5 | 3.41 |
| 273 | 465.5 | 2.88 |
| 274 | 620.7 | 1.24 |
| 275 | 485.5 | 3.31 |
| 276 | 515.7 | 1.98 |
| 277 | 588.7 | 2.05 |
| 278 | 542.5 | 2.35 |
| 279 | 597.5 | 3.65 |
| 280 | 561.5 | 1.78 |
| 281 | 499.1 | 3.98 |
| 282 | 575.5 | 3.05 |
| 283 | 569.5 | 3.45 |
| 284 | 493.5 | 3.13 |
| 285 | 607.5 | 1.54 |
| 286 | 563.5 | 3.32 |
| 287 | 567.5 | 2.85 |
| 288 | 570.5 | 1.33 |
| 289 | 573.5 | 1.27 |
| 290 | 606.5 | 1.62 |
| 291 | 573.5 | 1.73 |
| 292 | 590.7 | 2.16 |
| 293 | 550.5 | 1.79 |
| 294 | 592.7 | 1.79 |
| 295 | 587.5 | 1.34 |
| 296 | 620.7 | 1.71 |
| 297 | 587.5 | 1.79 |
| 298 | 604.5 | 2.23 |
| 299 | 564.5 | 1.88 |
| 300 | 606.5 | 1.86 |
| 301 | 620.7 | 1.78 |
| 302 | 619 | 1.42 |
| 303 | 630 | 1.49 |
| 304 | 606.5 | 1.71 |
| 305 | 525.5 | 1.24 |
| 306 | 525.5 | 1.25 |
| 307 | 649.7 | 1.41 |
| 308 | 589.5 | 2.13 |
| 309 | 609.5 | 2.18 |
| 310 | 623.7 | 2.23 |
| 311 | 595.5 | 2.12 |
| 312 | 549.7 | 2 |
| 313 | 539.5 | 1.32 |
| 314 | 539.6 | 1.31 |
| 315 | 575.7 | 2.08 |
| 316 | 561.5 | 2.02 |
| 317 | 561.5 | 2.04 |
| 318 | 575.5 | 2.09 |
| 319 | 620.4 | 1.61 |
| 320 | 634.4 | 1.68 |
| 321 | 633.7 | 1.47 |
| 322 | 633.7 | 1.5 |
| 323 | 651.5 | 1.42 |
| 324 | 665.5 | 1.48 |
| 325 | 663.7 | 1.42 |
| 326 | 663.7 | 1.45 |
| 327 | 620.5 | 1.32 |
| 328 | 634.7 | 1.41 |
| 329 | 620.5 | 1.3 |
| 330 | 634.5 | 1.35 |
| 331 | 605.5 | 1.48 |
| 332 | 619.7 | 1.56 |
| 333 | 647.7 | 1.41 |
| 334 | 647.7 | 1.49 |
| 335 | 633.5 | 1.45 |
| 336 | 633.5 | 1.47 |
| 337 | 638.5 | 1.26 |
| 338 | 637.5 | 1.39 |
| 339 | 679.7 | 1.49 |
| 340 | 693.7 | 1.52 |
| 341 | 666.5 | 1.34 |
| 342 | 691.5 | 1.51 |
| 343 | 665.7 | 1.41 |
| 344 | 665.5 | 1.42 |
| 345 | 679.7 | 1.46 |
| 346 | 677.7 | 1.44 |
| 347 | 663.7 | 1.39 |
| 348 | 637.7 | 1.34 |
| 349 | 652.5 | 1.26 |
| 350 | 638.5 | 1.18 |
| 351 | 651.5 | 1.46 |
| 352 | 665.5 | 1.49 |
| 353 | 638.5 | 1.26 |
| 354 | 637.7 | 1.42 |
| 355 | 667.5 | 1.47 |
| 356 | 681.7 | 1.52 |
| 357 | 654.7 | 1.29 |
| 358 | 679.7 | 1.46 |
| 359 | 653.7 | 1.41 |
| 360 | 651.5 | 1.45 |
| 361 | 665.5 | 1.5 |
| 362 | 638.5 | 1.29 |
| 363 | 663.7 | 1.44 |
| 364 | 675.7 | 1.56 |
| 365 | 689.5 | 1.63 |
| 366 | 662.5 | 1.38 |
| 367 | 695.7 | 2.02 |
| 368 | 709 | 2.01 |
| 369 | 647.7 | 1.52 |
| 370 | 661.7 | 1.55 |
| 371 | 663.7 | 1.45 |
| 372 | 677.7 | 1.5 |

TABLE 2-continued

| Cmpd # | LC/MS M + 1 | LC/RT min |
| --- | --- | --- |
| 373 | 633 | 1.42 |
| 374 | 633 | 1.42 |
| 375 | 661.6 | 1.53 |
| 376 | 707 | 1.56 |
| 377 | 661.6 | 1.61 |
| 378 | 634.6 | 1.26 |
| 379 | 730.9 | 1.31 |
| 380 | 634.6 | 1.37 |
| 381 | 703.9 | 1.16 |
| 382 | 636.7 | 1.33 |
| 383 | 649.7 | 1.48 |
| 384 | 715.7 | 1.61 |
| 385 | 663.7 | 1.54 |
| 386 | 622.7 | 1.28 |
| 387 | 688.7 | 1.43 |
| 388 | 647.7 | 1.43 |
| 389 | 691.7 | 1.53 |
| 390 | 664.7 | 1.32 |
| 391 | 651.7 | 1.47 |
| 392 | 733.7 | 2.07 |
| 393 | 706.7 | 1.82 |
| 394 | 638.5 | 0.95 |
| 395 | 693.6 | 1.63 |
| 396 | 693.6 | 1.7 |
| 397 | 638.5 | 1.24 |
| 398 | 651.7 | 1.47 |
| 399 | 651.7 | 1.47 |
| 400 | 707.7 | 1.58 |
| 401 | 707.7 | 1.53 |
| 402 | 710.9 | 1.5 |
| 403 | 737.7 | 1.68 |
| 404 | 634.5 | 1.32 |
| 405 | 661.7 | 1.49 |
| 406 | 634.5 | 1.3 |
| 407 | 661.5 | 1.49 |
| 408 | 710.7 | 1.51 |
| 409 | 737.7 | 1.69 |
| 410 | 633.5 | 1.4 |
| 411 | 680.7 | 2.29 |
| 412 | 647.7 | 1.5 |
| 413 | 620.5 | 1.27 |
| 414 | 630 | 1.5 |
| 415 | 621.6 | 1.59 |
| 416 | 535.5 | 1.92 |
| 417 | 508.6 | 1.62 |
| 418 | 648.7 | 1.3 |
| 419 | 675.7 | 1.52 |
| 420 | 549.6 | 1.51 |
| 421 | 632.4 | 1.88 |
| 422 | 634.6 | 1.44 |
| 423 | 620.6 | 1.83 |
| 424 | 520.4 | 1.65 |
| 425 | 605.4 | 1.52 |
| 426 | 607.4 | 1.12 |
| 427 | 593.4 | 1.52 |
| 428 | 591.6 | 1.7 |
| 429 | 707.4 | 1.77 |
| 430 | 707.4 | 1.91 |
| 431 | 707.4 | 1.77 |
| 432 | 707.4 | 1.87 |
| 433 | 709 | 1.49 |
| 434 | 709 | 1.49 |
| 435 | 623 | 1.21 |
| 436 | 680 | 1.29 |
| 437 | 680 | 1.29 |
| 438 | 682 | 1.3 |
| 439 | 733.6 | 1.68 |
| 440 | 733.6 | 1.7 |
| 441 | 706.6 | 1.45 |
| 442 | 706.4 | 1.5 |
| 443 | 649.7 | 1.21 |
| 444 | 676.5 | 1.44 |
| 445 | 680 | 1.48 |
| 446 | 680 | 1.33 |
| 447 | 645.5 | 1.98 |
| 448 | 672.6 | 2.42 |
| 449 | 669.5 | 3.2 |
| 450 | 693.6 | 2.75 |
| 451 | 664.5 | 2.98 |
| 452 | 694.7 | 3.12 |
| 453 | 657 | 3.05 |
| 454 | 657.5 | 3.1 |
| 455 | 652.5 | 1.98 |
| 456 | 652.5 | 1.98 |
| 457 | 717.1 | 2.68 |
| 458 | 638.5 | 1.94 |
| 459 | 638.5 | 2 |
| 460 | 695.2 | 2.3 |
| 461 | 681.3 | 2.45 |
| 462 | 625.4 | 2.87 |
| 463 | 652.4 | 3.31 |
| 464 | 637.3 | 3.29 |
| 465 | 624.5 | 1.91 |
| 466 | 651.2 | 2.13 |
| 467 | 637.5 | 1.97 |
| 468 | 625.4 | 2.94 |
| 469 | 638.5 | 3.2 |
| 470 | 624.5 | 1.98 |
| 471 | 651.2 | 2.21 |
| 472 | 637.2 | 2.13 |
| 473 | 652.5 | 1.94 |
| 474 | 679.5 | 2.13 |
| 475 | 652.5 | 1.98 |
| 476 | 679.5 | 2.16 |
| 477 | 605 | 1.36 |

Measuring CGRP Functional Antagonism Using SK-N-MC-BLA (4C10):

CGRP functional antagonism was characterized in a cell based transcriptional assay using a recombinant SK-N-MC line. To introduce the transcriptional reporter system, SK-N-MC cell line was transduced with a retroviral vector containing β-lactamase gene downstream of cAMP responsive promoter. The expression of β-lactamase is triggered by cAMP increase that is a downstream event of activation of endogenous CGRP receptor. Single clones were separated using Fluorescent Activated Cell Sorting (FACS) based on CGRP induced β-lactamase activity. β-lactamase activity was measured using a fluorescence energy transfer (FRET) dye, CCF4. CCF4 is a substrate of β-lactamase (Zlokarnik G, et al., Science, 279 (5347): 84-88, 1998) and cleaved into a product with different fluorescent signal from that of the parent. 4C10 clone was selected for dose dependent β-lactamase expression to different concentrations of CGRP and consistent pharmacology with previously published values. To evaluate functional antagonist activity of compounds in SK-N-MC (4C10) line, compounds were evaluated for their inhibition of β-lactamase expression in the presence of CGRP.

SK-N-MC (4C10) was cultured in Minimal Essential Media (MEM) (Invitrogen) supplemented with 1 mM non-essential amino acids solution (Invitrogen), 100 units/ml Penicillin-Streptomycin (Invitrogen), 1 mM sodium pyruvate (Invitrogen) and 10% fetal bovine serum. For the β-lactamase assay, low serum, 1% FBS in MEM was used. 30,000 cells were plated into each wells of poly-D-lysine coated 384-well plate (Becton Dickinson) a day prior to the assay. SK-N-MC (4C10) was preincubated with compounds for 30 min before the addition of 200 pM CGRP. The assay was incubated for 3 hours at 37° C. to allow β-lactamase expression. CCF4 dye was added and incubated for 2 hours at room temperature. The fluorescent signals were read using a fluorescence plate reader, Topology Compensatory Plate Reader (tcPR) at excitation wavelength, 400 nm and emission wavelengths, 460 nm for the product and 535 nm for the parent. The ratio of values at 460 to 535 nm was used to calculate percent of activation. Curve fitting and IC50 calculation were carried about using MOD3.

$I^{125}$-CGRP Binding Displacement Assay to Calculate $K_i$ of Compounds.

Purified SK-N-MC membrane was purchased from Perkin Elmer. The membrane was thawed quickly and placed on ice. The compounds were diluted with CGRP binding solution (25 mM Tris-HCl, pH7.4, 5 mM MgCl2, 0.1% BSA and 0.05% Tween). The membrane was diluted 1:20 with the binding solution and homogenized with Tissue Matster-50 Homogenizer (Omni International) for 30 sec. The homogenized membrane was added to compounds in the binding solution. After 10 minutes incubation at room temperature, the final concentration of 46 pM, I125-iodotyrosyl-Calcitonin-Gene-Related Peptide (GE healthcare) was added to the membrane and compounds. After 2 hour incubation at room temperature, the reaction was stopped by rapid filtration through 0.5% PEI treated GF/C filter plate (Perkin Elmer) and the filter plate was washed with ice-cold washing solution (50 mM Tris HCl, pH7.4, 5 mM MgCl2 and 0.1% BSA) using cell harvestor (Tomtec). The radioactivity of the filter plates were read on Topcount (Packard). The nonspecific binding was determined in the control reaction where 1 uM unlabelled CGRP was preincubated with the membrane prior to I125-CGRP addition. The total binding was determined in the control reaction of the membrane and I125-CGRP in the absence of compound. The percent displacement of I125-CGRP with compounds was calculated using nonspecific and total binding controls. The curve fitting was carried out using MOD3. Ki of compound was calculated by the equation of Cheng and Prusoff (Cheng Y., Prusoff W. H., Biochem. Pharmacol. 22: 3099-3108, 1973) using Kd of CGRP for the membrane and the amount of I125-CGRP used for the assay.

Exemplary compounds of the present invention in Table 1 were found to be antagonists of CGRP in the $I^{125}$-CGRP binding assay and in the CGRP functional antagonism assay described above.

$IC_{50}$ and Ki data for selected compounds of the present invention are shown below in Table 3. In Table 3, for both the $IC_{50}$ column and the Ki column, the symbols have the following meaning: "A" means <1 µM; "B" means between 1 µM and 5 µM; "C" means >5 µM and "ND" means no data.

TABLE 3

| Cmpd # | IC50 | Ki |
|---|---|---|
| 1 | A | A |
| 2 | A | A |
| 3 | A | A |
| 4 | A | ND |
| 5 | B | ND |
| 6 | A | ND |
| 7 | A | ND |
| 8 | A | A |
| 9 | A | A |
| 10 | A | A |
| 11 | A | ND |
| 12 | A | A |
| 13 | A | ND |
| 14 | A | A |
| 15 | A | A |
| 16 | A | A |
| 17 | ND | A |
| 18 | B | ND |
| 19 | C | C |
| 20 | A | A |

TABLE 3-continued

| Cmpd # | IC50 | Ki |
|---|---|---|
| 21 | A | ND |
| 22 | B | ND |
| 23 | A | ND |
| 24 | B | ND |
| 25 | A | ND |
| 26 | A | ND |
| 27 | C | ND |
| 28 | A | A |
| 29 | C | ND |
| 30 | B | A |
| 31 | A | ND |
| 32 | A | ND |
| 33 | A | A |
| 34 | A | ND |
| 35 | B | ND |
| 36 | A | ND |
| 37 | A | A |
| 38 | A | ND |
| 39 | ND | ND |
| 40 | ND | ND |
| 41 | A | A |
| 42 | ND | ND |
| 43 | B | A |
| 44 | A | A |
| 45 | C | ND |
| 46 | B | ND |
| 47 | A | ND |
| 48 | A | A |
| 49 | A | A |
| 50 | ND | ND |
| 51 | A | ND |
| 52 | ND | ND |
| 53 | C | C |
| 54 | A | A |
| 55 | B | ND |
| 56 | ND | ND |
| 57 | A | ND |
| 58 | A | A |
| 59 | A | ND |
| 60 | A | A |
| 61 | B | C |
| 62 | A | A |
| 63 | A | A |
| 64 | B | A |
| 65 | A | ND |
| 66 | A | A |
| 67 | A | A |
| 68 | ND | ND |
| 69 | A | ND |
| 70 | A | A |
| 71 | C | ND |
| 72 | ND | ND |
| 73 | A | ND |
| 74 | B | ND |
| 75 | B | ND |
| 76 | A | A |
| 77 | C | ND |
| 78 | A | A |
| 79 | A | A |
| 80 | A | A |
| 81 | ND | ND |
| 82 | B | ND |
| 83 | A | ND |
| 84 | A | A |
| 85 | C | ND |
| 86 | B | ND |
| 87 | B | B |
| 88 | A | A |
| 89 | A | ND |
| 90 | B | ND |
| 91 | A | ND |
| 92 | A | ND |
| 93 | A | A |
| 94 | C | ND |
| 95 | A | ND |
| 96 | B | ND |
| 97 | C | ND |

TABLE 3-continued

| Cmpd # | IC50 | Ki |
|---|---|---|
| 98 | B | ND |
| 99 | ND | ND |
| 100 | A | ND |
| 101 | C | ND |
| 102 | A | A |
| 103 | C | ND |
| 104 | C | C |
| 105 | C | C |
| 106 | A | A |
| 107 | A | A |
| 108 | C | ND |
| 109 | B | A |
| 110 | C | C |
| 111 | C | ND |
| 112 | C | ND |
| 113 | A | A |
| 114 | A | A |
| 115 | A | A |
| 116 | B | A |
| 117 | B | ND |
| 118 | B | A |
| 119 | ND | A |
| 120 | A | A |
| 121 | A | ND |
| 122 | C | A |
| 123 | A | ND |
| 124 | B | ND |
| 125 | A | ND |
| 126 | A | ND |
| 127 | B | C |
| 128 | B | A |
| 129 | ND | ND |
| 130 | B | ND |
| 131 | C | ND |
| 132 | B | ND |
| 133 | C | ND |
| 134 | A | ND |
| 135 | A | ND |
| 136 | A | ND |
| 137 | A | ND |
| 138 | A | ND |
| 139 | B | ND |
| 140 | ND | ND |
| 141 | C | ND |
| 142 | ND | ND |
| 143 | C | ND |
| 144 | A | A |
| 145 | A | A |
| 146 | C | ND |
| 147 | A | A |
| 148 | B | A |
| 149 | A | A |
| 150 | A | A |
| 151 | A | ND |
| 152 | A | ND |
| 153 | ND | ND |
| 154 | A | ND |
| 155 | A | ND |
| 156 | A | ND |
| 157 | C | ND |
| 158 | B | ND |
| 159 | A | A |
| 160 | A | A |
| 161 | A | ND |
| 162 | ND | ND |
| 163 | ND | ND |
| 164 | B | ND |
| 165 | A | ND |
| 166 | A | ND |
| 167 | C | ND |
| 168 | B | ND |
| 169 | B | A |
| 170 | A | A |
| 171 | A | A |
| 172 | A | A |
| 173 | ND | ND |
| 174 | A | A |
| 175 | A | A |
| 176 | B | A |
| 177 | B | ND |
| 178 | B | ND |
| 179 | A | ND |
| 180 | B | ND |
| 181 | A | ND |
| 182 | A | A |
| 183 | A | A |
| 184 | A | A |
| 185 | A | ND |
| 186 | C | ND |
| 187 | B | A |
| 188 | A | A |
| 189 | C | ND |
| 190 | C | B |
| 191 | A | ND |
| 192 | A | ND |
| 193 | ND | ND |
| 194 | A | A |
| 195 | B | C |
| 196 | B | ND |
| 197 | C | ND |
| 198 | A | A |
| 199 | ND | ND |
| 200 | C | ND |
| 201 | B | ND |
| 202 | A | A |
| 203 | B | A |
| 204 | B | B |
| 205 | B | ND |
| 206 | A | ND |
| 207 | A | ND |
| 208 | A | A |
| 209 | A | ND |
| 210 | A | ND |
| 211 | B | A |
| 212 | A | A |
| 213 | B | ND |
| 214 | B | ND |
| 215 | A | ND |
| 216 | ND | ND |
| 217 | A | ND |
| 218 | C | ND |
| 219 | B | ND |
| 220 | ND | ND |
| 221 | A | ND |
| 222 | A | ND |
| 223 | C | ND |
| 224 | A | A |
| 225 | A | A |
| 226 | B | A |
| 227 | A | A |
| 228 | B | ND |
| 229 | ND | ND |
| 230 | C | B |
| 231 | A | ND |
| 232 | B | ND |
| 233 | A | ND |
| 234 | A | ND |
| 235 | B | ND |
| 236 | B | A |
| 237 | A | C |
| 238 | B | ND |
| 239 | A | ND |
| 240 | B | A |
| 241 | B | ND |
| 242 | B | ND |
| 243 | B | ND |
| 244 | A | A |
| 245 | C | ND |
| 246 | A | ND |
| 247 | B | ND |
| 248 | A | C |
| 249 | A | ND |
| 250 | C | ND |
| 251 | C | B |

TABLE 3-continued

| Cmpd # | IC50 | Ki |
|---|---|---|
| 252 | A | ND |
| 253 | B | ND |
| 254 | B | ND |
| 255 | B | A |
| 256 | A | A |
| 257 | A | ND |
| 258 | B | ND |
| 259 | A | A |
| 260 | A | A |
| 261 | C | ND |
| 262 | B | ND |
| 263 | A | A |
| 264 | A | A |
| 265 | A | A |
| 266 | A | A |
| 267 | A | ND |
| 268 | A | A |
| 269 | B | ND |
| 270 | C | ND |
| 271 | A | A |
| 272 | B | ND |
| 273 | B | ND |
| 274 | A | ND |
| 275 | C | ND |
| 276 | B | ND |
| 277 | A | ND |
| 278 | A | A |
| 279 | A | A |
| 280 | A | ND |
| 281 | C | ND |
| 282 | A | A |
| 283 | B | A |
| 284 | B | ND |
| 285 | A | ND |
| 286 | B | C |
| 287 | B | B |
| 288 | A | A |
| 289 | A | A |
| 290 | A | A |
| 291 | A | ND |
| 292 | B | ND |
| 293 | A | ND |
| 294 | A | ND |
| 295 | A | A |
| 296 | A | A |
| 297 | A | A |
| 298 | A | ND |
| 299 | A | A |
| 300 | A | ND |
| 301 | A | A |
| 302 | A | A |
| 303 | A | A |
| 304 | ND | A |
| 305 | B | ND |
| 306 | C | C |
| 307 | A | A |
| 308 | A | ND |
| 309 | B | ND |
| 310 | A | ND |
| 311 | B | ND |
| 312 | A | ND |
| 313 | A | ND |
| 314 | C | ND |
| 315 | A | A |
| 316 | C | ND |
| 317 | B | A |
| 318 | A | ND |
| 319 | A | ND |
| 320 | A | ND |
| 321 | A | ND |
| 322 | B | ND |
| 323 | A | ND |
| 324 | A | A |
| 325 | A | ND |
| 326 | ND | ND |
| 327 | ND | ND |
| 328 | A | A |

TABLE 3-continued

| Cmpd # | IC50 | Ki |
|---|---|---|
| 329 | ND | ND |
| 330 | B | A |
| 331 | A | A |
| 332 | C | ND |
| 333 | B | ND |
| 334 | A | ND |
| 335 | A | A |
| 336 | A | A |
| 337 | ND | ND |
| 338 | A | ND |
| 339 | ND | ND |
| 340 | C | C |
| 341 | A | A |
| 342 | B | ND |
| 343 | ND | ND |
| 344 | A | ND |
| 345 | A | A |
| 346 | A | ND |
| 347 | A | A |
| 348 | B | C |
| 349 | A | A |
| 350 | A | A |
| 351 | B | A |
| 352 | A | ND |
| 353 | A | A |
| 354 | A | A |
| 355 | ND | ND |
| 356 | A | ND |
| 357 | A | A |
| 358 | C | ND |
| 359 | ND | ND |
| 360 | A | ND |
| 361 | B | ND |
| 362 | B | ND |
| 363 | A | A |
| 364 | C | ND |
| 365 | A | A |
| 366 | A | ND |
| 367 | A | A |
| 368 | ND | ND |
| 369 | B | ND |
| 370 | A | ND |
| 371 | A | A |
| 372 | C | ND |
| 373 | B | ND |
| 374 | B | B |
| 375 | A | A |
| 376 | A | ND |
| 377 | B | ND |
| 378 | A | ND |
| 379 | A | ND |
| 380 | A | A |
| 381 | C | ND |
| 382 | A | ND |
| 383 | B | ND |
| 384 | C | ND |
| 385 | B | ND |
| 386 | ND | ND |
| 387 | A | ND |
| 388 | C | ND |
| 389 | A | A |
| 390 | C | ND |
| 391 | C | C |
| 392 | C | ND |
| 393 | A | ND |
| 394 | A | A |
| 395 | C | ND |
| 396 | B | ND |
| 397 | C | C |
| 398 | C | ND |
| 399 | C | ND |
| 400 | A | A |
| 401 | A | A |
| 402 | A | A |
| 403 | B | A |
| 404 | B | ND |
| 405 | B | A |

TABLE 3-continued

| Cmpd # | IC50 | Ki |
|---|---|---|
| 406 | ND | A |
| 407 | A | A |
| 408 | A | ND |
| 409 | C | A |
| 410 | A | ND |
| 411 | B | ND |
| 412 | A | ND |
| 413 | A | ND |
| 414 | B | C |
| 415 | B | A |
| 416 | ND | ND |
| 417 | B | ND |
| 418 | C | ND |
| 419 | B | ND |
| 420 | C | ND |
| 421 | A | ND |
| 422 | A | ND |
| 423 | A | ND |
| 424 | A | ND |
| 425 | A | ND |
| 426 | B | ND |
| 427 | ND | ND |
| 428 | C | ND |
| 429 | ND | ND |
| 430 | C | ND |
| 431 | A | A |
| 432 | A | A |
| 433 | C | ND |
| 434 | A | A |
| 435 | B | A |
| 436 | A | A |
| 437 | A | A |
| 438 | A | ND |
| 439 | A | ND |
| 440 | ND | ND |
| 441 | A | ND |
| 442 | A | ND |
| 443 | A | ND |
| 444 | C | ND |
| 445 | B | ND |
| 446 | A | A |
| 447 | A | A |
| 448 | A | ND |
| 449 | ND | ND |
| 450 | ND | ND |
| 451 | B | ND |
| 452 | A | ND |
| 453 | A | ND |
| 454 | C | ND |
| 455 | B | ND |
| 456 | B | A |
| 457 | A | A |
| 458 | A | A |
| 459 | A | A |
| 460 | ND | ND |
| 461 | A | A |
| 462 | A | A |
| 463 | B | A |
| 464 | B | ND |
| 465 | B | ND |
| 466 | A | ND |
| 467 | B | ND |
| 468 | A | ND |
| 469 | A | A |
| 470 | A | A |
| 471 | A | A |
| 472 | A | ND |
| 473 | C | ND |
| 474 | B | A |
| 475 | A | A |
| 476 | C | ND |
| 477 | C | A |

What is claimed is:

1. A compound of formula I':

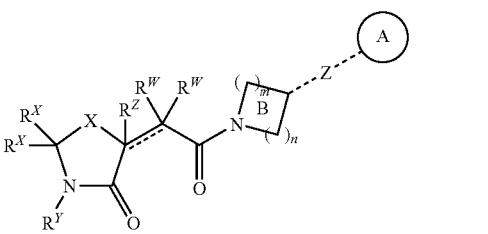

wherein:

X is S, SO, or $SO_2$;

Z is present or absent;
wherein:
when Z is present, then ring A is attached to ring B through a single bond;
when Z is absent, then ring A together with ring B forms a spirocyclic ring system;

ring A is a 4-7 membered heterocyclic or heteroaryl ring or a 10-14 membered bicyclic heteroaryl or heterocyclic ring, wherein said heterocyclic or heteroaryl ring has 1-4 heteroatoms selected from O, N, or S; wherein ring A is optionally substituted with up to 5 $R^1$ substituents;

m is 1-3;

n is 1-3; provided that m+n is $\leq 4$;

$R^Y$ is aryl, heteroaryl, cycloaliphatic, C1-C6 aliphatic, aryl-aliphatic-, or cycloaliphatic-aliphatic-; wherein $R^Y$ is optionally substituted with up to 5 $R^2$ substituents;

$R^X$ is hydrogen, halo, aryl, heteroaryl, C1-C6 aliphatic, aryl-C1-C6 aliphatic-, heteroaryl-C1-C6 aliphatic-, wherein $R^X$ is optionally substituted with up to 5 $R^3$ substituents;

or two $R^X$, taken together with the carbon atom that they are attached to, form a 3-9 membered cycloaliphatic or heterocyclic ring, wherein said heterocyclic ring has up to 3 heteroatoms selected from O, S, and N; wherein said ring is optionally substituted with up to 3 $R^3$ substituents;

wherein said ring formed by two $R^X$ is optionally substituted with up to 5 $R^4$ substituents;

$R^Z$ is absent, hydrogen, CN, C1-C6 aliphatic, halo-C1-C6 aliphatic, O-C1-C6 aliphatic, O-(halo-C1-C6 aliphatic), halo, aryl-C1-C6 aliphatic, or heteroaryl-C1-C6 aliphatic;

----- is a single or a double bond; provided that when it is a double bond, then $R^Z$ and one of $R^W$ is absent;

$R^W$ is independently, hydrogen, halo, oxo, C1-C6 aliphatic, halo-C1-C6 aliphatic, —O-C1-C6 aliphatic, —O-(halo-C1-C6 aliphatic), aryl, aryl-C1-C6 aliphatic-, C3-C7 cycloaliphatic; or two $R^W$ taken together form an optionally substituted C3-C7 cycloaliphatic or heterocyclic ring, wherein said heterocyclic ring has up to 3 heteroatoms selected from O, S, and N; wherein said ring formed by two $R^W$ is optionally substituted with up to 5 $R^5$ substituents;

wherein each occurrence of $R^1$, $R^2$, $R^3$, $R^4$, and $R^5$ is independently Q-$R^M$;

wherein Q is a bond or is a C1-C6 aliphatic chain wherein up to two non-adjacent methylene units of Q are optionally and independently replaced by CO, $CO_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR;

wherein each occurrence of R$^M$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R';

wherein each occurrence of R is independently selected from hydrogen or an optionally substituted C$_{1-6}$ aliphatic group wherein each occurrence of R' is independently selected from hydrogen or an optionally substituted group selected from C$_{1-8}$ aliphatic, C$_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form a 5-8 membered cycloalkyl, heterocyclyl, aryl, or heteroaryl ring having 0-3 heteroatoms independently selected from nitrogen, oxygen, or sulfur.

2. The compound according to claim 1, wherein ----- is a single bond.

3. The compound according to claim 1, wherein ----- is a single bond and both of R$^W$ are hydrogen.

4. The compound according to claim 1, wherein R$^Z$, if present, is C1-C6 alkyl, halo-C1-C6 alkyl- or —O-C1-C6 alkyl.

5. The compound according to claim 1, wherein at least one R$^W$ is C1-C6 alkyl, halo-C1-C6 alkyl- or —O-C1-C6 alkyl.

6. The compound according to claim 1, wherein R$^Y$ is C1-C6 aliphatic optionally substituted with one or more halo, OH, -C1-C4 alkoxy, -C1-C4 alkoxy carbonyl, or di-(C1-C4 alkyl) amino-.

7. The compound according to claim 6, wherein R$^Y$ is methyl, ethyl, propyl, isopropyl, butyl, t-butyl, 3,3-dimethyl-butyl, 3-methyl-butyl, 2-methyl-propyl, 2-methoxy-ethyl, 3-ethoxypropyl, 1-(methoxy carbonyl)-3-methyl-butyl, 1-(hydroxy methyl)-3-methyl-butyl, allyl, acetenyl, 2-(diethylamino)ethyl, 1-methyl-2-methoxy-ethyl, 3-hydroxy-2,2-dimethyl-propyl, 2,2,2-trifluoroethyl, 3,3,3-trifluoro-propyl, or 2,2,3,3,3-pentafluoro-propyl.

8. The compound according to claim 1, wherein R$^Y$ is C3-C8 cycloaliphatic or a C3-C8 cycloaliphatic substituted C1-C6 aliphatic-.

9. The compound according to claim 1, wherein R$^Y$ is optionally substituted phenyl or (optionally substituted phenyl)-substituted C1-C6 aliphatic.

10. The compound according to claim 1, wherein one R$^X$ is hydrogen and the other R$^X$ is phenyl or heteroaryl optionally substituted with one or more substituents independently selected from C1-C6 aliphatic, cyano, halo, halo-C1-C6 aliphatic, aryl-C1-C6 aliphatic, heteroaryl-C1-C6 aliphatic, aralkyloxy, di(C1-C6 aliphatic)amino, O-C1-C6 aliphatic, S(O)-C1-C6 aliphatic, or S(O)$_2$-C1-C6 aliphatic.

11. The compound according to claim 1, wherein two R$^X$, taken together with the carbon atom that they are attached to, form a 3-9 membered cycloaliphatic or heterocyclic, monocyclic, bicyclic, or tricyclic ring.

12. The compound according to claim 1, wherein said compound is of formula I'-A:

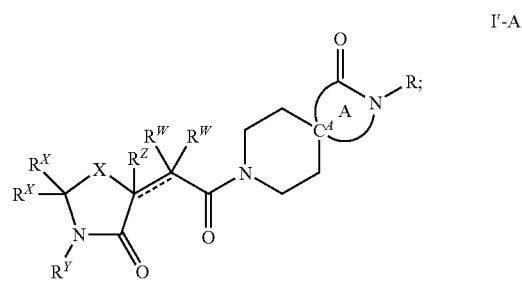

I'-A wherein:

ring A is a 4-7 membered heterocyclic ring that forms a spirocyclic ring system with said piperidine ring through carbon atom C$^A$, wherein ring A is optionally fused with a an optionally substituted phenyl or heteroaryl ring;

wherein said ring A, in addition to the nitrogen ring atom, has up to two additional ring heteroatoms selected from O, N, or S; and wherein ring A, in addition to the oxo group, is optionally substituted with up to 5 R$^1$ substituents.

13. The compound according to claim 12, wherein ring A is selected from:

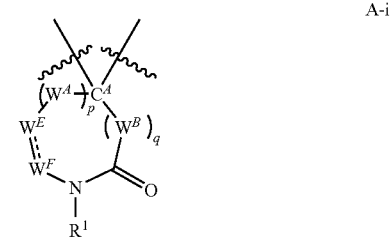

A-i

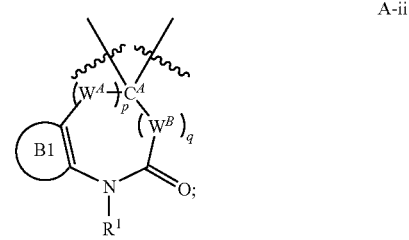

A-ii

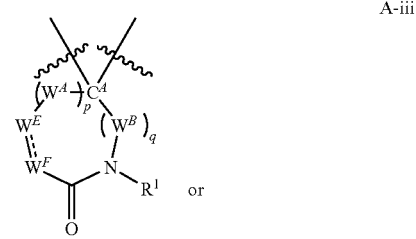

A-iii or

-continued

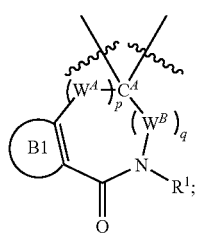

A-iv wherein:
p is 0-2;
q is 0-2; provided that p+q≦2;
each of $W^A$ and $W^B$ is independently selected from $NR^1$, O, S, SO, $SO_2$, $C(R^1)_2$, or $=CR^1$ (when p or q is 2);
$W^E$ is —$C(R^1)_2$, =$C(R^1)$—, =N—, or —$N(R^1)$—;
$W^F$ is absent or is selected from —$C(R^1)_2$, =$C(R^1)$—, =N—, or —$N(R^1)$—; provided that both of $W^E$ and $W^F$ are not simultaneously =N— or —$N(R^1)$—;
ring B1 is an optionally substituted phenyl or 5-6 membered heteroaryl ring; and
$R^1$ is as defined in claim 12.

14. The compound according to claim 1, wherein said compound is of formula I'-B:

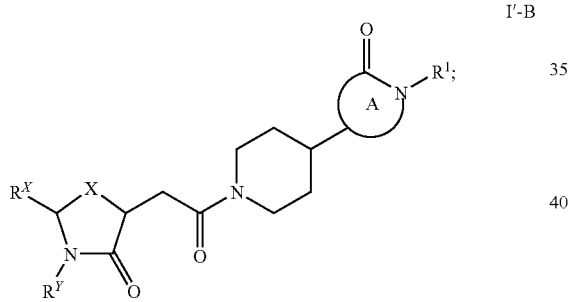

I'-B wherein ring A is a 4-7 membered heterocyclic ring optionally fused with an phenyl or heteroaryl ring that is optionally substituted with up to 5 $R^1$ substituents;
wherein said ring A, in addition to the nitrogen ring atom, contains up to two additional ring heteroatoms selected from O, N, or S; and
wherein ring A, in addition to the oxo group, is optionally substituted with up to 5 $R^1$ substituents.

15. The compound according to claim 14, wherein ring A is selected from:

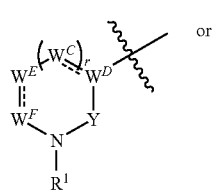

A-v or

-continued

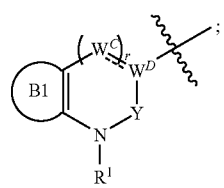

A-vi wherein:
$W^C$ is —$C(R^1)_2$, C(O), or =$CR^1$—;
r is 0-2;
$W^D$ is N or =C—;
$W^E$ is —$C(R^1)_2$, =$C(R^1)$—, =N—, or —$N(R^1)$—;
$W^F$ is absent or is selected from —$C(R^1)_2$, =$C(R^1)$—, =N—, or —$N(R^1)$—; provided that both of $W^E$ and $W^F$ are not simultaneously =N— or —$N(R^1)$—;
Y is C(O), S(O), or $S(O)_2$; and
ring B1 is a phenyl or 5-6 membered heteroaryl ring optionally substituted with up to 5 $R^1$ substituents; and ----- is a single or a double bond.

16. The compound according to claim 15, wherein ring A is selected from:

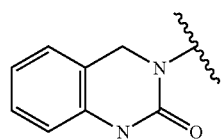

A-vi-a

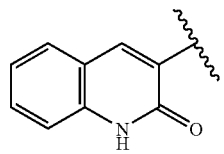

A-vi-b

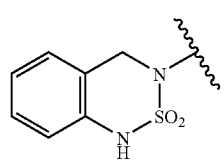

A-vi-c

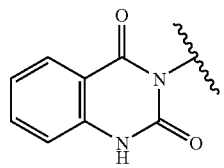

A-vi-d

A-vi-e

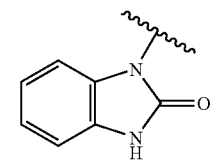

A-vi-f

-continued
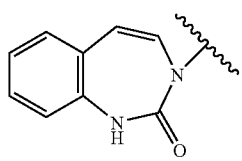
A-vi-g
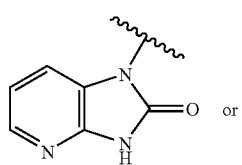
A-vi-h or
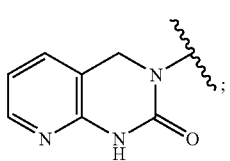
A-vi-I;
wherein said ring is optionally substituted with up to 4 R¹ substituents.
17. A compound selected from:
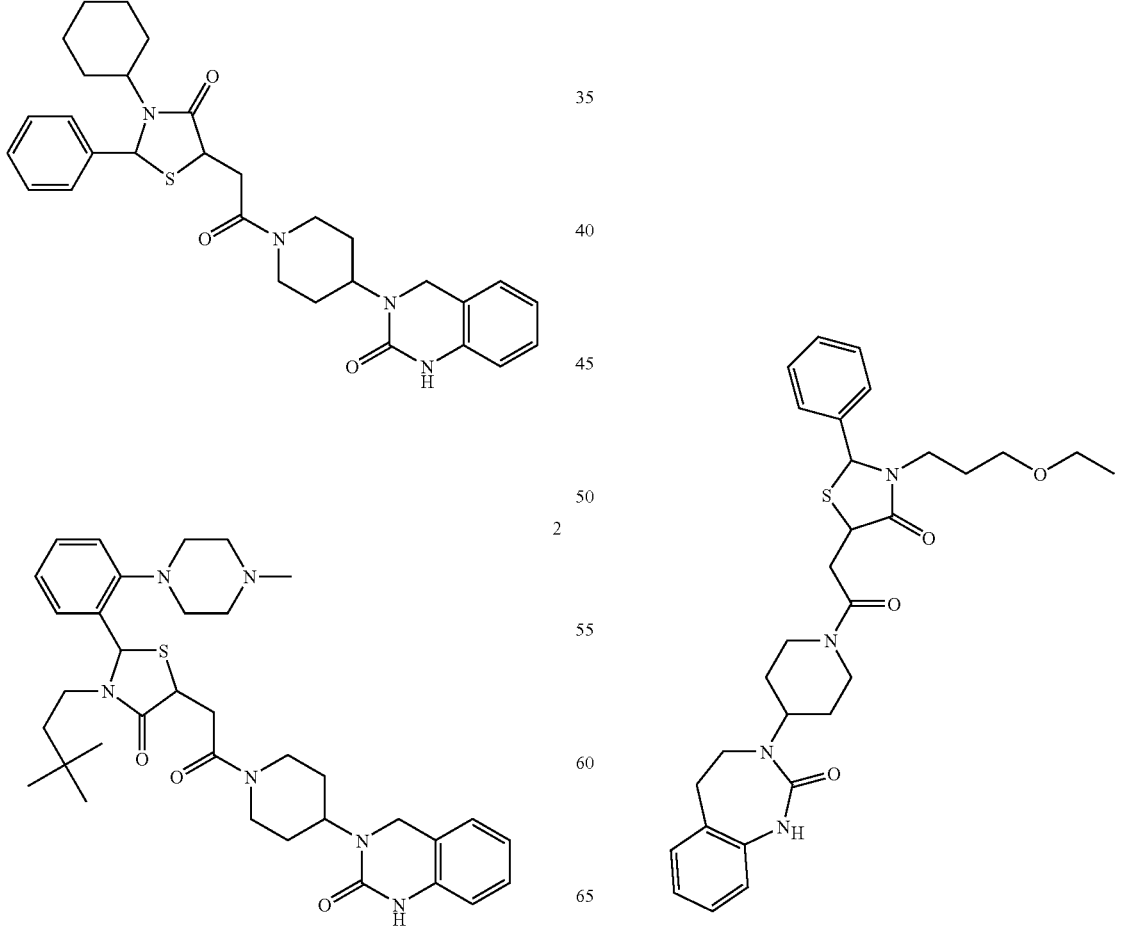
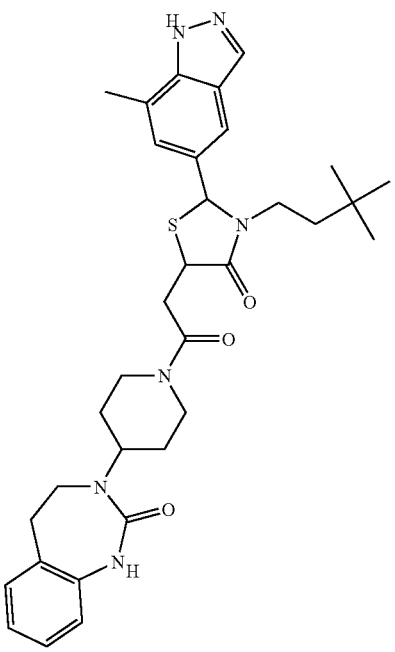

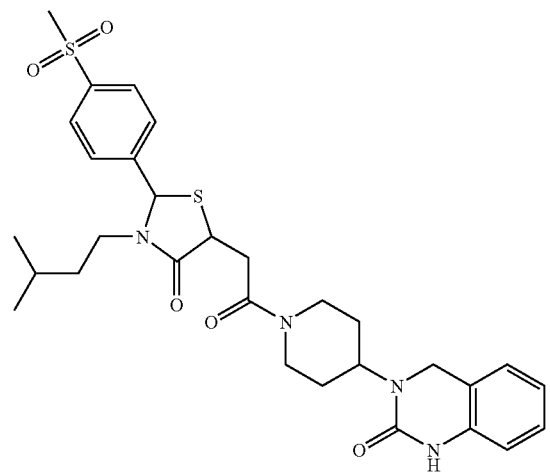
5
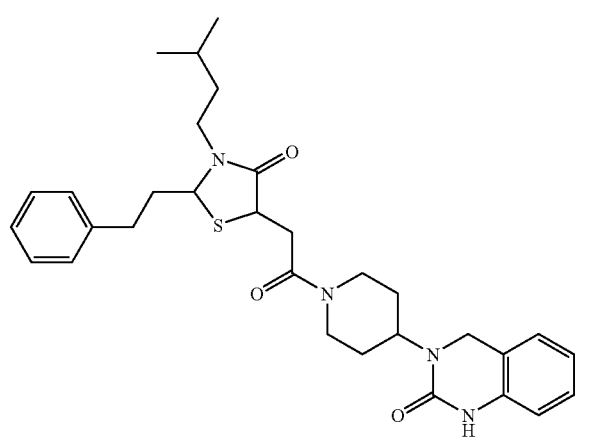
6
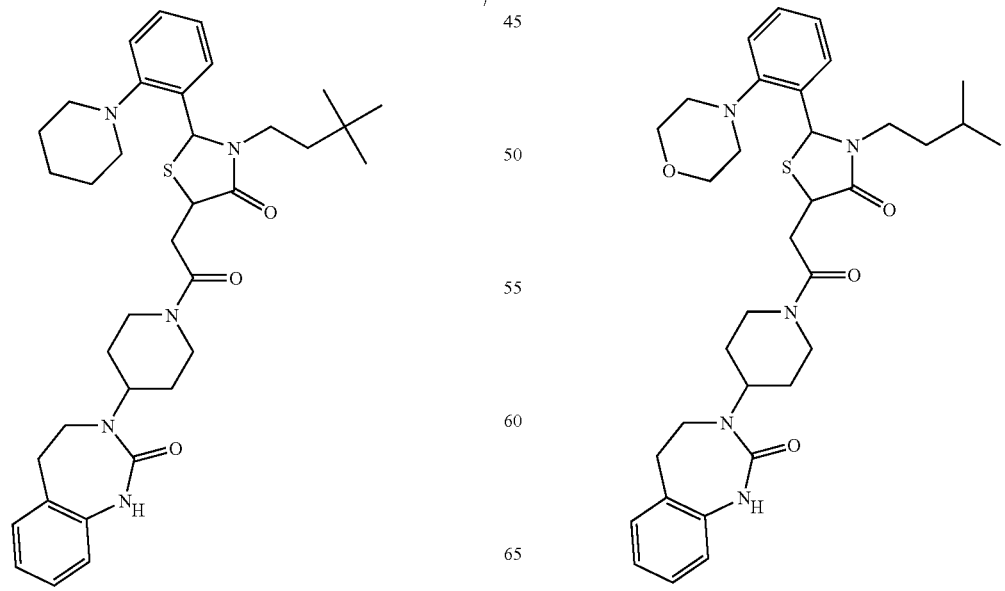
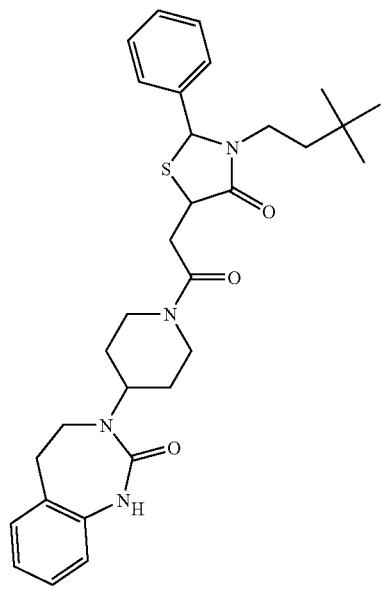
8
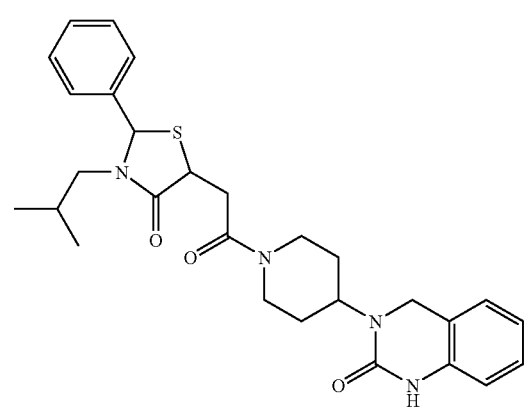
9

11
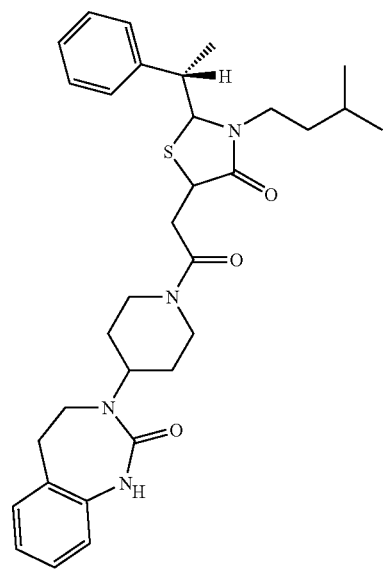
12
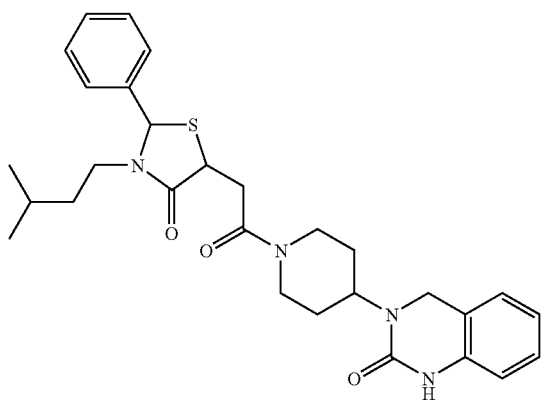
13
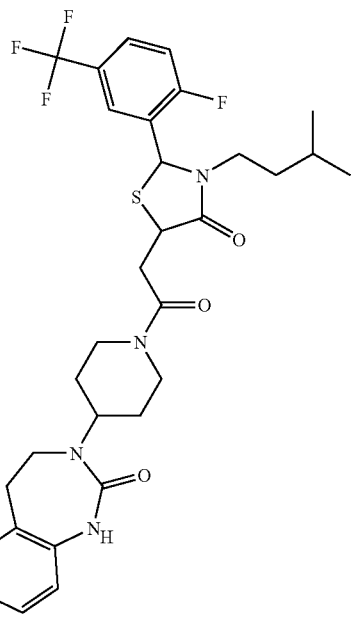
14
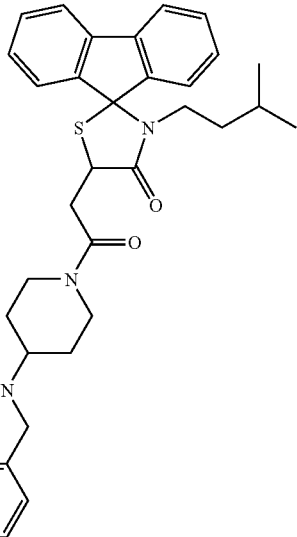
15
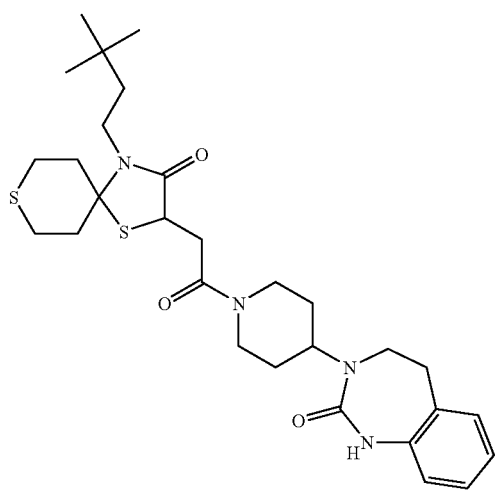
16
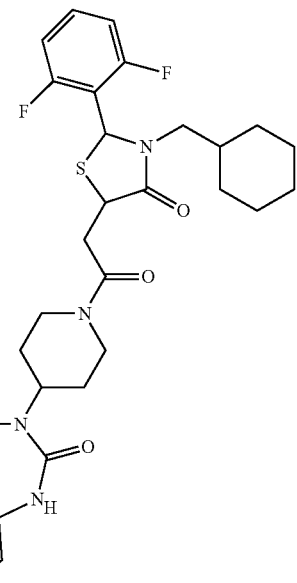

17
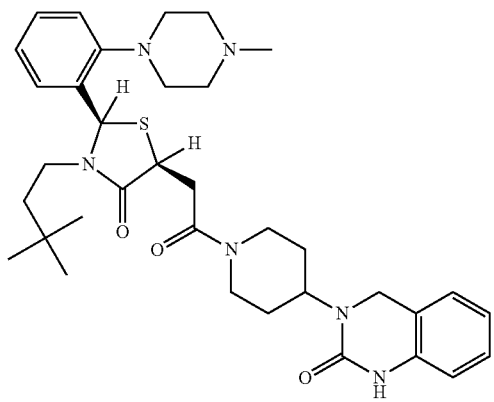
18
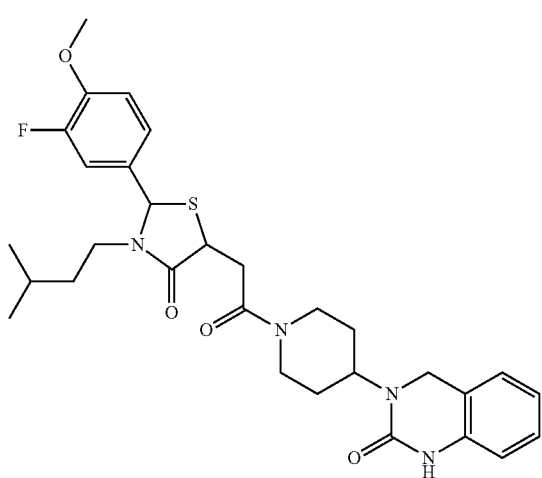
19
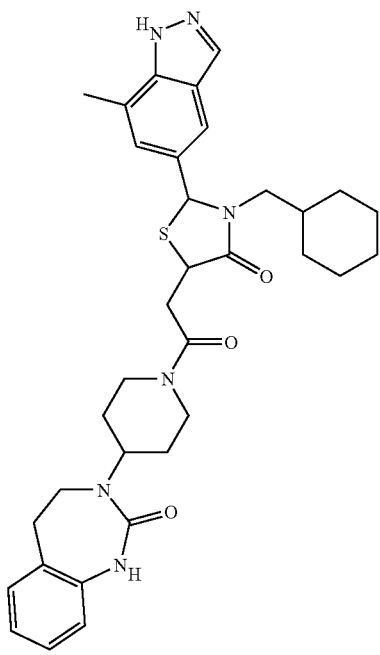
20
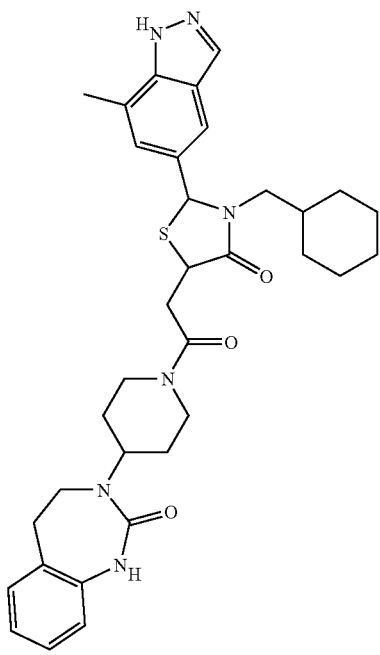
21
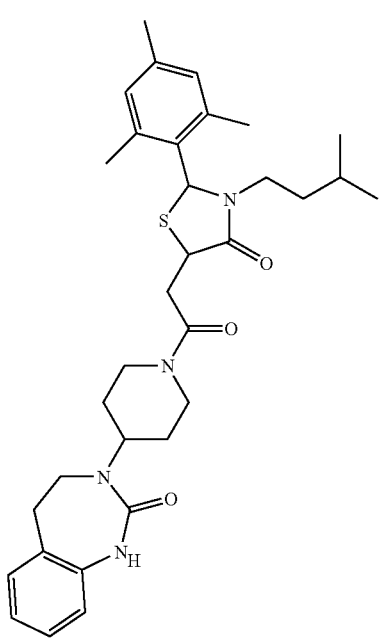

-continued
22
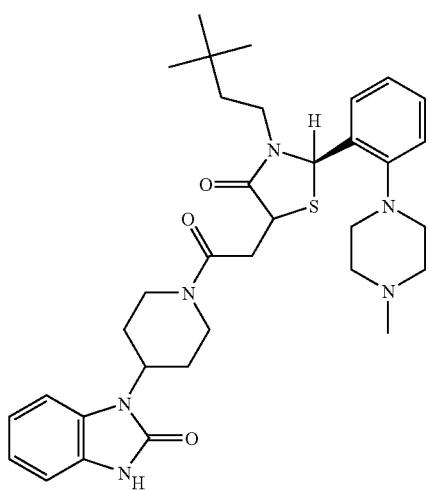
23
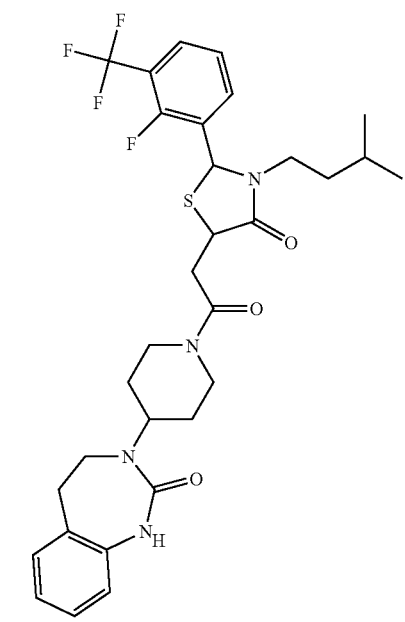
-continued
24
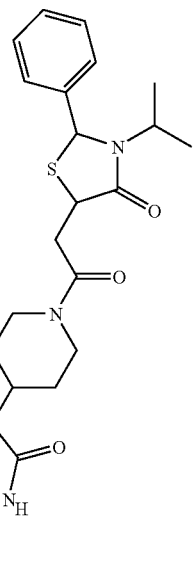
25
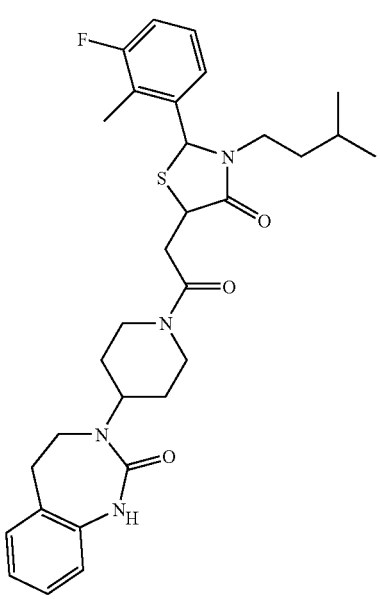
26

27
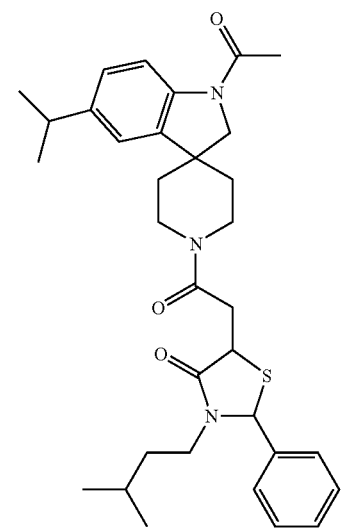
28
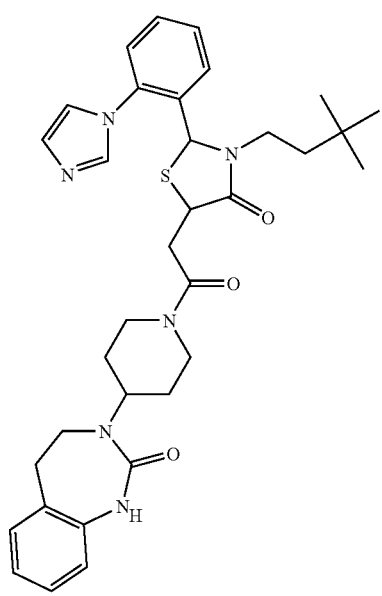
29
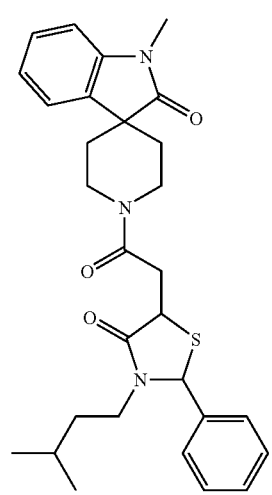
30
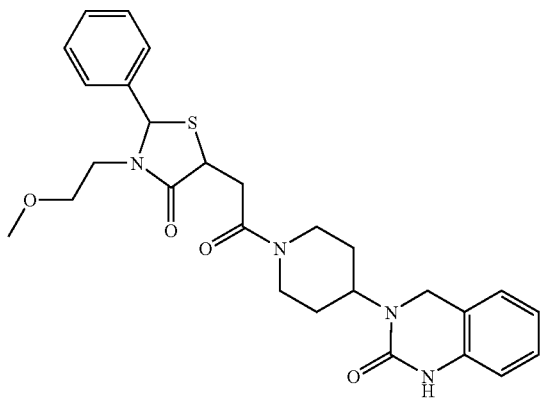
31
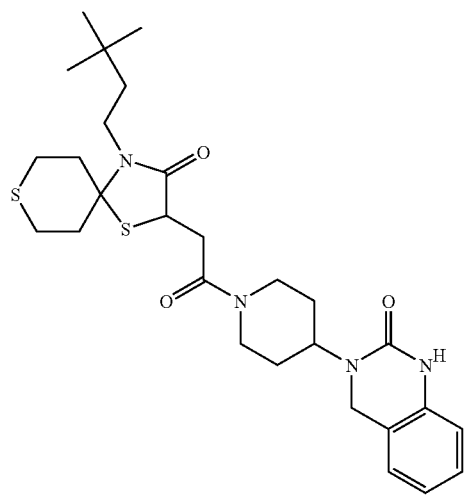
32
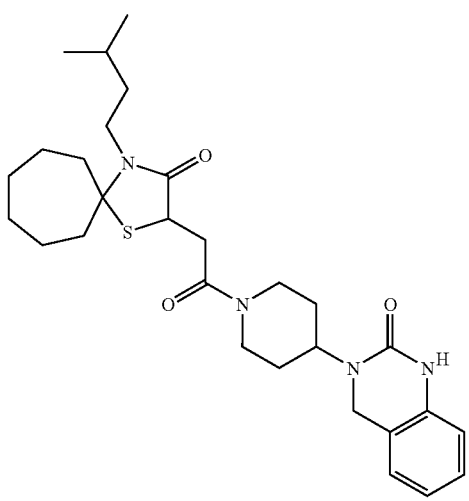

33
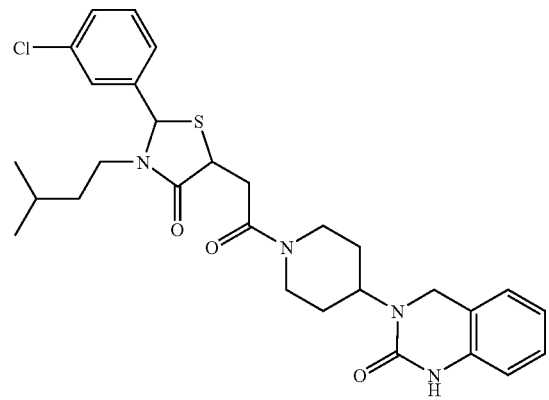
34
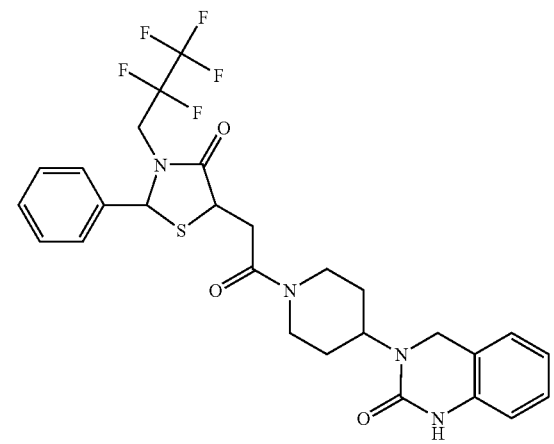
35
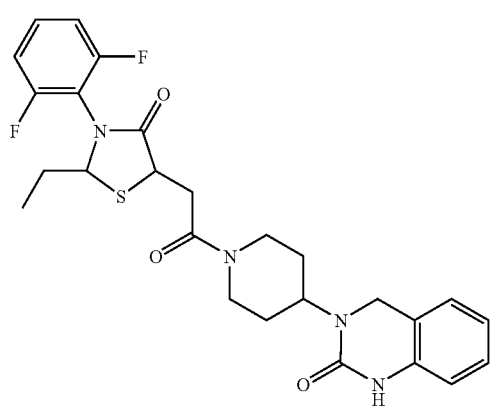
36
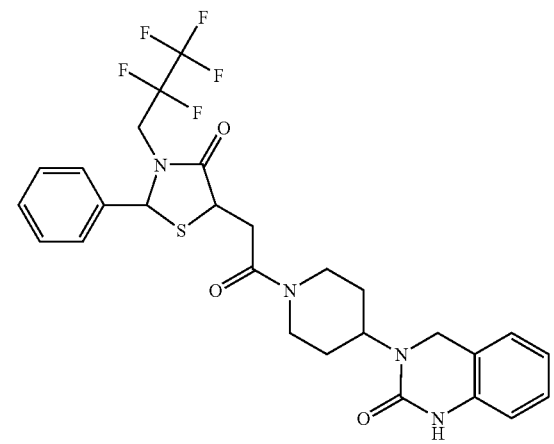
37
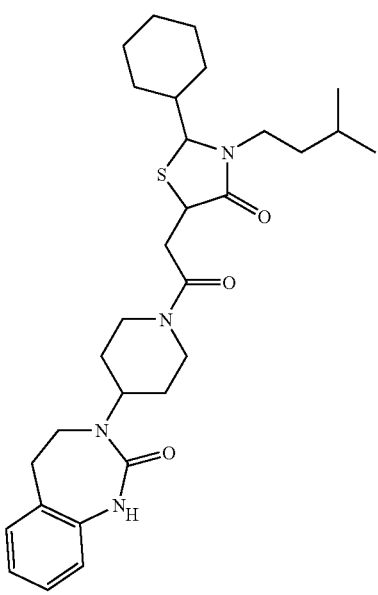
38
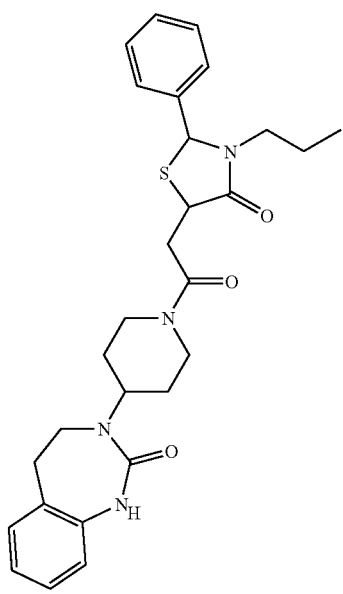

39
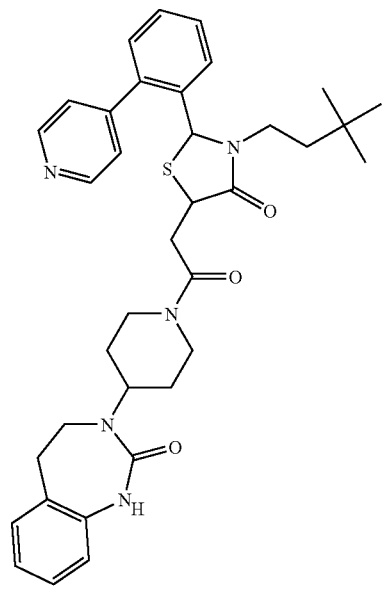
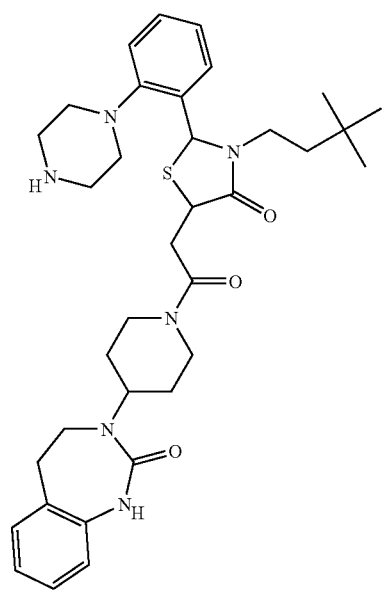
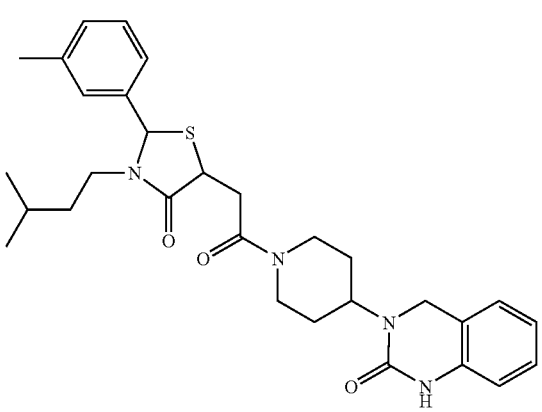
40
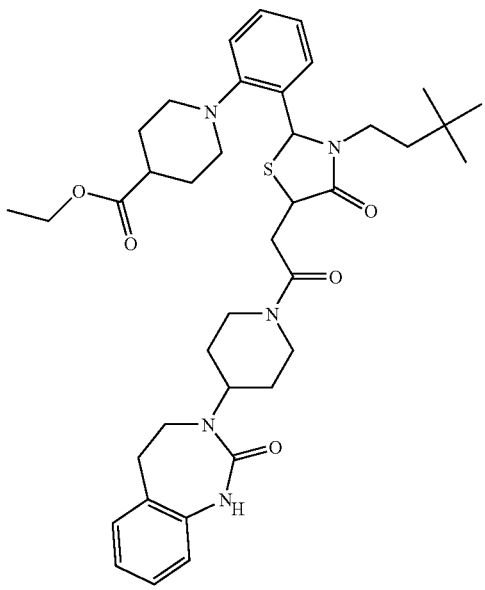
41
42
43
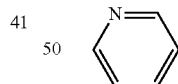
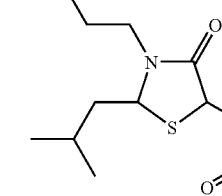

-continued
44
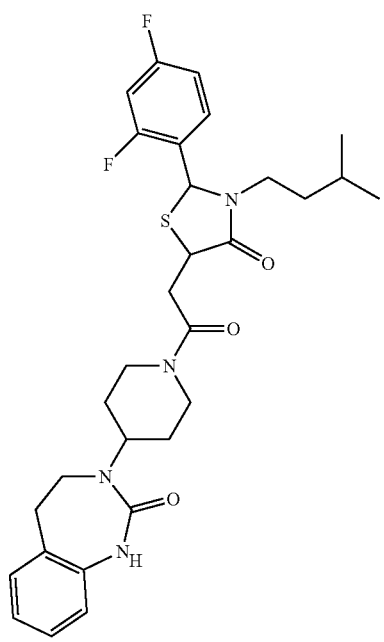
45
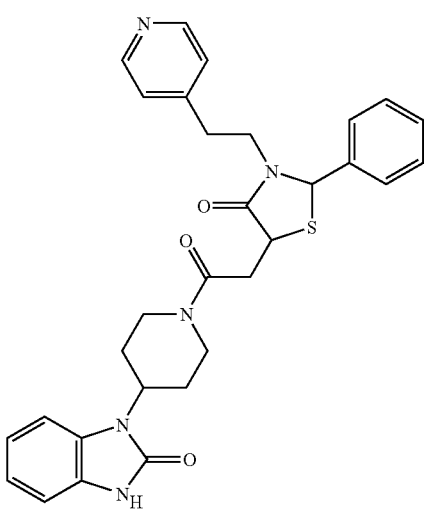
46
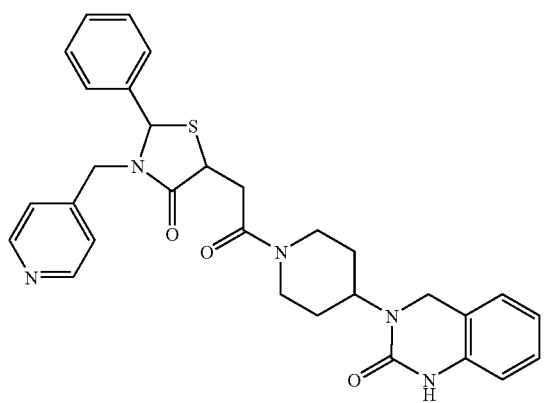
-continued
47
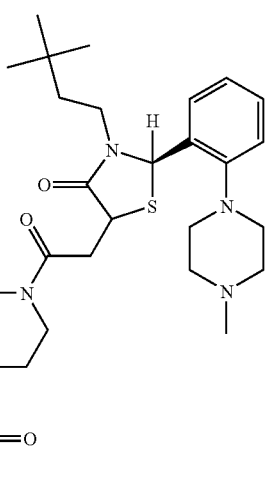
48
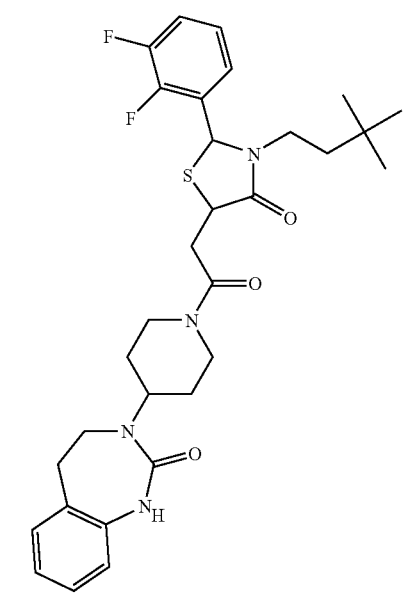
49
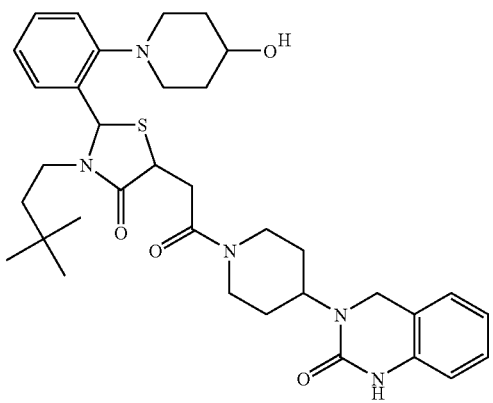

-continued
| 50 | |
|---|---|
| 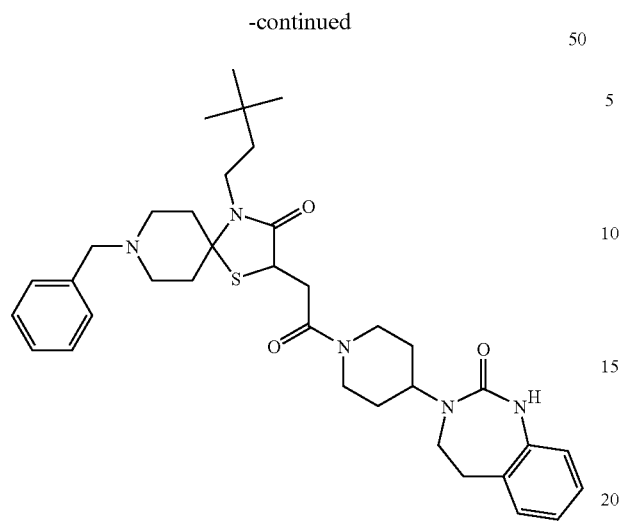 | 53 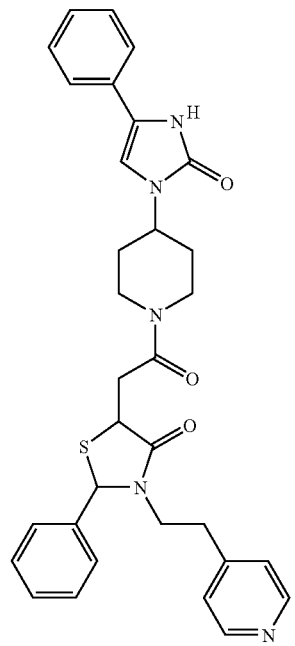 |
| 51 | |
| 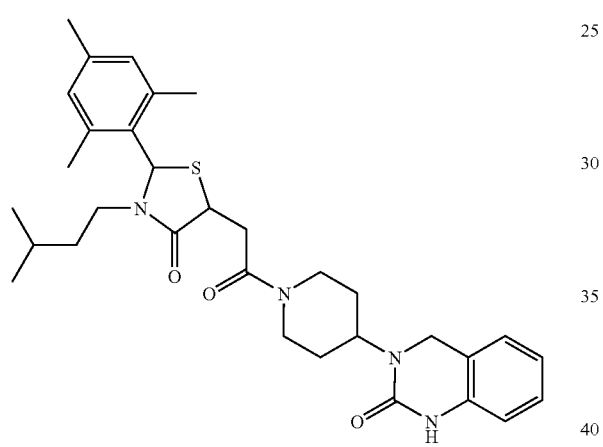 | 54 |
| 52 | 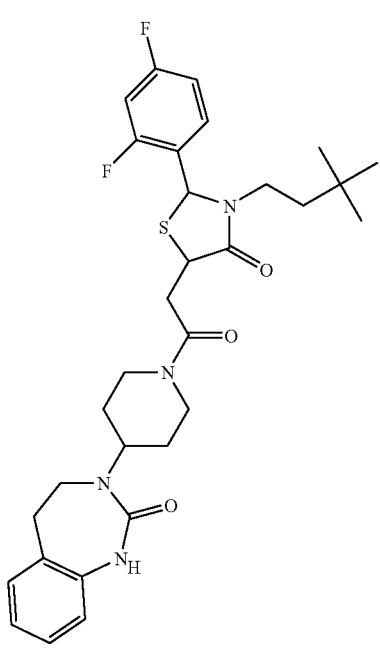 |
| 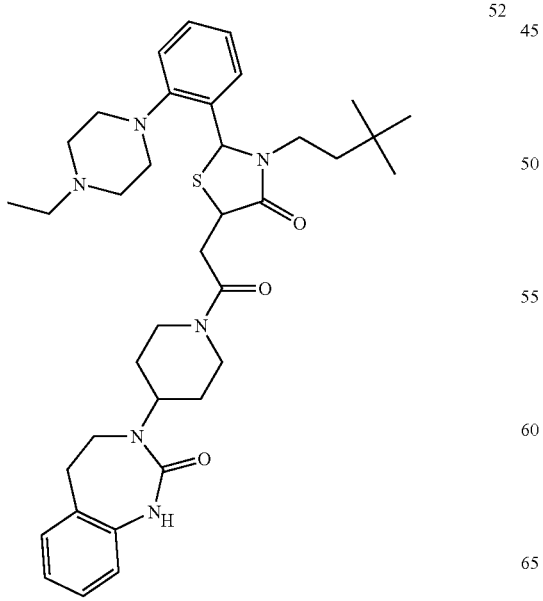 | |

295
-continued
55
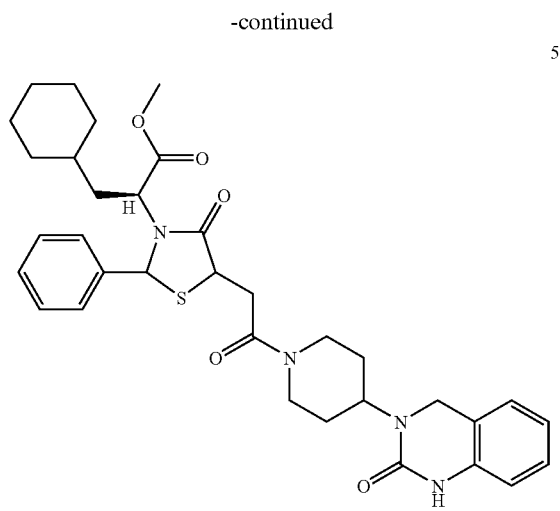
56
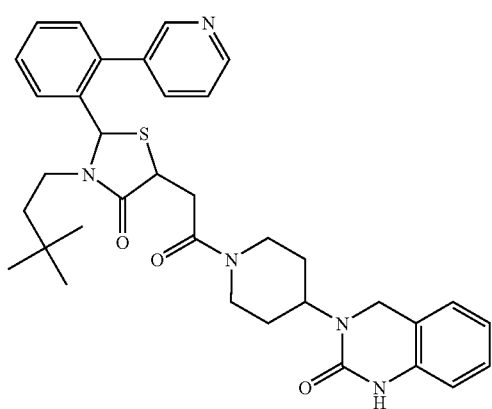
57
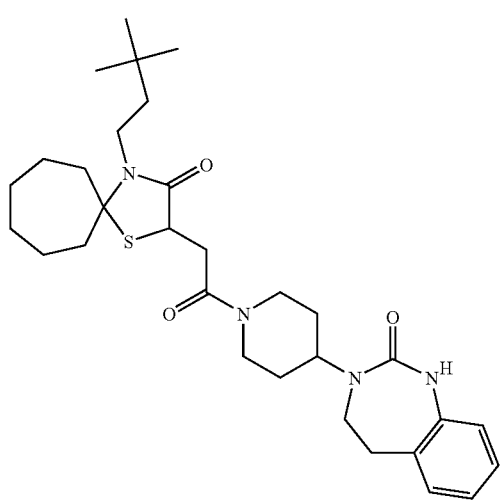
296
-continued
58
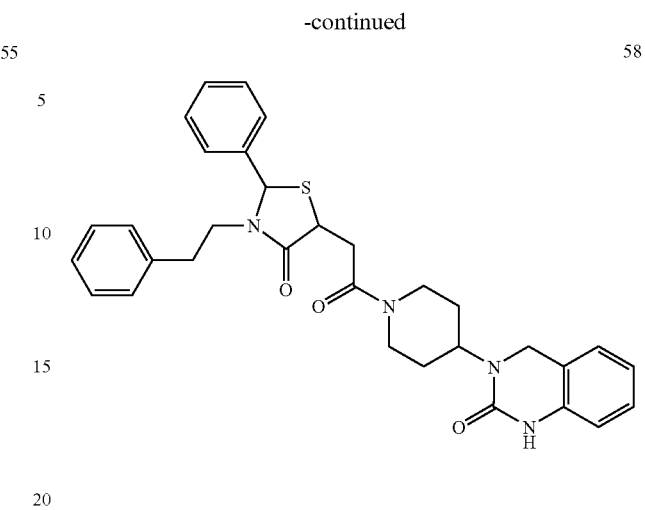
59
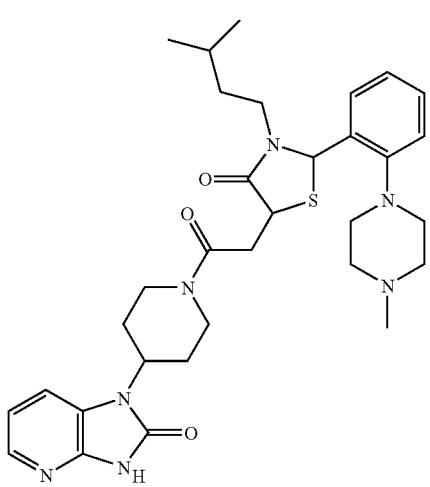
60
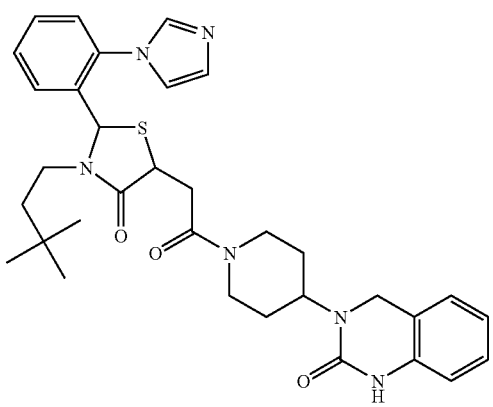

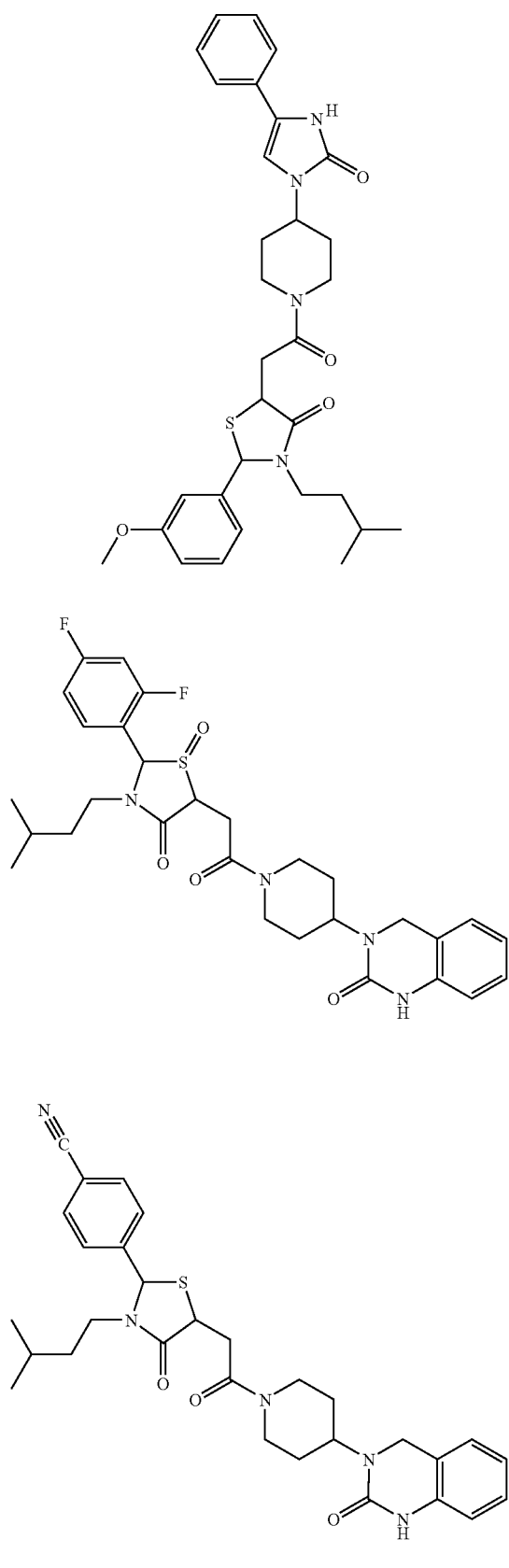
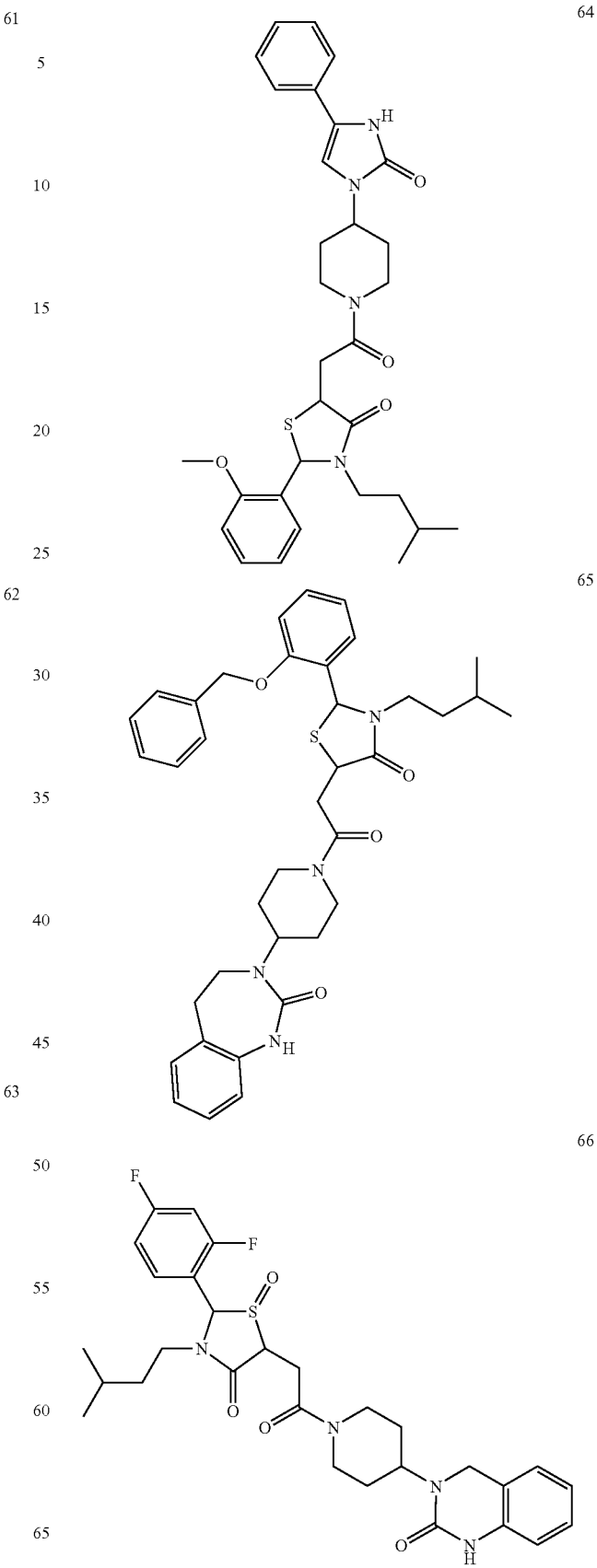

67
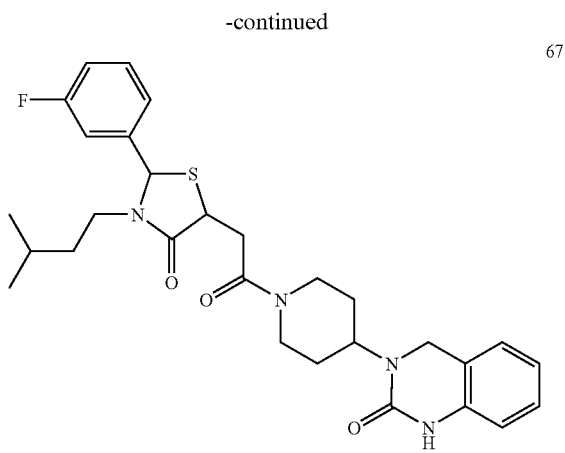
68
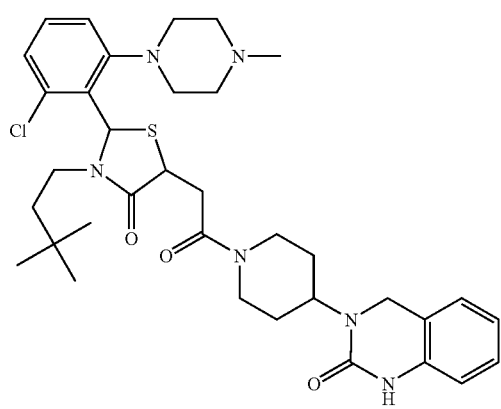
69
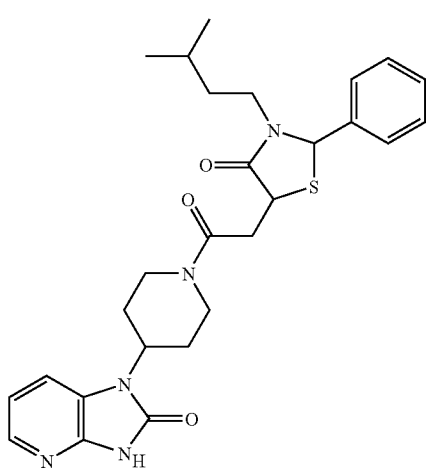
70
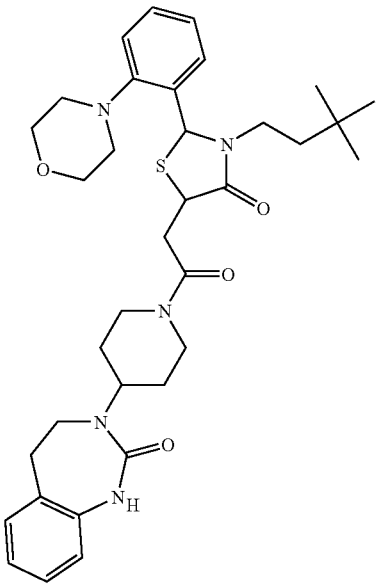
71
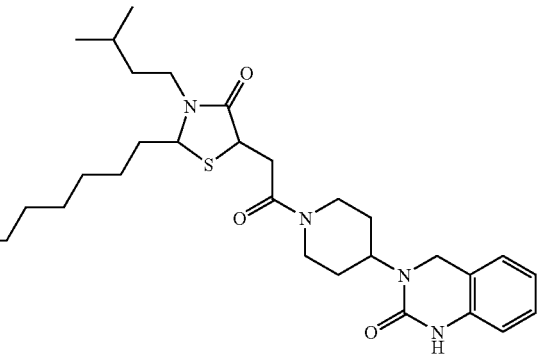
72
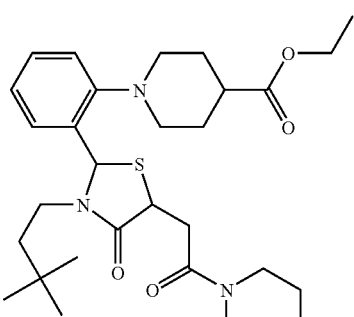
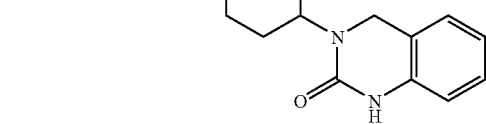

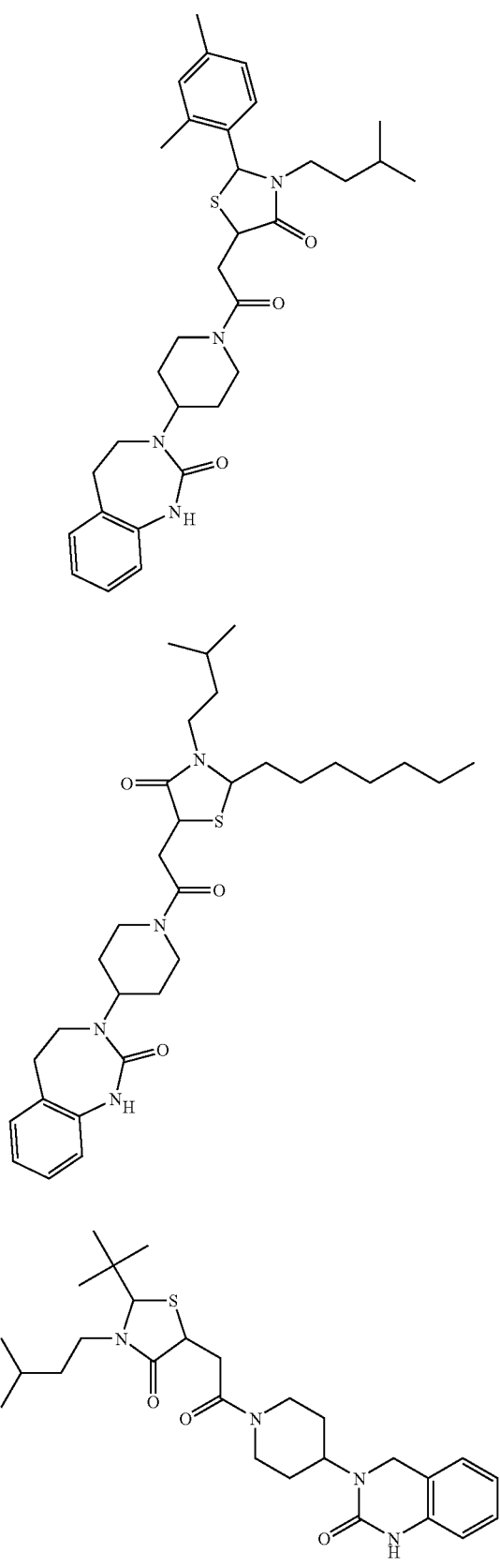
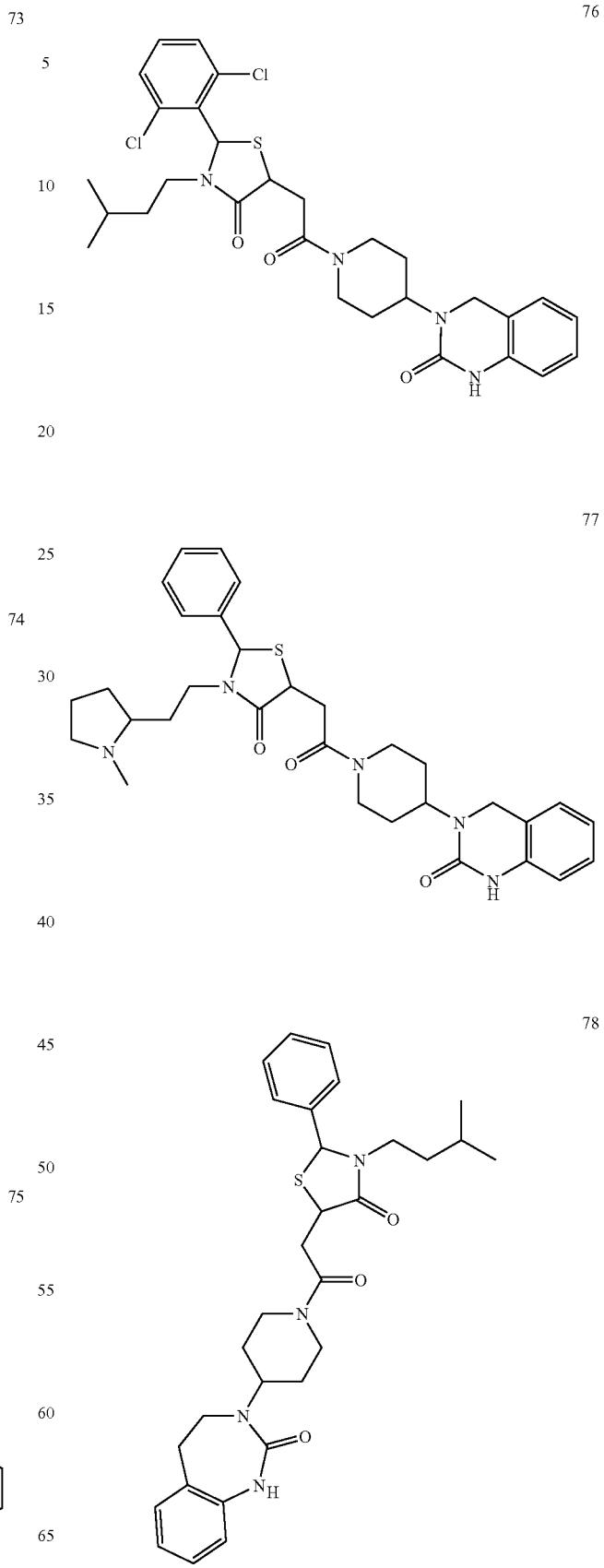

303
-continued
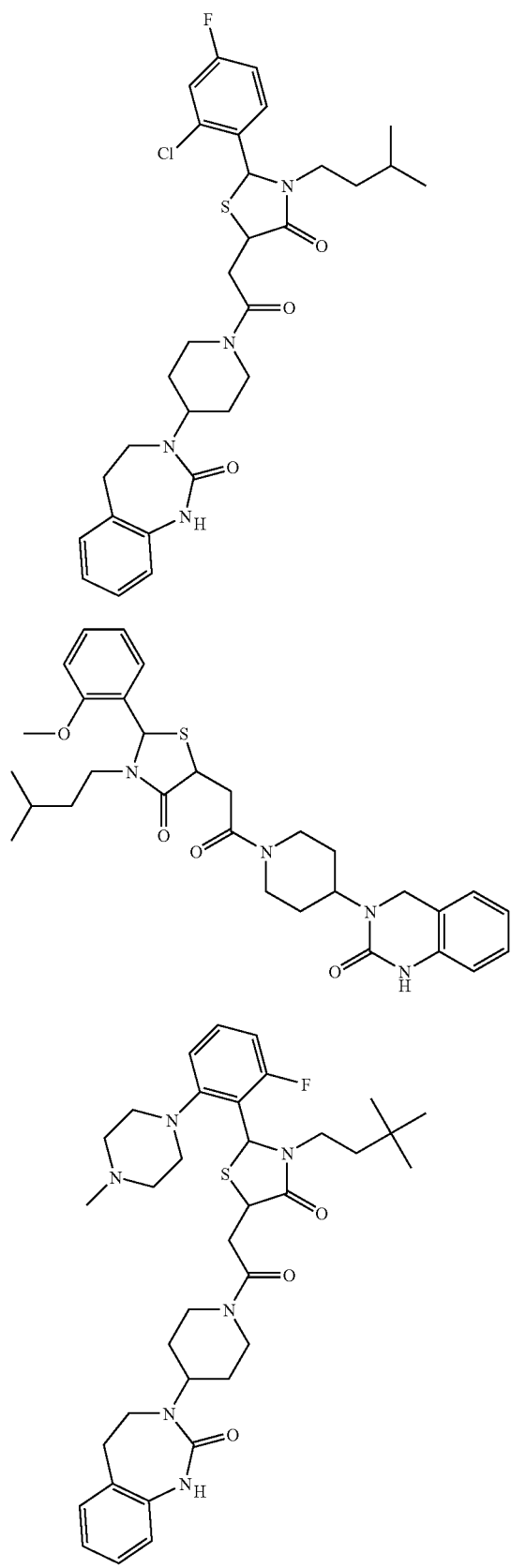
304
-continued
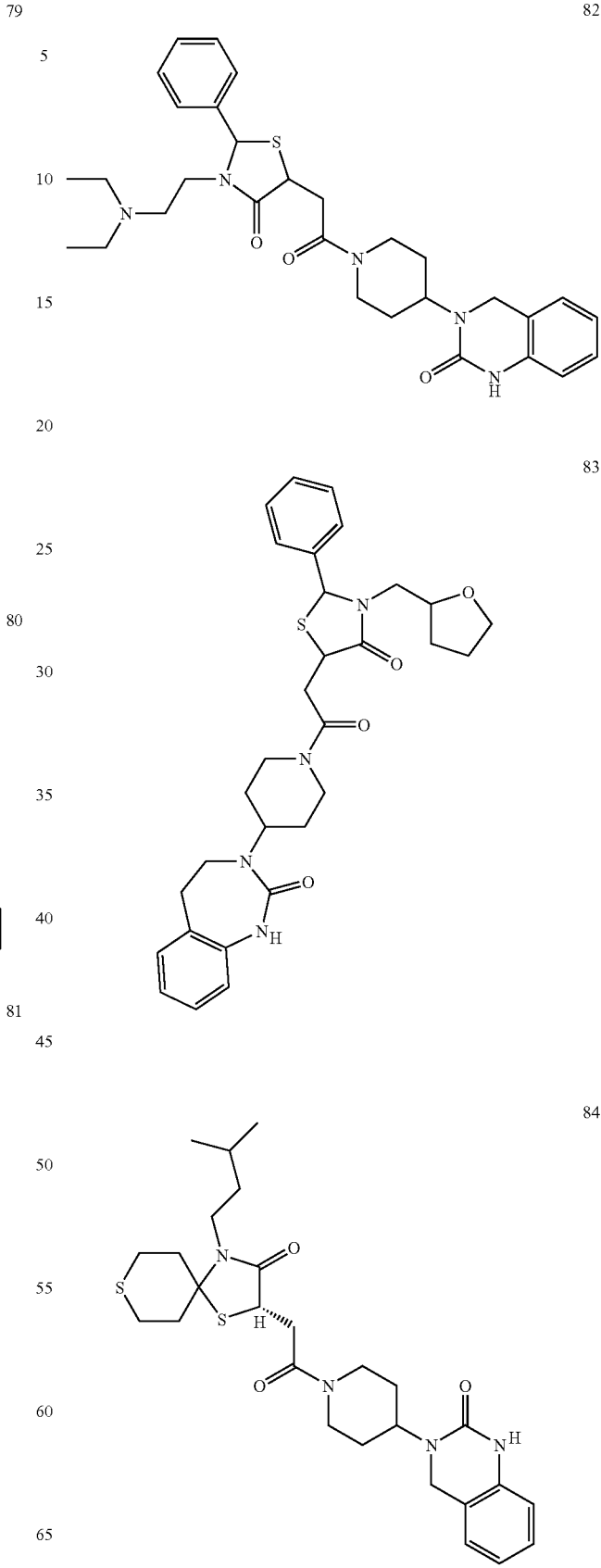

305
-continued
306
-continued
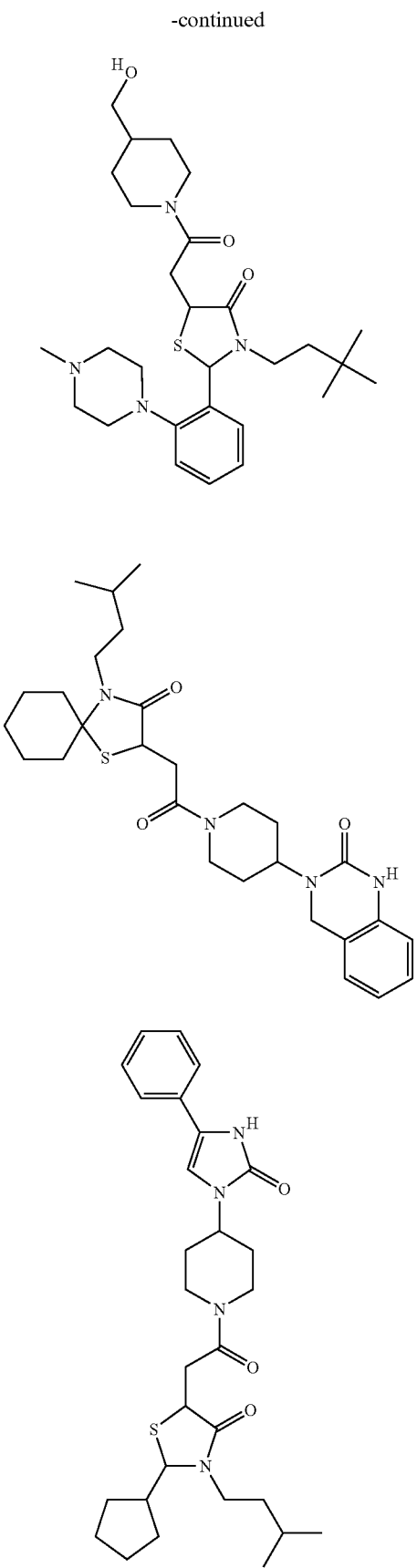
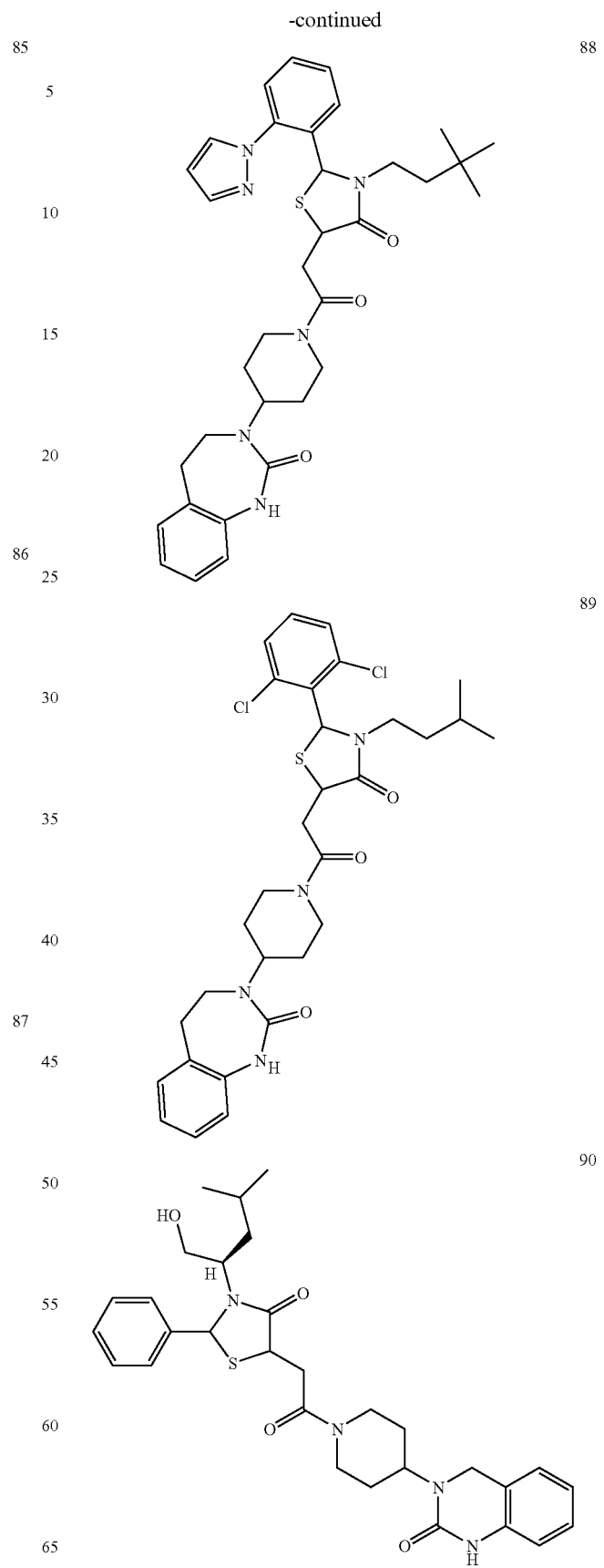

307
-continued
91
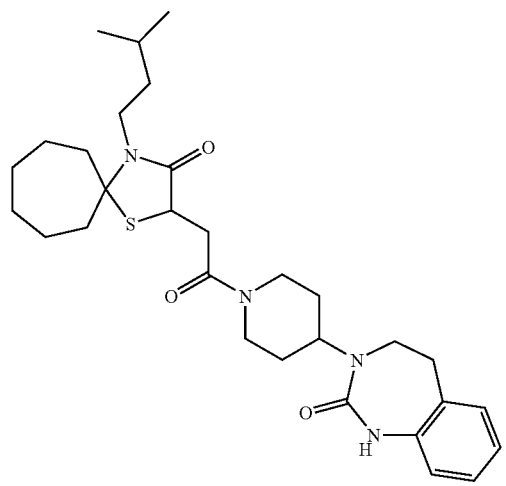
92
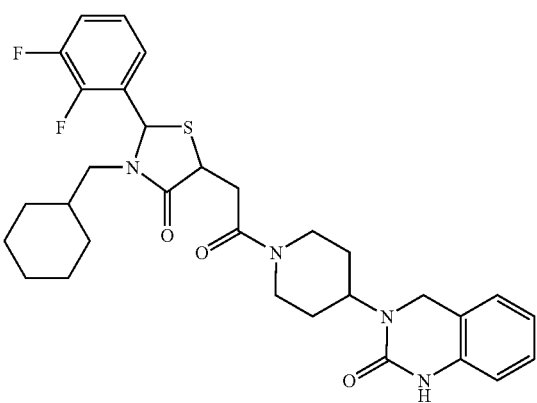
93
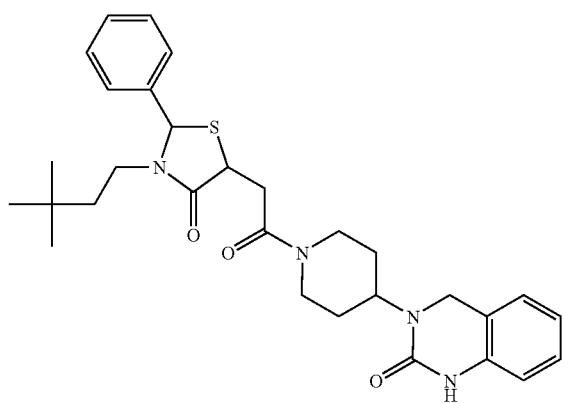
308
-continued
94
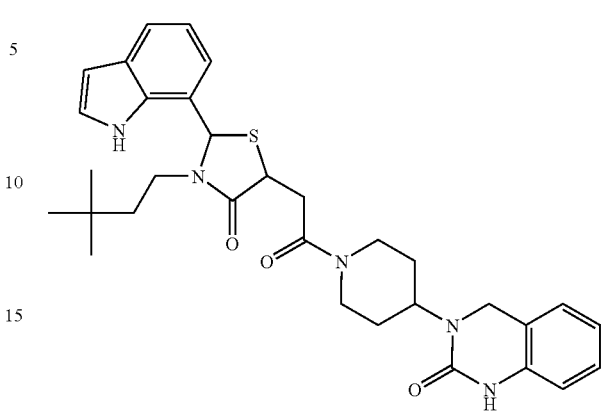
95
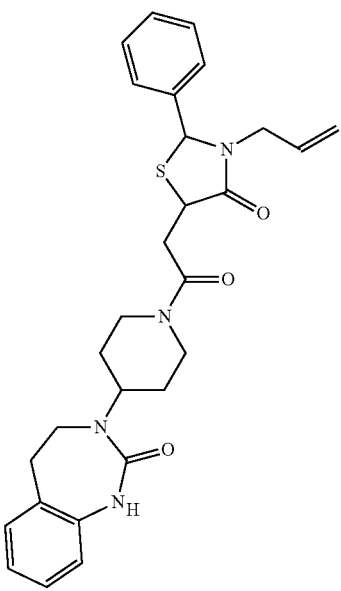
96

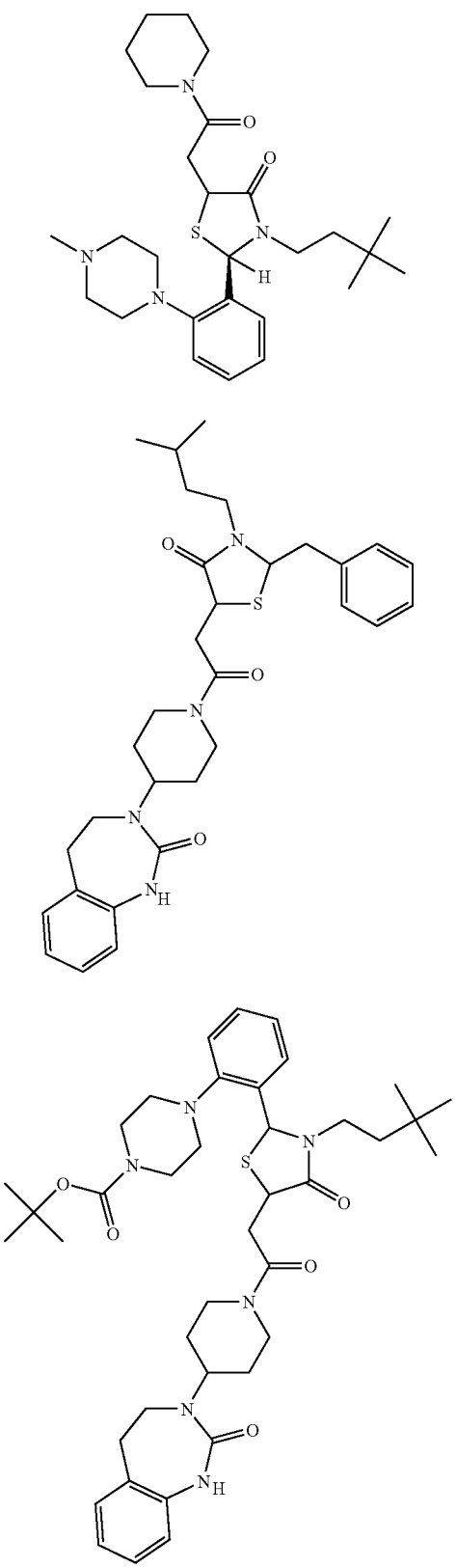
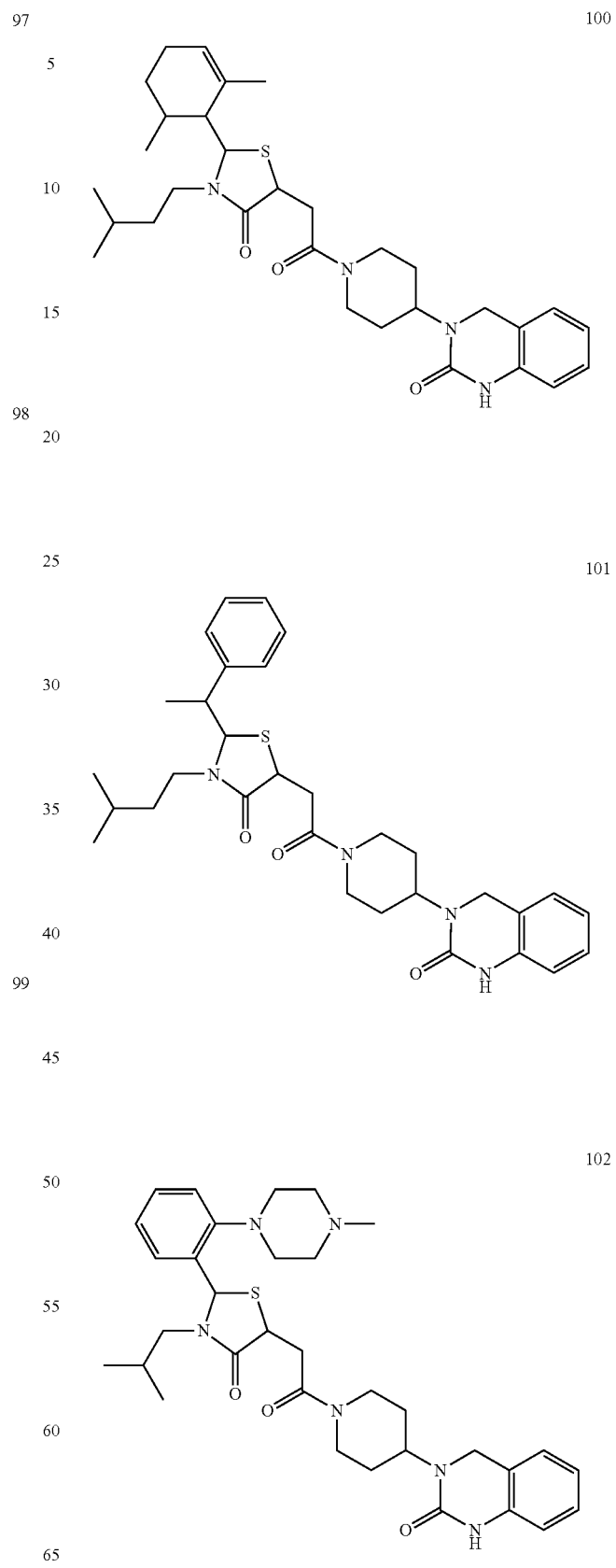

311
-continued
103
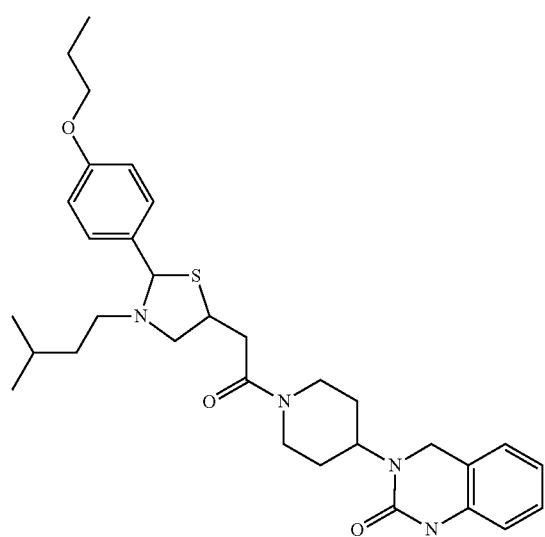
104
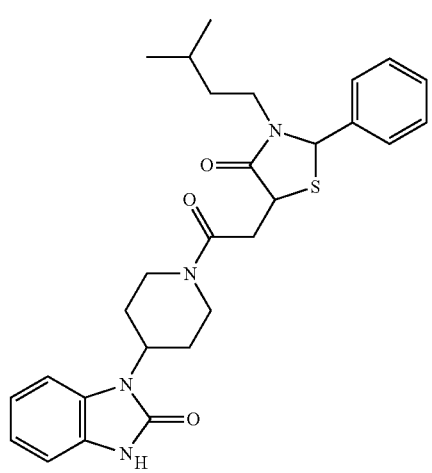
105
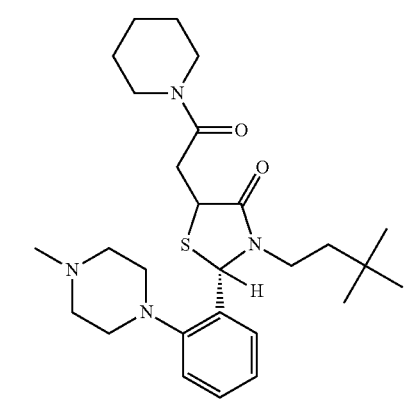
312
-continued
106
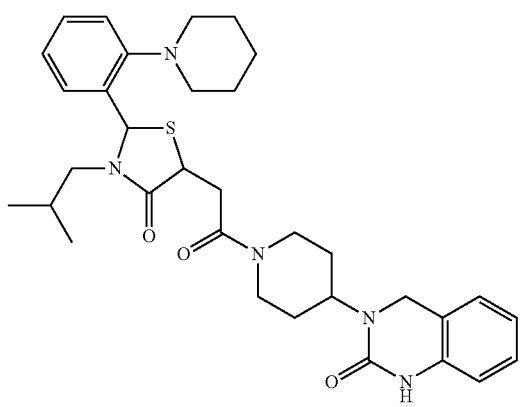
107
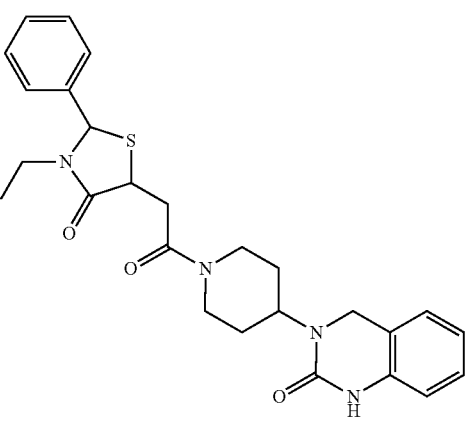
108
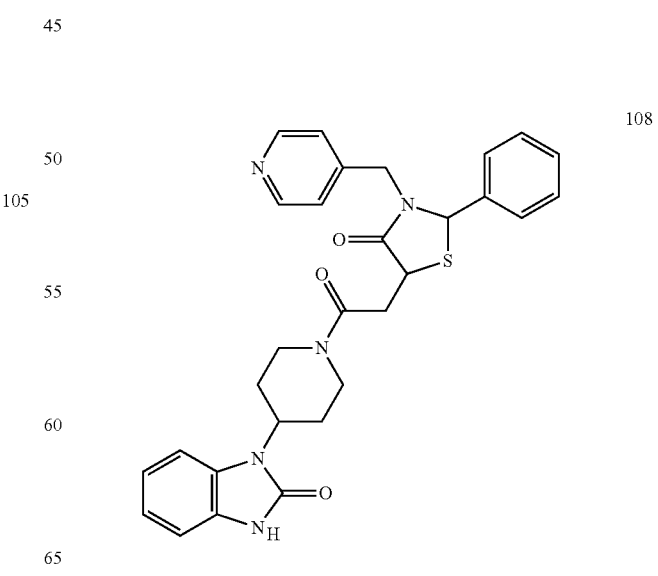

-continued
109
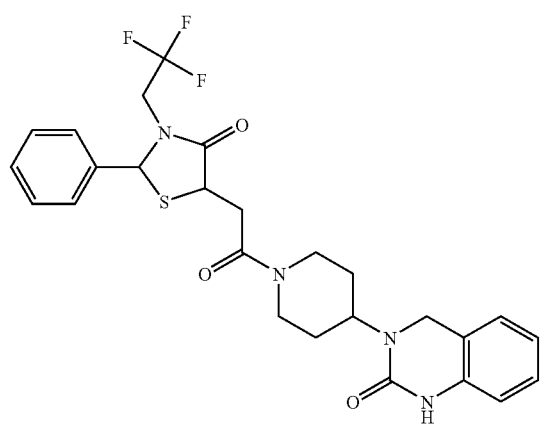
110
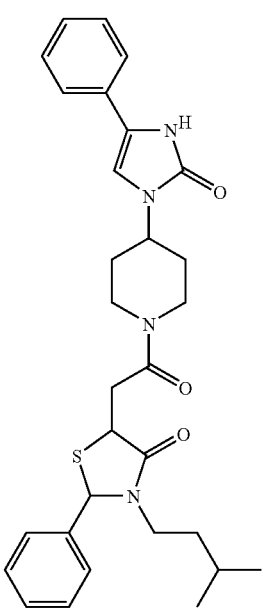
111
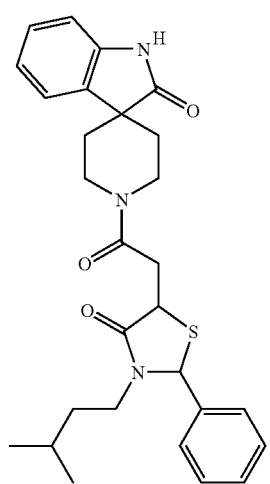
-continued
112
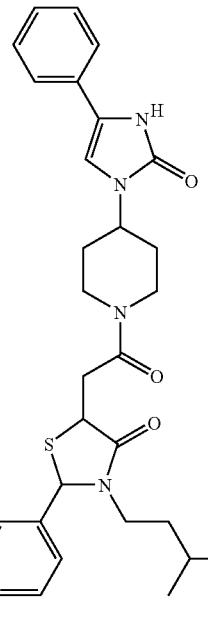
113
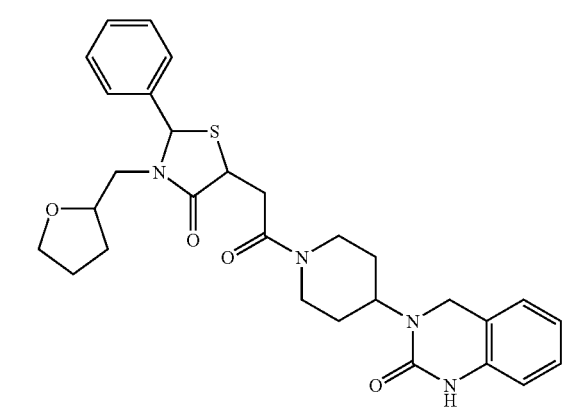
114
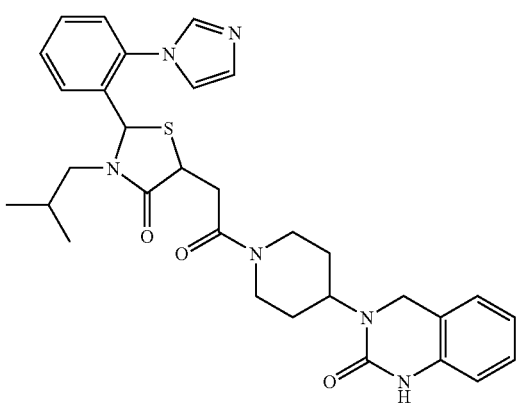

115
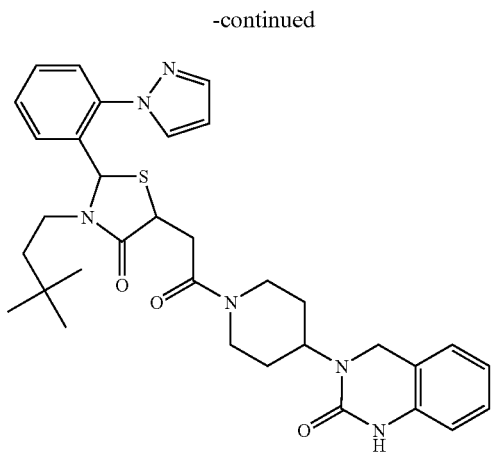
116
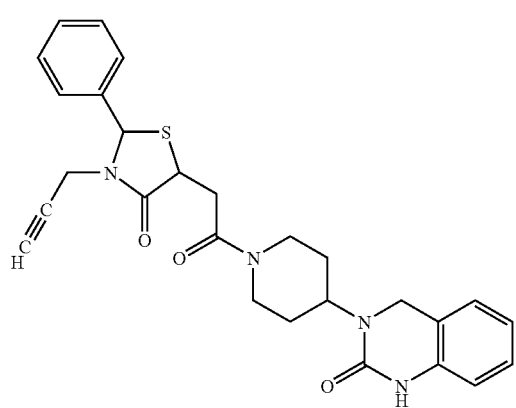
117
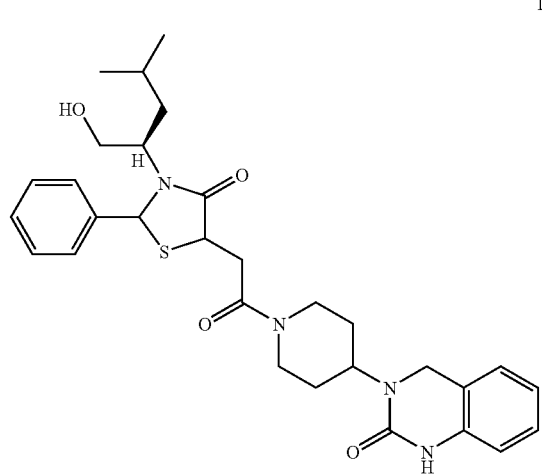
118
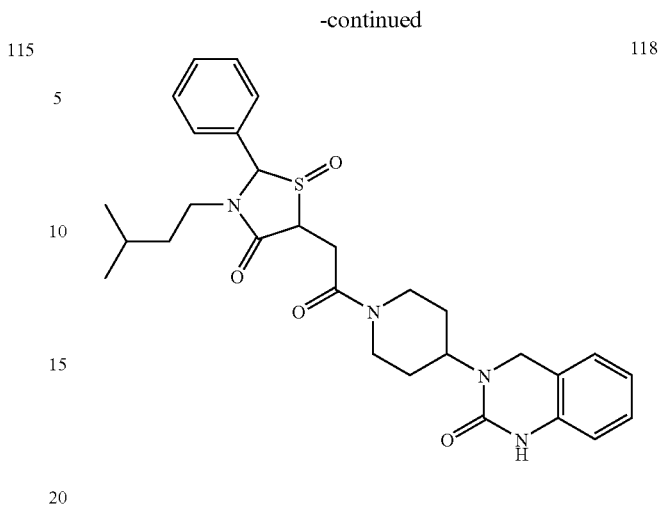
119
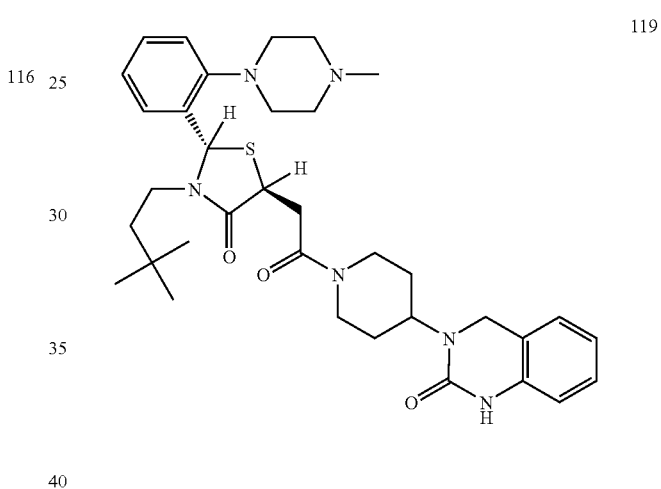
120
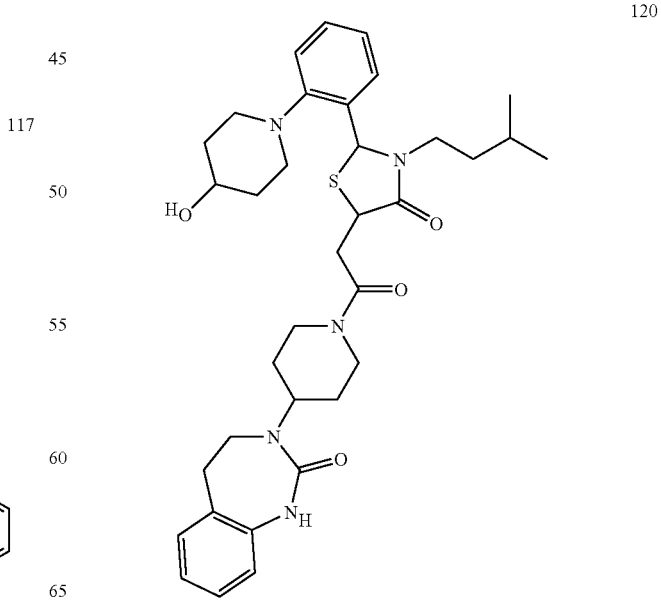

121
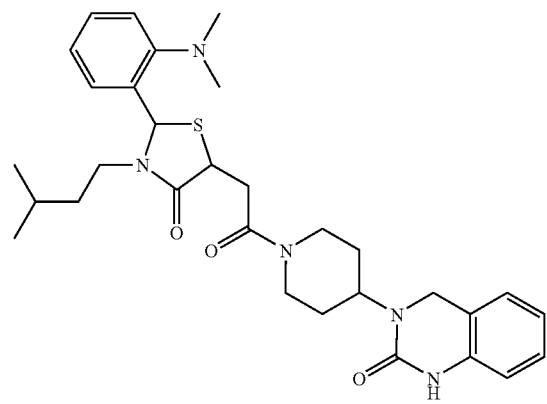
122
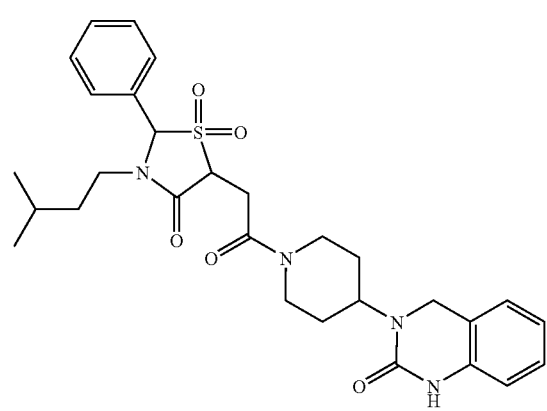
123
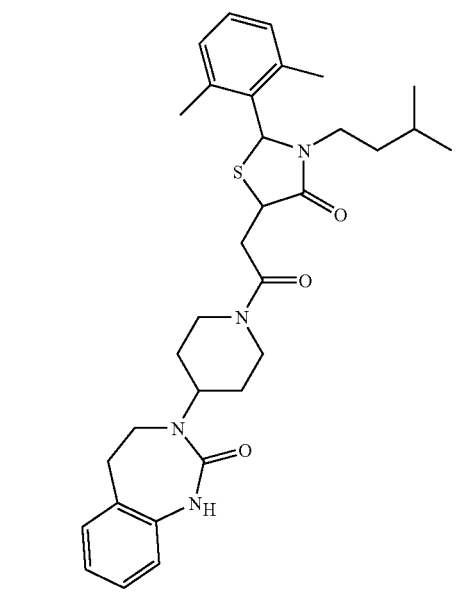
124
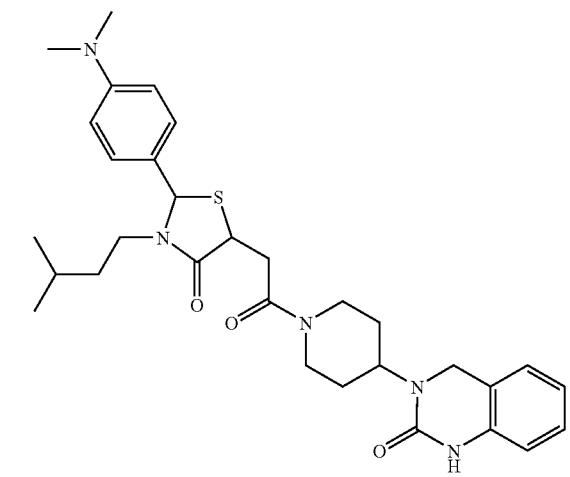
125
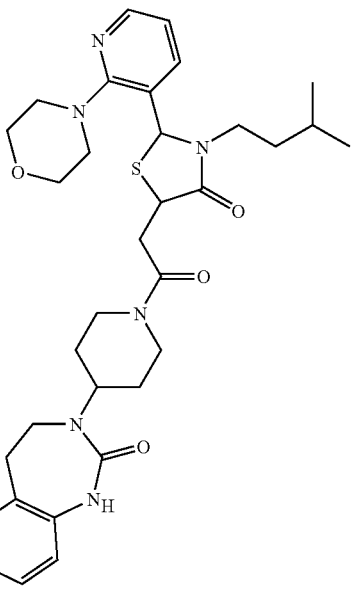
126
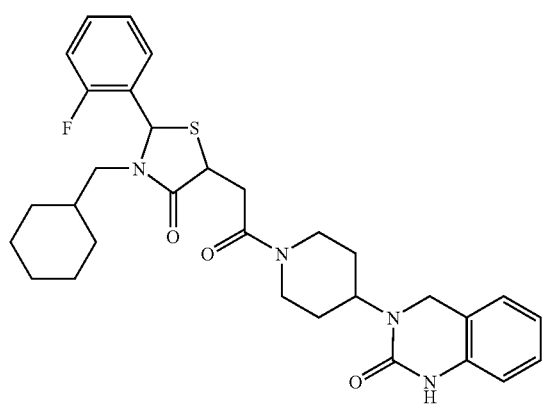

-continued
127
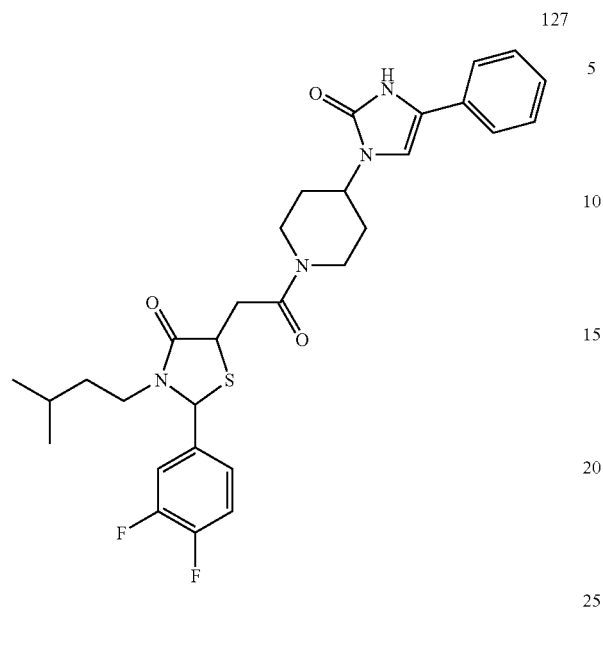
128
130
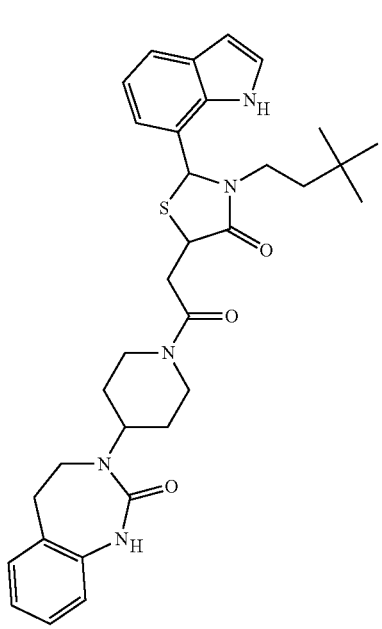
131
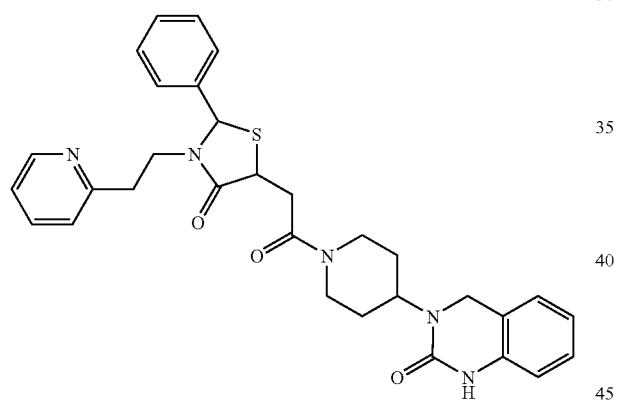
129
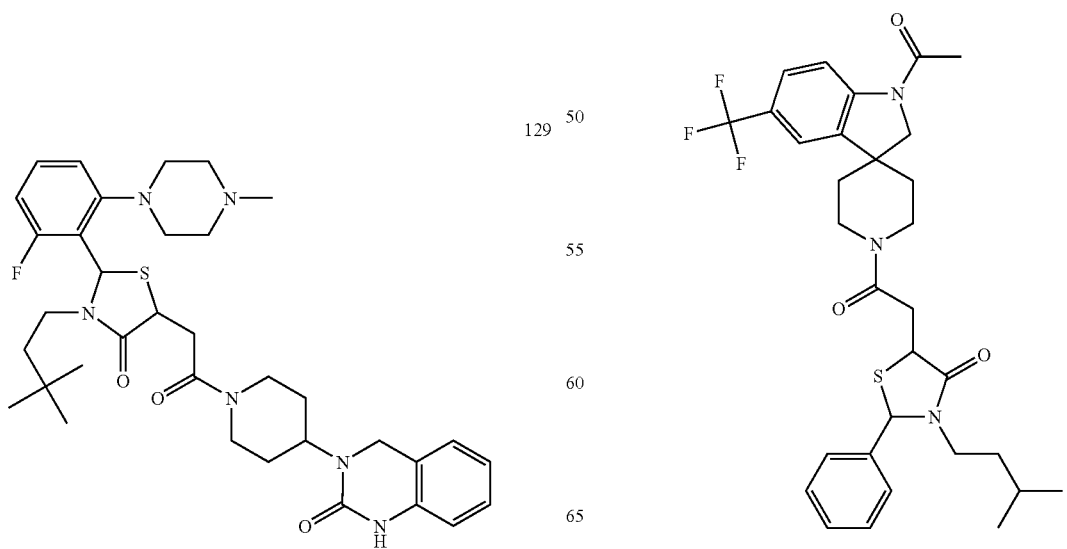

132
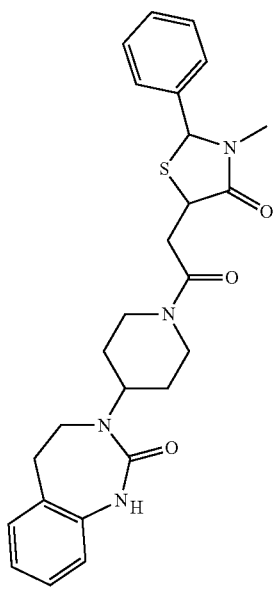
133
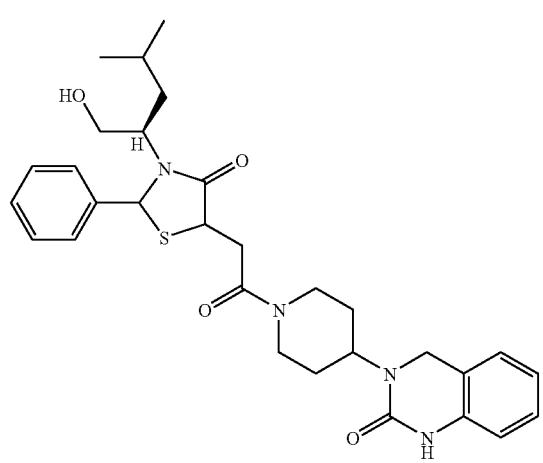
134
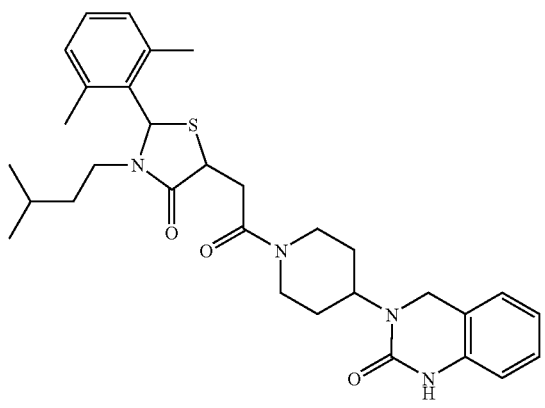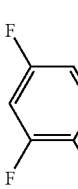
135
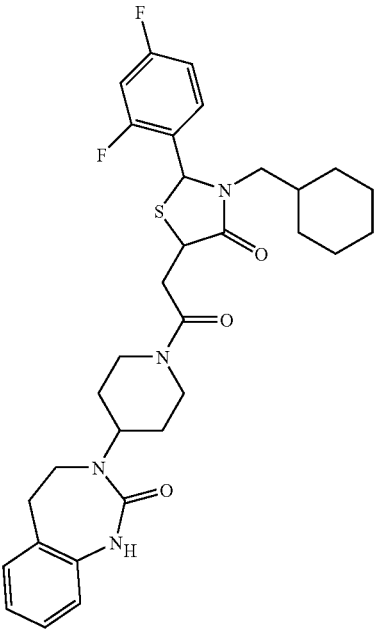
136
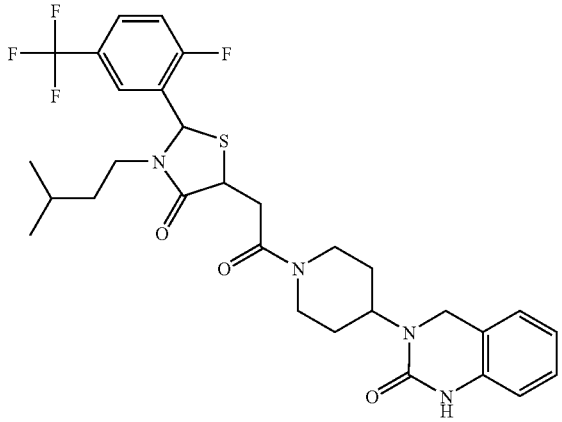
137
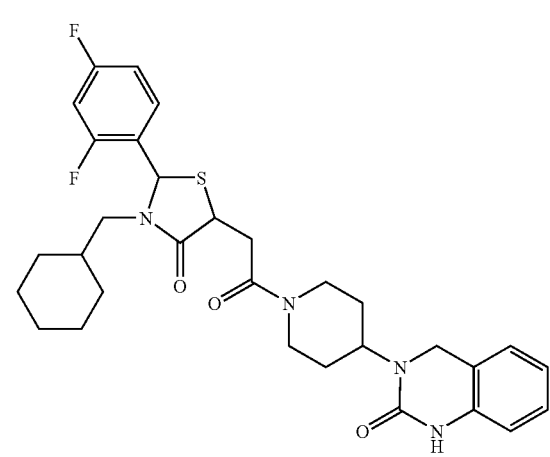

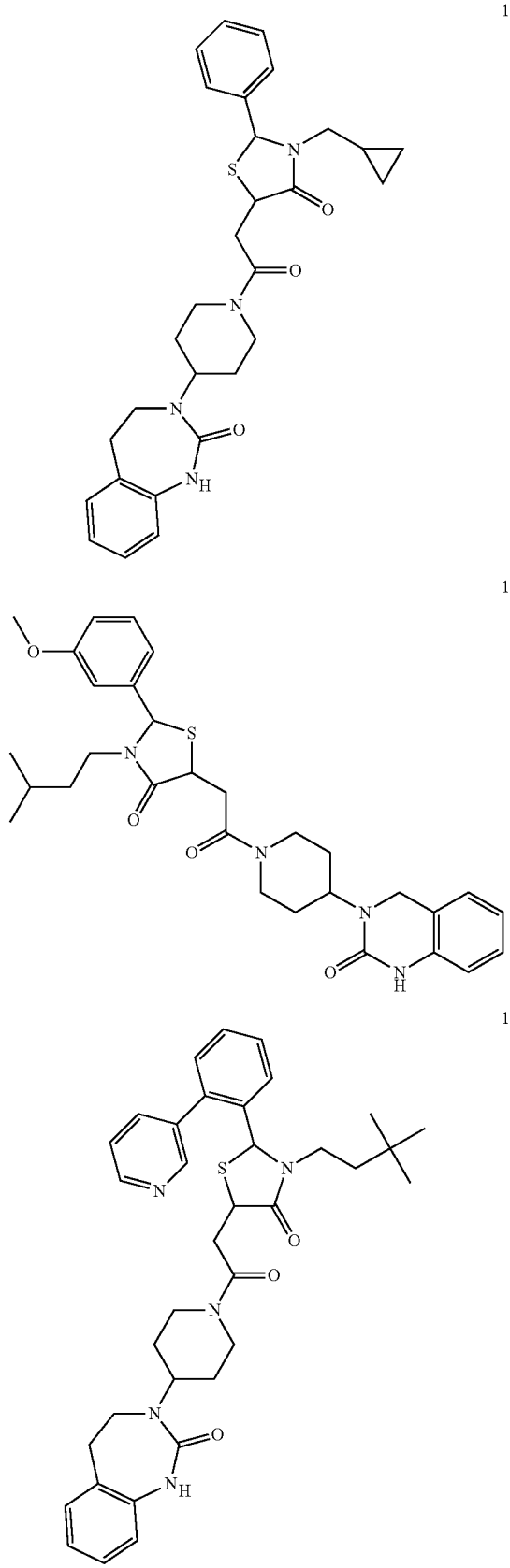
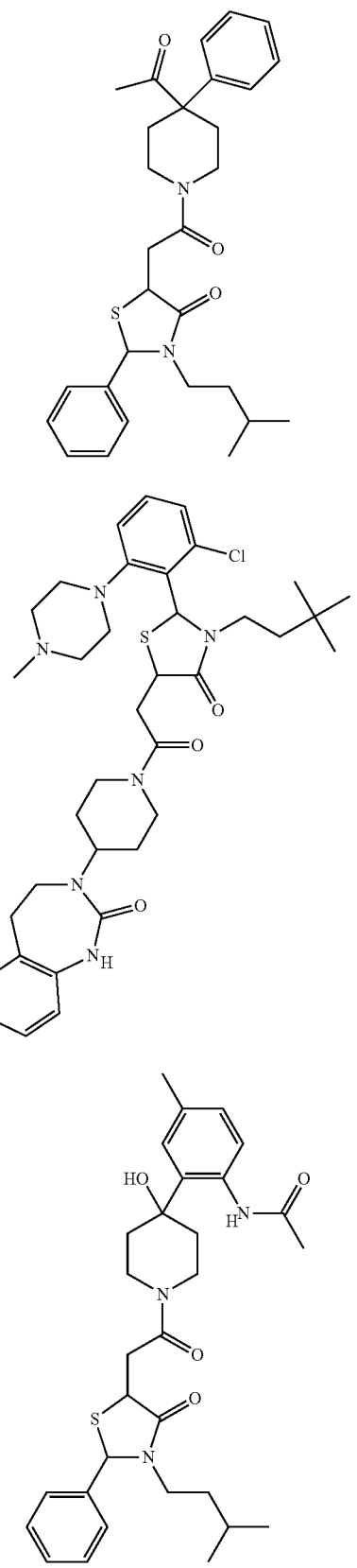

325

144

145

146

326

147

148

149

-continued
150
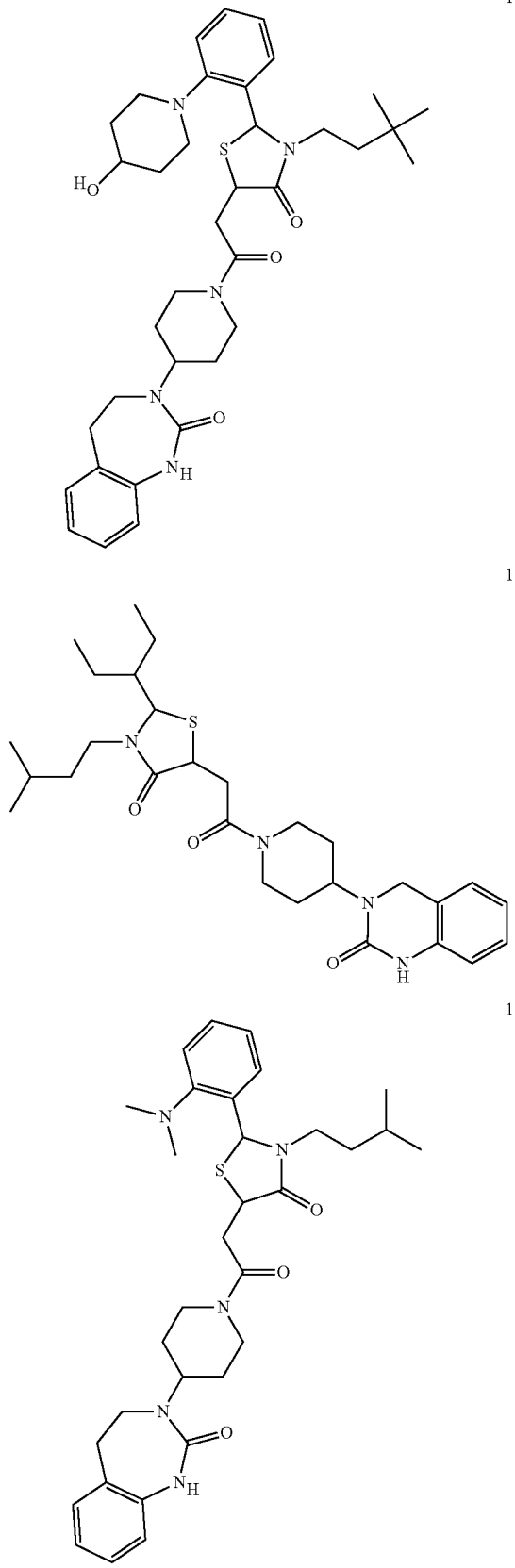
151
152
-continued
153
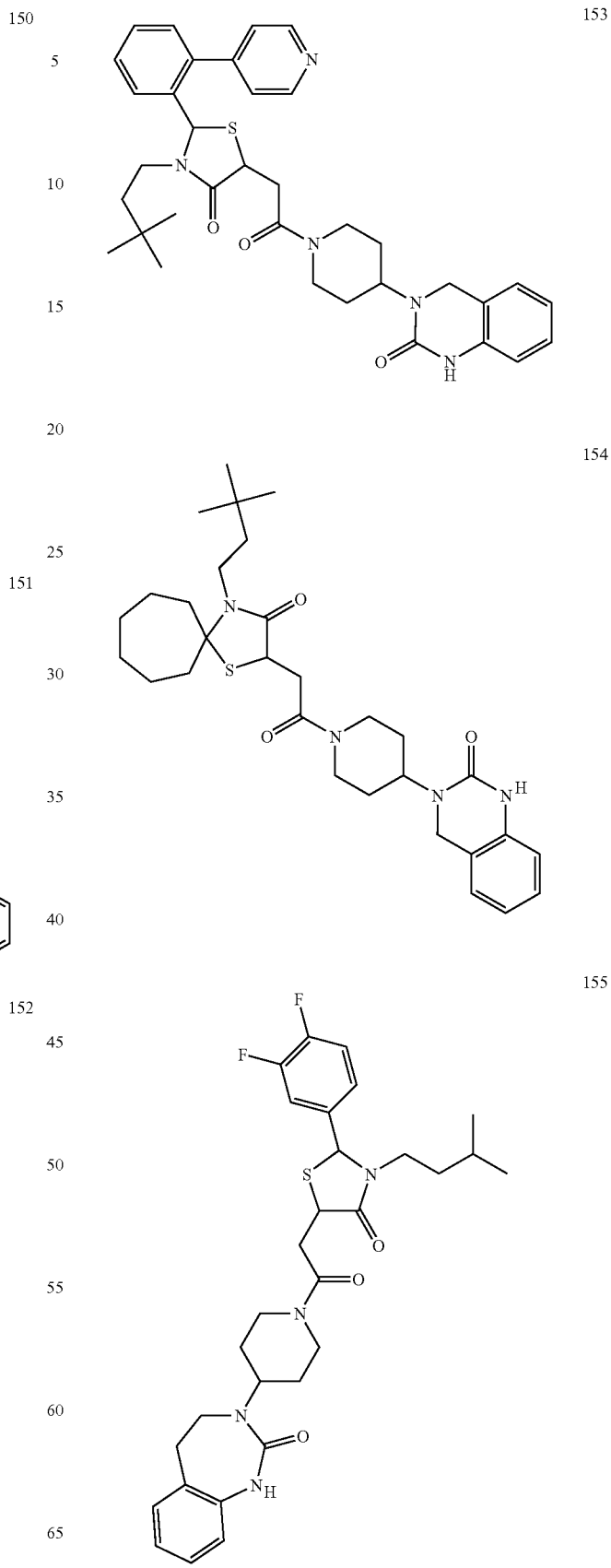
154
155

| 329 | 330 |
|---|---|
| -continued | -continued |
| 156 | 159 |
| 157 | 160 |
| 158 | 161 |

| 331 | 332 |
|---|---|
| -continued | -continued |
162
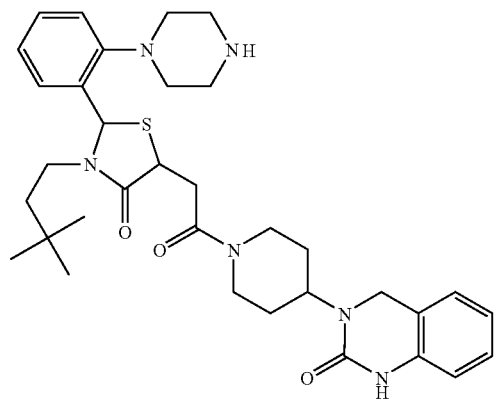
163
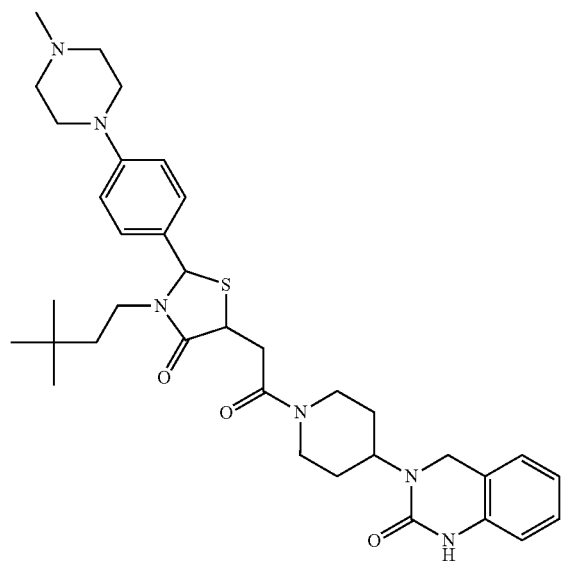
164
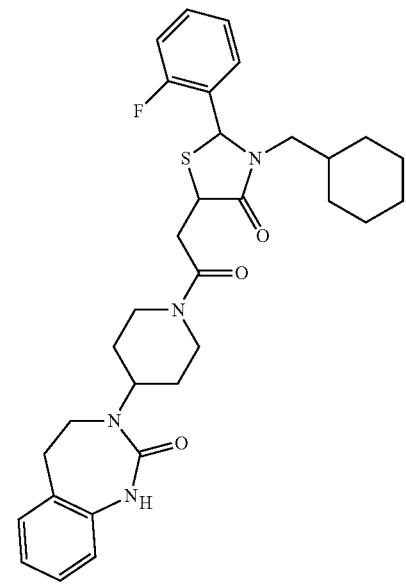
165
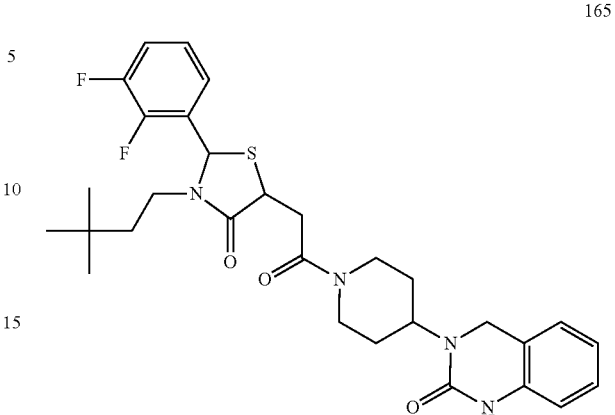
166
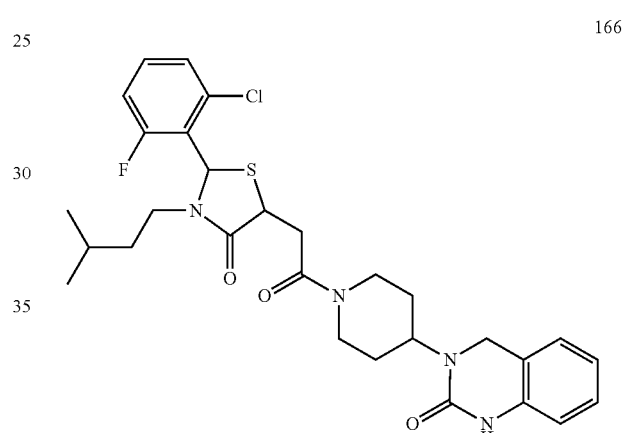
167
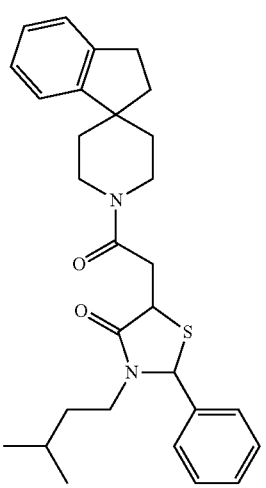

333
-continued
168
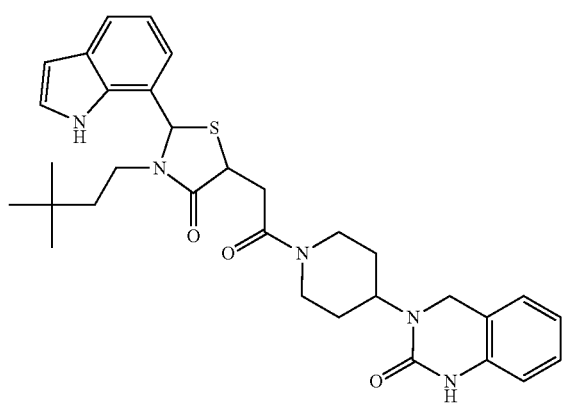
169
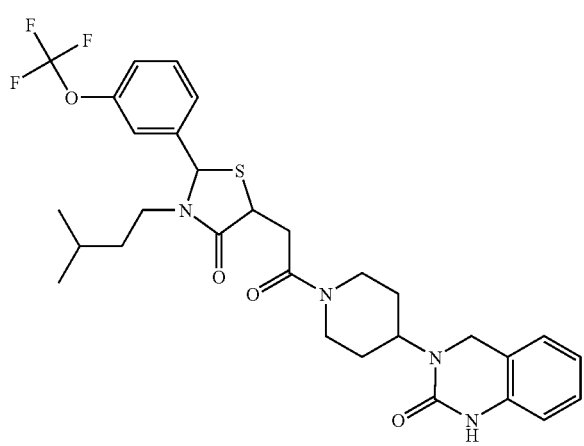
170
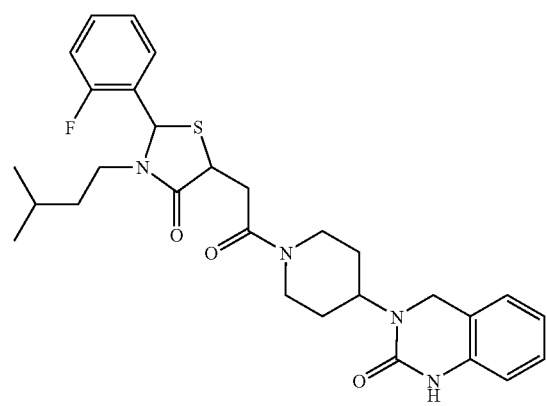
334
-continued
171
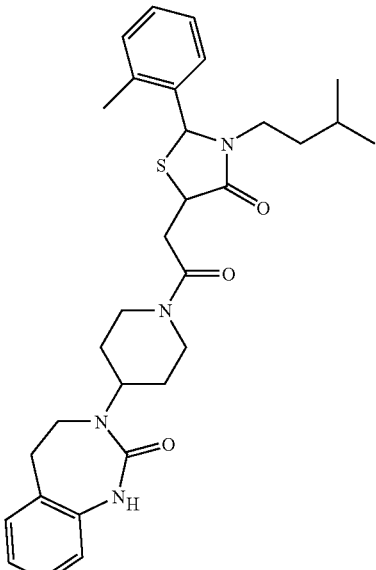
172
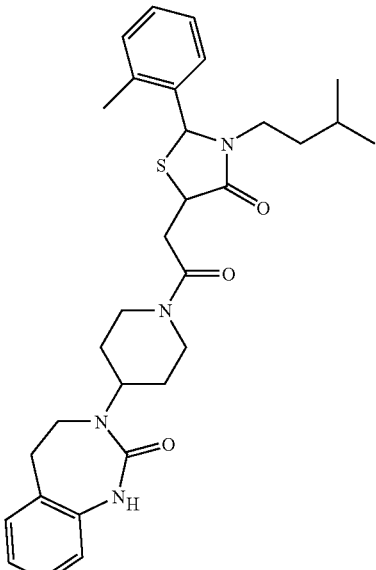
173
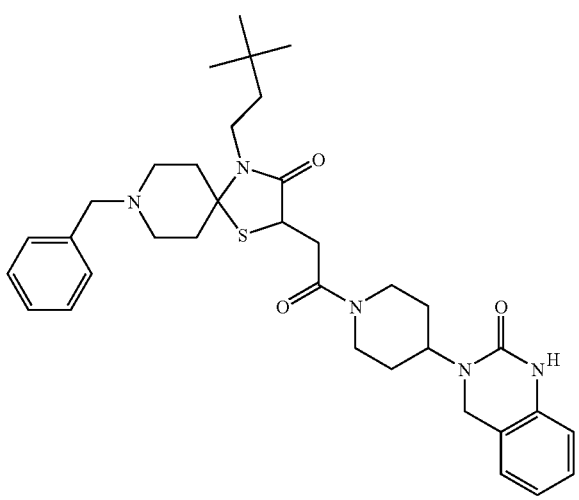

174 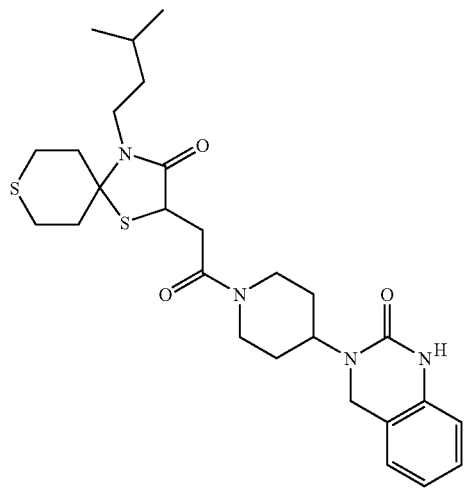
175 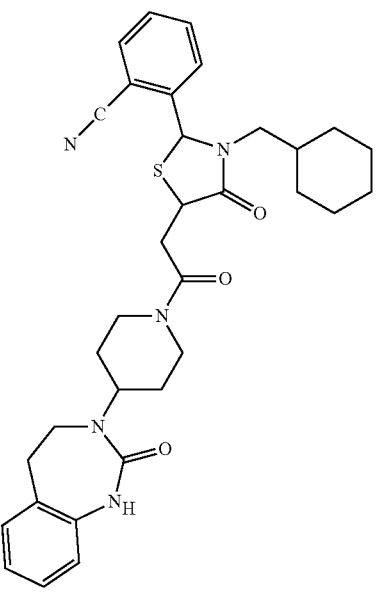
176 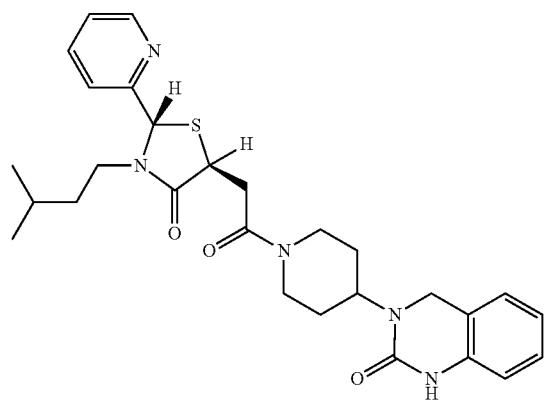
177 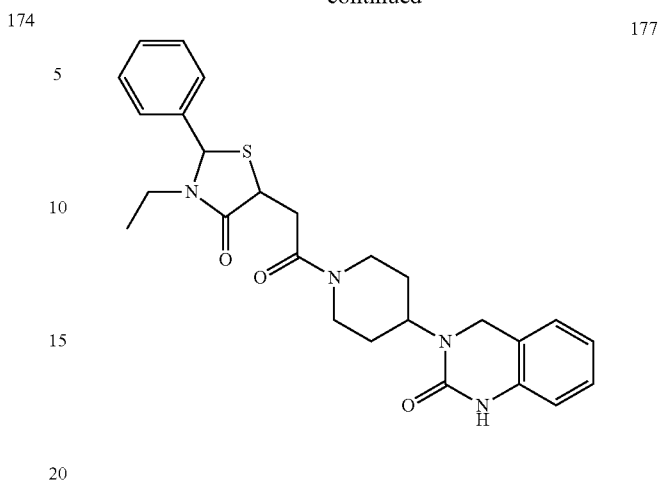
178 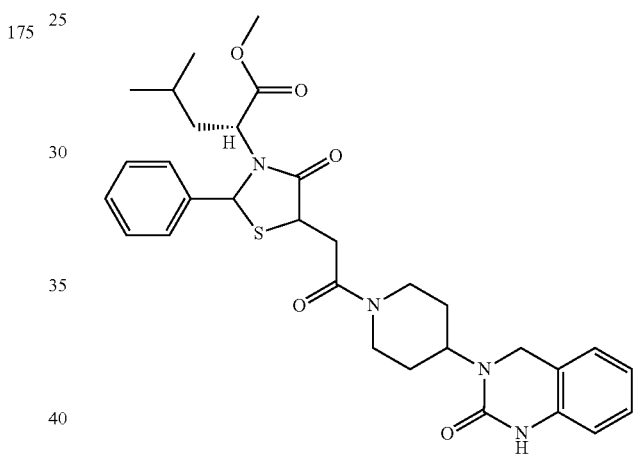
179 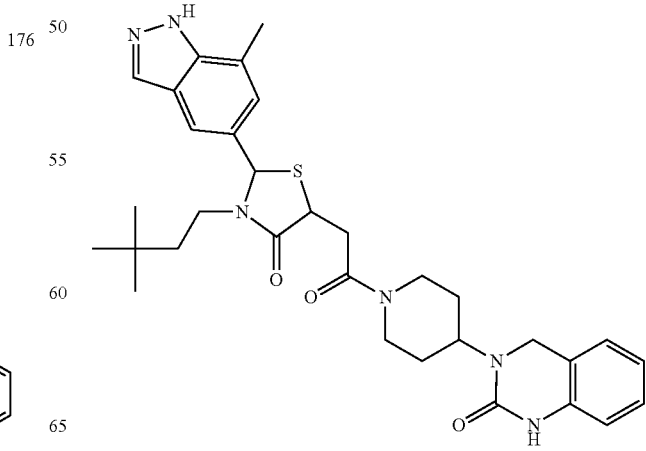

337
-continued
180
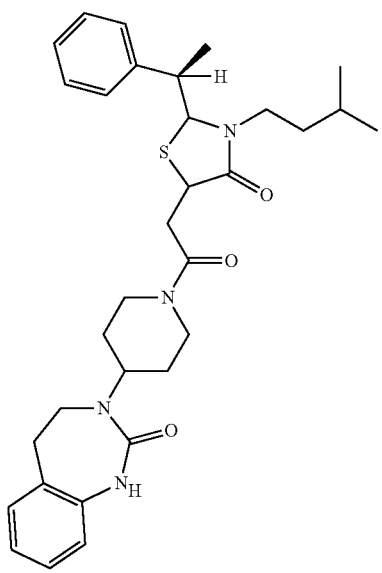
181
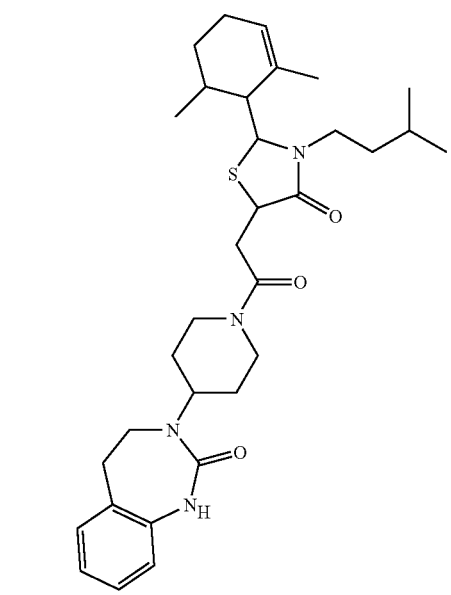
182
338
-continued
183
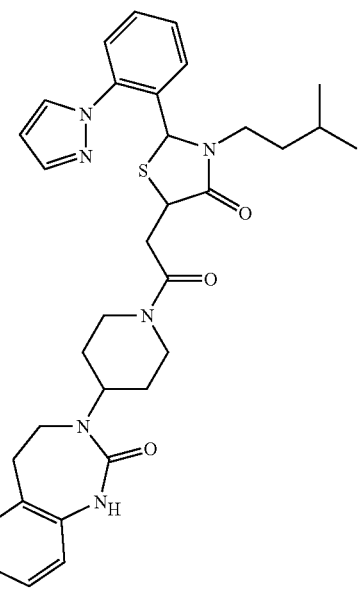
184
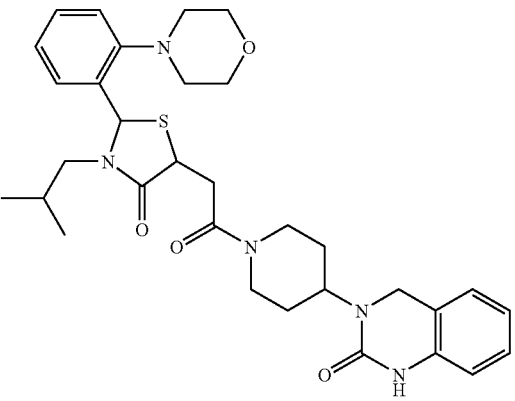
185
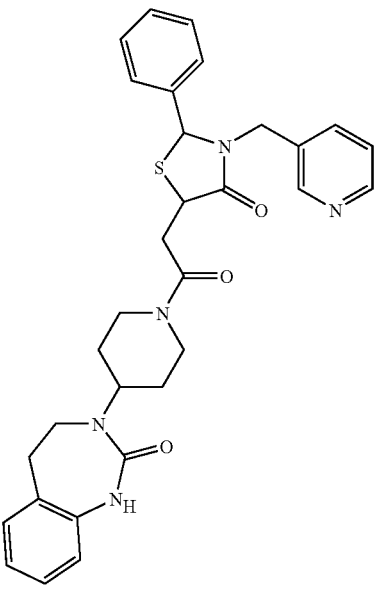

-continued
186
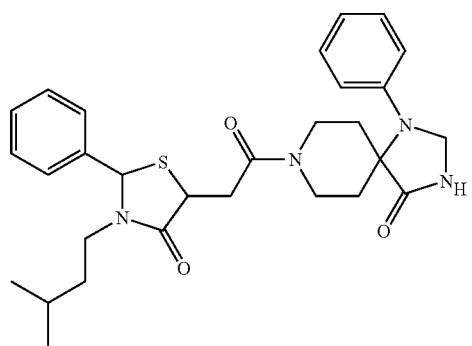
187
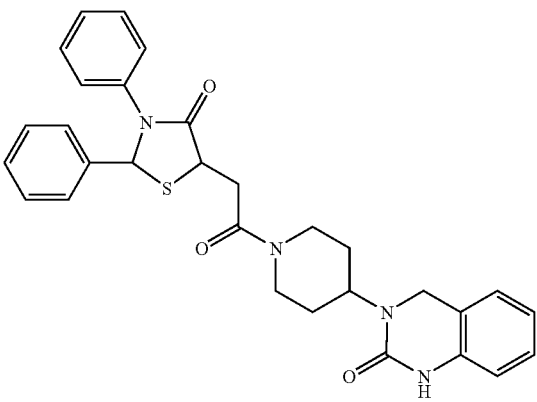
188
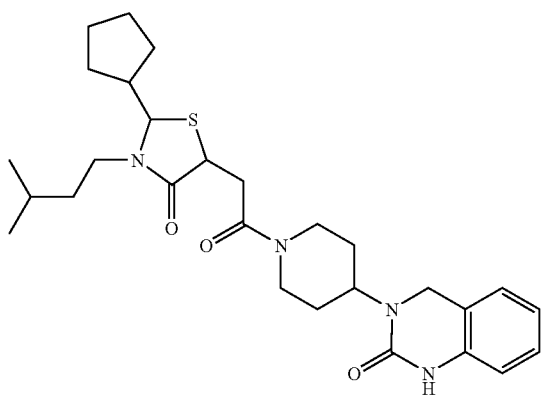
-continued
189
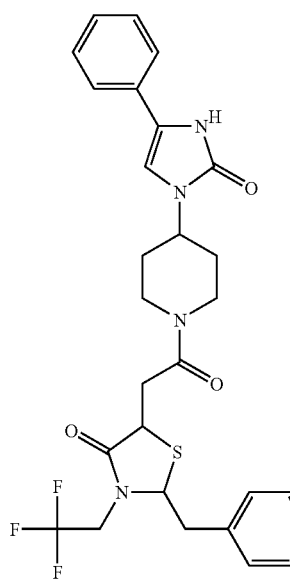
190
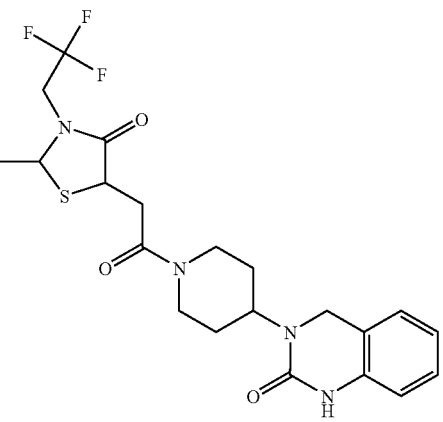
191
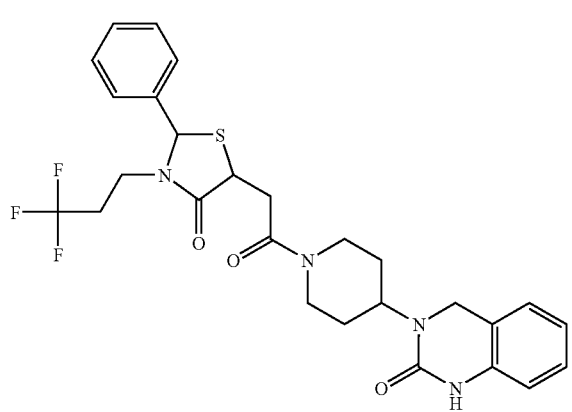

192
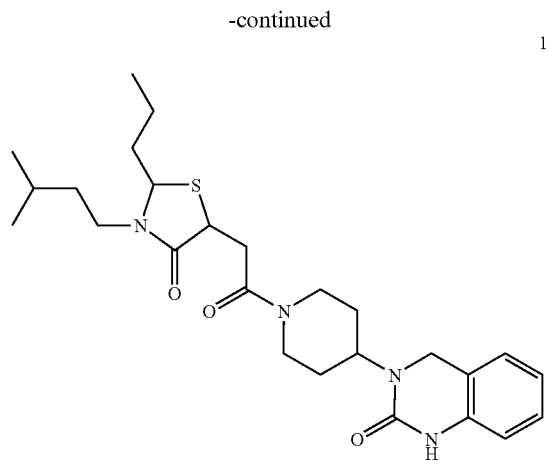
193
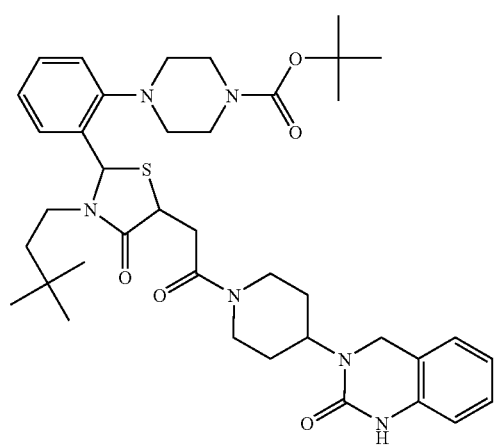
194
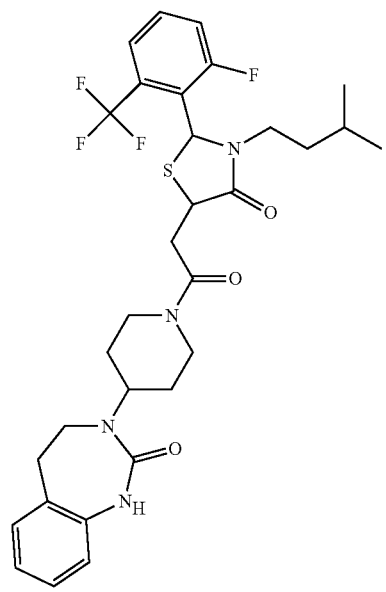
195
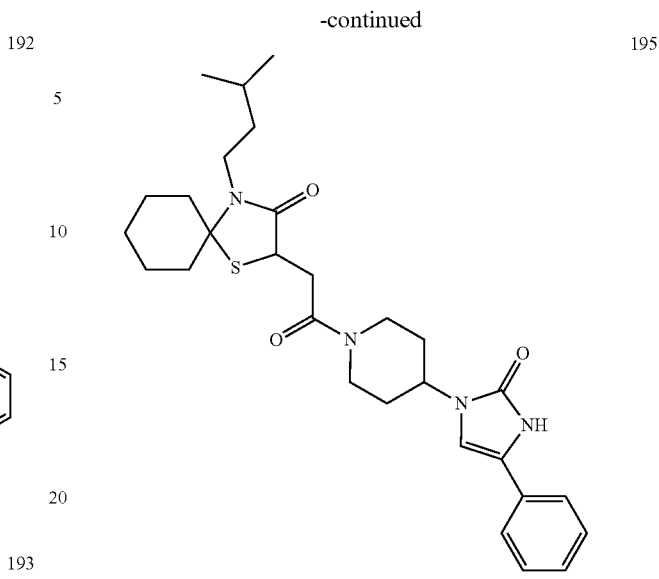
196
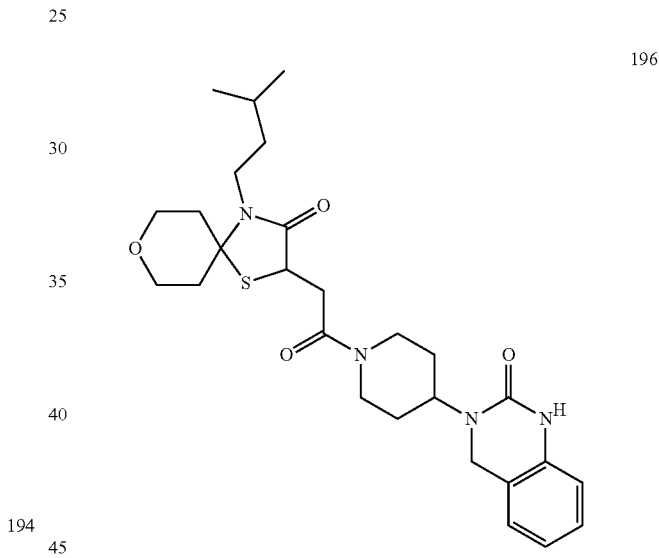
197
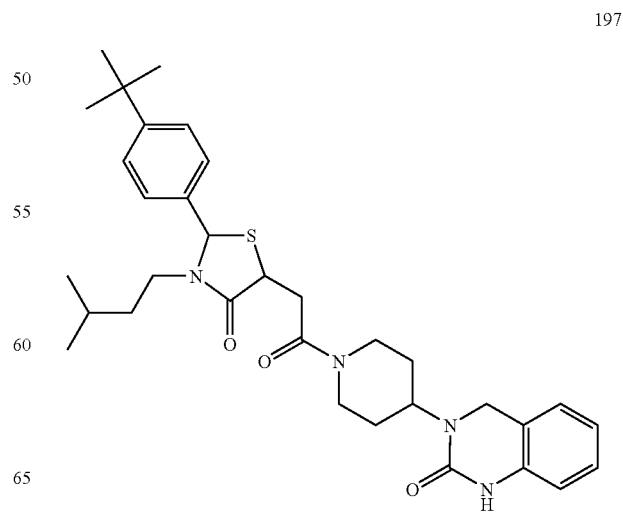

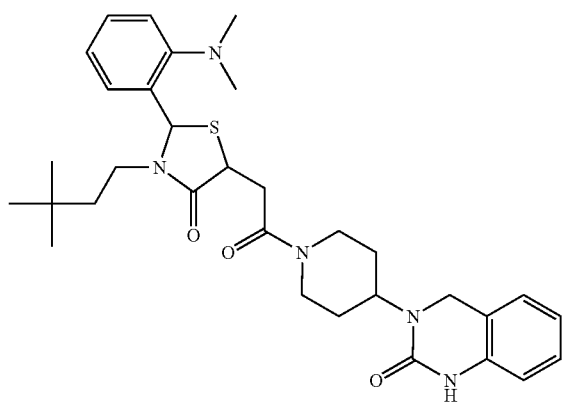
198
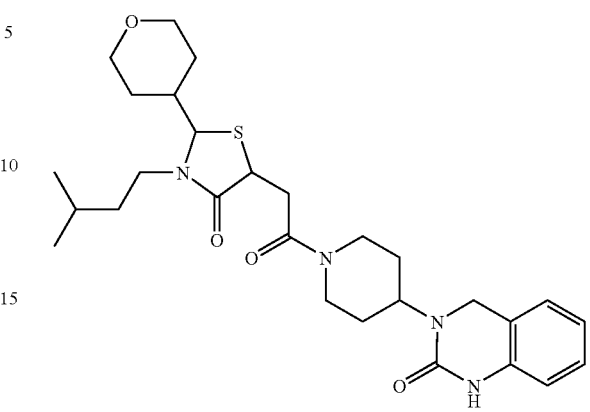
201
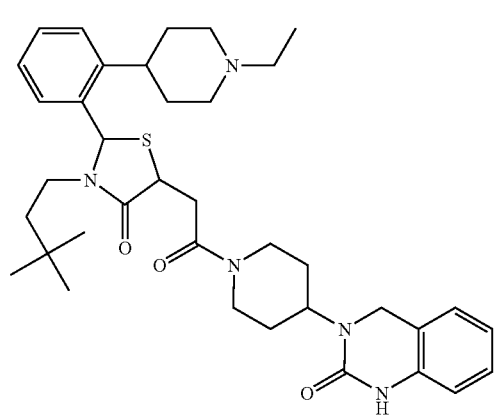
199
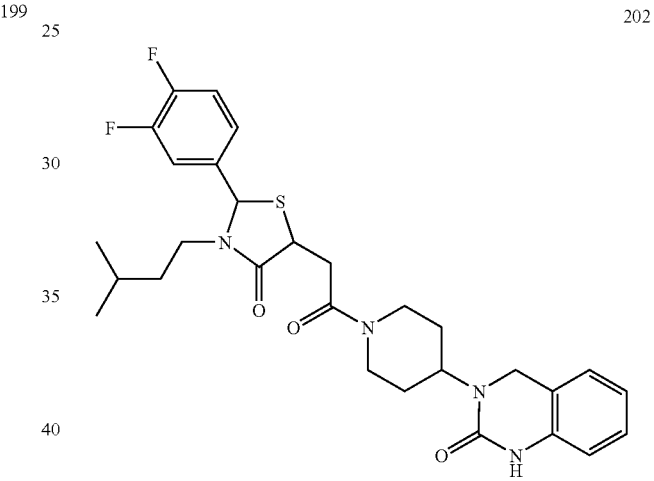
202
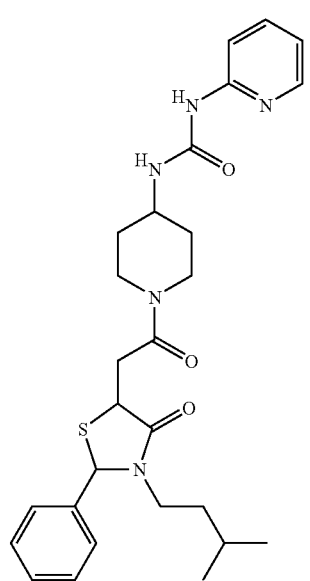
200
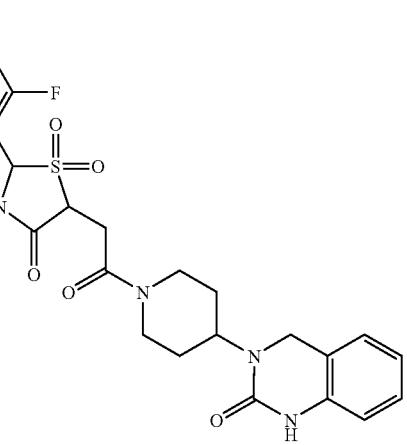
203

204
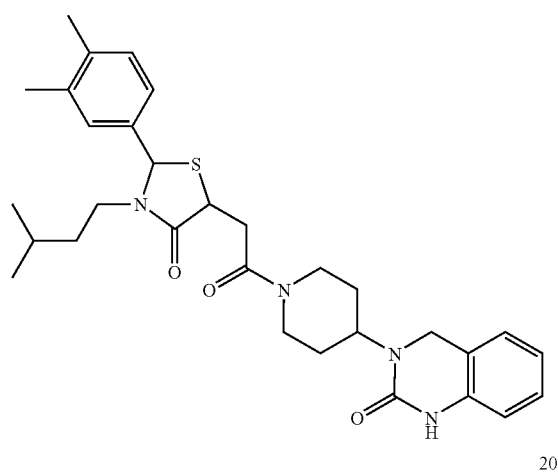
205
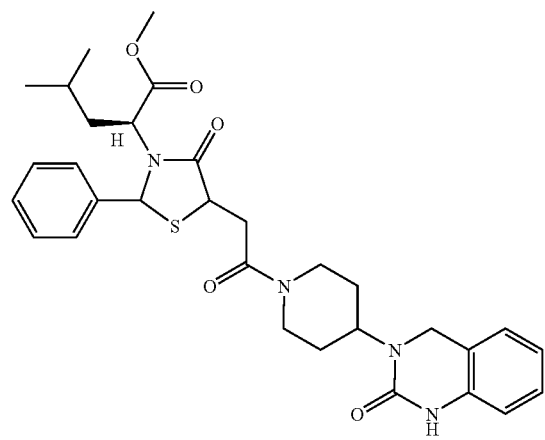
206
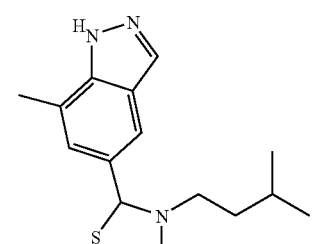
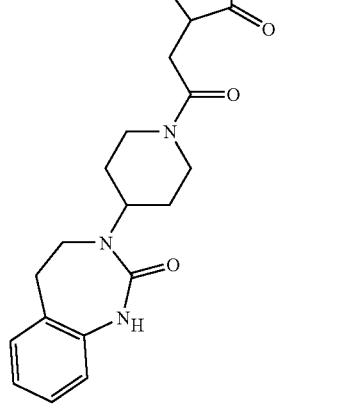
207
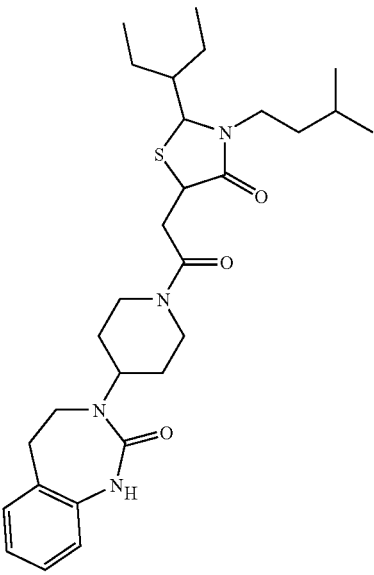
208
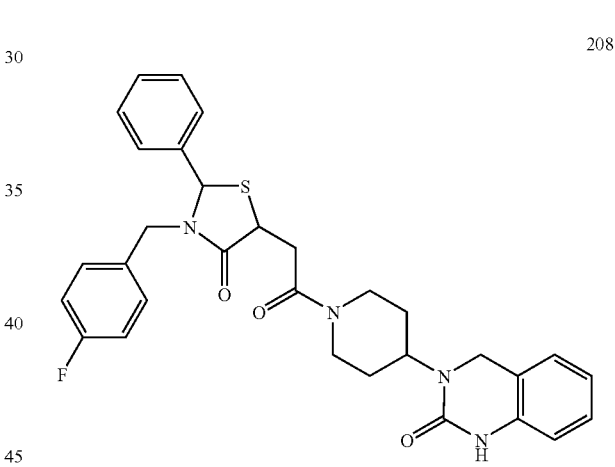
209
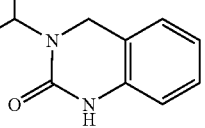

210 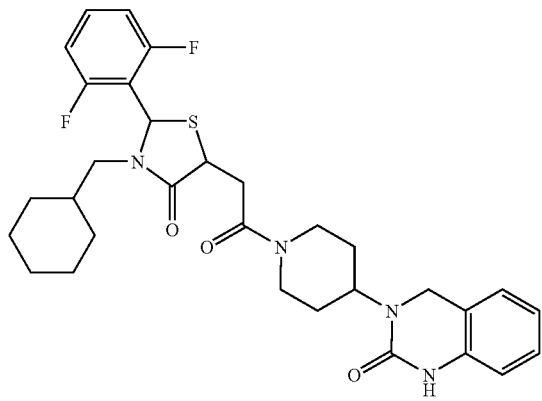
211 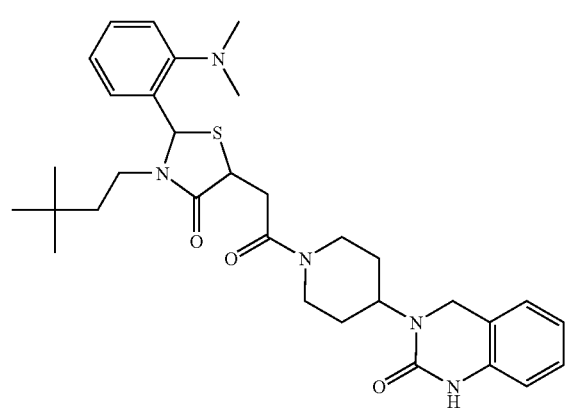
212 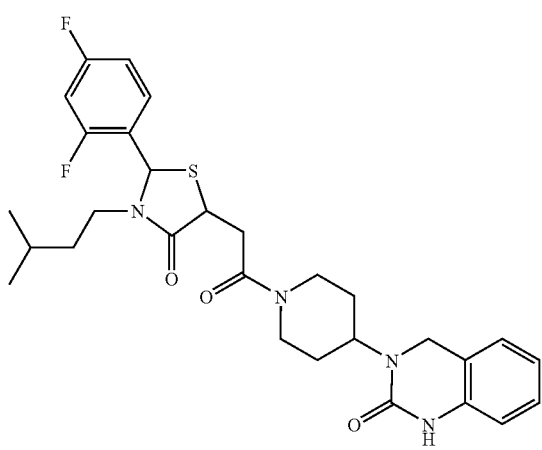
213 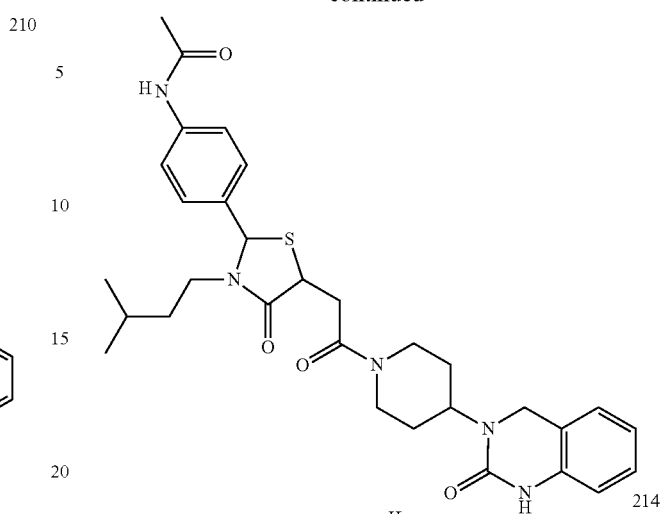
214 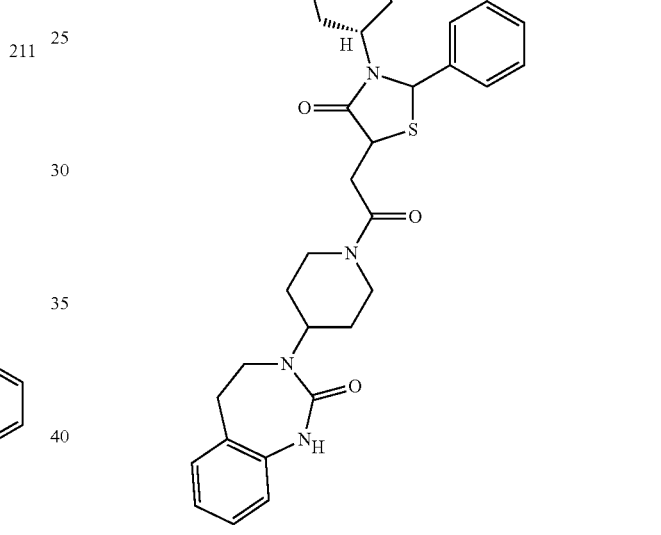
215 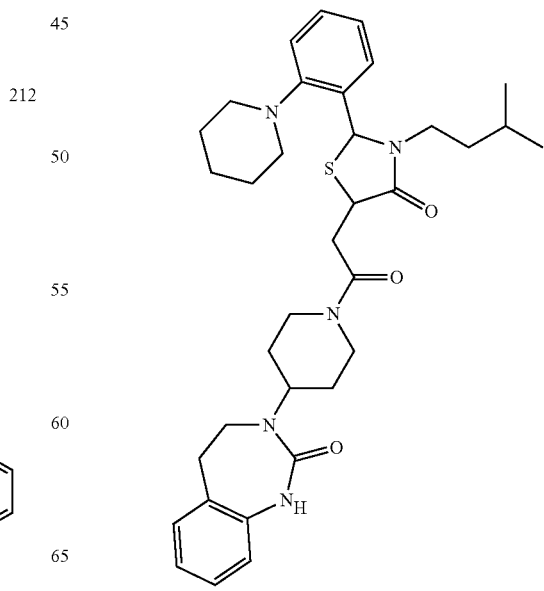

349
-continued
216
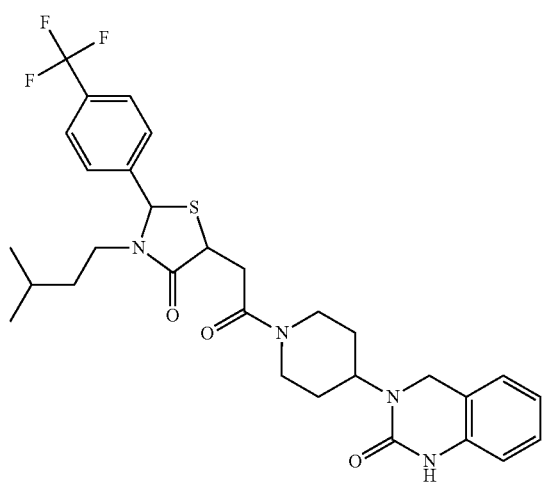
217
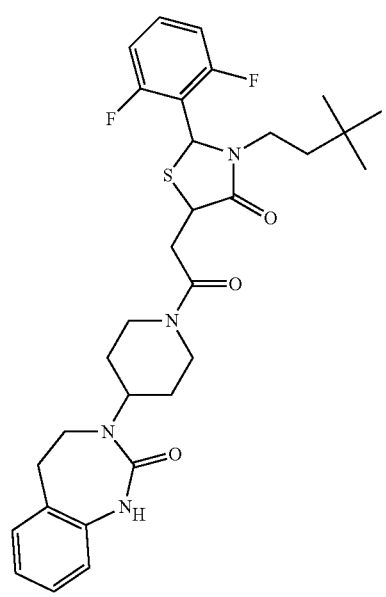
218
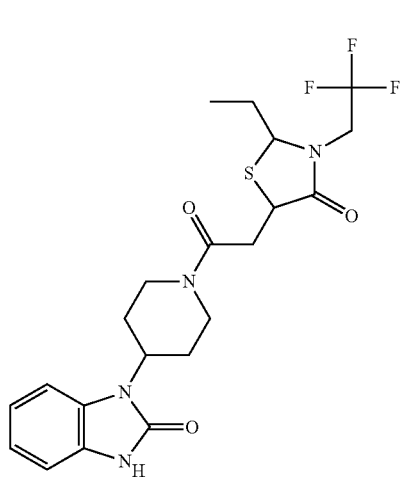
350
-continued
219
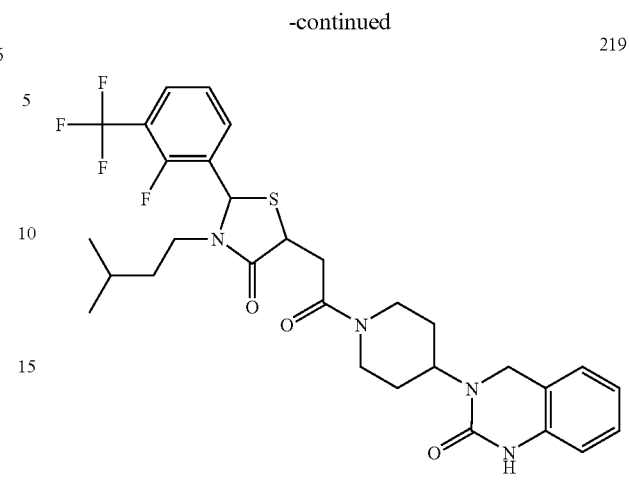
220
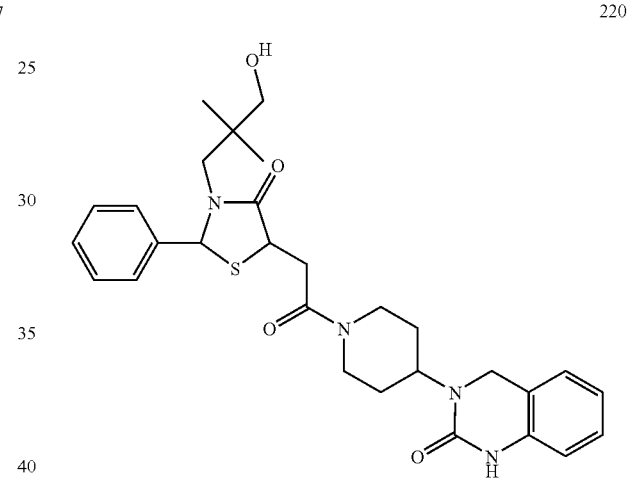
221
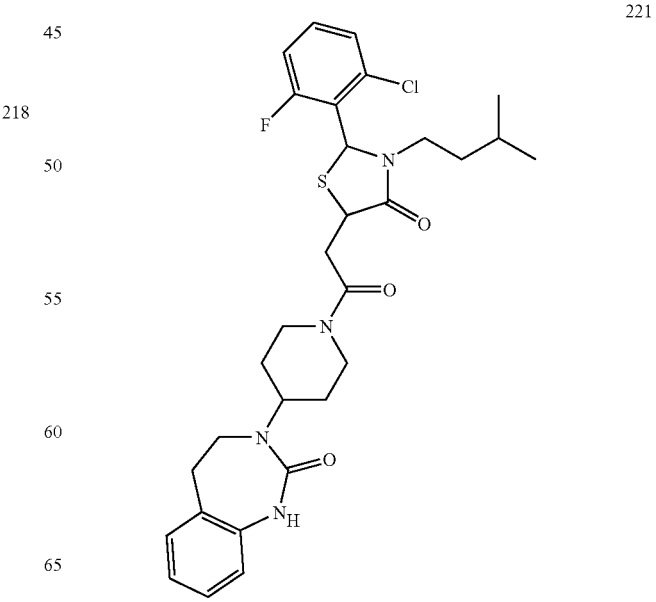

222
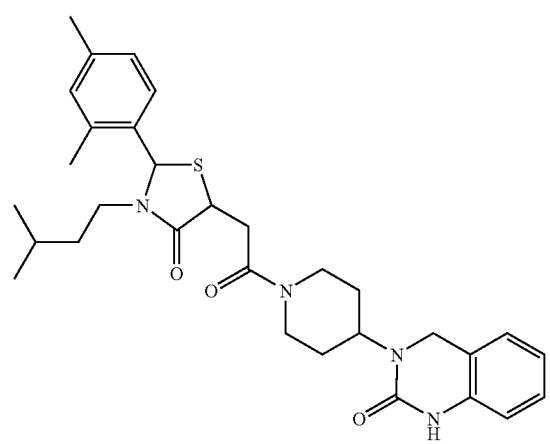
223
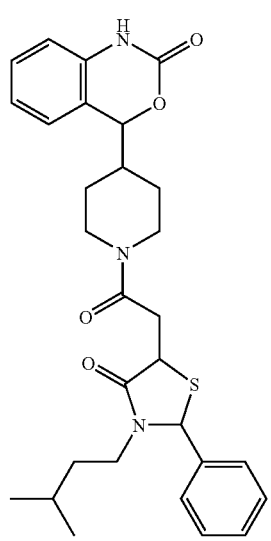
224
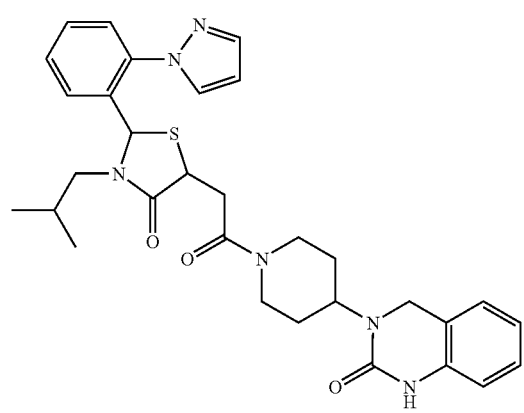
225
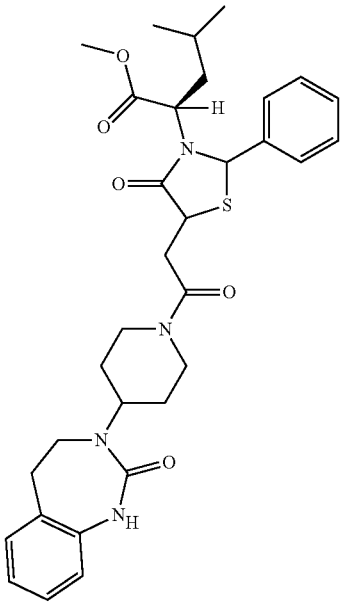
226
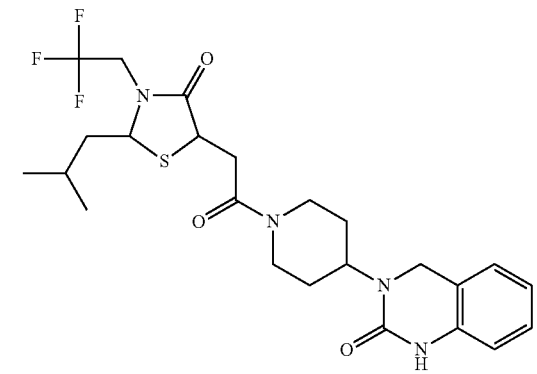
227
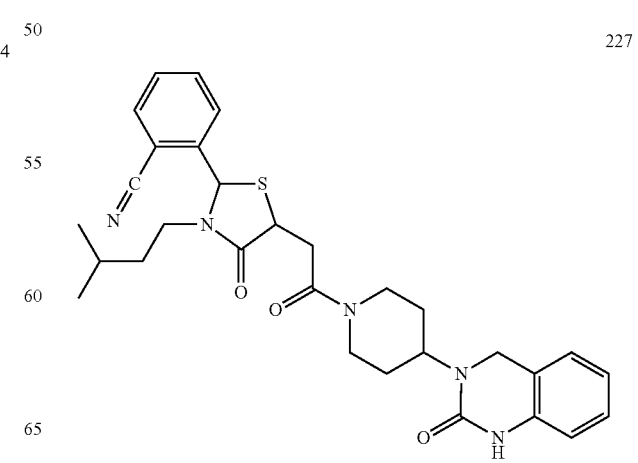

-continued
228
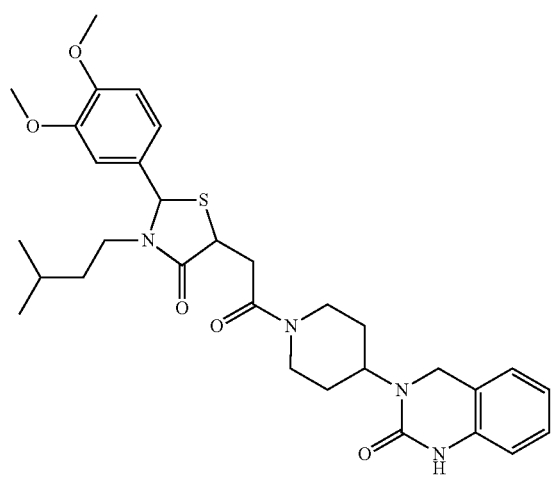
229
230
231
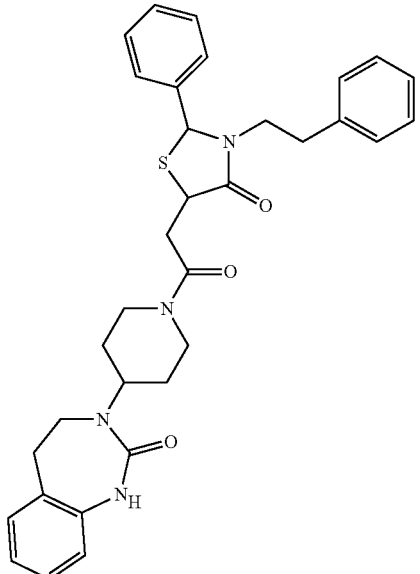
232
233
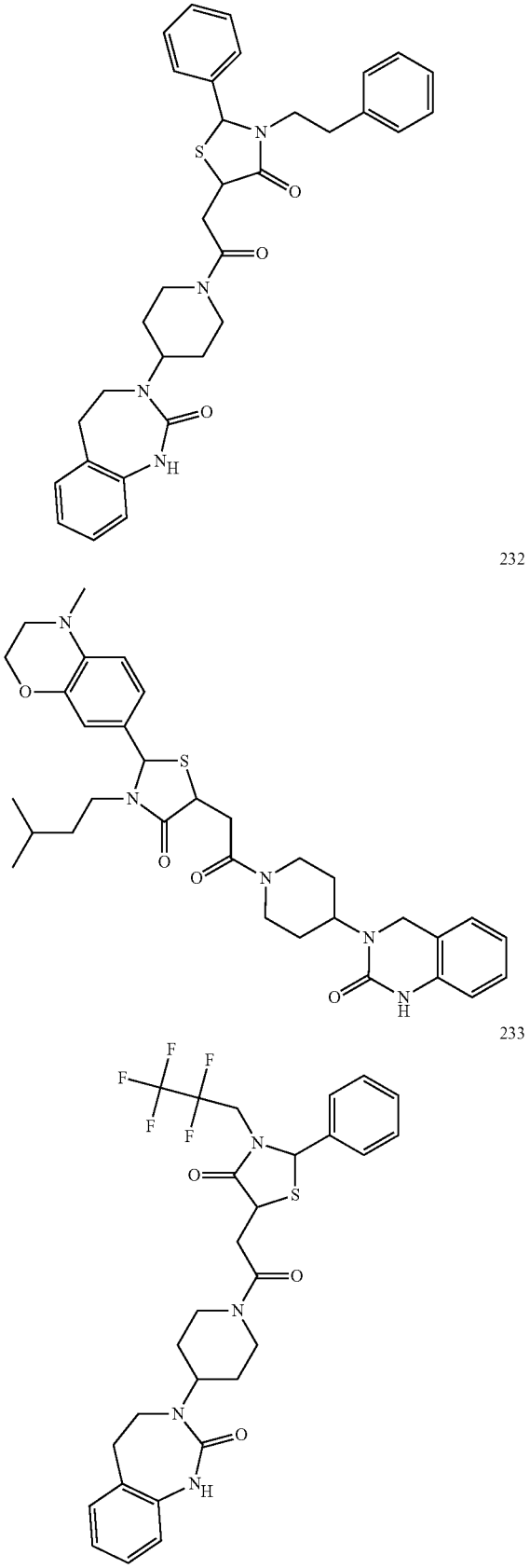

355
-continued
234
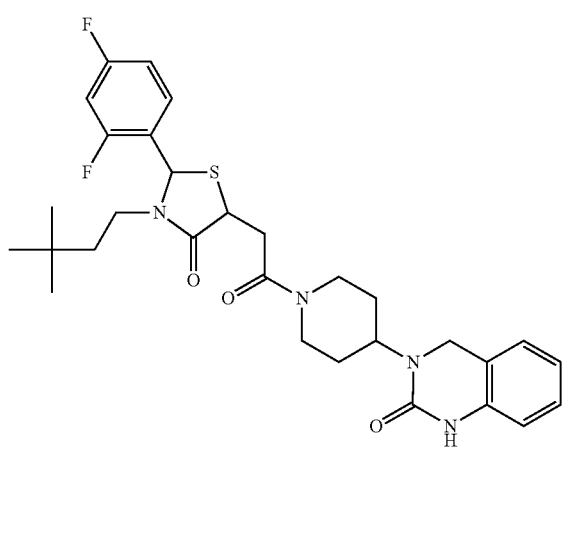
235
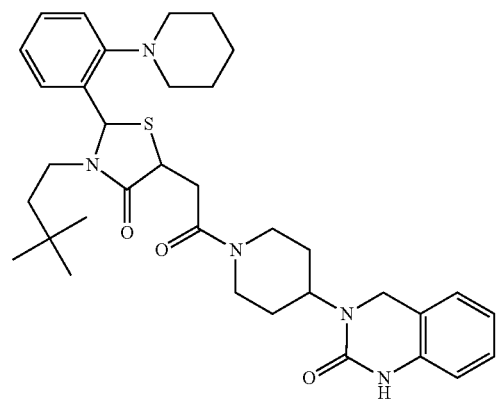
236
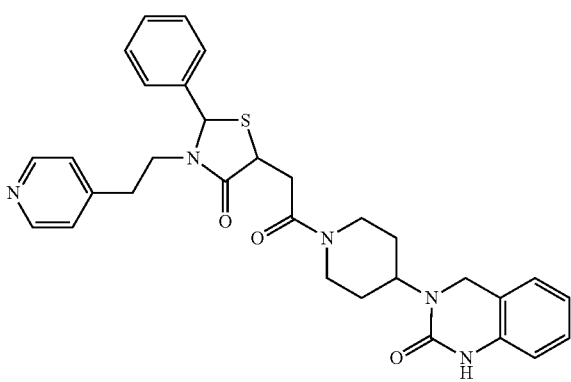
356
-continued
237
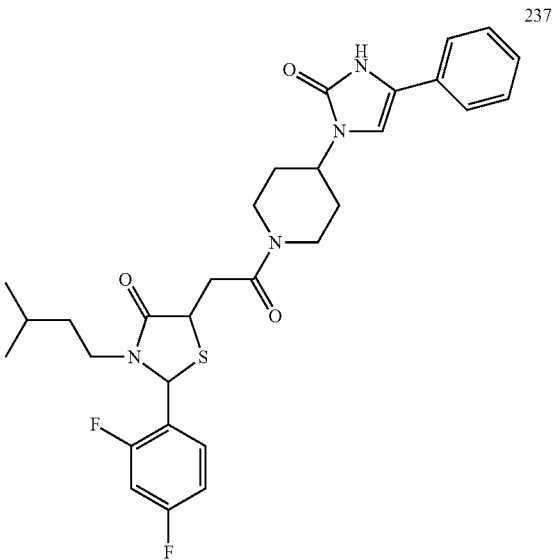
238
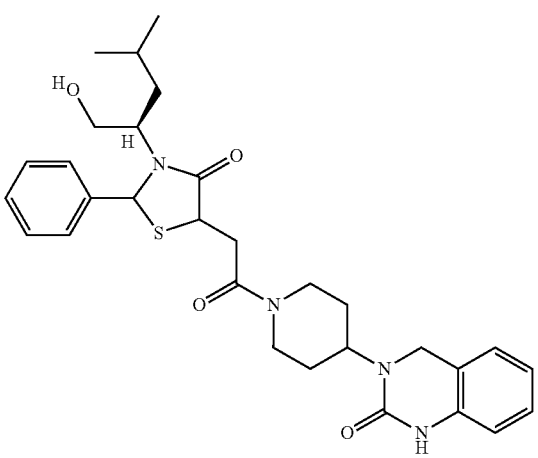
239
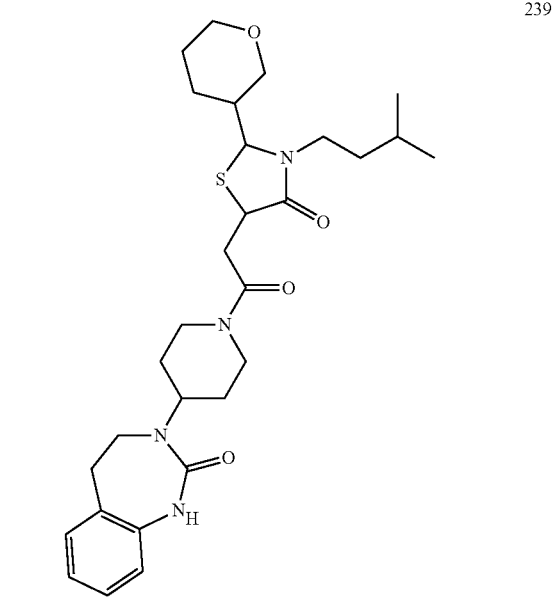

240
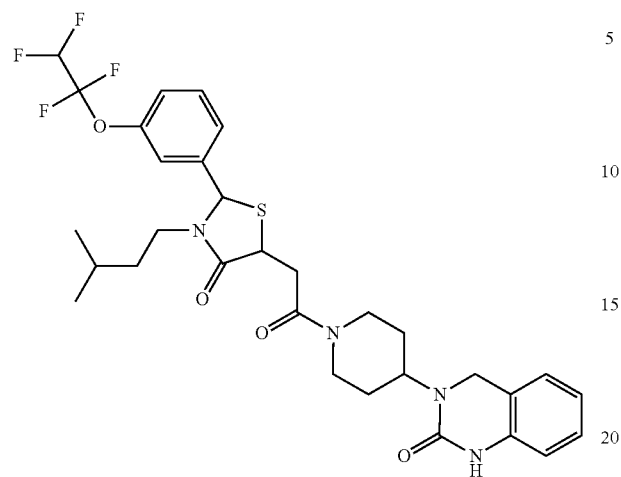
241
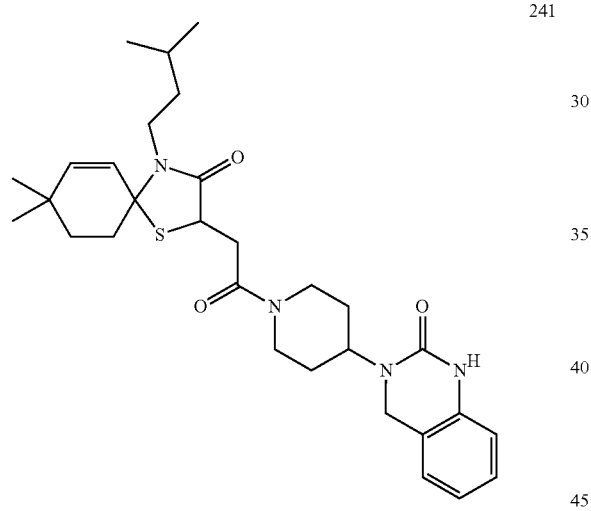
242
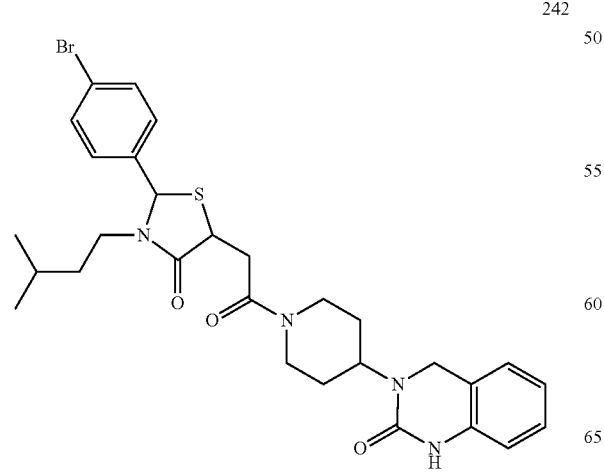
243
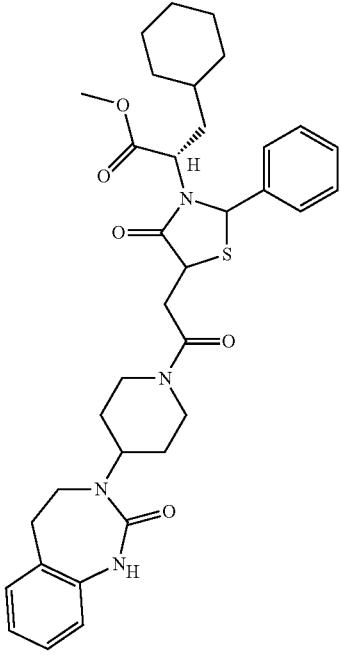
244
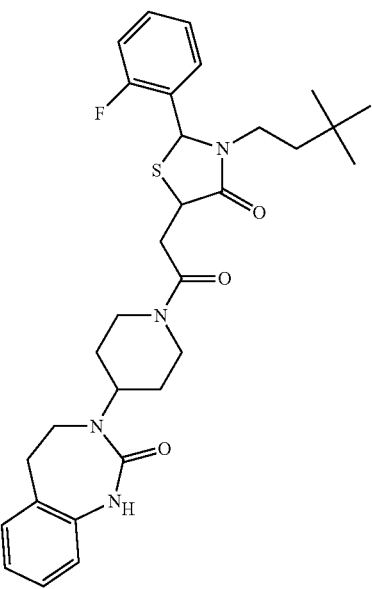

245 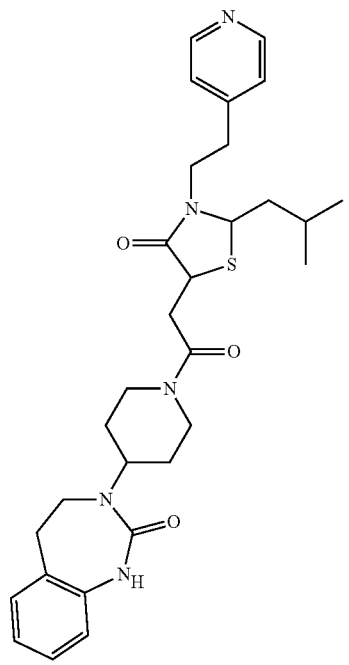
246 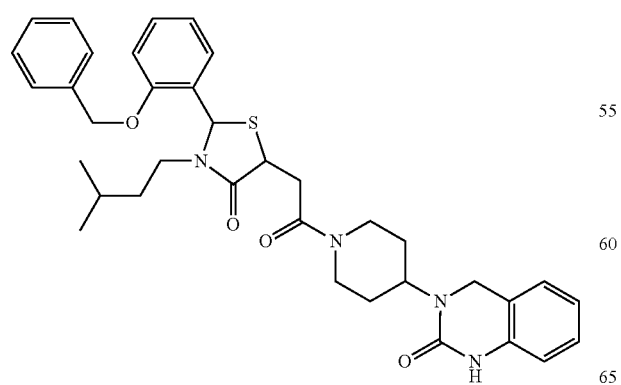
247 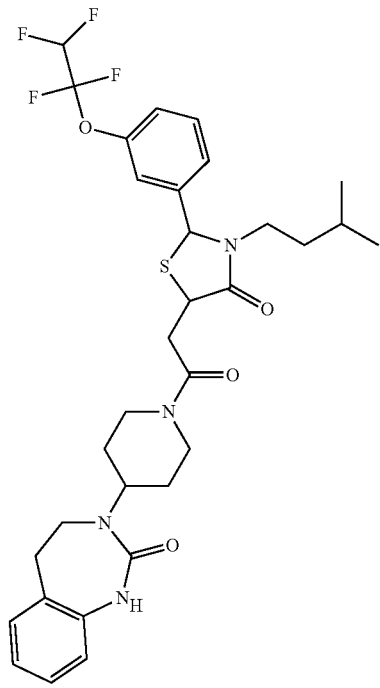
248 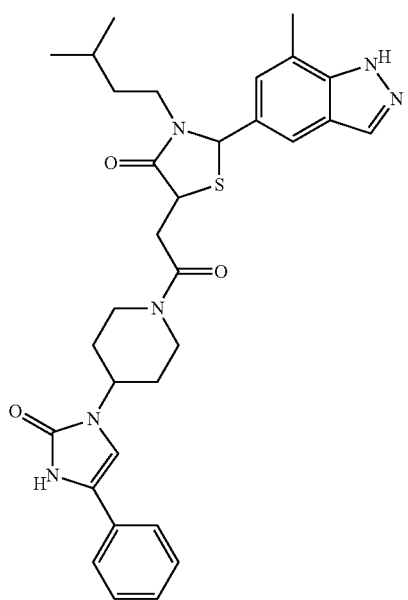

249
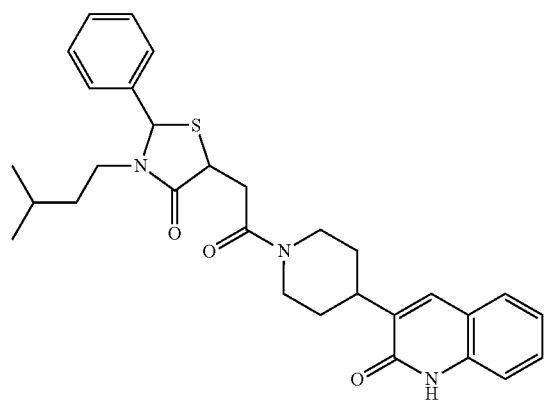
250
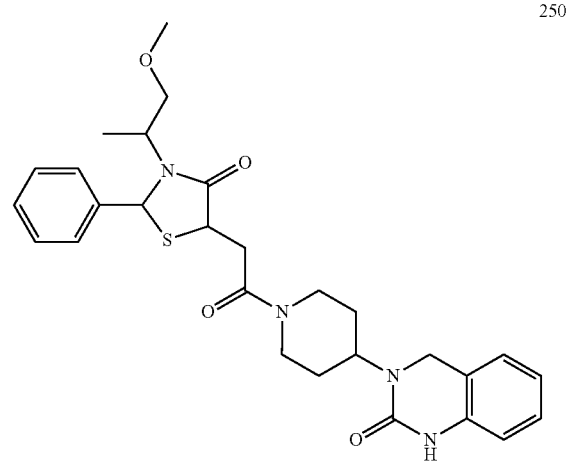
251
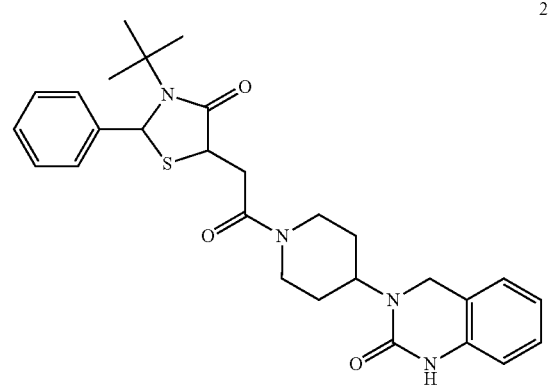
252
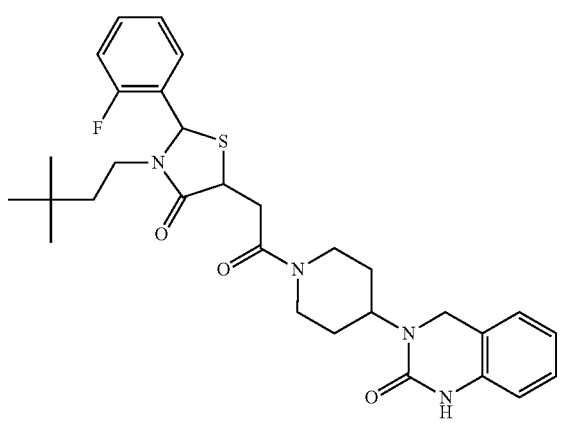
253
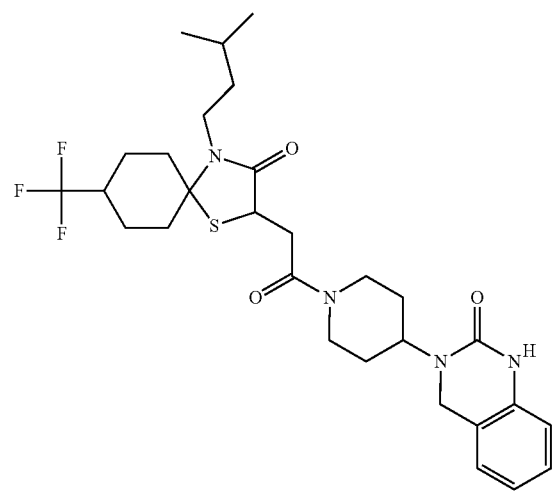
254
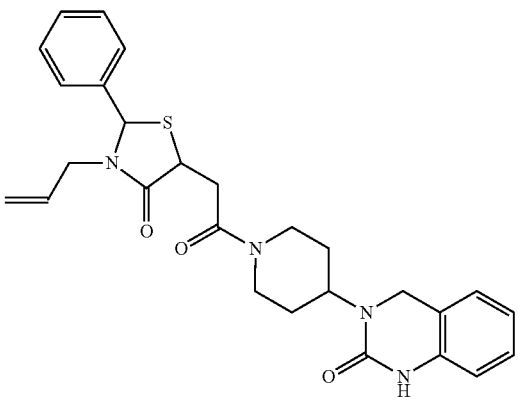

363
-continued
255
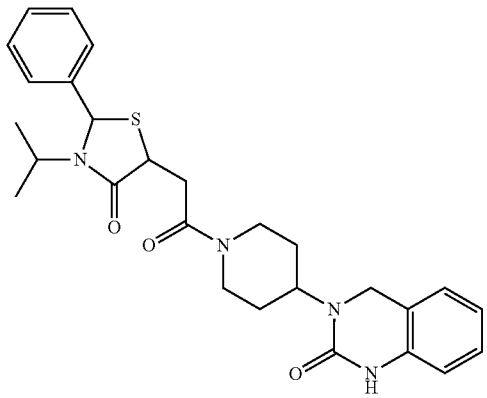
256
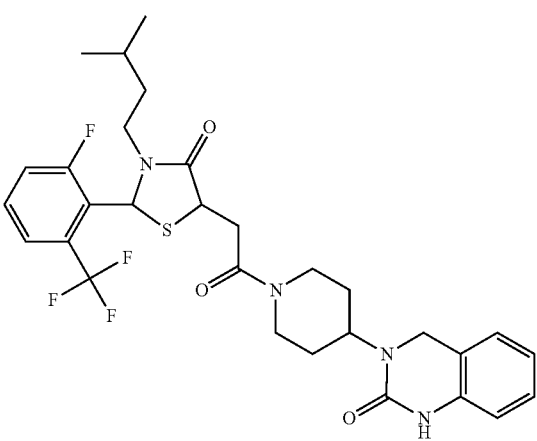
257
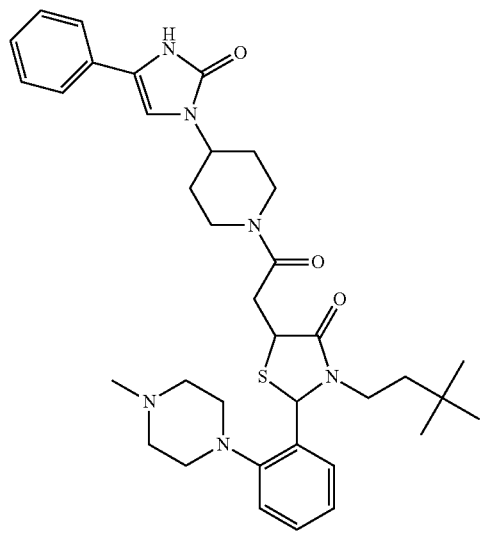
364
-continued
258
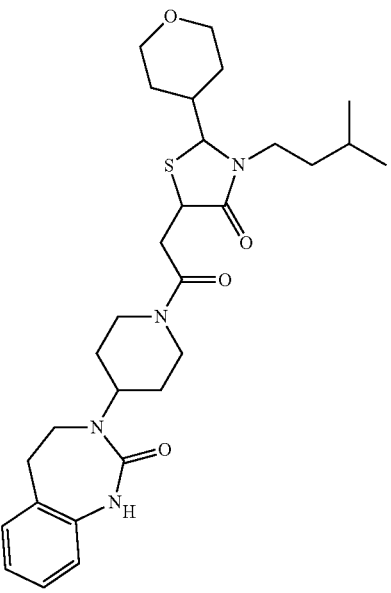
259
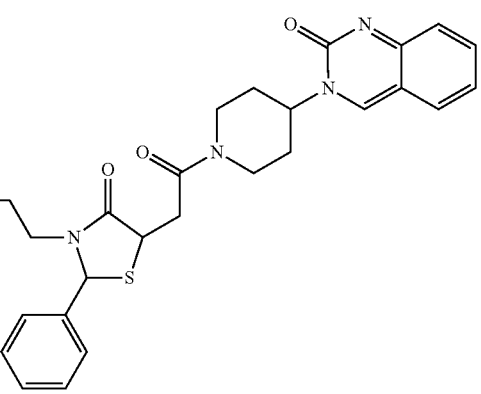
260
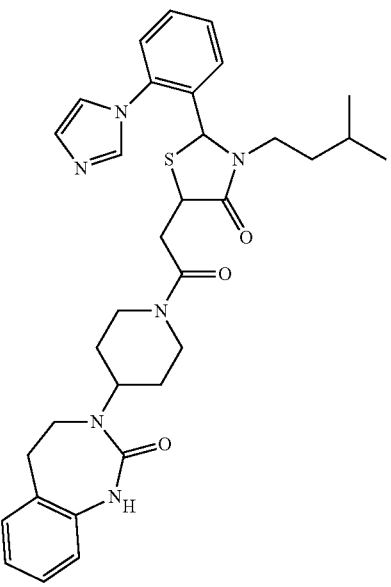

261
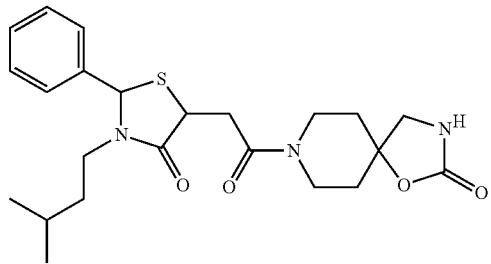
262
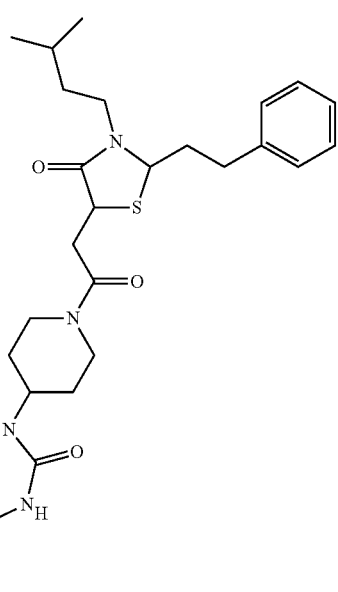
263
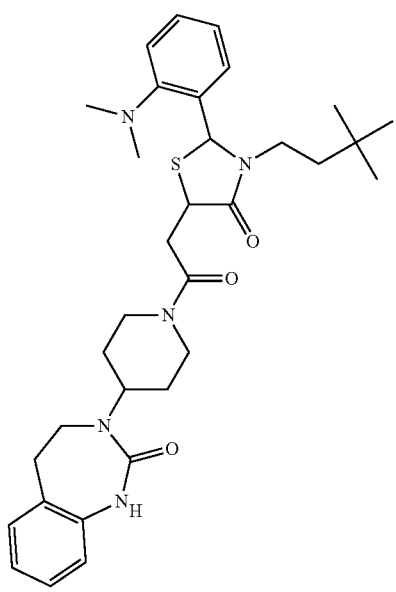
264
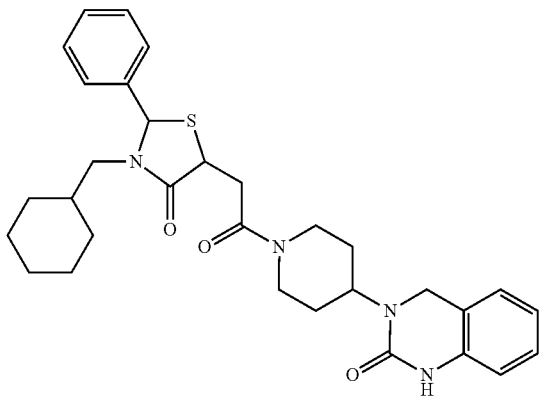
265
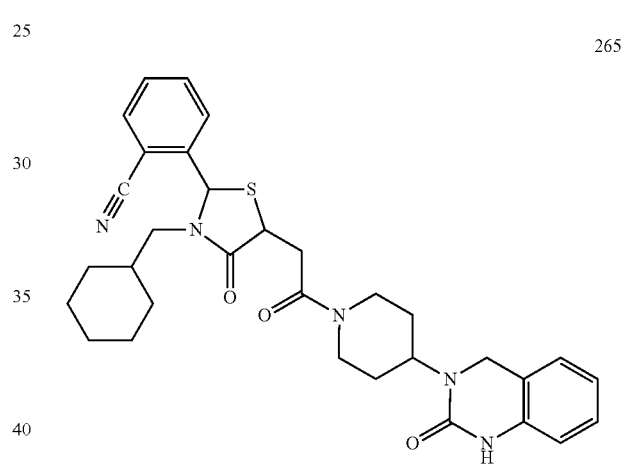
266
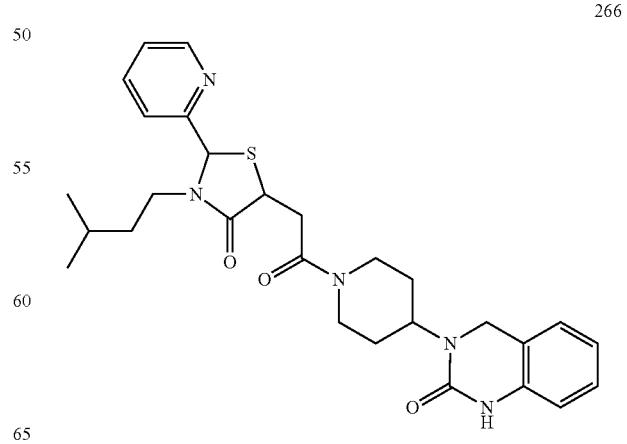

267
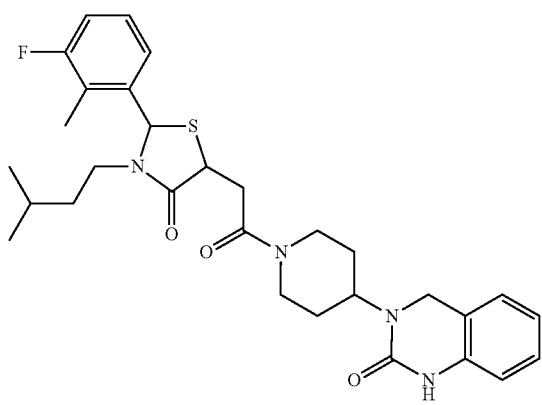
268
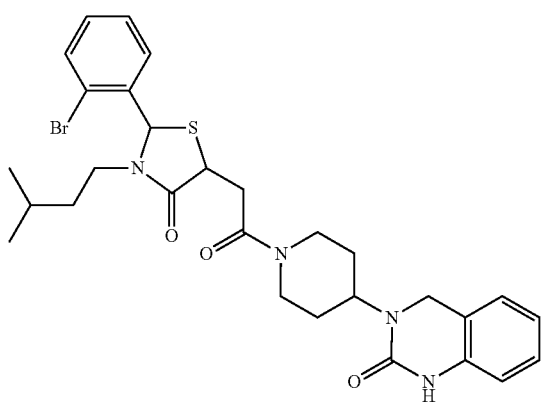
269
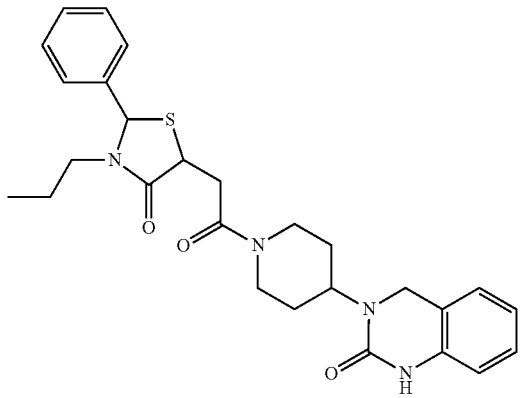
270
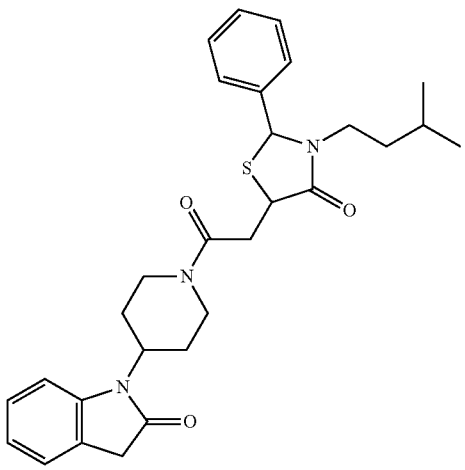
271
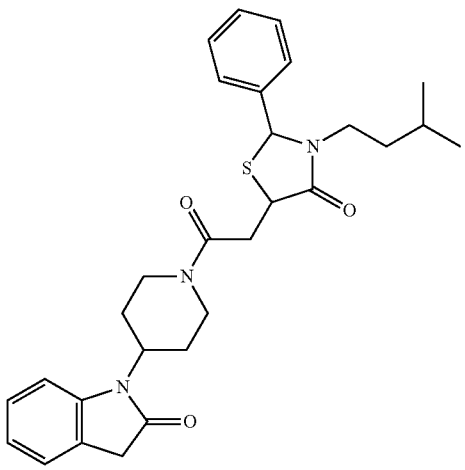
272
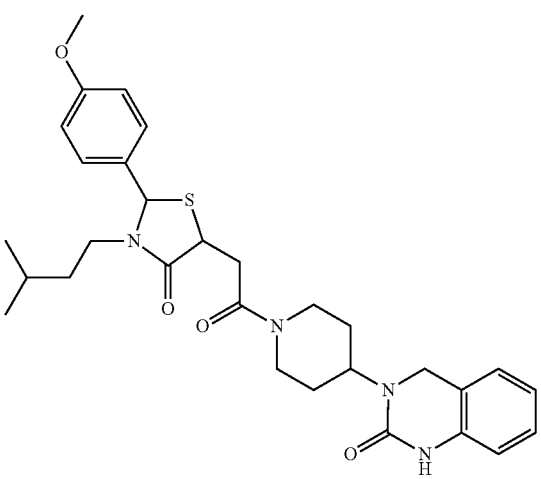

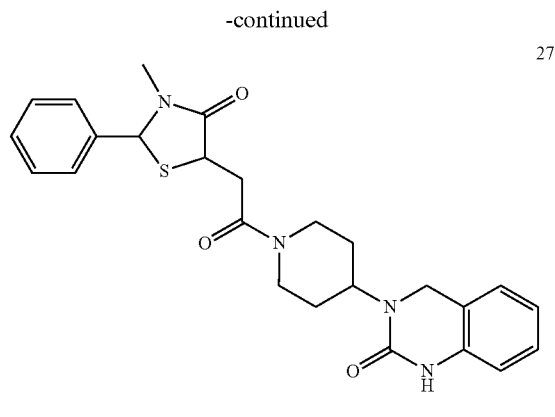
273
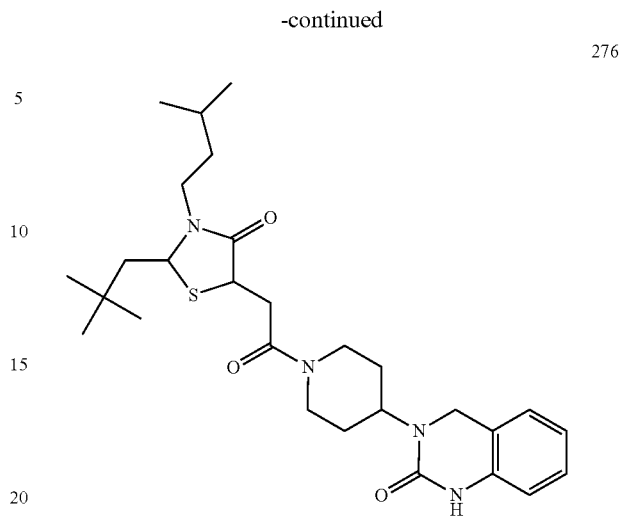
276
274
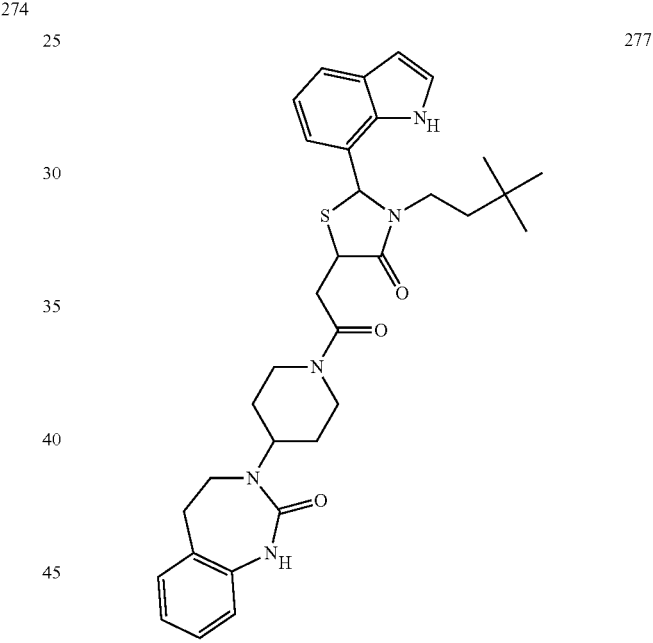
277
275
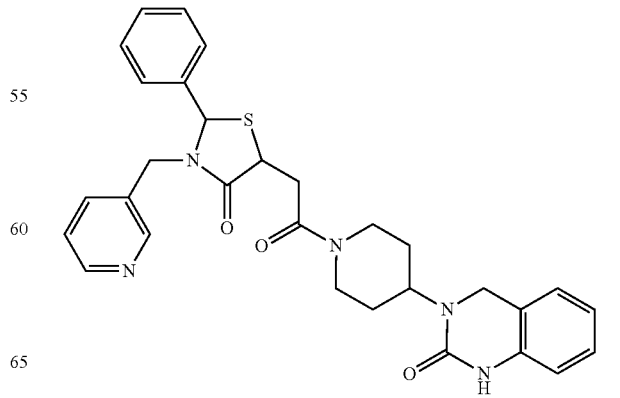
278

-continued
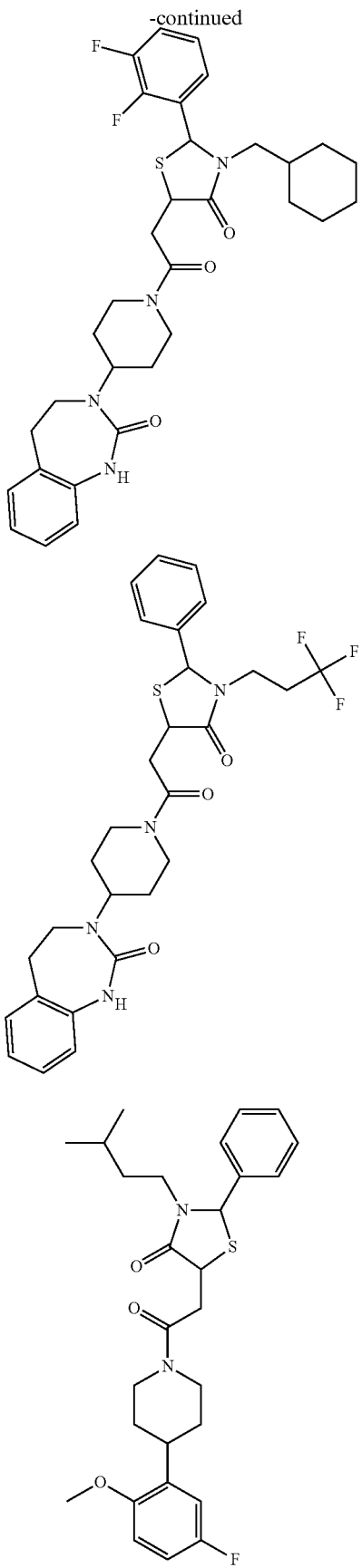
-continued
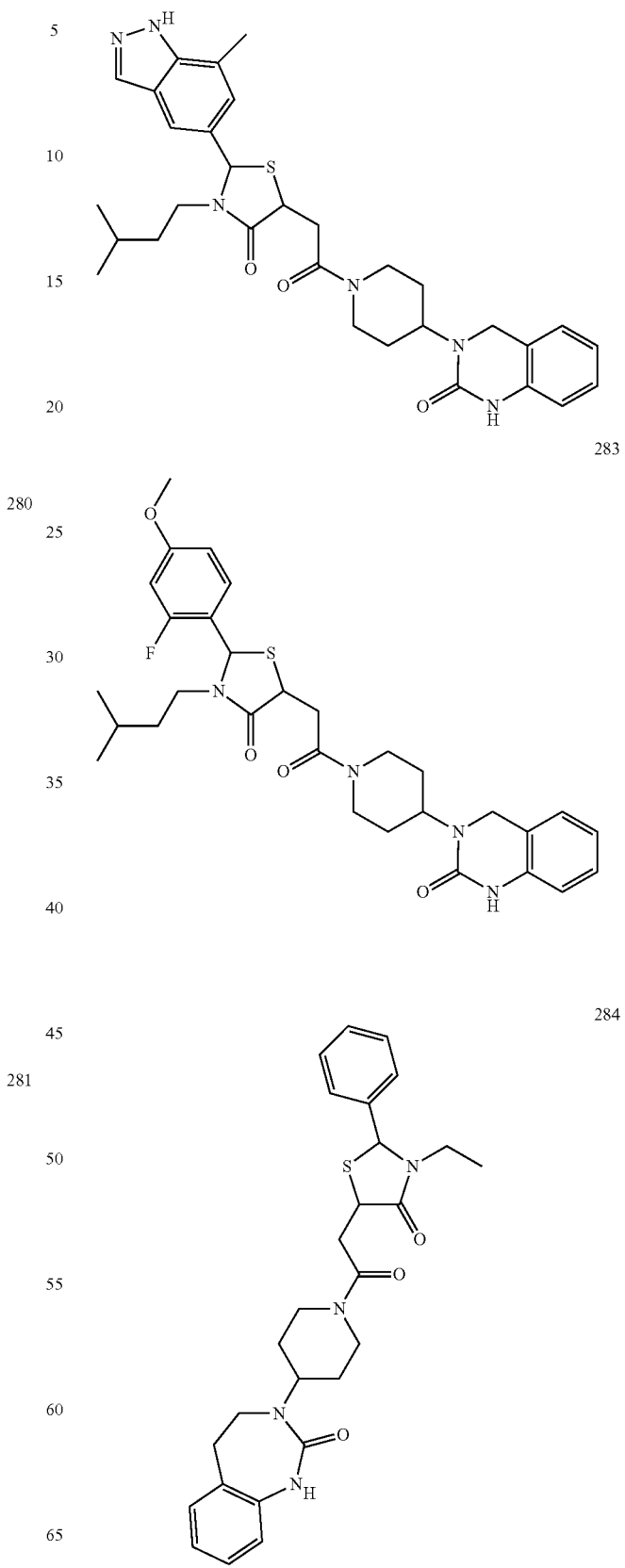

-continued
285
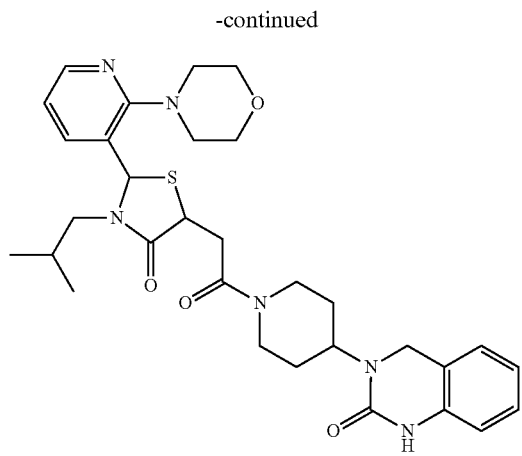
286
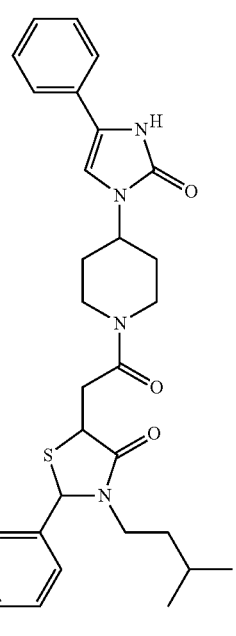
287
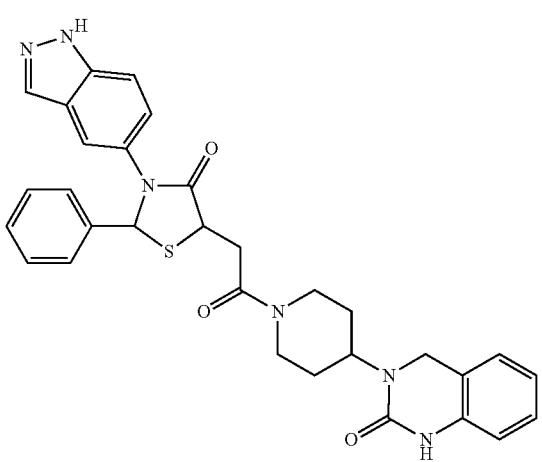
-continued
288
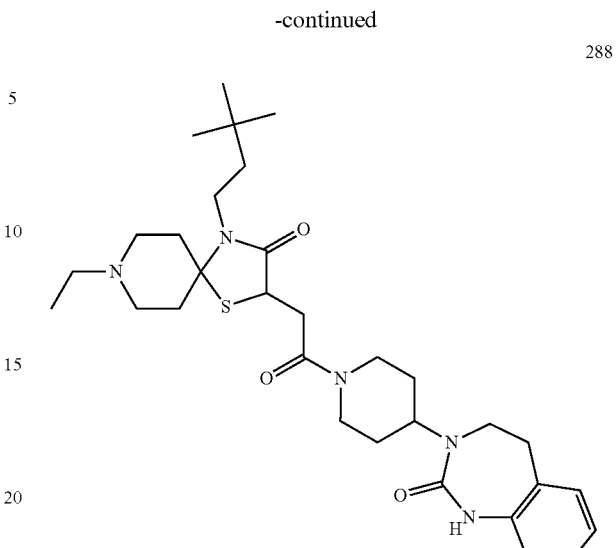
289
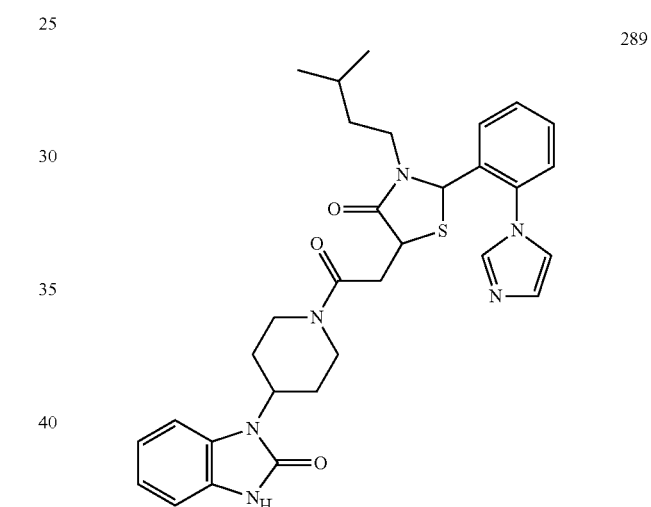
290
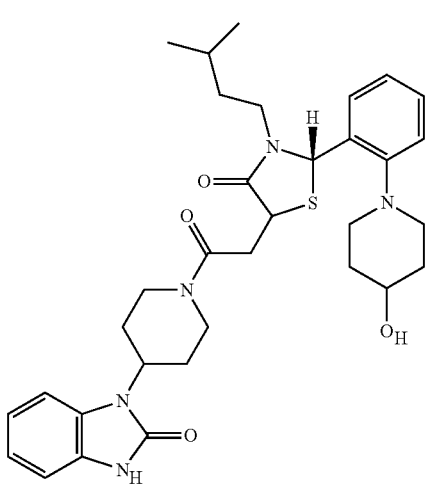

-continued
291
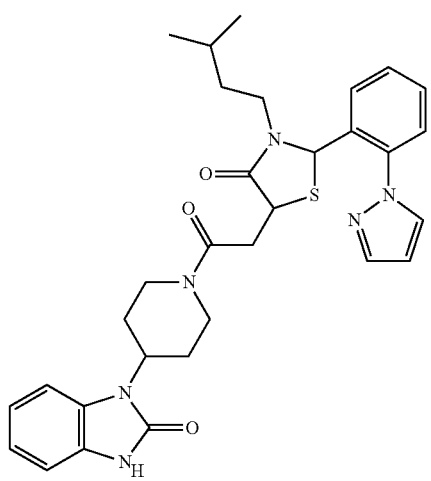
292
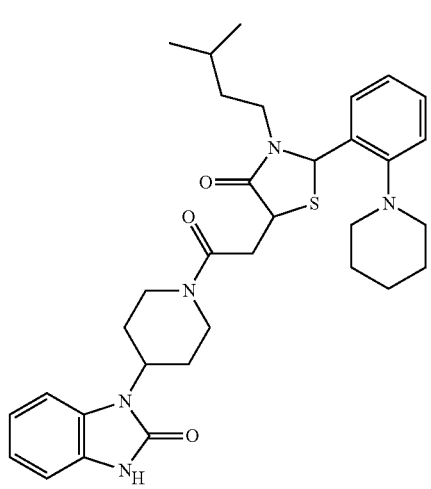
293
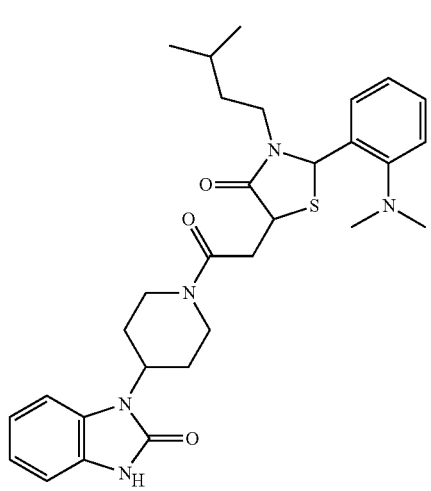
-continued
294
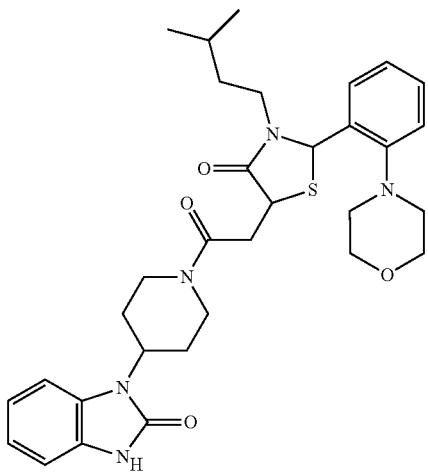
295
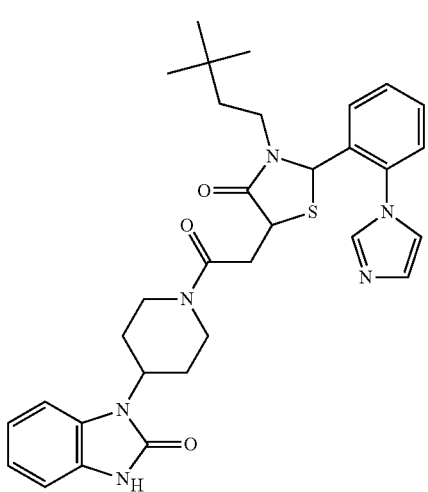
296
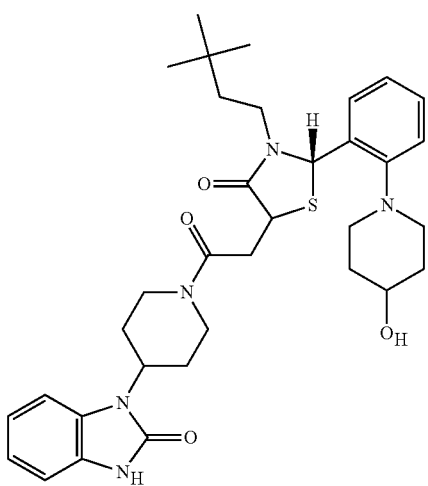

297
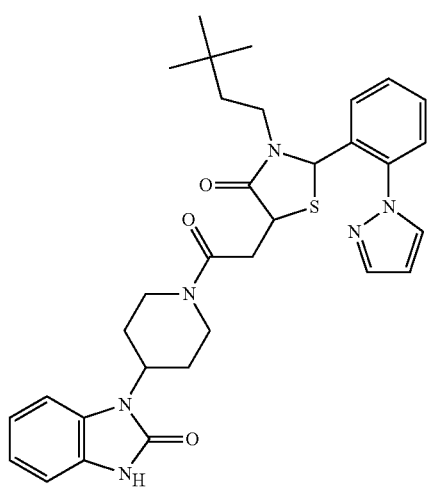
298
299
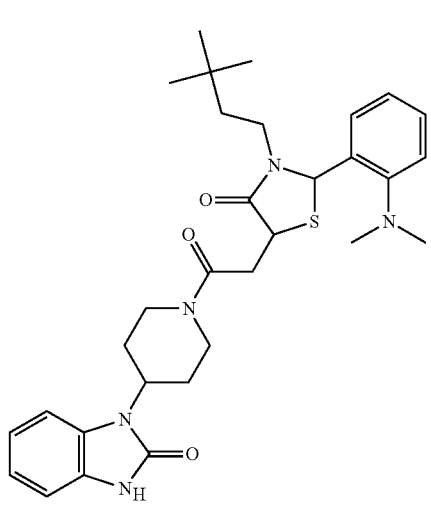
300
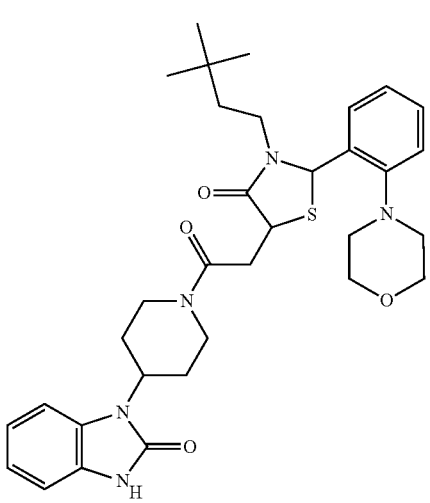
301
302

-continued
303
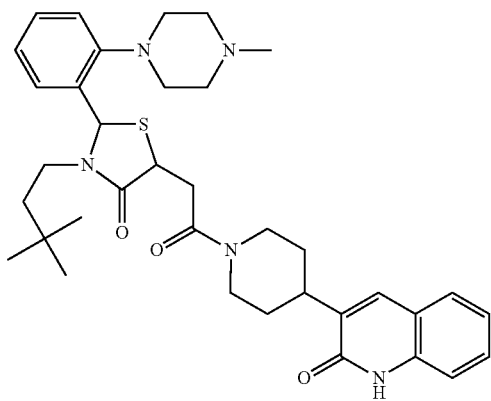
304
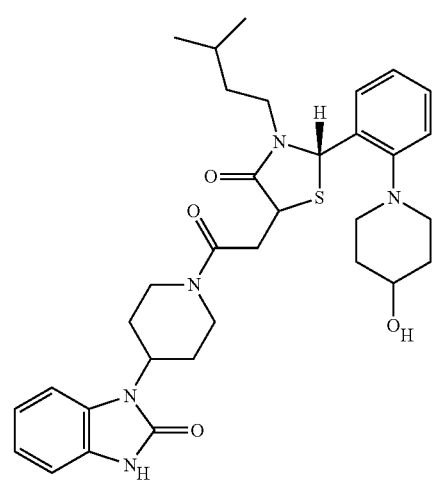
305
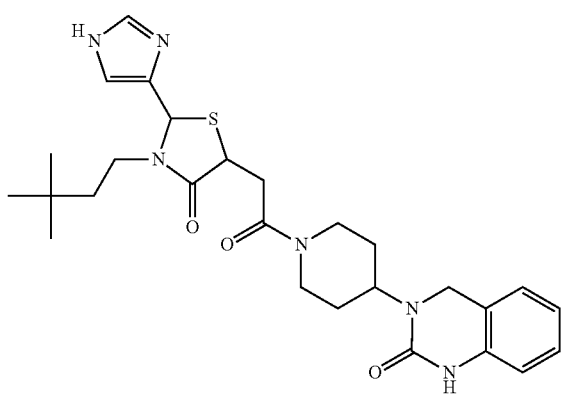
-continued
306
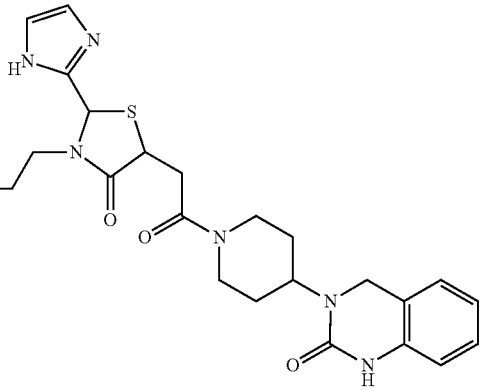
307
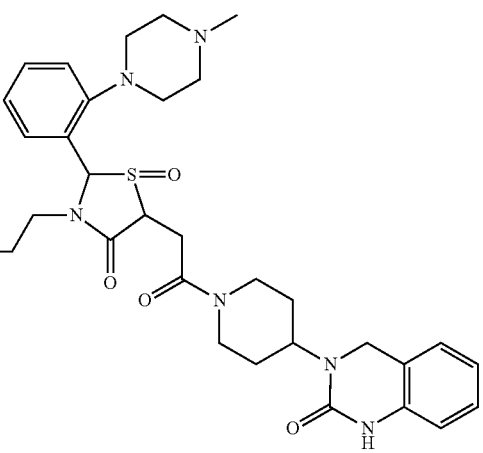
308
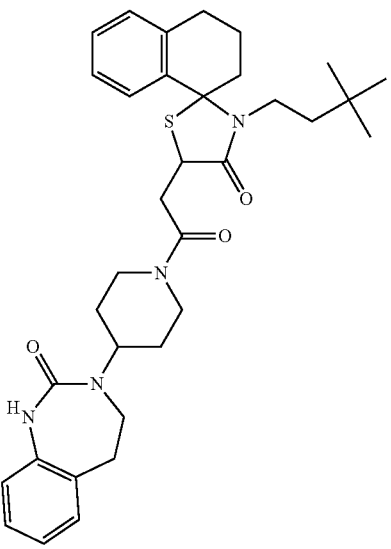

-continued
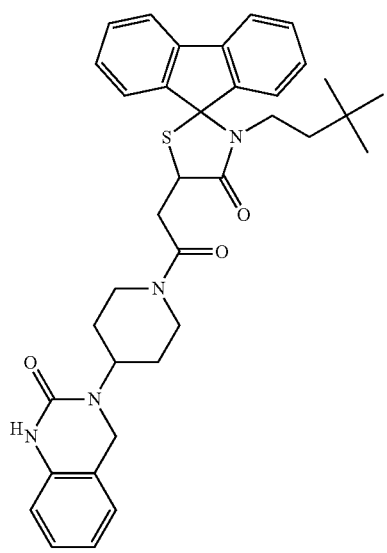
309
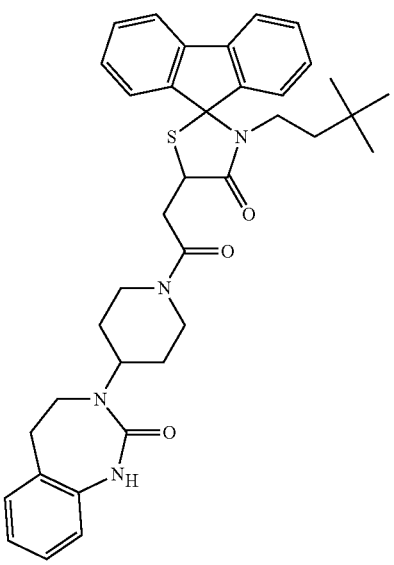
310
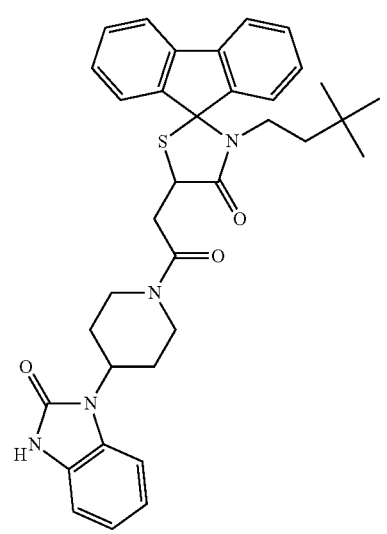
311
-continued
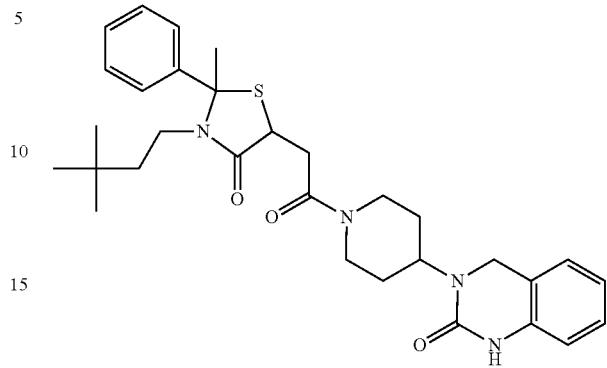
312
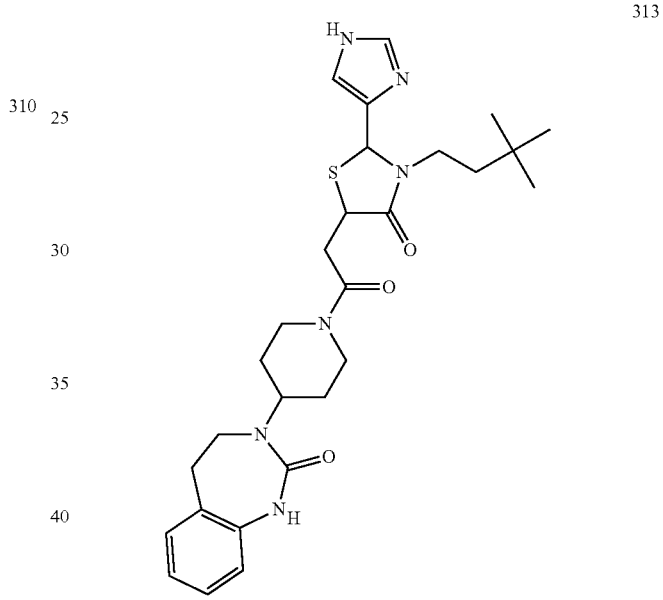
313
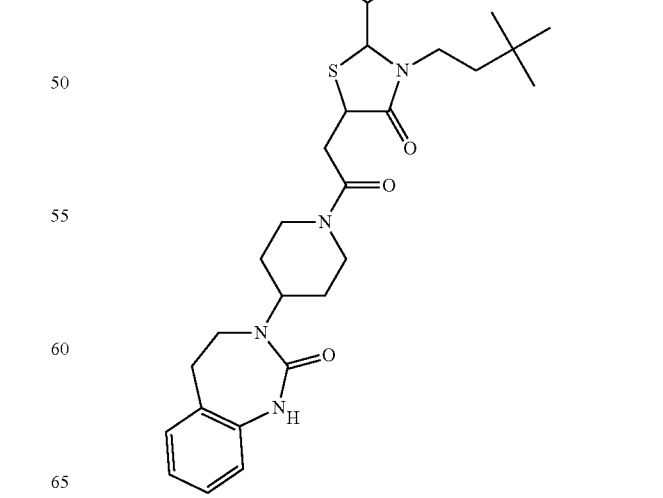
314

383
-continued
315
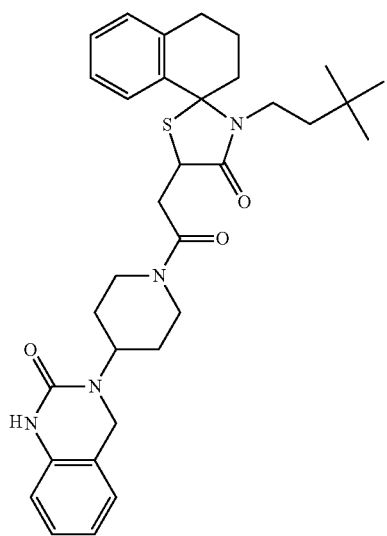
316
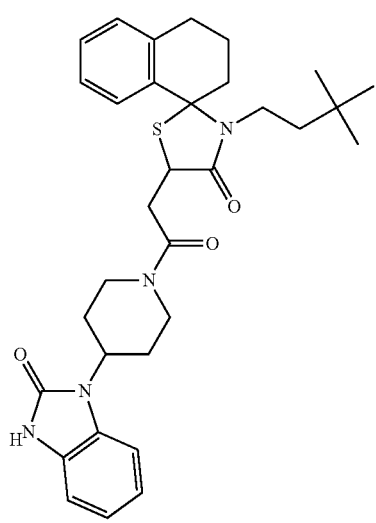
317
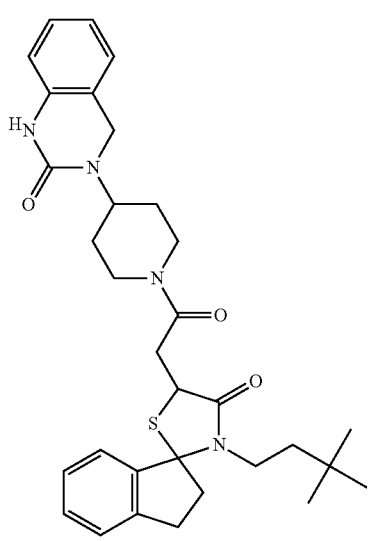
384
-continued
318
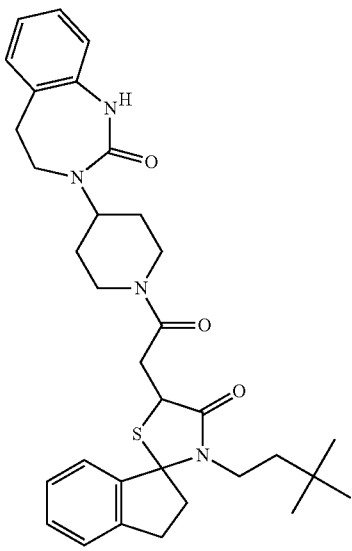
319
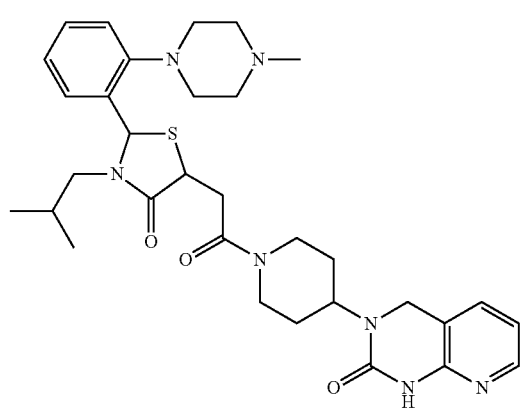
320
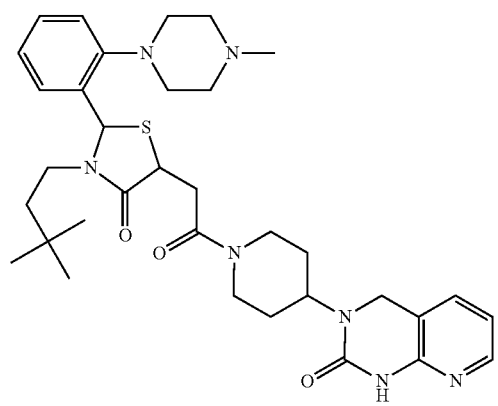

385
-continued
321
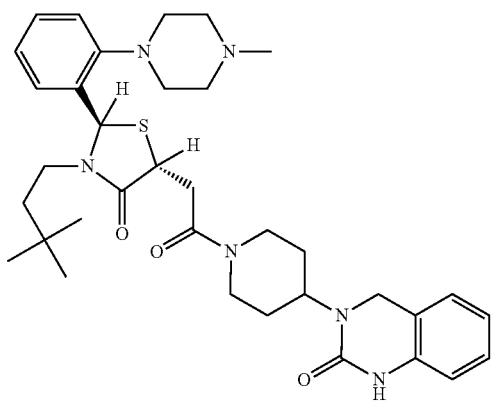
322
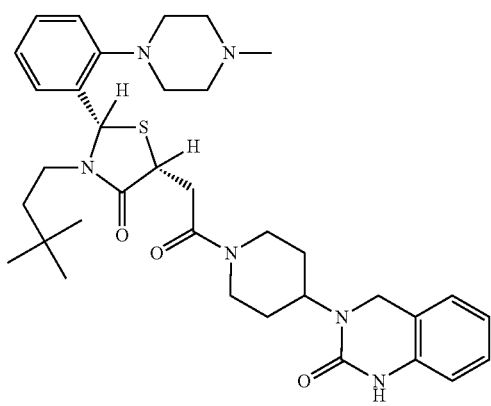
323
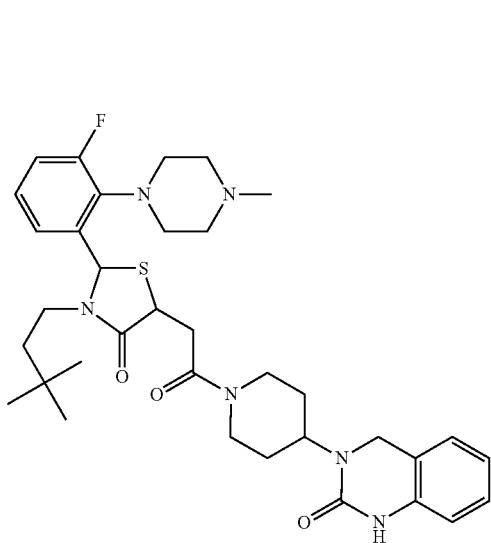
386
-continued
324
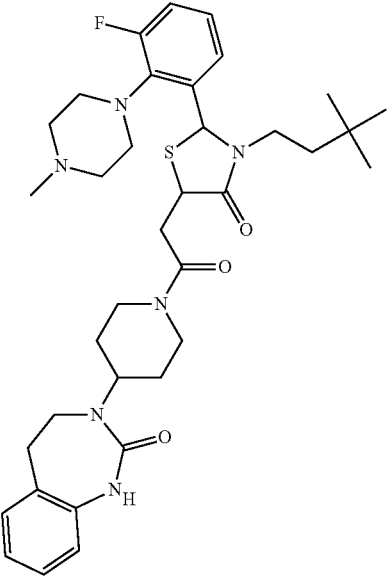
325
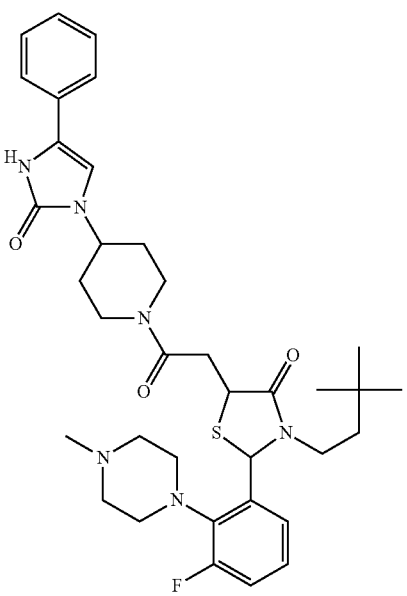

326
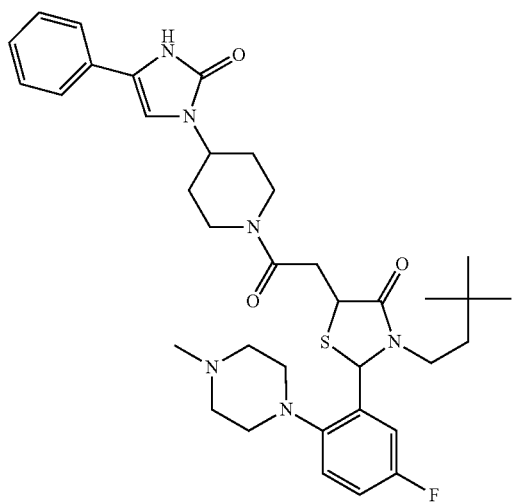
327
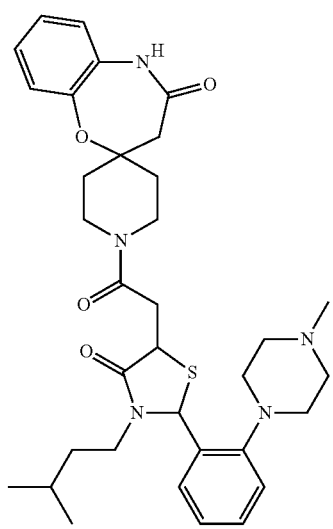
328
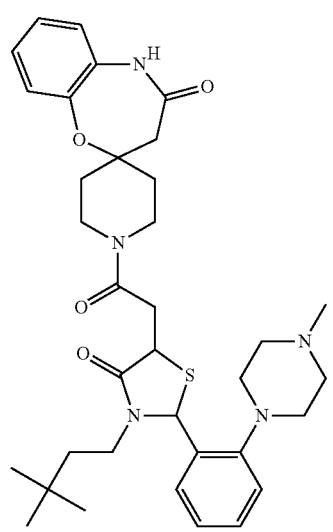
329
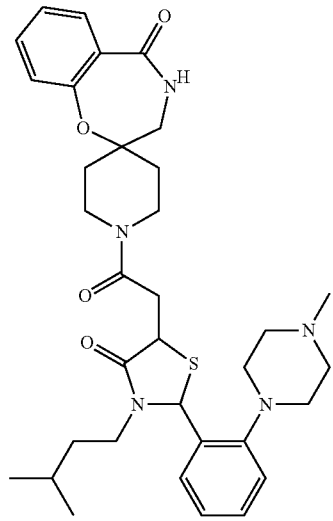
330
331

-continued
332
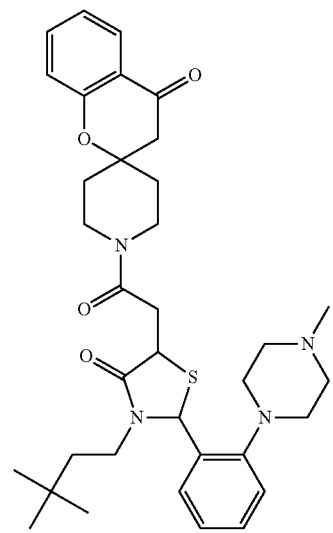
333
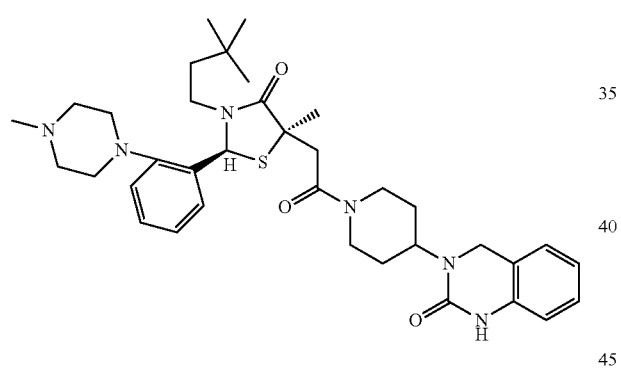
334
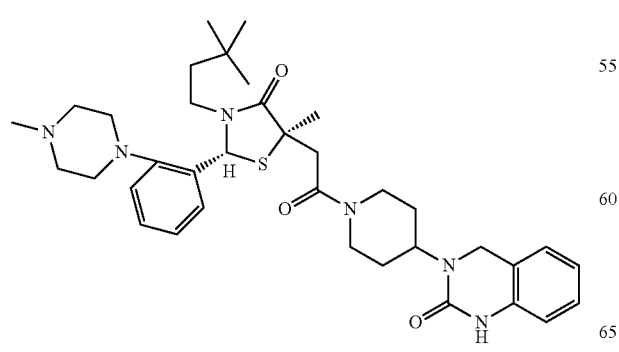
-continued
335
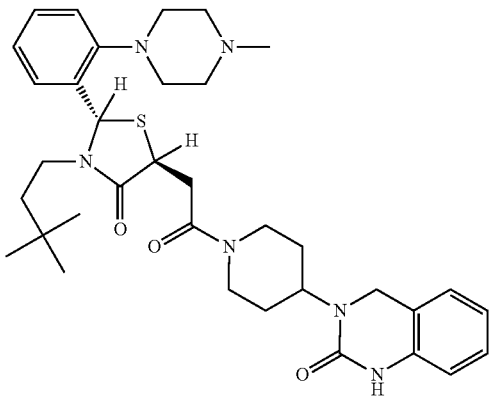
336
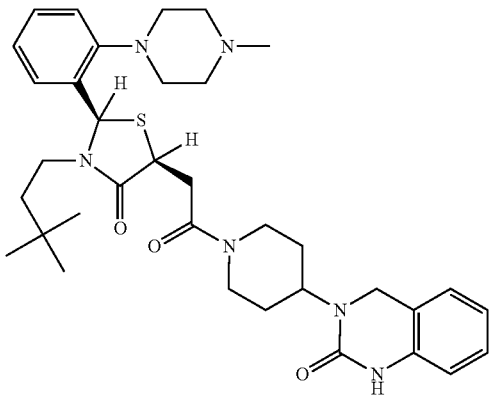
337
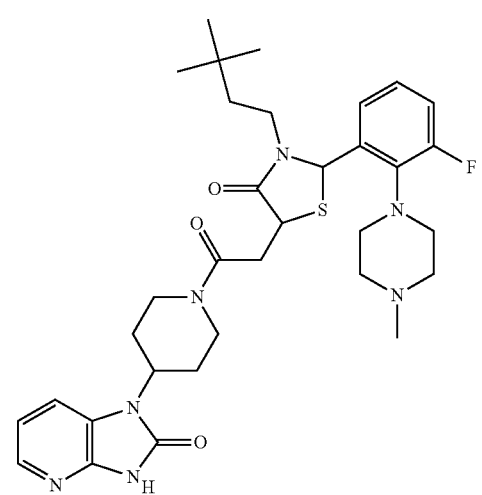

338
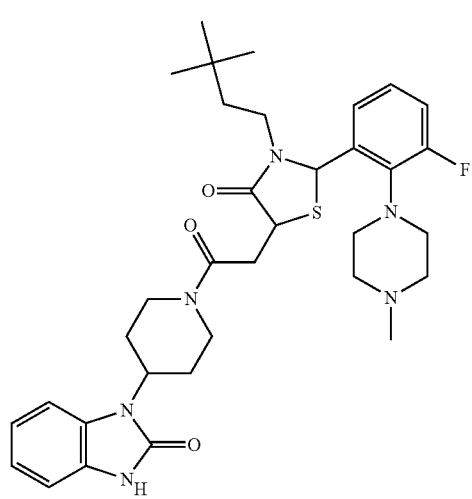
339
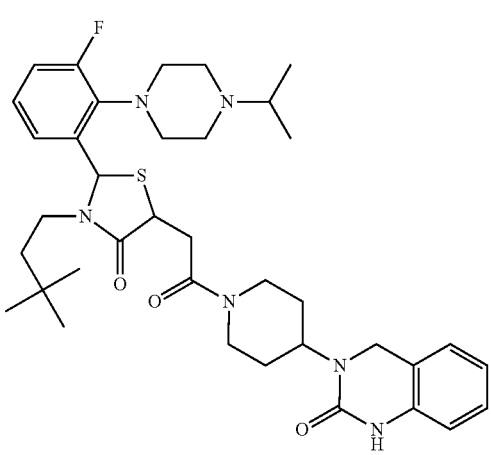
340
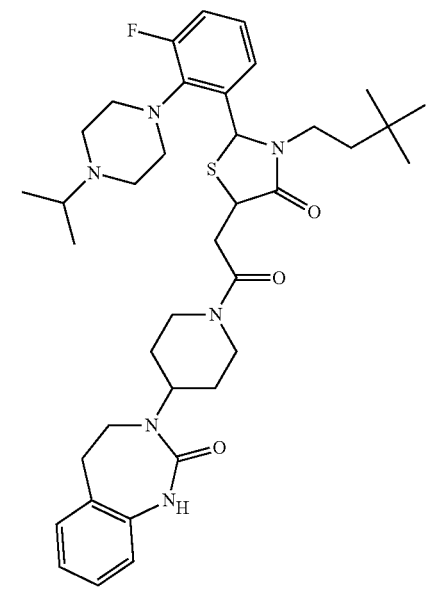
341
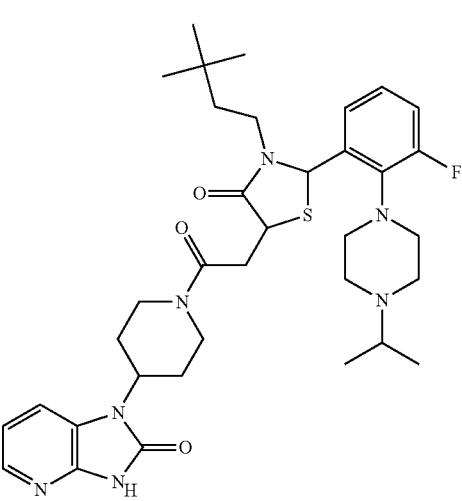
342
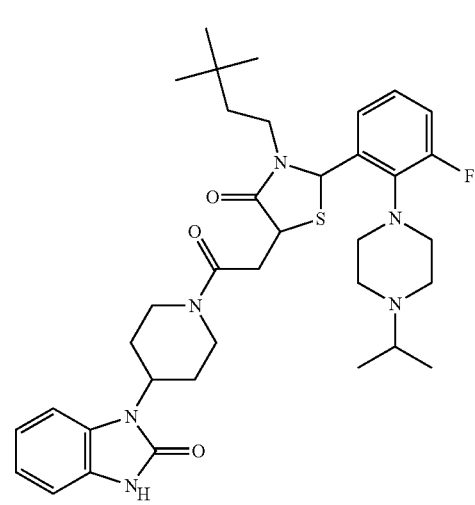
343

344
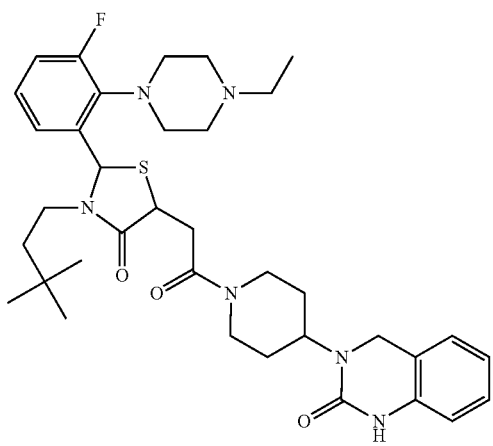
345
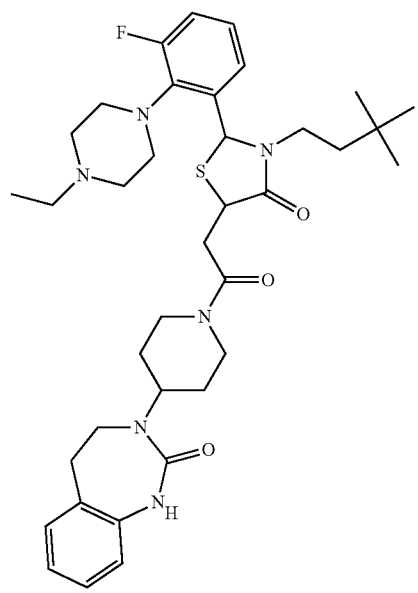
346
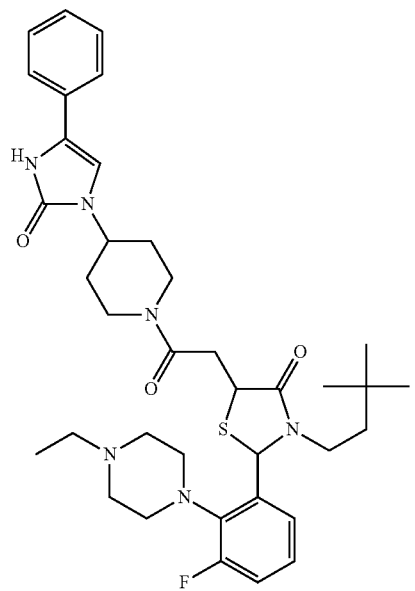
347
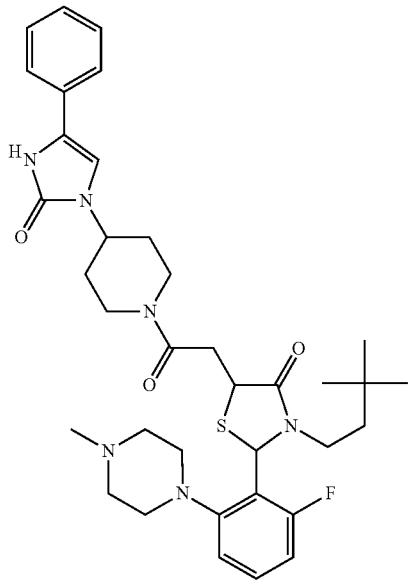
348
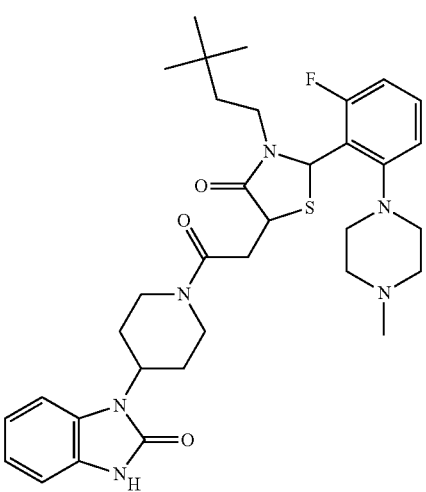
349
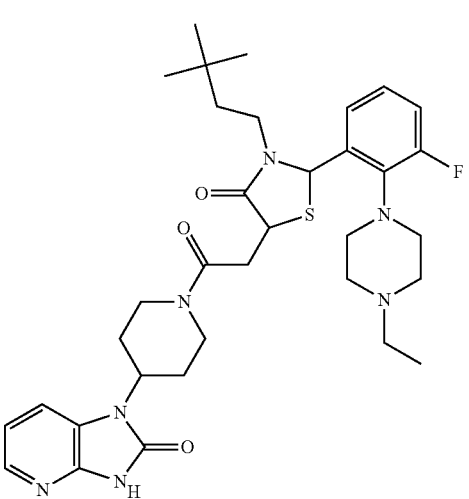

350
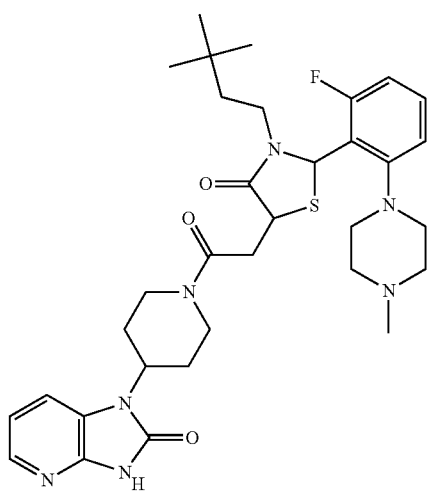
351
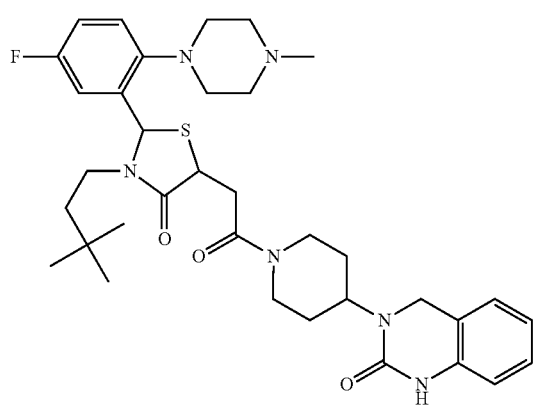
352
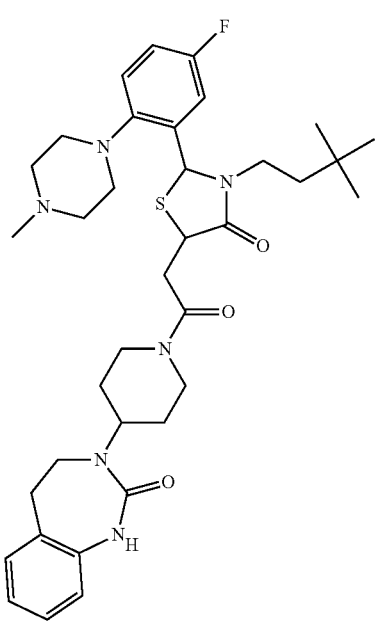
353
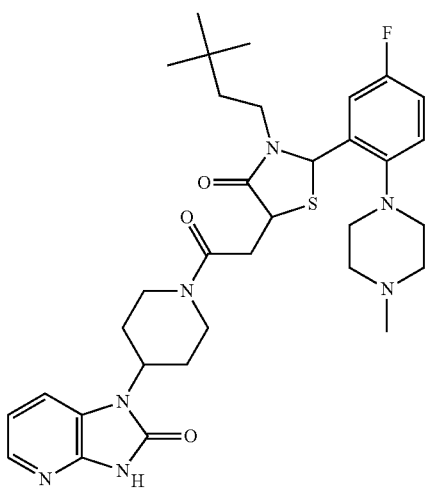
354
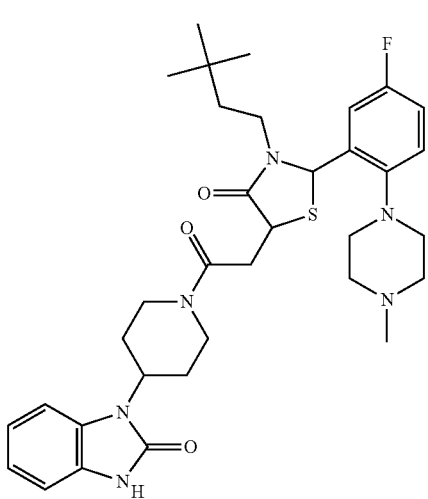
355
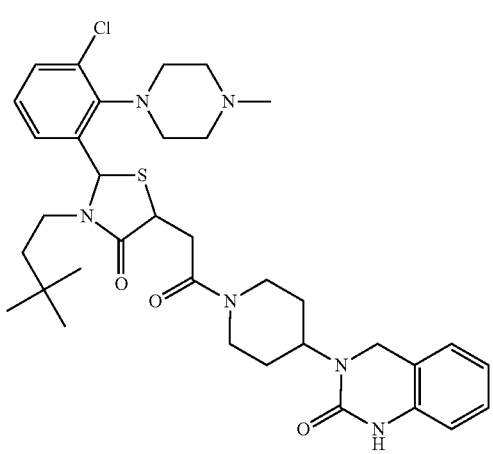

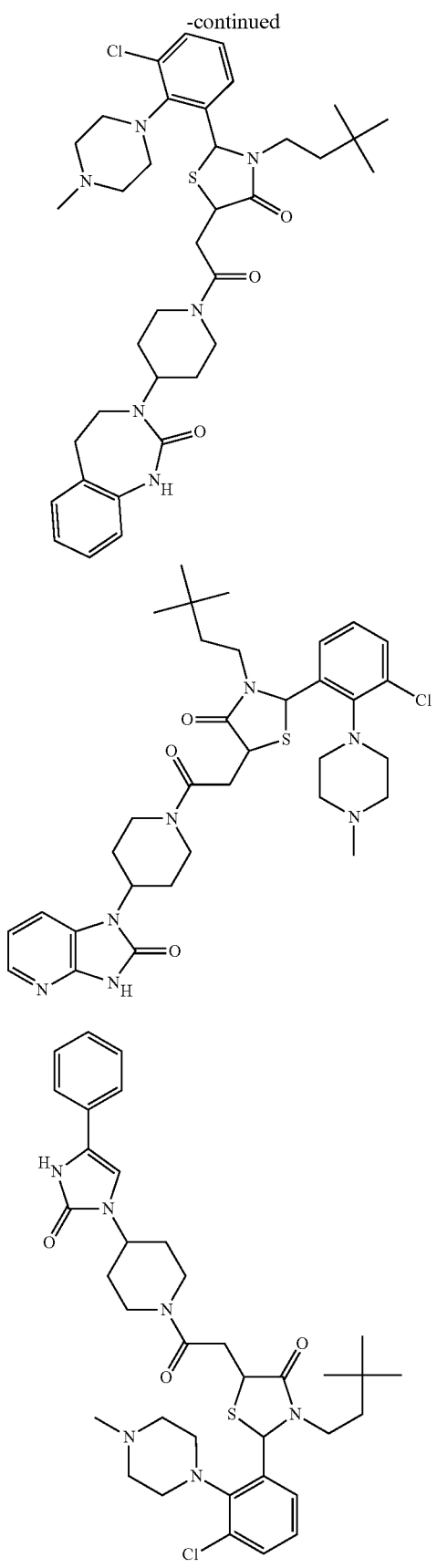
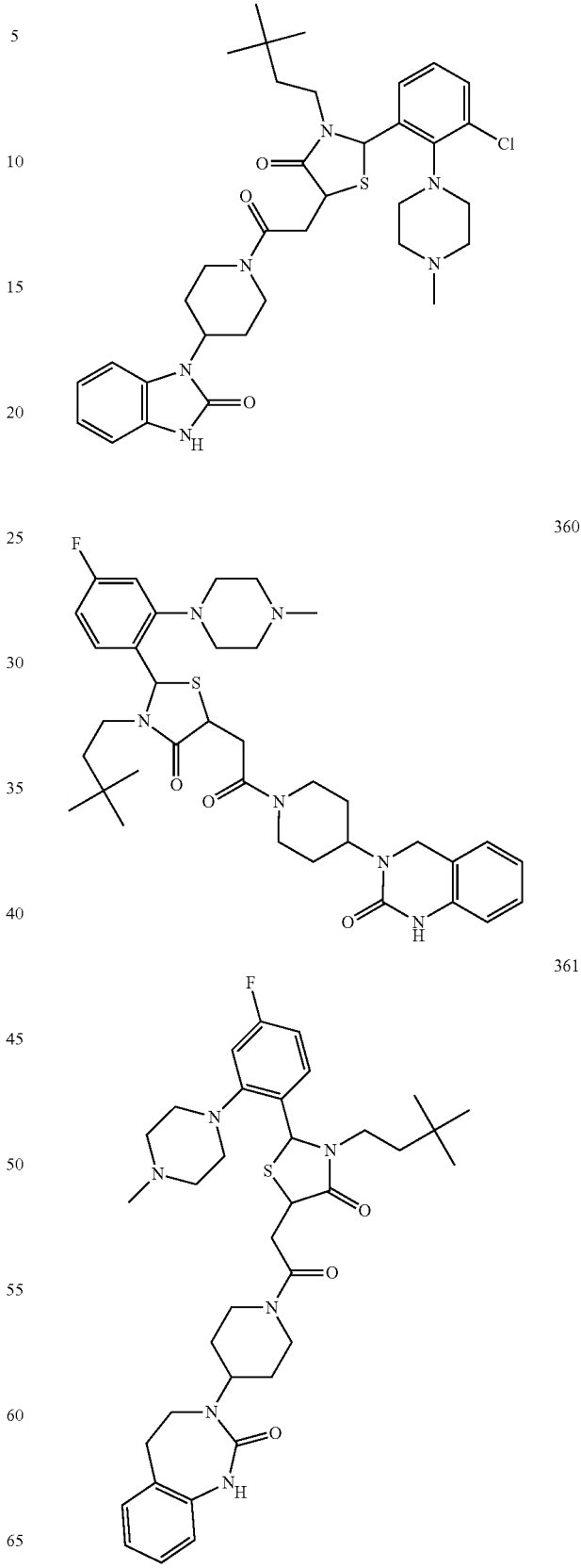

-continued
362
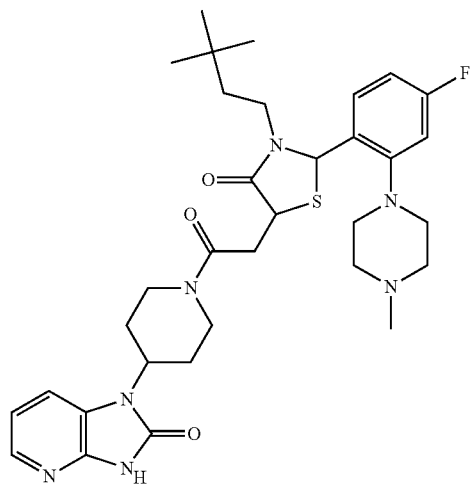
363
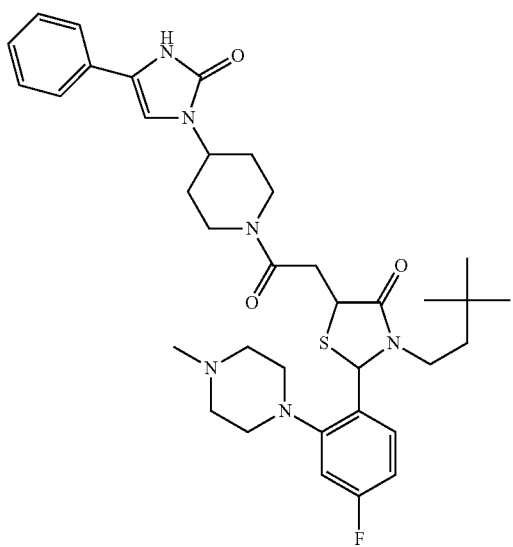
364
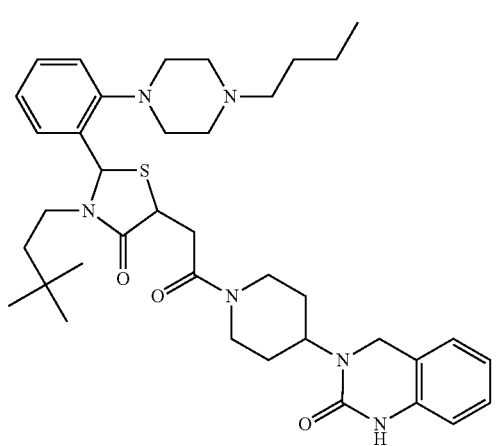
-continued
365
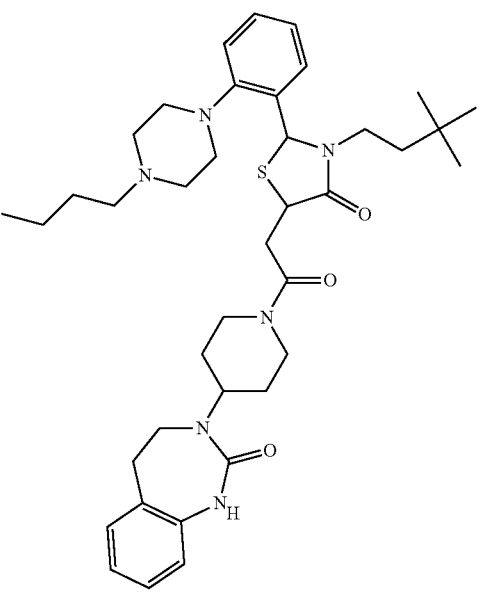
366
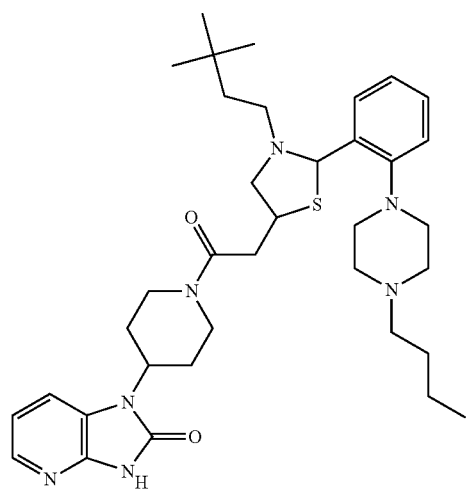
367
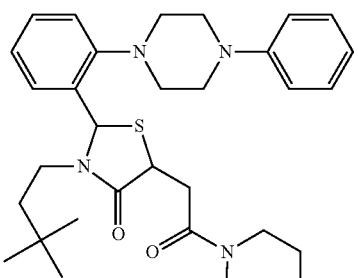
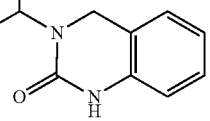

-continued
368
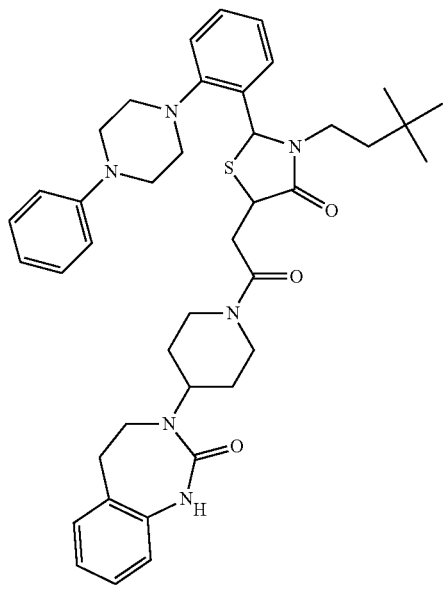
369
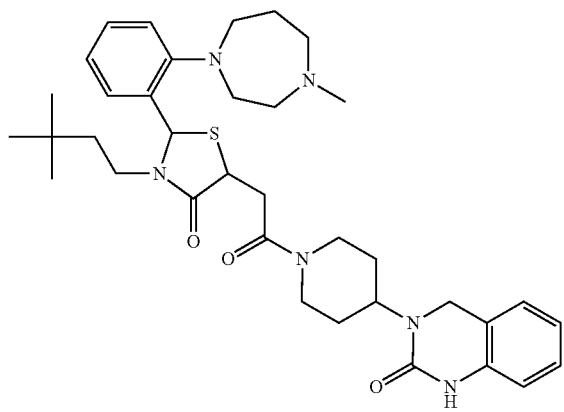
370
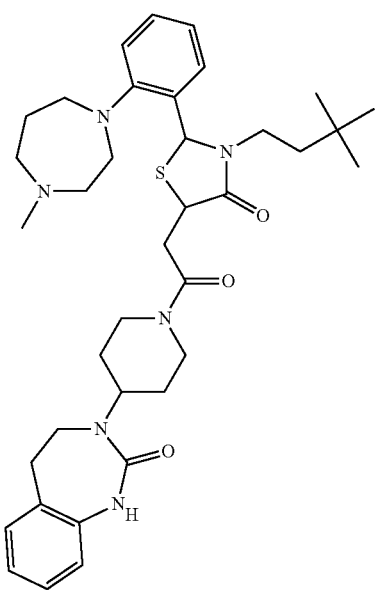
-continued
371
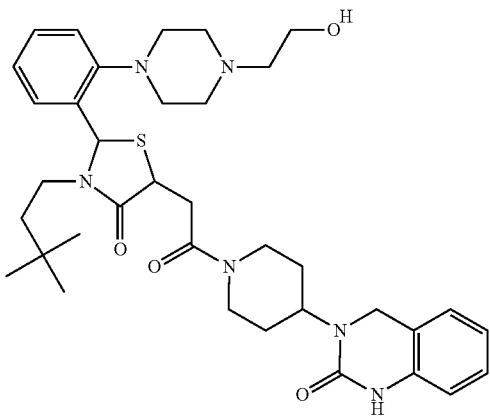
372
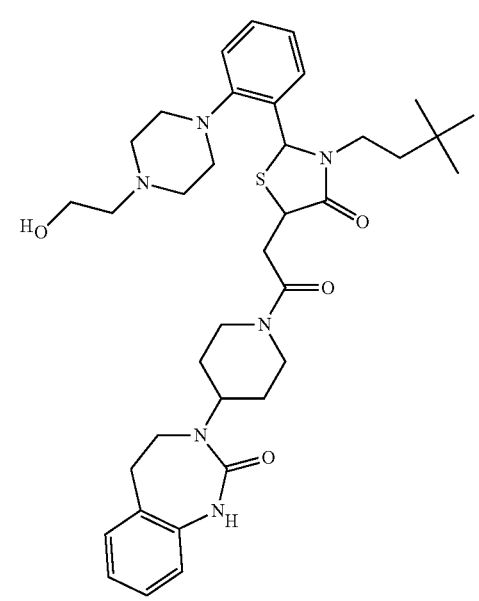
373
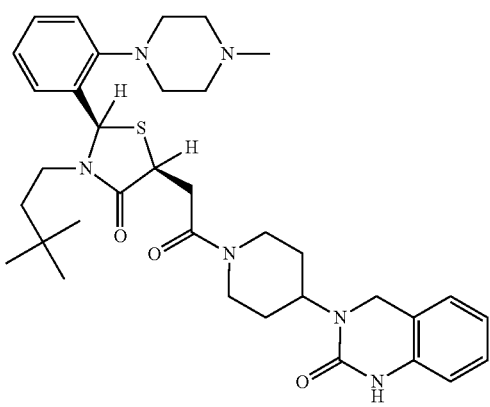

374
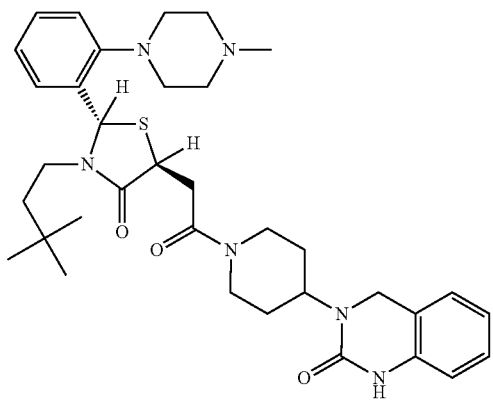
375
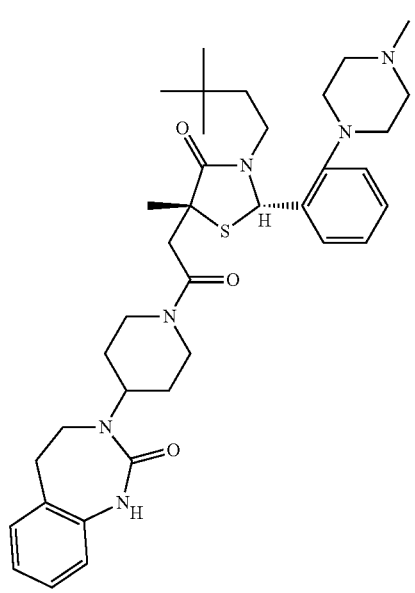
376
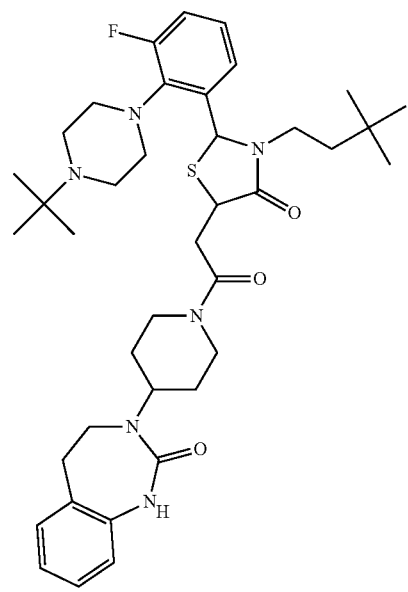
377
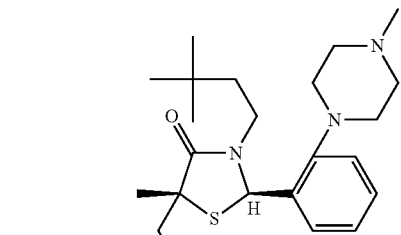
378
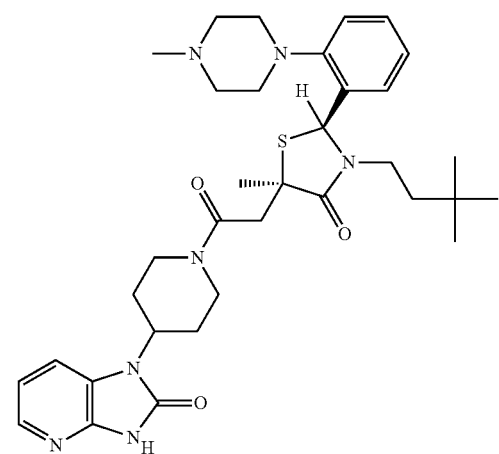
379
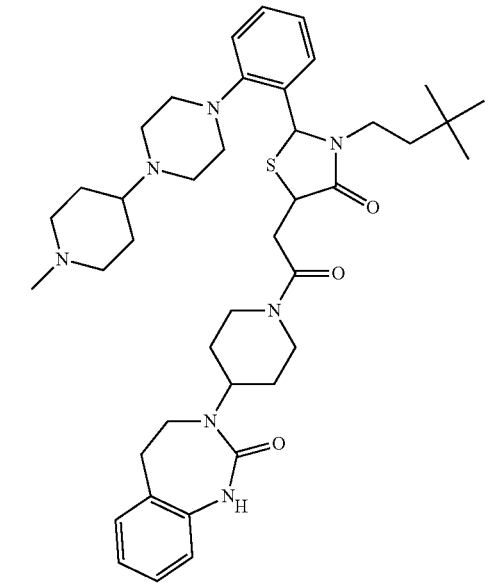

-continued
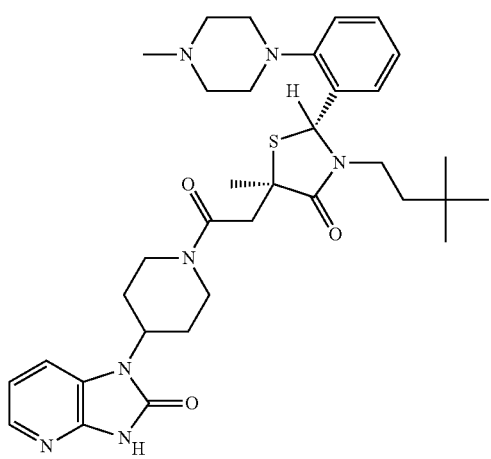
380
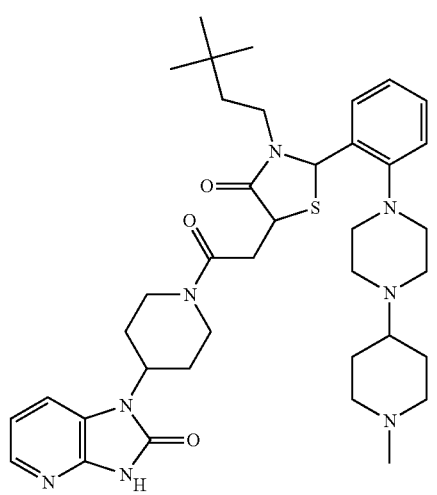
381
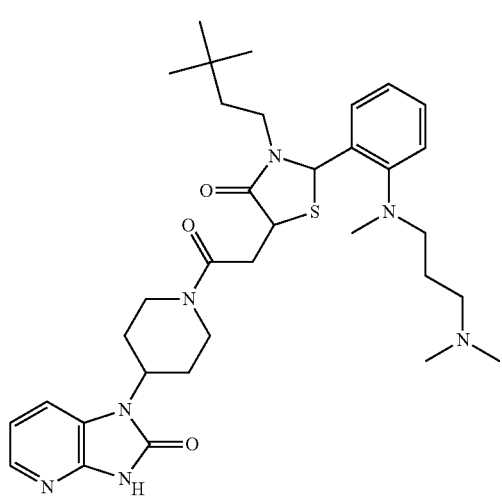
382
-continued
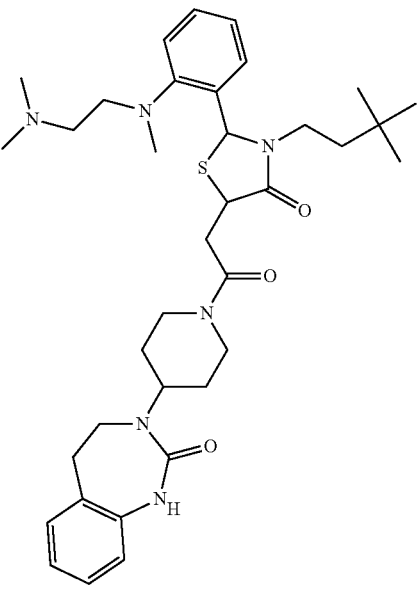
383
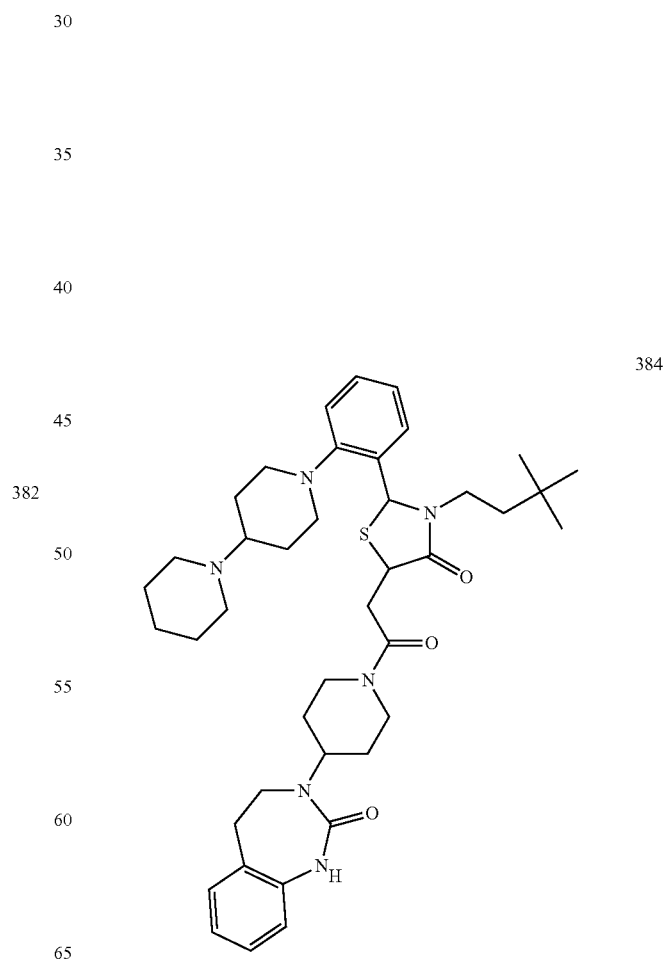
384

407
-continued
385
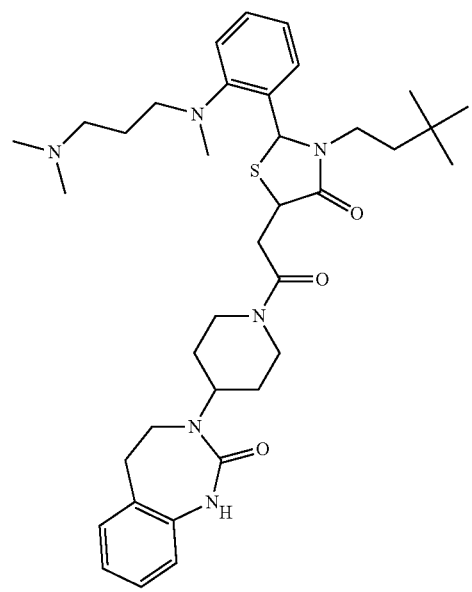
386
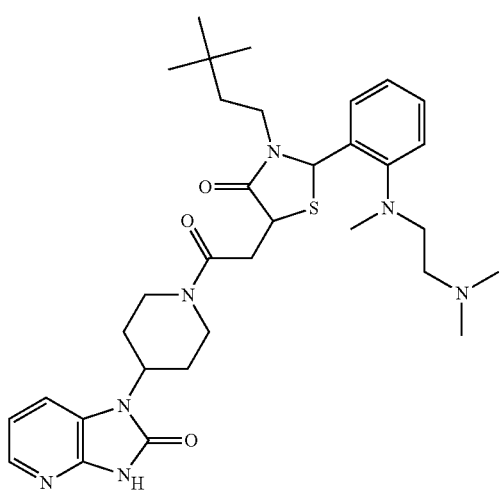
387
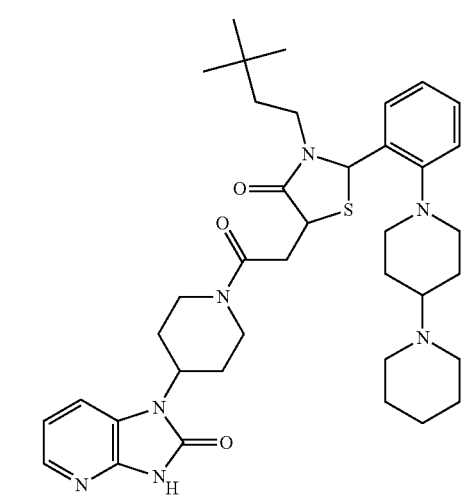
408
-continued
388
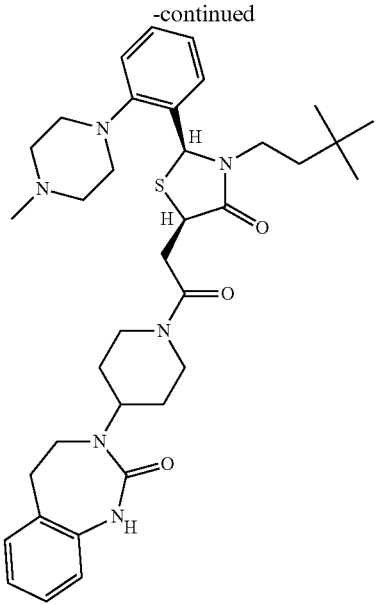
389
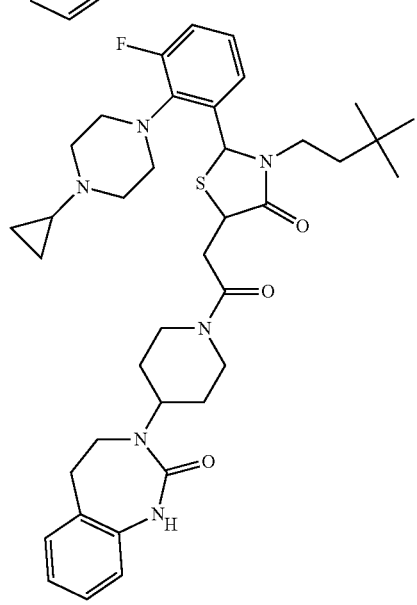
390
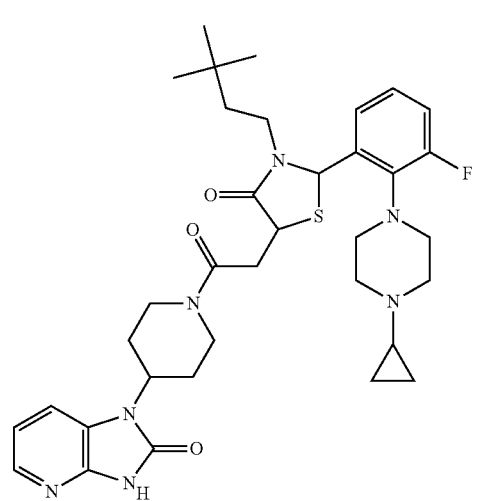

-continued
391
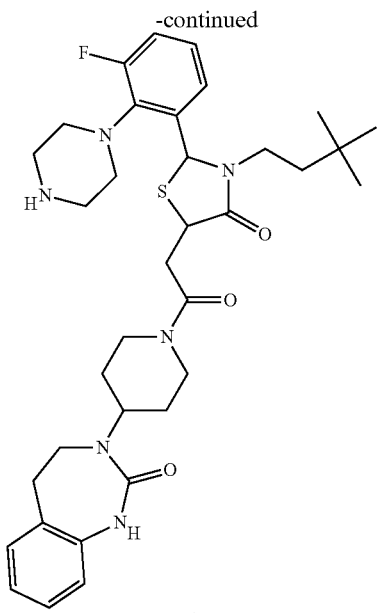
392
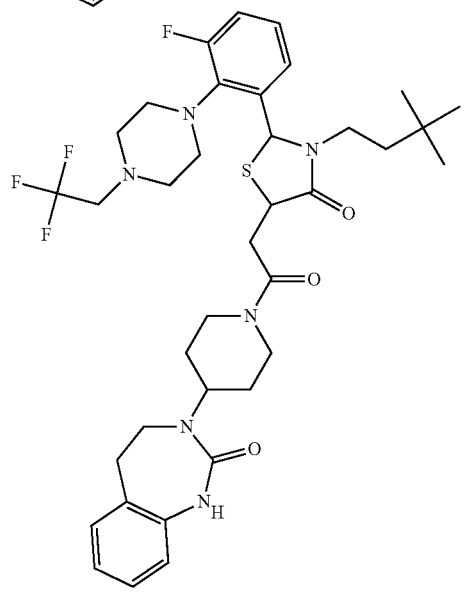
393
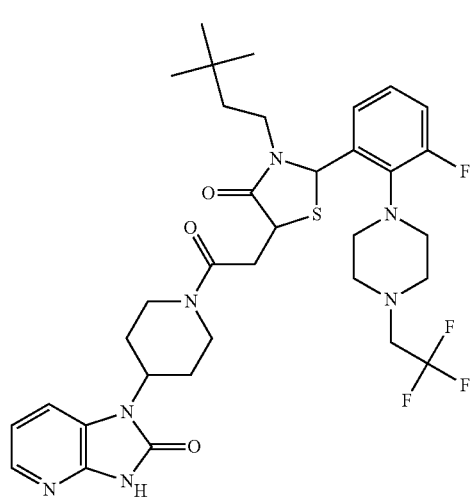
-continued
394
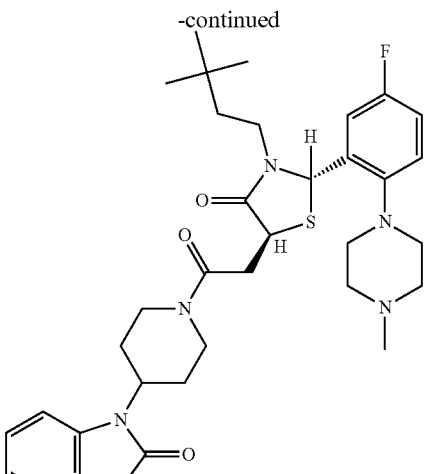
395
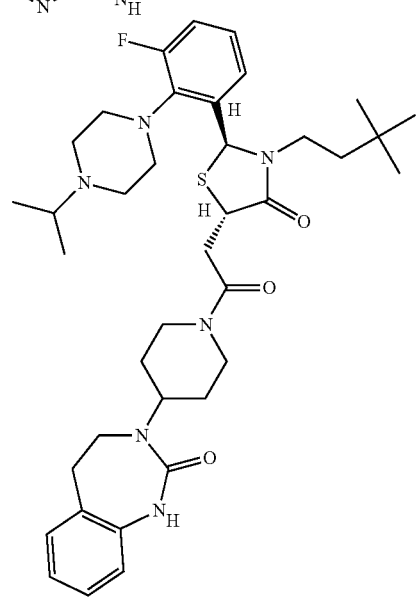
396
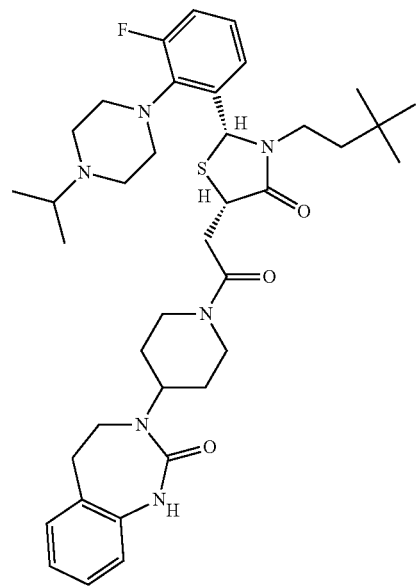

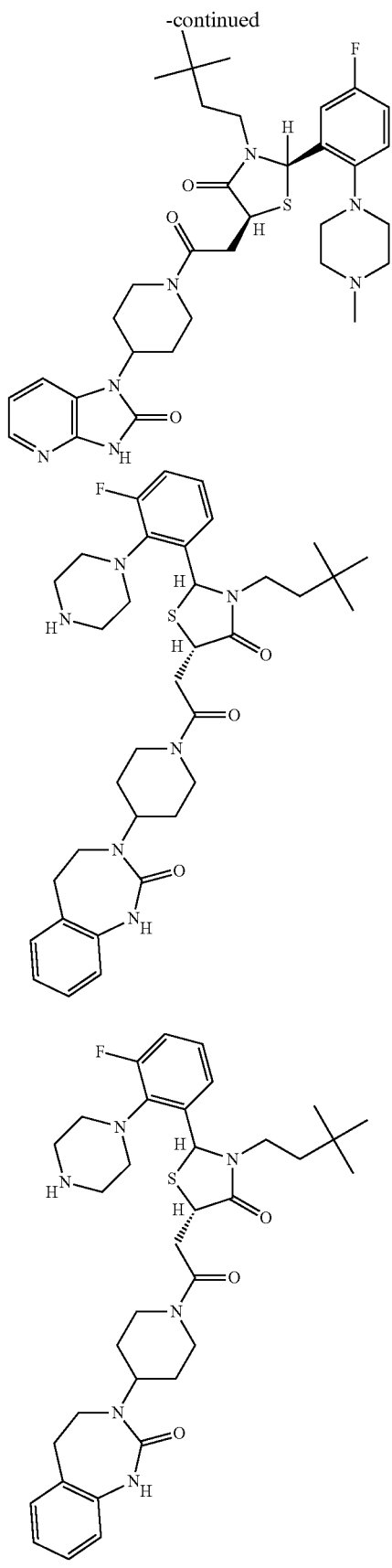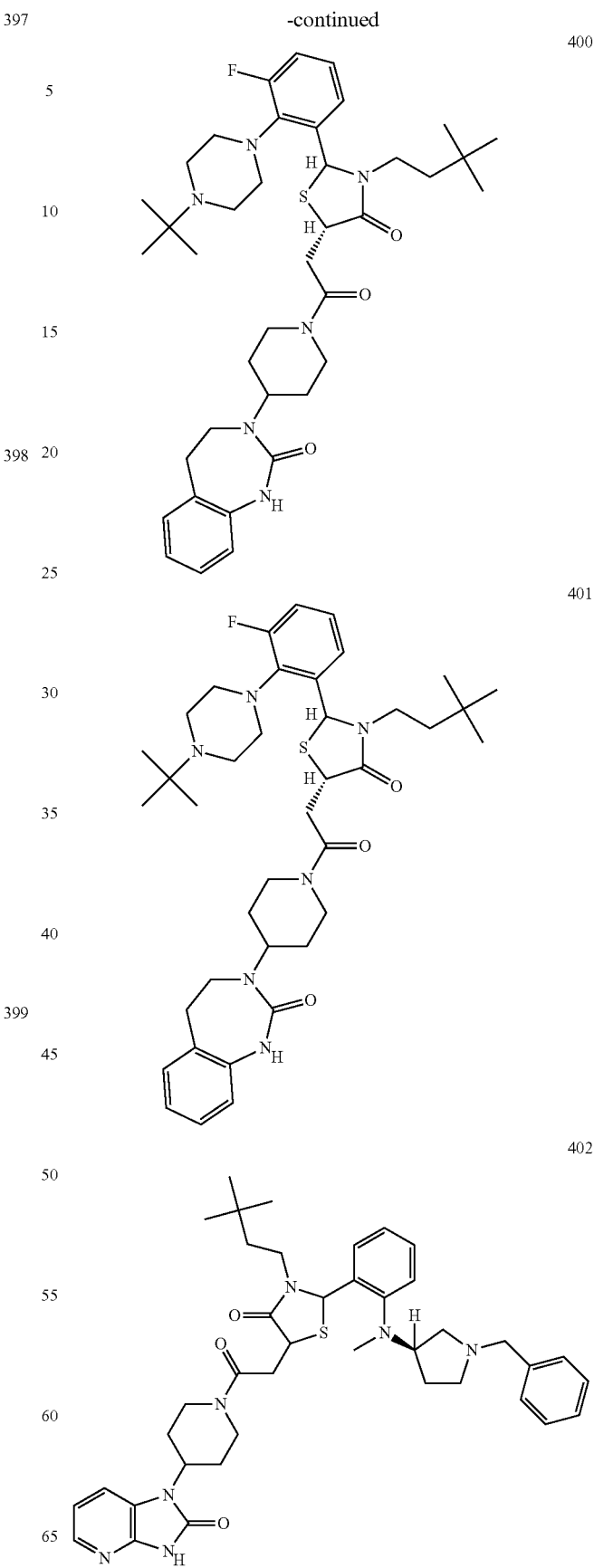

413
-continued
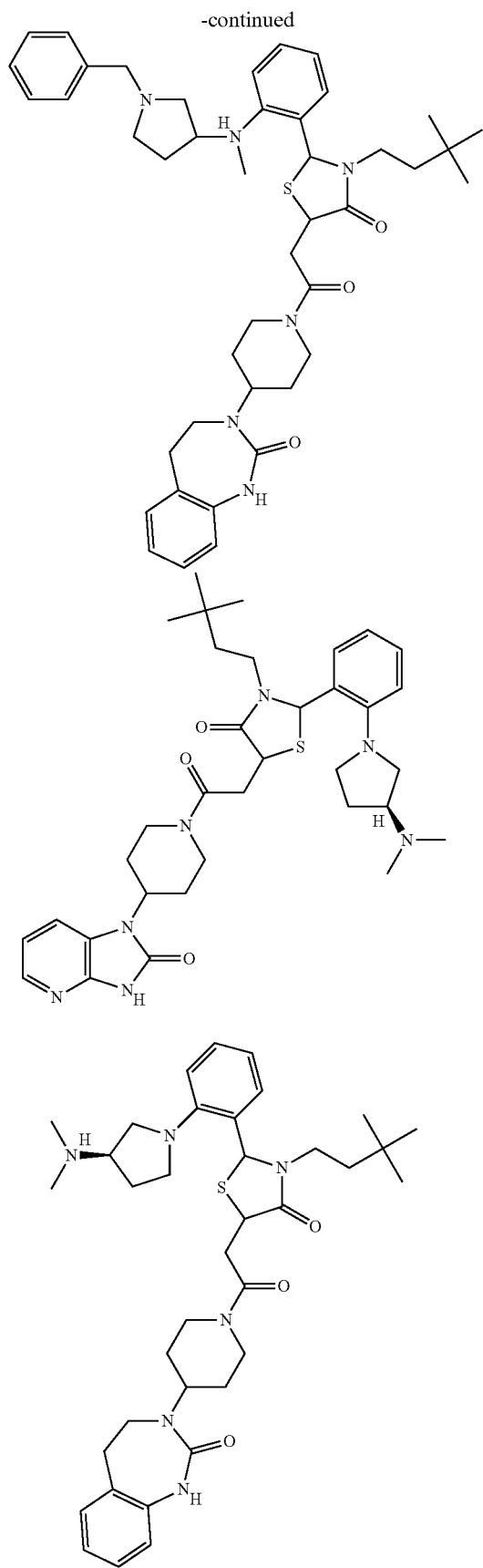
403
404
405
414
-continued
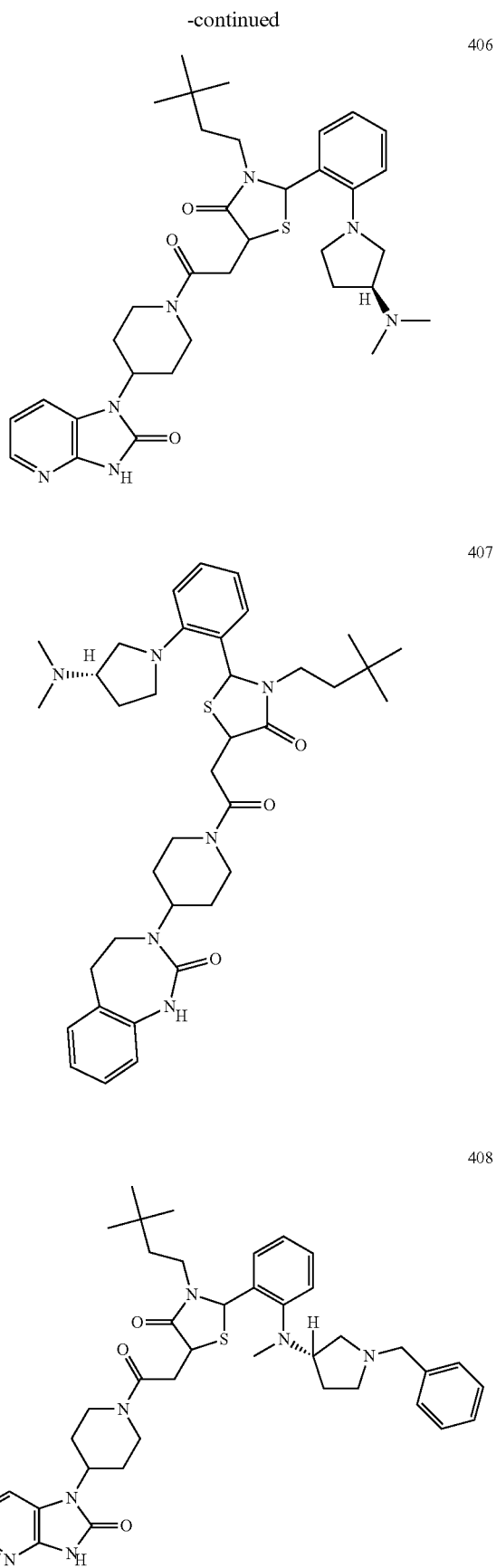
406
407
408

-continued
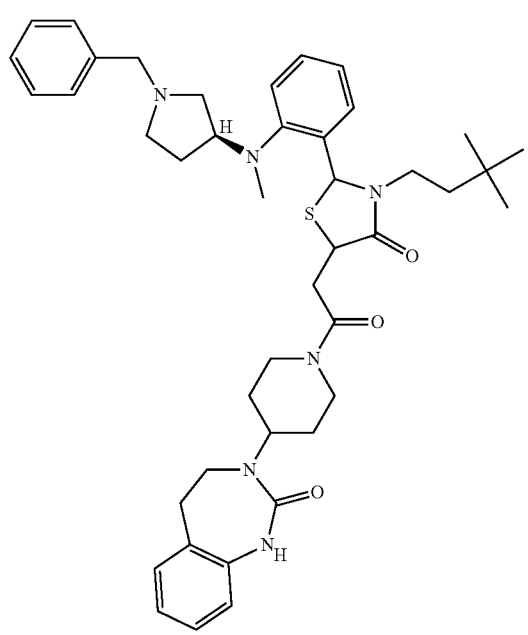
409
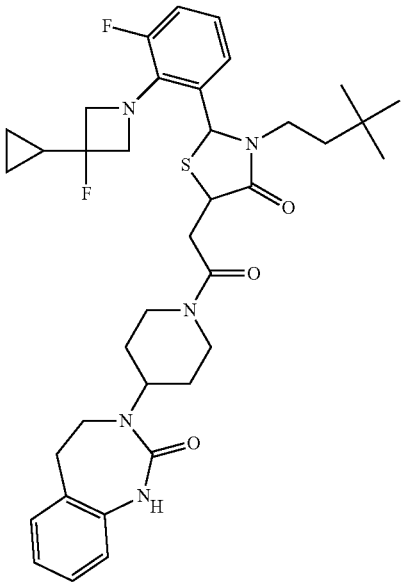
411
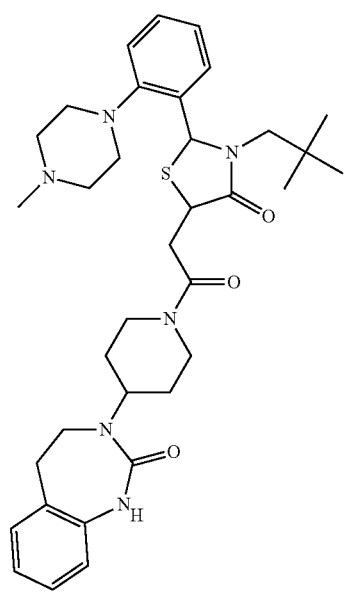
410
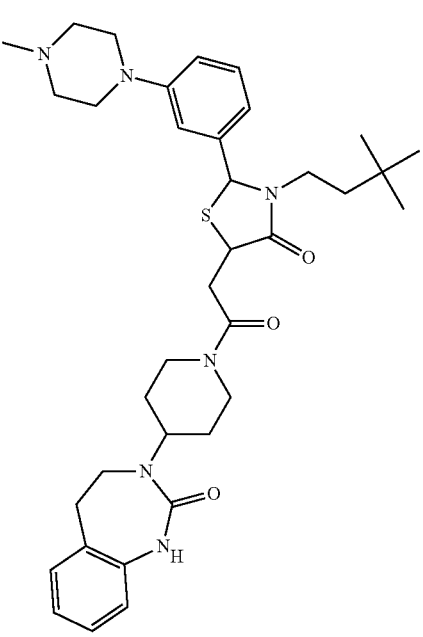
412

-continued
413
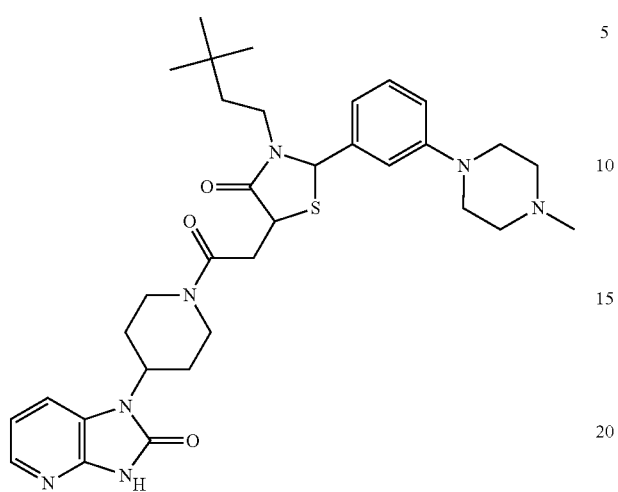
414
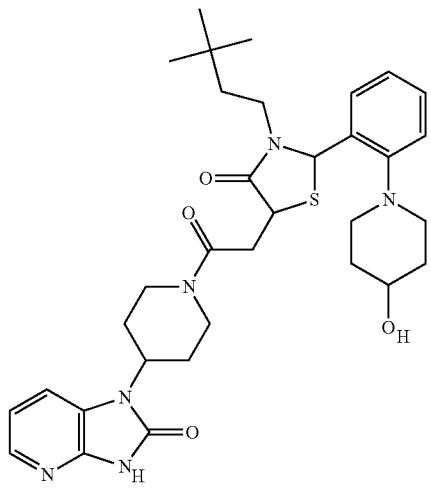
415
-continued
416
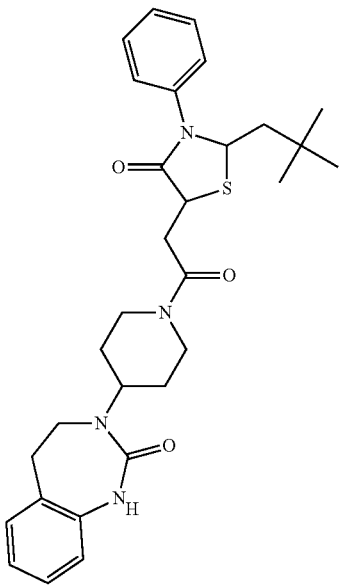
417
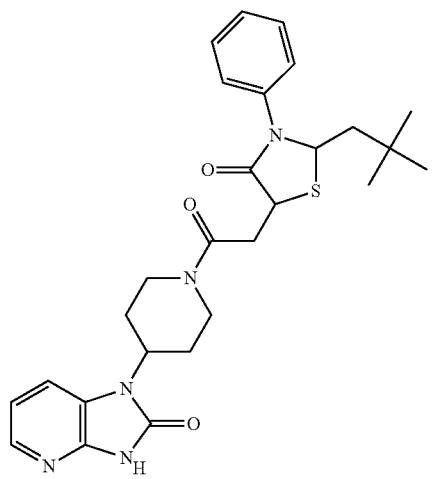
418
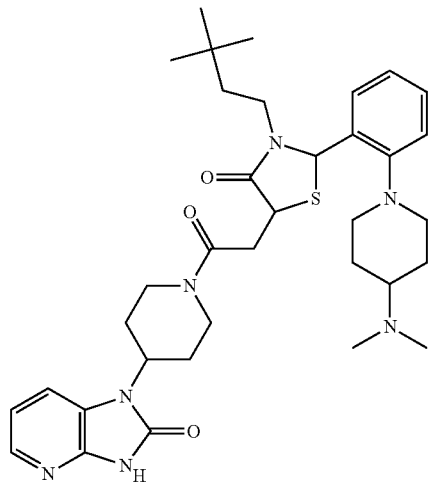

-continued
419
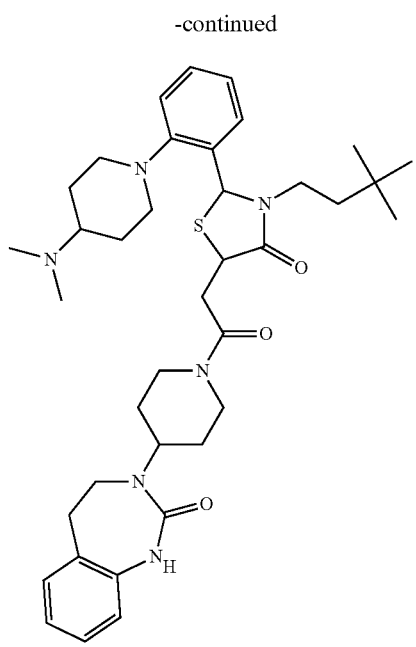
420
-continued
421
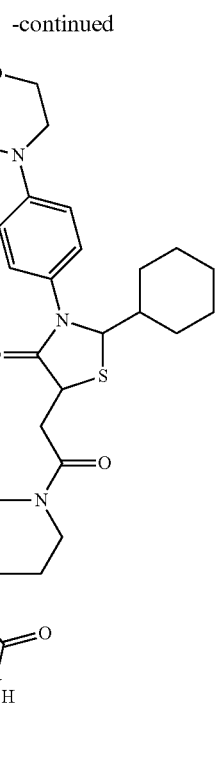
422
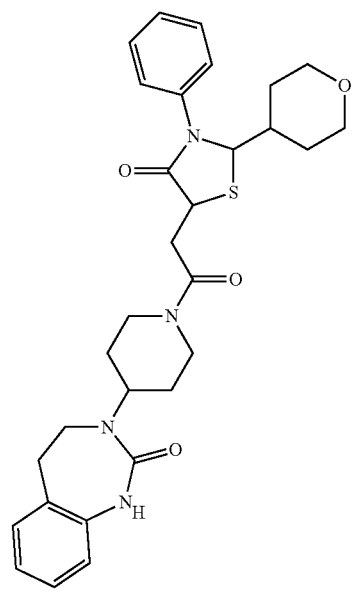
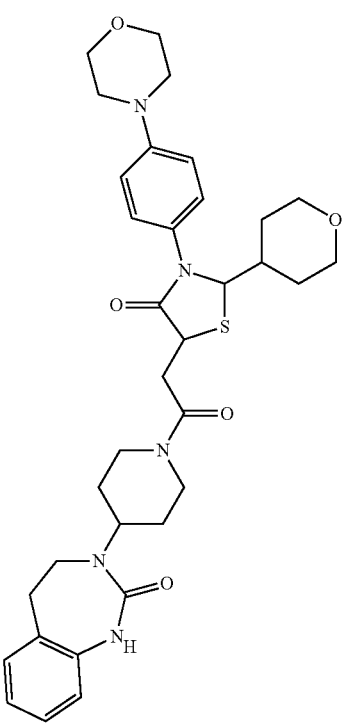

421
-continued
422
-continued
423
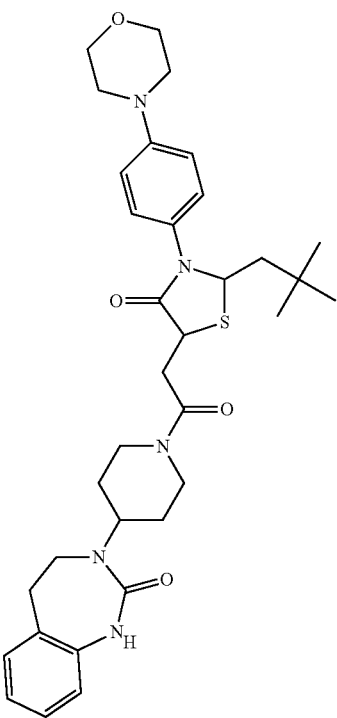
425
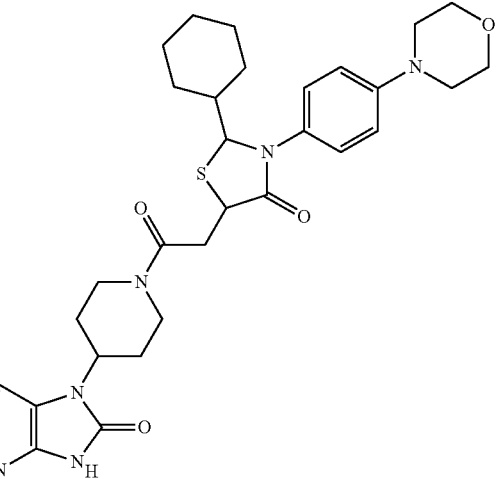
426
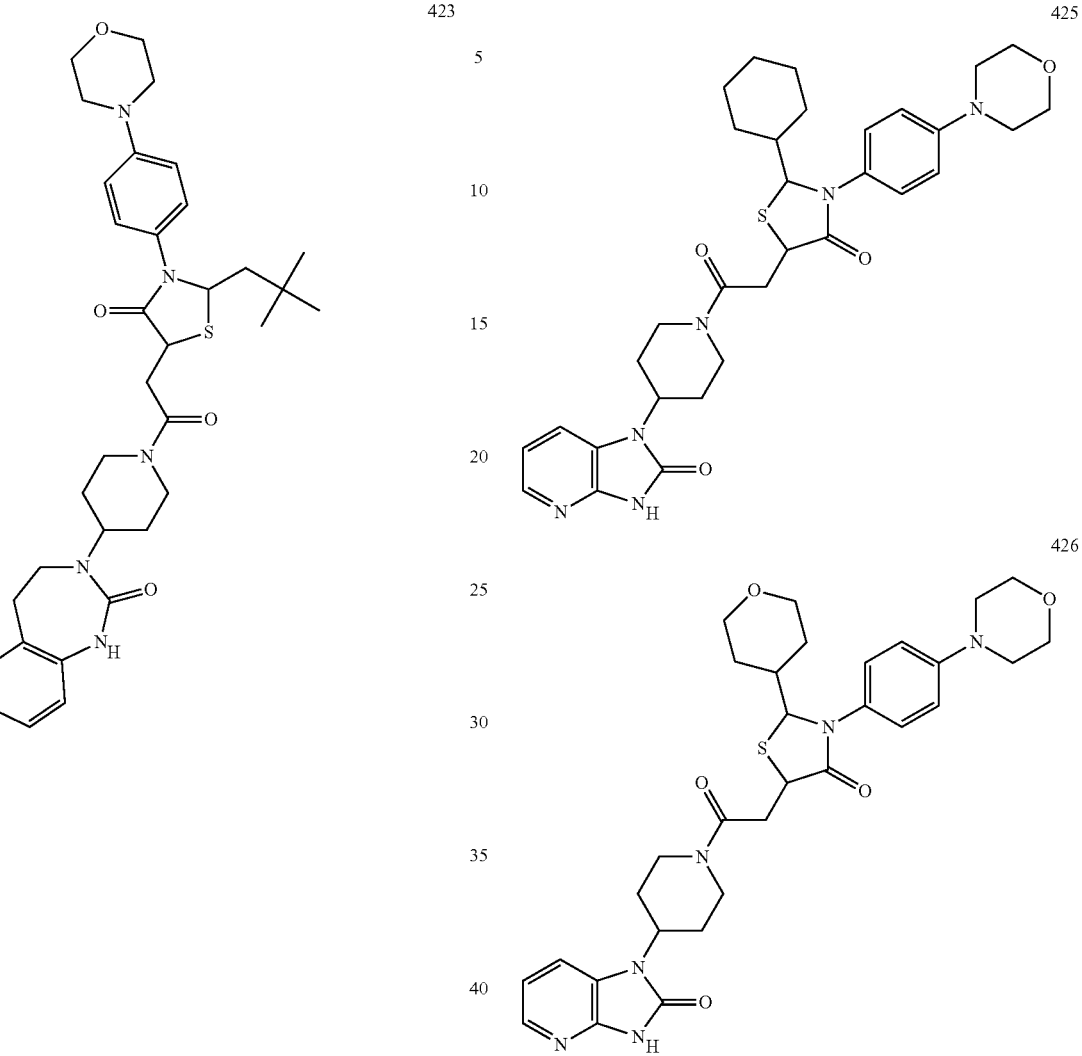
424
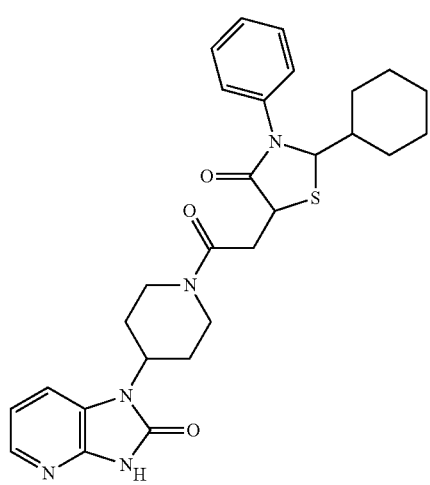
427
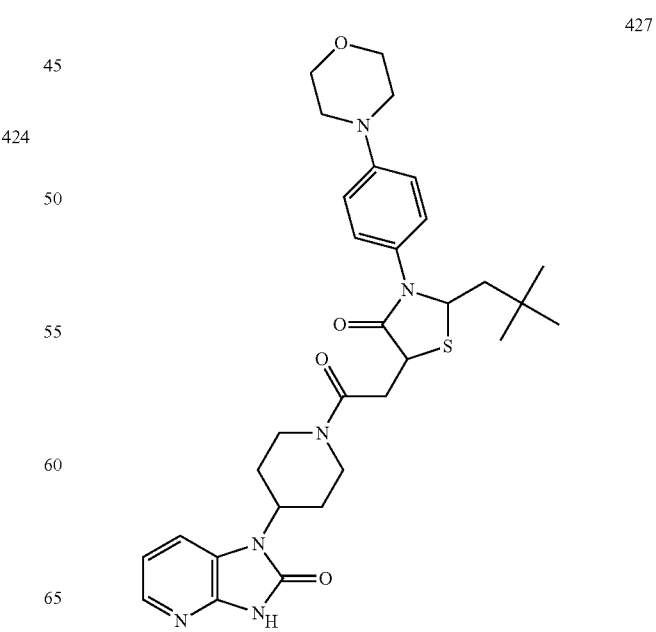

423
-continued
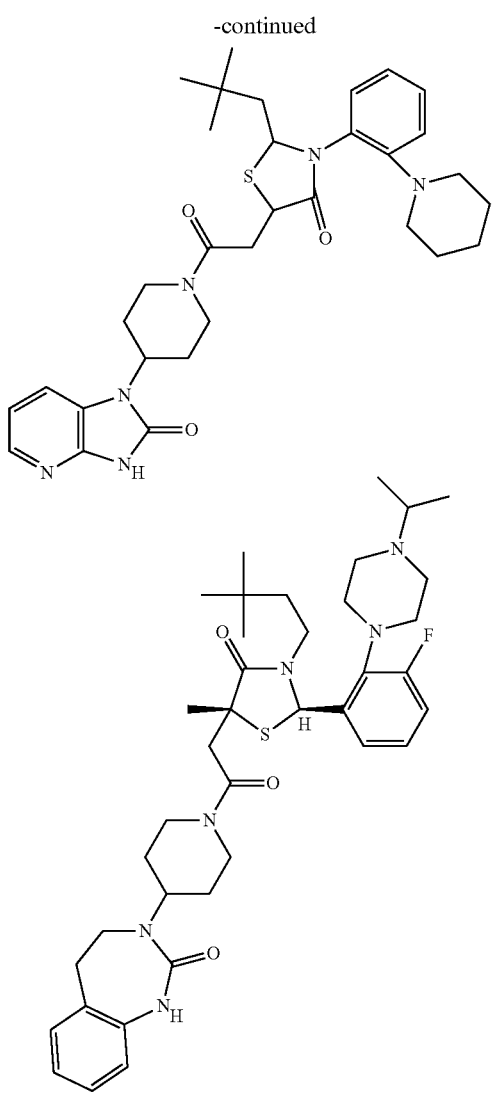
428
429
424
-continued
431
430
432

425
-continued
433
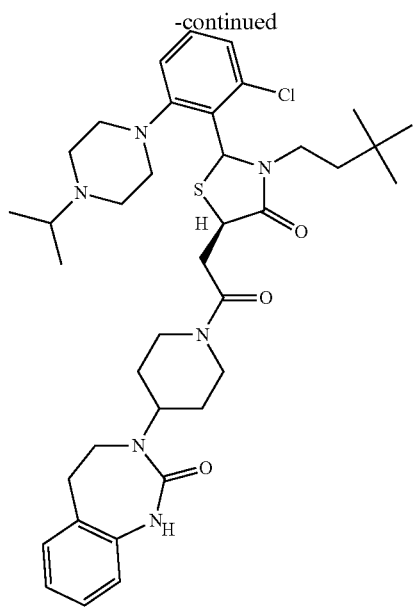
434
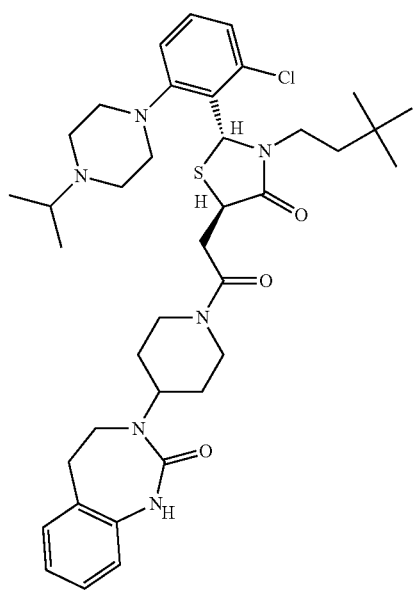
435
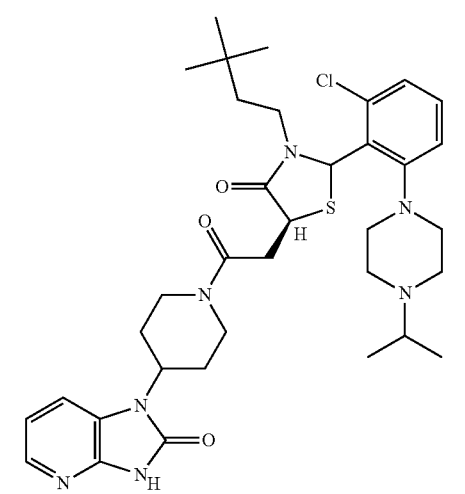
426
-continued
436
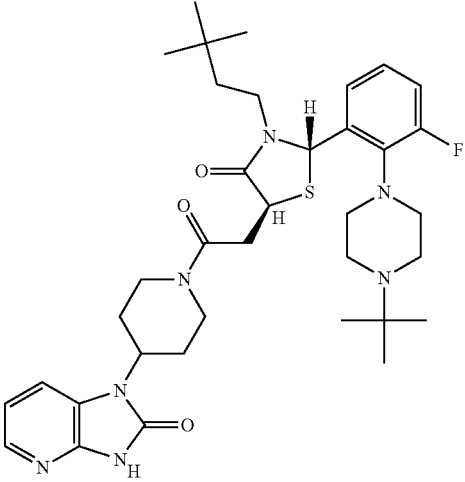
437
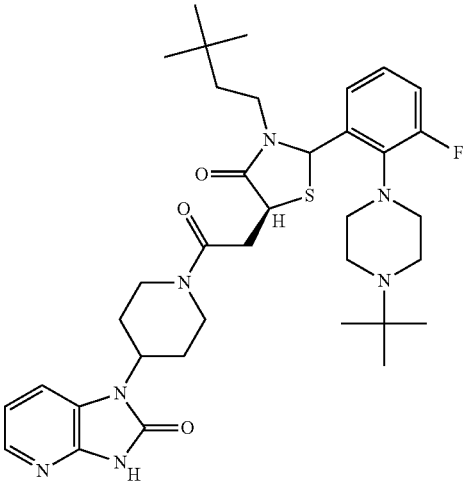
438

-continued
439
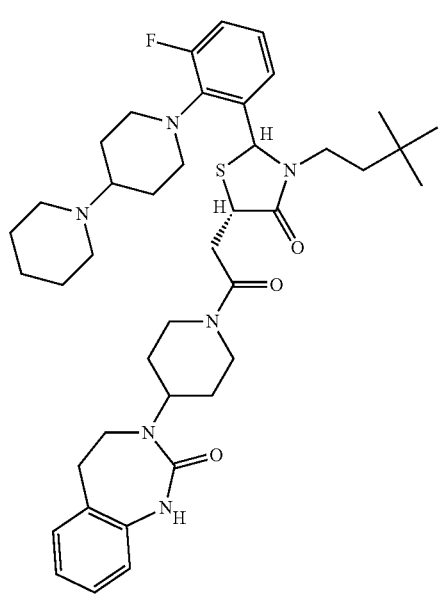
440
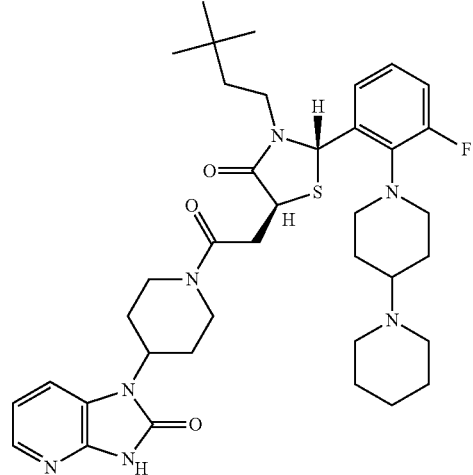
441
442
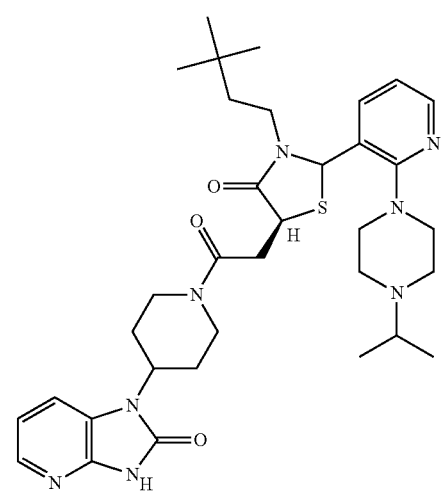
443
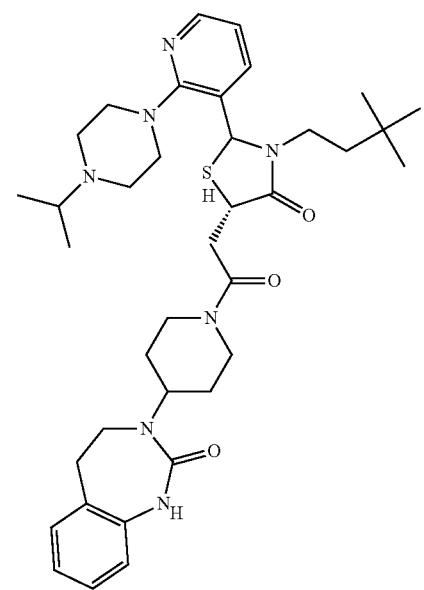
444

445
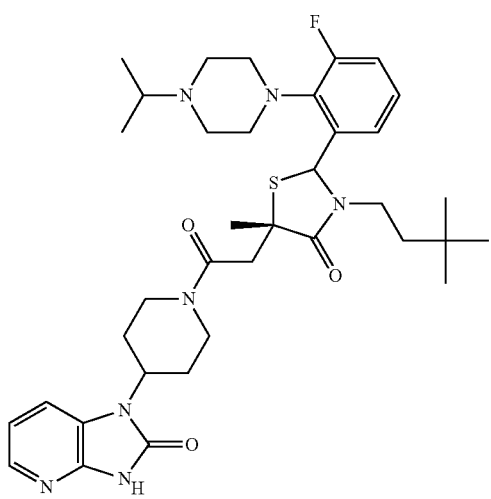
446
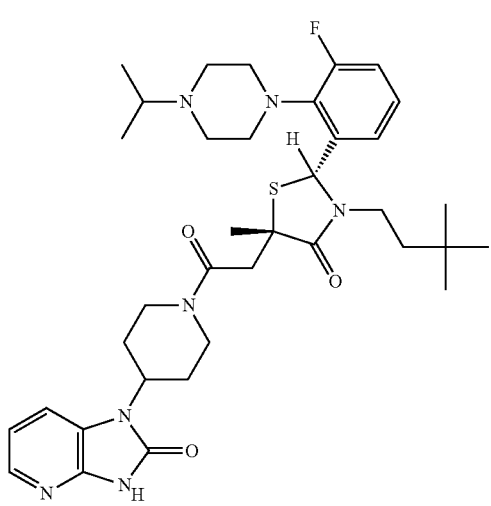
447
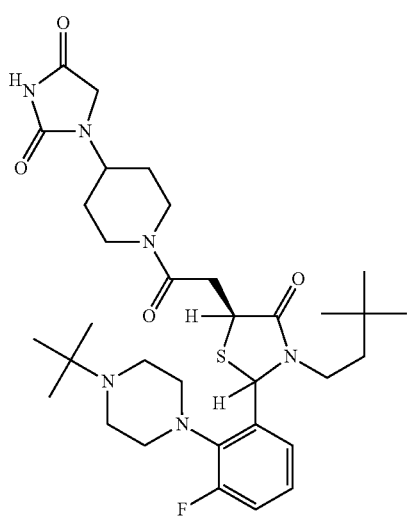
448
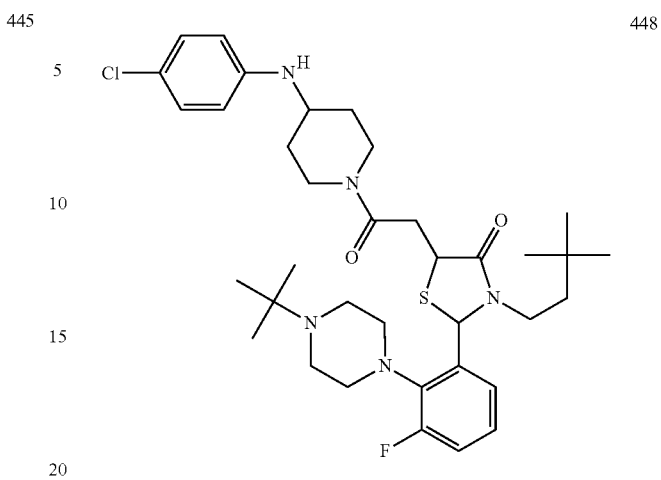
449
450
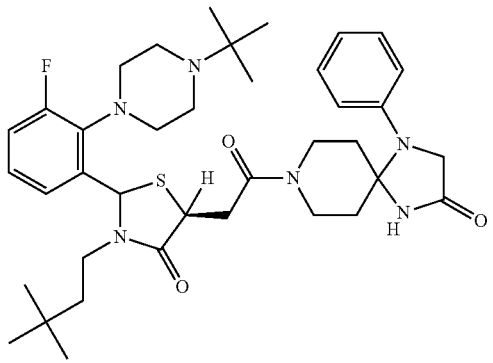

-continued
451
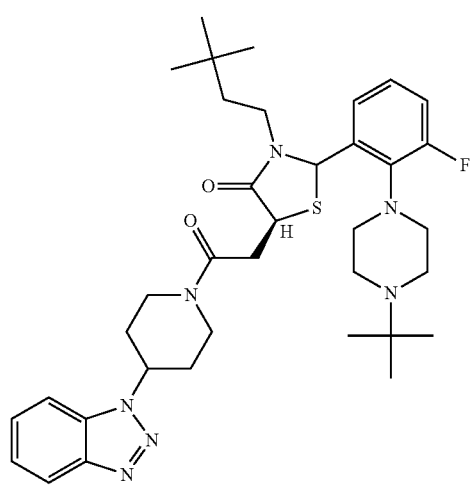
452
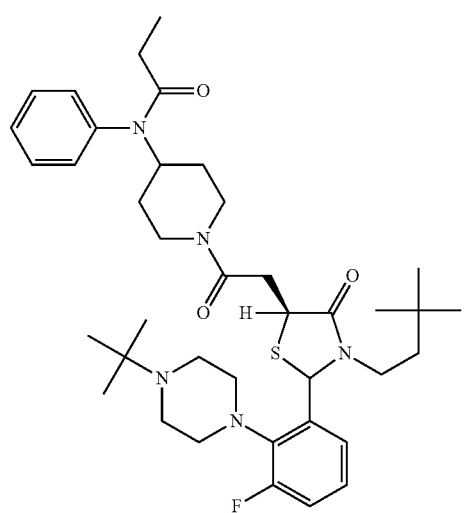
453
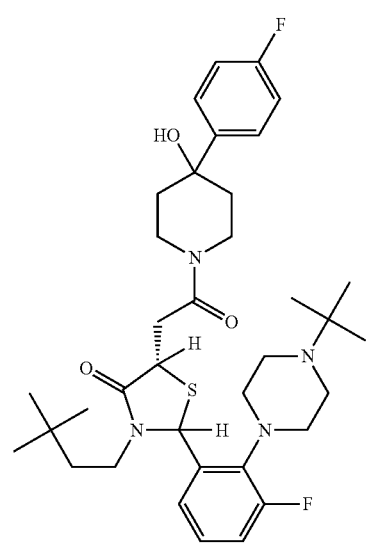
-continued
454
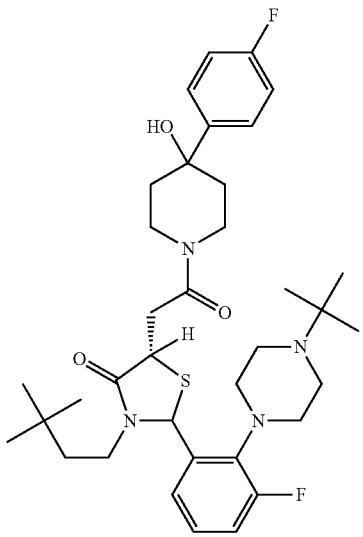
455
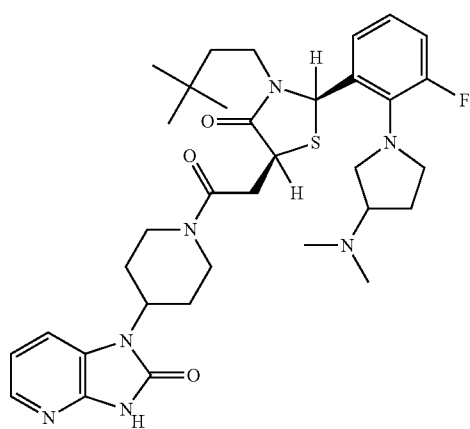
456
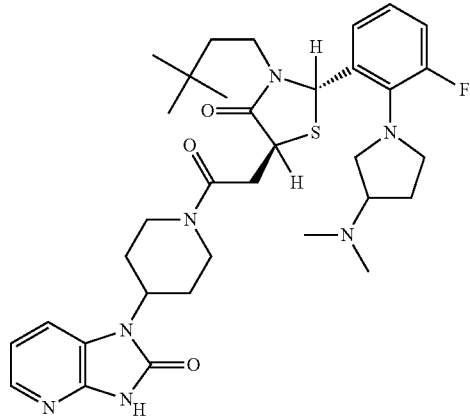

433
-continued
457
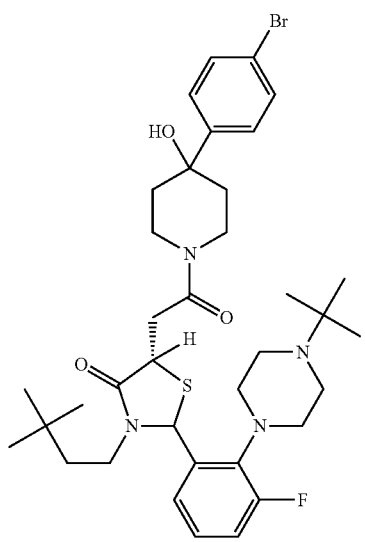
458
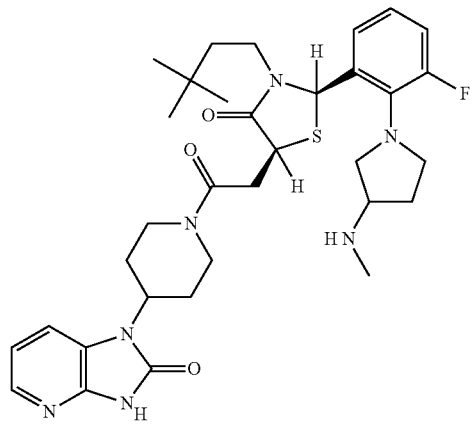
459
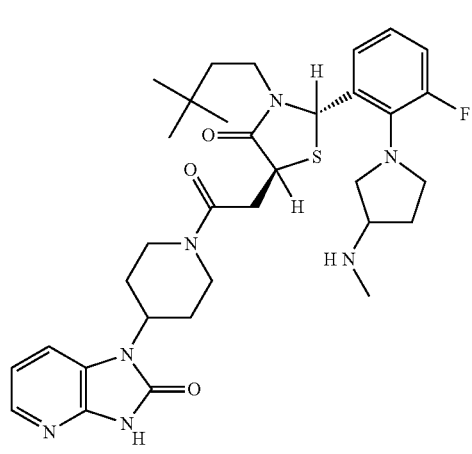
434
-continued
460
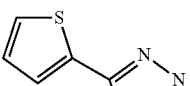
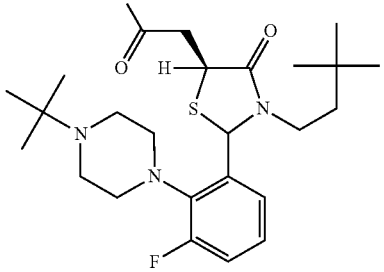
461
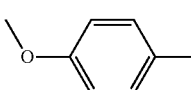
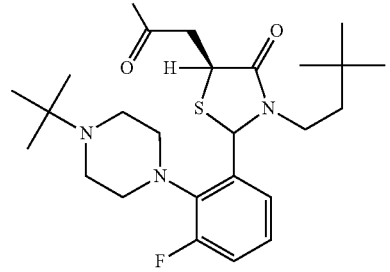
462
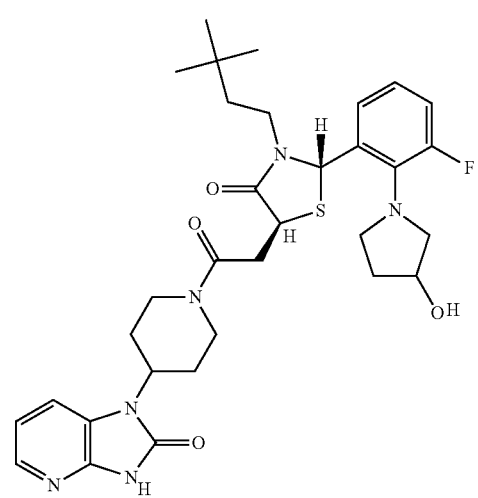

435
-continued
463
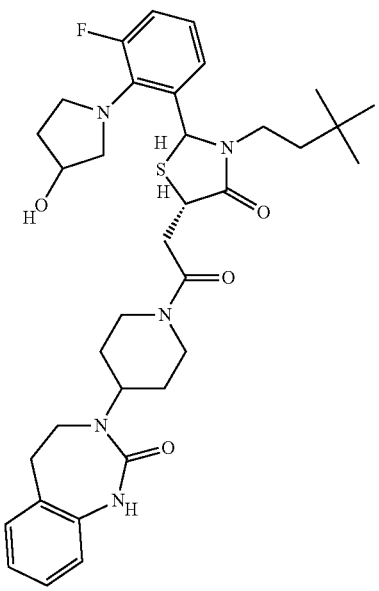
464
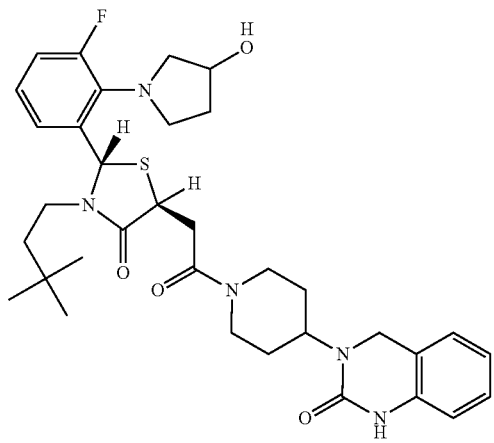
465
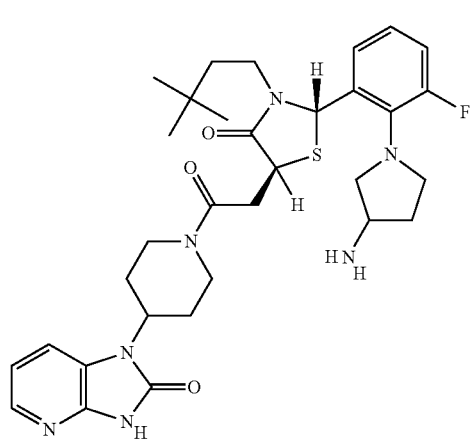
436
-continued
466
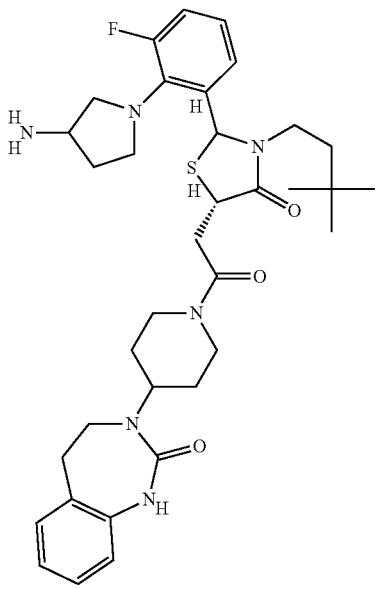
467
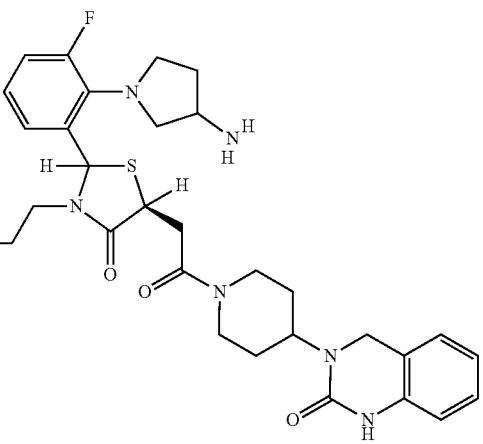
468
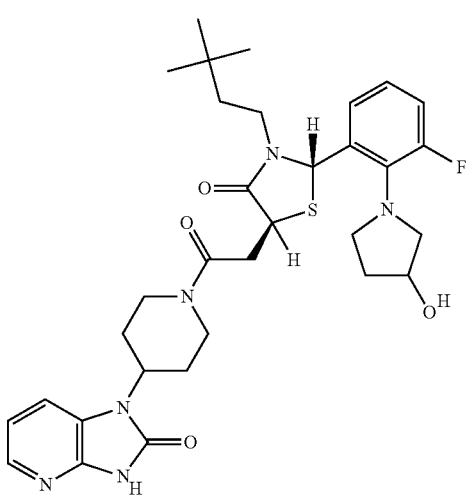

469
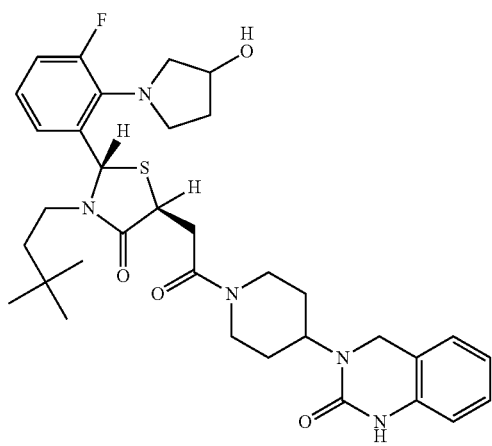
470
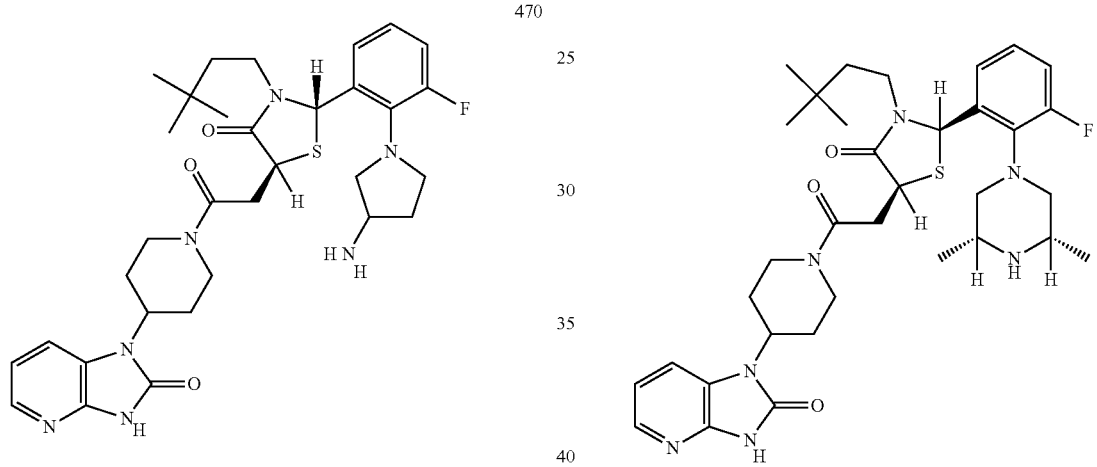
471
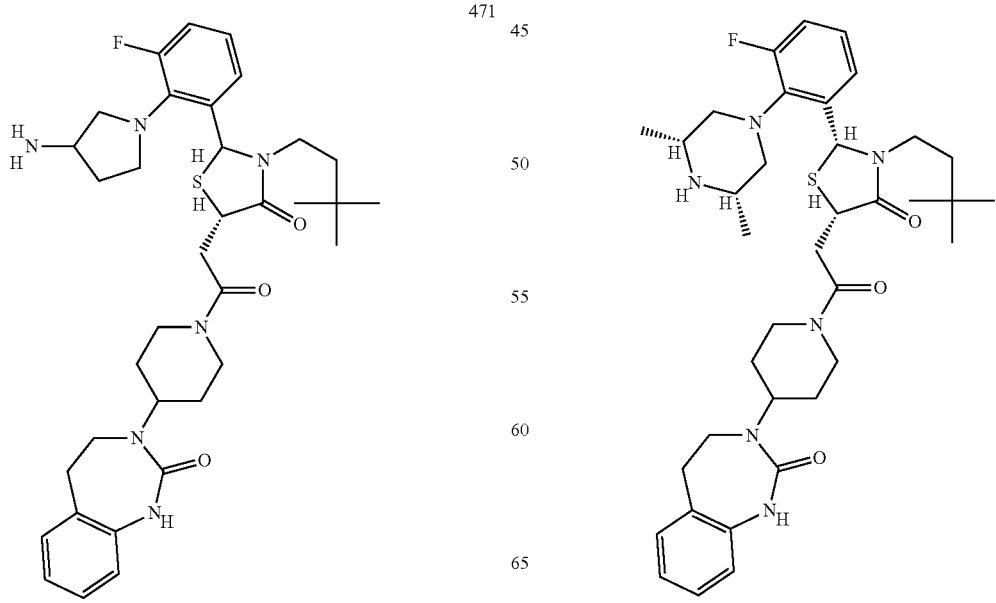
472
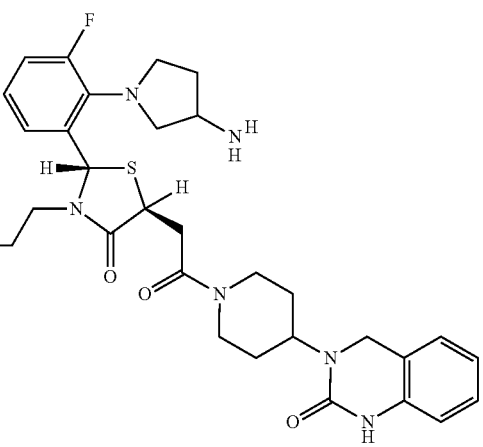
473
474

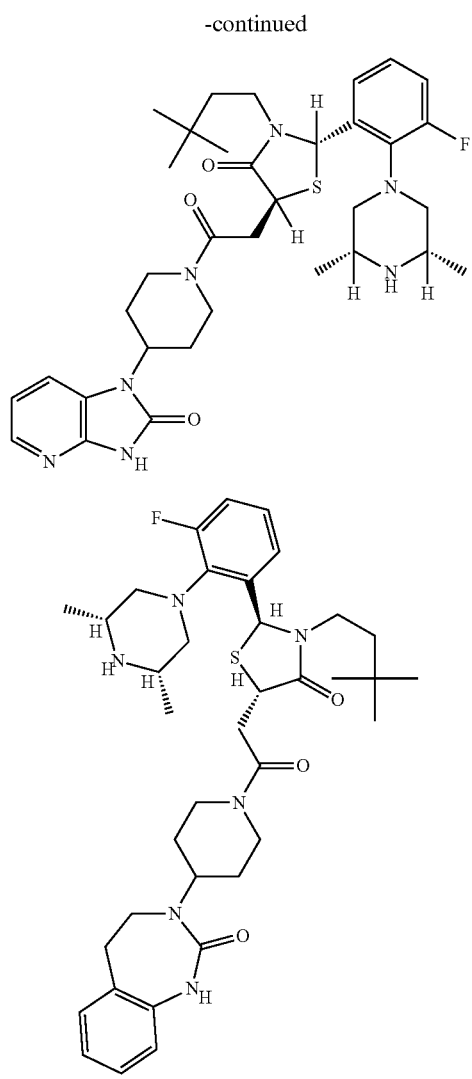

475

476

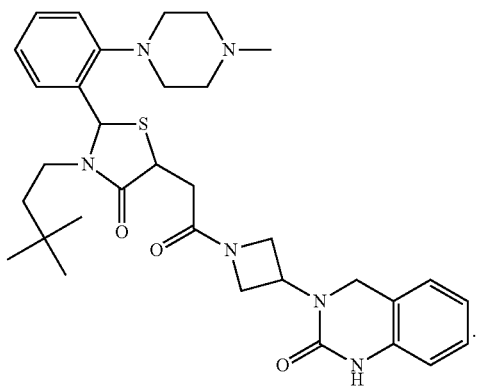

477

18. A pharmaceutical composition comprising a compound according to any one of claims 1, 2, 4, 5, 6, 7, 8, 9, 10, 11, 12, 13, 14, 15, 16 or 17, and a pharmaceutically acceptable carrier, adjuvant, or vehicle.

19. The pharmaceutical composition according to claim 18, further comprising an additional therapeutic agent.

20. A method of ameliorating, controlling or reducing the risk of one or more of the following conditions or diseases in a subject: headache; migraine; cluster headache; chronic tension type headache; neurogenic inflammation and inflammatory pain; or hot flashes in men and women; comprising administering a therapeutically effective amount of a compound according to claim 1 or claim 17 or a pharmaceutically acceptable composition comprising said compound to said subject in need thereof.

* * * * *